US008409816B2

(12) United States Patent
Urdea et al.

(10) Patent No.: US 8,409,816 B2
(45) Date of Patent: *Apr. 2, 2013

(54) DIABETES-RELATED BIOMARKERS AND METHODS OF USE THEREOF

(75) Inventors: Michael S. Urdea, Alamo, CA (US); Michael P. McKenna, Oakland, CA (US); Patrick A. Arensdorf, Palo Alto, CA (US)

(73) Assignee: Tethys Bioscience, Inc., Emeryville, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/253,578

(22) Filed: Oct. 5, 2011

(65) Prior Publication Data

US 2012/0179484 A1 Jul. 12, 2012

Related U.S. Application Data

(63) Continuation of application No. 12/106,070, filed on Apr. 18, 2008, now Pat. No. 8,119,358, which is a continuation-in-part of application No. 11/788,260, filed on Apr. 18, 2007, now abandoned, which is a continuation-in-part of application No. 11/546,874, filed on Oct. 11, 2006, now abandoned.

(60) Provisional application No. 60/725,462, filed on Oct. 11, 2005, provisional application No. 61/002,609, filed on Nov. 8, 2007.

(51) Int. Cl.
*G01N 31/00* (2006.01)
*G01N 33/53* (2006.01)

(52) U.S. Cl. ........ 435/7.21; 435/7.1; 436/501; 436/518; 424/9.1; 424/520; 530/300; 530/350

(58) Field of Classification Search ........................ None
See application file for complete search history.

(56) References Cited

U.S. PATENT DOCUMENTS

| | | | |
|---|---|---|---|
| 4,105,776 A | 8/1978 | Ondetti et al. |
| 4,230,767 A | 10/1980 | Isaka et al. |
| 4,230,797 A | 10/1980 | Boguslaski et al. |
| 4,231,938 A | 11/1980 | Monaghan et al. |
| 4,233,402 A | 11/1980 | Maggio et al. |
| 4,275,149 A | 6/1981 | Litman et al. |
| 4,302,386 A | 11/1981 | Stevens |
| 4,316,906 A | 2/1982 | Ondetti et al. |
| 4,337,201 A | 6/1982 | Petrillo, Jr. |
| 4,344,949 A | 8/1982 | Hoefle et al. |
| 4,346,227 A | 8/1982 | Terahara et al. |
| 4,374,829 A | 2/1983 | Harris et al. |
| 4,376,110 A | 3/1983 | David et al. |
| 4,410,520 A | 10/1983 | Watthey |
| 4,444,784 A | 4/1984 | Hoffman et al. |
| 4,508,729 A | 4/1985 | Vincent et al. |
| 4,512,924 A | 4/1985 | Attwood et al. |
| 4,587,258 A | 5/1986 | Gold et al. |
| 4,659,678 A | 4/1987 | Forrest et al. |
| 4,727,022 A | 2/1988 | Skold et al. |
| 4,739,073 A | 4/1988 | Kathawala |
| 4,772,684 A | 9/1988 | Brunck et al. |
| 4,780,401 A | 10/1988 | Heusser et al. |
| 4,816,463 A | 3/1989 | Blankley et al. |
| 4,845,079 A | 7/1989 | Luly et al. |
| 4,885,292 A | 12/1989 | Ryono et al. |
| 4,894,437 A | 1/1990 | TenBrink |
| 4,897,402 A | 1/1990 | Duggan et al. |
| 4,904,646 A | 2/1990 | Karanewsky et al. |
| 4,906,624 A | 3/1990 | Chucholowski et al. |
| 4,906,657 A | 3/1990 | Roth |
| 4,920,109 A | 4/1990 | Onishi et al. |
| 4,923,861 A | 5/1990 | Picard et al. |
| 4,929,620 A | 5/1990 | Chucholowski et al. |
| 4,939,143 A | 7/1990 | Regan et al. |
| 4,940,727 A | 7/1990 | Inamine et al. |
| 4,940,800 A | 7/1990 | Bertolini et al. |
| 4,946,860 A | 8/1990 | Morris et al. |
| 4,946,864 A | 8/1990 | Prugh et al. |
| 4,950,675 A | 8/1990 | Chucholowski |
| 4,957,940 A | 9/1990 | Roth |
| 4,963,538 A | 10/1990 | Duggan et al. |
| 4,968,693 A | 11/1990 | Joshua et al. |
| 4,970,231 A | 11/1990 | Lee et al. |
| 4,980,283 A | 12/1990 | Huang et al. |
| 4,992,429 A | 2/1991 | Ullrich et al. |
| 4,994,494 A | 2/1991 | Regan et al. |

(Continued)

FOREIGN PATENT DOCUMENTS

| EP | 253310 A2 | 1/1988 |
|---|---|---|
| WO | WO-95/00501 | 1/1995 |

(Continued)

OTHER PUBLICATIONS

U.S. Appl. No. 13/504,720, filed Apr. 27, 2012, McKenna et al.
U.S. Appl. No. 13/504,478, filed Aug. 15, 2012, McKenna et al.
Bayés et al., Obesity, adiponectin and inflammation as predictors of new-onset diabetes mellitus after kidney transplantation, *Am. J. Transplantation*, 7:416-22 (2007).
Biesenbach et al., Erythropoietin requirement in patients with type 2 diabetes mellitus on maintenance hemodialysis therapy. *Wiener Klinische Wochenschrift*, 116(24): 844-8 (2004).
Burke et al., Rapid rise in the incidence of type 2 diabetes from 1987 to 1996, *Arch. Intern. Med.*, 159:1450-56 (1999).
Burke et al., Reversion from type 2 diabetes to nondiabetic status, *Diabet. Care*, 21:1266-70 (1998).
Chen et al., Association between inflammation and insulin resistance in U.S. nondiabetic adults: Results from the Third National Health and Nutrition Examination Survey. *Diabetes Care*, 27(12): 2960-5 (2004).
Choi et al., Inflammation, insulin resistance, and glucose intolerance in acute myocardial infarction patients without a previous diagnosis of diabetes mellitus. *J. Clin. Endocrinol. Metab.* 90(1): 175-80 (2005).

(Continued)

*Primary Examiner* — Lisa Cook
(74) *Attorney, Agent, or Firm* — Marshall, Gerstein & Borun LLP

(57) ABSTRACT

The invention describes biomarkers which can be used to predict the likelihood that an individual will develop Diabetes. The biomarkers can also be used to screen large groups in order to identify individuals at risk of developing Diabetes.

38 Claims, 181 Drawing Sheets

U.S. PATENT DOCUMENTS

| | | |
|---|---|---|
| 4,996,234 A | 2/1991 | Regan et al. |
| 4,997,837 A | 3/1991 | Chucholowski et al. |
| 5,001,128 A | 3/1991 | Neuenschwander et al. |
| 5,001,144 A | 3/1991 | Regan et al. |
| 5,017,716 A | 5/1991 | Karanewsky et al. |
| 5,018,067 A | 5/1991 | Mohlenbrock et al. |
| 5,021,453 A | 6/1991 | Joshua et al. |
| 5,025,000 A | 6/1991 | Karanewsky |
| 5,034,512 A | 7/1991 | Hudspeth et al. |
| 5,036,053 A | 7/1991 | Himmelsbach et al. |
| 5,036,054 A | 7/1991 | Kaltenbronn et al. |
| 5,055,466 A | 10/1991 | Weller, III et al. |
| 5,063,207 A | 11/1991 | Doherty et al. |
| 5,063,208 A | 11/1991 | Rosenberg et al. |
| 5,064,825 A | 11/1991 | Chakravarty et al. |
| 5,064,965 A | 11/1991 | Ocain et al. |
| 5,066,643 A | 11/1991 | Abeles et al. |
| 5,071,837 A | 12/1991 | Doherty et al. |
| 5,073,566 A | 12/1991 | Lifer et al. |
| 5,075,451 A | 12/1991 | Ocain et al. |
| 5,081,127 A | 1/1992 | Carini et al. |
| 5,081,136 A | 1/1992 | Bertolini et al. |
| 5,085,992 A | 2/1992 | Chen et al. |
| 5,087,634 A | 2/1992 | Reitz et al. |
| 5,089,471 A | 2/1992 | Hanson et al. |
| 5,091,378 A | 2/1992 | Karanewsky et al. |
| 5,091,386 A | 2/1992 | Kesseler et al. |
| 5,095,006 A | 3/1992 | Bender et al. |
| 5,095,119 A | 3/1992 | Ocain et al. |
| 5,098,924 A | 3/1992 | Poss |
| 5,098,931 A | 3/1992 | Duggan et al. |
| 5,102,911 A | 4/1992 | Lee et al. |
| 5,104,869 A | 4/1992 | Albright et al. |
| 5,106,835 A | 4/1992 | Albright et al. |
| 5,112,857 A | 5/1992 | Vickers |
| 5,114,937 A | 5/1992 | Hamby et al. |
| 5,116,835 A | 5/1992 | Ruger et al. |
| 5,116,870 A | 5/1992 | Smith et al. |
| 5,130,306 A | 7/1992 | Duggan et al. |
| 5,132,312 A | 7/1992 | Regan et al. |
| 5,135,935 A | 8/1992 | Alberts et al. |
| 5,166,171 A | 11/1992 | Jendralla et al. |
| 5,182,298 A | 1/1993 | Helms et al. |
| 5,196,440 A | 3/1993 | Bertolini et al. |
| 5,202,327 A | 4/1993 | Robl |
| 5,250,435 A | 10/1993 | Cover et al. |
| 5,256,689 A | 10/1993 | Chiang |
| 5,260,332 A | 11/1993 | Dufresne |
| 5,262,435 A | 11/1993 | Joshua et al. |
| 5,273,995 A | 12/1993 | Roth |
| 5,276,021 A | 1/1994 | Karanewsky et al. |
| 5,283,256 A | 2/1994 | Dufresne et al. |
| 5,286,895 A | 2/1994 | Harris et al. |
| 5,302,604 A | 4/1994 | Byrne et al. |
| 5,317,031 A | 5/1994 | MacConnell et al. |
| 5,356,896 A | 10/1994 | Kabadi et al. |
| 5,369,125 A | 11/1994 | Berger et al. |
| 5,385,932 A | 1/1995 | Vickers |
| 5,474,995 A | 12/1995 | Ducharme et al. |
| 5,521,213 A | 5/1996 | Prasit et al. |
| 5,536,752 A | 7/1996 | Ducharme et al. |
| 5,543,297 A | 8/1996 | Cromlish et al. |
| 5,550,142 A | 8/1996 | Ducharme et al. |
| 5,552,422 A | 9/1996 | Gauthier et al. |
| 5,604,253 A | 2/1997 | Lau et al. |
| 5,604,260 A | 2/1997 | Guay et al. |
| 5,622,985 A | 4/1997 | Olukotun et al. |
| 5,639,780 A | 6/1997 | Lau et al. |
| 5,643,933 A | 7/1997 | Talley et al. |
| 5,677,318 A | 10/1997 | Lau et al. |
| 5,691,374 A | 11/1997 | Black et al. |
| 5,698,584 A | 12/1997 | Black et al. |
| 5,710,140 A | 1/1998 | Ducharme et al. |
| 5,733,909 A | 3/1998 | Black et al. |
| 5,744,305 A | 4/1998 | Fodor et al. |
| 5,789,413 A | 8/1998 | Black et al. |
| 5,817,700 A | 10/1998 | Dube et al. |
| 5,849,943 A | 12/1998 | Atkinson et al. |
| 5,861,419 A | 1/1999 | Dube et al. |
| 5,922,742 A | 7/1999 | Black et al. |
| 5,925,631 A | 7/1999 | Black et al. |
| 7,723,050 B2* | 5/2010 | Urdea et al. ............... 435/7.1 |
| 8,119,358 B2* | 2/2012 | Urdea et al. ............... 435/7.21 |
| 2002/0038227 A1 | 3/2002 | Fey et al. |
| 2003/0100486 A1 | 5/2003 | Ridker et al. |
| 2004/0122296 A1 | 6/2004 | Hatlestad et al. |
| 2004/0122297 A1 | 6/2004 | Stahmann et al. |
| 2004/0219606 A1 | 11/2004 | Halperin |
| 2005/0054005 A1 | 3/2005 | Ellis et al. |
| 2005/0074805 A1 | 4/2005 | Kochan et al. |
| 2005/0164233 A1 | 7/2005 | Byrne et al. |
| 2006/0040293 A1 | 2/2006 | Salonen et al. |
| 2007/0026458 A1 | 2/2007 | Polidori et al. |
| 2007/0218519 A1 | 9/2007 | Urdea et al. |
| 2007/0259377 A1 | 11/2007 | Urdea et al. |
| 2008/0300170 A1 | 12/2008 | Gelber et al. |
| 2009/0012716 A1 | 1/2009 | Urdea et al. |

FOREIGN PATENT DOCUMENTS

| | | |
|---|---|---|
| WO | WO-95/18799 | 7/1995 |
| WO | WO-02/48715 | 6/2002 |
| WO | WO-2004/056456 | 7/2004 |
| WO | WO-2004/088309 | 10/2004 |
| WO | WO-2004/092416 | 10/2004 |
| WO | WO-2006/008342 | 1/2006 |
| WO | WO-2006/072654 | 7/2006 |
| WO | WO-2007/044860 | 4/2007 |
| WO | WO-2007/128884 | 11/2007 |
| WO | WO-2007/133586 | 11/2007 |
| WO | WO-2007/146229 | 12/2007 |
| WO | WO-2008/131224 | 10/2008 |
| WO | WO-2008/156617 | 12/2008 |
| WO | WO-2011/059720 | 5/2011 |
| WO | WO-2011/059721 | 5/2011 |

OTHER PUBLICATIONS

Cook, Use and misuse of the receiver operating characteristic curve in risk prediction. *Circulation*, 115:928-35 (2007).

Dhindsa et al., Comparison of the micro- and macro-vascular effects of glimepiride and gliclazide in metformin-treatment patients with Type 2 diabetes: A double-bind, crossover study. *Br. J. Clin. Pharmacol.* 55(6): 616-9 (2003).

Eddy et al., Archimedes: A trial-validated model of diabetes, *Diabet. Care*, 26:3093-101 (2003).

Eddy et al., Validation of the archimedes diabetes model. *Diabetes Care.* 26: 3102-10 (2003).*

Edelman et al., Utility of hemoglobin A1c in predicting diabetes risk, *J. Gen. Intern. Med.*, 19:1175-1180 (2004).

Fleckenstein, History of Calcium antagonists. *Cir. Rev.* 52: Suppl 1: 13-16 (1983).

Ford et al., Diabetes and serum ferritin concentration among U.S. adults. *Diabetes Care*, 22(12): 1978-83 (1999).

Freeman et al., C-reactive protein is an independent predictor of risk for the development of diabetes in the west of Scotland coronary prevention study, *Diabetes*, 51:1596-600 (2002).

Fumeron et al., Ferritin and transferrin are both predictive of the onset of hyperglycemia in men and women over 3 years, *Diabetes Care*, 29(9):2090-4 (2006).

Gribble et al., Sulfonylurea sensitivity of adenosine triphosphate-sensitive potassium channels from cells and extrapancreatic tissues. *Metab. Clin. Exp.* 49(10): 3-6 (2000).

Griffin et al., Diabetes risk score: Toward earlier detection of type 2 diabetes in general practice. *Diabetes Metab. Res. Rev.* 16: 164-71 (2000).

Hanley et al., Metabolic and inflammation variable clusters and prediction of type 2 diabetes, *Diabetes*, 53:1773-81 (2004).

Hart et al., Variants in the sulphoylurea receptor gene: Association of the exon 16-3t variant with Type II diabetes mellitus in Dutch Caucasians. *Diabetologia*, 42(5): 617-20 (1999).

Heidemann et al., A dietary pattern protective against type 2 diabetes in the European prospective investigation into cancer and nutrition (EPIC)-Potsdam study cohort. *Diabetologia Metab.* 48(6): 1126-34 (2005).

Hu et al., Inflammatory markers and risk of developing type 2 diabetes in women, *Diabetes*, 53:693-700 (2004).

Iwasaki et al., Non-alcoholic fatty liver disease in Japanese Type 2 diabetes mellitus: Relation to regional adiposity, fatty acids and iron deposit. *Diabetologia*, 47(Suppl. 1): A464 (2004).

Jenkins et al., Effect of wheat bran on glycemic control and risk factors for cardiovascular disease in type 2 diabetes. *Diabetes Care*, 25(9): 1522-8 (2002).

Jiang et al., Body iron stores in relation to risk of type 2 diabetes in apparently healthy women. *JAMA*, 291(6): 711-7 (2004).

Kannel et al., A general cardiovascular risk profile: the Framingham Study. *Am. J. Cardiol.* 38: 46-51 (1976).

Kisner, Product development: the making of the Abbot Architecht. *Clin. Lab Manage Rev.*, 11(6):419-21 (1997).

Krakoff et al, Inflammatory markers, adiponectin, and risk of type 2 diabetes in the Pima Indian, *Diabetes Care*, 26(6):1745-51 (2003).

Lindstrom et al., The diabetes risk score: a practical tool to predict type 2 diabetes risk. *Diabetes Care*, 26: 725-31 (2003).

Ognibene et al., A new modular chemiluminescence immunoassay analyzer evaluated. *Clin. Chem. Lab. Med.*, 38(3):251-60 (2000).

O'Marcaigh et al., Estimating the predictive value of a diagnostic test, how to prevent misleading or confusing results. *Clin. Ped.*, 32(8):485-91 (1993).

Park et al., Three-year experience in using total laboratory automation system. *Southeast Asian J. Trop. Med. Public Health*, 33(Suppl. 2):68-73 (2002).

Pauli et al., The Abbott Architech c8000: analytical performance and productivity characteristic of a new analyzer applied to general chemistry testing. *Clin. Lab.*, 51(1-2):31-41 (2005).

Pepe et al., Limitations of the odds ratio in gauging the performance of a diagnostic, prognostic, or screening marker. *Am. J. Epidemiol*, 159(9):882-90 (2004).

Reis et al., Association of a variant in exon 31 of the sulfonylurea receptor 1 (SUR1) gene with type 2 diabetes mellitus in French Caucasians. *Hum. Genet.* 107(2): 138-44 (2000).

Ren et al., Altered mRNA expression of ATP-sensitive and inward rectifier potassium channel subunits in streptozotocin-induced diabetic rat heart and aorta. *J. Pharmacol. Sci.* 93(4): 478-83 (2003).

Seino et al., Gene targeting approach to clarification of ion channel function: Studies of Kir6.x null mice. *J. Physiol.* 554(2): 295-300 (2004).

Stern et al., Identification of person at high risk for type 2 diabetes mellitus: De we need the oral glucose tolerance test? *Ann. Intern. Med.* 136: 575-81 (2002).*

Stern et al., Predicting diabetes—Moving beyond impaired glucose tolerance. *Diabetes.* 42: 706-14 (1993).*

Stern et al., Predicting future cardiovascular disease, *Diabet. Care*, 25:1851-56 (2002).

Stern et al., Sex difference in the effects of sociocultural status on diabetes and cardiovascular risk factors in Mexican Americans, *Am. J. Epidemiol.*, 120:834-51 (1984).

Takahashi et al., The logistic regression and ROC analysis of group-based screening for predicting diabetes incidence in four years, *Kobe J. Med. Sci.*, 52(6):171-80 (2006).

Valenti et al., Effect of iron depletion on liver function and insulin resistance in patients with NASH and fatty liver. *Hepatol.* 42(4): Suppl 1: 619A-620A (2005).

Vasan, Biomarkers of cardiovascular disease: Molecular basis and practical considerations. *Circulation*, 113:2335-62 (2006).

Wilson et al., "Clinical Chemistry Analyzer Sub-System Level Performance," American Association for Clinical Chemistry Annual Meeting, Chicago, Illinois, Jul. 23-27, 2006.

Wirth et al., Post-translational modification detection using metastable ions in reflector matrix-assisted laser desorption/ionization-time of flight mass spectrometry. *Proteomics*, 2(10):1445-51 (2002).

Wong et al., Nonpeptide angiotensin II receptor antagonists. I. Pharmacological characterization of 2-n-butyl-4-chloro-1-(2-chlorobenzyl)imidazole-5-acetic acid, sodium salt (S-8307). *J. Pharmacol. Exp. Ther.* 247: 1-7 (1988).

Yuan et al., Serum CRP levels are equally evelated in newly diagnosed type 2 diabetes and impaired glucose tolerance and related to adiponectin levels and insulin sensitivity, *Diabetes Res. Clin. Pract.*, 72:244-50 (2006).

Ziegler et al., Type 2 diabetes as an inflammatory cardiovascular disorder. *Curr. Molec. Med.* 5(3): 309-22 (2005).

Zweig et al., ROC curve analysis: An example showing the relationships among serum lipid and apolipoprotein concentrations in identifying subjects with coronory artery disease. *Clin. Chem.*, 38(8):1425-8 (1992).

European Search Report, EP 09 01 0506, dated Apr. 6, 2010.

International Search Report and Written Opinion of the International Searching Authority established in WO-2008/131224.

Accelerated Examination Support Document in U.S. Appl. No. 12/501,385.

First Information Disclosure Statement in U.S. Appl. No. 12/501,385.

Second Information Disclosure Statement in U.S. Appl. No. 12/501,385.

Third Information Disclosure Statement in U.S. Appl. No. 12/501,385.

* cited by examiner

FIGURE 1

| No Previous Markers | | | | | | |
|---|---|---|---|---|---|---|
| Cutoff | C1 | P1 | C2 | P2 | C3 | P3 |
| 0 | 84 | 1 | 3486 | 1 | 95284 | 1 |
| 0.05 | 84 | 1 | 3486 | 1 | 95284 | 1 |
| 0.1 | 84 | 1 | 3486 | 1 | 95284 | 1 |
| 0.15 | 84 | 1 | 3486 | 1 | 95284 | 1 |
| 0.2 | 84 | 1 | 3486 | 1 | 95284 | 1 |
| 0.25 | 84 | 1 | 3486 | 1 | 95284 | 1 |
| 0.3 | 84 | 1 | 3486 | 1 | 95284 | 1 |
| 0.35 | 84 | 1 | 3486 | 1 | 95284 | 1 |
| 0.4 | 84 | 1 | 3486 | 1 | 95284 | 1 |
| 0.45 | 84 | 1 | 3469 | 0.995123 | 94481 | 0.991573 |
| 0.5 | 74 | 0.880952 | 3225 | 0.925129 | 86828 | 0.911255 |
| 0.55 | 34 | 0.404762 | 2141 | 0.614171 | 66909 | 0.702206 |
| 0.6 | 11 | 0.130952 | 942 | 0.270224 | 36627 | 0.384398 |
| 0.65 | 5 | 0.059524 | 399 | 0.114458 | 16302 | 0.171089 |
| 0.7 | 0 | 0 | 77 | 0.022088 | 3385 | 0.035525 |
| 0.75 | 0 | 0 | 1 | 0.000287 | 77 | 0.000808 |
| 0.8 | 0 | 0 | 0 | 0 | 0 | 0 |
| 0.85 | 0 | 0 | 0 | 0 | 0 | 0 |
| 0.9 | 0 | 0 | 0 | 0 | 0 | 0 |
| 0.95 | 0 | 0 | 0 | 0 | 0 | 0 |
| 1 | 0 | 0 | 0 | 0 | 0 | 0 |

FIGURE 2

| Position 1 | Position 2 | Position 3 |
|---|---|---|
| ACE | CRP | GLUCOSE |
| ADIPOQ | CRP | GLUCOSE |
| AGE | CRP | GLUCOSE |
| AGER | CRP | GLUCOSE |
| AHSG | CRP | GLUCOSE |
| ANG | CRP | GLUCOSE |
| APOA1 | CRP | GLUCOSE |
| APOB | CRP | GLUCOSE |
| APOE | CRP | GLUCOSE |
| BAX | CRP | GLUCOSE |
| BCL2 | CRP | GLUCOSE |
| BMI | CRP | GLUCOSE |
| C3 | CRP | GLUCOSE |
| CCL2 | CRP | GLUCOSE |
| CD14 | CRP | GLUCOSE |
| CD40 | CRP | GLUCOSE |
| CDK5 | CRP | GLUCOSE |
| CHOL | CRP | GLUCOSE |
| CRP | CTSB | GLUCOSE |
| CRP | DBP | GLUCOSE |
| CRP | DPP4 | GLUCOSE |
| CRP | EGF | GLUCOSE |
| CRP | ENG | GLUCOSE |
| CRP | FAS | GLUCOSE |
| CRP | FGA | GLUCOSE |
| CRP | FHx1 | GLUCOSE |
| CRP | FHx2 | GLUCOSE |
| CRP | FTH1 | GLUCOSE |
| CRP | GH1 | GLUCOSE |
| CRP | GLUCOSE | GPT |
| CRP | GLUCOSE | HBA1C |
| CRP | GLUCOSE | HDL |
| CRP | GLUCOSE | HEIGHT |
| CRP | GLUCOSE | HGF |
| CRP | GLUCOSE | HIP |
| CRP | GLUCOSE | HP |
| CRP | GLUCOSE | HSPA1B |
| CRP | GLUCOSE | ICAM1 |
| CRP | GLUCOSE | IGF1 |

FIGURE 2 (continued)

| Position 1 | Position 2 | Position 3 |
|---|---|---|
| CRP | GLUCOSE | IGF1R |
| CRP | GLUCOSE | IGFBP1 |
| CRP | GLUCOSE | IGFBP2 |
| CRP | GLUCOSE | IGFBP3 |
| CRP | GLUCOSE | IL18 |
| CRP | GLUCOSE | IL2RA |
| CRP | GLUCOSE | IL2RB |
| CRP | GLUCOSE | IL6 |
| CRP | GLUCOSE | IL6R |
| CRP | GLUCOSE | IL6ST |
| CRP | GLUCOSE | IL8 |
| CRP | GLUCOSE | INHBA |
| CRP | GLUCOSE | INSULIN-M |
| CRP | GLUCOSE | LDL |
| CRP | GLUCOSE | LEP |
| CRP | GLUCOSE | PLAT |
| CRP | GLUCOSE | POMC |
| CRP | GLUCOSE | Proinsulin |
| CRP | GLUCOSE | RETN |
| CRP | GLUCOSE | SBP |
| CRP | GLUCOSE | SCp |
| CRP | GLUCOSE | SELE |
| CRP | GLUCOSE | SELP |
| CRP | GLUCOSE | SERPINE1 |
| CRP | GLUCOSE | SEX |
| CRP | GLUCOSE | SGK |
| CRP | GLUCOSE | SHBG |
| CRP | GLUCOSE | TGFB1 |
| CRP | GLUCOSE | TIMP2 |
| CRP | GLUCOSE | TNFRSF1B |
| CRP | GLUCOSE | TRIG |
| CRP | GLUCOSE | VCAM1 |
| CRP | GLUCOSE | VEGF |
| CRP | GLUCOSE | VWF |
| CRP | GLUCOSE | WAIST |
| CRP | GLUCOSE | WEIGHT |
| CRP | GLUCOSE | WHr |
| GLUCOSE | HBA1C | INSULIN-M |

LDA - Complete Forward Selection - All Markers

FIGURE 5

| Variable | Units | Transform | Converters (n=83) | | | Non-Converters (n=236) | | | pvals |
|---|---|---|---|---|---|---|---|---|---|
| | | | Mean | SD | BT (Raw Mean) | Mean | SD | BT (Raw Mean) | |
| ADIPOQ | ng/ml | Log | 4.29 | 0.49 | 19309.48 | 4.38 | 0.46 | 24126.04 | 0.1066 |
| AGE | years | Raw | 50.07 | 6.32 | 50.07 | 48.81 | 6.32 | 48.81 | 0.1196 |
| BMI | kg/m² | Log | 1.48 | 0.06 | 30.17 | 1.46 | 0.05 | 28.58 | 0.0012 |
| CCL2 | ng/ml | Log | -0.79 | 0.50 | 0.16 | -0.86 | 0.24 | 0.14 | 0.0933 |
| CD40 | ng/ml | Log | -1.00 | 0.26 | 0.10 | -1.00 | 0.36 | 0.10 | 0.9657 |
| CHOL | mmol/L | Log | 0.77 | 0.07 | 5.86 | 0.76 | 0.08 | 5.72 | 0.2742 |
| CRP | ng/ml | Log | 3.62 | 0.53 | 4122.90 | 3.30 | 0.58 | 1987.13 | 1.6E-05 |
| DBP | mm Hg | Log | 1.94 | 0.06 | 86.86 | 1.92 | 0.06 | 84.12 | 0.0648 |
| EGF | ng/ml | Log | -0.43 | 0.29 | 0.37 | -0.39 | 0.29 | 0.40 | 0.3004 |
| ENG | ng/ml | Log | 0.11 | 0.26 | 1.30 | 0.19 | 0.27 | 1.55 | 0.0284 |
| FGA | ng/ml | Log | 6.23 | 0.31 | 1698371.56 | 6.24 | 0.30 | 1737402.00 | 0.7987 |
| FTH1 | ng/ml | Log | 2.79 | 0.58 | 610.40 | 2.67 | 0.53 | 468.82 | 0.0969 |
| GLUCOSE | mmol/L | Log | 0.78 | 0.04 | 5.97 | 0.75 | 0.04 | 5.59 | 1.5E-08 |
| GPT | ng/ml | Log | 0.44 | 0.22 | 2.75 | 0.35 | 0.25 | 2.25 | 0.0053 |
| HBA1C | percent | Sqrt | 0.79 | 0.03 | 6.10 | 0.77 | 0.03 | 5.85 | 3.8E-06 |
| HDL | mmol/L | Log | 0.08 | 0.12 | 1.21 | 0.11 | 0.12 | 1.30 | 0.0366 |
| HEIGHT | cm | Raw | 172.43 | 9.44 | 172.43 | 172.97 | 9.49 | 172.97 | 0.6572 |
| HIP | cm | Log | 2.03 | 0.04 | 106.35 | 2.02 | 0.04 | 105.12 | 0.3057 |
| HP | ng/ml | Log | 5.60 | 0.77 | 395666.07 | 5.70 | 0.74 | 500947.78 | 0.2777 |
| HSPA1B | ng/ml | Log | 0.36 | 0.27 | 2.29 | 0.30 | 0.19 | 1.99 | 0.0278 |
| IGF1R | ng/ml | Log | -0.63 | 0.41 | 0.23 | -0.69 | 0.38 | 0.20 | 0.2322 |
| IGFBP1 | ng/ml | Log | 0.72 | 0.58 | 5.23 | 0.78 | 0.45 | 6.00 | 0.3402 |
| IGFBP2 | ng/ml | Sqrt | 14.41 | 4.82 | 207.54 | 15.66 | 5.01 | 245.14 | 0.0451 |
| IL2RA | ng/ml | Log | -0.50 | 0.21 | 0.32 | -0.56 | 0.22 | 0.28 | 0.0262 |
| IL2RB | ng/ml | Log | -0.11 | 0.46 | 0.79 | -0.11 | 0.44 | 0.77 | 0.8737 |
| IL6R | ng/ml | Log | 1.32 | 0.19 | 20.80 | 1.31 | 0.21 | 20.26 | 0.6640 |
| INSULIN-M | ul U/ml | Log | 1.75 | 0.27 | 56.28 | 1.59 | 0.24 | 39.11 | 1.2E-06 |
| LEP | ng/ml | Log | 1.29 | 0.40 | 19.70 | 1.16 | 0.44 | 14.32 | 0.0117 |
| SBP | mm Hg | Log | 2.14 | 0.05 | 138.30 | 2.12 | 0.06 | 132.68 | 0.0127 |

FIGURE 5 (continued)

| SCp | pg/ml | Raw | 666.81 | 171.44 | 666.81 | 602.70 | 170.44 | 602.70 | 0.0035 |
|---|---|---|---|---|---|---|---|---|---|
| SHBG | ng/ml | Log | 3.72 | 0.31 | 5240.56 | 3.75 | 0.25 | 5670.75 | 0.2986 |
| TIMP2 | ng/ml | Sqrt | 8.31 | 1.80 | 69.01 | 7.99 | 1.73 | 63.80 | 0.1530 |
| TRIG | mmol/L | Log | 0.24 | 0.22 | 1.75 | 0.13 | 0.23 | 1.34 | 0.0001 |
| VWF | ng/ml | Log | 4.17 | 0.30 | 14765.56 | 4.14 | 0.25 | 13788.06 | 0.3786 |
| WAIST | cm | Log | 1.99 | 0.05 | 97.81 | 1.97 | 0.05 | 92.93 | 0.0008 |
| WEIGHT | kg | Log | 1.95 | 0.07 | 89.44 | 1.93 | 0.07 | 85.27 | 0.0189 |

FIGURE 6A

| Panel No. | Marker 1 | Marker 2 | Marker 3 |
|---|---|---|---|
| 3.1 | ADIPOQ | CRP | GLUCOSE |
| 3.2 | CRP | GLUCOSE | GPT |
| 3.3 | CRP | GLUCOSE | HBA1C |
| 3.4 | CRP | GLUCOSE | IGFBP2 |
| 3.5 | CRP | GLUCOSE | INSULIN-M |
| 3.6 | CRP | GLUCOSE | TRIG |
| 3.7 | GLUCOSE | HBA1C | INSULIN-M |

FIGURE 6B

| Panel No. | Marker 1 | Marker 2 | Marker 3 | Marker 4 |
|---|---|---|---|---|
| 4.1 | ADIPOQ | CRP | GLUCOSE | LEP |
| 4.2 | ADIPOQ | CRP | GLUCOSE | GPT |
| 4.3 | ADIPOQ | CRP | GLUCOSE | HBA1C |
| 4.4 | ADIPOQ | CRP | GLUCOSE | IGFBP2 |
| 4.5 | ADIPOQ | CRP | GLUCOSE | INSULIN-M |
| 4.6 | ADIPOQ | GLUCOSE | HSPA1B | LEP |
| 4.7 | CRP | GLUCOSE | GPT | HBA1C |
| 4.8 | CRP | GLUCOSE | GPT | HSPA1B |
| 4.9 | CRP | GLUCOSE | GPT | IGFBP2 |
| 4.10 | CRP | GLUCOSE | HBA1C | IGFBP2 |
| 4.11 | CRP | GLUCOSE | HBA1C | INSULIN-M |
| 4.12 | CRP | GLUCOSE | HBA1C | INSULIN-M |
| 4.13 | CRP | GLUCOSE | HBA1C | INSULIN-M |
| 4.14 | CRP | GLUCOSE | HBA1C | LEP |
| 4.15 | CRP | GLUCOSE | HSPA1B | LEP |
| 4.16 | CRP | GLUCOSE | IGFBP1 | LEP |
| 4.17 | CRP | GLUCOSE | IGFBP2 | TRIG |
| 4.18 | CRP | GLUCOSE | INSULIN-M | TRIG |
| 4.19 | CRP | GLUCOSE | INSULIN-M | TRIG |
| 4.20 | CRP | GLUCOSE | LEP | TRIG |
| 4.21 | CRP | GPT | HBA1C | INSULIN-M |
| 4.22 | CRP | HBA1C | INSULIN-M | TRIG |
| 4.23 | GLUCOSE | GPT | HBA1C | INSULIN-M |
| 4.24 | GLUCOSE | HBA1C | INSULIN-M | LEP |
| 4.25 | GLUCOSE | HBA1C | LEP | TRIG |

FIGURE 6C

| Panel No. | Marker 1 | Marker 2 | Marker 3 | Marker 4 | Marker 5 |
|---|---|---|---|---|---|
| 5.1 | ADIPOQ | CRP | GLUCOSE | GPT | HBA1C |
| 5.2 | ADIPOQ | CRP | GLUCOSE | GPT | HSPA1B |
| 5.3 | ADIPOQ | CRP | GLUCOSE | GPT | INSULIN-M |
| 5.4 | ADIPOQ | CRP | GLUCOSE | GPT | LEP |
| 5.5 | ADIPOQ | CRP | GLUCOSE | GPT | TRIG |
| 5.6 | ADIPOQ | CRP | GLUCOSE | HBA1C | HSPA1B |
| 5.7 | ADIPOQ | CRP | GLUCOSE | HBA1C | IGFBP1 |
| 5.8 | ADIPOQ | CRP | GLUCOSE | HBA1C | INSULIN-M |
| 5.9 | ADIPOQ | CRP | GLUCOSE | HBA1C | LEP |
| 5.10 | ADIPOQ | CRP | GLUCOSE | HBA1C | TRIG |
| 5.11 | ADIPOQ | CRP | GLUCOSE | HSPA1B | IGFBP1 |
| 5.12 | ADIPOQ | CRP | GLUCOSE | HSPA1B | INSULIN-M |
| 5.13 | ADIPOQ | CRP | GLUCOSE | HSPA1B | LEP |
| 5.14 | ADIPOQ | CRP | GLUCOSE | HSPA1B | TRIG |
| 5.15 | ADIPOQ | CRP | GLUCOSE | IGFBP1 | IGFBP2 |
| 5.16 | ADIPOQ | CRP | GLUCOSE | IGFBP1 | INSULIN-M |
| 5.17 | ADIPOQ | CRP | GLUCOSE | IGFBP1 | LEP |
| 5.18 | ADIPOQ | CRP | GLUCOSE | IGFBP1 | TRIG |
| 5.19 | ADIPOQ | CRP | GLUCOSE | IGFBP2 | LEP |
| 5.20 | ADIPOQ | CRP | GLUCOSE | INSULIN-M | LEP |
| 5.21 | ADIPOQ | CRP | GLUCOSE | INSULIN-M | TRIG |
| 5.22 | ADIPOQ | CRP | GLUCOSE | LEP | TRIG |
| 5.23 | ADIPOQ | CRP | GPT | HBA1C | INSULIN-M |
| 5.24 | ADIPOQ | GLUCOSE | GPT | HBA1C | INSULIN-M |
| 5.25 | ADIPOQ | GLUCOSE | GPT | HBA1C | LEP |
| 5.26 | ADIPOQ | GLUCOSE | GPT | INSULIN-M | LEP |
| 5.27 | ADIPOQ | GLUCOSE | HBA1C | IGFBP2 | LEP |
| 5.28 | ADIPOQ | GLUCOSE | HSPA1B | LEP | TRIG |
| 5.29 | CRP | GLUCOSE | GPT | HBA1C | HSPA1B |
| 5.30 | CRP | GLUCOSE | GPT | HBA1C | IGFBP1 |
| 5.31 | CRP | GLUCOSE | GPT | HBA1C | IGFBP2 |
| 5.32 | CRP | GLUCOSE | GPT | HBA1C | INSULIN-M |
| 5.33 | CRP | GLUCOSE | GPT | HBA1C | TRIG |
| 5.34 | CRP | GLUCOSE | GPT | HSPA1B | LEP |
| 5.35 | CRP | GLUCOSE | GPT | HSPA1B | TRIG |
| 5.36 | CRP | GLUCOSE | GPT | IGFBP1 | INSULIN-M |
| 5.37 | CRP | GLUCOSE | GPT | IGFBP2 | INSULIN-M |
| 5.38 | CRP | GLUCOSE | GPT | IGFBP2 | LEP |
| 5.39 | CRP | GLUCOSE | GPT | IGFBP2 | TRIG |
| 5.40 | CRP | GLUCOSE | GPT | INSULIN-M | LEP |

FIGURE 6C (continued)

| Panel No. | Marker 1 | Marker 2 | Marker 3 | Marker 4 | Marker 5 |
|---|---|---|---|---|---|
| 5.41 | CRP | GLUCOSE | GPT | INSULIN-M | TRIG |
| 5.42 | CRP | GLUCOSE | GPT | LEP | TRIG |
| 5.43 | CRP | GLUCOSE | HBA1C | HSPA1B | IGFBP1 |
| 5.44 | CRP | GLUCOSE | HBA1C | HSPA1B | IGFBP2 |
| 5.45 | CRP | GLUCOSE | HBA1C | HSPA1B | INSULIN-M |
| 5.46 | CRP | GLUCOSE | HBA1C | HSPA1B | TRIG |
| 5.47 | CRP | GLUCOSE | HBA1C | IGFBP1 | INSULIN-M |
| 5.48 | CRP | GLUCOSE | HBA1C | IGFBP1 | LEP |
| 5.49 | CRP | GLUCOSE | HBA1C | IGFBP1 | TRIG |
| 5.50 | CRP | GLUCOSE | HBA1C | INSULIN-M | LEP |
| 5.51 | CRP | GLUCOSE | HBA1C | INSULIN-M | TRIG |
| 5.52 | CRP | GLUCOSE | HSPA1B | IGFBP2 | INSULIN-M |
| 5.53 | CRP | GLUCOSE | HSPA1B | INSULIN-M | LEP |
| 5.54 | CRP | GLUCOSE | HSPA1B | INSULIN-M | TRIG |
| 5.55 | CRP | GLUCOSE | IGFBP1 | INSULIN-M | TRIG |
| 5.56 | CRP | GLUCOSE | IGFBP2 | INSULIN-M | TRIG |
| 5.57 | CRP | GLUCOSE | IGFBP2 | LEP | TRIG |
| 5.58 | CRP | HBA1C | HSPA1B | IGFBP1 | TRIG |
| 5.59 | GLUCOSE | GPT | HBA1C | HSPA1B | LEP |
| 5.60 | GLUCOSE | GPT | HBA1C | INSULIN-M | LEP |
| 5.61 | GLUCOSE | GPT | HBA1C | LEP | TRIG |
| 5.62 | GLUCOSE | GPT | HSPA1B | IGFBP2 | INSULIN-M |
| 5.63 | GLUCOSE | HBA1C | HSPA1B | IGFBP2 | INSULIN-M |
| 5.64 | GLUCOSE | HBA1C | HSPA1B | INSULIN-M | TRIG |
| 5.65 | GLUCOSE | HBA1C | HSPA1B | LEP | TRIG |

FIGURE 6D

| Panel No. | Marker 1 | Marker 2 | Marker 3 | Marker 4 | Marker 5 | Marker 6 |
|---|---|---|---|---|---|---|
| 6.1 | ADIPOQ | CRP | GLUCOSE | GPT | HBA1C | HSPA1B |
| 6.2 | ADIPOQ | CRP | GLUCOSE | GPT | HBA1C | IGFBP1 |
| 6.3 | ADIPOQ | CRP | GLUCOSE | GPT | HBA1C | IGFBP2 |
| 6.4 | ADIPOQ | CRP | GLUCOSE | GPT | HBA1C | INSULIN-M |
| 6.5 | ADIPOQ | CRP | GLUCOSE | GPT | HBA1C | LEP |
| 6.6 | ADIPOQ | CRP | GLUCOSE | GPT | HBA1C | TRIG |
| 6.7 | ADIPOQ | CRP | GLUCOSE | GPT | HSPA1B | INSULIN-M |
| 6.8 | ADIPOQ | CRP | GLUCOSE | GPT | HSPA1B | LEP |
| 6.9 | ADIPOQ | CRP | GLUCOSE | GPT | HSPA1B | TRIG |
| 6.10 | ADIPOQ | CRP | GLUCOSE | GPT | IGFBP1 | IGFBP2 |
| 6.11 | ADIPOQ | CRP | GLUCOSE | GPT | IGFBP1 | INSULIN-M |
| 6.12 | ADIPOQ | CRP | GLUCOSE | GPT | IGFBP1 | LEP |
| 6.13 | ADIPOQ | CRP | GLUCOSE | GPT | IGFBP2 | INSULIN-M |
| 6.14 | ADIPOQ | CRP | GLUCOSE | GPT | IGFBP2 | LEP |
| 6.15 | ADIPOQ | CRP | GLUCOSE | GPT | IGFBP2 | TRIG |
| 6.16 | ADIPOQ | CRP | GLUCOSE | GPT | INSULIN-M | LEP |
| 6.17 | ADIPOQ | CRP | GLUCOSE | GPT | INSULIN-M | TRIG |
| 6.18 | ADIPOQ | CRP | GLUCOSE | GPT | LEP | TRIG |
| 6.19 | ADIPOQ | CRP | GLUCOSE | HBA1C | HSPA1B | IGFBP1 |
| 6.20 | ADIPOQ | CRP | GLUCOSE | HBA1C | HSPA1B | IGFBP2 |
| 6.21 | ADIPOQ | CRP | GLUCOSE | HBA1C | HSPA1B | INSULIN-M |
| 6.22 | ADIPOQ | CRP | GLUCOSE | HBA1C | HSPA1B | LEP |
| 6.23 | ADIPOQ | CRP | GLUCOSE | HBA1C | HSPA1B | TRIG |
| 6.24 | ADIPOQ | CRP | GLUCOSE | HBA1C | IGFBP1 | IGFBP2 |
| 6.25 | ADIPOQ | CRP | GLUCOSE | HBA1C | IGFBP1 | INSULIN-M |
| 6.26 | ADIPOQ | CRP | GLUCOSE | HBA1C | IGFBP1 | LEP |
| 6.27 | ADIPOQ | CRP | GLUCOSE | HBA1C | IGFBP1 | TRIG |
| 6.28 | ADIPOQ | CRP | GLUCOSE | HBA1C | IGFBP2 | INSULIN-M |
| 6.29 | ADIPOQ | CRP | GLUCOSE | HBA1C | IGFBP2 | LEP |
| 6.30 | ADIPOQ | CRP | GLUCOSE | HBA1C | IGFBP2 | TRIG |
| 6.31 | ADIPOQ | CRP | GLUCOSE | HBA1C | INSULIN-M | LEP |
| 6.32 | ADIPOQ | CRP | GLUCOSE | HBA1C | INSULIN-M | TRIG |
| 6.33 | ADIPOQ | CRP | GLUCOSE | HBA1C | LEP | TRIG |
| 6.34 | ADIPOQ | CRP | GLUCOSE | HSPA1B | IGFBP1 | IGFBP2 |
| 6.35 | ADIPOQ | CRP | GLUCOSE | HSPA1B | IGFBP1 | INSULIN-M |
| 6.36 | ADIPOQ | CRP | GLUCOSE | HSPA1B | IGFBP1 | LEP |
| 6.37 | ADIPOQ | CRP | GLUCOSE | HSPA1B | IGFBP1 | TRIG |
| 6.38 | ADIPOQ | CRP | GLUCOSE | HSPA1B | IGFBP2 | INSULIN-M |
| 6.39 | ADIPOQ | CRP | GLUCOSE | HSPA1B | IGFBP2 | LEP |
| 6.40 | ADIPOQ | CRP | GLUCOSE | HSPA1B | INSULIN-M | LEP |

FIGURE 6D (continued)

| Panel No. | Marker 1 | Marker 2 | Marker 3 | Marker 4 | Marker 5 | Marker 6 |
|---|---|---|---|---|---|---|
| 6.41 | ADIPOQ | CRP | GLUCOSE | HSPA1B | INSULIN-M | TRIG |
| 6.42 | ADIPOQ | CRP | GLUCOSE | HSPA1B | LEP | TRIG |
| 6.43 | ADIPOQ | CRP | GLUCOSE | IGFBP1 | IGFBP2 | INSULIN-M |
| 6.44 | ADIPOQ | CRP | GLUCOSE | IGFBP1 | IGFBP2 | LEP |
| 6.45 | ADIPOQ | CRP | GLUCOSE | IGFBP1 | INSULIN-M | LEP |
| 6.46 | ADIPOQ | CRP | GLUCOSE | IGFBP1 | INSULIN-M | TRIG |
| 6.47 | ADIPOQ | CRP | GLUCOSE | IGFBP1 | LEP | TRIG |
| 6.48 | ADIPOQ | CRP | GLUCOSE | IGFBP2 | INSULIN-M | LEP |
| 6.49 | ADIPOQ | CRP | GLUCOSE | IGFBP2 | INSULIN-M | TRIG |
| 6.50 | ADIPOQ | CRP | GLUCOSE | IGFBP2 | LEP | TRIG |
| 6.51 | ADIPOQ | CRP | GLUCOSE | INSULIN-M | LEP | TRIG |
| 6.52 | ADIPOQ | CRP | GPT | HBA1C | HSPA1B | INSULIN-M |
| 6.53 | ADIPOQ | CRP | GPT | HBA1C | IGFBP2 | INSULIN-M |
| 6.54 | ADIPOQ | CRP | GPT | HBA1C | INSULIN-M | TRIG |
| 6.55 | ADIPOQ | GLUCOSE | GPT | HBA1C | HSPA1B | INSULIN-M |
| 6.56 | ADIPOQ | GLUCOSE | GPT | HBA1C | IGFBP2 | INSULIN-M |
| 6.57 | ADIPOQ | GLUCOSE | GPT | HBA1C | IGFBP2 | LEP |
| 6.58 | ADIPOQ | GLUCOSE | GPT | HBA1C | INSULIN-M | LEP |
| 6.59 | ADIPOQ | GLUCOSE | GPT | HBA1C | LEP | TRIG |
| 6.60 | ADIPOQ | GLUCOSE | GPT | HSPA1B | IGFBP2 | LEP |
| 6.61 | ADIPOQ | GLUCOSE | GPT | HSPA1B | INSULIN-M | LEP |
| 6.62 | ADIPOQ | GLUCOSE | GPT | HSPA1B | LEP | TRIG |
| 6.63 | ADIPOQ | GLUCOSE | GPT | IGFBP2 | LEP | TRIG |
| 6.64 | ADIPOQ | GLUCOSE | HBA1C | HSPA1B | IGFBP2 | INSULIN-M |
| 6.65 | ADIPOQ | GLUCOSE | HBA1C | HSPA1B | IGFBP2 | LEP |
| 6.66 | ADIPOQ | GLUCOSE | HBA1C | HSPA1B | INSULIN-M | LEP |
| 6.67 | ADIPOQ | GLUCOSE | HBA1C | HSPA1B | INSULIN-M | TRIG |
| 6.68 | ADIPOQ | GLUCOSE | HBA1C | HSPA1B | LEP | TRIG |
| 6.69 | ADIPOQ | GLUCOSE | HBA1C | IGFBP2 | LEP | TRIG |
| 6.70 | ADIPOQ | GLUCOSE | HBA1C | INSULIN-M | LEP | TRIG |
| 6.71 | ADIPOQ | GLUCOSE | HSPA1B | IGFBP1 | IGFBP2 | LEP |
| 6.72 | ADIPOQ | GLUCOSE | HSPA1B | IGFBP1 | LEP | TRIG |
| 6.73 | ADIPOQ | GLUCOSE | HSPA1B | IGFBP2 | INSULIN-M | LEP |
| 6.74 | ADIPOQ | GLUCOSE | HSPA1B | IGFBP2 | LEP | TRIG |
| 6.75 | ADIPOQ | GLUCOSE | HSPA1B | INSULIN-M | LEP | TRIG |
| 6.76 | CRP | GLUCOSE | GPT | HBA1C | HSPA1B | IGFBP1 |
| 6.77 | CRP | GLUCOSE | GPT | HBA1C | HSPA1B | IGFBP2 |
| 6.78 | CRP | GLUCOSE | GPT | HBA1C | HSPA1B | INSULIN-M |
| 6.79 | CRP | GLUCOSE | GPT | HBA1C | HSPA1B | LEP |
| 6.80 | CRP | GLUCOSE | GPT | HBA1C | HSPA1B | TRIG |

FIGURE 6D (continued)

| Panel No. | Marker 1 | Marker 2 | Marker 3 | Marker 4 | Marker 5 | Marker 6 |
|---|---|---|---|---|---|---|
| 6.81 | CRP | GLUCOSE | GPT | HBA1C | IGFBP1 | IGFBP2 |
| 6.82 | CRP | GLUCOSE | GPT | HBA1C | IGFBP1 | INSULIN-M |
| 6.83 | CRP | GLUCOSE | GPT | HBA1C | IGFBP1 | LEP |
| 6.84 | CRP | GLUCOSE | GPT | HBA1C | IGFBP1 | TRIG |
| 6.85 | CRP | GLUCOSE | GPT | HBA1C | IGFBP2 | INSULIN-M |
| 6.86 | CRP | GLUCOSE | GPT | HBA1C | INSULIN-M | LEP |
| 6.87 | CRP | GLUCOSE | GPT | HBA1C | INSULIN-M | TRIG |
| 6.88 | CRP | GLUCOSE | GPT | HBA1C | LEP | TRIG |
| 6.89 | CRP | GLUCOSE | GPT | HSPA1B | IGFBP2 | INSULIN-M |
| 6.90 | CRP | GLUCOSE | GPT | HSPA1B | IGFBP2 | LEP |
| 6.91 | CRP | GLUCOSE | GPT | HSPA1B | IGFBP2 | TRIG |
| 6.92 | CRP | GLUCOSE | GPT | HSPA1B | INSULIN-M | LEP |
| 6.93 | CRP | GLUCOSE | GPT | HSPA1B | INSULIN-M | TRIG |
| 6.94 | CRP | GLUCOSE | GPT | IGFBP1 | IGFBP2 | INSULIN-M |
| 6.95 | CRP | GLUCOSE | GPT | IGFBP1 | INSULIN-M | LEP |
| 6.96 | CRP | GLUCOSE | GPT | IGFBP1 | LEP | TRIG |
| 6.97 | CRP | GLUCOSE | GPT | IGFBP2 | INSULIN-M | TRIG |
| 6.98 | CRP | GLUCOSE | GPT | IGFBP2 | LEP | TRIG |
| 6.99 | CRP | GLUCOSE | GPT | INSULIN-M | LEP | TRIG |
| 6.100 | CRP | GLUCOSE | HBA1C | HSPA1B | IGFBP1 | INSULIN-M |
| 6.101 | CRP | GLUCOSE | HBA1C | HSPA1B | IGFBP1 | LEP |
| 6.102 | CRP | GLUCOSE | HBA1C | HSPA1B | IGFBP1 | TRIG |
| 6.103 | CRP | GLUCOSE | HBA1C | HSPA1B | IGFBP2 | INSULIN-M |
| 6.104 | CRP | GLUCOSE | HBA1C | HSPA1B | IGFBP2 | LEP |
| 6.105 | CRP | GLUCOSE | HBA1C | HSPA1B | INSULIN-M | LEP |
| 6.106 | CRP | GLUCOSE | HBA1C | HSPA1B | INSULIN-M | TRIG |
| 6.107 | CRP | GLUCOSE | HBA1C | HSPA1B | LEP | TRIG |
| 6.108 | CRP | GLUCOSE | HBA1C | IGFBP1 | IGFBP2 | INSULIN-M |
| 6.109 | CRP | GLUCOSE | HBA1C | IGFBP1 | IGFBP2 | TRIG |
| 6.110 | CRP | GLUCOSE | HBA1C | IGFBP1 | INSULIN-M | LEP |
| 6.111 | CRP | GLUCOSE | HBA1C | IGFBP1 | INSULIN-M | TRIG |
| 6.112 | CRP | GLUCOSE | HBA1C | IGFBP1 | LEP | TRIG |
| 6.113 | CRP | GLUCOSE | HBA1C | IGFBP2 | INSULIN-M | LEP |
| 6.114 | CRP | GLUCOSE | HBA1C | IGFBP2 | INSULIN-M | TRIG |
| 6.115 | CRP | GLUCOSE | HBA1C | IGFBP2 | LEP | TRIG |
| 6.116 | CRP | GLUCOSE | HBA1C | INSULIN-M | LEP | TRIG |
| 6.117 | CRP | GLUCOSE | HSPA1B | IGFBP1 | IGFBP2 | INSULIN-M |
| 6.118 | CRP | GLUCOSE | HSPA1B | IGFBP1 | LEP | TRIG |
| 6.119 | CRP | GLUCOSE | HSPA1B | IGFBP2 | INSULIN-M | LEP |
| 6.120 | CRP | GLUCOSE | HSPA1B | IGFBP2 | INSULIN-M | TRIG |

FIGURE 6D (continued)

| Panel No. | Marker 1 | Marker 2 | Marker 3 | Marker 4 | Marker 5 | Marker 6 |
|---|---|---|---|---|---|---|
| 6.121 | CRP | GLUCOSE | HSPA1B | IGFBP2 | LEP | TRIG |
| 6.122 | CRP | GLUCOSE | IGFBP1 | IGFBP2 | INSULIN-M | TRIG |
| 6.123 | CRP | GLUCOSE | IGFBP1 | INSULIN-M | LEP | TRIG |
| 6.124 | CRP | GLUCOSE | IGFBP2 | INSULIN-M | LEP | TRIG |
| 6.125 | CRP | GPT | HBA1C | HSPA1B | INSULIN-M | TRIG |
| 6.126 | GLUCOSE | GPT | HBA1C | HSPA1B | IGFBP2 | INSULIN-M |
| 6.127 | GLUCOSE | GPT | HBA1C | HSPA1B | IGFBP2 | LEP |
| 6.128 | GLUCOSE | GPT | HBA1C | IGFBP2 | INSULIN-M | LEP |
| 6.129 | GLUCOSE | GPT | HBA1C | INSULIN-M | LEP | TRIG |
| 6.130 | GLUCOSE | HBA1C | HSPA1B | IGFBP1 | IGFBP2 | INSULIN-M |
| 6.131 | GLUCOSE | HBA1C | HSPA1B | IGFBP2 | INSULIN-M | LEP |
| 6.132 | GLUCOSE | HBA1C | HSPA1B | IGFBP2 | INSULIN-M | TRIG |
| 6.133 | GLUCOSE | HBA1C | HSPA1B | IGFBP2 | LEP | TRIG |
| 6.134 | GLUCOSE | HBA1C | IGFBP1 | INSULIN-M | LEP | TRIG |

FIGURE 6E

| Panel No. | Marker 1 | Marker 2 | Marker 3 | Marker 4 | Marker 5 | Marker 6 | Marker 7 |
|---|---|---|---|---|---|---|---|
| 7.1 | ADIPOQ | CRP | GLUCOSE | GPT | HBA1C | HSPA1B | INSULIN-M |
| 7.2 | ADIPOQ | CRP | GLUCOSE | GPT | HBA1C | HSPA1B | LEP |
| 7.3 | ADIPOQ | CRP | GLUCOSE | GPT | HBA1C | HSPA1B | LEP |
| 7.4 | ADIPOQ | CRP | GLUCOSE | GPT | HBA1C | HSPA1B | LEP |
| 7.5 | ADIPOQ | CRP | GLUCOSE | GPT | HBA1C | HSPA1B | TRIG |
| 7.6 | ADIPOQ | CRP | GLUCOSE | GPT | HBA1C | IGFBP1 | LEP |
| 7.7 | ADIPOQ | CRP | GLUCOSE | GPT | HBA1C | IGFBP1 | LEP |
| 7.8 | ADIPOQ | CRP | GLUCOSE | GPT | HBA1C | IGFBP1 | LEP |
| 7.9 | ADIPOQ | CRP | GLUCOSE | GPT | HBA1C | IGFBP1 | TRIG |
| 7.10 | ADIPOQ | CRP | GLUCOSE | GPT | HBA1C | IGFBP2 | LEP |
| 7.11 | ADIPOQ | CRP | GLUCOSE | GPT | HBA1C | IGFBP2 | LEP |
| 7.12 | ADIPOQ | CRP | GLUCOSE | GPT | HBA1C | IGFBP2 | TRIG |
| 7.13 | ADIPOQ | CRP | GLUCOSE | GPT | HBA1C | INSULIN-M | LEP |
| 7.14 | ADIPOQ | CRP | GLUCOSE | GPT | HBA1C | INSULIN-M | TRIG |
| 7.15 | ADIPOQ | CRP | GLUCOSE | GPT | HBA1C | LEP | IGFBP2 |
| 7.16 | ADIPOQ | CRP | GLUCOSE | GPT | HSPA1B | IGFBP1 | INSULIN-M |
| 7.17 | ADIPOQ | CRP | GLUCOSE | GPT | HSPA1B | IGFBP1 | LEP |
| 7.18 | ADIPOQ | CRP | GLUCOSE | GPT | HSPA1B | IGFBP1 | TRIG |
| 7.19 | ADIPOQ | CRP | GLUCOSE | GPT | HSPA1B | IGFBP2 | LEP |
| 7.20 | ADIPOQ | CRP | GLUCOSE | GPT | HSPA1B | IGFBP2 | TRIG |
| 7.21 | ADIPOQ | CRP | GLUCOSE | GPT | HSPA1B | INSULIN-M | TRIG |
| 7.22 | ADIPOQ | CRP | GLUCOSE | GPT | HSPA1B | INSULIN-M | TRIG |
| 7.23 | ADIPOQ | CRP | GLUCOSE | GPT | HSPA1B | LEP | TRIG |
| 7.24 | ADIPOQ | CRP | GLUCOSE | GPT | IGFBP1 | IGFBP2 | LEP |
| 7.25 | ADIPOQ | CRP | GLUCOSE | GPT | IGFBP1 | IGFBP2 | TRIG |
| 7.26 | ADIPOQ | CRP | GLUCOSE | GPT | IGFBP1 | IGFBP2 | INSULIN-M |
| 7.27 | ADIPOQ | CRP | GLUCOSE | GPT | IGFBP1 | INSULIN-M | INSULIN-M |
| 7.28 | ADIPOQ | CRP | GLUCOSE | GPT | IGFBP1 | INSULIN-M | TRIG |
| 7.29 | ADIPOQ | CRP | GLUCOSE | GPT | IGFBP1 | LEP | INSULIN-M |
| 7.30 | ADIPOQ | CRP | GLUCOSE | GPT | IGFBP2 | INSULIN-M | LEP |
| 7.31 | ADIPOQ | CRP | GLUCOSE | GPT | IGFBP2 | INSULIN-M | TRIG |
| 7.32 | ADIPOQ | CRP | GLUCOSE | GPT | IGFBP2 | LEP | IGFBP2 |
| 7.33 | ADIPOQ | CRP | GLUCOSE | GPT | INSULIN-M | LEP | INSULIN-M |
| 7.34 | ADIPOQ | CRP | GLUCOSE | HBA1C | HSPA1B | IGFBP1 | IGFBP1 |
| 7.35 | ADIPOQ | CRP | GLUCOSE | HBA1C | HSPA1B | IGFBP1 | LEP |
| 7.36 | ADIPOQ | CRP | GLUCOSE | HBA1C | HSPA1B | IGFBP1 | TRIG |
| 7.37 | ADIPOQ | CRP | GLUCOSE | HBA1C | HSPA1B | IGFBP2 | LEP |
| 7.38 | ADIPOQ | CRP | GLUCOSE | HBA1C | HSPA1B | IGFBP2 | TRIG |
| 7.39 | ADIPOQ | CRP | GLUCOSE | HBA1C | HSPA1B | IGFBP2 | TRIG |
| 7.40 | ADIPOQ | CRP | GLUCOSE | HBA1C | HSPA1B | INSULIN-M | IGFBP2 |

FIGURE 6E (continued)

| Panel No. | Marker 1 | Marker 2 | Marker 3 | Marker 4 | Marker 5 | Marker 6 | Marker 7 |
|---|---|---|---|---|---|---|---|
| 7.41 | ADIPOQ | CRP | GLUCOSE | HBA1C | HSPA1B | INSULIN-M | TRIG |
| 7.42 | ADIPOQ | CRP | GLUCOSE | HBA1C | HSPA1B | LEP | LEP |
| 7.43 | ADIPOQ | CRP | GLUCOSE | HBA1C | IGFBP1 | IGFBP2 | LEP |
| 7.44 | ADIPOQ | CRP | GLUCOSE | HBA1C | IGFBP1 | IGFBP2 | TRIG |
| 7.45 | ADIPOQ | CRP | GLUCOSE | HBA1C | IGFBP1 | IGFBP2 | TRIG |
| 7.46 | ADIPOQ | CRP | GLUCOSE | HBA1C | IGFBP1 | INSULIN-M | TRIG |
| 7.47 | ADIPOQ | CRP | GLUCOSE | HBA1C | IGFBP1 | LEP | TRIG |
| 7.48 | ADIPOQ | CRP | GLUCOSE | HBA1C | IGFBP2 | INSULIN-M | INSULIN-M |
| 7.49 | ADIPOQ | CRP | GLUCOSE | HBA1C | IGFBP2 | INSULIN-M | TRIG |
| 7.50 | ADIPOQ | CRP | GLUCOSE | HBA1C | IGFBP2 | LEP | TRIG |
| 7.51 | ADIPOQ | CRP | GLUCOSE | HBA1C | INSULIN-M | LEP | TRIG |
| 7.52 | ADIPOQ | CRP | GLUCOSE | HSPA1B | IGFBP1 | IGFBP2 | INSULIN-M |
| 7.53 | ADIPOQ | CRP | GLUCOSE | HSPA1B | IGFBP1 | IGFBP2 | INSULIN-M |
| 7.54 | ADIPOQ | CRP | GLUCOSE | HSPA1B | IGFBP1 | IGFBP2 | TRIG |
| 7.55 | ADIPOQ | CRP | GLUCOSE | HSPA1B | IGFBP1 | INSULIN-M | TRIG |
| 7.56 | ADIPOQ | CRP | GLUCOSE | HSPA1B | IGFBP1 | LEP | TRIG |
| 7.57 | ADIPOQ | CRP | GLUCOSE | HSPA1B | IGFBP2 | INSULIN-M | LEP |
| 7.58 | ADIPOQ | CRP | GLUCOSE | HSPA1B | IGFBP2 | INSULIN-M | LEP |
| 7.59 | ADIPOQ | CRP | GLUCOSE | HSPA1B | IGFBP2 | LEP | TRIG |
| 7.60 | ADIPOQ | CRP | GLUCOSE | HSPA1B | INSULIN-M | LEP | LEP |
| 7.61 | ADIPOQ | CRP | GLUCOSE | IGFBP1 | IGFBP2 | INSULIN-M | TRIG |
| 7.62 | ADIPOQ | CRP | GLUCOSE | IGFBP1 | IGFBP2 | INSULIN-M | TRIG |
| 7.63 | ADIPOQ | CRP | GLUCOSE | IGFBP1 | IGFBP2 | LEP | TRIG |
| 7.64 | ADIPOQ | CRP | GLUCOSE | IGFBP2 | INSULIN-M | LEP | TRIG |
| 7.65 | ADIPOQ | CRP | GPT | HBA1C | HSPA1B | IGFBP2 | INSULIN-M |
| 7.66 | ADIPOQ | CRP | GPT | HBA1C | HSPA1B | IGFBP2 | TRIG |
| 7.67 | ADIPOQ | CRP | GPT | HBA1C | HSPA1B | INSULIN-M | TRIG |
| 7.68 | ADIPOQ | CRP | HBA1C | HSPA1B | IGFBP2 | INSULIN-M | LEP |
| 7.69 | ADIPOQ | CRP | HBA1C | HSPA1B | IGFBP2 | INSULIN-M | TRIG |
| 7.70 | ADIPOQ | CRP | HBA1C | HSPA1B | INSULIN-M | LEP | TRIG |
| 7.71 | ADIPOQ | GLUCOSE | GPT | HBA1C | HSPA1B | IGFBP1 | LEP |
| 7.72 | ADIPOQ | GLUCOSE | GPT | HBA1C | HSPA1B | IGFBP2 | LEP |
| 7.73 | ADIPOQ | GLUCOSE | GPT | HBA1C | HSPA1B | IGFBP2 | TRIG |
| 7.74 | ADIPOQ | GLUCOSE | GPT | HBA1C | HSPA1B | INSULIN-M | INSULIN-M |
| 7.75 | ADIPOQ | GLUCOSE | GPT | HBA1C | HSPA1B | INSULIN-M | LEP |
| 7.76 | ADIPOQ | GLUCOSE | GPT | HBA1C | HSPA1B | LEP | TRIG |
| 7.77 | ADIPOQ | GLUCOSE | GPT | HBA1C | IGFBP1 | INSULIN-M | TRIG |
| 7.78 | ADIPOQ | GLUCOSE | GPT | HBA1C | IGFBP2 | INSULIN-M | LEP |
| 7.79 | ADIPOQ | GLUCOSE | GPT | HBA1C | IGFBP2 | LEP | INSULIN-M |
| 7.80 | ADIPOQ | GLUCOSE | GPT | HSPA1B | IGFBP1 | INSULIN-M | TRIG |

FIGURE 6E (continued)

| Panel No. | Marker 1 | Marker 2 | Marker 3 | Marker 4 | Marker 5 | Marker 6 | Marker 7 |
|---|---|---|---|---|---|---|---|
| 7.81 | ADIPOQ | GLUCOSE | GPT | HSPA1B | IGFBP2 | LEP | LEP |
| 7.82 | ADIPOQ | GLUCOSE | GPT | HSPA1B | INSULIN-M | LEP | LEP |
| 7.83 | ADIPOQ | GLUCOSE | GPT | IGFBP1 | IGFBP2 | INSULIN-M | TRIG |
| 7.84 | ADIPOQ | GLUCOSE | HBA1C | HSPA1B | IGFBP1 | IGFBP2 | LEP |
| 7.85 | ADIPOQ | GLUCOSE | HBA1C | HSPA1B | IGFBP1 | INSULIN-M | TRIG |
| 7.86 | ADIPOQ | GLUCOSE | HBA1C | HSPA1B | IGFBP1 | LEP | LEP |
| 7.87 | ADIPOQ | GLUCOSE | HBA1C | HSPA1B | IGFBP2 | INSULIN-M | INSULIN-M |
| 7.88 | ADIPOQ | GLUCOSE | HBA1C | HSPA1B | IGFBP2 | INSULIN-M | TRIG |
| 7.89 | ADIPOQ | GLUCOSE | HBA1C | HSPA1B | IGFBP2 | LEP | TRIG |
| 7.90 | ADIPOQ | GLUCOSE | HBA1C | HSPA1B | INSULIN-M | LEP | TRIG |
| 7.91 | ADIPOQ | GLUCOSE | HBA1C | IGFBP2 | INSULIN-M | LEP | TRIG |
| 7.92 | ADIPOQ | GLUCOSE | HSPA1B | IGFBP2 | INSULIN-M | LEP | TRIG |
| 7.93 | CRP | GLUCOSE | GPT | HBA1C | HSPA1B | IGFBP1 | INSULIN-M |
| 7.94 | CRP | GLUCOSE | GPT | HBA1C | HSPA1B | IGFBP1 | LEP |
| 7.95 | CRP | GLUCOSE | GPT | HBA1C | HSPA1B | IGFBP2 | INSULIN-M |
| 7.96 | CRP | GLUCOSE | GPT | HBA1C | HSPA1B | IGFBP2 | LEP |
| 7.97 | CRP | GLUCOSE | GPT | HBA1C | HSPA1B | IGFBP2 | TRIG |
| 7.98 | CRP | GLUCOSE | GPT | HBA1C | HSPA1B | INSULIN-M | TRIG |
| 7.99 | CRP | GLUCOSE | GPT | HBA1C | HSPA1B | INSULIN-M | TRIG |
| 7.100 | CRP | GLUCOSE | GPT | HBA1C | HSPA1B | LEP | TRIG |
| 7.101 | CRP | GLUCOSE | GPT | HBA1C | IGFBP1 | IGFBP2 | LEP |
| 7.102 | CRP | GLUCOSE | GPT | HBA1C | IGFBP1 | IGFBP2 | TRIG |
| 7.103 | CRP | GLUCOSE | GPT | HBA1C | IGFBP1 | IGFBP2 | TRIG |
| 7.104 | CRP | GLUCOSE | GPT | HBA1C | IGFBP1 | INSULIN-M | TRIG |
| 7.105 | CRP | GLUCOSE | GPT | HBA1C | IGFBP1 | INSULIN-M | TRIG |
| 7.106 | CRP | GLUCOSE | GPT | HBA1C | IGFBP1 | LEP | LEP |
| 7.107 | CRP | GLUCOSE | GPT | HBA1C | IGFBP2 | INSULIN-M | TRIG |
| 7.108 | CRP | GLUCOSE | GPT | HBA1C | IGFBP2 | INSULIN-M | TRIG |
| 7.109 | CRP | GLUCOSE | GPT | HBA1C | IGFBP2 | LEP | INSULIN-M |
| 7.110 | CRP | GLUCOSE | GPT | HBA1C | INSULIN-M | LEP | LEP |
| 7.111 | CRP | GLUCOSE | GPT | HSPA1B | IGFBP1 | IGFBP2 | INSULIN-M |
| 7.112 | CRP | GLUCOSE | GPT | HSPA1B | IGFBP1 | INSULIN-M | LEP |
| 7.113 | CRP | GLUCOSE | GPT | HSPA1B | IGFBP1 | LEP | TRIG |
| 7.114 | CRP | GLUCOSE | GPT | HSPA1B | IGFBP2 | INSULIN-M | LEP |
| 7.115 | CRP | GLUCOSE | GPT | HSPA1B | IGFBP2 | INSULIN-M | TRIG |
| 7.116 | CRP | GLUCOSE | GPT | HSPA1B | INSULIN-M | LEP | TRIG |
| 7.117 | CRP | GLUCOSE | GPT | IGFBP1 | IGFBP2 | INSULIN-M | TRIG |
| 7.118 | CRP | GLUCOSE | GPT | IGFBP1 | INSULIN-M | LEP | TRIG |
| 7.119 | CRP | GLUCOSE | HBA1C | HSPA1B | IGFBP1 | IGFBP2 | LEP |
| 7.120 | CRP | GLUCOSE | HBA1C | HSPA1B | IGFBP1 | IGFBP2 | TRIG |

FIGURE 6E (continued)

| Panel No. | Marker 1 | Marker 2 | Marker 3 | Marker 4 | Marker 5 | Marker 6 | Marker 7 |
|---|---|---|---|---|---|---|---|
| 7.121 | CRP | GLUCOSE | HBA1C | HSPA1B | IGFBP1 | IGFBP2 | TRIG |
| 7.122 | CRP | GLUCOSE | HBA1C | HSPA1B | IGFBP1 | INSULIN-M | INSULIN-M |
| 7.123 | CRP | GLUCOSE | HBA1C | HSPA1B | IGFBP1 | INSULIN-M | TRIG |
| 7.124 | CRP | GLUCOSE | HBA1C | HSPA1B | IGFBP1 | LEP | TRIG |
| 7.125 | CRP | GLUCOSE | HBA1C | HSPA1B | IGFBP2 | INSULIN-M | LEP |
| 7.126 | CRP | GLUCOSE | HBA1C | HSPA1B | IGFBP2 | INSULIN-M | LEP |
| 7.127 | CRP | GLUCOSE | HBA1C | HSPA1B | IGFBP2 | LEP | TRIG |
| 7.128 | CRP | GLUCOSE | HBA1C | HSPA1B | INSULIN-M | LEP | TRIG |
| 7.129 | CRP | GLUCOSE | HBA1C | IGFBP1 | IGFBP2 | INSULIN-M | TRIG |
| 7.130 | CRP | GLUCOSE | HBA1C | IGFBP1 | IGFBP2 | LEP | LEP |
| 7.131 | CRP | GLUCOSE | HBA1C | IGFBP1 | INSULIN-M | LEP | TRIG |
| 7.132 | CRP | GLUCOSE | HBA1C | IGFBP2 | INSULIN-M | LEP | TRIG |
| 7.133 | CRP | GLUCOSE | HSPA1B | IGFBP1 | IGFBP2 | LEP | TRIG |
| 7.134 | CRP | GLUCOSE | HSPA1B | IGFBP1 | INSULIN-M | LEP | TRIG |
| 7.135 | CRP | GLUCOSE | HSPA1B | IGFBP2 | INSULIN-M | LEP | TRIG |
| 7.136 | CRP | GLUCOSE | IGFBP1 | IGFBP2 | INSULIN-M | LEP | TRIG |
| 7.137 | CRP | GPT | HBA1C | HSPA1B | IGFBP1 | IGFBP2 | TRIG |
| 7.138 | GLUCOSE | GPT | HBA1C | HSPA1B | IGFBP1 | INSULIN-M | TRIG |
| 7.139 | GLUCOSE | GPT | HBA1C | HSPA1B | IGFBP1 | INSULIN-M | TRIG |
| 7.140 | GLUCOSE | GPT | HBA1C | HSPA1B | IGFBP2 | INSULIN-M | LEP |
| 7.141 | GLUCOSE | GPT | HBA1C | HSPA1B | IGFBP2 | INSULIN-M | TRIG |
| 7.142 | GLUCOSE | GPT | HBA1C | HSPA1B | IGFBP2 | LEP | LEP |
| 7.143 | GLUCOSE | GPT | HBA1C | HSPA1B | INSULIN-M | LEP | INSULIN-M |
| 7.144 | GLUCOSE | GPT | HBA1C | IGFBP2 | INSULIN-M | LEP | TRIG |
| 7.145 | GLUCOSE | GPT | HSPA1B | IGFBP1 | INSULIN-M | LEP | TRIG |
| 7.146 | GLUCOSE | GPT | HSPA1B | IGFBP2 | INSULIN-M | LEP | TRIG |
| 7.147 | GLUCOSE | HBA1C | HSPA1B | IGFBP1 | IGFBP2 | INSULIN-M | LEP |

FIGURE 6F

| Panel No. | Marker 1 | Marker 2 | Marker 3 | Marker 4 | Marker 5 | Marker 6 | Marker 7 | Marker 8 |
|---|---|---|---|---|---|---|---|---|
| 8.1 | ADIPOQ | CRP | GLUCOSE | GPT | HBA1C | HSPA1B | IGFBP2 | INSULIN-M |
| 8.2 | ADIPOQ | CRP | GLUCOSE | GPT | HBA1C | HSPA1B | IGFBP2 | LEP |
| 8.3 | ADIPOQ | CRP | GLUCOSE | GPT | HBA1C | HSPA1B | INSULIN-M | LEP |
| 8.4 | ADIPOQ | CRP | GLUCOSE | GPT | HBA1C | HSPA1B | INSULIN-M | LEP |
| 8.5 | ADIPOQ | CRP | GLUCOSE | GPT | HBA1C | HSPA1B | INSULIN-M | LEP |
| 8.6 | ADIPOQ | CRP | GLUCOSE | GPT | HBA1C | HSPA1B | INSULIN-M | LEP |
| 8.7 | ADIPOQ | CRP | GLUCOSE | GPT | HBA1C | HSPA1B | LEP | TRIG |
| 8.8 | ADIPOQ | CRP | GLUCOSE | GPT | HBA1C | HSPA1B | LEP | TRIG |
| 8.9 | ADIPOQ | CRP | GLUCOSE | GPT | HBA1C | HSPA1B | LEP | TRIG |
| 8.10 | ADIPOQ | CRP | GLUCOSE | GPT | HBA1C | IGFBP1 | IGFBP1 | IGFBP2 |
| 8.11 | ADIPOQ | CRP | GLUCOSE | GPT | HBA1C | IGFBP1 | IGFBP2 | INSULIN-M |
| 8.12 | ADIPOQ | CRP | GLUCOSE | GPT | HBA1C | IGFBP1 | INSULIN-M | LEP |
| 8.13 | ADIPOQ | CRP | GLUCOSE | GPT | HBA1C | IGFBP1 | INSULIN-M | TRIG |
| 8.14 | ADIPOQ | CRP | GLUCOSE | GPT | HBA1C | IGFBP1 | LEP | TRIG |
| 8.15 | ADIPOQ | CRP | GLUCOSE | GPT | HBA1C | IGFBP1 | LEP | TRIG |
| 8.16 | ADIPOQ | CRP | GLUCOSE | GPT | HBA1C | IGFBP2 | IGFBP2 | TRIG |
| 8.17 | ADIPOQ | CRP | GLUCOSE | GPT | HBA1C | IGFBP2 | INSULIN-M | TRIG |
| 8.18 | ADIPOQ | CRP | GLUCOSE | GPT | HBA1C | IGFBP2 | INSULIN-M | TRIG |
| 8.19 | ADIPOQ | CRP | GLUCOSE | GPT | HBA1C | INSULIN-M | LEP | TRIG |
| 8.20 | ADIPOQ | CRP | GLUCOSE | GPT | HSPA1B | IGFBP1 | IGFBP2 | LEP |
| 8.21 | ADIPOQ | CRP | GLUCOSE | GPT | HSPA1B | IGFBP1 | INSULIN-M | LEP |
| 8.22 | ADIPOQ | CRP | GLUCOSE | GPT | HSPA1B | IGFBP1 | INSULIN-M | LEP |
| 8.23 | ADIPOQ | CRP | GLUCOSE | GPT | HSPA1B | IGFBP1 | INSULIN-M | LEP |
| 8.24 | ADIPOQ | CRP | GLUCOSE | GPT | HSPA1B | IGFBP1 | LEP | TRIG |
| 8.25 | ADIPOQ | CRP | GLUCOSE | GPT | HSPA1B | IGFBP2 | INSULIN-M | TRIG |
| 8.26 | ADIPOQ | CRP | GLUCOSE | GPT | HSPA1B | IGFBP2 | LEP | TRIG |
| 8.27 | ADIPOQ | CRP | GLUCOSE | GPT | HSPA1B | IGFBP2 | LEP | TRIG |
| 8.28 | ADIPOQ | CRP | GLUCOSE | GPT | HSPA1B | INSULIN-M | IGFBP2 | LEP |
| 8.29 | ADIPOQ | CRP | GLUCOSE | GPT | IGFBP1 | IGFBP2 | IGFBP2 | INSULIN-M |
| 8.30 | ADIPOQ | CRP | GLUCOSE | GPT | IGFBP1 | IGFBP2 | INSULIN-M | LEP |
| 8.31 | ADIPOQ | CRP | GLUCOSE | GPT | IGFBP1 | IGFBP2 | LEP | TRIG |
| 8.32 | ADIPOQ | CRP | GLUCOSE | GPT | IGFBP1 | INSULIN-M | IGFBP1 | LEP |
| 8.33 | ADIPOQ | CRP | GLUCOSE | GPT | IGFBP2 | INSULIN-M | IGFBP1 | TRIG |
| 8.34 | ADIPOQ | CRP | GLUCOSE | HBA1C | HSPA1B | IGFBP1 | IGFBP1 | INSULIN-M |
| 8.35 | ADIPOQ | CRP | GLUCOSE | HBA1C | HSPA1B | IGFBP1 | INSULIN-M | TRIG |
| 8.36 | ADIPOQ | CRP | GLUCOSE | HBA1C | HSPA1B | IGFBP1 | LEP | TRIG |
| 8.37 | ADIPOQ | CRP | GLUCOSE | HBA1C | HSPA1B | IGFBP1 | LEP | TRIG |
| 8.38 | ADIPOQ | CRP | GLUCOSE | HBA1C | HSPA1B | IGFBP1 | LEP | TRIG |
| 8.39 | ADIPOQ | CRP | GLUCOSE | HBA1C | HSPA1B | IGFBP1 | LEP | TRIG |
| 8.40 | ADIPOQ | CRP | GLUCOSE | HBA1C | HSPA1B | IGFBP2 | IGFBP2 | TRIG |

FIGURE 6F (continued)

| Panel No. | Marker 1 | Marker 2 | Marker 3 | Marker 4 | Marker 5 | Marker 6 | Marker 7 | Marker 8 |
|---|---|---|---|---|---|---|---|---|
| 8.41 | ADIPOQ | CRP | GLUCOSE | HBA1C | HSPA1B | IGFBP2 | INSULIN-M | TRIG |
| 8.42 | ADIPOQ | CRP | GLUCOSE | HBA1C | HSPA1B | IGFBP2 | INSULIN-M | TRIG |
| 8.43 | ADIPOQ | CRP | GLUCOSE | HBA1C | HSPA1B | INSULIN-M | LEP | TRIG |
| 8.44 | ADIPOQ | CRP | GLUCOSE | HBA1C | IGFBP1 | IGFBP2 | INSULIN-M | TRIG |
| 8.45 | ADIPOQ | CRP | GLUCOSE | HBA1C | IGFBP1 | IGFBP2 | LEP | TRIG |
| 8.46 | ADIPOQ | CRP | GLUCOSE | HBA1C | IGFBP1 | IGFBP2 | LEP | TRIG |
| 8.47 | ADIPOQ | CRP | GLUCOSE | HBA1C | IGFBP1 | INSULIN-M | LEP | TRIG |
| 8.48 | ADIPOQ | CRP | GLUCOSE | HBA1C | IGFBP2 | INSULIN-M | LEP | TRIG |
| 8.49 | ADIPOQ | CRP | GLUCOSE | HSPA1B | IGFBP1 | IGFBP2 | IGFBP2 | INSULIN-M |
| 8.50 | ADIPOQ | CRP | GLUCOSE | HSPA1B | IGFBP1 | IGFBP2 | INSULIN-M | LEP |
| 8.51 | ADIPOQ | CRP | GLUCOSE | HSPA1B | IGFBP1 | INSULIN-M | LEP | TRIG |
| 8.52 | ADIPOQ | CRP | GLUCOSE | HSPA1B | IGFBP2 | INSULIN-M | IGFBP2 | LEP |
| 8.53 | ADIPOQ | CRP | GLUCOSE | IGFBP1 | IGFBP2 | INSULIN-M | INSULIN-M | TRIG |
| 8.54 | ADIPOQ | CRP | GPT | HBA1C | HSPA1B | IGFBP2 | INSULIN-M | LEP |
| 8.55 | ADIPOQ | CRP | GPT | HBA1C | HSPA1B | IGFBP2 | INSULIN-M | TRIG |
| 8.56 | ADIPOQ | GLUCOSE | GPT | HBA1C | HSPA1B | IGFBP1 | INSULIN-M | LEP |
| 8.57 | ADIPOQ | GLUCOSE | GPT | HBA1C | HSPA1B | IGFBP1 | LEP | TRIG |
| 8.58 | ADIPOQ | GLUCOSE | GPT | HBA1C | HSPA1B | IGFBP1 | LEP | TRIG |
| 8.59 | ADIPOQ | GLUCOSE | GPT | HBA1C | HSPA1B | IGFBP2 | IGFBP2 | LEP |
| 8.60 | ADIPOQ | GLUCOSE | GPT | HBA1C | HSPA1B | IGFBP2 | LEP | TRIG |
| 8.61 | ADIPOQ | GLUCOSE | GPT | HBA1C | HSPA1B | IGFBP2 | LEP | TRIG |
| 8.62 | ADIPOQ | GLUCOSE | GPT | HBA1C | HSPA1B | INSULIN-M | IGFBP2 | INSULIN-M |
| 8.63 | ADIPOQ | GLUCOSE | GPT | HBA1C | IGFBP1 | IGFBP2 | LEP | TRIG |
| 8.64 | ADIPOQ | GLUCOSE | GPT | HBA1C | IGFBP2 | INSULIN-M | INSULIN-M | LEP |
| 8.65 | ADIPOQ | GLUCOSE | GPT | HSPA1B | IGFBP1 | IGFBP2 | INSULIN-M | TRIG |
| 8.66 | ADIPOQ | GLUCOSE | GPT | HSPA1B | IGFBP1 | INSULIN-M | LEP | TRIG |
| 8.67 | ADIPOQ | GLUCOSE | GPT | HSPA1B | IGFBP2 | INSULIN-M | LEP | TRIG |
| 8.68 | ADIPOQ | GLUCOSE | HBA1C | HSPA1B | IGFBP1 | IGFBP2 | INSULIN-M | LEP |
| 8.69 | ADIPOQ | GLUCOSE | HBA1C | HSPA1B | IGFBP1 | IGFBP2 | LEP | TRIG |
| 8.70 | ADIPOQ | GLUCOSE | HBA1C | HSPA1B | IGFBP1 | IGFBP2 | LEP | TRIG |
| 8.71 | ADIPOQ | GLUCOSE | HBA1C | HSPA1B | IGFBP2 | INSULIN-M | INSULIN-M | TRIG |
| 8.72 | CRP | GLUCOSE | GPT | HBA1C | HSPA1B | IGFBP1 | IGFBP2 | TRIG |
| 8.73 | CRP | GLUCOSE | GPT | HBA1C | HSPA1B | IGFBP1 | INSULIN-M | LEP |
| 8.74 | CRP | GLUCOSE | GPT | HBA1C | HSPA1B | IGFBP1 | INSULIN-M | TRIG |
| 8.75 | CRP | GLUCOSE | GPT | HBA1C | HSPA1B | IGFBP1 | INSULIN-M | TRIG |
| 8.76 | CRP | GLUCOSE | GPT | HBA1C | HSPA1B | IGFBP1 | LEP | TRIG |
| 8.77 | CRP | GLUCOSE | GPT | HBA1C | HSPA1B | IGFBP1 | LEP | TRIG |
| 8.78 | CRP | GLUCOSE | GPT | HBA1C | HSPA1B | IGFBP2 | IGFBP2 | LEP |
| 8.79 | CRP | GLUCOSE | GPT | HBA1C | HSPA1B | IGFBP2 | LEP | TRIG |
| 8.80 | CRP | GLUCOSE | GPT | HBA1C | HSPA1B | IGFBP2 | LEP | TRIG |

FIGURE 6F (continued)

| Panel No. | Marker 1 | Marker 2 | Marker 3 | Marker 4 | Marker 5 | Marker 6 | Marker 7 | Marker 8 |
|---|---|---|---|---|---|---|---|---|
| 8.81 | CRP | GLUCOSE | GPT | HBA1C | HSPA1B | INSULIN-M | LEP | TRIG |
| 8.82 | CRP | GLUCOSE | GPT | HBA1C | IGFBP1 | IGFBP2 | INSULIN-M | LEP |
| 8.83 | CRP | GLUCOSE | GPT | HBA1C | IGFBP1 | IGFBP2 | LEP | TRIG |
| 8.84 | CRP | GLUCOSE | GPT | HBA1C | IGFBP1 | IGFBP2 | LEP | TRIG |
| 8.85 | CRP | GLUCOSE | GPT | HBA1C | IGFBP1 | INSULIN-M | INSULIN-M | TRIG |
| 8.86 | CRP | GLUCOSE | GPT | HBA1C | IGFBP2 | INSULIN-M | IGFBP2 | INSULIN-M |
| 8.87 | CRP | GLUCOSE | GPT | HSPA1B | IGFBP1 | IGFBP2 | INSULIN-M | LEP |
| 8.88 | CRP | GLUCOSE | GPT | HSPA1B | IGFBP1 | IGFBP2 | INSULIN-M | LEP |
| 8.89 | CRP | GLUCOSE | GPT | HSPA1B | IGFBP1 | IGFBP2 | INSULIN-M | TRIG |
| 8.90 | CRP | GLUCOSE | GPT | HSPA1B | IGFBP1 | INSULIN-M | LEP | TRIG |
| 8.91 | CRP | GLUCOSE | GPT | HSPA1B | IGFBP2 | INSULIN-M | LEP | TRIG |
| 8.92 | CRP | GLUCOSE | GPT | IGFBP1 | IGFBP2 | INSULIN-M | LEP | TRIG |
| 8.93 | CRP | GLUCOSE | HBA1C | HSPA1B | IGFBP1 | IGFBP2 | LEP | TRIG |
| 8.94 | CRP | GLUCOSE | HBA1C | HSPA1B | IGFBP1 | INSULIN-M | LEP | TRIG |
| 8.95 | CRP | GLUCOSE | HBA1C | HSPA1B | IGFBP2 | INSULIN-M | LEP | TRIG |
| 8.96 | CRP | GLUCOSE | HBA1C | IGFBP1 | IGFBP2 | INSULIN-M | LEP | TRIG |
| 8.97 | CRP | GPT | HBA1C | HSPA1B | IGFBP1 | IGFBP2 | INSULIN-M | TRIG |
| 8.98 | GLUCOSE | GPT | HBA1C | HSPA1B | IGFBP1 | IGFBP2 | INSULIN-M | LEP |
| 8.99 | GLUCOSE | GPT | HBA1C | HSPA1B | IGFBP1 | IGFBP2 | LEP | TRIG |
| 8.100 | GLUCOSE | GPT | HBA1C | HSPA1B | IGFBP2 | INSULIN-M | INSULIN-M | TRIG |

FIGURE 6G

| Panel No. | Marker 1 | Marker 2 | Marker 3 | Marker 4 | Marker 5 | Marker 6 | Marker 7 | Marker 8 | Marker 9 |
|---|---|---|---|---|---|---|---|---|---|
| 9.1 | ADIPOQ | CRP | GLUCOSE | GPT | HBA1C | HSPA1B | IGFBP1 | IGFBP2 | INSULIN-M |
| 9.2 | ADIPOQ | CRP | GLUCOSE | GPT | HBA1C | HSPA1B | IGFBP1 | IGFBP2 | LEP |
| 9.3 | ADIPOQ | CRP | GLUCOSE | GPT | HBA1C | HSPA1B | IGFBP1 | LEP | TRIG |
| 9.4 | ADIPOQ | CRP | GLUCOSE | GPT | HBA1C | HSPA1B | IGFBP2 | INSULIN-M | LEP |
| 9.5 | ADIPOQ | CRP | GLUCOSE | GPT | HBA1C | HSPA1B | IGFBP2 | INSULIN-M | TRIG |
| 9.6 | ADIPOQ | CRP | GLUCOSE | GPT | HBA1C | HSPA1B | IGFBP2 | INSULIN-M | TRIG |
| 9.7 | ADIPOQ | CRP | GLUCOSE | GPT | HBA1C | HSPA1B | IGFBP2 | LEP | TRIG |
| 9.8 | ADIPOQ | CRP | GLUCOSE | GPT | HBA1C | HSPA1B | IGFBP2 | LEP | TRIG |
| 9.9 | ADIPOQ | CRP | GLUCOSE | GPT | HBA1C | HSPA1B | INSULIN-M | LEP | TRIG |
| 9.10 | ADIPOQ | CRP | GLUCOSE | GPT | HBA1C | HSPA1B | INSULIN-M | LEP | TRIG |
| 9.11 | ADIPOQ | CRP | GLUCOSE | GPT | HBA1C | IGFBP1 | IGFBP2 | INSULIN-M | LEP |
| 9.12 | ADIPOQ | CRP | GLUCOSE | GPT | HBA1C | IGFBP1 | IGFBP2 | LEP | TRIG |
| 9.13 | ADIPOQ | CRP | GLUCOSE | GPT | HBA1C | IGFBP1 | IGFBP2 | LEP | TRIG |
| 9.14 | ADIPOQ | CRP | GLUCOSE | GPT | HBA1C | IGFBP1 | INSULIN-M | LEP | TRIG |
| 9.15 | ADIPOQ | CRP | GLUCOSE | GPT | HBA1C | IGFBP2 | INSULIN-M | LEP | TRIG |
| 9.16 | ADIPOQ | CRP | GLUCOSE | GPT | HSPA1B | IGFBP1 | IGFBP1 | INSULIN-M | LEP |
| 9.17 | ADIPOQ | CRP | GLUCOSE | GPT | HSPA1B | IGFBP1 | IGFBP2 | INSULIN-M | LEP |
| 9.18 | ADIPOQ | CRP | GLUCOSE | GPT | HSPA1B | IGFBP1 | IGFBP2 | INSULIN-M | LEP |
| 9.19 | ADIPOQ | CRP | GLUCOSE | GPT | HSPA1B | IGFBP2 | INSULIN-M | LEP | TRIG |
| 9.20 | ADIPOQ | CRP | GLUCOSE | GPT | IGFBP1 | IGFBP2 | INSULIN-M | LEP | TRIG |
| 9.21 | ADIPOQ | CRP | GLUCOSE | HBA1C | HSPA1B | IGFBP1 | IGFBP1 | INSULIN-M | TRIG |
| 9.22 | ADIPOQ | CRP | GLUCOSE | HBA1C | HSPA1B | IGFBP1 | INSULIN-M | LEP | TRIG |
| 9.23 | ADIPOQ | CRP | GLUCOSE | HBA1C | HSPA1B | IGFBP1 | INSULIN-M | LEP | TRIG |
| 9.24 | ADIPOQ | CRP | GLUCOSE | HBA1C | HSPA1B | IGFBP1 | INSULIN-M | LEP | TRIG |
| 9.25 | ADIPOQ | CRP | GLUCOSE | HBA1C | HSPA1B | IGFBP2 | IGFBP1 | IGFBP2 | TRIG |
| 9.26 | ADIPOQ | CRP | GLUCOSE | HBA1C | IGFBP1 | IGFBP2 | IGFBP2 | INSULIN-M | TRIG |
| 9.27 | ADIPOQ | CRP | GLUCOSE | HSPA1B | IGFBP1 | IGFBP2 | INSULIN-M | LEP | TRIG |
| 9.28 | ADIPOQ | CRP | GPT | HBA1C | HSPA1B | IGFBP1 | IGFBP2 | INSULIN-M | LEP |
| 9.29 | ADIPOQ | CRP | GPT | HBA1C | HSPA1B | IGFBP1 | IGFBP2 | INSULIN-M | TRIG |
| 9.30 | ADIPOQ | GLUCOSE | GPT | HBA1C | HSPA1B | IGFBP1 | IGFBP2 | INSULIN-M | LEP |
| 9.31 | ADIPOQ | GLUCOSE | GPT | HBA1C | HSPA1B | IGFBP1 | IGFBP2 | LEP | TRIG |
| 9.32 | ADIPOQ | GLUCOSE | GPT | HBA1C | HSPA1B | IGFBP1 | INSULIN-M | LEP | TRIG |
| 9.33 | ADIPOQ | GLUCOSE | GPT | HBA1C | HSPA1B | IGFBP1 | INSULIN-M | LEP | TRIG |
| 9.34 | ADIPOQ | GLUCOSE | GPT | HBA1C | HSPA1B | IGFBP2 | INSULIN-M | LEP | TRIG |
| 9.35 | ADIPOQ | GLUCOSE | GPT | HBA1C | IGFBP1 | IGFBP2 | IGFBP2 | INSULIN-M | TRIG |
| 9.36 | ADIPOQ | GLUCOSE | GPT | HSPA1B | IGFBP1 | IGFBP2 | INSULIN-M | LEP | TRIG |
| 9.37 | ADIPOQ | GLUCOSE | HBA1C | HSPA1B | IGFBP1 | IGFBP2 | INSULIN-M | LEP | TRIG |
| 9.38 | CRP | GLUCOSE | GPT | HSPA1B | IGFBP1 | IGFBP2 | INSULIN-M | LEP | TRIG |
| 9.39 | CRP | GLUCOSE | GPT | HBA1C | HSPA1B | IGFBP1 | IGFBP2 | INSULIN-M | LEP |
| 9.40 | CRP | GLUCOSE | GPT | HBA1C | HSPA1B | IGFBP1 | IGFBP2 | INSULIN-M | TRIG |
| 9.41 | CRP | GLUCOSE | GPT | HBA1C | HSPA1B | IGFBP1 | IGFBP2 | LEP | TRIG |
| 9.42 | CRP | GLUCOSE | GPT | HBA1C | HSPA1B | IGFBP1 | INSULIN-M | LEP | TRIG |
| 9.43 | CRP | GLUCOSE | GPT | HBA1C | HSPA1B | IGFBP2 | INSULIN-M | LEP | TRIG |
| 9.44 | CRP | GLUCOSE | GPT | HBA1C | IGFBP1 | IGFBP2 | INSULIN-M | LEP | TRIG |

FIGURE 6H

| Panel No. | Marker 1 | Marker 2 | Marker 3 | Marker 4 | Marker 5 | Marker 6 | Marker 7 | Marker 8 | Marker 9 | Marker 10 |
|---|---|---|---|---|---|---|---|---|---|---|
| 10.1 | ADIPOQ | CRP | GLUCOSE | GPT | HBA1C | HSPA1B | IGFBP1 | IGFBP2 | INSULIN-M | LEP |
| 10.2 | ADIPOQ | CRP | GLUCOSE | GPT | HBA1C | HSPA1B | IGFBP1 | IGFBP2 | INSULIN-M | TRIG |
| 10.3 | ADIPOQ | CRP | GLUCOSE | GPT | HBA1C | HSPA1B | IGFBP1 | IGFBP2 | LEP | TRIG |
| 10.4 | ADIPOQ | CRP | GLUCOSE | GPT | HBA1C | HSPA1B | IGFBP1 | INSULIN-M | LEP | TRIG |
| 10.5 | ADIPOQ | CRP | GLUCOSE | GPT | HBA1C | HSPA1B | IGFBP2 | INSULIN-M | LEP | TRIG |
| 10.6 | ADIPOQ | CRP | GLUCOSE | GPT | HBA1C | IGFBP1 | IGFBP2 | INSULIN-M | LEP | TRIG |
| 10.7 | ADIPOQ | CRP | GLUCOSE | GPT | HSPA1B | IGFBP1 | IGFBP2 | INSULIN-M | LEP | TRIG |
| 10.8 | ADIPOQ | CRP | GLUCOSE | HBA1C | HSPA1B | IGFBP1 | IGFBP2 | INSULIN-M | LEP | TRIG |
| 10.9 | ADIPOQ | CRP | GPT | HBA1C | HSPA1B | IGFBP1 | IGFBP2 | INSULIN-M | LEP | TRIG |
| 10.10 | ADIPOQ | GLUCOSE | GPT | HBA1C | HSPA1B | IGFBP1 | IGFBP2 | INSULIN-M | LEP | TRIG |
| 10.11 | CRP | GLUCOSE | GPT | HBA1C | HSPA1B | IGFBP1 | IGFBP2 | INSULIN-M | LEP | TRIG |

FIGURE 6I

| Panel No. | Marker 1 | Marker 2 | Marker 3 | Marker 4 | Marker 5 | Marker 6 | Marker 7 | Marker 8 |
|---|---|---|---|---|---|---|---|---|
| 11.1 | ADIPOQ | CRP | GLUCOSE | GPT | HBA1C | HSPA1B | IGFBP1 | IGFBP2 |

| Panel No. | Marker 9 | Marker 10 | Marker 11 |
|---|---|---|---|
| 11.1 continued | INSULIN-M | LEP | TRIG |

FIGURE 7A

| Panel No. | Marker 1 | Marker 2 | Marker 3 |
|---|---|---|---|
| 7.3.1 | ADIPOQ | CRP | GLUCOSE |
| 7.3.2 | CCL2 | CRP | GLUCOSE |
| 7.3.3 | CD40 | CRP | GLUCOSE |
| 7.3.4 | CRP | EGF | GLUCOSE |
| 7.3.5 | CRP | ENG | GLUCOSE |
| 7.3.6 | CRP | FGA | GLUCOSE |
| 7.3.7 | CRP | FTH1 | GLUCOSE |
| 7.3.8 | CRP | GLUCOSE | GPT |
| 7.3.9 | CRP | GLUCOSE | HBA1C |
| 7.3.10 | CRP | GLUCOSE | HP |
| 7.3.11 | CRP | GLUCOSE | HSPA1B |
| 7.3.12 | CRP | GLUCOSE | IGF1R |
| 7.3.13 | CRP | GLUCOSE | IGFBP1 |
| 7.3.14 | CRP | GLUCOSE | IGFBP2 |
| 7.3.15 | CRP | GLUCOSE | IL2RA |
| 7.3.16 | CRP | GLUCOSE | IL2RB |
| 7.3.17 | CRP | GLUCOSE | IL6R |
| 7.3.18 | CRP | GLUCOSE | INSULIN-M |
| 7.3.19 | CRP | GLUCOSE | LEP |
| 7.3.20 | CRP | GLUCOSE | SCp |
| 7.3.21 | CRP | GLUCOSE | SHBG |
| 7.3.22 | CRP | GLUCOSE | TIMP2 |
| 7.3.23 | CRP | GLUCOSE | TRIG |
| 7.3.24 | CRP | GLUCOSE | VWF |
| 7.3.25 | GLUCOSE | HBA1C | INSULIN-M |

FIGURE 7B

| Panel No. | Marker 1 | Marker 2 | Marker 3 | Marker 4 |
|---|---|---|---|---|
| 7.4.1 | ADIPOQ | CCL2 | CRP | GLUCOSE |
| 7.4.2 | ADIPOQ | CD40 | CRP | GLUCOSE |
| 7.4.3 | ADIPOQ | CRP | EGF | GLUCOSE |
| 7.4.4 | ADIPOQ | CRP | ENG | GLUCOSE |
| 7.4.5 | ADIPOQ | CRP | FGA | GLUCOSE |
| 7.4.6 | ADIPOQ | CRP | FTH1 | GLUCOSE |
| 7.4.7 | ADIPOQ | CRP | GLUCOSE | GPT |
| 7.4.8 | ADIPOQ | CRP | GLUCOSE | HBA1C |
| 7.4.9 | ADIPOQ | CRP | GLUCOSE | HP |
| 7.4.10 | ADIPOQ | CRP | GLUCOSE | HSPA1B |
| 7.4.11 | ADIPOQ | CRP | GLUCOSE | IGF1R |
| 7.4.12 | ADIPOQ | CRP | GLUCOSE | IGFBP1 |
| 7.4.13 | ADIPOQ | CRP | GLUCOSE | IGFBP2 |
| 7.4.14 | ADIPOQ | CRP | GLUCOSE | IL2RA |
| 7.4.15 | ADIPOQ | CRP | GLUCOSE | IL2RB |
| 7.4.16 | ADIPOQ | CRP | GLUCOSE | IL6R |
| 7.4.17 | ADIPOQ | CRP | GLUCOSE | INSULIN-M |
| 7.4.18 | ADIPOQ | CRP | GLUCOSE | LEP |
| 7.4.19 | ADIPOQ | CRP | GLUCOSE | SCp |
| 7.4.20 | ADIPOQ | CRP | GLUCOSE | SHBG |
| 7.4.21 | ADIPOQ | CRP | GLUCOSE | TIMP2 |
| 7.4.22 | ADIPOQ | CRP | GLUCOSE | TRIG |
| 7.4.23 | ADIPOQ | CRP | GLUCOSE | VWF |
| 7.4.24 | ADIPOQ | GLUCOSE | GPT | LEP |
| 7.4.25 | ADIPOQ | GLUCOSE | HBA1C | INSULIN-M |
| 7.4.26 | ADIPOQ | GLUCOSE | HBA1C | LEP |
| 7.4.27 | ADIPOQ | GLUCOSE | HSPA1B | LEP |
| 7.4.28 | ADIPOQ | GLUCOSE | IGFBP2 | LEP |
| 7.4.29 | ADIPOQ | GLUCOSE | INSULIN-M | LEP |
| 7.4.30 | ADIPOQ | GLUCOSE | LEP | TRIG |
| 7.4.31 | ADIPOQ | GLUCOSE | LEP | VWF |
| 7.4.32 | CCL2 | CD40 | CRP | GLUCOSE |
| 7.4.33 | CCL2 | CRP | EGF | GLUCOSE |
| 7.4.34 | CCL2 | CRP | ENG | GLUCOSE |
| 7.4.35 | CCL2 | CRP | FGA | GLUCOSE |
| 7.4.36 | CCL2 | CRP | FTH1 | GLUCOSE |
| 7.4.37 | CCL2 | CRP | GLUCOSE | GPT |
| 7.4.38 | CCL2 | CRP | GLUCOSE | HBA1C |
| 7.4.39 | CCL2 | CRP | GLUCOSE | HP |
| 7.4.40 | CCL2 | CRP | GLUCOSE | HSPA1B |

FIGURE 7B (continued)

| Panel No. | Marker 1 | Marker 2 | Marker 3 | Marker 4 |
|---|---|---|---|---|
| 7.4.41 | CCL2 | CRP | GLUCOSE | IGF1R |
| 7.4.42 | CCL2 | CRP | GLUCOSE | IGFBP1 |
| 7.4.43 | CCL2 | CRP | GLUCOSE | IGFBP2 |
| 7.4.44 | CCL2 | CRP | GLUCOSE | IL2RA |
| 7.4.45 | CCL2 | CRP | GLUCOSE | IL2RB |
| 7.4.46 | CCL2 | CRP | GLUCOSE | IL6R |
| 7.4.47 | CCL2 | CRP | GLUCOSE | INSULIN-M |
| 7.4.48 | CCL2 | CRP | GLUCOSE | LEP |
| 7.4.49 | CCL2 | CRP | GLUCOSE | SCp |
| 7.4.50 | CCL2 | CRP | GLUCOSE | SHBG |
| 7.4.51 | CCL2 | CRP | GLUCOSE | TIMP2 |
| 7.4.52 | CCL2 | CRP | GLUCOSE | TRIG |
| 7.4.53 | CCL2 | CRP | GLUCOSE | VWF |
| 7.4.54 | CCL2 | CRP | HBA1C | INSULIN-M |
| 7.4.55 | CCL2 | GLUCOSE | HBA1C | INSULIN-M |
| 7.4.56 | CCL2 | GLUCOSE | HBA1C | LEP |
| 7.4.57 | CCL2 | GLUCOSE | HSPA1B | INSULIN-M |
| 7.4.58 | CCL2 | GLUCOSE | LEP | TRIG |
| 7.4.59 | CD40 | CRP | EGF | GLUCOSE |
| 7.4.60 | CD40 | CRP | ENG | GLUCOSE |
| 7.4.61 | CD40 | CRP | FGA | GLUCOSE |
| 7.4.62 | CD40 | CRP | FTH1 | GLUCOSE |
| 7.4.63 | CD40 | CRP | GLUCOSE | GPT |
| 7.4.64 | CD40 | CRP | GLUCOSE | HBA1C |
| 7.4.65 | CD40 | CRP | GLUCOSE | HP |
| 7.4.66 | CD40 | CRP | GLUCOSE | HSPA1B |
| 7.4.67 | CD40 | CRP | GLUCOSE | IGF1R |
| 7.4.68 | CD40 | CRP | GLUCOSE | IGFBP1 |
| 7.4.69 | CD40 | CRP | GLUCOSE | IGFBP2 |
| 7.4.70 | CD40 | CRP | GLUCOSE | IL2RA |
| 7.4.71 | CD40 | CRP | GLUCOSE | IL2RB |
| 7.4.72 | CD40 | CRP | GLUCOSE | IL6R |
| 7.4.73 | CD40 | CRP | GLUCOSE | INSULIN-M |
| 7.4.74 | CD40 | CRP | GLUCOSE | LEP |
| 7.4.75 | CD40 | CRP | GLUCOSE | SCp |
| 7.4.76 | CD40 | CRP | GLUCOSE | SHBG |
| 7.4.77 | CD40 | CRP | GLUCOSE | TIMP2 |
| 7.4.78 | CD40 | CRP | GLUCOSE | TRIG |
| 7.4.79 | CD40 | CRP | GLUCOSE | VWF |
| 7.4.80 | CD40 | GLUCOSE | HBA1C | INSULIN-M |

FIGURE 7B (continued)

| Panel No. | Marker 1 | Marker 2 | Marker 3 | Marker 4 |
|---|---|---|---|---|
| 7.4.81 | CRP | EGF | ENG | GLUCOSE |
| 7.4.82 | CRP | EGF | FGA | GLUCOSE |
| 7.4.83 | CRP | EGF | FTH1 | GLUCOSE |
| 7.4.84 | CRP | EGF | GLUCOSE | GPT |
| 7.4.85 | CRP | EGF | GLUCOSE | HBA1C |
| 7.4.86 | CRP | EGF | GLUCOSE | HP |
| 7.4.87 | CRP | EGF | GLUCOSE | HSPA1B |
| 7.4.88 | CRP | EGF | GLUCOSE | IGF1R |
| 7.4.89 | CRP | EGF | GLUCOSE | IGFBP1 |
| 7.4.90 | CRP | EGF | GLUCOSE | IGFBP2 |
| 7.4.91 | CRP | EGF | GLUCOSE | IL2RA |
| 7.4.92 | CRP | EGF | GLUCOSE | IL2RB |
| 7.4.93 | CRP | EGF | GLUCOSE | IL6R |
| 7.4.94 | CRP | EGF | GLUCOSE | INSULIN-M |
| 7.4.95 | CRP | EGF | GLUCOSE | LEP |
| 7.4.96 | CRP | EGF | GLUCOSE | SCp |
| 7.4.97 | CRP | EGF | GLUCOSE | SHBG |
| 7.4.98 | CRP | EGF | GLUCOSE | TIMP2 |
| 7.4.99 | CRP | EGF | GLUCOSE | TRIG |
| 7.4.100 | CRP | EGF | GLUCOSE | VWF |
| 7.4.101 | CRP | EGF | HBA1C | INSULIN-M |
| 7.4.102 | CRP | EGF | HBA1C | TRIG |
| 7.4.103 | CRP | ENG | FGA | GLUCOSE |
| 7.4.104 | CRP | ENG | FTH1 | GLUCOSE |
| 7.4.105 | CRP | ENG | GLUCOSE | GPT |
| 7.4.106 | CRP | ENG | GLUCOSE | HBA1C |
| 7.4.107 | CRP | ENG | GLUCOSE | HP |
| 7.4.108 | CRP | ENG | GLUCOSE | HSPA1B |
| 7.4.109 | CRP | ENG | GLUCOSE | IGF1R |
| 7.4.110 | CRP | ENG | GLUCOSE | IGFBP1 |
| 7.4.111 | CRP | ENG | GLUCOSE | IGFBP2 |
| 7.4.112 | CRP | ENG | GLUCOSE | IL2RA |
| 7.4.113 | CRP | ENG | GLUCOSE | IL2RB |
| 7.4.114 | CRP | ENG | GLUCOSE | IL6R |
| 7.4.115 | CRP | ENG | GLUCOSE | INSULIN-M |
| 7.4.116 | CRP | ENG | GLUCOSE | LEP |
| 7.4.117 | CRP | ENG | GLUCOSE | SCp |
| 7.4.118 | CRP | ENG | GLUCOSE | SHBG |
| 7.4.119 | CRP | ENG | GLUCOSE | TIMP2 |
| 7.4.120 | CRP | ENG | GLUCOSE | TRIG |

FIGURE 7B (continued)

| Panel No. | Marker 1 | Marker 2 | Marker 3 | Marker 4 |
|---|---|---|---|---|
| 7.4.121 | CRP | ENG | GLUCOSE | VWF |
| 7.4.122 | CRP | ENG | HBA1C | INSULIN-M |
| 7.4.123 | CRP | ENG | HBA1C | TRIG |
| 7.4.124 | CRP | FGA | FTH1 | GLUCOSE |
| 7.4.125 | CRP | FGA | GLUCOSE | GPT |
| 7.4.126 | CRP | FGA | GLUCOSE | HBA1C |
| 7.4.127 | CRP | FGA | GLUCOSE | HP |
| 7.4.128 | CRP | FGA | GLUCOSE | HSPA1B |
| 7.4.129 | CRP | FGA | GLUCOSE | IGF1R |
| 7.4.130 | CRP | FGA | GLUCOSE | IGFBP1 |
| 7.4.131 | CRP | FGA | GLUCOSE | IGFBP2 |
| 7.4.132 | CRP | FGA | GLUCOSE | IL2RA |
| 7.4.133 | CRP | FGA | GLUCOSE | IL2RB |
| 7.4.134 | CRP | FGA | GLUCOSE | IL6R |
| 7.4.135 | CRP | FGA | GLUCOSE | INSULIN-M |
| 7.4.136 | CRP | FGA | GLUCOSE | LEP |
| 7.4.137 | CRP | FGA | GLUCOSE | SCp |
| 7.4.138 | CRP | FGA | GLUCOSE | SHBG |
| 7.4.139 | CRP | FGA | GLUCOSE | TIMP2 |
| 7.4.140 | CRP | FGA | GLUCOSE | TRIG |
| 7.4.141 | CRP | FGA | GLUCOSE | VWF |
| 7.4.142 | CRP | FTH1 | GLUCOSE | GPT |
| 7.4.143 | CRP | FTH1 | GLUCOSE | HBA1C |
| 7.4.144 | CRP | FTH1 | GLUCOSE | HP |
| 7.4.145 | CRP | FTH1 | GLUCOSE | HSPA1B |
| 7.4.146 | CRP | FTH1 | GLUCOSE | IGF1R |
| 7.4.147 | CRP | FTH1 | GLUCOSE | IGFBP1 |
| 7.4.148 | CRP | FTH1 | GLUCOSE | IGFBP2 |
| 7.4.149 | CRP | FTH1 | GLUCOSE | IL2RA |
| 7.4.150 | CRP | FTH1 | GLUCOSE | IL2RB |
| 7.4.151 | CRP | FTH1 | GLUCOSE | IL6R |
| 7.4.152 | CRP | FTH1 | GLUCOSE | INSULIN-M |
| 7.4.153 | CRP | FTH1 | GLUCOSE | LEP |
| 7.4.154 | CRP | FTH1 | GLUCOSE | SCp |
| 7.4.155 | CRP | FTH1 | GLUCOSE | SHBG |
| 7.4.156 | CRP | FTH1 | GLUCOSE | TIMP2 |
| 7.4.157 | CRP | FTH1 | GLUCOSE | TRIG |
| 7.4.158 | CRP | FTH1 | GLUCOSE | VWF |
| 7.4.159 | CRP | FTH1 | HBA1C | INSULIN-M |
| 7.4.160 | CRP | GLUCOSE | GPT | HBA1C |

FIGURE 7B (continued)

| Panel No. | Marker 1 | Marker 2 | Marker 3 | Marker 4 |
|---|---|---|---|---|
| 7.4.161 | CRP | GLUCOSE | GPT | HP |
| 7.4.162 | CRP | GLUCOSE | GPT | HSPA1B |
| 7.4.163 | CRP | GLUCOSE | GPT | IGF1R |
| 7.4.164 | CRP | GLUCOSE | GPT | IGFBP1 |
| 7.4.165 | CRP | GLUCOSE | GPT | IGFBP2 |
| 7.4.166 | CRP | GLUCOSE | GPT | IL2RA |
| 7.4.167 | CRP | GLUCOSE | GPT | IL2RB |
| 7.4.168 | CRP | GLUCOSE | GPT | IL6R |
| 7.4.169 | CRP | GLUCOSE | GPT | INSULIN-M |
| 7.4.170 | CRP | GLUCOSE | GPT | LEP |
| 7.4.171 | CRP | GLUCOSE | GPT | SCp |
| 7.4.172 | CRP | GLUCOSE | GPT | SHBG |
| 7.4.173 | CRP | GLUCOSE | GPT | TIMP2 |
| 7.4.174 | CRP | GLUCOSE | GPT | TRIG |
| 7.4.175 | CRP | GLUCOSE | GPT | VWF |
| 7.4.176 | CRP | GLUCOSE | HBA1C | HP |
| 7.4.177 | CRP | GLUCOSE | HBA1C | HSPA1B |
| 7.4.178 | CRP | GLUCOSE | HBA1C | IGF1R |
| 7.4.179 | CRP | GLUCOSE | HBA1C | IGFBP1 |
| 7.4.180 | CRP | GLUCOSE | HBA1C | IGFBP2 |
| 7.4.181 | CRP | GLUCOSE | HBA1C | IL2RA |
| 7.4.182 | CRP | GLUCOSE | HBA1C | IL2RB |
| 7.4.183 | CRP | GLUCOSE | HBA1C | IL6R |
| 7.4.184 | CRP | GLUCOSE | HBA1C | INSULIN-M |
| 7.4.185 | CRP | GLUCOSE | HBA1C | LEP |
| 7.4.186 | CRP | GLUCOSE | HBA1C | SCp |
| 7.4.187 | CRP | GLUCOSE | HBA1C | SHBG |
| 7.4.188 | CRP | GLUCOSE | HBA1C | TIMP2 |
| 7.4.189 | CRP | GLUCOSE | HBA1C | TRIG |
| 7.4.190 | CRP | GLUCOSE | HBA1C | VWF |
| 7.4.191 | CRP | GLUCOSE | HP | HSPA1B |
| 7.4.192 | CRP | GLUCOSE | HP | IGF1R |
| 7.4.193 | CRP | GLUCOSE | HP | IGFBP1 |
| 7.4.194 | CRP | GLUCOSE | HP | IGFBP2 |
| 7.4.195 | CRP | GLUCOSE | HP | IL2RA |
| 7.4.196 | CRP | GLUCOSE | HP | IL2RB |
| 7.4.197 | CRP | GLUCOSE | HP | IL6R |
| 7.4.198 | CRP | GLUCOSE | HP | INSULIN-M |
| 7.4.199 | CRP | GLUCOSE | HP | LEP |
| 7.4.200 | CRP | GLUCOSE | HP | SCp |

FIGURE 7B (continued)

| Panel No. | Marker 1 | Marker 2 | Marker 3 | Marker 4 |
|---|---|---|---|---|
| 7.4.201 | CRP | GLUCOSE | HP | SHBG |
| 7.4.202 | CRP | GLUCOSE | HP | TIMP2 |
| 7.4.203 | CRP | GLUCOSE | HP | TRIG |
| 7.4.204 | CRP | GLUCOSE | HP | VWF |
| 7.4.205 | CRP | GLUCOSE | HSPA1B | IGF1R |
| 7.4.206 | CRP | GLUCOSE | HSPA1B | IGFBP1 |
| 7.4.207 | CRP | GLUCOSE | HSPA1B | IGFBP2 |
| 7.4.208 | CRP | GLUCOSE | HSPA1B | IL2RA |
| 7.4.209 | CRP | GLUCOSE | HSPA1B | IL2RB |
| 7.4.210 | CRP | GLUCOSE | HSPA1B | IL6R |
| 7.4.211 | CRP | GLUCOSE | HSPA1B | INSULIN-M |
| 7.4.212 | CRP | GLUCOSE | HSPA1B | LEP |
| 7.4.213 | CRP | GLUCOSE | HSPA1B | SCp |
| 7.4.214 | CRP | GLUCOSE | HSPA1B | SHBG |
| 7.4.215 | CRP | GLUCOSE | HSPA1B | TIMP2 |
| 7.4.216 | CRP | GLUCOSE | HSPA1B | TRIG |
| 7.4.217 | CRP | GLUCOSE | HSPA1B | VWF |
| 7.4.218 | CRP | GLUCOSE | IGF1R | IGFBP1 |
| 7.4.219 | CRP | GLUCOSE | IGF1R | IGFBP2 |
| 7.4.220 | CRP | GLUCOSE | IGF1R | IL2RA |
| 7.4.221 | CRP | GLUCOSE | IGF1R | IL2RB |
| 7.4.222 | CRP | GLUCOSE | IGF1R | IL6R |
| 7.4.223 | CRP | GLUCOSE | IGF1R | INSULIN-M |
| 7.4.224 | CRP | GLUCOSE | IGF1R | LEP |
| 7.4.225 | CRP | GLUCOSE | IGF1R | SCp |
| 7.4.226 | CRP | GLUCOSE | IGF1R | SHBG |
| 7.4.227 | CRP | GLUCOSE | IGF1R | TIMP2 |
| 7.4.228 | CRP | GLUCOSE | IGF1R | TRIG |
| 7.4.229 | CRP | GLUCOSE | IGF1R | VWF |
| 7.4.230 | CRP | GLUCOSE | IGFBP1 | IGFBP2 |
| 7.4.231 | CRP | GLUCOSE | IGFBP1 | IL2RA |
| 7.4.232 | CRP | GLUCOSE | IGFBP1 | IL2RB |
| 7.4.233 | CRP | GLUCOSE | IGFBP1 | IL6R |
| 7.4.234 | CRP | GLUCOSE | IGFBP1 | INSULIN-M |
| 7.4.235 | CRP | GLUCOSE | IGFBP1 | LEP |
| 7.4.236 | CRP | GLUCOSE | IGFBP1 | SCp |
| 7.4.237 | CRP | GLUCOSE | IGFBP1 | SHBG |
| 7.4.238 | CRP | GLUCOSE | IGFBP1 | TIMP2 |
| 7.4.239 | CRP | GLUCOSE | IGFBP1 | TRIG |
| 7.4.240 | CRP | GLUCOSE | IGFBP1 | VWF |

FIGURE 7B (continued)

| Panel No. | Marker 1 | Marker 2 | Marker 3 | Marker 4 |
|---|---|---|---|---|
| 7.4.241 | CRP | GLUCOSE | IGFBP2 | IL2RA |
| 7.4.242 | CRP | GLUCOSE | IGFBP2 | IL2RB |
| 7.4.243 | CRP | GLUCOSE | IGFBP2 | IL6R |
| 7.4.244 | CRP | GLUCOSE | IGFBP2 | INSULIN-M |
| 7.4.245 | CRP | GLUCOSE | IGFBP2 | LEP |
| 7.4.246 | CRP | GLUCOSE | IGFBP2 | SCp |
| 7.4.247 | CRP | GLUCOSE | IGFBP2 | SHBG |
| 7.4.248 | CRP | GLUCOSE | IGFBP2 | TIMP2 |
| 7.4.249 | CRP | GLUCOSE | IGFBP2 | TRIG |
| 7.4.250 | CRP | GLUCOSE | IGFBP2 | VWF |
| 7.4.251 | CRP | GLUCOSE | IL2RA | IL2RB |
| 7.4.252 | CRP | GLUCOSE | IL2RA | IL6R |
| 7.4.253 | CRP | GLUCOSE | IL2RA | INSULIN-M |
| 7.4.254 | CRP | GLUCOSE | IL2RA | LEP |
| 7.4.255 | CRP | GLUCOSE | IL2RA | SCp |
| 7.4.256 | CRP | GLUCOSE | IL2RA | SHBG |
| 7.4.257 | CRP | GLUCOSE | IL2RA | TIMP2 |
| 7.4.258 | CRP | GLUCOSE | IL2RA | TRIG |
| 7.4.259 | CRP | GLUCOSE | IL2RA | VWF |
| 7.4.260 | CRP | GLUCOSE | IL2RB | IL6R |
| 7.4.261 | CRP | GLUCOSE | IL2RB | INSULIN-M |
| 7.4.262 | CRP | GLUCOSE | IL2RB | LEP |
| 7.4.263 | CRP | GLUCOSE | IL2RB | SCp |
| 7.4.264 | CRP | GLUCOSE | IL2RB | SHBG |
| 7.4.265 | CRP | GLUCOSE | IL2RB | TIMP2 |
| 7.4.266 | CRP | GLUCOSE | IL2RB | TRIG |
| 7.4.267 | CRP | GLUCOSE | IL2RB | VWF |
| 7.4.268 | CRP | GLUCOSE | IL6R | INSULIN-M |
| 7.4.269 | CRP | GLUCOSE | IL6R | LEP |
| 7.4.270 | CRP | GLUCOSE | IL6R | SCp |
| 7.4.271 | CRP | GLUCOSE | IL6R | SHBG |
| 7.4.272 | CRP | GLUCOSE | IL6R | TIMP2 |
| 7.4.273 | CRP | GLUCOSE | IL6R | TRIG |
| 7.4.274 | CRP | GLUCOSE | IL6R | VWF |
| 7.4.275 | CRP | GLUCOSE | INSULIN-M | LEP |
| 7.4.276 | CRP | GLUCOSE | INSULIN-M | SCp |
| 7.4.277 | CRP | GLUCOSE | INSULIN-M | SHBG |
| 7.4.278 | CRP | GLUCOSE | INSULIN-M | TIMP2 |
| 7.4.279 | CRP | GLUCOSE | INSULIN-M | TRIG |
| 7.4.280 | CRP | GLUCOSE | INSULIN-M | VWF |

FIGURE 7B (continued)

| Panel No. | Marker 1 | Marker 2 | Marker 3 | Marker 4 |
|---|---|---|---|---|
| 7.4.281 | CRP | GLUCOSE | LEP | SCp |
| 7.4.282 | CRP | GLUCOSE | LEP | SHBG |
| 7.4.283 | CRP | GLUCOSE | LEP | TIMP2 |
| 7.4.284 | CRP | GLUCOSE | LEP | TRIG |
| 7.4.285 | CRP | GLUCOSE | LEP | VWF |
| 7.4.286 | CRP | GLUCOSE | SCp | SHBG |
| 7.4.287 | CRP | GLUCOSE | SCp | TIMP2 |
| 7.4.288 | CRP | GLUCOSE | SCp | TRIG |
| 7.4.289 | CRP | GLUCOSE | SCp | VWF |
| 7.4.290 | CRP | GLUCOSE | SHBG | TIMP2 |
| 7.4.291 | CRP | GLUCOSE | SHBG | TRIG |
| 7.4.292 | CRP | GLUCOSE | SHBG | VWF |
| 7.4.293 | CRP | GLUCOSE | TIMP2 | TRIG |
| 7.4.294 | CRP | GLUCOSE | TIMP2 | VWF |
| 7.4.295 | CRP | GLUCOSE | TRIG | VWF |
| 7.4.296 | CRP | GPT | HBA1C | INSULIN-M |
| 7.4.297 | CRP | HBA1C | HP | INSULIN-M |
| 7.4.298 | CRP | HBA1C | HP | TRIG |
| 7.4.299 | CRP | HBA1C | HSPA1B | INSULIN-M |
| 7.4.300 | CRP | HBA1C | HSPA1B | TRIG |
| 7.4.301 | CRP | HBA1C | INSULIN-M | TRIG |
| 7.4.302 | CRP | HBA1C | TIMP2 | TRIG |
| 7.4.303 | EGF | GLUCOSE | HBA1C | INSULIN-M |
| 7.4.304 | EGF | GLUCOSE | HBA1C | LEP |
| 7.4.305 | ENG | GLUCOSE | HBA1C | INSULIN-M |
| 7.4.306 | ENG | GLUCOSE | HBA1C | LEP |
| 7.4.307 | ENG | GLUCOSE | HSPA1B | INSULIN-M |
| 7.4.308 | ENG | GLUCOSE | HSPA1B | LEP |
| 7.4.309 | ENG | GLUCOSE | LEP | TRIG |
| 7.4.310 | FGA | GLUCOSE | HBA1C | INSULIN-M |
| 7.4.311 | FTH1 | GLUCOSE | HBA1C | INSULIN-M |
| 7.4.312 | FTH1 | GLUCOSE | HBA1C | LEP |
| 7.4.313 | GLUCOSE | GPT | HBA1C | INSULIN-M |
| 7.4.314 | GLUCOSE | GPT | HBA1C | LEP |
| 7.4.315 | GLUCOSE | GPT | HSPA1B | LEP |
| 7.4.316 | GLUCOSE | GPT | INSULIN-M | LEP |
| 7.4.317 | GLUCOSE | GPT | LEP | TRIG |
| 7.4.318 | GLUCOSE | HBA1C | HP | INSULIN-M |
| 7.4.319 | GLUCOSE | HBA1C | HSPA1B | INSULIN-M |
| 7.4.320 | GLUCOSE | HBA1C | HSPA1B | LEP |

FIGURE 7B (continued)

| Panel No. | Marker 1 | Marker 2 | Marker 3 | Marker 4 |
|---|---|---|---|---|
| 7.4.321 | GLUCOSE | HBA1C | IGF1R | INSULIN-M |
| 7.4.322 | GLUCOSE | HBA1C | IGFBP1 | INSULIN-M |
| 7.4.323 | GLUCOSE | HBA1C | IGFBP2 | INSULIN-M |
| 7.4.324 | GLUCOSE | HBA1C | IL2RA | INSULIN-M |
| 7.4.325 | GLUCOSE | HBA1C | IL2RB | INSULIN-M |
| 7.4.326 | GLUCOSE | HBA1C | IL6R | INSULIN-M |
| 7.4.327 | GLUCOSE | HBA1C | INSULIN-M | LEP |
| 7.4.328 | GLUCOSE | HBA1C | INSULIN-M | SCp |
| 7.4.329 | GLUCOSE | HBA1C | INSULIN-M | SHBG |
| 7.4.330 | GLUCOSE | HBA1C | INSULIN-M | TIMP2 |
| 7.4.331 | GLUCOSE | HBA1C | INSULIN-M | TRIG |
| 7.4.332 | GLUCOSE | HBA1C | INSULIN-M | VWF |
| 7.4.333 | GLUCOSE | HBA1C | LEP | TRIG |
| 7.4.334 | GLUCOSE | HSPA1B | IGFBP2 | INSULIN-M |
| 7.4.335 | GLUCOSE | HSPA1B | IL2RA | INSULIN-M |
| 7.4.336 | GLUCOSE | HSPA1B | IL2RA | LEP |
| 7.4.337 | GLUCOSE | HSPA1B | INSULIN-M | LEP |
| 7.4.338 | GLUCOSE | HSPA1B | LEP | TRIG |

Figure 7C

| Panel No. | Marker 1 | Marker 2 | Marker 3 | Marker 4 | Marker 5 |
|---|---|---|---|---|---|
| 7.5.1 | ADIPOQ | CCL2 | CRP | EGF | GLUCOSE |
| 7.5.2 | ADIPOQ | CCL2 | CRP | ENG | GLUCOSE |
| 7.5.3 | ADIPOQ | CCL2 | CRP | GLUCOSE | GPT |
| 7.5.4 | ADIPOQ | CCL2 | CRP | GLUCOSE | HBA1C |
| 7.5.5 | ADIPOQ | CCL2 | CRP | GLUCOSE | HP |
| 7.5.6 | ADIPOQ | CCL2 | CRP | GLUCOSE | HSPA1B |
| 7.5.7 | ADIPOQ | CCL2 | CRP | GLUCOSE | IGFBP2 |
| 7.5.8 | ADIPOQ | CCL2 | CRP | GLUCOSE | IL2RA |
| 7.5.9 | ADIPOQ | CCL2 | CRP | GLUCOSE | INSULIN-M |
| 7.5.10 | ADIPOQ | CCL2 | CRP | GLUCOSE | LEP |
| 7.5.11 | ADIPOQ | CCL2 | CRP | GLUCOSE | TIMP2 |
| 7.5.12 | ADIPOQ | CCL2 | CRP | GLUCOSE | TRIG |
| 7.5.13 | ADIPOQ | CCL2 | CRP | GLUCOSE | VWF |
| 7.5.14 | ADIPOQ | CD40 | CRP | GLUCOSE | HBA1C |
| 7.5.15 | ADIPOQ | CD40 | CRP | GLUCOSE | INSULIN-M |
| 7.5.16 | ADIPOQ | CD40 | CRP | GLUCOSE | LEP |
| 7.5.17 | ADIPOQ | CRP | EGF | GLUCOSE | GPT |
| 7.5.18 | ADIPOQ | CRP | EGF | GLUCOSE | HBA1C |
| 7.5.19 | ADIPOQ | CRP | EGF | GLUCOSE | LEP |
| 7.5.20 | ADIPOQ | CRP | EGF | GLUCOSE | TRIG |
| 7.5.21 | ADIPOQ | CRP | ENG | GLUCOSE | GPT |
| 7.5.22 | ADIPOQ | CRP | ENG | GLUCOSE | HBA1C |
| 7.5.23 | ADIPOQ | CRP | ENG | GLUCOSE | HSPA1B |
| 7.5.24 | ADIPOQ | CRP | ENG | GLUCOSE | IL2RA |
| 7.5.25 | ADIPOQ | CRP | ENG | GLUCOSE | INSULIN-M |
| 7.5.26 | ADIPOQ | CRP | ENG | GLUCOSE | LEP |
| 7.5.27 | ADIPOQ | CRP | ENG | GLUCOSE | TIMP2 |
| 7.5.28 | ADIPOQ | CRP | ENG | GLUCOSE | TRIG |
| 7.5.29 | ADIPOQ | CRP | ENG | GLUCOSE | VWF |
| 7.5.30 | ADIPOQ | CRP | FGA | GLUCOSE | GPT |
| 7.5.31 | ADIPOQ | CRP | FGA | GLUCOSE | HBA1C |
| 7.5.32 | ADIPOQ | CRP | FGA | GLUCOSE | LEP |
| 7.5.33 | ADIPOQ | CRP | FTH1 | GLUCOSE | HBA1C |
| 7.5.34 | ADIPOQ | CRP | FTH1 | GLUCOSE | INSULIN-M |
| 7.5.35 | ADIPOQ | CRP | FTH1 | GLUCOSE | LEP |
| 7.5.36 | ADIPOQ | CRP | GLUCOSE | GPT | HBA1C |
| 7.5.37 | ADIPOQ | CRP | GLUCOSE | GPT | HP |
| 7.5.38 | ADIPOQ | CRP | GLUCOSE | GPT | HSPA1B |
| 7.5.39 | ADIPOQ | CRP | GLUCOSE | GPT | IGFBP2 |
| 7.5.40 | ADIPOQ | CRP | GLUCOSE | GPT | IL2RA |

FIGURE 7C (continued)

| Panel No. | Marker 1 | Marker 2 | Marker 3 | Marker 4 | Marker 5 |
|---|---|---|---|---|---|
| 7.5.41 | ADIPOQ | CRP | GLUCOSE | GPT | INSULIN-M |
| 7.5.42 | ADIPOQ | CRP | GLUCOSE | GPT | LEP |
| 7.5.43 | ADIPOQ | CRP | GLUCOSE | GPT | TIMP2 |
| 7.5.44 | ADIPOQ | CRP | GLUCOSE | GPT | TRIG |
| 7.5.45 | ADIPOQ | CRP | GLUCOSE | GPT | VWF |
| 7.5.46 | ADIPOQ | CRP | GLUCOSE | HBA1C | HP |
| 7.5.47 | ADIPOQ | CRP | GLUCOSE | HBA1C | HSPA1B |
| 7.5.48 | ADIPOQ | CRP | GLUCOSE | HBA1C | IGF1R |
| 7.5.49 | ADIPOQ | CRP | GLUCOSE | HBA1C | IGFBP1 |
| 7.5.50 | ADIPOQ | CRP | GLUCOSE | HBA1C | IGFBP2 |
| 7.5.51 | ADIPOQ | CRP | GLUCOSE | HBA1C | IL2RA |
| 7.5.52 | ADIPOQ | CRP | GLUCOSE | HBA1C | IL2RB |
| 7.5.53 | ADIPOQ | CRP | GLUCOSE | HBA1C | IL6R |
| 7.5.54 | ADIPOQ | CRP | GLUCOSE | HBA1C | INSULIN-M |
| 7.5.55 | ADIPOQ | CRP | GLUCOSE | HBA1C | LEP |
| 7.5.56 | ADIPOQ | CRP | GLUCOSE | HBA1C | SCp |
| 7.5.57 | ADIPOQ | CRP | GLUCOSE | HBA1C | SHBG |
| 7.5.58 | ADIPOQ | CRP | GLUCOSE | HBA1C | TIMP2 |
| 7.5.59 | ADIPOQ | CRP | GLUCOSE | HBA1C | TRIG |
| 7.5.60 | ADIPOQ | CRP | GLUCOSE | HBA1C | VWF |
| 7.5.61 | ADIPOQ | CRP | GLUCOSE | HP | HSPA1B |
| 7.5.62 | ADIPOQ | CRP | GLUCOSE | HP | INSULIN-M |
| 7.5.63 | ADIPOQ | CRP | GLUCOSE | HP | LEP |
| 7.5.64 | ADIPOQ | CRP | GLUCOSE | HP | TRIG |
| 7.5.65 | ADIPOQ | CRP | GLUCOSE | HSPA1B | IL2RA |
| 7.5.66 | ADIPOQ | CRP | GLUCOSE | HSPA1B | INSULIN-M |
| 7.5.67 | ADIPOQ | CRP | GLUCOSE | HSPA1B | LEP |
| 7.5.68 | ADIPOQ | CRP | GLUCOSE | HSPA1B | TIMP2 |
| 7.5.69 | ADIPOQ | CRP | GLUCOSE | HSPA1B | TRIG |
| 7.5.70 | ADIPOQ | CRP | GLUCOSE | IGF1R | LEP |
| 7.5.71 | ADIPOQ | CRP | GLUCOSE | IGFBP1 | LEP |
| 7.5.72 | ADIPOQ | CRP | GLUCOSE | IGFBP2 | INSULIN-M |
| 7.5.73 | ADIPOQ | CRP | GLUCOSE | IGFBP2 | LEP |
| 7.5.74 | ADIPOQ | CRP | GLUCOSE | IL2RA | LEP |
| 7.5.75 | ADIPOQ | CRP | GLUCOSE | IL2RB | LEP |
| 7.5.76 | ADIPOQ | CRP | GLUCOSE | IL2RB | TRIG |
| 7.5.77 | ADIPOQ | CRP | GLUCOSE | IL6R | LEP |
| 7.5.78 | ADIPOQ | CRP | GLUCOSE | INSULIN-M | LEP |
| 7.5.79 | ADIPOQ | CRP | GLUCOSE | INSULIN-M | SCp |
| 7.5.80 | ADIPOQ | CRP | GLUCOSE | INSULIN-M | SHBG |

FIGURE 7C (continued)

| Panel No. | Marker 1 | Marker 2 | Marker 3 | Marker 4 | Marker 5 |
|---|---|---|---|---|---|
| 7.5.81 | ADIPOQ | CRP | GLUCOSE | INSULIN-M | TIMP2 |
| 7.5.82 | ADIPOQ | CRP | GLUCOSE | INSULIN-M | TRIG |
| 7.5.83 | ADIPOQ | CRP | GLUCOSE | INSULIN-M | VWF |
| 7.5.84 | ADIPOQ | CRP | GLUCOSE | LEP | SCp |
| 7.5.85 | ADIPOQ | CRP | GLUCOSE | LEP | SHBG |
| 7.5.86 | ADIPOQ | CRP | GLUCOSE | LEP | TIMP2 |
| 7.5.87 | ADIPOQ | CRP | GLUCOSE | LEP | TRIG |
| 7.5.88 | ADIPOQ | CRP | GLUCOSE | LEP | VWF |
| 7.5.89 | ADIPOQ | CRP | GLUCOSE | TIMP2 | TRIG |
| 7.5.90 | ADIPOQ | CRP | GLUCOSE | TRIG | VWF |
| 7.5.91 | ADIPOQ | GLUCOSE | HBA1C | HSPA1B | LEP |
| 7.5.92 | CCL2 | CD40 | CRP | GLUCOSE | HBA1C |
| 7.5.93 | CCL2 | CD40 | CRP | GLUCOSE | INSULIN-M |
| 7.5.94 | CCL2 | CRP | EGF | GLUCOSE | HBA1C |
| 7.5.95 | CCL2 | CRP | EGF | GLUCOSE | INSULIN-M |
| 7.5.96 | CCL2 | CRP | EGF | GLUCOSE | TRIG |
| 7.5.97 | CCL2 | CRP | ENG | GLUCOSE | GPT |
| 7.5.98 | CCL2 | CRP | ENG | GLUCOSE | HBA1C |
| 7.5.99 | CCL2 | CRP | ENG | GLUCOSE | HP |
| 7.5.100 | CCL2 | CRP | ENG | GLUCOSE | HSPA1B |
| 7.5.101 | CCL2 | CRP | ENG | GLUCOSE | IL2RA |
| 7.5.102 | CCL2 | CRP | ENG | GLUCOSE | INSULIN-M |
| 7.5.103 | CCL2 | CRP | ENG | GLUCOSE | LEP |
| 7.5.104 | CCL2 | CRP | ENG | GLUCOSE | TRIG |
| 7.5.105 | CCL2 | CRP | FGA | GLUCOSE | HBA1C |
| 7.5.106 | CCL2 | CRP | FGA | GLUCOSE | INSULIN-M |
| 7.5.107 | CCL2 | CRP | FGA | GLUCOSE | TRIG |
| 7.5.108 | CCL2 | CRP | FTH1 | GLUCOSE | HBA1C |
| 7.5.109 | CCL2 | CRP | GLUCOSE | GPT | HBA1C |
| 7.5.110 | CCL2 | CRP | GLUCOSE | GPT | HP |
| 7.5.111 | CCL2 | CRP | GLUCOSE | GPT | IL2RA |
| 7.5.112 | CCL2 | CRP | GLUCOSE | GPT | INSULIN-M |
| 7.5.113 | CCL2 | CRP | GLUCOSE | GPT | LEP |
| 7.5.114 | CCL2 | CRP | GLUCOSE | GPT | TRIG |
| 7.5.115 | CCL2 | CRP | GLUCOSE | HBA1C | HP |
| 7.5.116 | CCL2 | CRP | GLUCOSE | HBA1C | HSPA1B |
| 7.5.117 | CCL2 | CRP | GLUCOSE | HBA1C | IGF1R |
| 7.5.118 | CCL2 | CRP | GLUCOSE | HBA1C | IGFBP1 |
| 7.5.119 | CCL2 | CRP | GLUCOSE | HBA1C | IGFBP2 |
| 7.5.120 | CCL2 | CRP | GLUCOSE | HBA1C | IL2RA |

FIGURE 7C (continued)

| Panel No. | Marker 1 | Marker 2 | Marker 3 | Marker 4 | Marker 5 |
|---|---|---|---|---|---|
| 7.5.121 | CCL2 | CRP | GLUCOSE | HBA1C | IL2RB |
| 7.5.122 | CCL2 | CRP | GLUCOSE | HBA1C | IL6R |
| 7.5.123 | CCL2 | CRP | GLUCOSE | HBA1C | INSULIN-M |
| 7.5.124 | CCL2 | CRP | GLUCOSE | HBA1C | LEP |
| 7.5.125 | CCL2 | CRP | GLUCOSE | HBA1C | SCp |
| 7.5.126 | CCL2 | CRP | GLUCOSE | HBA1C | SHBG |
| 7.5.127 | CCL2 | CRP | GLUCOSE | HBA1C | TIMP2 |
| 7.5.128 | CCL2 | CRP | GLUCOSE | HBA1C | TRIG |
| 7.5.129 | CCL2 | CRP | GLUCOSE | HBA1C | VWF |
| 7.5.130 | CCL2 | CRP | GLUCOSE | HP | HSPA1B |
| 7.5.131 | CCL2 | CRP | GLUCOSE | HP | IGFBP2 |
| 7.5.132 | CCL2 | CRP | GLUCOSE | HP | INSULIN-M |
| 7.5.133 | CCL2 | CRP | GLUCOSE | HP | LEP |
| 7.5.134 | CCL2 | CRP | GLUCOSE | HP | SHBG |
| 7.5.135 | CCL2 | CRP | GLUCOSE | HP | TIMP2 |
| 7.5.136 | CCL2 | CRP | GLUCOSE | HP | TRIG |
| 7.5.137 | CCL2 | CRP | GLUCOSE | HSPA1B | INSULIN-M |
| 7.5.138 | CCL2 | CRP | GLUCOSE | HSPA1B | LEP |
| 7.5.139 | CCL2 | CRP | GLUCOSE | HSPA1B | TRIG |
| 7.5.140 | CCL2 | CRP | GLUCOSE | IGF1R | INSULIN-M |
| 7.5.141 | CCL2 | CRP | GLUCOSE | IGFBP1 | INSULIN-M |
| 7.5.142 | CCL2 | CRP | GLUCOSE | IGFBP2 | INSULIN-M |
| 7.5.143 | CCL2 | CRP | GLUCOSE | IL2RA | INSULIN-M |
| 7.5.144 | CCL2 | CRP | GLUCOSE | IL2RA | TRIG |
| 7.5.145 | CCL2 | CRP | GLUCOSE | IL2RB | INSULIN-M |
| 7.5.146 | CCL2 | CRP | GLUCOSE | IL6R | INSULIN-M |
| 7.5.147 | CCL2 | CRP | GLUCOSE | INSULIN-M | LEP |
| 7.5.148 | CCL2 | CRP | GLUCOSE | INSULIN-M | SCp |
| 7.5.149 | CCL2 | CRP | GLUCOSE | INSULIN-M | SHBG |
| 7.5.150 | CCL2 | CRP | GLUCOSE | INSULIN-M | TIMP2 |
| 7.5.151 | CCL2 | CRP | GLUCOSE | INSULIN-M | TRIG |
| 7.5.152 | CCL2 | CRP | GLUCOSE | INSULIN-M | VWF |
| 7.5.153 | CCL2 | CRP | GLUCOSE | LEP | TRIG |
| 7.5.154 | CCL2 | CRP | GLUCOSE | TIMP2 | TRIG |
| 7.5.155 | CCL2 | GLUCOSE | GPT | HBA1C | INSULIN-M |
| 7.5.156 | CCL2 | GLUCOSE | HBA1C | HSPA1B | INSULIN-M |
| 7.5.157 | CD40 | CRP | ENG | GLUCOSE | INSULIN-M |
| 7.5.158 | CD40 | CRP | GLUCOSE | GPT | HBA1C |
| 7.5.159 | CD40 | CRP | GLUCOSE | GPT | INSULIN-M |
| 7.5.160 | CD40 | CRP | GLUCOSE | HBA1C | HP |

FIGURE 7C (continued)

| Panel No. | Marker 1 | Marker 2 | Marker 3 | Marker 4 | Marker 5 |
|---|---|---|---|---|---|
| 7.5.161 | CD40 | CRP | GLUCOSE | HBA1C | INSULIN-M |
| 7.5.162 | CD40 | CRP | GLUCOSE | HBA1C | TRIG |
| 7.5.163 | CD40 | CRP | GLUCOSE | HP | INSULIN-M |
| 7.5.164 | CRP | EGF | ENG | GLUCOSE | HBA1C |
| 7.5.165 | CRP | EGF | ENG | GLUCOSE | INSULIN-M |
| 7.5.166 | CRP | EGF | ENG | GLUCOSE | TRIG |
| 7.5.167 | CRP | EGF | FGA | GLUCOSE | HBA1C |
| 7.5.168 | CRP | EGF | FTH1 | GLUCOSE | HBA1C |
| 7.5.169 | CRP | EGF | GLUCOSE | GPT | HBA1C |
| 7.5.170 | CRP | EGF | GLUCOSE | GPT | IL2RA |
| 7.5.171 | CRP | EGF | GLUCOSE | GPT | INSULIN-M |
| 7.5.172 | CRP | EGF | GLUCOSE | GPT | LEP |
| 7.5.173 | CRP | EGF | GLUCOSE | GPT | TRIG |
| 7.5.174 | CRP | EGF | GLUCOSE | HBA1C | HP |
| 7.5.175 | CRP | EGF | GLUCOSE | HBA1C | HSPA1B |
| 7.5.176 | CRP | EGF | GLUCOSE | HBA1C | IGF1R |
| 7.5.177 | CRP | EGF | GLUCOSE | HBA1C | IGFBP2 |
| 7.5.178 | CRP | EGF | GLUCOSE | HBA1C | IL2RA |
| 7.5.179 | CRP | EGF | GLUCOSE | HBA1C | IL2RB |
| 7.5.180 | CRP | EGF | GLUCOSE | HBA1C | INSULIN-M |
| 7.5.181 | CRP | EGF | GLUCOSE | HBA1C | LEP |
| 7.5.182 | CRP | EGF | GLUCOSE | HBA1C | SHBG |
| 7.5.183 | CRP | EGF | GLUCOSE | HBA1C | TIMP2 |
| 7.5.184 | CRP | EGF | GLUCOSE | HBA1C | TRIG |
| 7.5.185 | CRP | EGF | GLUCOSE | HP | INSULIN-M |
| 7.5.186 | CRP | EGF | GLUCOSE | HSPA1B | IL2RA |
| 7.5.187 | CRP | EGF | GLUCOSE | HSPA1B | INSULIN-M |
| 7.5.188 | CRP | EGF | GLUCOSE | HSPA1B | TRIG |
| 7.5.189 | CRP | EGF | GLUCOSE | IGFBP2 | INSULIN-M |
| 7.5.190 | CRP | EGF | GLUCOSE | IL2RA | TRIG |
| 7.5.191 | CRP | EGF | GLUCOSE | INSULIN-M | SHBG |
| 7.5.192 | CRP | EGF | GLUCOSE | INSULIN-M | TRIG |
| 7.5.193 | CRP | EGF | GLUCOSE | LEP | TRIG |
| 7.5.194 | CRP | EGF | GLUCOSE | SHBG | TRIG |
| 7.5.195 | CRP | EGF | GLUCOSE | TIMP2 | TRIG |
| 7.5.196 | CRP | EGF | GLUCOSE | TRIG | VWF |
| 7.5.197 | CRP | ENG | FGA | GLUCOSE | INSULIN-M |
| 7.5.198 | CRP | ENG | FGA | GLUCOSE | TRIG |
| 7.5.199 | CRP | ENG | FTH1 | GLUCOSE | HBA1C |
| 7.5.200 | CRP | ENG | FTH1 | GLUCOSE | INSULIN-M |

FIGURE 7C (continued)

| Panel No. | Marker 1 | Marker 2 | Marker 3 | Marker 4 | Marker 5 |
|---|---|---|---|---|---|
| 7.5.201 | CRP | ENG | FTH1 | GLUCOSE | TRIG |
| 7.5.202 | CRP | ENG | GLUCOSE | GPT | HBA1C |
| 7.5.203 | CRP | ENG | GLUCOSE | GPT | IGFBP2 |
| 7.5.204 | CRP | ENG | GLUCOSE | GPT | IL2RA |
| 7.5.205 | CRP | ENG | GLUCOSE | GPT | IL2RB |
| 7.5.206 | CRP | ENG | GLUCOSE | GPT | INSULIN-M |
| 7.5.207 | CRP | ENG | GLUCOSE | GPT | LEP |
| 7.5.208 | CRP | ENG | GLUCOSE | GPT | TIMP2 |
| 7.5.209 | CRP | ENG | GLUCOSE | GPT | TRIG |
| 7.5.210 | CRP | ENG | GLUCOSE | HBA1C | HP |
| 7.5.211 | CRP | ENG | GLUCOSE | HBA1C | HSPA1B |
| 7.5.212 | CRP | ENG | GLUCOSE | HBA1C | IGF1R |
| 7.5.213 | CRP | ENG | GLUCOSE | HBA1C | IGFBP1 |
| 7.5.214 | CRP | ENG | GLUCOSE | HBA1C | IL2RA |
| 7.5.215 | CRP | ENG | GLUCOSE | HBA1C | IL2RB |
| 7.5.216 | CRP | ENG | GLUCOSE | HBA1C | INSULIN-M |
| 7.5.217 | CRP | ENG | GLUCOSE | HBA1C | LEP |
| 7.5.218 | CRP | ENG | GLUCOSE | HBA1C | SCp |
| 7.5.219 | CRP | ENG | GLUCOSE | HBA1C | SHBG |
| 7.5.220 | CRP | ENG | GLUCOSE | HBA1C | TIMP2 |
| 7.5.221 | CRP | ENG | GLUCOSE | HBA1C | TRIG |
| 7.5.222 | CRP | ENG | GLUCOSE | HBA1C | VWF |
| 7.5.223 | CRP | ENG | GLUCOSE | HP | INSULIN-M |
| 7.5.224 | CRP | ENG | GLUCOSE | HP | TRIG |
| 7.5.225 | CRP | ENG | GLUCOSE | HSPA1B | IL2RA |
| 7.5.226 | CRP | ENG | GLUCOSE | HSPA1B | INSULIN-M |
| 7.5.227 | CRP | ENG | GLUCOSE | HSPA1B | LEP |
| 7.5.228 | CRP | ENG | GLUCOSE | HSPA1B | TRIG |
| 7.5.229 | CRP | ENG | GLUCOSE | IGF1R | INSULIN-M |
| 7.5.230 | CRP | ENG | GLUCOSE | IGFBP1 | INSULIN-M |
| 7.5.231 | CRP | ENG | GLUCOSE | IGFBP1 | TRIG |
| 7.5.232 | CRP | ENG | GLUCOSE | IGFBP2 | INSULIN-M |
| 7.5.233 | CRP | ENG | GLUCOSE | IGFBP2 | TRIG |
| 7.5.234 | CRP | ENG | GLUCOSE | IL2RA | INSULIN-M |
| 7.5.235 | CRP | ENG | GLUCOSE | IL2RA | TRIG |
| 7.5.236 | CRP | ENG | GLUCOSE | IL2RB | INSULIN-M |
| 7.5.237 | CRP | ENG | GLUCOSE | IL2RB | TRIG |
| 7.5.238 | CRP | ENG | GLUCOSE | IL6R | INSULIN-M |
| 7.5.239 | CRP | ENG | GLUCOSE | IL6R | TRIG |
| 7.5.240 | CRP | ENG | GLUCOSE | INSULIN-M | LEP |

FIGURE 7C (continued)

| Panel No. | Marker 1 | Marker 2 | Marker 3 | Marker 4 | Marker 5 |
|---|---|---|---|---|---|
| 7.5.241 | CRP | ENG | GLUCOSE | INSULIN-M | SCp |
| 7.5.242 | CRP | ENG | GLUCOSE | INSULIN-M | SHBG |
| 7.5.243 | CRP | ENG | GLUCOSE | INSULIN-M | TIMP2 |
| 7.5.244 | CRP | ENG | GLUCOSE | INSULIN-M | TRIG |
| 7.5.245 | CRP | ENG | GLUCOSE | INSULIN-M | VWF |
| 7.5.246 | CRP | ENG | GLUCOSE | LEP | TRIG |
| 7.5.247 | CRP | ENG | GLUCOSE | SCp | TRIG |
| 7.5.248 | CRP | ENG | GLUCOSE | SHBG | TRIG |
| 7.5.249 | CRP | ENG | GLUCOSE | TIMP2 | TRIG |
| 7.5.250 | CRP | ENG | GLUCOSE | TRIG | VWF |
| 7.5.251 | CRP | FGA | GLUCOSE | GPT | HBA1C |
| 7.5.252 | CRP | FGA | GLUCOSE | GPT | IL2RA |
| 7.5.253 | CRP | FGA | GLUCOSE | GPT | INSULIN-M |
| 7.5.254 | CRP | FGA | GLUCOSE | GPT | LEP |
| 7.5.255 | CRP | FGA | GLUCOSE | HBA1C | HP |
| 7.5.256 | CRP | FGA | GLUCOSE | HBA1C | INSULIN-M |
| 7.5.257 | CRP | FGA | GLUCOSE | HBA1C | TRIG |
| 7.5.258 | CRP | FGA | GLUCOSE | HP | INSULIN-M |
| 7.5.259 | CRP | FGA | GLUCOSE | HSPA1B | INSULIN-M |
| 7.5.260 | CRP | FGA | GLUCOSE | INSULIN-M | TRIG |
| 7.5.261 | CRP | FTH1 | GLUCOSE | GPT | HBA1C |
| 7.5.262 | CRP | FTH1 | GLUCOSE | GPT | INSULIN-M |
| 7.5.263 | CRP | FTH1 | GLUCOSE | HBA1C | HP |
| 7.5.264 | CRP | FTH1 | GLUCOSE | HBA1C | INSULIN-M |
| 7.5.265 | CRP | FTH1 | GLUCOSE | HBA1C | LEP |
| 7.5.266 | CRP | FTH1 | GLUCOSE | HBA1C | TRIG |
| 7.5.267 | CRP | FTH1 | GLUCOSE | HP | INSULIN-M |
| 7.5.268 | CRP | FTH1 | GLUCOSE | INSULIN-M | TRIG |
| 7.5.269 | CRP | GLUCOSE | GPT | HBA1C | HP |
| 7.5.270 | CRP | GLUCOSE | GPT | HBA1C | HSPA1B |
| 7.5.271 | CRP | GLUCOSE | GPT | HBA1C | IGF1R |
| 7.5.272 | CRP | GLUCOSE | GPT | HBA1C | IGFBP1 |
| 7.5.273 | CRP | GLUCOSE | GPT | HBA1C | IGFBP2 |
| 7.5.274 | CRP | GLUCOSE | GPT | HBA1C | IL2RA |
| 7.5.275 | CRP | GLUCOSE | GPT | HBA1C | IL2RB |
| 7.5.276 | CRP | GLUCOSE | GPT | HBA1C | IL6R |
| 7.5.277 | CRP | GLUCOSE | GPT | HBA1C | INSULIN-M |
| 7.5.278 | CRP | GLUCOSE | GPT | HBA1C | LEP |
| 7.5.279 | CRP | GLUCOSE | GPT | HBA1C | SCp |
| 7.5.280 | CRP | GLUCOSE | GPT | HBA1C | SHBG |

FIGURE 7C (continued)

| Panel No. | Marker 1 | Marker 2 | Marker 3 | Marker 4 | Marker 5 |
|---|---|---|---|---|---|
| 7.5.281 | CRP | GLUCOSE | GPT | HBA1C | TIMP2 |
| 7.5.282 | CRP | GLUCOSE | GPT | HBA1C | TRIG |
| 7.5.283 | CRP | GLUCOSE | GPT | HBA1C | VWF |
| 7.5.284 | CRP | GLUCOSE | GPT | HP | IGFBP2 |
| 7.5.285 | CRP | GLUCOSE | GPT | HP | IL2RA |
| 7.5.286 | CRP | GLUCOSE | GPT | HP | IL2RB |
| 7.5.287 | CRP | GLUCOSE | GPT | HP | INSULIN-M |
| 7.5.288 | CRP | GLUCOSE | GPT | HP | LEP |
| 7.5.289 | CRP | GLUCOSE | GPT | HP | TRIG |
| 7.5.290 | CRP | GLUCOSE | GPT | HSPA1B | INSULIN-M |
| 7.5.291 | CRP | GLUCOSE | GPT | IGF1R | INSULIN-M |
| 7.5.292 | CRP | GLUCOSE | GPT | IGFBP1 | INSULIN-M |
| 7.5.293 | CRP | GLUCOSE | GPT | IGFBP2 | INSULIN-M |
| 7.5.294 | CRP | GLUCOSE | GPT | IL2RA | INSULIN-M |
| 7.5.295 | CRP | GLUCOSE | GPT | IL2RA | LEP |
| 7.5.296 | CRP | GLUCOSE | GPT | IL2RA | TRIG |
| 7.5.297 | CRP | GLUCOSE | GPT | IL2RB | INSULIN-M |
| 7.5.298 | CRP | GLUCOSE | GPT | IL2RB | LEP |
| 7.5.299 | CRP | GLUCOSE | GPT | IL2RB | TRIG |
| 7.5.300 | CRP | GLUCOSE | GPT | IL6R | INSULIN-M |
| 7.5.301 | CRP | GLUCOSE | GPT | INSULIN-M | LEP |
| 7.5.302 | CRP | GLUCOSE | GPT | INSULIN-M | SCp |
| 7.5.303 | CRP | GLUCOSE | GPT | INSULIN-M | SHBG |
| 7.5.304 | CRP | GLUCOSE | GPT | INSULIN-M | TIMP2 |
| 7.5.305 | CRP | GLUCOSE | GPT | INSULIN-M | TRIG |
| 7.5.306 | CRP | GLUCOSE | GPT | INSULIN-M | VWF |
| 7.5.307 | CRP | GLUCOSE | GPT | LEP | TRIG |
| 7.5.308 | CRP | GLUCOSE | GPT | TIMP2 | TRIG |
| 7.5.309 | CRP | GLUCOSE | HBA1C | HP | HSPA1B |
| 7.5.310 | CRP | GLUCOSE | HBA1C | HP | IGF1R |
| 7.5.311 | CRP | GLUCOSE | HBA1C | HP | IGFBP1 |
| 7.5.312 | CRP | GLUCOSE | HBA1C | HP | IGFBP2 |
| 7.5.313 | CRP | GLUCOSE | HBA1C | HP | IL2RA |
| 7.5.314 | CRP | GLUCOSE | HBA1C | HP | IL2RB |
| 7.5.315 | CRP | GLUCOSE | HBA1C | HP | IL6R |
| 7.5.316 | CRP | GLUCOSE | HBA1C | HP | INSULIN-M |
| 7.5.317 | CRP | GLUCOSE | HBA1C | HP | LEP |
| 7.5.318 | CRP | GLUCOSE | HBA1C | HP | SCp |
| 7.5.319 | CRP | GLUCOSE | HBA1C | HP | SHBG |
| 7.5.320 | CRP | GLUCOSE | HBA1C | HP | TIMP2 |

FIGURE 7C (continued)

| Panel No. | Marker 1 | Marker 2 | Marker 3 | Marker 4 | Marker 5 |
|---|---|---|---|---|---|
| 7.5.321 | CRP | GLUCOSE | HBA1C | HP | TRIG |
| 7.5.322 | CRP | GLUCOSE | HBA1C | HP | VWF |
| 7.5.323 | CRP | GLUCOSE | HBA1C | HSPA1B | IL2RA |
| 7.5.324 | CRP | GLUCOSE | HBA1C | HSPA1B | IL2RB |
| 7.5.325 | CRP | GLUCOSE | HBA1C | HSPA1B | INSULIN-M |
| 7.5.326 | CRP | GLUCOSE | HBA1C | HSPA1B | LEP |
| 7.5.327 | CRP | GLUCOSE | HBA1C | HSPA1B | TIMP2 |
| 7.5.328 | CRP | GLUCOSE | HBA1C | HSPA1B | TRIG |
| 7.5.329 | CRP | GLUCOSE | HBA1C | IGF1R | INSULIN-M |
| 7.5.330 | CRP | GLUCOSE | HBA1C | IGF1R | LEP |
| 7.5.331 | CRP | GLUCOSE | HBA1C | IGF1R | TRIG |
| 7.5.332 | CRP | GLUCOSE | HBA1C | IGFBP1 | INSULIN-M |
| 7.5.333 | CRP | GLUCOSE | HBA1C | IGFBP1 | TRIG |
| 7.5.334 | CRP | GLUCOSE | HBA1C | IGFBP2 | INSULIN-M |
| 7.5.335 | CRP | GLUCOSE | HBA1C | IGFBP2 | TRIG |
| 7.5.336 | CRP | GLUCOSE | HBA1C | IL2RA | INSULIN-M |
| 7.5.337 | CRP | GLUCOSE | HBA1C | IL2RA | TIMP2 |
| 7.5.338 | CRP | GLUCOSE | HBA1C | IL2RA | TRIG |
| 7.5.339 | CRP | GLUCOSE | HBA1C | IL2RB | INSULIN-M |
| 7.5.340 | CRP | GLUCOSE | HBA1C | IL2RB | LEP |
| 7.5.341 | CRP | GLUCOSE | HBA1C | IL2RB | TRIG |
| 7.5.342 | CRP | GLUCOSE | HBA1C | IL6R | INSULIN-M |
| 7.5.343 | CRP | GLUCOSE | HBA1C | IL6R | LEP |
| 7.5.344 | CRP | GLUCOSE | HBA1C | IL6R | TIMP2 |
| 7.5.345 | CRP | GLUCOSE | HBA1C | IL6R | TRIG |
| 7.5.346 | CRP | GLUCOSE | HBA1C | INSULIN-M | LEP |
| 7.5.347 | CRP | GLUCOSE | HBA1C | INSULIN-M | SCp |
| 7.5.348 | CRP | GLUCOSE | HBA1C | INSULIN-M | SHBG |
| 7.5.349 | CRP | GLUCOSE | HBA1C | INSULIN-M | TIMP2 |
| 7.5.350 | CRP | GLUCOSE | HBA1C | INSULIN-M | TRIG |
| 7.5.351 | CRP | GLUCOSE | HBA1C | INSULIN-M | VWF |
| 7.5.352 | CRP | GLUCOSE | HBA1C | LEP | TRIG |
| 7.5.353 | CRP | GLUCOSE | HBA1C | SCp | TRIG |
| 7.5.354 | CRP | GLUCOSE | HBA1C | SHBG | TRIG |
| 7.5.355 | CRP | GLUCOSE | HBA1C | TIMP2 | TRIG |
| 7.5.356 | CRP | GLUCOSE | HBA1C | TRIG | VWF |
| 7.5.357 | CRP | GLUCOSE | HP | HSPA1B | INSULIN-M |
| 7.5.358 | CRP | GLUCOSE | HP | HSPA1B | TRIG |
| 7.5.359 | CRP | GLUCOSE | HP | IGFBP2 | INSULIN-M |
| 7.5.360 | CRP | GLUCOSE | HP | IGFBP2 | TRIG |

FIGURE 7C (continued)

| Panel No. | Marker 1 | Marker 2 | Marker 3 | Marker 4 | Marker 5 |
|---|---|---|---|---|---|
| 7.5.361 | CRP | GLUCOSE | HP | IL2RA | INSULIN-M |
| 7.5.362 | CRP | GLUCOSE | HP | IL2RB | INSULIN-M |
| 7.5.363 | CRP | GLUCOSE | HP | IL2RB | TRIG |
| 7.5.364 | CRP | GLUCOSE | HP | IL6R | INSULIN-M |
| 7.5.365 | CRP | GLUCOSE | HP | INSULIN-M | LEP |
| 7.5.366 | CRP | GLUCOSE | HP | INSULIN-M | SCp |
| 7.5.367 | CRP | GLUCOSE | HP | INSULIN-M | SHBG |
| 7.5.368 | CRP | GLUCOSE | HP | INSULIN-M | TIMP2 |
| 7.5.369 | CRP | GLUCOSE | HP | INSULIN-M | TRIG |
| 7.5.370 | CRP | GLUCOSE | HP | INSULIN-M | VWF |
| 7.5.371 | CRP | GLUCOSE | HP | LEP | TRIG |
| 7.5.372 | CRP | GLUCOSE | HP | SHBG | TRIG |
| 7.5.373 | CRP | GLUCOSE | HP | TIMP2 | TRIG |
| 7.5.374 | CRP | GLUCOSE | HP | TRIG | VWF |
| 7.5.375 | CRP | GLUCOSE | HSPA1B | IGFBP2 | INSULIN-M |
| 7.5.376 | CRP | GLUCOSE | HSPA1B | IL2RA | INSULIN-M |
| 7.5.377 | CRP | GLUCOSE | HSPA1B | IL2RA | LEP |
| 7.5.378 | CRP | GLUCOSE | HSPA1B | IL2RA | TRIG |
| 7.5.379 | CRP | GLUCOSE | HSPA1B | IL2RB | INSULIN-M |
| 7.5.380 | CRP | GLUCOSE | HSPA1B | INSULIN-M | LEP |
| 7.5.381 | CRP | GLUCOSE | HSPA1B | INSULIN-M | TIMP2 |
| 7.5.382 | CRP | GLUCOSE | HSPA1B | INSULIN-M | TRIG |
| 7.5.383 | CRP | GLUCOSE | HSPA1B | LEP | TRIG |
| 7.5.384 | CRP | GLUCOSE | HSPA1B | TIMP2 | TRIG |
| 7.5.385 | CRP | GLUCOSE | IGFBP2 | INSULIN-M | TRIG |
| 7.5.386 | CRP | GLUCOSE | IGFBP2 | LEP | TRIG |
| 7.5.387 | CRP | GLUCOSE | IL2RA | INSULIN-M | TRIG |
| 7.5.388 | CRP | GLUCOSE | IL2RA | LEP | TRIG |
| 7.5.389 | CRP | GLUCOSE | IL2RA | TIMP2 | TRIG |
| 7.5.390 | CRP | GLUCOSE | IL2RB | LEP | TRIG |
| 7.5.391 | CRP | GLUCOSE | IL6R | INSULIN-M | TRIG |
| 7.5.392 | CRP | GLUCOSE | INSULIN-M | LEP | TRIG |
| 7.5.393 | CRP | GLUCOSE | INSULIN-M | SCp | TRIG |
| 7.5.394 | CRP | GLUCOSE | INSULIN-M | SHBG | TRIG |
| 7.5.395 | CRP | GLUCOSE | INSULIN-M | TIMP2 | TRIG |
| 7.5.396 | CRP | GLUCOSE | INSULIN-M | TRIG | VWF |
| 7.5.397 | CRP | GLUCOSE | LEP | TIMP2 | TRIG |
| 7.5.398 | GLUCOSE | GPT | HBA1C | INSULIN-M | LEP |
| 7.5.399 | GLUCOSE | HBA1C | HSPA1B | IGFBP2 | INSULIN-M |
| 7.5.400 | GLUCOSE | HBA1C | HSPA1B | INSULIN-M | LEP |

FIGURE 7D

| Panel No. | Marker 1 | Marker 2 | Marker 3 | Marker 4 | Marker 5 | Marker 6 |
|---|---|---|---|---|---|---|
| 7.6.1 | ADIPOQ | CCL2 | CRP | EGF | GLUCOSE | HBA1C |
| 7.6.2 | ADIPOQ | CCL2 | CRP | ENG | GLUCOSE | GPT |
| 7.6.3 | ADIPOQ | CCL2 | CRP | ENG | GLUCOSE | HBA1C |
| 7.6.4 | ADIPOQ | CCL2 | CRP | ENG | GLUCOSE | LEP |
| 7.6.5 | ADIPOQ | CCL2 | CRP | GLUCOSE | GPT | HBA1C |
| 7.6.6 | ADIPOQ | CCL2 | CRP | GLUCOSE | GPT | HP |
| 7.6.7 | ADIPOQ | CCL2 | CRP | GLUCOSE | GPT | INSULIN-M |
| 7.6.8 | ADIPOQ | CCL2 | CRP | GLUCOSE | GPT | LEP |
| 7.6.9 | ADIPOQ | CCL2 | CRP | GLUCOSE | HBA1C | HP |
| 7.6.10 | ADIPOQ | CCL2 | CRP | GLUCOSE | HBA1C | HSPA1B |
| 7.6.11 | ADIPOQ | CCL2 | CRP | GLUCOSE | HBA1C | INSULIN-M |
| 7.6.12 | ADIPOQ | CCL2 | CRP | GLUCOSE | HBA1C | LEP |
| 7.6.13 | ADIPOQ | CCL2 | CRP | GLUCOSE | HBA1C | TIMP2 |
| 7.6.14 | ADIPOQ | CCL2 | CRP | GLUCOSE | HBA1C | TRIG |
| 7.6.15 | ADIPOQ | CCL2 | CRP | GLUCOSE | HP | HSPA1B |
| 7.6.16 | ADIPOQ | CCL2 | CRP | GLUCOSE | HP | LEP |
| 7.6.17 | ADIPOQ | CCL2 | CRP | GLUCOSE | HSPA1B | INSULIN-M |
| 7.6.18 | ADIPOQ | CCL2 | CRP | GLUCOSE | HSPA1B | LEP |
| 7.6.19 | ADIPOQ | CD40 | CRP | GLUCOSE | GPT | LEP |
| 7.6.20 | ADIPOQ | CD40 | CRP | GLUCOSE | HBA1C | INSULIN-M |
| 7.6.21 | ADIPOQ | CD40 | CRP | GLUCOSE | HSPA1B | LEP |
| 7.6.22 | ADIPOQ | CRP | EGF | GLUCOSE | GPT | HBA1C |
| 7.6.23 | ADIPOQ | CRP | EGF | GLUCOSE | GPT | LEP |
| 7.6.24 | ADIPOQ | CRP | EGF | GLUCOSE | HBA1C | INSULIN-M |
| 7.6.25 | ADIPOQ | CRP | EGF | GLUCOSE | HBA1C | LEP |
| 7.6.26 | ADIPOQ | CRP | EGF | GLUCOSE | HBA1C | TRIG |
| 7.6.27 | ADIPOQ | CRP | EGF | GLUCOSE | HSPA1B | LEP |
| 7.6.28 | ADIPOQ | CRP | ENG | GLUCOSE | GPT | HBA1C |
| 7.6.29 | ADIPOQ | CRP | ENG | GLUCOSE | GPT | INSULIN-M |
| 7.6.30 | ADIPOQ | CRP | ENG | GLUCOSE | GPT | LEP |
| 7.6.31 | ADIPOQ | CRP | ENG | GLUCOSE | HBA1C | HP |
| 7.6.32 | ADIPOQ | CRP | ENG | GLUCOSE | HBA1C | INSULIN-M |
| 7.6.33 | ADIPOQ | CRP | ENG | GLUCOSE | HBA1C | LEP |
| 7.6.34 | ADIPOQ | CRP | ENG | GLUCOSE | HBA1C | TRIG |
| 7.6.35 | ADIPOQ | CRP | ENG | GLUCOSE | HSPA1B | INSULIN-M |
| 7.6.36 | ADIPOQ | CRP | ENG | GLUCOSE | HSPA1B | LEP |
| 7.6.37 | ADIPOQ | CRP | ENG | GLUCOSE | LEP | TRIG |
| 7.6.38 | ADIPOQ | CRP | FGA | GLUCOSE | GPT | LEP |
| 7.6.39 | ADIPOQ | CRP | FGA | GLUCOSE | HBA1C | INSULIN-M |
| 7.6.40 | ADIPOQ | CRP | FGA | GLUCOSE | HBA1C | LEP |

FIGURE 7D (continued)

| Panel No. | Marker 1 | Marker 2 | Marker 3 | Marker 4 | Marker 5 | Marker 6 |
|---|---|---|---|---|---|---|
| 7.6.41 | ADIPOQ | CRP | FGA | GLUCOSE | HSPA1B | LEP |
| 7.6.42 | ADIPOQ | CRP | FTH1 | GLUCOSE | GPT | LEP |
| 7.6.43 | ADIPOQ | CRP | FTH1 | GLUCOSE | HBA1C | INSULIN-M |
| 7.6.44 | ADIPOQ | CRP | FTH1 | GLUCOSE | HBA1C | LEP |
| 7.6.45 | ADIPOQ | CRP | FTH1 | GLUCOSE | HSPA1B | LEP |
| 7.6.46 | ADIPOQ | CRP | GLUCOSE | GPT | HBA1C | HP |
| 7.6.47 | ADIPOQ | CRP | GLUCOSE | GPT | HBA1C | HSPA1B |
| 7.6.48 | ADIPOQ | CRP | GLUCOSE | GPT | HBA1C | IGF1R |
| 7.6.49 | ADIPOQ | CRP | GLUCOSE | GPT | HBA1C | IGFBP2 |
| 7.6.50 | ADIPOQ | CRP | GLUCOSE | GPT | HBA1C | IL2RB |
| 7.6.51 | ADIPOQ | CRP | GLUCOSE | GPT | HBA1C | INSULIN-M |
| 7.6.52 | ADIPOQ | CRP | GLUCOSE | GPT | HBA1C | LEP |
| 7.6.53 | ADIPOQ | CRP | GLUCOSE | GPT | HBA1C | TIMP2 |
| 7.6.54 | ADIPOQ | CRP | GLUCOSE | GPT | HBA1C | TRIG |
| 7.6.55 | ADIPOQ | CRP | GLUCOSE | GPT | HP | IGFBP2 |
| 7.6.56 | ADIPOQ | CRP | GLUCOSE | GPT | HP | INSULIN-M |
| 7.6.57 | ADIPOQ | CRP | GLUCOSE | GPT | HP | LEP |
| 7.6.58 | ADIPOQ | CRP | GLUCOSE | GPT | HSPA1B | LEP |
| 7.6.59 | ADIPOQ | CRP | GLUCOSE | GPT | IGF1R | LEP |
| 7.6.60 | ADIPOQ | CRP | GLUCOSE | GPT | IGFBP1 | LEP |
| 7.6.61 | ADIPOQ | CRP | GLUCOSE | GPT | IGFBP2 | INSULIN-M |
| 7.6.62 | ADIPOQ | CRP | GLUCOSE | GPT | IGFBP2 | LEP |
| 7.6.63 | ADIPOQ | CRP | GLUCOSE | GPT | IL2RA | LEP |
| 7.6.64 | ADIPOQ | CRP | GLUCOSE | GPT | IL2RB | LEP |
| 7.6.65 | ADIPOQ | CRP | GLUCOSE | GPT | IL6R | LEP |
| 7.6.66 | ADIPOQ | CRP | GLUCOSE | GPT | INSULIN-M | LEP |
| 7.6.67 | ADIPOQ | CRP | GLUCOSE | GPT | LEP | SCp |
| 7.6.68 | ADIPOQ | CRP | GLUCOSE | GPT | LEP | SHBG |
| 7.6.69 | ADIPOQ | CRP | GLUCOSE | GPT | LEP | TIMP2 |
| 7.6.70 | ADIPOQ | CRP | GLUCOSE | GPT | LEP | TRIG |
| 7.6.71 | ADIPOQ | CRP | GLUCOSE | GPT | LEP | VWF |
| 7.6.72 | ADIPOQ | CRP | GLUCOSE | HBA1C | HP | HSPA1B |
| 7.6.73 | ADIPOQ | CRP | GLUCOSE | HBA1C | HP | IGFBP2 |
| 7.6.74 | ADIPOQ | CRP | GLUCOSE | HBA1C | HP | INSULIN-M |
| 7.6.75 | ADIPOQ | CRP | GLUCOSE | HBA1C | HP | LEP |
| 7.6.76 | ADIPOQ | CRP | GLUCOSE | HBA1C | HP | TIMP2 |
| 7.6.77 | ADIPOQ | CRP | GLUCOSE | HBA1C | HP | TRIG |
| 7.6.78 | ADIPOQ | CRP | GLUCOSE | HBA1C | HSPA1B | INSULIN-M |
| 7.6.79 | ADIPOQ | CRP | GLUCOSE | HBA1C | HSPA1B | LEP |
| 7.6.80 | ADIPOQ | CRP | GLUCOSE | HBA1C | HSPA1B | TRIG |

FIGURE 7D (continued)

| Panel No. | Marker 1 | Marker 2 | Marker 3 | Marker 4 | Marker 5 | Marker 6 |
|---|---|---|---|---|---|---|
| 7.6.81 | ADIPOQ | CRP | GLUCOSE | HBA1C | IGF1R | LEP |
| 7.6.82 | ADIPOQ | CRP | GLUCOSE | HBA1C | IGFBP1 | INSULIN-M |
| 7.6.83 | ADIPOQ | CRP | GLUCOSE | HBA1C | IGFBP2 | INSULIN-M |
| 7.6.84 | ADIPOQ | CRP | GLUCOSE | HBA1C | IGFBP2 | TIMP2 |
| 7.6.85 | ADIPOQ | CRP | GLUCOSE | HBA1C | IL2RB | INSULIN-M |
| 7.6.86 | ADIPOQ | CRP | GLUCOSE | HBA1C | IL6R | INSULIN-M |
| 7.6.87 | ADIPOQ | CRP | GLUCOSE | HBA1C | IL6R | LEP |
| 7.6.88 | ADIPOQ | CRP | GLUCOSE | HBA1C | INSULIN-M | LEP |
| 7.6.89 | ADIPOQ | CRP | GLUCOSE | HBA1C | INSULIN-M | SCp |
| 7.6.90 | ADIPOQ | CRP | GLUCOSE | HBA1C | INSULIN-M | SHBG |
| 7.6.91 | ADIPOQ | CRP | GLUCOSE | HBA1C | INSULIN-M | TIMP2 |
| 7.6.92 | ADIPOQ | CRP | GLUCOSE | HBA1C | INSULIN-M | TRIG |
| 7.6.93 | ADIPOQ | CRP | GLUCOSE | HBA1C | INSULIN-M | VWF |
| 7.6.94 | ADIPOQ | CRP | GLUCOSE | HBA1C | LEP | TIMP2 |
| 7.6.95 | ADIPOQ | CRP | GLUCOSE | HBA1C | LEP | TRIG |
| 7.6.96 | ADIPOQ | CRP | GLUCOSE | HBA1C | TIMP2 | TRIG |
| 7.6.97 | ADIPOQ | CRP | GLUCOSE | HP | HSPA1B | INSULIN-M |
| 7.6.98 | ADIPOQ | CRP | GLUCOSE | HP | HSPA1B | LEP |
| 7.6.99 | ADIPOQ | CRP | GLUCOSE | HP | LEP | TRIG |
| 7.6.100 | ADIPOQ | CRP | GLUCOSE | HSPA1B | IGF1R | LEP |
| 7.6.101 | ADIPOQ | CRP | GLUCOSE | HSPA1B | IGFBP1 | LEP |
| 7.6.102 | ADIPOQ | CRP | GLUCOSE | HSPA1B | IGFBP2 | LEP |
| 7.6.103 | ADIPOQ | CRP | GLUCOSE | HSPA1B | IL2RA | LEP |
| 7.6.104 | ADIPOQ | CRP | GLUCOSE | HSPA1B | IL2RB | LEP |
| 7.6.105 | ADIPOQ | CRP | GLUCOSE | HSPA1B | IL6R | LEP |
| 7.6.106 | ADIPOQ | CRP | GLUCOSE | HSPA1B | INSULIN-M | LEP |
| 7.6.107 | ADIPOQ | CRP | GLUCOSE | HSPA1B | LEP | SCp |
| 7.6.108 | ADIPOQ | CRP | GLUCOSE | HSPA1B | LEP | SHBG |
| 7.6.109 | ADIPOQ | CRP | GLUCOSE | HSPA1B | LEP | TIMP2 |
| 7.6.110 | ADIPOQ | CRP | GLUCOSE | HSPA1B | LEP | TRIG |
| 7.6.111 | ADIPOQ | CRP | GLUCOSE | HSPA1B | LEP | VWF |
| 7.6.112 | ADIPOQ | CRP | GLUCOSE | LEP | SCp | TRIG |
| 7.6.113 | ADIPOQ | CRP | GLUCOSE | LEP | TRIG | VWF |
| 7.6.114 | CCL2 | CD40 | CRP | GLUCOSE | HBA1C | HP |
| 7.6.115 | CCL2 | CD40 | CRP | GLUCOSE | HBA1C | INSULIN-M |
| 7.6.116 | CCL2 | CRP | EGF | GLUCOSE | GPT | HBA1C |
| 7.6.117 | CCL2 | CRP | EGF | GLUCOSE | HBA1C | HP |
| 7.6.118 | CCL2 | CRP | EGF | GLUCOSE | HBA1C | HSPA1B |
| 7.6.119 | CCL2 | CRP | EGF | GLUCOSE | HBA1C | INSULIN-M |
| 7.6.120 | CCL2 | CRP | EGF | GLUCOSE | HBA1C | TRIG |

FIGURE 7D (continued)

| Panel No. | Marker 1 | Marker 2 | Marker 3 | Marker 4 | Marker 5 | Marker 6 |
|---|---|---|---|---|---|---|
| 7.6.121 | CCL2 | CRP | EGF | GLUCOSE | HSPA1B | INSULIN-M |
| 7.6.122 | CCL2 | CRP | ENG | FTH1 | GLUCOSE | HBA1C |
| 7.6.123 | CCL2 | CRP | ENG | GLUCOSE | GPT | HBA1C |
| 7.6.124 | CCL2 | CRP | ENG | GLUCOSE | GPT | HP |
| 7.6.125 | CCL2 | CRP | ENG | GLUCOSE | GPT | INSULIN-M |
| 7.6.126 | CCL2 | CRP | ENG | GLUCOSE | HBA1C | HP |
| 7.6.127 | CCL2 | CRP | ENG | GLUCOSE | HBA1C | HSPA1B |
| 7.6.128 | CCL2 | CRP | ENG | GLUCOSE | HBA1C | INSULIN-M |
| 7.6.129 | CCL2 | CRP | ENG | GLUCOSE | HBA1C | LEP |
| 7.6.130 | CCL2 | CRP | ENG | GLUCOSE | HBA1C | TRIG |
| 7.6.131 | CCL2 | CRP | ENG | GLUCOSE | HSPA1B | INSULIN-M |
| 7.6.132 | CCL2 | CRP | FGA | GLUCOSE | GPT | HBA1C |
| 7.6.133 | CCL2 | CRP | FGA | GLUCOSE | HBA1C | HP |
| 7.6.134 | CCL2 | CRP | FGA | GLUCOSE | HBA1C | INSULIN-M |
| 7.6.135 | CCL2 | CRP | FGA | GLUCOSE | HBA1C | TRIG |
| 7.6.136 | CCL2 | CRP | FTH1 | GLUCOSE | GPT | HBA1C |
| 7.6.137 | CCL2 | CRP | FTH1 | GLUCOSE | HBA1C | HP |
| 7.6.138 | CCL2 | CRP | FTH1 | GLUCOSE | HBA1C | INSULIN-M |
| 7.6.139 | CCL2 | CRP | GLUCOSE | GPT | HBA1C | HP |
| 7.6.140 | CCL2 | CRP | GLUCOSE | GPT | HBA1C | IGFBP1 |
| 7.6.141 | CCL2 | CRP | GLUCOSE | GPT | HBA1C | IGFBP2 |
| 7.6.142 | CCL2 | CRP | GLUCOSE | GPT | HBA1C | IL2RB |
| 7.6.143 | CCL2 | CRP | GLUCOSE | GPT | HBA1C | IL6R |
| 7.6.144 | CCL2 | CRP | GLUCOSE | GPT | HBA1C | INSULIN-M |
| 7.6.145 | CCL2 | CRP | GLUCOSE | GPT | HBA1C | LEP |
| 7.6.146 | CCL2 | CRP | GLUCOSE | GPT | HBA1C | SHBG |
| 7.6.147 | CCL2 | CRP | GLUCOSE | GPT | HBA1C | TIMP2 |
| 7.6.148 | CCL2 | CRP | GLUCOSE | GPT | HBA1C | TRIG |
| 7.6.149 | CCL2 | CRP | GLUCOSE | GPT | HBA1C | VWF |
| 7.6.150 | CCL2 | CRP | GLUCOSE | GPT | HP | IL2RA |
| 7.6.151 | CCL2 | CRP | GLUCOSE | GPT | HP | INSULIN-M |
| 7.6.152 | CCL2 | CRP | GLUCOSE | GPT | HP | LEP |
| 7.6.153 | CCL2 | CRP | GLUCOSE | GPT | HP | SHBG |
| 7.6.154 | CCL2 | CRP | GLUCOSE | GPT | HP | TRIG |
| 7.6.155 | CCL2 | CRP | GLUCOSE | GPT | HSPA1B | INSULIN-M |
| 7.6.156 | CCL2 | CRP | GLUCOSE | GPT | IGFBP2 | INSULIN-M |
| 7.6.157 | CCL2 | CRP | GLUCOSE | HBA1C | HP | HSPA1B |
| 7.6.158 | CCL2 | CRP | GLUCOSE | HBA1C | HP | IGFBP1 |
| 7.6.159 | CCL2 | CRP | GLUCOSE | HBA1C | HP | IGFBP2 |
| 7.6.160 | CCL2 | CRP | GLUCOSE | HBA1C | HP | IL2RB |

FIGURE 7D (continued)

| Panel No. | Marker 1 | Marker 2 | Marker 3 | Marker 4 | Marker 5 | Marker 6 |
|---|---|---|---|---|---|---|
| 7.6.161 | CCL2 | CRP | GLUCOSE | HBA1C | HP | IL6R |
| 7.6.162 | CCL2 | CRP | GLUCOSE | HBA1C | HP | INSULIN-M |
| 7.6.163 | CCL2 | CRP | GLUCOSE | HBA1C | HP | LEP |
| 7.6.164 | CCL2 | CRP | GLUCOSE | HBA1C | HP | SCp |
| 7.6.165 | CCL2 | CRP | GLUCOSE | HBA1C | HP | SHBG |
| 7.6.166 | CCL2 | CRP | GLUCOSE | HBA1C | HP | TIMP2 |
| 7.6.167 | CCL2 | CRP | GLUCOSE | HBA1C | HP | TRIG |
| 7.6.168 | CCL2 | CRP | GLUCOSE | HBA1C | HSPA1B | INSULIN-M |
| 7.6.169 | CCL2 | CRP | GLUCOSE | HBA1C | HSPA1B | TRIG |
| 7.6.170 | CCL2 | CRP | GLUCOSE | HBA1C | IGF1R | INSULIN-M |
| 7.6.171 | CCL2 | CRP | GLUCOSE | HBA1C | IGFBP1 | INSULIN-M |
| 7.6.172 | CCL2 | CRP | GLUCOSE | HBA1C | IGFBP2 | INSULIN-M |
| 7.6.173 | CCL2 | CRP | GLUCOSE | HBA1C | IL2RA | INSULIN-M |
| 7.6.174 | CCL2 | CRP | GLUCOSE | HBA1C | IL2RB | INSULIN-M |
| 7.6.175 | CCL2 | CRP | GLUCOSE | HBA1C | IL2RB | TRIG |
| 7.6.176 | CCL2 | CRP | GLUCOSE | HBA1C | IL6R | INSULIN-M |
| 7.6.177 | CCL2 | CRP | GLUCOSE | HBA1C | IL6R | TRIG |
| 7.6.178 | CCL2 | CRP | GLUCOSE | HBA1C | INSULIN-M | LEP |
| 7.6.179 | CCL2 | CRP | GLUCOSE | HBA1C | INSULIN-M | SCp |
| 7.6.180 | CCL2 | CRP | GLUCOSE | HBA1C | INSULIN-M | SHBG |
| 7.6.181 | CCL2 | CRP | GLUCOSE | HBA1C | INSULIN-M | TIMP2 |
| 7.6.182 | CCL2 | CRP | GLUCOSE | HBA1C | INSULIN-M | TRIG |
| 7.6.183 | CCL2 | CRP | GLUCOSE | HBA1C | INSULIN-M | VWF |
| 7.6.184 | CCL2 | CRP | GLUCOSE | HBA1C | LEP | TRIG |
| 7.6.185 | CCL2 | CRP | GLUCOSE | HBA1C | TIMP2 | TRIG |
| 7.6.186 | CCL2 | CRP | GLUCOSE | HP | HSPA1B | INSULIN-M |
| 7.6.187 | CCL2 | CRP | GLUCOSE | HP | HSPA1B | LEP |
| 7.6.188 | CCL2 | CRP | GLUCOSE | HP | HSPA1B | TRIG |
| 7.6.189 | CCL2 | CRP | GLUCOSE | HP | IGFBP2 | INSULIN-M |
| 7.6.190 | CCL2 | CRP | GLUCOSE | HP | INSULIN-M | SCp |
| 7.6.191 | CCL2 | CRP | GLUCOSE | HP | INSULIN-M | SHBG |
| 7.6.192 | CCL2 | CRP | GLUCOSE | HP | INSULIN-M | TIMP2 |
| 7.6.193 | CCL2 | CRP | GLUCOSE | HSPA1B | IL2RA | INSULIN-M |
| 7.6.194 | CCL2 | CRP | GLUCOSE | HSPA1B | INSULIN-M | TIMP2 |
| 7.6.195 | CCL2 | CRP | GLUCOSE | HSPA1B | TIMP2 | TRIG |
| 7.6.196 | CD40 | CRP | ENG | GLUCOSE | GPT | INSULIN-M |
| 7.6.197 | CD40 | CRP | ENG | GLUCOSE | HBA1C | INSULIN-M |
| 7.6.198 | CD40 | CRP | ENG | GLUCOSE | HBA1C | TRIG |
| 7.6.199 | CD40 | CRP | GLUCOSE | GPT | HBA1C | HP |
| 7.6.200 | CD40 | CRP | GLUCOSE | GPT | HBA1C | INSULIN-M |

FIGURE 7D (continued)

| Panel No. | Marker 1 | Marker 2 | Marker 3 | Marker 4 | Marker 5 | Marker 6 |
|---|---|---|---|---|---|---|
| 7.6.201 | CD40 | CRP | GLUCOSE | GPT | HP | INSULIN-M |
| 7.6.202 | CD40 | CRP | GLUCOSE | HBA1C | HP | INSULIN-M |
| 7.6.203 | CD40 | CRP | GLUCOSE | HBA1C | HP | TRIG |
| 7.6.204 | CD40 | CRP | GLUCOSE | HBA1C | INSULIN-M | TRIG |
| 7.6.205 | CD40 | CRP | GLUCOSE | HBA1C | TIMP2 | TRIG |
| 7.6.206 | CRP | EGF | ENG | GLUCOSE | GPT | INSULIN-M |
| 7.6.207 | CRP | EGF | ENG | GLUCOSE | HBA1C | INSULIN-M |
| 7.6.208 | CRP | EGF | ENG | GLUCOSE | HBA1C | TRIG |
| 7.6.209 | CRP | EGF | FGA | GLUCOSE | HBA1C | INSULIN-M |
| 7.6.210 | CRP | EGF | FTH1 | GLUCOSE | HBA1C | INSULIN-M |
| 7.6.211 | CRP | EGF | GLUCOSE | GPT | HBA1C | HP |
| 7.6.212 | CRP | EGF | GLUCOSE | GPT | HBA1C | INSULIN-M |
| 7.6.213 | CRP | EGF | GLUCOSE | GPT | HBA1C | LEP |
| 7.6.214 | CRP | EGF | GLUCOSE | GPT | HBA1C | TRIG |
| 7.6.215 | CRP | EGF | GLUCOSE | HBA1C | HP | INSULIN-M |
| 7.6.216 | CRP | EGF | GLUCOSE | HBA1C | HP | TRIG |
| 7.6.217 | CRP | EGF | GLUCOSE | HBA1C | HSPA1B | INSULIN-M |
| 7.6.218 | CRP | EGF | GLUCOSE | HBA1C | HSPA1B | LEP |
| 7.6.219 | CRP | EGF | GLUCOSE | HBA1C | HSPA1B | TRIG |
| 7.6.220 | CRP | EGF | GLUCOSE | HBA1C | IGFBP2 | INSULIN-M |
| 7.6.221 | CRP | EGF | GLUCOSE | HBA1C | IL2RB | TRIG |
| 7.6.222 | CRP | EGF | GLUCOSE | HBA1C | INSULIN-M | SHBG |
| 7.6.223 | CRP | EGF | GLUCOSE | HBA1C | INSULIN-M | TIMP2 |
| 7.6.224 | CRP | EGF | GLUCOSE | HBA1C | INSULIN-M | TRIG |
| 7.6.225 | CRP | EGF | GLUCOSE | HBA1C | LEP | TRIG |
| 7.6.226 | CRP | EGF | GLUCOSE | HBA1C | SHBG | TRIG |
| 7.6.227 | CRP | EGF | GLUCOSE | HBA1C | TIMP2 | TRIG |
| 7.6.228 | CRP | EGF | GLUCOSE | HSPA1B | TIMP2 | TRIG |
| 7.6.229 | CRP | ENG | FGA | GLUCOSE | GPT | INSULIN-M |
| 7.6.230 | CRP | ENG | FGA | GLUCOSE | HBA1C | INSULIN-M |
| 7.6.231 | CRP | ENG | FGA | GLUCOSE | HBA1C | TRIG |
| 7.6.232 | CRP | ENG | FTH1 | GLUCOSE | GPT | HBA1C |
| 7.6.233 | CRP | ENG | FTH1 | GLUCOSE | GPT | INSULIN-M |
| 7.6.234 | CRP | ENG | FTH1 | GLUCOSE | HBA1C | INSULIN-M |
| 7.6.235 | CRP | ENG | FTH1 | GLUCOSE | HBA1C | LEP |
| 7.6.236 | CRP | ENG | FTH1 | GLUCOSE | HBA1C | TRIG |
| 7.6.237 | CRP | ENG | FTH1 | GLUCOSE | HSPA1B | INSULIN-M |
| 7.6.238 | CRP | ENG | GLUCOSE | GPT | HBA1C | HP |
| 7.6.239 | CRP | ENG | GLUCOSE | GPT | HBA1C | IGF1R |
| 7.6.240 | CRP | ENG | GLUCOSE | GPT | HBA1C | IGFBP2 |

FIGURE 7D (continued)

| Panel No. | Marker 1 | Marker 2 | Marker 3 | Marker 4 | Marker 5 | Marker 6 |
|---|---|---|---|---|---|---|
| 7.6.241 | CRP | ENG | GLUCOSE | GPT | HBA1C | IL2RB |
| 7.6.242 | CRP | ENG | GLUCOSE | GPT | HBA1C | INSULIN-M |
| 7.6.243 | CRP | ENG | GLUCOSE | GPT | HBA1C | LEP |
| 7.6.244 | CRP | ENG | GLUCOSE | GPT | HBA1C | TIMP2 |
| 7.6.245 | CRP | ENG | GLUCOSE | GPT | HBA1C | TRIG |
| 7.6.246 | CRP | ENG | GLUCOSE | GPT | HP | INSULIN-M |
| 7.6.247 | CRP | ENG | GLUCOSE | GPT | HSPA1B | INSULIN-M |
| 7.6.248 | CRP | ENG | GLUCOSE | GPT | IGFBP1 | INSULIN-M |
| 7.6.249 | CRP | ENG | GLUCOSE | GPT | IGFBP2 | INSULIN-M |
| 7.6.250 | CRP | ENG | GLUCOSE | GPT | IL2RA | INSULIN-M |
| 7.6.251 | CRP | ENG | GLUCOSE | GPT | IL6R | INSULIN-M |
| 7.6.252 | CRP | ENG | GLUCOSE | GPT | INSULIN-M | LEP |
| 7.6.253 | CRP | ENG | GLUCOSE | GPT | INSULIN-M | SCp |
| 7.6.254 | CRP | ENG | GLUCOSE | GPT | INSULIN-M | SHBG |
| 7.6.255 | CRP | ENG | GLUCOSE | GPT | INSULIN-M | TIMP2 |
| 7.6.256 | CRP | ENG | GLUCOSE | GPT | INSULIN-M | TRIG |
| 7.6.257 | CRP | ENG | GLUCOSE | GPT | INSULIN-M | VWF |
| 7.6.258 | CRP | ENG | GLUCOSE | GPT | LEP | TRIG |
| 7.6.259 | CRP | ENG | GLUCOSE | HBA1C | HP | INSULIN-M |
| 7.6.260 | CRP | ENG | GLUCOSE | HBA1C | HP | TRIG |
| 7.6.261 | CRP | ENG | GLUCOSE | HBA1C | HSPA1B | INSULIN-M |
| 7.6.262 | CRP | ENG | GLUCOSE | HBA1C | HSPA1B | TRIG |
| 7.6.263 | CRP | ENG | GLUCOSE | HBA1C | IGF1R | INSULIN-M |
| 7.6.264 | CRP | ENG | GLUCOSE | HBA1C | IGF1R | TRIG |
| 7.6.265 | CRP | ENG | GLUCOSE | HBA1C | IGFBP1 | INSULIN-M |
| 7.6.266 | CRP | ENG | GLUCOSE | HBA1C | IGFBP1 | TRIG |
| 7.6.267 | CRP | ENG | GLUCOSE | HBA1C | IGFBP2 | INSULIN-M |
| 7.6.268 | CRP | ENG | GLUCOSE | HBA1C | IGFBP2 | TRIG |
| 7.6.269 | CRP | ENG | GLUCOSE | HBA1C | IL2RA | INSULIN-M |
| 7.6.270 | CRP | ENG | GLUCOSE | HBA1C | IL2RA | TRIG |
| 7.6.271 | CRP | ENG | GLUCOSE | HBA1C | IL2RB | INSULIN-M |
| 7.6.272 | CRP | ENG | GLUCOSE | HBA1C | IL2RB | TRIG |
| 7.6.273 | CRP | ENG | GLUCOSE | HBA1C | IL6R | INSULIN-M |
| 7.6.274 | CRP | ENG | GLUCOSE | HBA1C | IL6R | TRIG |
| 7.6.275 | CRP | ENG | GLUCOSE | HBA1C | INSULIN-M | LEP |
| 7.6.276 | CRP | ENG | GLUCOSE | HBA1C | INSULIN-M | SCp |
| 7.6.277 | CRP | ENG | GLUCOSE | HBA1C | INSULIN-M | SHBG |
| 7.6.278 | CRP | ENG | GLUCOSE | HBA1C | INSULIN-M | TIMP2 |
| 7.6.279 | CRP | ENG | GLUCOSE | HBA1C | INSULIN-M | TRIG |
| 7.6.280 | CRP | ENG | GLUCOSE | HBA1C | INSULIN-M | VWF |

FIGURE 7D (continued)

| Panel No. | Marker 1 | Marker 2 | Marker 3 | Marker 4 | Marker 5 | Marker 6 |
|---|---|---|---|---|---|---|
| 7.6.281 | CRP | ENG | GLUCOSE | HBA1C | LEP | TRIG |
| 7.6.282 | CRP | ENG | GLUCOSE | HBA1C | SCp | TRIG |
| 7.6.283 | CRP | ENG | GLUCOSE | HBA1C | SHBG | TRIG |
| 7.6.284 | CRP | ENG | GLUCOSE | HBA1C | TIMP2 | TRIG |
| 7.6.285 | CRP | ENG | GLUCOSE | HBA1C | TRIG | VWF |
| 7.6.286 | CRP | ENG | GLUCOSE | HP | HSPA1B | INSULIN-M |
| 7.6.287 | CRP | ENG | GLUCOSE | HP | INSULIN-M | SHBG |
| 7.6.288 | CRP | ENG | GLUCOSE | HSPA1B | IGFBP2 | INSULIN-M |
| 7.6.289 | CRP | ENG | GLUCOSE | HSPA1B | IL2RA | INSULIN-M |
| 7.6.290 | CRP | ENG | GLUCOSE | HSPA1B | IL2RA | TRIG |
| 7.6.291 | CRP | ENG | GLUCOSE | HSPA1B | INSULIN-M | LEP |
| 7.6.292 | CRP | ENG | GLUCOSE | HSPA1B | INSULIN-M | SHBG |
| 7.6.293 | CRP | ENG | GLUCOSE | HSPA1B | LEP | TRIG |
| 7.6.294 | CRP | FGA | GLUCOSE | GPT | HBA1C | HP |
| 7.6.295 | CRP | FGA | GLUCOSE | GPT | HBA1C | INSULIN-M |
| 7.6.296 | CRP | FGA | GLUCOSE | GPT | HP | INSULIN-M |
| 7.6.297 | CRP | FGA | GLUCOSE | HBA1C | HP | INSULIN-M |
| 7.6.298 | CRP | FGA | GLUCOSE | HBA1C | HP | TRIG |
| 7.6.299 | CRP | FGA | GLUCOSE | HBA1C | HSPA1B | INSULIN-M |
| 7.6.300 | CRP | FGA | GLUCOSE | HBA1C | INSULIN-M | TRIG |
| 7.6.301 | CRP | FGA | GLUCOSE | HBA1C | TIMP2 | TRIG |
| 7.6.302 | CRP | FTH1 | GLUCOSE | GPT | HBA1C | HP |
| 7.6.303 | CRP | FTH1 | GLUCOSE | GPT | HBA1C | INSULIN-M |
| 7.6.304 | CRP | FTH1 | GLUCOSE | HBA1C | HP | INSULIN-M |
| 7.6.305 | CRP | FTH1 | GLUCOSE | HBA1C | HP | TRIG |
| 7.6.306 | CRP | FTH1 | GLUCOSE | HBA1C | INSULIN-M | TRIG |
| 7.6.307 | CRP | FTH1 | GLUCOSE | HBA1C | TIMP2 | TRIG |
| 7.6.308 | CRP | GLUCOSE | GPT | HBA1C | HP | HSPA1B |
| 7.6.309 | CRP | GLUCOSE | GPT | HBA1C | HP | IGF1R |
| 7.6.310 | CRP | GLUCOSE | GPT | HBA1C | HP | IGFBP1 |
| 7.6.311 | CRP | GLUCOSE | GPT | HBA1C | HP | IGFBP2 |
| 7.6.312 | CRP | GLUCOSE | GPT | HBA1C | HP | IL2RA |
| 7.6.313 | CRP | GLUCOSE | GPT | HBA1C | HP | IL2RB |
| 7.6.314 | CRP | GLUCOSE | GPT | HBA1C | HP | INSULIN-M |
| 7.6.315 | CRP | GLUCOSE | GPT | HBA1C | HP | LEP |
| 7.6.316 | CRP | GLUCOSE | GPT | HBA1C | HP | SCp |
| 7.6.317 | CRP | GLUCOSE | GPT | HBA1C | HP | SHBG |
| 7.6.318 | CRP | GLUCOSE | GPT | HBA1C | HP | TIMP2 |
| 7.6.319 | CRP | GLUCOSE | GPT | HBA1C | HP | TRIG |
| 7.6.320 | CRP | GLUCOSE | GPT | HBA1C | HP | VWF |

FIGURE 7D (continued)

| Panel No. | Marker 1 | Marker 2 | Marker 3 | Marker 4 | Marker 5 | Marker 6 |
|---|---|---|---|---|---|---|
| 7.6.321 | CRP | GLUCOSE | GPT | HBA1C | HSPA1B | INSULIN-M |
| 7.6.322 | CRP | GLUCOSE | GPT | HBA1C | IGF1R | INSULIN-M |
| 7.6.323 | CRP | GLUCOSE | GPT | HBA1C | IGFBP1 | INSULIN-M |
| 7.6.324 | CRP | GLUCOSE | GPT | HBA1C | IGFBP2 | INSULIN-M |
| 7.6.325 | CRP | GLUCOSE | GPT | HBA1C | IL2RA | INSULIN-M |
| 7.6.326 | CRP | GLUCOSE | GPT | HBA1C | IL2RB | INSULIN-M |
| 7.6.327 | CRP | GLUCOSE | GPT | HBA1C | IL2RB | LEP |
| 7.6.328 | CRP | GLUCOSE | GPT | HBA1C | IL2RB | TRIG |
| 7.6.329 | CRP | GLUCOSE | GPT | HBA1C | IL6R | INSULIN-M |
| 7.6.330 | CRP | GLUCOSE | GPT | HBA1C | INSULIN-M | LEP |
| 7.6.331 | CRP | GLUCOSE | GPT | HBA1C | INSULIN-M | SCp |
| 7.6.332 | CRP | GLUCOSE | GPT | HBA1C | INSULIN-M | SHBG |
| 7.6.333 | CRP | GLUCOSE | GPT | HBA1C | INSULIN-M | TIMP2 |
| 7.6.334 | CRP | GLUCOSE | GPT | HBA1C | INSULIN-M | TRIG |
| 7.6.335 | CRP | GLUCOSE | GPT | HBA1C | INSULIN-M | VWF |
| 7.6.336 | CRP | GLUCOSE | GPT | HBA1C | LEP | TRIG |
| 7.6.337 | CRP | GLUCOSE | GPT | HBA1C | TIMP2 | TRIG |
| 7.6.338 | CRP | GLUCOSE | GPT | HP | HSPA1B | INSULIN-M |
| 7.6.339 | CRP | GLUCOSE | GPT | HP | IGFBP2 | INSULIN-M |
| 7.6.340 | CRP | GLUCOSE | GPT | HP | INSULIN-M | LEP |
| 7.6.341 | CRP | GLUCOSE | GPT | HP | INSULIN-M | SCp |
| 7.6.342 | CRP | GLUCOSE | GPT | HP | INSULIN-M | SHBG |
| 7.6.343 | CRP | GLUCOSE | GPT | HP | INSULIN-M | TRIG |
| 7.6.344 | CRP | GLUCOSE | GPT | HP | LEP | TRIG |
| 7.6.345 | CRP | GLUCOSE | HBA1C | HP | HSPA1B | INSULIN-M |
| 7.6.346 | CRP | GLUCOSE | HBA1C | HP | HSPA1B | TRIG |
| 7.6.347 | CRP | GLUCOSE | HBA1C | HP | IGF1R | INSULIN-M |
| 7.6.348 | CRP | GLUCOSE | HBA1C | HP | IGF1R | TRIG |
| 7.6.349 | CRP | GLUCOSE | HBA1C | HP | IGFBP1 | INSULIN-M |
| 7.6.350 | CRP | GLUCOSE | HBA1C | HP | IGFBP1 | TRIG |
| 7.6.351 | CRP | GLUCOSE | HBA1C | HP | IGFBP2 | INSULIN-M |
| 7.6.352 | CRP | GLUCOSE | HBA1C | HP | IGFBP2 | TRIG |
| 7.6.353 | CRP | GLUCOSE | HBA1C | HP | IL2RA | INSULIN-M |
| 7.6.354 | CRP | GLUCOSE | HBA1C | HP | IL2RA | TRIG |
| 7.6.355 | CRP | GLUCOSE | HBA1C | HP | IL2RB | INSULIN-M |
| 7.6.356 | CRP | GLUCOSE | HBA1C | HP | IL2RB | TRIG |
| 7.6.357 | CRP | GLUCOSE | HBA1C | HP | IL6R | INSULIN-M |
| 7.6.358 | CRP | GLUCOSE | HBA1C | HP | IL6R | TRIG |
| 7.6.359 | CRP | GLUCOSE | HBA1C | HP | INSULIN-M | LEP |
| 7.6.360 | CRP | GLUCOSE | HBA1C | HP | INSULIN-M | SCp |

FIGURE 7D (continued)

| Panel No. | Marker 1 | Marker 2 | Marker 3 | Marker 4 | Marker 5 | Marker 6 |
|---|---|---|---|---|---|---|
| 7.6.361 | CRP | GLUCOSE | HBA1C | HP | INSULIN-M | SHBG |
| 7.6.362 | CRP | GLUCOSE | HBA1C | HP | INSULIN-M | TIMP2 |
| 7.6.363 | CRP | GLUCOSE | HBA1C | HP | INSULIN-M | TRIG |
| 7.6.364 | CRP | GLUCOSE | HBA1C | HP | INSULIN-M | VWF |
| 7.6.365 | CRP | GLUCOSE | HBA1C | HP | LEP | TRIG |
| 7.6.366 | CRP | GLUCOSE | HBA1C | HP | SCp | TRIG |
| 7.6.367 | CRP | GLUCOSE | HBA1C | HP | SHBG | TRIG |
| 7.6.368 | CRP | GLUCOSE | HBA1C | HP | TIMP2 | TRIG |
| 7.6.369 | CRP | GLUCOSE | HBA1C | HP | TRIG | VWF |
| 7.6.370 | CRP | GLUCOSE | HBA1C | HSPA1B | IGFBP2 | INSULIN-M |
| 7.6.371 | CRP | GLUCOSE | HBA1C | HSPA1B | IL2RA | INSULIN-M |
| 7.6.372 | CRP | GLUCOSE | HBA1C | HSPA1B | IL2RA | TRIG |
| 7.6.373 | CRP | GLUCOSE | HBA1C | HSPA1B | IL2RB | INSULIN-M |
| 7.6.374 | CRP | GLUCOSE | HBA1C | HSPA1B | IL2RB | TRIG |
| 7.6.375 | CRP | GLUCOSE | HBA1C | HSPA1B | IL6R | INSULIN-M |
| 7.6.376 | CRP | GLUCOSE | HBA1C | HSPA1B | INSULIN-M | LEP |
| 7.6.377 | CRP | GLUCOSE | HBA1C | HSPA1B | INSULIN-M | TIMP2 |
| 7.6.378 | CRP | GLUCOSE | HBA1C | HSPA1B | INSULIN-M | TRIG |
| 7.6.379 | CRP | GLUCOSE | HBA1C | HSPA1B | LEP | TRIG |
| 7.6.380 | CRP | GLUCOSE | HBA1C | HSPA1B | TIMP2 | TRIG |
| 7.6.381 | CRP | GLUCOSE | HBA1C | IGFBP1 | INSULIN-M | TRIG |
| 7.6.382 | CRP | GLUCOSE | HBA1C | IGFBP2 | INSULIN-M | TRIG |
| 7.6.383 | CRP | GLUCOSE | HBA1C | IGFBP2 | TIMP2 | TRIG |
| 7.6.384 | CRP | GLUCOSE | HBA1C | IL2RA | TIMP2 | TRIG |
| 7.6.385 | CRP | GLUCOSE | HBA1C | IL2RB | INSULIN-M | TRIG |
| 7.6.386 | CRP | GLUCOSE | HBA1C | IL2RB | TIMP2 | TRIG |
| 7.6.387 | CRP | GLUCOSE | HBA1C | IL6R | INSULIN-M | TIMP2 |
| 7.6.388 | CRP | GLUCOSE | HBA1C | IL6R | INSULIN-M | TRIG |
| 7.6.389 | CRP | GLUCOSE | HBA1C | IL6R | TIMP2 | TRIG |
| 7.6.390 | CRP | GLUCOSE | HBA1C | INSULIN-M | LEP | TRIG |
| 7.6.391 | CRP | GLUCOSE | HBA1C | INSULIN-M | SCp | TRIG |
| 7.6.392 | CRP | GLUCOSE | HBA1C | INSULIN-M | SHBG | TRIG |
| 7.6.393 | CRP | GLUCOSE | HBA1C | INSULIN-M | TIMP2 | TRIG |
| 7.6.394 | CRP | GLUCOSE | HBA1C | LEP | TIMP2 | TRIG |
| 7.6.395 | CRP | GLUCOSE | HBA1C | SCp | TIMP2 | TRIG |
| 7.6.396 | CRP | GLUCOSE | HBA1C | TIMP2 | TRIG | VWF |
| 7.6.397 | CRP | GLUCOSE | HP | HSPA1B | IGFBP2 | INSULIN-M |
| 7.6.398 | CRP | GLUCOSE | HP | INSULIN-M | SHBG | TRIG |
| 7.6.399 | CRP | GLUCOSE | HSPA1B | IL2RA | TIMP2 | TRIG |
| 7.6.400 | ENG | GLUCOSE | HBA1C | HSPA1B | LEP | TRIG |

FIGURE 7E

| Panel No. | Marker 1 | Marker 2 | Marker 3 | Marker 4 | Marker 5 | Marker 6 | Marker 7 |
|---|---|---|---|---|---|---|---|
| 7.7.1 | ADIPOQ | CCL2 | CRP | EGF | GLUCOSE | HSPA1B | LEP |
| 7.7.2 | ADIPOQ | CCL2 | CRP | ENG | GLUCOSE | GPT | HBA1C |
| 7.7.3 | ADIPOQ | CCL2 | CRP | ENG | GLUCOSE | GPT | LEP |
| 7.7.4 | ADIPOQ | CCL2 | CRP | ENG | GLUCOSE | HBA1C | INSULIN-M |
| 7.7.5 | ADIPOQ | CCL2 | CRP | GLUCOSE | GPT | HBA1C | HP |
| 7.7.6 | ADIPOQ | CCL2 | CRP | GLUCOSE | GPT | HBA1C | IGFBP2 |
| 7.7.7 | ADIPOQ | CCL2 | CRP | GLUCOSE | GPT | HBA1C | INSULIN-M |
| 7.7.8 | ADIPOQ | CCL2 | CRP | GLUCOSE | GPT | HBA1C | LEP |
| 7.7.9 | ADIPOQ | CCL2 | CRP | GLUCOSE | GPT | HBA1C | TIMP2 |
| 7.7.10 | ADIPOQ | CCL2 | CRP | GLUCOSE | GPT | HP | LEP |
| 7.7.11 | ADIPOQ | CCL2 | CRP | GLUCOSE | GPT | HSPA1B | LEP |
| 7.7.12 | ADIPOQ | CCL2 | CRP | GLUCOSE | HBA1C | HP | HSPA1B |
| 7.7.13 | ADIPOQ | CCL2 | CRP | GLUCOSE | HBA1C | HP | INSULIN-M |
| 7.7.14 | ADIPOQ | CCL2 | CRP | GLUCOSE | HBA1C | HP | LEP |
| 7.7.15 | ADIPOQ | CCL2 | CRP | GLUCOSE | HBA1C | HP | SHBG |
| 7.7.16 | ADIPOQ | CCL2 | CRP | GLUCOSE | HBA1C | HP | TIMP2 |
| 7.7.17 | ADIPOQ | CCL2 | CRP | GLUCOSE | HBA1C | HP | TRIG |
| 7.7.18 | ADIPOQ | CCL2 | CRP | GLUCOSE | HBA1C | HSPA1B | INSULIN-M |
| 7.7.19 | ADIPOQ | CCL2 | CRP | GLUCOSE | HBA1C | HSPA1B | LEP |
| 7.7.20 | ADIPOQ | CCL2 | CRP | GLUCOSE | HBA1C | LEP | TRIG |
| 7.7.21 | ADIPOQ | CCL2 | CRP | GLUCOSE | HBA1C | TIMP2 | TRIG |
| 7.7.22 | ADIPOQ | CCL2 | CRP | GLUCOSE | HP | HSPA1B | LEP |
| 7.7.23 | ADIPOQ | CCL2 | CRP | GLUCOSE | HSPA1B | IGFBP2 | LEP |
| 7.7.24 | ADIPOQ | CCL2 | CRP | GLUCOSE | HSPA1B | INSULIN-M | LEP |
| 7.7.25 | ADIPOQ | CCL2 | CRP | GLUCOSE | HSPA1B | LEP | TRIG |
| 7.7.26 | ADIPOQ | CD40 | CRP | GLUCOSE | GPT | HBA1C | LEP |
| 7.7.27 | ADIPOQ | CRP | EGF | GLUCOSE | GPT | HBA1C | LEP |
| 7.7.28 | ADIPOQ | CRP | EGF | GLUCOSE | GPT | HSPA1B | LEP |
| 7.7.29 | ADIPOQ | CRP | EGF | GLUCOSE | HBA1C | LEP | TRIG |
| 7.7.30 | ADIPOQ | CRP | EGF | GLUCOSE | HSPA1B | IGFBP2 | LEP |
| 7.7.31 | ADIPOQ | CRP | EGF | GLUCOSE | HSPA1B | LEP | TRIG |
| 7.7.32 | ADIPOQ | CRP | ENG | FTH1 | GLUCOSE | GPT | LEP |
| 7.7.33 | ADIPOQ | CRP | ENG | FTH1 | GLUCOSE | HSPA1B | LEP |
| 7.7.34 | ADIPOQ | CRP | ENG | GLUCOSE | GPT | HBA1C | INSULIN-M |
| 7.7.35 | ADIPOQ | CRP | ENG | GLUCOSE | GPT | HBA1C | LEP |
| 7.7.36 | ADIPOQ | CRP | ENG | GLUCOSE | GPT | HP | LEP |
| 7.7.37 | ADIPOQ | CRP | ENG | GLUCOSE | GPT | HSPA1B | LEP |
| 7.7.38 | ADIPOQ | CRP | ENG | GLUCOSE | GPT | IGFBP2 | LEP |
| 7.7.39 | ADIPOQ | CRP | ENG | GLUCOSE | GPT | LEP | TRIG |
| 7.7.40 | ADIPOQ | CRP | ENG | GLUCOSE | HBA1C | HP | INSULIN-M |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.41 | ADIPOQ | CRP | ENG | GLUCOSE | HBA1C | HP | LEP |
| 7.7.42 | ADIPOQ | CRP | ENG | GLUCOSE | HBA1C | HSPA1B | INSULIN-M |
| 7.7.43 | ADIPOQ | CRP | ENG | GLUCOSE | HBA1C | HSPA1B | LEP |
| 7.7.44 | ADIPOQ | CRP | ENG | GLUCOSE | HBA1C | HSPA1B | TRIG |
| 7.7.45 | ADIPOQ | CRP | ENG | GLUCOSE | HBA1C | INSULIN-M | SHBG |
| 7.7.46 | ADIPOQ | CRP | ENG | GLUCOSE | HBA1C | LEP | TRIG |
| 7.7.47 | ADIPOQ | CRP | ENG | GLUCOSE | HBA1C | TIMP2 | TRIG |
| 7.7.48 | ADIPOQ | CRP | ENG | GLUCOSE | HP | HSPA1B | LEP |
| 7.7.49 | ADIPOQ | CRP | ENG | GLUCOSE | HSPA1B | IGFBP2 | LEP |
| 7.7.50 | ADIPOQ | CRP | ENG | GLUCOSE | HSPA1B | IL2RA | LEP |
| 7.7.51 | ADIPOQ | CRP | ENG | GLUCOSE | HSPA1B | INSULIN-M | LEP |
| 7.7.52 | ADIPOQ | CRP | ENG | GLUCOSE | HSPA1B | LEP | TRIG |
| 7.7.53 | ADIPOQ | CRP | FGA | GLUCOSE | GPT | HBA1C | INSULIN-M |
| 7.7.54 | ADIPOQ | CRP | FGA | GLUCOSE | GPT | HBA1C | LEP |
| 7.7.55 | ADIPOQ | CRP | FTH1 | GLUCOSE | GPT | HBA1C | LEP |
| 7.7.56 | ADIPOQ | CRP | FTH1 | GLUCOSE | GPT | HP | LEP |
| 7.7.57 | ADIPOQ | CRP | FTH1 | GLUCOSE | GPT | HSPA1B | LEP |
| 7.7.58 | ADIPOQ | CRP | FTH1 | GLUCOSE | HP | HSPA1B | LEP |
| 7.7.59 | ADIPOQ | CRP | GLUCOSE | GPT | HBA1C | HP | IGF1R |
| 7.7.60 | ADIPOQ | CRP | GLUCOSE | GPT | HBA1C | HP | IGFBP2 |
| 7.7.61 | ADIPOQ | CRP | GLUCOSE | GPT | HBA1C | HP | IL2RB |
| 7.7.62 | ADIPOQ | CRP | GLUCOSE | GPT | HBA1C | HP | INSULIN-M |
| 7.7.63 | ADIPOQ | CRP | GLUCOSE | GPT | HBA1C | HP | LEP |
| 7.7.64 | ADIPOQ | CRP | GLUCOSE | GPT | HBA1C | HP | SHBG |
| 7.7.65 | ADIPOQ | CRP | GLUCOSE | GPT | HBA1C | HP | TIMP2 |
| 7.7.66 | ADIPOQ | CRP | GLUCOSE | GPT | HBA1C | HP | TRIG |
| 7.7.67 | ADIPOQ | CRP | GLUCOSE | GPT | HBA1C | HSPA1B | INSULIN-M |
| 7.7.68 | ADIPOQ | CRP | GLUCOSE | GPT | HBA1C | HSPA1B | LEP |
| 7.7.69 | ADIPOQ | CRP | GLUCOSE | GPT | HBA1C | IGF1R | LEP |
| 7.7.70 | ADIPOQ | CRP | GLUCOSE | GPT | HBA1C | IGFBP1 | LEP |
| 7.7.71 | ADIPOQ | CRP | GLUCOSE | GPT | HBA1C | IGFBP2 | INSULIN-M |
| 7.7.72 | ADIPOQ | CRP | GLUCOSE | GPT | HBA1C | IGFBP2 | LEP |
| 7.7.73 | ADIPOQ | CRP | GLUCOSE | GPT | HBA1C | IGFBP2 | TIMP2 |
| 7.7.74 | ADIPOQ | CRP | GLUCOSE | GPT | HBA1C | IL2RA | LEP |
| 7.7.75 | ADIPOQ | CRP | GLUCOSE | GPT | HBA1C | IL2RB | LEP |
| 7.7.76 | ADIPOQ | CRP | GLUCOSE | GPT | HBA1C | IL6R | LEP |
| 7.7.77 | ADIPOQ | CRP | GLUCOSE | GPT | HBA1C | INSULIN-M | LEP |
| 7.7.78 | ADIPOQ | CRP | GLUCOSE | GPT | HBA1C | INSULIN-M | SHBG |
| 7.7.79 | ADIPOQ | CRP | GLUCOSE | GPT | HBA1C | INSULIN-M | TIMP2 |
| 7.7.80 | ADIPOQ | CRP | GLUCOSE | GPT | HBA1C | LEP | SHBG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.81 | ADIPOQ | CRP | GLUCOSE | GPT | HBA1C | LEP | TIMP2 |
| 7.7.82 | ADIPOQ | CRP | GLUCOSE | GPT | HBA1C | LEP | TRIG |
| 7.7.83 | ADIPOQ | CRP | GLUCOSE | GPT | HBA1C | LEP | VWF |
| 7.7.84 | ADIPOQ | CRP | GLUCOSE | GPT | HBA1C | TIMP2 | TRIG |
| 7.7.85 | ADIPOQ | CRP | GLUCOSE | GPT | HP | HSPA1B | LEP |
| 7.7.86 | ADIPOQ | CRP | GLUCOSE | GPT | HP | IGFBP2 | INSULIN-M |
| 7.7.87 | ADIPOQ | CRP | GLUCOSE | GPT | HP | IGFBP2 | LEP |
| 7.7.88 | ADIPOQ | CRP | GLUCOSE | GPT | HP | INSULIN-M | LEP |
| 7.7.89 | ADIPOQ | CRP | GLUCOSE | GPT | HP | INSULIN-M | SHBG |
| 7.7.90 | ADIPOQ | CRP | GLUCOSE | GPT | HP | LEP | SHBG |
| 7.7.91 | ADIPOQ | CRP | GLUCOSE | GPT | HP | LEP | TRIG |
| 7.7.92 | ADIPOQ | CRP | GLUCOSE | GPT | HP | LEP | VWF |
| 7.7.93 | ADIPOQ | CRP | GLUCOSE | GPT | HSPA1B | IGF1R | LEP |
| 7.7.94 | ADIPOQ | CRP | GLUCOSE | GPT | HSPA1B | IGFBP2 | LEP |
| 7.7.95 | ADIPOQ | CRP | GLUCOSE | GPT | HSPA1B | IL2RA | LEP |
| 7.7.96 | ADIPOQ | CRP | GLUCOSE | GPT | HSPA1B | IL2RB | LEP |
| 7.7.97 | ADIPOQ | CRP | GLUCOSE | GPT | HSPA1B | INSULIN-M | LEP |
| 7.7.98 | ADIPOQ | CRP | GLUCOSE | GPT | HSPA1B | LEP | TIMP2 |
| 7.7.99 | ADIPOQ | CRP | GLUCOSE | GPT | HSPA1B | LEP | TRIG |
| 7.7.100 | ADIPOQ | CRP | GLUCOSE | GPT | IGFBP2 | LEP | TIMP2 |
| 7.7.101 | ADIPOQ | CRP | GLUCOSE | HBA1C | HP | HSPA1B | IGFBP2 |
| 7.7.102 | ADIPOQ | CRP | GLUCOSE | HBA1C | HP | HSPA1B | INSULIN-M |
| 7.7.103 | ADIPOQ | CRP | GLUCOSE | HBA1C | HP | HSPA1B | LEP |
| 7.7.104 | ADIPOQ | CRP | GLUCOSE | HBA1C | HP | HSPA1B | TRIG |
| 7.7.105 | ADIPOQ | CRP | GLUCOSE | HBA1C | HP | IGFBP2 | INSULIN-M |
| 7.7.106 | ADIPOQ | CRP | GLUCOSE | HBA1C | HP | IGFBP2 | LEP |
| 7.7.107 | ADIPOQ | CRP | GLUCOSE | HBA1C | HP | INSULIN-M | LEP |
| 7.7.108 | ADIPOQ | CRP | GLUCOSE | HBA1C | HP | INSULIN-M | SHBG |
| 7.7.109 | ADIPOQ | CRP | GLUCOSE | HBA1C | HP | INSULIN-M | TIMP2 |
| 7.7.110 | ADIPOQ | CRP | GLUCOSE | HBA1C | HP | INSULIN-M | TRIG |
| 7.7.111 | ADIPOQ | CRP | GLUCOSE | HBA1C | HP | LEP | TIMP2 |
| 7.7.112 | ADIPOQ | CRP | GLUCOSE | HBA1C | HP | LEP | TRIG |
| 7.7.113 | ADIPOQ | CRP | GLUCOSE | HBA1C | HP | SHBG | TRIG |
| 7.7.114 | ADIPOQ | CRP | GLUCOSE | HBA1C | HP | TIMP2 | TRIG |
| 7.7.115 | ADIPOQ | CRP | GLUCOSE | HBA1C | HSPA1B | IGF1R | LEP |
| 7.7.116 | ADIPOQ | CRP | GLUCOSE | HBA1C | HSPA1B | IGFBP2 | INSULIN-M |
| 7.7.117 | ADIPOQ | CRP | GLUCOSE | HBA1C | HSPA1B | IGFBP2 | LEP |
| 7.7.118 | ADIPOQ | CRP | GLUCOSE | HBA1C | HSPA1B | INSULIN-M | LEP |
| 7.7.119 | ADIPOQ | CRP | GLUCOSE | HBA1C | HSPA1B | LEP | TIMP2 |
| 7.7.120 | ADIPOQ | CRP | GLUCOSE | HBA1C | HSPA1B | LEP | TRIG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.121 | ADIPOQ | CRP | GLUCOSE | HBA1C | HSPA1B | TIMP2 | TRIG |
| 7.7.122 | ADIPOQ | CRP | GLUCOSE | HBA1C | LEP | TIMP2 | TRIG |
| 7.7.123 | ADIPOQ | CRP | GLUCOSE | HP | HSPA1B | IGFBP2 | LEP |
| 7.7.124 | ADIPOQ | CRP | GLUCOSE | HP | HSPA1B | IL2RA | LEP |
| 7.7.125 | ADIPOQ | CRP | GLUCOSE | HP | HSPA1B | LEP | TIMP2 |
| 7.7.126 | ADIPOQ | CRP | GLUCOSE | HP | HSPA1B | LEP | TRIG |
| 7.7.127 | ADIPOQ | CRP | GLUCOSE | HSPA1B | IGFBP2 | IL2RB | LEP |
| 7.7.128 | ADIPOQ | CRP | GLUCOSE | HSPA1B | IGFBP2 | INSULIN-M | LEP |
| 7.7.129 | ADIPOQ | CRP | GLUCOSE | HSPA1B | IGFBP2 | LEP | TRIG |
| 7.7.130 | ADIPOQ | CRP | GLUCOSE | HSPA1B | IL6R | LEP | TRIG |
| 7.7.131 | ADIPOQ | CRP | GLUCOSE | HSPA1B | LEP | TIMP2 | TRIG |
| 7.7.132 | CCL2 | CD40 | CRP | GLUCOSE | GPT | HBA1C | HP |
| 7.7.133 | CCL2 | CD40 | CRP | GLUCOSE | GPT | HBA1C | INSULIN-M |
| 7.7.134 | CCL2 | CD40 | CRP | GLUCOSE | HBA1C | HP | INSULIN-M |
| 7.7.135 | CCL2 | CRP | EGF | ENG | GLUCOSE | HBA1C | INSULIN-M |
| 7.7.136 | CCL2 | CRP | EGF | GLUCOSE | GPT | HBA1C | HP |
| 7.7.137 | CCL2 | CRP | EGF | GLUCOSE | GPT | HBA1C | INSULIN-M |
| 7.7.138 | CCL2 | CRP | EGF | GLUCOSE | GPT | HBA1C | TRIG |
| 7.7.139 | CCL2 | CRP | EGF | GLUCOSE | HBA1C | HP | INSULIN-M |
| 7.7.140 | CCL2 | CRP | EGF | GLUCOSE | HBA1C | HSPA1B | INSULIN-M |
| 7.7.141 | CCL2 | CRP | EGF | GLUCOSE | HBA1C | HSPA1B | TRIG |
| 7.7.142 | CCL2 | CRP | EGF | GLUCOSE | HBA1C | INSULIN-M | SHBG |
| 7.7.143 | CCL2 | CRP | EGF | GLUCOSE | HBA1C | TIMP2 | TRIG |
| 7.7.144 | CCL2 | CRP | ENG | FGA | GLUCOSE | HBA1C | INSULIN-M |
| 7.7.145 | CCL2 | CRP | ENG | FTH1 | GLUCOSE | GPT | HBA1C |
| 7.7.146 | CCL2 | CRP | ENG | FTH1 | GLUCOSE | HBA1C | INSULIN-M |
| 7.7.147 | CCL2 | CRP | ENG | FTH1 | GLUCOSE | HBA1C | LEP |
| 7.7.148 | CCL2 | CRP | ENG | GLUCOSE | GPT | HBA1C | HP |
| 7.7.149 | CCL2 | CRP | ENG | GLUCOSE | GPT | HBA1C | INSULIN-M |
| 7.7.150 | CCL2 | CRP | ENG | GLUCOSE | GPT | HBA1C | LEP |
| 7.7.151 | CCL2 | CRP | ENG | GLUCOSE | GPT | HBA1C | TIMP2 |
| 7.7.152 | CCL2 | CRP | ENG | GLUCOSE | GPT | HBA1C | TRIG |
| 7.7.153 | CCL2 | CRP | ENG | GLUCOSE | GPT | HP | INSULIN-M |
| 7.7.154 | CCL2 | CRP | ENG | GLUCOSE | GPT | HSPA1B | INSULIN-M |
| 7.7.155 | CCL2 | CRP | ENG | GLUCOSE | GPT | INSULIN-M | SHBG |
| 7.7.156 | CCL2 | CRP | ENG | GLUCOSE | HBA1C | HP | HSPA1B |
| 7.7.157 | CCL2 | CRP | ENG | GLUCOSE | HBA1C | HP | INSULIN-M |
| 7.7.158 | CCL2 | CRP | ENG | GLUCOSE | HBA1C | HP | TRIG |
| 7.7.159 | CCL2 | CRP | ENG | GLUCOSE | HBA1C | HSPA1B | INSULIN-M |
| 7.7.160 | CCL2 | CRP | ENG | GLUCOSE | HBA1C | HSPA1B | TRIG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.161 | CCL2 | CRP | ENG | GLUCOSE | HBA1C | IGFBP2 | INSULIN-M |
| 7.7.162 | CCL2 | CRP | ENG | GLUCOSE | HBA1C | IL6R | INSULIN-M |
| 7.7.163 | CCL2 | CRP | ENG | GLUCOSE | HBA1C | INSULIN-M | LEP |
| 7.7.164 | CCL2 | CRP | ENG | GLUCOSE | HBA1C | INSULIN-M | SCp |
| 7.7.165 | CCL2 | CRP | ENG | GLUCOSE | HBA1C | INSULIN-M | SHBG |
| 7.7.166 | CCL2 | CRP | ENG | GLUCOSE | HBA1C | INSULIN-M | TIMP2 |
| 7.7.167 | CCL2 | CRP | ENG | GLUCOSE | HBA1C | INSULIN-M | TRIG |
| 7.7.168 | CCL2 | CRP | ENG | GLUCOSE | HBA1C | LEP | TRIG |
| 7.7.169 | CCL2 | CRP | ENG | GLUCOSE | HBA1C | SHBG | TRIG |
| 7.7.170 | CCL2 | CRP | ENG | GLUCOSE | HBA1C | TIMP2 | TRIG |
| 7.7.171 | CCL2 | CRP | ENG | GLUCOSE | HP | HSPA1B | INSULIN-M |
| 7.7.172 | CCL2 | CRP | FGA | GLUCOSE | GPT | HBA1C | HP |
| 7.7.173 | CCL2 | CRP | FGA | GLUCOSE | GPT | HBA1C | INSULIN-M |
| 7.7.174 | CCL2 | CRP | FGA | GLUCOSE | HBA1C | HP | INSULIN-M |
| 7.7.175 | CCL2 | CRP | FGA | GLUCOSE | HBA1C | HSPA1B | INSULIN-M |
| 7.7.176 | CCL2 | CRP | FTH1 | GLUCOSE | GPT | HBA1C | HP |
| 7.7.177 | CCL2 | CRP | FTH1 | GLUCOSE | GPT | HBA1C | INSULIN-M |
| 7.7.178 | CCL2 | CRP | FTH1 | GLUCOSE | HBA1C | HP | INSULIN-M |
| 7.7.179 | CCL2 | CRP | GLUCOSE | GPT | HBA1C | HP | HSPA1B |
| 7.7.180 | CCL2 | CRP | GLUCOSE | GPT | HBA1C | HP | IGF1R |
| 7.7.181 | CCL2 | CRP | GLUCOSE | GPT | HBA1C | HP | IGFBP1 |
| 7.7.182 | CCL2 | CRP | GLUCOSE | GPT | HBA1C | HP | IGFBP2 |
| 7.7.183 | CCL2 | CRP | GLUCOSE | GPT | HBA1C | HP | IL2RA |
| 7.7.184 | CCL2 | CRP | GLUCOSE | GPT | HBA1C | HP | IL2RB |
| 7.7.185 | CCL2 | CRP | GLUCOSE | GPT | HBA1C | HP | IL6R |
| 7.7.186 | CCL2 | CRP | GLUCOSE | GPT | HBA1C | HP | INSULIN-M |
| 7.7.187 | CCL2 | CRP | GLUCOSE | GPT | HBA1C | HP | LEP |
| 7.7.188 | CCL2 | CRP | GLUCOSE | GPT | HBA1C | HP | SCp |
| 7.7.189 | CCL2 | CRP | GLUCOSE | GPT | HBA1C | HP | SHBG |
| 7.7.190 | CCL2 | CRP | GLUCOSE | GPT | HBA1C | HP | TIMP2 |
| 7.7.191 | CCL2 | CRP | GLUCOSE | GPT | HBA1C | HP | TRIG |
| 7.7.192 | CCL2 | CRP | GLUCOSE | GPT | HBA1C | HP | VWF |
| 7.7.193 | CCL2 | CRP | GLUCOSE | GPT | HBA1C | HSPA1B | INSULIN-M |
| 7.7.194 | CCL2 | CRP | GLUCOSE | GPT | HBA1C | IGF1R | INSULIN-M |
| 7.7.195 | CCL2 | CRP | GLUCOSE | GPT | HBA1C | IGFBP1 | INSULIN-M |
| 7.7.196 | CCL2 | CRP | GLUCOSE | GPT | HBA1C | IGFBP2 | INSULIN-M |
| 7.7.197 | CCL2 | CRP | GLUCOSE | GPT | HBA1C | IL2RB | INSULIN-M |
| 7.7.198 | CCL2 | CRP | GLUCOSE | GPT | HBA1C | IL6R | INSULIN-M |
| 7.7.199 | CCL2 | CRP | GLUCOSE | GPT | HBA1C | INSULIN-M | LEP |
| 7.7.200 | CCL2 | CRP | GLUCOSE | GPT | HBA1C | INSULIN-M | SCp |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.201 | CCL2 | CRP | GLUCOSE | GPT | HBA1C | INSULIN-M | SHBG |
| 7.7.202 | CCL2 | CRP | GLUCOSE | GPT | HBA1C | INSULIN-M | TIMP2 |
| 7.7.203 | CCL2 | CRP | GLUCOSE | GPT | HBA1C | INSULIN-M | TRIG |
| 7.7.204 | CCL2 | CRP | GLUCOSE | GPT | HBA1C | INSULIN-M | VWF |
| 7.7.205 | CCL2 | CRP | GLUCOSE | GPT | HBA1C | TIMP2 | TRIG |
| 7.7.206 | CCL2 | CRP | GLUCOSE | GPT | HP | HSPA1B | INSULIN-M |
| 7.7.207 | CCL2 | CRP | GLUCOSE | GPT | HP | IGFBP2 | INSULIN-M |
| 7.7.208 | CCL2 | CRP | GLUCOSE | GPT | HP | IL2RA | INSULIN-M |
| 7.7.209 | CCL2 | CRP | GLUCOSE | GPT | HP | INSULIN-M | LEP |
| 7.7.210 | CCL2 | CRP | GLUCOSE | GPT | HP | INSULIN-M | SHBG |
| 7.7.211 | CCL2 | CRP | GLUCOSE | HBA1C | HP | HSPA1B | IGFBP2 |
| 7.7.212 | CCL2 | CRP | GLUCOSE | HBA1C | HP | HSPA1B | INSULIN-M |
| 7.7.213 | CCL2 | CRP | GLUCOSE | HBA1C | HP | HSPA1B | LEP |
| 7.7.214 | CCL2 | CRP | GLUCOSE | HBA1C | HP | HSPA1B | TRIG |
| 7.7.215 | CCL2 | CRP | GLUCOSE | HBA1C | HP | IGF1R | INSULIN-M |
| 7.7.216 | CCL2 | CRP | GLUCOSE | HBA1C | HP | IGFBP1 | INSULIN-M |
| 7.7.217 | CCL2 | CRP | GLUCOSE | HBA1C | HP | IGFBP1 | TRIG |
| 7.7.218 | CCL2 | CRP | GLUCOSE | HBA1C | HP | IGFBP2 | INSULIN-M |
| 7.7.219 | CCL2 | CRP | GLUCOSE | HBA1C | HP | IGFBP2 | TRIG |
| 7.7.220 | CCL2 | CRP | GLUCOSE | HBA1C | HP | IL2RA | INSULIN-M |
| 7.7.221 | CCL2 | CRP | GLUCOSE | HBA1C | HP | IL2RB | INSULIN-M |
| 7.7.222 | CCL2 | CRP | GLUCOSE | HBA1C | HP | IL6R | INSULIN-M |
| 7.7.223 | CCL2 | CRP | GLUCOSE | HBA1C | HP | IL6R | TRIG |
| 7.7.224 | CCL2 | CRP | GLUCOSE | HBA1C | HP | INSULIN-M | LEP |
| 7.7.225 | CCL2 | CRP | GLUCOSE | HBA1C | HP | INSULIN-M | SCp |
| 7.7.226 | CCL2 | CRP | GLUCOSE | HBA1C | HP | INSULIN-M | SHBG |
| 7.7.227 | CCL2 | CRP | GLUCOSE | HBA1C | HP | INSULIN-M | TIMP2 |
| 7.7.228 | CCL2 | CRP | GLUCOSE | HBA1C | HP | INSULIN-M | TRIG |
| 7.7.229 | CCL2 | CRP | GLUCOSE | HBA1C | HP | INSULIN-M | VWF |
| 7.7.230 | CCL2 | CRP | GLUCOSE | HBA1C | HP | LEP | TRIG |
| 7.7.231 | CCL2 | CRP | GLUCOSE | HBA1C | HP | SHBG | TRIG |
| 7.7.232 | CCL2 | CRP | GLUCOSE | HBA1C | HP | TIMP2 | TRIG |
| 7.7.233 | CCL2 | CRP | GLUCOSE | HBA1C | HSPA1B | IGFBP2 | INSULIN-M |
| 7.7.234 | CCL2 | CRP | GLUCOSE | HBA1C | HSPA1B | IL6R | INSULIN-M |
| 7.7.235 | CCL2 | CRP | GLUCOSE | HBA1C | HSPA1B | INSULIN-M | SCp |
| 7.7.236 | CCL2 | CRP | GLUCOSE | HBA1C | HSPA1B | INSULIN-M | TIMP2 |
| 7.7.237 | CCL2 | CRP | GLUCOSE | HBA1C | HSPA1B | INSULIN-M | TRIG |
| 7.7.238 | CCL2 | CRP | GLUCOSE | HBA1C | HSPA1B | INSULIN-M | VWF |
| 7.7.239 | CCL2 | CRP | GLUCOSE | HBA1C | HSPA1B | LEP | TRIG |
| 7.7.240 | CCL2 | CRP | GLUCOSE | HBA1C | HSPA1B | TIMP2 | TRIG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.241 | CCL2 | CRP | GLUCOSE | HBA1C | IL6R | INSULIN-M | TIMP2 |
| 7.7.242 | CCL2 | CRP | GLUCOSE | HBA1C | IL6R | TIMP2 | TRIG |
| 7.7.243 | CCL2 | CRP | GLUCOSE | HBA1C | INSULIN-M | SCp | TRIG |
| 7.7.244 | CCL2 | CRP | GLUCOSE | HBA1C | INSULIN-M | TIMP2 | TRIG |
| 7.7.245 | CCL2 | CRP | GLUCOSE | HP | HSPA1B | INSULIN-M | SHBG |
| 7.7.246 | CCL2 | CRP | GLUCOSE | HP | HSPA1B | INSULIN-M | TIMP2 |
| 7.7.247 | CD40 | CRP | ENG | GLUCOSE | GPT | HBA1C | INSULIN-M |
| 7.7.248 | CD40 | CRP | GLUCOSE | GPT | HBA1C | HP | INSULIN-M |
| 7.7.249 | CRP | EGF | ENG | GLUCOSE | GPT | HBA1C | INSULIN-M |
| 7.7.250 | CRP | EGF | ENG | GLUCOSE | HBA1C | INSULIN-M | SHBG |
| 7.7.251 | CRP | EGF | GLUCOSE | GPT | HBA1C | HP | INSULIN-M |
| 7.7.252 | CRP | EGF | GLUCOSE | GPT | HBA1C | IGFBP2 | INSULIN-M |
| 7.7.253 | CRP | EGF | GLUCOSE | GPT | HBA1C | INSULIN-M | SHBG |
| 7.7.254 | CRP | EGF | GLUCOSE | HBA1C | HP | INSULIN-M | SHBG |
| 7.7.255 | CRP | EGF | GLUCOSE | HBA1C | HP | SHBG | TRIG |
| 7.7.256 | CRP | EGF | GLUCOSE | HBA1C | HSPA1B | IGFBP2 | INSULIN-M |
| 7.7.257 | CRP | EGF | GLUCOSE | HBA1C | HSPA1B | IL2RA | TRIG |
| 7.7.258 | CRP | EGF | GLUCOSE | HBA1C | HSPA1B | LEP | TRIG |
| 7.7.259 | CRP | EGF | GLUCOSE | HBA1C | HSPA1B | TIMP2 | TRIG |
| 7.7.260 | CRP | EGF | GLUCOSE | HSPA1B | IL2RA | TIMP2 | TRIG |
| 7.7.261 | CRP | ENG | FGA | GLUCOSE | GPT | HBA1C | INSULIN-M |
| 7.7.262 | CRP | ENG | FTH1 | GLUCOSE | GPT | HBA1C | INSULIN-M |
| 7.7.263 | CRP | ENG | FTH1 | GLUCOSE | GPT | HBA1C | LEP |
| 7.7.264 | CRP | ENG | FTH1 | GLUCOSE | GPT | HBA1C | TRIG |
| 7.7.265 | CRP | ENG | FTH1 | GLUCOSE | HBA1C | HP | INSULIN-M |
| 7.7.266 | CRP | ENG | FTH1 | GLUCOSE | HBA1C | HSPA1B | INSULIN-M |
| 7.7.267 | CRP | ENG | FTH1 | GLUCOSE | HBA1C | INSULIN-M | LEP |
| 7.7.268 | CRP | ENG | FTH1 | GLUCOSE | HBA1C | INSULIN-M | SHBG |
| 7.7.269 | CRP | ENG | FTH1 | GLUCOSE | HBA1C | LEP | TRIG |
| 7.7.270 | CRP | ENG | GLUCOSE | GPT | HBA1C | HP | IGFBP2 |
| 7.7.271 | CRP | ENG | GLUCOSE | GPT | HBA1C | HP | IL2RB |
| 7.7.272 | CRP | ENG | GLUCOSE | GPT | HBA1C | HP | INSULIN-M |
| 7.7.273 | CRP | ENG | GLUCOSE | GPT | HBA1C | HP | LEP |
| 7.7.274 | CRP | ENG | GLUCOSE | GPT | HBA1C | HP | SHBG |
| 7.7.275 | CRP | ENG | GLUCOSE | GPT | HBA1C | HP | TRIG |
| 7.7.276 | CRP | ENG | GLUCOSE | GPT | HBA1C | HSPA1B | INSULIN-M |
| 7.7.277 | CRP | ENG | GLUCOSE | GPT | HBA1C | IGF1R | INSULIN-M |
| 7.7.278 | CRP | ENG | GLUCOSE | GPT | HBA1C | IGFBP1 | INSULIN-M |
| 7.7.279 | CRP | ENG | GLUCOSE | GPT | HBA1C | IGFBP2 | IL2RA |
| 7.7.280 | CRP | ENG | GLUCOSE | GPT | HBA1C | IGFBP2 | INSULIN-M |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.281 | CRP | ENG | GLUCOSE | GPT | HBA1C | IL2RA | INSULIN-M |
| 7.7.282 | CRP | ENG | GLUCOSE | GPT | HBA1C | IL2RA | TRIG |
| 7.7.283 | CRP | ENG | GLUCOSE | GPT | HBA1C | IL2RB | INSULIN-M |
| 7.7.284 | CRP | ENG | GLUCOSE | GPT | HBA1C | IL2RB | LEP |
| 7.7.285 | CRP | ENG | GLUCOSE | GPT | HBA1C | IL2RB | TRIG |
| 7.7.286 | CRP | ENG | GLUCOSE | GPT | HBA1C | IL6R | INSULIN-M |
| 7.7.287 | CRP | ENG | GLUCOSE | GPT | HBA1C | INSULIN-M | LEP |
| 7.7.288 | CRP | ENG | GLUCOSE | GPT | HBA1C | INSULIN-M | SCp |
| 7.7.289 | CRP | ENG | GLUCOSE | GPT | HBA1C | INSULIN-M | SHBG |
| 7.7.290 | CRP | ENG | GLUCOSE | GPT | HBA1C | INSULIN-M | TIMP2 |
| 7.7.291 | CRP | ENG | GLUCOSE | GPT | HBA1C | INSULIN-M | TRIG |
| 7.7.292 | CRP | ENG | GLUCOSE | GPT | HBA1C | INSULIN-M | VWF |
| 7.7.293 | CRP | ENG | GLUCOSE | GPT | HBA1C | LEP | TRIG |
| 7.7.294 | CRP | ENG | GLUCOSE | GPT | HBA1C | TIMP2 | TRIG |
| 7.7.295 | CRP | ENG | GLUCOSE | GPT | HP | IGFBP2 | INSULIN-M |
| 7.7.296 | CRP | ENG | GLUCOSE | GPT | HP | INSULIN-M | SHBG |
| 7.7.297 | CRP | ENG | GLUCOSE | GPT | HSPA1B | IGFBP2 | IL2RA |
| 7.7.298 | CRP | ENG | GLUCOSE | GPT | HSPA1B | IGFBP2 | INSULIN-M |
| 7.7.299 | CRP | ENG | GLUCOSE | GPT | HSPA1B | IL2RA | INSULIN-M |
| 7.7.300 | CRP | ENG | GLUCOSE | GPT | HSPA1B | IL2RA | TRIG |
| 7.7.301 | CRP | ENG | GLUCOSE | GPT | HSPA1B | INSULIN-M | LEP |
| 7.7.302 | CRP | ENG | GLUCOSE | GPT | HSPA1B | INSULIN-M | SHBG |
| 7.7.303 | CRP | ENG | GLUCOSE | GPT | IGFBP2 | INSULIN-M | SCp |
| 7.7.304 | CRP | ENG | GLUCOSE | HBA1C | HP | HSPA1B | INSULIN-M |
| 7.7.305 | CRP | ENG | GLUCOSE | HBA1C | HP | HSPA1B | TRIG |
| 7.7.306 | CRP | ENG | GLUCOSE | HBA1C | HP | IGFBP2 | INSULIN-M |
| 7.7.307 | CRP | ENG | GLUCOSE | HBA1C | HP | INSULIN-M | SHBG |
| 7.7.308 | CRP | ENG | GLUCOSE | HBA1C | HP | INSULIN-M | TRIG |
| 7.7.309 | CRP | ENG | GLUCOSE | HBA1C | HP | LEP | TRIG |
| 7.7.310 | CRP | ENG | GLUCOSE | HBA1C | HP | SHBG | TRIG |
| 7.7.311 | CRP | ENG | GLUCOSE | HBA1C | HSPA1B | IGFBP2 | INSULIN-M |
| 7.7.312 | CRP | ENG | GLUCOSE | HBA1C | HSPA1B | IL2RA | INSULIN-M |
| 7.7.313 | CRP | ENG | GLUCOSE | HBA1C | HSPA1B | IL2RA | TRIG |
| 7.7.314 | CRP | ENG | GLUCOSE | HBA1C | HSPA1B | IL2RB | TRIG |
| 7.7.315 | CRP | ENG | GLUCOSE | HBA1C | HSPA1B | INSULIN-M | SHBG |
| 7.7.316 | CRP | ENG | GLUCOSE | HBA1C | HSPA1B | INSULIN-M | TIMP2 |
| 7.7.317 | CRP | ENG | GLUCOSE | HBA1C | HSPA1B | INSULIN-M | TRIG |
| 7.7.318 | CRP | ENG | GLUCOSE | HBA1C | HSPA1B | LEP | TRIG |
| 7.7.319 | CRP | ENG | GLUCOSE | HBA1C | HSPA1B | TIMP2 | TRIG |
| 7.7.320 | CRP | ENG | GLUCOSE | HBA1C | IL2RB | LEP | TRIG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.321 | CRP | ENG | GLUCOSE | HBA1C | INSULIN-M | LEP | TRIG |
| 7.7.322 | CRP | ENG | GLUCOSE | HBA1C | INSULIN-M | SCp | TRIG |
| 7.7.323 | CRP | ENG | GLUCOSE | HBA1C | INSULIN-M | SHBG | TRIG |
| 7.7.324 | CRP | ENG | GLUCOSE | HBA1C | INSULIN-M | TIMP2 | TRIG |
| 7.7.325 | CRP | ENG | GLUCOSE | HSPA1B | IL2RA | LEP | TRIG |
| 7.7.326 | CRP | ENG | GLUCOSE | HSPA1B | IL2RA | TIMP2 | TRIG |
| 7.7.327 | CRP | FGA | GLUCOSE | GPT | HBA1C | HP | INSULIN-M |
| 7.7.328 | CRP | FGA | GLUCOSE | GPT | HBA1C | INSULIN-M | TIMP2 |
| 7.7.329 | CRP | FGA | GLUCOSE | HBA1C | HP | HSPA1B | INSULIN-M |
| 7.7.330 | CRP | FGA | GLUCOSE | HBA1C | HP | INSULIN-M | SHBG |
| 7.7.331 | CRP | FTH1 | GLUCOSE | GPT | HBA1C | HP | INSULIN-M |
| 7.7.332 | CRP | FTH1 | GLUCOSE | GPT | HBA1C | HP | LEP |
| 7.7.333 | CRP | FTH1 | GLUCOSE | HBA1C | HP | IGFBP2 | INSULIN-M |
| 7.7.334 | CRP | FTH1 | GLUCOSE | HBA1C | HP | INSULIN-M | SHBG |
| 7.7.335 | CRP | FTH1 | GLUCOSE | HBA1C | HP | INSULIN-M | TRIG |
| 7.7.336 | CRP | GLUCOSE | GPT | HBA1C | HP | HSPA1B | IL2RB |
| 7.7.337 | CRP | GLUCOSE | GPT | HBA1C | HP | HSPA1B | INSULIN-M |
| 7.7.338 | CRP | GLUCOSE | GPT | HBA1C | HP | IGF1R | IGFBP2 |
| 7.7.339 | CRP | GLUCOSE | GPT | HBA1C | HP | IGF1R | INSULIN-M |
| 7.7.340 | CRP | GLUCOSE | GPT | HBA1C | HP | IGF1R | TRIG |
| 7.7.341 | CRP | GLUCOSE | GPT | HBA1C | HP | IGFBP1 | INSULIN-M |
| 7.7.342 | CRP | GLUCOSE | GPT | HBA1C | HP | IGFBP2 | IL2RB |
| 7.7.343 | CRP | GLUCOSE | GPT | HBA1C | HP | IGFBP2 | INSULIN-M |
| 7.7.344 | CRP | GLUCOSE | GPT | HBA1C | HP | IGFBP2 | LEP |
| 7.7.345 | CRP | GLUCOSE | GPT | HBA1C | HP | IGFBP2 | SHBG |
| 7.7.346 | CRP | GLUCOSE | GPT | HBA1C | HP | IGFBP2 | TIMP2 |
| 7.7.347 | CRP | GLUCOSE | GPT | HBA1C | HP | IGFBP2 | TRIG |
| 7.7.348 | CRP | GLUCOSE | GPT | HBA1C | HP | IL2RA | INSULIN-M |
| 7.7.349 | CRP | GLUCOSE | GPT | HBA1C | HP | IL2RB | INSULIN-M |
| 7.7.350 | CRP | GLUCOSE | GPT | HBA1C | HP | IL2RB | LEP |
| 7.7.351 | CRP | GLUCOSE | GPT | HBA1C | HP | IL2RB | SHBG |
| 7.7.352 | CRP | GLUCOSE | GPT | HBA1C | HP | IL2RB | TRIG |
| 7.7.353 | CRP | GLUCOSE | GPT | HBA1C | HP | IL6R | INSULIN-M |
| 7.7.354 | CRP | GLUCOSE | GPT | HBA1C | HP | INSULIN-M | LEP |
| 7.7.355 | CRP | GLUCOSE | GPT | HBA1C | HP | INSULIN-M | SCp |
| 7.7.356 | CRP | GLUCOSE | GPT | HBA1C | HP | INSULIN-M | SHBG |
| 7.7.357 | CRP | GLUCOSE | GPT | HBA1C | HP | INSULIN-M | TIMP2 |
| 7.7.358 | CRP | GLUCOSE | GPT | HBA1C | HP | INSULIN-M | TRIG |
| 7.7.359 | CRP | GLUCOSE | GPT | HBA1C | HP | INSULIN-M | VWF |
| 7.7.360 | CRP | GLUCOSE | GPT | HBA1C | HP | LEP | SHBG |

FIGURE 7E (continued)

| Panel No. | Marker 1 | Marker 2 | Marker 3 | Marker 4 | Marker 5 | Marker 6 | Marker 7 |
|---|---|---|---|---|---|---|---|
| 7.7.361 | CRP | GLUCOSE | GPT | HBA1C | HP | LEP | TIMP2 |
| 7.7.362 | CRP | GLUCOSE | GPT | HBA1C | HP | LEP | TRIG |
| 7.7.363 | CRP | GLUCOSE | GPT | HBA1C | HP | SHBG | TRIG |
| 7.7.364 | CRP | GLUCOSE | GPT | HBA1C | HP | TIMP2 | TRIG |
| 7.7.365 | CRP | GLUCOSE | GPT | HBA1C | HSPA1B | IGFBP2 | INSULIN-M |
| 7.7.366 | CRP | GLUCOSE | GPT | HBA1C | IGFBP2 | IL2RB | INSULIN-M |
| 7.7.367 | CRP | GLUCOSE | GPT | HBA1C | IGFBP2 | INSULIN-M | SCp |
| 7.7.368 | CRP | GLUCOSE | GPT | HBA1C | IGFBP2 | INSULIN-M | TIMP2 |
| 7.7.369 | CRP | GLUCOSE | GPT | HBA1C | IL6R | INSULIN-M | TIMP2 |
| 7.7.370 | CRP | GLUCOSE | GPT | HP | IGFBP2 | INSULIN-M | SCp |
| 7.7.371 | CRP | GLUCOSE | GPT | HP | IGFBP2 | INSULIN-M | SHBG |
| 7.7.372 | CRP | GLUCOSE | GPT | HP | IGFBP2 | INSULIN-M | TIMP2 |
| 7.7.373 | CRP | GLUCOSE | HBA1C | HP | HSPA1B | IGFBP2 | INSULIN-M |
| 7.7.374 | CRP | GLUCOSE | HBA1C | HP | HSPA1B | IGFBP2 | TRIG |
| 7.7.375 | CRP | GLUCOSE | HBA1C | HP | HSPA1B | IL2RA | INSULIN-M |
| 7.7.376 | CRP | GLUCOSE | HBA1C | HP | HSPA1B | INSULIN-M | LEP |
| 7.7.377 | CRP | GLUCOSE | HBA1C | HP | HSPA1B | INSULIN-M | SHBG |
| 7.7.378 | CRP | GLUCOSE | HBA1C | HP | HSPA1B | INSULIN-M | TIMP2 |
| 7.7.379 | CRP | GLUCOSE | HBA1C | HP | HSPA1B | INSULIN-M | TRIG |
| 7.7.380 | CRP | GLUCOSE | HBA1C | HP | HSPA1B | LEP | TRIG |
| 7.7.381 | CRP | GLUCOSE | HBA1C | HP | HSPA1B | TIMP2 | TRIG |
| 7.7.382 | CRP | GLUCOSE | HBA1C | HP | IGFBP2 | INSULIN-M | SHBG |
| 7.7.383 | CRP | GLUCOSE | HBA1C | HP | IGFBP2 | INSULIN-M | TIMP2 |
| 7.7.384 | CRP | GLUCOSE | HBA1C | HP | IGFBP2 | INSULIN-M | TRIG |
| 7.7.385 | CRP | GLUCOSE | HBA1C | HP | IGFBP2 | TIMP2 | TRIG |
| 7.7.386 | CRP | GLUCOSE | HBA1C | HP | IL6R | INSULIN-M | SHBG |
| 7.7.387 | CRP | GLUCOSE | HBA1C | HP | INSULIN-M | LEP | TRIG |
| 7.7.388 | CRP | GLUCOSE | HBA1C | HP | INSULIN-M | SCp | SHBG |
| 7.7.389 | CRP | GLUCOSE | HBA1C | HP | INSULIN-M | SCp | TRIG |
| 7.7.390 | CRP | GLUCOSE | HBA1C | HP | INSULIN-M | SHBG | TIMP2 |
| 7.7.391 | CRP | GLUCOSE | HBA1C | HP | INSULIN-M | SHBG | TRIG |
| 7.7.392 | CRP | GLUCOSE | HBA1C | HP | INSULIN-M | SHBG | VWF |
| 7.7.393 | CRP | GLUCOSE | HBA1C | HP | INSULIN-M | TIMP2 | TRIG |
| 7.7.394 | CRP | GLUCOSE | HBA1C | HP | SHBG | TIMP2 | TRIG |
| 7.7.395 | CRP | GLUCOSE | HBA1C | HSPA1B | IL2RA | TIMP2 | TRIG |
| 7.7.396 | CRP | GLUCOSE | HBA1C | HSPA1B | IL2RB | TIMP2 | TRIG |
| 7.7.397 | CRP | GLUCOSE | HBA1C | HSPA1B | IL6R | TIMP2 | TRIG |
| 7.7.398 | CRP | GLUCOSE | HBA1C | HSPA1B | INSULIN-M | TIMP2 | TRIG |
| 7.7.399 | CRP | GLUCOSE | HBA1C | HSPA1B | LEP | TIMP2 | TRIG |
| 7.7.400 | ENG | GLUCOSE | HBA1C | HSPA1B | IL2RA | LEP | TRIG |

FIGURE 8

| Clinical Parameters | Traditional Laboratory Risk Factors | Tier 1 Markers | Tier 2 Markers | Tier 3 Markers |
|---|---|---|---|---|
| • Age (AGE)<br>• Body Mass Index (BMI)<br>• Diastolic Blood Pressure (DBP)<br>• Family History (FHX)<br>• Gestational Diabetes Mellitus (GDM), Past<br>• Height (HT)<br>• Hip Circumference (Hip)<br>• Race (RACE)<br>• Sex (SEX)<br>• Systolic Blood Pressure (SBP)<br>• Waist Circumference (Waist)<br>• WHr<br>• Weight (WT) | • Cholesterol (CHOL)<br>• Glucose (fasting plasma glucose (FPG/Glucose) or with oral glucose tolerance test (OGTT))<br>• HBA1c (Glycosylated Hemoglobin (HBA1/HBA1C)<br>• High Density Lipoprotein (HDL/HDLC)<br>• Low Density Lipoprotein (LDL/LDLC)<br>• Very Low Density Lipoprotein (VLDLC)<br>• Triglycerides (TRIG) | • CRP<br>• INSULIN-M<br>• GLUCOSE<br>• TRIG<br>• HBA1C | • GPT<br>• HSPA1B<br>• IGFBP2<br>• LEP<br>• ADIPOQ<br>• IGFBP1 | • CCL2<br>• ENG<br>• HP<br>• IL2RA<br>• SCp<br>• SHBG<br>• TIMP2<br>• FGA<br>• VWF<br>• APOA2<br>• CD40<br>• EGF<br>• FTH1<br>• IGF1R<br>• IL2RB<br>• IL6R<br>• MMP9 |

FIGURE 9

| Glycemic Control | Acute Phase Response Signalling | Lipoprotein Metabolism | Adipocyte Signalling | Liver/Hepatic Signalling | Inflammatory Blood and Endothelial Cell Signalling |
|---|---|---|---|---|---|
| • GLU<br>• HBA1C | • CRP<br>• FGA<br>• FTH1<br>• HP<br>• IL6<br>• IL6R<br>• IL18<br>• VWF | • APOA1<br>• APOA2<br>• APOB<br>• APOE<br>• CHOL<br>• TRIG | • ADIPOQ<br>• DPP4<br>• INHBA<br>• INS<br>• IGF1R<br>• IGFBP1<br>• IGFBP2<br>• LEP<br>• SHBG | • ENG<br>• EGF<br>• IL6<br>• IL6R<br>• IL8<br>• GPT(ALT) | • CCL2<br>• DPP4<br>• FAS<br>• IL2RA<br>• IL6<br>• IL8<br>• MMP9<br>• SELP<br>• TIMP1<br>• TIMP2<br>• VCAM1<br>• VEGF |

FIGURE 10

9 candidate blood markers with significant p value

| | Transform | Converters (n=83) | | | Non - Converters (n=236) | | | pvals |
|---|---|---|---|---|---|---|---|---|
| | | Mean | SD | BT | Mean | SD | BT | |
| GLUCOSE | Log | 0.78 | 0.039 | 6.0 | 0.75 | 0.039 | 5.6 | 1.5E-08 |
| INSULIN | Log | 1.75 | 0.268 | 56.3 | 1.59 | 0.242 | 39.1 | 1.2E-06 |
| HBA1C | Log | 0.79 | 0.031 | 6.1 | 0.77 | 0.033 | 5.8 | 3.8E-06 |
| CRP | Log | 3.62 | 0.527 | 4122.9 | 3.30 | 0.577 | 1987.1 | 1.6E-05 |
| TRIG | Log | 0.24 | 0.222 | 1.8 | 0.13 | 0.231 | 1.3 | 0.0001 |
| WHr | Raw | 0.92 | 0.078 | 0.9 | 0.89 | 0.079 | 0.9 | 0.0004 |
| WAIST | Log | 1.99 | 0.052 | 97.8 | 1.97 | 0.051 | 92.9 | 0.0008 |
| BMI | Log | 1.48 | 0.056 | 30.2 | 1.46 | 0.054 | 28.6 | 0.0012 |
| SCp | Raw | 666.81 | 171.439 | 666.8 | 602.70 | 170.438 | 602.7 | 0.0035 |
| GPT | Log | 0.44 | 0.224 | 2.8 | 0.35 | 0.252 | 2.2 | 0.0053 |
| LEP | Log | 1.29 | 0.405 | 19.7 | 1.16 | 0.439 | 14.3 | 0.0117 |
| SBP | Log | 2.14 | 0.049 | 138.3 | 2.12 | 0.058 | 132.7 | 0.0127 |
| SERPINE1 | Sqrt | 7.11 | 1.785 | 50.5 | 6.56 | 1.674 | 43.0 | 0.0139 |
| WEIGHT | Log | 1.95 | 0.070 | 89.4 | 1.93 | 0.068 | 85.3 | 0.0189 |
| IL18 | Log | -0.47 | 0.178 | 0.3 | -0.54 | 0.253 | 0.3 | 0.0225 |

Permutation test → pval<0.024 is non-random

FIGURE 11

A. Top interactions

| Marker 1 | | Marker 2 |
|---|---|---|
| GLUCOSE | x | INSULIN |
| CRP | x | INSULIN |
| CRP | x | GLUCOSE |
| INSULIN | x | SELP |
| APOA1 | x | INSULIN |
| LEP | x | TRIG |
| INSULIN | x | VWF |
| CHOL | x | INSULIN |
| APOB | x | INSULIN |
| FGA | x | INSULIN |
| INSULIN | x | Proinsulin |
| APOA1 | x | GLUCOSE |
| IL6ST | x | INSULIN |
| GLUCOSE | x | VWF |
| CRP | x | TRIG |
| INSULIN | x | TRIG |
| ACE | x | INSULIN |
| DPP4 | x | INSULIN |

B. Individual Markers comprising interaction terms

Marker
ACE
APOA1
APOB
CHOL
CRP
DPP4
FGA
GLUCOSE
IL6ST
INSULIN
LEP
Proinsulin
SELP
TRIG
VCAM1
VWF

FIGURE 12

Markers of Interest

ADIPOQ
ANG
C3
CCL2
CDK5
CRP
ENG
GLUCOSE
GPT
HP
HSPA1B
IGFBP2
IL2RA
INSULIN-M
LEP
SHBG
TIMP2
TRIG

FIGURE 14

|           | DRS1    | DRS2    | DRS3    |
|-----------|---------|---------|---------|
| AUC       | 0.798   | 0.769   | 0.780   |
| AUC.SE    | 0.0007  | 0.0008  | 0.0008  |
| Pearson   | 0.426   | 0.396   | 0.422   |
| Pearson.p | 4.2E-15 | 4.2E-13 | 8.7E-15 |
| Spearman  | 0.421   | 0.385   | 0.408   |
| Spearman.p| 9.8E-15 | 2.2E-12 | 7.1E-14 |

|       | 1       | 2   | 3         | 4    | 5      | 6      | 7      | 8   | 9    |
|-------|---------|-----|-----------|------|--------|--------|--------|-----|------|
| DRS1: | GLUCOSE | CRP | INSULIN-M | GPT  | HSPA1B | IGFBP2 | ADIPOQ | LEP | TRIG |
| DRS2: | GLUCOSE | CRP | INSULIN-M | TRIG |        |        |        |     |      |
| DRS3: | GLUCOSE | CRP | INSULIN-M | TRIG | HBA1C  |        |        |     |      |

Pearson is the standard correlation coefficient, spearman is a correlation of ranks p values test the hypothesis that the coefficient = 0

FIGURE 15

| Clinical Parameters | Traditional Laboratory Risk Factors | Core Biomarkers I | Core Biomarkers II | Additional Biomarkers I | Additional Biomarkers II |
|---|---|---|---|---|---|
| - Age (AGE)<br>- Body Mass Index (BMI)<br>- Diastolic Blood Pressure (DBP)<br>- Family History (FHX)<br>- Gestational Diabetes Mellitus (GDM), Past<br>- Height (HT)<br>- Hip Circumference (Hip)<br>- Race (RACE)<br>- Sex (SEX)<br>- Systolic Blood Pressure (SBP)<br>- Waist Circumference (Waist)<br>- Weight (WT) | - Cholesterol (CHOL)<br>- Glucose (fasting plasma glucose (FPG/Glucose) or with oral glucose tolerance test (OGTT))<br>- HBA1c (Glycosylated Hemoglobin (HBA1/HBA1C)<br>- High Density Lipoprotein (HDL/HDLC)<br>- Low Density Lipoprotein (LDL/LDLC)<br>- Very Low Density Lipoprotein (VLDLC)<br>- Triglycerides (TRIG) | - Adiponectin (ADIPOQ)<br>- C-Reactive Protein (CRP)<br>- Fibrinogen alpha chain (FGA)<br>- Insulin Pro-insulin, and soluble C-Peptide (any and/or all of which, INS)<br>- Leptin (LEP) | - Advanced Glycosylation End Product-Specific Receptor (AGER)<br>- Alpha-2-HS-Glycoprotein (AHSG)<br>- Angiogenin (ANG)<br>- Apolipoprotein E (APOE)<br>- CD14 molecule (CD14)<br>- Ferritin (FTH1)<br>- Insulin-like growth factor binding protein 1 (IGFBP1)<br>- Interleukin 2 Receptor, Alpha (IL2RA)<br>- Vascular Cell Adhesion Molecule 1 (VCAM1)<br>- Vascular Endothelial Growth Factor (VEGF)<br>- Von Willebrand Factor (VWF) | - Chemokine (C-C motif) ligand 2 aka monocyte chemoattractant protein-1 (CCL2)<br>- Cyclin-dependent kinase 5 (CDK5)<br>- Complement Component 3 (C3)<br>- Fas aka TNF receptor superfamily, member 6 (FAS)<br>- Hepatocyte Growth Factor (HGF)<br>- Interleukin 18 (IL18)<br>- Inhibin, Beta A aka Activin-A (INHBA)<br>- Resistin (RETN)<br>- Selectin-P (SELP)<br>- Tumor Necrosis Factor Receptor Superfamily, member 1 B (TNFRSF1B) | - Angiotensin-Converting Enzyme (ACE)<br>- Complement Component C4 (C4A)<br>- Complement Factor D (Adipsin) (CFD)<br>- Dipeptidyl-Peptidase 4 (CD26) (DPP4)<br>- Haptoglobin (HP)<br>- Interleukin 8 (IL8)<br>- Matrix Metallopeptidase 2 (MMP2)<br>- Selectin E (SELE)<br>- Tumor Necrosis Factor (TNF-Alpha) (TNF)<br>- Tumor Necrosis Factor Superfamily Member 1A (TNFRSF1A) |

FIGURE 18

| Variable | | Controls/Non-Converters (120) | Converters/Cases (47) | p | OR | CI |
|---|---|---|---|---|---|---|
| Family History | No | 14 | 6 | 0.8449 | | |
| | Yes | 106 | 41 | | 0.90 | (0.34-2.69) |
| Glucose Status | NGT | 55 | 14 | 0.1009 | | |
| | IFG | 18 | 5 | | 1.09 | (0.32-3.31) |
| | IGT | 34 | 18 | | 2.08 | (0.92-4.78) |
| | IFG & IGT | 13 | 10 | | 3.02 | (1.09-8.39) |
| Sex | Male | 60 | 25 | 0.7106 | | |
| | Female | 60 | 22 | | 0.88 | (0.45-1.73) |

| Variable | Units | Transform | Non - Converters (n=120) | | | | Converters (n=47) | | | | pvals |
|---|---|---|---|---|---|---|---|---|---|---|---|
| | | | N | Mean | SD | BT (Raw Mean) | N | Mean | SD | BT (Raw Mean) | |
| BMI | kg/m2 | Log | 120 | 1.46 | 0.05 | 28.5 | 47 | 1.46 | 0.05 | 29.1 | 0.2655 |
| AGE | years | Square | 120 | 3,082.81 | 998.08 | 55.5 | 47 | 3,146.58 | 919.92 | 56.1 | 0.7049 |
| WAIST | cm | Log | 120 | 1.97 | 0.05 | 94.1 | 47 | 1.99 | 0.05 | 98.2 | 0.0271 |
| SBP | mm Hg | Log | 120 | 2.13 | 0.05 | 135.6 | 47 | 2.16 | 0.06 | 144.3 | 0.0061 |
| DBP | mm Hg | Log | 120 | 1.92 | 0.05 | 82.6 | 47 | 1.93 | 0.05 | 85.9 | 0.0539 |
| Glucose | nmol/L | Raw | 120 | 5.89 | 0.57 | 5.9 | 47 | 5.94 | 0.62 | 5.9 | 0.6218 |
| Insulin | uIU/ml | Log | 117 | 0.88 | 0.21 | 7.7 | 46 | 1.07 | 0.28 | 11.6 | 0.0000 |
| HBA1C | percent | Raw | 93 | 5.51 | 0.55 | 5.5 | 41 | 5.79 | 0.43 | 5.8 | 0.0034 |
| CHOL | mmol/L | Log | 114 | 0.78 | 0.08 | 6.0 | 44 | 0.77 | 0.08 | 5.8 | 0.3665 |
| TRIG | mmol/L | Log | 114 | 0.13 | 0.21 | 1.3 | 44 | 0.19 | 0.22 | 1.5 | 0.1206 |
| HDL | mmol/L | Log | 115 | 0.12 | 0.10 | 1.3 | 44 | 0.08 | 0.10 | 1.2 | 0.0106 |
| ACE | ng/ml | Log | 93 | 2.28 | 0.17 | 192.1 | 37 | 2.21 | 0.24 | 160.5 | 0.0354 |
| ADIPOQ | ng/ml | Log | 120 | 4.18 | 0.31 | 14,980.6 | 47 | 3.97 | 0.33 | 9,388.8 | 0.0002 |
| AGER | ng/ml | Log | 120 | (0.88) | 0.41 | 0.1 | 47 | (0.97) | 0.43 | 0.1 | 0.1929 |
| AHSG | ng/ml | Log | 120 | 6.21 | 0.12 | 1,603,578.7 | 47 | 6.20 | 0.10 | 1,588,769.2 | 0.8422 |
| ANG | ng/ml | Log | 119 | 2.52 | 0.30 | 332.8 | 46 | 2.58 | 0.28 | 384.2 | 0.2234 |
| APOA2 | ng/ml | Log | 120 | 4.51 | 0.53 | 32,668.1 | 46 | 4.58 | 0.57 | 37,724.7 | 0.5040 |
| APOE | ng/ml | Log | 94 | 4.48 | 0.35 | 30,120.1 | 37 | 4.44 | 0.32 | 27,510.1 | 0.5539 |
| C3 | ng/ml | Log | 94 | 6.09 | 0.29 | 1,240,086.9 | 37 | 6.15 | 0.31 | 1,420,122.3 | 0.3048 |
| CCL2 | ng/ml | Log | 120 | (0.89) | 0.27 | 0.1 | 47 | (0.90) | 0.29 | 0.1 | 0.7503 |
| CD14 | ng/ml | Log | 120 | 3.14 | 0.17 | 1,385.8 | 47 | 3.17 | 0.16 | 1,491.2 | 0.2717 |
| CD36 | ng/ml | Log | 120 | 0.92 | 0.54 | 8.3 | 47 | 0.95 | 0.42 | 8.9 | 0.7441 |
| CD40 | ng/ml | Log | 120 | (1.09) | 0.40 | 0.1 | 46 | (1.11) | 0.39 | 0.1 | 0.7815 |
| CD40LG | ng/ml | Log | 120 | (0.69) | 0.26 | 0.2 | 47 | (0.72) | 0.22 | 0.2 | 0.5541 |
| CDK5 | ng/ml | Log | 120 | 2.07 | 0.19 | 116.4 | 47 | 2.06 | 0.17 | 113.5 | 0.7303 |
| CRP | ng/ml | Log | 120 | 3.15 | 0.56 | 1,424.4 | 47 | 3.50 | 0.51 | 3,172.0 | 0.0003 |
| DPP4 | ng/ml | Log | 94 | 2.61 | 0.32 | 404.1 | 37 | 2.56 | 0.37 | 355.7 | 0.3959 |
| EGF | ng/ml | Log | 120 | (0.15) | 0.40 | 0.7 | 46 | (0.17) | 0.31 | 0.7 | 0.8324 |
| FAS | ng/ml | Log | 120 | 0.11 | 0.24 | 1.3 | 47 | 0.11 | 0.22 | 1.3 | 0.9680 |
| FASLG | ng/ml | Log | 120 | (0.98) | 0.20 | 0.1 | 46 | (1.02) | 0.21 | 0.1 | 0.2359 |
| FGA | ng/ml | Log | 120 | 5.54 | 0.46 | 346,906.9 | 46 | 5.37 | 0.38 | 235,418.9 | 0.0291 |
| FTH1 | ng/ml | Log | 120 | 2.80 | 0.55 | 635.4 | 47 | 2.72 | 0.57 | 520.9 | 0.3695 |
| HGF | ng/ml | Log | 120 | (0.18) | 0.23 | 0.7 | 47 | (0.09) | 0.24 | 0.8 | 0.0328 |
| ICAM1 | ng/ml | Log | 91 | 2.85 | 0.65 | 704.2 | 36 | 2.81 | 0.72 | 650.0 | 0.7936 |
| IGFBP1 | ng/ml | Log | 120 | 0.65 | 0.37 | 4.5 | 47 | 0.65 | 0.44 | 4.5 | 0.9993 |
| IGFBP3 | ng/ml | Log | 120 | 1.52 | 0.43 | 32.8 | 46 | 1.56 | 0.40 | 36.5 | 0.5364 |
| IL18 | ng/ml | Log | 120 | (0.84) | 0.17 | 0.1 | 47 | (0.79) | 0.23 | 0.2 | 0.1617 |
| IL2 | ng/ml | Log | 120 | (0.26) | 0.84 | 0.6 | 46 | (0.24) | 0.93 | 0.6 | 0.9027 |
| IL2RA | ng/ml | Log | 120 | (0.49) | 0.22 | 0.3 | 46 | (0.48) | 0.27 | 0.3 | 0.6937 |
| IL6R | ng/ml | Log | 120 | 0.70 | 0.17 | 5.1 | 47 | 0.75 | 0.18 | 5.6 | 0.1540 |
| IL6ST | ng/ml | Log | 120 | 2.07 | 0.35 | 118.2 | 46 | 1.99 | 0.38 | 96.6 | 0.1585 |
| IL8 | ng/ml | Log | 120 | (1.86) | 0.60 | 0.0 | 46 | (1.83) | 0.70 | 0.0 | 0.7787 |
| INHBA | ng/ml | Log | 120 | (0.28) | 0.42 | 0.5 | 46 | (0.23) | 0.48 | 0.6 | 0.5650 |
| LEP | ng/ml | Log | 119 | 1.22 | 0.42 | 16.5 | 47 | 1.29 | 0.38 | 19.6 | 0.2968 |
| MMP2 | ng/ml | Log | 120 | 1.89 | 0.37 | 78.1 | 47 | 1.91 | 0.32 | 80.5 | 0.8327 |
| MMP9 | ng/ml | Log | 120 | 2.39 | 0.32 | 243.7 | 47 | 2.46 | 0.24 | 288.9 | 0.1508 |
| RETN | ng/ml | Log | 120 | 1.23 | 0.21 | 17.1 | 46 | 1.28 | 0.23 | 19.1 | 0.2028 |
| SELE | ng/ml | Log | 115 | 1.51 | 0.27 | 32.6 | 46 | 1.55 | 0.24 | 35.2 | 0.4615 |
| SELP | ng/ml | Log | 94 | 2.17 | 0.31 | 147.8 | 37 | 2.15 | 0.27 | 140.2 | 0.6968 |
| TNFRSF1B | ng/ml | Log | 120 | 0.59 | 0.19 | 3.9 | 46 | 0.62 | 0.21 | 4.1 | 0.4655 |
| VCAM1 | ng/ml | Log | 120 | 2.53 | 0.15 | 339.5 | 47 | 2.52 | 0.18 | 335.0 | 0.8294 |
| VEGF | ng/ml | Log | 120 | (0.83) | 0.36 | 0.1 | 46 | (0.82) | 0.39 | 0.2 | 0.8580 |
| VWF | ng/ml | Log | 120 | 4.22 | 0.30 | 16,666.2 | 47 | 4.18 | 0.35 | 15,080.2 | 0.4289 |

FIGURE 21

| Model | Marker Selection | AUC Fitted | AUC 10-Fold CV | Parameters Included |
|---|---|---|---|---|
| Clinical (LDA) | Stepwise | 0.67 | 0.61 | Waist, SBP |
| Stern et al. (2002) | | | 0.63 | Age, Sex, Fasting Glucose, SBP, HDLC, BMI, Family History, Race |
| LDA | Univariate | 0.71 | 0.71 | Insulin |
| LDA | Bivariate | 0.75 | 0.74 | ADIPOQ, CRP |
| LDA | Trivariate | 0.79 | 0.76 | ADIPOQ, IGFBP1, Insulin |
| Logistic Regression | Forward (AIC) | 0.86 | 0.61 | Insulin, ADIPOQ, IGFBP1, CRP, HBA1C, FGA, AGER |
| Logistic Regression | Backward (AIC) | 0.91 | 0.57 | SBP, Glucose, Insulin, HBA1C, CHOL, TRIG, ADIPOQ, APOA2, CRP, DPP4, EGF, FAS, FGA, IGFBP1, IL6ST, INHBA, MMP2, RETN, TNFRSF1B, VCAM1, VWF |
| LDA | Forward (T2) | 0.86 | 0.76 | Insulin, HBA1C, ADIPOQ, CRP, FAS, FGA, IGFBP1, RETN, VCAM1, VWF |
| LDA | Backward (T2) | 0.86 | 0.74 | Insulin, HBA1C, ADIPOQ, CRP, FAS, FGA, IGFBP1, RETN, VCAM1, VWF |
| LDA | Stepwise (T2) | 0.85 | 0.78 | Insulin, HBA1C, ADIPOQ, CRP, FAS, FGA, IGFBP1 |
| LDA | ELDA | 0.83 | 0.76 | DBP, Insulin, HBA1C, ADIPOQ, CRP, FGA |
| SVM | KW (5) | 0.80 | 0.75 | Insulin, HBA1C, ADIPOQ, CRP, HGF |
| SVM | RF (9) | 0.97 | 0.73 | BMI, Insulin, HBA1C, HDLC, ADIPOQ, ANG, CRP, FGA, HGF |

FIGURE 25

| Variable | Units | Transform | Non-Converters (n=236) | | | | Converters (n=100) | | | | Diabetics (n=48) | | | | pvals | KW |
|---|---|---|---|---|---|---|---|---|---|---|---|---|---|---|---|---|
| | | | N | Mean | SD | BT (Raw Mean) | N | Mean | SD | BT (Raw Mean) | N | Mean | SD | BT (Raw Mean) | | |
| Glucose | mmol/L | Raw | 236 | 5.61 | 0.50 | 5.6 | 100 | 5.95 | 0.55 | 5.9 | 48 | 8.91 | 3.84 | 8.9 | 2.32E-37 | 6.37E-23 |
| Insulin | pmol/L | Log | 236 | 1.59 | 0.24 | 39.1 | 100 | 1.72 | 0.27 | 52.6 | 47 | 1.80 | 0.21 | 63.0 | 1.02E-08 | 2.08E-08 |
| POMC | ng/ml | Log | 236 | 1.23 | 0.33 | 17.1 | 100 | 1.27 | 0.34 | 18.6 | 48 | 1.50 | 0.22 | 31.4 | 2.72E-06 | 7.66E-07 |
| TRIG | mmol/L | Log | 236 | 0.13 | 0.23 | 1.3 | 100 | 0.22 | 0.23 | 1.7 | 48 | 0.27 | 0.25 | 1.9 | 3.25E-05 | 1.53E-05 |
| CRP | ng/ml | Log | 236 | 3.30 | 0.58 | 1,987.1 | 100 | 3.58 | 0.53 | 3,837.6 | 48 | 3.51 | 0.54 | 3,271.4 | 4.70E-05 | 2.62E-05 |
| Waist | cm | Log | 235 | 1.97 | 0.05 | 92.8 | 100 | 1.98 | 0.06 | 95.2 | 48 | 2.00 | 0.06 | 100.5 | 1.35E-04 | 6.25E-04 |
| HGF | ng/ml | Log | 236 | (0.07) | 0.27 | 0.9 | 100 | (0.04) | 0.20 | 0.9 | 48 | 0.09 | 0.15 | 1.2 | 4.70E-05 | 2.62E-08 |
| FTH1 | ng/ml | Log | 236 | 2.67 | 0.53 | 468.8 | 100 | 2.78 | 0.56 | 603.3 | 48 | 3.00 | 0.60 | 1,008.0 | 2.56E-04 | 6.25E-04 |
| SELP | ng/ml | Log | 236 | 2.65 | 0.29 | 442.9 | 100 | 2.73 | 0.30 | 531.4 | 48 | 2.81 | 0.28 | 642.4 | 5.62E-04 | 3.26E-04 |
| APOA1 | ng/ml | Log | 236 | 6.60 | 0.24 | 3,940,732.2 | 100 | 6.59 | 0.20 | 3,877,087.1 | 48 | 6.72 | 0.26 | 5,269,204.8 | 8.70E-04 | 1.28E-03 |
| ADIPOQ | ng/ml | Log | 236 | 4.38 | 0.46 | 24,126.0 | 100 | 4.32 | 0.48 | 20,672.6 | 48 | 4.13 | 0.31 | 13,557.6 | 0.002 | 0.002 |
| SBP | mm Hg | Log | 236 | 2.12 | 0.06 | 132.7 | 100 | 2.14 | 0.06 | 136.9 | 48 | 2.15 | 0.07 | 142.3 | 0.002 | 0.000 |
| BMI | kg/m2 | Log | 236 | 1.16 | 0.44 | 14.3 | 100 | 1.26 | 0.42 | 18.4 | 48 | 1.36 | 0.44 | 22.9 | 0.003 | 0.000 |
| LEP | ng/ml | Log | 236 | 1.46 | 0.05 | 28.6 | 100 | 1.46 | 0.07 | 29.0 | 48 | 1.49 | 0.07 | 30.7 | 0.005 | 0.004 |
| SCp | pg/ml | Sqrt | 209 | 24.14 | 3.64 | 582.6 | 72 | 25.22 | 4.05 | 635.9 | 33 | 26.11 | 5.01 | 682.0 | 0.005 | 0.003 |
| IGFBP3 | ng/ml | Log | 236 | 1.85 | 0.18 | 71.3 | 100 | 1.84 | 0.17 | 68.7 | 48 | 1.77 | 0.12 | 58.9 | 0.008 | 0.008 |
| IL2RA | ng/ml | Log | 236 | (0.56) | 0.22 | 0.3 | 100 | (0.51) | 0.20 | 0.3 | 48 | (0.61) | 0.18 | 0.2 | 0.009 | 0.001 |
| IL18 | ng/ml | Log | 236 | (0.54) | 0.25 | 0.3 | 100 | (0.48) | 0.18 | 0.3 | 48 | (0.59) | 0.25 | 0.3 | 0.016 | 0.005 |
| SELE | ng/ml | Log | 236 | 1.90 | 0.29 | 78.8 | 100 | 1.94 | 0.28 | 86.9 | 48 | 2.01 | 0.24 | 101.4 | 0.020 | 0.002 |
| VCAM1 | ng/ml | Log | 236 | 2.60 | 0.17 | 394.2 | 100 | 2.60 | 0.18 | 393.6 | 48 | 2.67 | 0.16 | 465.1 | 0.038 | 0.046 |
| VEGF | ng/ml | Log | 236 | (0.59) | 0.32 | 0.3 | 100 | (0.51) | 0.22 | 0.3 | 48 | (0.51) | 0.29 | 0.3 | 0.039 | 0.018 |
| Age | years | Raw | 236 | 48.81 | 6.32 | 48.8 | 100 | 49.60 | 6.79 | 49.6 | 48 | 51.26 | 6.43 | 51.3 | 0.043 | 0.055 |
| C3 | ng/ml | Log | 236 | 6.62 | 0.64 | 4,199,760.5 | 100 | 6.56 | 0.57 | 3,641,204.8 | 48 | 6.40 | 0.40 | 2,518,435.9 | 0.051 | 0.043 |
| TNFRSF1B | ng/ml | Log | 236 | 0.60 | 0.18 | 4.0 | 100 | 0.64 | 0.18 | 4.4 | 48 | 0.64 | 0.16 | 4.4 | 0.061 | 0.346 |
| HDLC | mmol/L | Log | 236 | 0.11 | 0.12 | 1.3 | 100 | 0.09 | 0.12 | 1.2 | 48 | 0.08 | 0.11 | 1.2 | 0.067 | 0.065 |
| CCL2 | ng/ml | Log | 236 | (0.86) | 0.24 | 0.1 | 100 | (0.79) | 0.46 | 0.2 | 48 | (0.84) | 0.29 | 0.1 | 0.130 | 0.139 |
| DBP | mm Hg | Log | 236 | 1.92 | 0.06 | 84.1 | 100 | 1.94 | 0.06 | 86.4 | 48 | 1.94 | 0.05 | 86.5 | 0.138 | 0.563 |
| VWF | ng/ml | Log | 236 | 4.14 | 0.25 | 13,788.1 | 100 | 4.17 | 0.28 | 14,781.2 | 47 | 4.21 | 0.30 | 16,293.4 | 0.170 | 0.205 |
| Hip | cm | Log | 235 | 2.02 | 0.04 | 105.0 | 100 | 2.02 | 0.04 | 104.9 | 48 | 2.03 | 0.04 | 107.5 | 0.204 | 0.278 |
| IL6ST | ng/ml | Log | 236 | 2.44 | 0.20 | 275.0 | 100 | 2.46 | 0.22 | 291.1 | 48 | 2.49 | 0.19 | 310.1 | 0.219 | 0.342 |
| WT | kg/m2 | Log | 236 | 1.93 | 0.07 | 85.3 | 100 | 1.93 | 0.08 | 85.9 | 48 | 1.95 | 0.08 | 89.3 | 0.226 | 0.238 |
| AHSG | ng/ml | Log | 204 | 5.83 | 0.55 | 668,647.2 | 85 | 5.75 | 0.52 | 567,482.2 | 48 | 5.91 | 0.22 | 813,085.2 | 0.229 | 0.521 |
| HT | cm | Raw | 236 | 172.97 | 9.49 | 173.0 | 100 | 172.40 | 9.11 | 172.4 | 48 | 170.85 | 10.66 | 170.9 | 0.232 | 0.513 |
| LDL | mmol/L | Sqrt | 232 | 1.92 | 0.24 | 3.7 | 97 | 1.93 | 0.25 | 3.7 | 45 | 1.89 | 0.23 | 3.6 | 0.370 | 0.443 |
| FGA | ng/ml | Log | 236 | 6.24 | 0.30 | 1,737,402.0 | 100 | 6.23 | 0.30 | 1,716,234.3 | 48 | 6.19 | 0.28 | 1,555,943.7 | 0.570 | 0.753 |
| ICAM1 | ng/ml | Log | 236 | 2.95 | 0.27 | 898.6 | 100 | 2.97 | 0.28 | 926.0 | 48 | 2.92 | 0.22 | 838.0 | 0.600 | 0.543 |
| IL8 | mmol/L | Log | 236 | (2.08) | 0.41 | 0.0 | 100 | (2.04) | 0.39 | 0.0 | 48 | (2.06) | 0.29 | 0.0 | 0.658 | 0.814 |
| CHOL | ng/ml | Log | 236 | 0.76 | 0.08 | 5.7 | 100 | 0.77 | 0.08 | 5.8 | 48 | 0.76 | 0.08 | 5.8 | 0.685 | 0.629 |
| IL6R | ng/ml | Log | 236 | 1.31 | 0.21 | 20.3 | 100 | 1.32 | 0.18 | 20.8 | 48 | 1.33 | 0.22 | 21.3 | 0.693 | 0.618 |
| AGER | ng/ml | Log | 236 | (1.09) | 0.34 | 0.1 | 100 | (1.11) | 0.38 | 0.1 | 48 | (1.13) | 0.35 | 0.1 | 0.747 | 0.791 |
| CDK5 | ng/ml | Log | 236 | 1.71 | 0.25 | 51.6 | 100 | 1.70 | 0.25 | 50.0 | 48 | 1.69 | 0.29 | 48.6 | 0.748 | 0.503 |
| IGF1 | ng/ml | Log | 236 | 1.02 | 0.40 | 10.4 | 100 | 1.03 | 0.46 | 10.6 | 48 | 1.06 | 0.34 | 11.4 | 0.766 | 0.542 |
| INHBA | ng/ml | Log | 236 | 0.52 | 0.31 | 3.3 | 100 | 0.52 | 0.32 | 3.3 | 48 | 0.49 | 0.33 | 3.1 | 0.815 | 0.796 |
| CD14 | ng/ml | Log | 236 | 3.55 | 0.34 | 3,552.3 | 202 | 3.56 | 0.37 | 3,626.5 | 48 | 3.53 | 0.26 | 3,368.9 | 0.845 | 0.723 |
| ANG | ng/ml | Log | 236 | 2.64 | 0.32 | 432.9 | 86 | 2.65 | 0.35 | 444.7 | 48 | 2.62 | 0.44 | 412.5 | 0.866 | 0.816 |
| APOE | ng/ml | Log | 231 | 4.70 | 0.33 | 50,602.9 | 100 | 4.69 | 0.35 | 48,821.5 | 48 | 4.71 | 0.29 | 51,028.5 | 0.871 | 0.799 |
| DPP4 | ng/ml | Log | 236 | 2.69 | 0.23 | 490.1 | 94 | 2.70 | 0.23 | 498.4 | 48 | 2.68 | 0.18 | 479.9 | 0.914 | 0.969 |
| IGFBP1 | ng/ml | Log | 236 | 0.78 | 0.45 | 6.0 | 100 | 0.76 | 0.56 | 5.7 | 48 | 0.78 | 0.42 | 6.1 | 0.935 | 0.967 |
| ACE | ng/ml | Log | 236 | 2.29 | 0.19 | 194.0 | 99 | 2.29 | 0.20 | 194.4 | 48 | 2.30 | 0.36 | 198.1 | 0.966 | 0.466 |

FIG. 26B

| | HT | WT | Waist | Hip | Age | BMI | SBP | DBP | CHOL | HDLC | LDL | TRIG | SCp | Insulin | Glucose | ACE |
|---|---|---|---|---|---|---|---|---|---|---|---|---|---|---|---|---|
| AGER | 0.08 | (0.03) | (0.05) | (0.11) | (0.05) | (0.10) | (0.14) | (0.13) | 0.05 | (0.10) | 0.03 | 0.09 | (0.00) | (0.02) | (0.10) | 0.15 |
| AHSG | (0.05) | (0.00) | (0.01) | 0.00 | 0.06 | 0.04 | (0.03) | (0.02) | 0.04 | 0.04 | 0.03 | (0.00) | 0.03 | 0.05 | 0.05 | 0.05 |
| ANG | 0.06 | 0.08 | 0.08 | (0.01) | (0.00) | 0.05 | 0.07 | 0.07 | 0.15 | 0.03 | 0.11 | 0.15 | 0.05 | 0.07 | 0.10 | 0.14 |
| APOA1 | (0.02) | (0.09) | (0.12) | (0.05) | (0.13) | (0.10) | 0.02 | (0.01) | 0.12 | 0.24 | 0.06 | (0.03) | (0.01) | (0.05) | (0.03) | 0.16 |
| APOE | 0.10 | 0.08 | 0.10 | 0.02 | 0.01 | 0.02 | 0.02 | 0.05 | 0.15 | (0.14) | 0.16 | 0.16 | 0.09 | 0.09 | 0.09 | 0.11 |
| C3 | (0.14) | (0.04) | (0.02) | (0.00) | 0.08 | 0.06 | (0.05) | (0.03) | 0.08 | (0.07) | 0.10 | 0.07 | (0.03) | 0.02 | 0.02 | (0.00) |
| CCL2 | (0.08) | (0.03) | (0.01) | (0.01) | (0.03) | (0.03) | 0.00 | (0.03) | (0.05) | (0.08) | (0.03) | 0.05 | 0.00 | 0.09 | (0.01) | 0.11 |
| CD14 | (0.06) | (0.02) | (0.04) | 0.01 | 0.12 | 0.03 | (0.02) | (0.04) | 0.10 | 0.00 | 0.10 | 0.01 | 0.06 | 0.07 | (0.02) | 0.28 |
| CDK5 | 0.02 | (0.02) | (0.03) | (0.03) | (0.04) | (0.04) | (0.05) | (0.09) | (0.01) | (0.03) | (0.02) | (0.01) | (0.01) | (0.06) | (0.02) | 0.03 |
| CRP | (0.13) | 0.23 | 0.29 | 0.30 | 0.15 | 0.39 | 0.15 | 0.13 | 0.06 | (0.04) | 0.06 | 0.06 | 0.21 | 0.33 | 0.10 | 0.08 |
| DPP4 | (0.03) | 0.03 | 0.11 | 0.04 | 0.03 | 0.06 | 0.12 | 0.11 | 0.04 | (0.04) | (0.01) | 0.04 | 0.02 | 0.10 | (0.02) | 0.29 |
| FGA | (0.04) | (0.00) | (0.02) | 0.09 | 0.20 | 0.03 | 0.01 | (0.04) | 0.11 | 0.01 | 0.12 | 0.02 | 0.05 | 0.06 | (0.05) | 0.16 |
| FTH1 | 0.35 | 0.19 | 0.25 | (0.12) | 0.11 | (0.05) | 0.24 | 0.21 | 0.22 | (0.11) | 0.16 | 0.24 | 0.12 | 0.09 | 0.25 | 0.20 |
| HGF | (0.19) | (0.02) | 0.06 | 0.07 | (0.04) | 0.13 | (0.02) | (0.05) | (0.05) | (0.13) | (0.04) | 0.08 | 0.10 | 0.16 | (0.01) | 0.09 |
| ICAM1 | (0.08) | (0.01) | 0.05 | 0.01 | 0.01 | 0.05 | (0.02) | (0.01) | (0.04) | (0.05) | (0.05) | 0.04 | 0.04 | 0.06 | (0.08) | 0.36 |
| IGF1 | 0.09 | 0.08 | 0.02 | (0.00) | (0.17) | 0.02 | (0.03) | 0.00 | (0.16) | (0.12) | (0.12) | (0.03) | 0.06 | 0.22 | (0.03) | 0.06 |

Min Max: 1.00 / 0.05 – (0.5) / 0.05 – (0.50) / (1.00)

| | ADIPOQ | AGER | AHSG | ANG | APOA1 | APOE | C3 | CCL2 | CD14 | CDK5 | CRP | DPP4 | FGA | FTH1 | HGF | ICAM1 |
|---|---|---|---|---|---|---|---|---|---|---|---|---|---|---|---|---|
| IGFBP1 | 0.09 | (0.01) | 0.03 | (0.05) | 0.15 | (0.29) | 0.06 | 0.12 | 0.03 | 0.07 | 0.02 | 0.05 | 0.09 | (0.20) | 0.09 | 0.08 |
| IGFBP3 | 0.21 | (0.03) | 0.08 | 0.13 | 0.11 | 0.58 | (0.07) | (0.04) | (0.05) | (0.14) | (0.09) | 0.20 | 0.08 | 0.10 | 0.01 | 0.00 |
| IL18 | (0.05) | 0.09 | (0.06) | 0.12 | (0.00) | 0.11 | (0.09) | 0.28 | 0.07 | 0.09 | 0.21 | 0.08 | 0.07 | 0.14 | 0.38 | 0.22 |
| IL2RA | (0.13) | 0.07 | (0.01) | 0.06 | 0.11 | (0.19) | 0.06 | 0.29 | 0.03 | 0.04 | 0.12 | (0.14) | 0.21 | (0.10) | 0.27 | 0.13 |
| IL6R | 0.15 | 0.04 | 0.22 | 0.08 | 0.15 | 0.13 | 0.04 | 0.04 | 0.10 | 0.02 | 0.14 | 0.49 | 0.14 | 0.06 | 0.15 | 0.19 |
| IL6ST | 0.20 | 0.06 | 0.10 | 0.12 | 0.25 | 0.20 | (0.04) | 0.10 | 0.05 | (0.05) | 0.07 | 0.57 | 0.09 | 0.16 | 0.11 | 0.32 |
| IL8 | 0.06 | 0.11 | 0.14 | 0.17 | 0.03 | 0.11 | (0.10) | 0.41 | 0.15 | (0.02) | 0.06 | 0.23 | (0.04) | 0.11 | 0.21 | 0.05 |
| INHBA | (0.02) | (0.14) | (0.02) | (0.02) | 0.01 | (0.00) | (0.05) | 0.03 | (0.09) | 0.15 | (0.05) | 0.01 | (0.05) | (0.02) | 0.30 | 0.06 |
| LEP | 0.35 | (0.08) | 0.07 | 0.02 | 0.13 | 0.01 | 0.06 | 0.06 | 0.11 | (0.07) | 0.36 | 0.20 | 0.15 | 0.29 | 0.20 | 0.12 |
| POMC | (0.15) | 0.06 | 0.01 | (0.19) | (0.25) | (0.04) | 0.04 | 0.24 | (0.26) | (0.17) | (0.07) | 0.11 | (0.06) | (0.08) | 0.12 | 0.03 |
| SELE | (0.12) | (0.15) | 0.03 | 0.08 | 0.08 | (0.08) | (0.03) | 0.09 | 0.01 | 0.16 | 0.04 | 0.04 | 0.01 | 0.16 | 0.31 | 0.24 |
| SELP | 0.17 | 0.10 | (0.16) | 0.15 | 0.13 | 0.14 | (0.05) | 0.14 | 0.32 | (0.07) | 0.24 | 0.19 | 0.23 | 0.19 | 0.16 | 0.35 |
| TNFRSF1B | 0.04 | 0.03 | (0.05) | 0.13 | 0.08 | 0.05 | 0.00 | 0.11 | 0.22 | (0.14) | 0.25 | 0.09 | 0.31 | 0.05 | 0.07 | 0.20 |
| VCAM1 | 0.17 | 0.02 | 0.02 | 0.10 | 0.19 | 0.27 | (0.08) | 0.04 | 0.05 | (0.03) | (0.01) | 0.25 | 0.19 | 0.11 | 0.01 | 0.34 |
| VEGF | 0.06 | 0.05 | 0.03 | 0.06 | (0.03) | (0.10) | 0.08 | 0.12 | 0.05 | (0.07) | 0.22 | (0.06) | 0.03 | (0.04) | 0.19 | 0.03 |
| VWF | 0.22 | 0.00 | 0.03 | 0.20 | 0.27 | 0.08 | 0.05 | 0.00 | 0.20 | (0.03) | 0.24 | 0.15 | 0.43 | 0.00 | 0.13 | 0.29 |

Min Max
1.00
0.05
–
(0.5)
0.05
–
(0.50)
(1.00)

FIGURE 29

| Parameter | Example 1 | Example 2 | Clinical Parameters | Traditional Laboratory Risk Markers | Core Biomarkers I | Core Biomarkers II | Additional Biomarkers I | Additional Biomarkers II |
|---|---|---|---|---|---|---|---|---|
| AGE | x | x | x | | | | | |
| BMI | x | x | x | | | | | |
| DBP | x | x | x | | | | | |
| FHX | x | x | x | | | | | |
| GDM | | | x | | | | | |
| Hip | x | | x | | | | | |
| HT | x | | x | | | | | |
| RACE | | | x | | | | | |
| SBP | x | x | x | | | | | |
| SEX | x | x | x | | | | | |
| WAIST | x | x | x | | | | | |
| WT | x | | x | | | | | |
| CHOL | x | x | | x | | | | |
| Glucose | x | x | | x | | | | |
| HBA1C | x | | | x | | | | |
| HDL/HDLC | x | x | | x | | | | |
| LDL/LDLC | x | | | x | | | | |
| VLDL | | | | x | | | | |
| TRIG | x | x | | x | | | | |
| ACE | x | x | | | | | | x |
| ADIPOQ | x | x | | | x | | | |
| AGER | x | x | | | | x | | |
| AHSG | x | x | | | | x | | |
| ANG | x | x | | | | x | | |
| APOA1 | | x | | | | | | |
| APOA2 | x | | | | | | | |
| APOE | x | x | | | | x | | |
| C3 | x | x | | | | | x | |
| C4A | | | | | | | | x |
| CCL2 | x | x | | | | | x | |
| CD14 | x | x | | | | x | | |
| CD36 | x | | | | | | | |
| CD40 | x | | | | | | | |
| CD40LG | x | | | | | | | |
| CDK5 | x | x | | | | | x | |
| CFD | | | | | | | | x |
| CRP | x | x | | | x | | | |
| DPP4 | x | x | | | | | | x |
| EGF | x | | | | | | | |
| FAS | x | | | | | | x | |
| FASLG | x | | | | | | | |
| FGA | x | x | | | x | | | |
| FTH1 | x | x | | | | x | | |
| HGF | x | x | | | | | x | |
| HP | | | | | | | | x |
| ICAM1 | x | x | | | | | | |
| IGF1 | | x | | | | | | |
| IGFBP1 | x | x | | | | x | | |
| IGFBP3 | x | x | | | | | | |
| IL18 | x | x | | | | | x | |
| IL2 | x | | | | | | | |
| IL2RA | x | x | | | | x | | |
| IL6R | x | x | | | | | | |
| IL6ST | x | x | | | | | | |
| IL8 | x | x | | | | | | x |
| INHBA | x | x | | | | | x | |
| Insulin | x | x | | | x | | | |
| LEP | x | x | | | x | | | |
| MMP2 | x | | | | | | | x |
| MMP9 | x | | | | | | | |
| POMC | | x | | | | | | |
| RETN | x | | | | | | x | |
| SCp/sCP | x | | | | x | | | |
| SELE | x | x | | | | | | x |
| SELP | x | x | | | | | x | |
| TNF | | | | | | | | x |
| TNFRSF1A | | | | | | | | x |
| TNFRSF1B | x | x | | | | | x | |
| VCAM1 | x | x | | | | x | | |
| VEGF | x | x | | | | x | | |
| VWF | x | x | | | | x | | |

FIG. 30A

| | ALL PARAMETERS, TOTAL EXAMPLE 1 POPULATION | | | | | | | ALL PARAMETERS, BASE EXAMPLE 1 POPULATION ONLY | | | | | | |
|---|---|---|---|---|---|---|---|---|---|---|---|---|---|---|
| | LDA-FWD | LDA-BWD | LDA-SWS | SVMI-KW5 | SVMI-RF9 | LDA-ELDA3 | LDA-ELDA2 | LDA-FWD | LDA-BWD | LDA-SWS | SVMI-KW5 | SVMI-RF9 | LDA-ELDA3 | LDA-ELDA2 |
| BMI | | | | | | | | | | | | x | | |
| SBP | | | | x | | | | | | | | | | |
| DBP | | | | | | x | x | | | | | | x | x |
| Glucose | | | | | | x | x | | | | | | | |
| Insulin | x | x | x | x | x | x | x | x | x | x | x | x | x | x |
| HBA1C | x | x | x | x | x | x | x | x | x | | x | x | x | x |
| TRIG | | | | | | | | | | | | x | x | x |
| HDL | | | | | | | | | | | | x | | x |
| ADIPOQ | x | x | x | x | x | x | x | | | x | x | x | x | x |
| AGER | x | x | | | | | | | | | | x | | |
| ANG | x | x | | | | | | | | | | | | |
| APOE | | | | | | | | | | | | | | |
| C3 | | | | | | | | | | | | | | x |
| CD36 | | | | | | | | | | | | | | x |
| CD40LG | | | | | x | | | | | | | | | |
| CRP | x | x | x | x | x | x | x | x | x | x | x | | x | x |
| FAS | x | | | | x | x | x | x | x | x | | | | |
| FASLG | | | | | x | x | x | | | | | | | |
| FGA | x | x | x | | | | | x | | x | | x | | x |
| HGF | x | x | | | | | | | | x | x | | x | x |
| IGFBP1 | | | | | x | | x | | | | | | | |
| IGFBP3 | | | | | | | x | | | | | | | |
| IL2 | | | | | | | | | | | | | | |
| IL18 | | | | | | | x | | | | | | | x |
| INHBA | | | | | | | | | | | | | | x |
| LEP | | | | | | | x | | | | | | | |
| MMP2 | | | | | | | | | | | | | | |
| MMP9 | | | | | | | | | | | | | | x |
| RETN | | | | | | | | | | | x | | | |
| SELP | | | | | | | | | x | | x | | | |
| VWF | | x | | | | | | | x | | | | | |
| AUC | 0.82 | 0.82 | 0.80 | 0.78 | 0.96 | 0.77 | 0.79 | 0.86 | 0.86 | 0.85 | 0.80 | 0.97 | 0.83 | 0.84 |

FIG. 30B

| | LDA-FWD | LDA-BWD | LDA-SWS | SVMl-KW5 | SVMl-RF9 | LDA-ELDA3 | LDA-ELDA2 | | LDA-FWD | LDA-BWD | LDA-SWS | SVMl-KW5 | SVMl-RF9 | LDA-ELDA3 | LDA-ELDA2 |
|---|---|---|---|---|---|---|---|---|---|---|---|---|---|---|---|
| | BLOOD BIOMARKERS ONLY, TOTAL EXAMPLE 1 POPULATION | | | | | | | | BLOOD BIOMARKERS ONLY, BASE EXAMPLE 1 POPULATION ONLY | | | | | | |
| Insulin | X | X | X | X | X | X | X | | X | X | X | X | X | X | X |
| HBA1C | X | X | X | X | X | X | X | | X | X | X | X | X | X | X |
| TRIG | | | | | X | | | | | | | | | | |
| ACE | | | | | | | X | | | | | | X | | X |
| ADIPOQ | X | X | X | X | X | X | X | | | | | | | | X |
| AGER | X | X | X | | X | X | X | | | | | | | X | X |
| ANG | | | | | | | X | | | | | | | | X |
| APOA2 | X | | | | | | X | | | | | | | | X |
| APOE | | X | | | | | X | | | | | | | | |
| CD14 | | | | | | | | | | | | | | | X |
| CD36 | | | | | | | X | | | | | | X | | X |
| CD40LG | | | | | | | | | | | | | | | |
| CRP | X | X | X | X | | X | X | | X | X | X | X | X | X | X |
| EGF | | | | | | | | | | | | | | | |
| FAS | | | | | | | X | | | X | | | X | | |
| FASLG | | | | | | | X | | | | | | | | |
| FGA | X | X | X | X | X | X | X | | X | X | X | | X | | X |
| FTH1 | | | | | | | | | | | | | | | X |
| HGF | X | X | | | | | X | | | | X | X | | | X |
| IGFBP1 | | X | | | X | | | | X | | | | X | | X |
| IGFBP3 | | | | | X | | | | | | | | X | | X |
| IL2 | | | | | | | | | | | | | | | |
| IL18 | | | | | | | X | | | | | | | | X |
| LEP | | | | | | | X | | | | | | | | |
| MMP9 | | | | | | | X | | | | | | | | |
| SELP | | | | | | | | | | | | | X | | X |
| VCAM1 | | X | | | | | | | X | X | | | | | |
| VWF | | | | | | | X | | X | X | | | | | |
| AUC | 0.82 | 0.82 | 0.80 | 0.79 | 0.98 | 0.80 | 0.80 | | 0.86 | 0.87 | 0.84 | 0.80 | 0.94 | 0.82 | 0.86 |

FIG. 30C

| Parameter | ALL PARAMETERS, TOTAL EXAMPLE 2 POPULATION | | | | | | | ALL PARAMETERS, BASE EXAMPLE 2 POPULATION ONLY | | | | | | |
|---|---|---|---|---|---|---|---|---|---|---|---|---|---|---|
| | LDA-FWD | LDA-BWD | LDA-SWS | SVMI-KW5 | SVMI-RF9 | LDA-ELDA3 | LDA-ELDA2 | LDA-FWD | LDA-BWD | LDA-SWS | SVMI-KW5 | SVMI-RF9 | LDA-ELDA3 | LDA-ELDA2 |
| Waist | | | | | X | | | | | | | | | |
| BMI | | X | | | X | | | | | | X | X | | |
| SBP | | X | | | | | | | | | | | | |
| CHOL | | X | | | | | | | | | | | | |
| HDLC | | X | | | | | | | | | | | | |
| LDL | | X | | | | | | | | | | | | |
| TRIG | | X | | X | X | | X | | X | | X | X | | X |
| SCp | | X | | X | | | X | | | | | | X | X |
| Insulin | X | X | X | X | | | X | X | X | X | X | X | | X |
| Glucose | X | | X | X | X | X | | X | X | X | X | X | X | X |
| ADIPOQ | | X | X | | | X | | X | X | X | | X | | |
| AHSG | X | | X | | | | | | | | | | | |
| C3 | | X | | | | | | | | | | | | |
| CD14 | | | | | | | | | | | | X | | |
| CRP | X | | X | X | X | X | X | X | X | X | X | X | X | X |
| FTH1 | | | | | | | X | | | | | | | |
| IL18 | | | | | X | | | | | | | X | | X |
| IL2RA | | | | | X | | | | | | | | | X |
| LEP | | X | | | | | | | | | | X | | X |
| VEGF | | X | | | | | X | | | | | | | X |
| VWF | | | | | X | | | | | | | X | | |
| AUC | 0.75 | 0.80 | 0.75 | 0.74 | 0.97 | 0.72 | 0.74 | 0.77 | 0.77 | 0.77 | 0.77 | 0.99 | 0.76 | 0.78 |

FIG. 30D

BLOOD BIOMARKERS ONLY, TOTAL EXAMPLE 2 POPULATION

| | LDA-FWD | LDA-BWD | LDA-SWS | SVMI-KW5 | SVMI-RF9 | LDA-ELDA3 | LDA-ELDA2 |
|---|---|---|---|---|---|---|---|
| SCp | X | | | X | | X | X |
| Insulin | X | X | X | X | X | | X |
| Glucose | | X | X | X | X | X | X |
| ADIPOQ | X | X | X | | X | | |
| AHSG | | | | | | | |
| ANG | | | | | | | X |
| CCL2 | | | | | | | |
| CD14 | | | | | | | |
| CRP | X | X | X | X | X | X | X |
| FTH1 | | | | | X | | X |
| IGFBP1 | | | | | | | |
| IL2RA | | | | | | | |
| INHBA | | | | | | | |
| LEP | | | | | X | | X |
| SELE | | | | | | | X |
| SELP | | | | | | | X |
| VCAM1 | | | | | | | X |
| VEGF | | | | | X | | |
| VWF | | | | | | | |
| AUC | 0.74 | 0.74 | 0.74 | 0.74 | 0.97 | 0.72 | 0.75 |

BLOOD BIOMARKERS ONLY, BASE EXAMPLE 2 POPULATION

| | LDA-FWD | LDA-BWD | LDA-SWS | SVMI-KW5 | SVMI-RF9 | LDA-ELDA3 | LDA-ELDA2 |
|---|---|---|---|---|---|---|---|
| SCp | X | X | | X | | X | X |
| Insulin | X | X | X | X | X | X | X |
| Glucose | X | X | X | X | X | X | X |
| ADIPOQ | X | X | X | | | | X |
| AHSG | | | | | | | |
| ANG | | | | | | | |
| CCL2 | | | | | | | X |
| CD14 | | | | | X | | |
| CRP | X | X | X | X | X | X | X |
| FTH1 | | | | | | | |
| IGFBP1 | | | | | | | X |
| IL2RA | | | | | X | | |
| INHBA | | X | | | | | |
| LEP | X | X | | | | | X |
| SELE | | | | | | | |
| SELP | | | | | | | |
| VCAM1 | | | | X | X | | |
| VEGF | | | | | | | X |
| VWF | | | | | | | |
| AUC | 0.79 | 0.79 | 0.77 | 0.77 | 0.99 | 0.77 | 0.79 |

FIGURE 31

Exhaustive Enumeration of All Univariate, Bivariate, and Trivariate LDA Models
Number of Multi-Parameter Panels Meeting Selected AUC Hurdle Rates

| Number | Number of Parameters | All Combinations | 0.50 | 0.55 | 0.60 | 0.65 | 0.70 | 0.75 |
|---|---|---|---|---|---|---|---|---|
| Example 1 - Total | Univariate | 53 | 48 | 21 | 7 | 3 | - | - |
|  | Bivariate | 1,378 | 1,368 | 952 | 410 | 174 | 2 | - |
|  | Trivariate | 23,426 | 23,409 | 20,023 | 10,650 | 4,753 | 456 | 5 |
| Example 1 - Base | Univariate | 53 | 50 | 23 | 10 | 3 | 1 | - |
|  | Bivariate | 1,378 | 1,372 | 988 | 519 | 214 | 73 | 2 |
|  | Trivariate | 23,426 | 23,407 | 20,398 | 12,856 | 5,917 | 2,431 | 159 |
| Example 2 - Total | Univariate | 49 | 45 | 16 | 5 | 2 | - | - |
|  | Bivariate | 1,176 | 1,169 | 735 | 275 | 108 | 3 | - |
|  | Trivariate | 18,424 | 18,410 | 13,564 | 6,970 | 2,849 | 164 | - |
| Example 2 - Base | Univariate | 49 | 47 | 22 | 9 | 4 | 1 | - |
|  | Bivariate | 1,176 | 1,174 | 875 | 425 | 210 | 50 | 1 |
|  | Trivariate | 18,424 | 18,422 | 16,563 | 10,612 | 5,332 | 1,270 | 48 |

| Percent | Number of Parameters | All Combinations | 0.50 | 0.55 | 0.60 | 0.65 | 0.70 | 0.75 |
|---|---|---|---|---|---|---|---|---|
| Example 1 - Total | Univariate | 100.000% | 90.566% | 39.623% | 13.208% | 5.660% | 0.000% | 0.000% |
|  | Bivariate | 100.000% | 99.274% | 69.086% | 29.753% | 12.627% | 0.145% | 0.000% |
|  | Trivariate | 100.000% | 99.927% | 85.473% | 45.462% | 20.289% | 1.947% | 0.021% |
| Example 1 - Base | Univariate | 100.000% | 94.340% | 43.396% | 18.868% | 5.660% | 1.887% | 0.000% |
|  | Bivariate | 100.000% | 99.565% | 71.698% | 37.663% | 15.530% | 5.298% | 0.145% |
|  | Trivariate | 100.000% | 99.919% | 87.074% | 54.879% | 25.258% | 10.377% | 0.679% |
| Example 2 - Total | Univariate | 100.000% | 91.837% | 32.653% | 10.204% | 4.082% | 0.000% | 0.000% |
|  | Bivariate | 100.000% | 99.405% | 62.500% | 23.384% | 9.184% | 0.255% | 0.000% |
|  | Trivariate | 100.000% | 99.924% | 73.621% | 37.831% | 15.464% | 0.890% | 0.021% |
| Example 2 - Base | Univariate | 100.000% | 95.918% | 44.898% | 18.367% | 8.163% | 2.041% | 0.000% |
|  | Bivariate | 100.000% | 99.830% | 74.405% | 36.139% | 17.857% | 4.252% | 0.085% |
|  | Trivariate | 100.000% | 99.989% | 89.899% | 57.599% | 28.941% | 6.893% | 0.261% |

FIGURE 36

| Bins | C1 | P1 | C2 | P2 | C3 | P3 |
|---|---|---|---|---|---|---|
| 0 | 65 | 1 | 2080 | 1 | 43680 | 1 |
| 0.05 | 65 | 1 | 2080 | 1 | 43680 | 1 |
| 0.1 | 65 | 1 | 2080 | 1 | 43680 | 1 |
| 0.15 | 65 | 1 | 2080 | 1 | 43680 | 1 |
| 0.2 | 65 | 1 | 2080 | 1 | 43680 | 1 |
| 0.25 | 65 | 1 | 2080 | 1 | 43680 | 1 |
| 0.3 | 65 | 1 | 2080 | 1 | 43680 | 1 |
| 0.35 | 65 | 1 | 2080 | 1 | 43680 | 1 |
| 0.4 | 65 | 1 | 2080 | 1 | 43680 | 1 |
| 0.45 | 65 | 1 | 2080 | 1 | 43680 | 1 |
| 0.5 | 65 | 1 | 2077 | 0.998558 | 43663 | 0.999611 |
| 0.55 | 22 | 0.338462 | 1222 | 0.5875 | 33950 | 0.777244 |
| 0.6 | 7 | 0.107692 | 453 | 0.217788 | 14973 | 0.342788 |
| 0.65 | 3 | 0.046154 | 201 | 0.096635 | 6771 | 0.155014 |
| 0.7 | 1 | 0.015385 | 65 | 0.03125 | 2099 | 0.048054 |
| 0.75 | 0 | 0 | 1 | 0.000481 | 101 | 0.002312 |
| 0.8 | 0 | 0 | 0 | 0 | 0 | 0 |
| 0.85 | 0 | 0 | 0 | 0 | 0 | 0 |
| 0.9 | 0 | 0 | 0 | 0 | 0 | 0 |
| 0.95 | 0 | 0 | 0 | 0 | 0 | 0 |
| 1 | 0 | 0 | 0 | 0 | 0 | 0 |

FIGURE 37

| | | |
|---|---|---|
| ACE | CRP | GLUCOSE |
| ADIPOQ | CRP | GLUCOSE |
| AGER | CRP | GLUCOSE |
| AHSG | CRP | GLUCOSE |
| ANG | CRP | GLUCOSE |
| APOA1 | CRP | GLUCOSE |
| APOB | CRP | GLUCOSE |
| APOE | CRP | GLUCOSE |
| BAX | CRP | GLUCOSE |
| BCL2 | CRP | GLUCOSE |
| C3 | CRP | GLUCOSE |
| CCL2 | CRP | GLUCOSE |
| CD14 | CRP | GLUCOSE |
| CD40 | CRP | GLUCOSE |
| CDK5 | CRP | GLUCOSE |
| CHOL | CRP | GLUCOSE |
| CRP | CTSB | GLUCOSE |
| CRP | DPP4 | GLUCOSE |
| CRP | EGF | GLUCOSE |
| CRP | ENG | GLUCOSE |
| CRP | FAS | GLUCOSE |
| CRP | FGA | GLUCOSE |
| CRP | FTH1 | GLUCOSE |
| CRP | GH1 | GLUCOSE |
| CRP | GLUCOSE | GPT |
| CRP | GLUCOSE | HBA1C |
| CRP | GLUCOSE | HDL |
| CRP | GLUCOSE | HGF |
| CRP | GLUCOSE | HP |
| CRP | GLUCOSE | HSPA1B |
| CRP | GLUCOSE | ICAM1 |
| CRP | GLUCOSE | IGF1 |
| CRP | GLUCOSE | IGF1R |
| CRP | GLUCOSE | IGFBP1 |
| CRP | GLUCOSE | IGFBP2 |
| CRP | GLUCOSE | IGFBP3 |
| CCL2 | GLUCOSE | IL18 |
| CRP | GLUCOSE | IL18 |
| GLUCOSE | HBA1C | IL18 |
| GLUCOSE | HSPA1B | IL18 |

FIGURE 37 (continued)

| | | |
|---|---|---|
| CRP | GLUCOSE | IL2RA |
| CRP | GLUCOSE | IL2RB |
| CRP | GLUCOSE | IL6 |
| CRP | GLUCOSE | IL6R |
| CRP | GLUCOSE | IL6ST |
| CRP | GLUCOSE | IL8 |
| CRP | GLUCOSE | INHBA |
| ADIPOQ | GLUCOSE | INSULIN |
| BCL2 | GLUCOSE | INSULIN |
| C3 | GLUCOSE | INSULIN |
| CCL2 | GLUCOSE | INSULIN |
| CD14 | GLUCOSE | INSULIN |
| CDK5 | GLUCOSE | INSULIN |
| CRP | GLUCOSE | INSULIN |
| DPP4 | GLUCOSE | INSULIN |
| FTH1 | GLUCOSE | INSULIN |
| GH1 | GLUCOSE | INSULIN |
| GLUCOSE | GPT | INSULIN |
| GLUCOSE | HBA1C | INSULIN |
| GLUCOSE | HGF | INSULIN |
| GLUCOSE | HSPA1B | INSULIN |
| GLUCOSE | IGF1 | INSULIN |
| GLUCOSE | IL18 | INSULIN |
| GLUCOSE | IL2RA | INSULIN |
| GLUCOSE | IL6ST | INSULIN |
| GLUCOSE | IL8 | INSULIN |
| CRP | GLUCOSE | LDL |
| GLUCOSE | INSULIN | LDL |
| CRP | GLUCOSE | LEP |
| FTH1 | GLUCOSE | LEP |
| GLUCOSE | IL18 | LEP |
| GLUCOSE | INSULIN | LEP |
| CRP | GLUCOSE | PLAT |
| GLUCOSE | IL18 | PLAT |
| GLUCOSE | INSULIN | PLAT |
| CRP | GLUCOSE | POMC |
| CRP | GLUCOSE | Proinsulin |
| CRP | GLUCOSE | RETN |
| CRP | GLUCOSE | SELE |
| CRP | GLUCOSE | SELP |

FIGURE 37 (continued)

| | | |
|---|---|---|
| GLUCOSE | INSULIN | SELP |
| CRP | GLUCOSE | SERPINE1 |
| CRP | GLUCOSE | SGK |
| GLUCOSE | IL18 | SGK |
| GLUCOSE | INSULIN | SGK |
| CRP | GLUCOSE | SHBG |
| CRP | GLUCOSE | TGFB1 |
| CRP | GLUCOSE | TIMP2 |
| CRP | GLUCOSE | TNFRSF1B |
| GLUCOSE | INSULIN | TNFRSF1B |
| CRP | GLUCOSE | TRIG |
| GLUCOSE | HBA1C | TRIG |
| GLUCOSE | IL18 | TRIG |
| GLUCOSE | INSULIN | TRIG |
| GLUCOSE | LEP | TRIG |
| CRP | GLUCOSE | VCAM1 |
| GLUCOSE | INSULIN | VCAM1 |
| CRP | GLUCOSE | VEGF |
| GLUCOSE | INSULIN | VEGF |
| CRP | GLUCOSE | VWF |
| GLUCOSE | INSULIN | VWF |

FIGURE 38

| | | | |
|---|---|---|---|
| ADIPOQ | ANG | CRP | GLUCOSE |
| ADIPOQ | C3 | CRP | GLUCOSE |
| ADIPOQ | C3 | GLUCOSE | INSULIN |
| ADIPOQ | CCL2 | CRP | GLUCOSE |
| ADIPOQ | CCL2 | GLUCOSE | IL18 |
| ADIPOQ | CCL2 | GLUCOSE | INSULIN |
| ADIPOQ | CCL2 | GLUCOSE | LEP |
| ADIPOQ | CDK5 | CRP | GLUCOSE |
| ADIPOQ | CDK5 | GLUCOSE | INSULIN |
| ADIPOQ | CRP | ENG | GLUCOSE |
| ADIPOQ | CRP | FTH1 | GLUCOSE |
| ADIPOQ | CRP | GLUCOSE | GPT |
| ADIPOQ | CRP | GLUCOSE | HBA1C |
| ADIPOQ | CRP | GLUCOSE | HDL |
| ADIPOQ | CRP | GLUCOSE | HGF |
| ADIPOQ | CRP | GLUCOSE | HSPA1B |
| ADIPOQ | CRP | GLUCOSE | IGFBP1 |
| ADIPOQ | CRP | GLUCOSE | IGFBP2 |
| ADIPOQ | CRP | GLUCOSE | IL18 |
| ADIPOQ | CRP | GLUCOSE | IL2RA |
| ADIPOQ | CRP | GLUCOSE | INHBA |
| ADIPOQ | CRP | GLUCOSE | INSULIN |
| ADIPOQ | CRP | GLUCOSE | LEP |
| ADIPOQ | CRP | GLUCOSE | PLAT |
| ADIPOQ | CRP | GLUCOSE | SERPINE1 |
| ADIPOQ | CRP | GLUCOSE | TRIG |
| ADIPOQ | CRP | GLUCOSE | VEGF |
| ADIPOQ | CRP | GLUCOSE | VWF |
| ADIPOQ | ENG | GLUCOSE | INSULIN |
| ADIPOQ | FTH1 | GLUCOSE | IL18 |
| ADIPOQ | FTH1 | GLUCOSE | INSULIN |
| ADIPOQ | FTH1 | GLUCOSE | LEP |
| ADIPOQ | GLUCOSE | GPT | INSULIN |
| ADIPOQ | GLUCOSE | GPT | LEP |
| ADIPOQ | GLUCOSE | HBA1C | IL18 |
| ADIPOQ | GLUCOSE | HBA1C | INSULIN |
| ADIPOQ | GLUCOSE | HBA1C | LEP |
| ADIPOQ | GLUCOSE | HBA1C | TRIG |
| ADIPOQ | GLUCOSE | HDL | INSULIN |
| ADIPOQ | GLUCOSE | HDL | LEP |

FIGURE 38 (continued)

| ADIPOQ | GLUCOSE | HGF | INSULIN |
|---|---|---|---|
| ADIPOQ | GLUCOSE | HSPA1B | IL18 |
| ADIPOQ | GLUCOSE | HSPA1B | INSULIN |
| ADIPOQ | GLUCOSE | HSPA1B | LEP |
| ADIPOQ | GLUCOSE | IGFBP1 | INSULIN |
| ADIPOQ | GLUCOSE | IGFBP2 | IL18 |
| ADIPOQ | GLUCOSE | IGFBP2 | INSULIN |
| ADIPOQ | GLUCOSE | IL18 | INSULIN |
| ADIPOQ | GLUCOSE | IL18 | LEP |
| ADIPOQ | GLUCOSE | IL18 | PLAT |
| ADIPOQ | GLUCOSE | IL18 | TRIG |
| ADIPOQ | GLUCOSE | IL18 | VEGF |
| ADIPOQ | GLUCOSE | IL18 | VWF |
| ADIPOQ | GLUCOSE | IL2RA | INSULIN |
| ADIPOQ | GLUCOSE | IL2RA | LEP |
| ADIPOQ | GLUCOSE | INSULIN | LEP |
| ADIPOQ | GLUCOSE | INSULIN | PLAT |
| ADIPOQ | GLUCOSE | INSULIN | TRIG |
| ADIPOQ | GLUCOSE | INSULIN | VEGF |
| ADIPOQ | GLUCOSE | INSULIN | VWF |
| ADIPOQ | GLUCOSE | LEP | PLAT |
| ADIPOQ | GLUCOSE | LEP | TRIG |
| ADIPOQ | GLUCOSE | LEP | VEGF |
| ADIPOQ | GLUCOSE | LEP | VWF |
| ANG | C3 | CRP | GLUCOSE |
| ANG | C3 | GLUCOSE | INSULIN |
| ANG | CCL2 | CRP | GLUCOSE |
| ANG | CCL2 | GLUCOSE | IL18 |
| ANG | CCL2 | GLUCOSE | INSULIN |
| ANG | CDK5 | CRP | GLUCOSE |
| ANG | CDK5 | GLUCOSE | INSULIN |
| ANG | CRP | ENG | GLUCOSE |
| ANG | CRP | FTH1 | GLUCOSE |
| ANG | CRP | GLUCOSE | GPT |
| ANG | CRP | GLUCOSE | HBA1C |
| ANG | CRP | GLUCOSE | HDL |
| ANG | CRP | GLUCOSE | HGF |
| ANG | CRP | GLUCOSE | HSPA1B |
| ANG | CRP | GLUCOSE | IGFBP1 |
| ANG | CRP | GLUCOSE | IGFBP2 |

FIGURE 38 (continued)

| ANG | CRP | GLUCOSE | IL18 |
|---|---|---|---|
| ANG | CRP | GLUCOSE | IL2RA |
| ANG | CRP | GLUCOSE | INHBA |
| ANG | CRP | GLUCOSE | INSULIN |
| ANG | CRP | GLUCOSE | LEP |
| ANG | CRP | GLUCOSE | PLAT |
| ANG | CRP | GLUCOSE | SERPINE1 |
| ANG | CRP | GLUCOSE | TRIG |
| ANG | CRP | GLUCOSE | VEGF |
| ANG | CRP | GLUCOSE | VWF |
| ANG | ENG | GLUCOSE | INSULIN |
| ANG | FTH1 | GLUCOSE | IL18 |
| ANG | FTH1 | GLUCOSE | INSULIN |
| ANG | FTH1 | GLUCOSE | LEP |
| ANG | GLUCOSE | GPT | INSULIN |
| ANG | GLUCOSE | HBA1C | IL18 |
| ANG | GLUCOSE | HBA1C | INSULIN |
| ANG | GLUCOSE | HBA1C | LEP |
| ANG | GLUCOSE | HBA1C | TRIG |
| ANG | GLUCOSE | HDL | INSULIN |
| ANG | GLUCOSE | HGF | INSULIN |
| ANG | GLUCOSE | HSPA1B | IL18 |
| ANG | GLUCOSE | HSPA1B | INSULIN |
| ANG | GLUCOSE | IGFBP2 | INSULIN |
| ANG | GLUCOSE | IL18 | INSULIN |
| ANG | GLUCOSE | IL18 | LEP |
| ANG | GLUCOSE | IL18 | PLAT |
| ANG | GLUCOSE | IL18 | TRIG |
| ANG | GLUCOSE | IL18 | VWF |
| ANG | GLUCOSE | IL2RA | INSULIN |
| ANG | GLUCOSE | INSULIN | LEP |
| ANG | GLUCOSE | INSULIN | PLAT |
| ANG | GLUCOSE | INSULIN | TRIG |
| ANG | GLUCOSE | INSULIN | VEGF |
| ANG | GLUCOSE | INSULIN | VWF |
| ANG | GLUCOSE | LEP | TRIG |
| C3 | CCL2 | CRP | GLUCOSE |
| C3 | CCL2 | GLUCOSE | IL18 |
| C3 | CCL2 | GLUCOSE | INSULIN |
| C3 | CDK5 | CRP | GLUCOSE |

FIGURE 38 (continued)

| | | | |
|---|---|---|---|
| C3 | CDK5 | GLUCOSE | INSULIN |
| C3 | CRP | ENG | GLUCOSE |
| C3 | CRP | FTH1 | GLUCOSE |
| C3 | CRP | GLUCOSE | GPT |
| C3 | CRP | GLUCOSE | HBA1C |
| C3 | CRP | GLUCOSE | HDL |
| C3 | CRP | GLUCOSE | HGF |
| C3 | CRP | GLUCOSE | HSPA1B |
| C3 | CRP | GLUCOSE | IGFBP1 |
| C3 | CRP | GLUCOSE | IGFBP2 |
| C3 | CRP | GLUCOSE | IL18 |
| C3 | CRP | GLUCOSE | IL2RA |
| C3 | CRP | GLUCOSE | INHBA |
| C3 | CRP | GLUCOSE | INSULIN |
| C3 | CRP | GLUCOSE | LEP |
| C3 | CRP | GLUCOSE | PLAT |
| C3 | CRP | GLUCOSE | SERPINE1 |
| C3 | CRP | GLUCOSE | TRIG |
| C3 | CRP | GLUCOSE | VEGF |
| C3 | CRP | GLUCOSE | VWF |
| C3 | ENG | GLUCOSE | INSULIN |
| C3 | FTH1 | GLUCOSE | IL18 |
| C3 | FTH1 | GLUCOSE | INSULIN |
| C3 | FTH1 | GLUCOSE | LEP |
| C3 | GLUCOSE | GPT | INSULIN |
| C3 | GLUCOSE | HBA1C | IL18 |
| C3 | GLUCOSE | HBA1C | INSULIN |
| C3 | GLUCOSE | HBA1C | LEP |
| C3 | GLUCOSE | HBA1C | TRIG |
| C3 | GLUCOSE | HDL | INSULIN |
| C3 | GLUCOSE | HGF | INSULIN |
| C3 | GLUCOSE | HSPA1B | INSULIN |
| C3 | GLUCOSE | IGFBP1 | INSULIN |
| C3 | GLUCOSE | IGFBP2 | INSULIN |
| C3 | GLUCOSE | IL18 | INSULIN |
| C3 | GLUCOSE | IL18 | LEP |
| C3 | GLUCOSE | IL18 | TRIG |
| C3 | GLUCOSE | IL2RA | INSULIN |
| C3 | GLUCOSE | INHBA | INSULIN |
| C3 | GLUCOSE | INSULIN | LEP |

FIGURE 38 (continued)

| | | | |
|---|---|---|---|
| C3 | GLUCOSE | INSULIN | PLAT |
| C3 | GLUCOSE | INSULIN | SERPINE1 |
| C3 | GLUCOSE | INSULIN | TRIG |
| C3 | GLUCOSE | INSULIN | VEGF |
| C3 | GLUCOSE | INSULIN | VWF |
| C3 | GLUCOSE | LEP | TRIG |
| CCL2 | CDK5 | CRP | GLUCOSE |
| CCL2 | CDK5 | GLUCOSE | IL18 |
| CCL2 | CDK5 | GLUCOSE | INSULIN |
| CCL2 | CRP | ENG | GLUCOSE |
| CCL2 | CRP | FTH1 | GLUCOSE |
| CCL2 | CRP | GLUCOSE | GPT |
| CCL2 | CRP | GLUCOSE | HBA1C |
| CCL2 | CRP | GLUCOSE | HDL |
| CCL2 | CRP | GLUCOSE | HGF |
| CCL2 | CRP | GLUCOSE | HSPA1B |
| CCL2 | CRP | GLUCOSE | IGFBP1 |
| CCL2 | CRP | GLUCOSE | IGFBP2 |
| CCL2 | CRP | GLUCOSE | IL18 |
| CCL2 | CRP | GLUCOSE | IL2RA |
| CCL2 | CRP | GLUCOSE | INHBA |
| CCL2 | CRP | GLUCOSE | INSULIN |
| CCL2 | CRP | GLUCOSE | LEP |
| CCL2 | CRP | GLUCOSE | PLAT |
| CCL2 | CRP | GLUCOSE | SERPINE1 |
| CCL2 | CRP | GLUCOSE | TRIG |
| CCL2 | CRP | GLUCOSE | VEGF |
| CCL2 | CRP | GLUCOSE | VWF |
| CCL2 | ENG | GLUCOSE | IL18 |
| CCL2 | ENG | GLUCOSE | INSULIN |
| CCL2 | FTH1 | GLUCOSE | HBA1C |
| CCL2 | FTH1 | GLUCOSE | HGF |
| CCL2 | FTH1 | GLUCOSE | IL18 |
| CCL2 | FTH1 | GLUCOSE | IL2RA |
| CCL2 | FTH1 | GLUCOSE | INSULIN |
| CCL2 | FTH1 | GLUCOSE | LEP |
| CCL2 | FTH1 | GLUCOSE | PLAT |
| CCL2 | FTH1 | GLUCOSE | TRIG |
| CCL2 | GLUCOSE | GPT | IL18 |
| CCL2 | GLUCOSE | GPT | INSULIN |

FIGURE 38 (continued)

| | | | |
|---|---|---|---|
| CCL2 | GLUCOSE | GPT | LEP |
| CCL2 | GLUCOSE | HBA1C | HDL |
| CCL2 | GLUCOSE | HBA1C | HGF |
| CCL2 | GLUCOSE | HBA1C | HSPA1B |
| CCL2 | GLUCOSE | HBA1C | IL18 |
| CCL2 | GLUCOSE | HBA1C | INSULIN |
| CCL2 | GLUCOSE | HBA1C | LEP |
| CCL2 | GLUCOSE | HBA1C | PLAT |
| CCL2 | GLUCOSE | HBA1C | TRIG |
| CCL2 | GLUCOSE | HBA1C | VWF |
| CCL2 | GLUCOSE | HDL | IL18 |
| CCL2 | GLUCOSE | HDL | INSULIN |
| CCL2 | GLUCOSE | HDL | LEP |
| CCL2 | GLUCOSE | HGF | IL18 |
| CCL2 | GLUCOSE | HGF | INSULIN |
| CCL2 | GLUCOSE | HGF | PLAT |
| CCL2 | GLUCOSE | HGF | TRIG |
| CCL2 | GLUCOSE | HSPA1B | IL18 |
| CCL2 | GLUCOSE | HSPA1B | INSULIN |
| CCL2 | GLUCOSE | HSPA1B | LEP |
| CCL2 | GLUCOSE | IGFBP1 | IL18 |
| CCL2 | GLUCOSE | IGFBP1 | INSULIN |
| CCL2 | GLUCOSE | IGFBP2 | IL18 |
| CCL2 | GLUCOSE | IGFBP2 | INSULIN |
| CCL2 | GLUCOSE | IL18 | IL2RA |
| CCL2 | GLUCOSE | IL18 | INSULIN |
| CCL2 | GLUCOSE | IL18 | LEP |
| CCL2 | GLUCOSE | IL18 | PLAT |
| CCL2 | GLUCOSE | IL18 | SERPINE1 |
| CCL2 | GLUCOSE | IL18 | TRIG |
| CCL2 | GLUCOSE | IL18 | VEGF |
| CCL2 | GLUCOSE | IL18 | VWF |
| CCL2 | GLUCOSE | IL2RA | INSULIN |
| CCL2 | GLUCOSE | IL2RA | LEP |
| CCL2 | GLUCOSE | IL2RA | TRIG |
| CCL2 | GLUCOSE | INHBA | INSULIN |
| CCL2 | GLUCOSE | INSULIN | LEP |
| CCL2 | GLUCOSE | INSULIN | PLAT |
| CCL2 | GLUCOSE | INSULIN | SERPINE1 |
| CCL2 | GLUCOSE | INSULIN | TRIG |

FIGURE 38 (continued)

| | | | |
|---|---|---|---|
| CCL2 | GLUCOSE | INSULIN | VEGF |
| CCL2 | GLUCOSE | INSULIN | VWF |
| CCL2 | GLUCOSE | LEP | PLAT |
| CCL2 | GLUCOSE | LEP | TRIG |
| CCL2 | GLUCOSE | LEP | VEGF |
| CCL2 | GLUCOSE | LEP | VWF |
| CCL2 | GLUCOSE | PLAT | TRIG |
| CCL2 | GLUCOSE | TRIG | VEGF |
| CCL2 | GLUCOSE | TRIG | VWF |
| CDK5 | CRP | ENG | GLUCOSE |
| CDK5 | CRP | FTH1 | GLUCOSE |
| CDK5 | CRP | GLUCOSE | GPT |
| CDK5 | CRP | GLUCOSE | HBA1C |
| CDK5 | CRP | GLUCOSE | HDL |
| CDK5 | CRP | GLUCOSE | HGF |
| CDK5 | CRP | GLUCOSE | HSPA1B |
| CDK5 | CRP | GLUCOSE | IGFBP1 |
| CDK5 | CRP | GLUCOSE | IGFBP2 |
| CDK5 | CRP | GLUCOSE | IL18 |
| CDK5 | CRP | GLUCOSE | IL2RA |
| CDK5 | CRP | GLUCOSE | INHBA |
| CDK5 | CRP | GLUCOSE | INSULIN |
| CDK5 | CRP | GLUCOSE | LEP |
| CDK5 | CRP | GLUCOSE | PLAT |
| CDK5 | CRP | GLUCOSE | SERPINE1 |
| CDK5 | CRP | GLUCOSE | TRIG |
| CDK5 | CRP | GLUCOSE | VEGF |
| CDK5 | CRP | GLUCOSE | VWF |
| CDK5 | ENG | GLUCOSE | INSULIN |
| CDK5 | FTH1 | GLUCOSE | IL18 |
| CDK5 | FTH1 | GLUCOSE | INSULIN |
| CDK5 | FTH1 | GLUCOSE | LEP |
| CDK5 | GLUCOSE | GPT | INSULIN |
| CDK5 | GLUCOSE | HBA1C | IL18 |
| CDK5 | GLUCOSE | HBA1C | INSULIN |
| CDK5 | GLUCOSE | HBA1C | LEP |
| CDK5 | GLUCOSE | HBA1C | TRIG |
| CDK5 | GLUCOSE | HDL | INSULIN |
| CDK5 | GLUCOSE | HGF | INSULIN |
| CDK5 | GLUCOSE | HSPA1B | IL18 |

FIGURE 38 (continued)

| | | | |
|---|---|---|---|
| CDK5 | GLUCOSE | HSPA1B | INSULIN |
| CDK5 | GLUCOSE | IGFBP1 | INSULIN |
| CDK5 | GLUCOSE | IGFBP2 | INSULIN |
| CDK5 | GLUCOSE | IL18 | IL2RA |
| CDK5 | GLUCOSE | IL18 | INSULIN |
| CDK5 | GLUCOSE | IL18 | LEP |
| CDK5 | GLUCOSE | IL18 | PLAT |
| CDK5 | GLUCOSE | IL18 | TRIG |
| CDK5 | GLUCOSE | IL18 | VEGF |
| CDK5 | GLUCOSE | IL2RA | INSULIN |
| CDK5 | GLUCOSE | INHBA | INSULIN |
| CDK5 | GLUCOSE | INSULIN | LEP |
| CDK5 | GLUCOSE | INSULIN | PLAT |
| CDK5 | GLUCOSE | INSULIN | SERPINE1 |
| CDK5 | GLUCOSE | INSULIN | TRIG |
| CDK5 | GLUCOSE | INSULIN | VEGF |
| CDK5 | GLUCOSE | INSULIN | VWF |
| CDK5 | GLUCOSE | LEP | TRIG |
| CRP | ENG | FTH1 | GLUCOSE |
| CRP | ENG | GLUCOSE | GPT |
| CRP | ENG | GLUCOSE | HBA1C |
| CRP | ENG | GLUCOSE | HDL |
| CRP | ENG | GLUCOSE | HGF |
| CRP | ENG | GLUCOSE | HSPA1B |
| CRP | ENG | GLUCOSE | IGFBP1 |
| CRP | ENG | GLUCOSE | IGFBP2 |
| CRP | ENG | GLUCOSE | IL18 |
| CRP | ENG | GLUCOSE | IL2RA |
| CRP | ENG | GLUCOSE | INHBA |
| CRP | ENG | GLUCOSE | INSULIN |
| CRP | ENG | GLUCOSE | LEP |
| CRP | ENG | GLUCOSE | PLAT |
| CRP | ENG | GLUCOSE | SERPINE1 |
| CRP | ENG | GLUCOSE | TRIG |
| CRP | ENG | GLUCOSE | VEGF |
| CRP | ENG | GLUCOSE | VWF |
| CRP | FTH1 | GLUCOSE | GPT |
| CRP | FTH1 | GLUCOSE | HBA1C |
| CRP | FTH1 | GLUCOSE | HDL |
| CRP | FTH1 | GLUCOSE | HGF |

FIGURE 38 (continued)

| | | | |
|---|---|---|---|
| CRP | FTH1 | GLUCOSE | HSPA1B |
| CRP | FTH1 | GLUCOSE | IGFBP1 |
| CRP | FTH1 | GLUCOSE | IGFBP2 |
| CRP | FTH1 | GLUCOSE | IL18 |
| CRP | FTH1 | GLUCOSE | IL2RA |
| CRP | FTH1 | GLUCOSE | INHBA |
| CRP | FTH1 | GLUCOSE | INSULIN |
| CRP | FTH1 | GLUCOSE | LEP |
| CRP | FTH1 | GLUCOSE | PLAT |
| CRP | FTH1 | GLUCOSE | SERPINE1 |
| CRP | FTH1 | GLUCOSE | TRIG |
| CRP | FTH1 | GLUCOSE | VEGF |
| CRP | FTH1 | GLUCOSE | VWF |
| CRP | GLUCOSE | GPT | HBA1C |
| CRP | GLUCOSE | GPT | HDL |
| CRP | GLUCOSE | GPT | HGF |
| CRP | GLUCOSE | GPT | HSPA1B |
| CRP | GLUCOSE | GPT | IGFBP1 |
| CRP | GLUCOSE | GPT | IGFBP2 |
| CRP | GLUCOSE | GPT | IL18 |
| CRP | GLUCOSE | GPT | IL2RA |
| CRP | GLUCOSE | GPT | INHBA |
| CRP | GLUCOSE | GPT | INSULIN |
| CRP | GLUCOSE | GPT | LEP |
| CRP | GLUCOSE | GPT | PLAT |
| CRP | GLUCOSE | GPT | SERPINE1 |
| CRP | GLUCOSE | GPT | TRIG |
| CRP | GLUCOSE | GPT | VEGF |
| CRP | GLUCOSE | GPT | VWF |
| CRP | GLUCOSE | HBA1C | HDL |
| CRP | GLUCOSE | HBA1C | HGF |
| CRP | GLUCOSE | HBA1C | HSPA1B |
| CRP | GLUCOSE | HBA1C | IGFBP1 |
| CRP | GLUCOSE | HBA1C | IGFBP2 |
| CRP | GLUCOSE | HBA1C | IL18 |
| CRP | GLUCOSE | HBA1C | IL2RA |
| CRP | GLUCOSE | HBA1C | INHBA |
| CRP | GLUCOSE | HBA1C | INSULIN |
| CRP | GLUCOSE | HBA1C | LEP |
| CRP | GLUCOSE | HBA1C | PLAT |

FIGURE 38 (continued)

| | | | |
|---|---|---|---|
| CRP | GLUCOSE | HBA1C | SERPINE1 |
| CRP | GLUCOSE | HBA1C | TRIG |
| CRP | GLUCOSE | HBA1C | VEGF |
| CRP | GLUCOSE | HBA1C | VWF |
| CRP | GLUCOSE | HDL | HGF |
| CRP | GLUCOSE | HDL | HSPA1B |
| CRP | GLUCOSE | HDL | IGFBP1 |
| CRP | GLUCOSE | HDL | IGFBP2 |
| CRP | GLUCOSE | HDL | IL18 |
| CRP | GLUCOSE | HDL | IL2RA |
| CRP | GLUCOSE | HDL | INHBA |
| CRP | GLUCOSE | HDL | INSULIN |
| CRP | GLUCOSE | HDL | LEP |
| CRP | GLUCOSE | HDL | PLAT |
| CRP | GLUCOSE | HDL | SERPINE1 |
| CRP | GLUCOSE | HDL | TRIG |
| CRP | GLUCOSE | HDL | VEGF |
| CRP | GLUCOSE | HDL | VWF |
| CRP | GLUCOSE | HGF | HSPA1B |
| CRP | GLUCOSE | HGF | IGFBP1 |
| CRP | GLUCOSE | HGF | IGFBP2 |
| CRP | GLUCOSE | HGF | IL18 |
| CRP | GLUCOSE | HGF | IL2RA |
| CRP | GLUCOSE | HGF | INHBA |
| CRP | GLUCOSE | HGF | INSULIN |
| CRP | GLUCOSE | HGF | LEP |
| CRP | GLUCOSE | HGF | PLAT |
| CRP | GLUCOSE | HGF | SERPINE1 |
| CRP | GLUCOSE | HGF | TRIG |
| CRP | GLUCOSE | HGF | VEGF |
| CRP | GLUCOSE | HGF | VWF |
| CRP | GLUCOSE | HSPA1B | IGFBP1 |
| CRP | GLUCOSE | HSPA1B | IGFBP2 |
| CRP | GLUCOSE | HSPA1B | IL18 |
| CRP | GLUCOSE | HSPA1B | IL2RA |
| CRP | GLUCOSE | HSPA1B | INHBA |
| CRP | GLUCOSE | HSPA1B | INSULIN |
| CRP | GLUCOSE | HSPA1B | LEP |
| CRP | GLUCOSE | HSPA1B | PLAT |
| CRP | GLUCOSE | HSPA1B | SERPINE1 |

FIGURE 38 (continued)

| | | | |
|---|---|---|---|
| CRP | GLUCOSE | HSPA1B | TRIG |
| CRP | GLUCOSE | HSPA1B | VEGF |
| CRP | GLUCOSE | HSPA1B | VWF |
| CRP | GLUCOSE | IGFBP1 | IGFBP2 |
| CRP | GLUCOSE | IGFBP1 | IL18 |
| CRP | GLUCOSE | IGFBP1 | IL2RA |
| CRP | GLUCOSE | IGFBP1 | INHBA |
| CRP | GLUCOSE | IGFBP1 | INSULIN |
| CRP | GLUCOSE | IGFBP1 | LEP |
| CRP | GLUCOSE | IGFBP1 | PLAT |
| CRP | GLUCOSE | IGFBP1 | SERPINE1 |
| CRP | GLUCOSE | IGFBP1 | TRIG |
| CRP | GLUCOSE | IGFBP1 | VEGF |
| CRP | GLUCOSE | IGFBP1 | VWF |
| CRP | GLUCOSE | IGFBP2 | IL18 |
| CRP | GLUCOSE | IGFBP2 | IL2RA |
| CRP | GLUCOSE | IGFBP2 | INHBA |
| CRP | GLUCOSE | IGFBP2 | INSULIN |
| CRP | GLUCOSE | IGFBP2 | LEP |
| CRP | GLUCOSE | IGFBP2 | PLAT |
| CRP | GLUCOSE | IGFBP2 | SERPINE1 |
| CRP | GLUCOSE | IGFBP2 | TRIG |
| CRP | GLUCOSE | IGFBP2 | VEGF |
| CRP | GLUCOSE | IGFBP2 | VWF |
| CRP | GLUCOSE | IL18 | IL2RA |
| CRP | GLUCOSE | IL18 | INHBA |
| CRP | GLUCOSE | IL18 | INSULIN |
| CRP | GLUCOSE | IL18 | LEP |
| CRP | GLUCOSE | IL18 | PLAT |
| CRP | GLUCOSE | IL18 | SERPINE1 |
| CRP | GLUCOSE | IL18 | TRIG |
| CRP | GLUCOSE | IL18 | VEGF |
| CRP | GLUCOSE | IL18 | VWF |
| CRP | GLUCOSE | IL2RA | INHBA |
| CRP | GLUCOSE | IL2RA | INSULIN |
| CRP | GLUCOSE | IL2RA | LEP |
| CRP | GLUCOSE | IL2RA | PLAT |
| CRP | GLUCOSE | IL2RA | SERPINE1 |
| CRP | GLUCOSE | IL2RA | TRIG |
| CRP | GLUCOSE | IL2RA | VEGF |

FIGURE 38 (continued)

| CRP | GLUCOSE | IL2RA | VWF |
|---|---|---|---|
| CRP | GLUCOSE | INHBA | INSULIN |
| CRP | GLUCOSE | INHBA | LEP |
| CRP | GLUCOSE | INHBA | PLAT |
| CRP | GLUCOSE | INHBA | SERPINE1 |
| CRP | GLUCOSE | INHBA | TRIG |
| CRP | GLUCOSE | INHBA | VEGF |
| CRP | GLUCOSE | INHBA | VWF |
| CRP | GLUCOSE | INSULIN | LEP |
| CRP | GLUCOSE | INSULIN | PLAT |
| CRP | GLUCOSE | INSULIN | SERPINE1 |
| CRP | GLUCOSE | INSULIN | TRIG |
| CRP | GLUCOSE | INSULIN | VEGF |
| CRP | GLUCOSE | INSULIN | VWF |
| CRP | GLUCOSE | LEP | PLAT |
| CRP | GLUCOSE | LEP | SERPINE1 |
| CRP | GLUCOSE | LEP | TRIG |
| CRP | GLUCOSE | LEP | VEGF |
| CRP | GLUCOSE | LEP | VWF |
| CRP | GLUCOSE | PLAT | SERPINE1 |
| CRP | GLUCOSE | PLAT | TRIG |
| CRP | GLUCOSE | PLAT | VEGF |
| CRP | GLUCOSE | PLAT | VWF |
| CRP | GLUCOSE | SERPINE1 | TRIG |
| CRP | GLUCOSE | SERPINE1 | VEGF |
| CRP | GLUCOSE | SERPINE1 | VWF |
| CRP | GLUCOSE | TRIG | VEGF |
| CRP | GLUCOSE | TRIG | VWF |
| CRP | GLUCOSE | VEGF | VWF |
| ENG | FTH1 | GLUCOSE | HBA1C |
| ENG | FTH1 | GLUCOSE | IL18 |
| ENG | FTH1 | GLUCOSE | INSULIN |
| ENG | FTH1 | GLUCOSE | LEP |
| ENG | GLUCOSE | GPT | IL18 |
| ENG | GLUCOSE | GPT | INSULIN |
| ENG | GLUCOSE | HBA1C | IL18 |
| ENG | GLUCOSE | HBA1C | INSULIN |
| ENG | GLUCOSE | HBA1C | LEP |
| ENG | GLUCOSE | HBA1C | TRIG |
| ENG | GLUCOSE | HDL | INSULIN |

FIGURE 38 (continued)

| | | | |
|---|---|---|---|
| ENG | GLUCOSE | HGF | IL18 |
| ENG | GLUCOSE | HGF | INSULIN |
| ENG | GLUCOSE | HSPA1B | IL18 |
| ENG | GLUCOSE | HSPA1B | INSULIN |
| ENG | GLUCOSE | IGFBP1 | INSULIN |
| ENG | GLUCOSE | IGFBP2 | IL18 |
| ENG | GLUCOSE | IGFBP2 | INSULIN |
| ENG | GLUCOSE | IL18 | IL2RA |
| ENG | GLUCOSE | IL18 | INSULIN |
| ENG | GLUCOSE | IL18 | LEP |
| ENG | GLUCOSE | IL18 | PLAT |
| ENG | GLUCOSE | IL18 | TRIG |
| ENG | GLUCOSE | IL18 | VEGF |
| ENG | GLUCOSE | IL18 | VWF |
| ENG | GLUCOSE | IL2RA | INSULIN |
| ENG | GLUCOSE | INSULIN | LEP |
| ENG | GLUCOSE | INSULIN | PLAT |
| ENG | GLUCOSE | INSULIN | SERPINE1 |
| ENG | GLUCOSE | INSULIN | TRIG |
| ENG | GLUCOSE | INSULIN | VEGF |
| ENG | GLUCOSE | INSULIN | VWF |
| ENG | GLUCOSE | LEP | TRIG |
| FTH1 | GLUCOSE | GPT | HBA1C |
| FTH1 | GLUCOSE | GPT | HGF |
| FTH1 | GLUCOSE | GPT | IL18 |
| FTH1 | GLUCOSE | GPT | INSULIN |
| FTH1 | GLUCOSE | GPT | LEP |
| FTH1 | GLUCOSE | HBA1C | HDL |
| FTH1 | GLUCOSE | HBA1C | HGF |
| FTH1 | GLUCOSE | HBA1C | HSPA1B |
| FTH1 | GLUCOSE | HBA1C | IGFBP2 |
| FTH1 | GLUCOSE | HBA1C | IL18 |
| FTH1 | GLUCOSE | HBA1C | IL2RA |
| FTH1 | GLUCOSE | HBA1C | INSULIN |
| FTH1 | GLUCOSE | HBA1C | LEP |
| FTH1 | GLUCOSE | HBA1C | PLAT |
| FTH1 | GLUCOSE | HBA1C | SERPINE1 |
| FTH1 | GLUCOSE | HBA1C | TRIG |
| FTH1 | GLUCOSE | HBA1C | VEGF |
| FTH1 | GLUCOSE | HBA1C | VWF |

FIGURE 38 (continued)

| | | | |
|---|---|---|---|
| FTH1 | GLUCOSE | HDL | IL18 |
| FTH1 | GLUCOSE | HDL | INSULIN |
| FTH1 | GLUCOSE | HDL | LEP |
| FTH1 | GLUCOSE | HGF | IL18 |
| FTH1 | GLUCOSE | HGF | IL2RA |
| FTH1 | GLUCOSE | HGF | INSULIN |
| FTH1 | GLUCOSE | HGF | LEP |
| FTH1 | GLUCOSE | HGF | PLAT |
| FTH1 | GLUCOSE | HGF | TRIG |
| FTH1 | GLUCOSE | HSPA1B | IL18 |
| FTH1 | GLUCOSE | HSPA1B | INSULIN |
| FTH1 | GLUCOSE | HSPA1B | LEP |
| FTH1 | GLUCOSE | IGFBP1 | IL18 |
| FTH1 | GLUCOSE | IGFBP1 | INSULIN |
| FTH1 | GLUCOSE | IGFBP1 | LEP |
| FTH1 | GLUCOSE | IGFBP2 | IL18 |
| FTH1 | GLUCOSE | IGFBP2 | INSULIN |
| FTH1 | GLUCOSE | IGFBP2 | LEP |
| FTH1 | GLUCOSE | IL18 | IL2RA |
| FTH1 | GLUCOSE | IL18 | INHBA |
| FTH1 | GLUCOSE | IL18 | INSULIN |
| FTH1 | GLUCOSE | IL18 | LEP |
| FTH1 | GLUCOSE | IL18 | PLAT |
| FTH1 | GLUCOSE | IL18 | SERPINE1 |
| FTH1 | GLUCOSE | IL18 | TRIG |
| FTH1 | GLUCOSE | IL18 | VEGF |
| FTH1 | GLUCOSE | IL18 | VWF |
| FTH1 | GLUCOSE | IL2RA | INSULIN |
| FTH1 | GLUCOSE | IL2RA | LEP |
| FTH1 | GLUCOSE | IL2RA | TRIG |
| FTH1 | GLUCOSE | IL2RA | VEGF |
| FTH1 | GLUCOSE | INHBA | INSULIN |
| FTH1 | GLUCOSE | INHBA | LEP |
| FTH1 | GLUCOSE | INSULIN | LEP |
| FTH1 | GLUCOSE | INSULIN | PLAT |
| FTH1 | GLUCOSE | INSULIN | SERPINE1 |
| FTH1 | GLUCOSE | INSULIN | TRIG |
| FTH1 | GLUCOSE | INSULIN | VEGF |
| FTH1 | GLUCOSE | INSULIN | VWF |
| FTH1 | GLUCOSE | LEP | PLAT |

FIGURE 38 (continued)

| | | | |
|---|---|---|---|
| FTH1 | GLUCOSE | LEP | SERPINE1 |
| FTH1 | GLUCOSE | LEP | TRIG |
| FTH1 | GLUCOSE | LEP | VEGF |
| FTH1 | GLUCOSE | LEP | VWF |
| FTH1 | GLUCOSE | TRIG | VEGF |
| GLUCOSE | GPT | HBA1C | HDL |
| GLUCOSE | GPT | HBA1C | HGF |
| GLUCOSE | GPT | HBA1C | IL18 |
| GLUCOSE | GPT | HBA1C | INSULIN |
| GLUCOSE | GPT | HBA1C | LEP |
| GLUCOSE | GPT | HBA1C | TRIG |
| GLUCOSE | GPT | HDL | IL18 |
| GLUCOSE | GPT | HDL | INSULIN |
| GLUCOSE | GPT | HDL | LEP |
| GLUCOSE | GPT | HGF | IL18 |
| GLUCOSE | GPT | HGF | INSULIN |
| GLUCOSE | GPT | HSPA1B | IL18 |
| GLUCOSE | GPT | HSPA1B | INSULIN |
| GLUCOSE | GPT | IGFBP1 | INSULIN |
| GLUCOSE | GPT | IGFBP2 | IL18 |
| GLUCOSE | GPT | IGFBP2 | INSULIN |
| GLUCOSE | GPT | IL18 | IL2RA |
| GLUCOSE | GPT | IL18 | INSULIN |
| GLUCOSE | GPT | IL18 | LEP |
| GLUCOSE | GPT | IL18 | PLAT |
| GLUCOSE | GPT | IL18 | TRIG |
| GLUCOSE | GPT | IL18 | VEGF |
| GLUCOSE | GPT | IL18 | VWF |
| GLUCOSE | GPT | IL2RA | INSULIN |
| GLUCOSE | GPT | INHBA | INSULIN |
| GLUCOSE | GPT | INSULIN | LEP |
| GLUCOSE | GPT | INSULIN | PLAT |
| GLUCOSE | GPT | INSULIN | SERPINE1 |
| GLUCOSE | GPT | INSULIN | TRIG |
| GLUCOSE | GPT | INSULIN | VEGF |
| GLUCOSE | GPT | INSULIN | VWF |
| GLUCOSE | GPT | LEP | TRIG |
| GLUCOSE | GPT | LEP | VEGF |
| GLUCOSE | HBA1C | HDL | HGF |
| GLUCOSE | HBA1C | HDL | HSPA1B |

FIGURE 38 (continued)

| GLUCOSE | HBA1C | HDL | IL18 |
|---|---|---|---|
| GLUCOSE | HBA1C | HDL | IL2RA |
| GLUCOSE | HBA1C | HDL | INSULIN |
| GLUCOSE | HBA1C | HDL | LEP |
| GLUCOSE | HBA1C | HDL | PLAT |
| GLUCOSE | HBA1C | HDL | TRIG |
| GLUCOSE | HBA1C | HDL | VEGF |
| GLUCOSE | HBA1C | HDL | VWF |
| GLUCOSE | HBA1C | HGF | HSPA1B |
| GLUCOSE | HBA1C | HGF | IL18 |
| GLUCOSE | HBA1C | HGF | INSULIN |
| GLUCOSE | HBA1C | HGF | LEP |
| GLUCOSE | HBA1C | HGF | PLAT |
| GLUCOSE | HBA1C | HGF | TRIG |
| GLUCOSE | HBA1C | HSPA1B | IL18 |
| GLUCOSE | HBA1C | HSPA1B | INSULIN |
| GLUCOSE | HBA1C | HSPA1B | LEP |
| GLUCOSE | HBA1C | HSPA1B | TRIG |
| GLUCOSE | HBA1C | IGFBP1 | IL18 |
| GLUCOSE | HBA1C | IGFBP1 | INSULIN |
| GLUCOSE | HBA1C | IGFBP1 | LEP |
| GLUCOSE | HBA1C | IGFBP1 | TRIG |
| GLUCOSE | HBA1C | IGFBP2 | IL18 |
| GLUCOSE | HBA1C | IGFBP2 | INSULIN |
| GLUCOSE | HBA1C | IGFBP2 | LEP |
| GLUCOSE | HBA1C | IGFBP2 | TRIG |
| GLUCOSE | HBA1C | IL18 | IL2RA |
| GLUCOSE | HBA1C | IL18 | INHBA |
| GLUCOSE | HBA1C | IL18 | INSULIN |
| GLUCOSE | HBA1C | IL18 | LEP |
| GLUCOSE | HBA1C | IL18 | PLAT |
| GLUCOSE | HBA1C | IL18 | SERPINE1 |
| GLUCOSE | HBA1C | IL18 | TRIG |
| GLUCOSE | HBA1C | IL18 | VEGF |
| GLUCOSE | HBA1C | IL18 | VWF |
| GLUCOSE | HBA1C | IL2RA | INSULIN |
| GLUCOSE | HBA1C | IL2RA | LEP |
| GLUCOSE | HBA1C | IL2RA | PLAT |
| GLUCOSE | HBA1C | IL2RA | TRIG |
| GLUCOSE | HBA1C | INHBA | INSULIN |

FIGURE 38 (continued)

| GLUCOSE | HBA1C | INSULIN | LEP |
|---|---|---|---|
| GLUCOSE | HBA1C | INSULIN | PLAT |
| GLUCOSE | HBA1C | INSULIN | SERPINE1 |
| GLUCOSE | HBA1C | INSULIN | TRIG |
| GLUCOSE | HBA1C | INSULIN | VEGF |
| GLUCOSE | HBA1C | INSULIN | VWF |
| GLUCOSE | HBA1C | LEP | PLAT |
| GLUCOSE | HBA1C | LEP | SERPINE1 |
| GLUCOSE | HBA1C | LEP | TRIG |
| GLUCOSE | HBA1C | LEP | VEGF |
| GLUCOSE | HBA1C | LEP | VWF |
| GLUCOSE | HBA1C | PLAT | TRIG |
| GLUCOSE | HBA1C | SERPINE1 | TRIG |
| GLUCOSE | HBA1C | TRIG | VEGF |
| GLUCOSE | HBA1C | TRIG | VWF |
| GLUCOSE | HDL | HGF | IL18 |
| GLUCOSE | HDL | HGF | INSULIN |
| GLUCOSE | HDL | HSPA1B | IL18 |
| GLUCOSE | HDL | HSPA1B | INSULIN |
| GLUCOSE | HDL | HSPA1B | LEP |
| GLUCOSE | HDL | IGFBP2 | INSULIN |
| GLUCOSE | HDL | IL18 | IL2RA |
| GLUCOSE | HDL | IL18 | INSULIN |
| GLUCOSE | HDL | IL18 | LEP |
| GLUCOSE | HDL | IL18 | PLAT |
| GLUCOSE | HDL | IL18 | TRIG |
| GLUCOSE | HDL | IL18 | VEGF |
| GLUCOSE | HDL | IL18 | VWF |
| GLUCOSE | HDL | IL2RA | INSULIN |
| GLUCOSE | HDL | IL2RA | LEP |
| GLUCOSE | HDL | INSULIN | LEP |
| GLUCOSE | HDL | INSULIN | PLAT |
| GLUCOSE | HDL | INSULIN | SERPINE1 |
| GLUCOSE | HDL | INSULIN | TRIG |
| GLUCOSE | HDL | INSULIN | VEGF |
| GLUCOSE | HDL | INSULIN | VWF |
| GLUCOSE | HDL | LEP | PLAT |
| GLUCOSE | HDL | LEP | TRIG |
| GLUCOSE | HDL | LEP | VEGF |
| GLUCOSE | HDL | LEP | VWF |

FIGURE 38 (continued)

| | | | |
|---|---|---|---|
| GLUCOSE | HGF | HSPA1B | IL18 |
| GLUCOSE | HGF | HSPA1B | INSULIN |
| GLUCOSE | HGF | IGFBP1 | INSULIN |
| GLUCOSE | HGF | IGFBP2 | IL18 |
| GLUCOSE | HGF | IGFBP2 | INSULIN |
| GLUCOSE | HGF | IL18 | IL2RA |
| GLUCOSE | HGF | IL18 | INSULIN |
| GLUCOSE | HGF | IL18 | LEP |
| GLUCOSE | HGF | IL18 | PLAT |
| GLUCOSE | HGF | IL18 | TRIG |
| GLUCOSE | HGF | IL18 | VEGF |
| GLUCOSE | HGF | IL18 | VWF |
| GLUCOSE | HGF | IL2RA | INSULIN |
| GLUCOSE | HGF | IL2RA | TRIG |
| GLUCOSE | HGF | INHBA | INSULIN |
| GLUCOSE | HGF | INSULIN | LEP |
| GLUCOSE | HGF | INSULIN | PLAT |
| GLUCOSE | HGF | INSULIN | SERPINE1 |
| GLUCOSE | HGF | INSULIN | TRIG |
| GLUCOSE | HGF | INSULIN | VEGF |
| GLUCOSE | HGF | INSULIN | VWF |
| GLUCOSE | HGF | LEP | TRIG |
| GLUCOSE | HGF | PLAT | TRIG |
| GLUCOSE | HSPA1B | IGFBP1 | IL18 |
| GLUCOSE | HSPA1B | IGFBP1 | INSULIN |
| GLUCOSE | HSPA1B | IGFBP2 | IL18 |
| GLUCOSE | HSPA1B | IGFBP2 | INSULIN |
| GLUCOSE | HSPA1B | IL18 | IL2RA |
| GLUCOSE | HSPA1B | IL18 | INHBA |
| GLUCOSE | HSPA1B | IL18 | INSULIN |
| GLUCOSE | HSPA1B | IL18 | LEP |
| GLUCOSE | HSPA1B | IL18 | PLAT |
| GLUCOSE | HSPA1B | IL18 | TRIG |
| GLUCOSE | HSPA1B | IL18 | VEGF |
| GLUCOSE | HSPA1B | IL18 | VWF |
| GLUCOSE | HSPA1B | IL2RA | INSULIN |
| GLUCOSE | HSPA1B | IL2RA | TRIG |
| GLUCOSE | HSPA1B | INHBA | INSULIN |
| GLUCOSE | HSPA1B | INSULIN | LEP |
| GLUCOSE | HSPA1B | INSULIN | PLAT |

FIGURE 38 (continued)

| GLUCOSE | HSPA1B | INSULIN | SERPINE1 |
|---|---|---|---|
| GLUCOSE | HSPA1B | INSULIN | TRIG |
| GLUCOSE | HSPA1B | INSULIN | VEGF |
| GLUCOSE | HSPA1B | INSULIN | VWF |
| GLUCOSE | HSPA1B | LEP | TRIG |
| GLUCOSE | HSPA1B | LEP | VEGF |
| GLUCOSE | IGFBP1 | IL18 | INSULIN |
| GLUCOSE | IGFBP1 | IL18 | LEP |
| GLUCOSE | IGFBP1 | IL18 | PLAT |
| GLUCOSE | IGFBP1 | IL18 | TRIG |
| GLUCOSE | IGFBP1 | IL18 | VEGF |
| GLUCOSE | IGFBP1 | IL18 | VWF |
| GLUCOSE | IGFBP1 | IL2RA | INSULIN |
| GLUCOSE | IGFBP1 | INSULIN | LEP |
| GLUCOSE | IGFBP1 | INSULIN | PLAT |
| GLUCOSE | IGFBP1 | INSULIN | TRIG |
| GLUCOSE | IGFBP1 | INSULIN | VEGF |
| GLUCOSE | IGFBP1 | INSULIN | VWF |
| GLUCOSE | IGFBP1 | LEP | TRIG |
| GLUCOSE | IGFBP2 | IL18 | IL2RA |
| GLUCOSE | IGFBP2 | IL18 | INSULIN |
| GLUCOSE | IGFBP2 | IL18 | LEP |
| GLUCOSE | IGFBP2 | IL18 | PLAT |
| GLUCOSE | IGFBP2 | IL18 | TRIG |
| GLUCOSE | IGFBP2 | IL18 | VEGF |
| GLUCOSE | IGFBP2 | IL18 | VWF |
| GLUCOSE | IGFBP2 | IL2RA | INSULIN |
| GLUCOSE | IGFBP2 | INSULIN | LEP |
| GLUCOSE | IGFBP2 | INSULIN | PLAT |
| GLUCOSE | IGFBP2 | INSULIN | SERPINE1 |
| GLUCOSE | IGFBP2 | INSULIN | TRIG |
| GLUCOSE | IGFBP2 | INSULIN | VEGF |
| GLUCOSE | IGFBP2 | INSULIN | VWF |
| GLUCOSE | IGFBP2 | LEP | TRIG |
| GLUCOSE | IL18 | IL2RA | INSULIN |
| GLUCOSE | IL18 | IL2RA | LEP |
| GLUCOSE | IL18 | IL2RA | PLAT |
| GLUCOSE | IL18 | IL2RA | TRIG |
| GLUCOSE | IL18 | IL2RA | VEGF |
| GLUCOSE | IL18 | IL2RA | VWF |

FIGURE 38 (continued)

| GLUCOSE | IL18 | INHBA | INSULIN |
|---------|------|-------|---------|
| GLUCOSE | IL18 | INHBA | LEP |
| GLUCOSE | IL18 | INHBA | PLAT |
| GLUCOSE | IL18 | INHBA | TRIG |
| GLUCOSE | IL18 | INSULIN | LEP |
| GLUCOSE | IL18 | INSULIN | PLAT |
| GLUCOSE | IL18 | INSULIN | SERPINE1 |
| GLUCOSE | IL18 | INSULIN | TRIG |
| GLUCOSE | IL18 | INSULIN | VEGF |
| GLUCOSE | IL18 | INSULIN | VWF |
| GLUCOSE | IL18 | LEP | PLAT |
| GLUCOSE | IL18 | LEP | SERPINE1 |
| GLUCOSE | IL18 | LEP | TRIG |
| GLUCOSE | IL18 | LEP | VEGF |
| GLUCOSE | IL18 | LEP | VWF |
| GLUCOSE | IL18 | PLAT | SERPINE1 |
| GLUCOSE | IL18 | PLAT | TRIG |
| GLUCOSE | IL18 | PLAT | VEGF |
| GLUCOSE | IL18 | PLAT | VWF |
| GLUCOSE | IL18 | SERPINE1 | TRIG |
| GLUCOSE | IL18 | SERPINE1 | VWF |
| GLUCOSE | IL18 | TRIG | VEGF |
| GLUCOSE | IL18 | TRIG | VWF |
| GLUCOSE | IL18 | VEGF | VWF |
| GLUCOSE | IL2RA | INHBA | INSULIN |
| GLUCOSE | IL2RA | INSULIN | LEP |
| GLUCOSE | IL2RA | INSULIN | PLAT |
| GLUCOSE | IL2RA | INSULIN | SERPINE1 |
| GLUCOSE | IL2RA | INSULIN | TRIG |
| GLUCOSE | IL2RA | INSULIN | VEGF |
| GLUCOSE | IL2RA | INSULIN | VWF |
| GLUCOSE | IL2RA | LEP | PLAT |
| GLUCOSE | IL2RA | LEP | TRIG |
| GLUCOSE | IL2RA | LEP | VEGF |
| GLUCOSE | IL2RA | PLAT | TRIG |
| GLUCOSE | IL2RA | TRIG | VEGF |
| GLUCOSE | IL2RA | TRIG | VWF |
| GLUCOSE | INHBA | INSULIN | LEP |
| GLUCOSE | INHBA | INSULIN | PLAT |
| GLUCOSE | INHBA | INSULIN | TRIG |

FIGURE 38 (continued)

| GLUCOSE | INHBA   | INSULIN  | VEGF     |
|---------|---------|----------|----------|
| GLUCOSE | INHBA   | INSULIN  | VWF      |
| GLUCOSE | INHBA   | LEP      | TRIG     |
| GLUCOSE | INSULIN | LEP      | PLAT     |
| GLUCOSE | INSULIN | LEP      | SERPINE1 |
| GLUCOSE | INSULIN | LEP      | TRIG     |
| GLUCOSE | INSULIN | LEP      | VEGF     |
| GLUCOSE | INSULIN | LEP      | VWF      |
| GLUCOSE | INSULIN | PLAT     | SERPINE1 |
| GLUCOSE | INSULIN | PLAT     | TRIG     |
| GLUCOSE | INSULIN | PLAT     | VEGF     |
| GLUCOSE | INSULIN | PLAT     | VWF      |
| GLUCOSE | INSULIN | SERPINE1 | TRIG     |
| GLUCOSE | INSULIN | SERPINE1 | VEGF     |
| GLUCOSE | INSULIN | SERPINE1 | VWF      |
| GLUCOSE | INSULIN | TRIG     | VEGF     |
| GLUCOSE | INSULIN | TRIG     | VWF      |
| GLUCOSE | INSULIN | VEGF     | VWF      |
| GLUCOSE | LEP     | PLAT     | TRIG     |
| GLUCOSE | LEP     | PLAT     | VEGF     |
| GLUCOSE | LEP     | TRIG     | VEGF     |
| GLUCOSE | LEP     | TRIG     | VWF      |
| GLUCOSE | LEP     | VEGF     | VWF      |
| GLUCOSE | PLAT    | TRIG     | VEGF     |
| GLUCOSE | PLAT    | TRIG     | VWF      |
| GLUCOSE | TRIG    | VEGF     | VWF      |

FIGURE 39

| | | | | |
|---|---|---|---|---|
| ADIPOQ | ANG | CRP | GLUCOSE | INSULIN |
| ADIPOQ | C3 | CRP | GLUCOSE | HBA1C |
| ADIPOQ | CCL2 | CRP | FTH1 | GLUCOSE |
| ADIPOQ | CCL2 | CRP | GLUCOSE | HBA1C |
| ADIPOQ | CCL2 | CRP | GLUCOSE | INSULIN |
| ADIPOQ | CCL2 | CRP | GLUCOSE | PLAT |
| ADIPOQ | CDK5 | CRP | GLUCOSE | HBA1C |
| ADIPOQ | CDK5 | CRP | GLUCOSE | INSULIN |
| ADIPOQ | CRP | ENG | FTH1 | GLUCOSE |
| ADIPOQ | CRP | ENG | GLUCOSE | HBA1C |
| ADIPOQ | CRP | ENG | GLUCOSE | INSULIN |
| ADIPOQ | CRP | FTH1 | GLUCOSE | HBA1C |
| ADIPOQ | CRP | FTH1 | GLUCOSE | IL18 |
| ADIPOQ | CRP | FTH1 | GLUCOSE | INSULIN |
| ADIPOQ | CRP | FTH1 | GLUCOSE | LEP |
| ADIPOQ | CRP | GLUCOSE | GPT | HBA1C |
| ADIPOQ | CRP | GLUCOSE | HBA1C | IL18 |
| ADIPOQ | CRP | GLUCOSE | HBA1C | INSULIN |
| ADIPOQ | CRP | GLUCOSE | HBA1C | LEP |
| ADIPOQ | CRP | GLUCOSE | HBA1C | PLAT |
| ADIPOQ | CRP | GLUCOSE | HBA1C | TRIG |
| ADIPOQ | CRP | GLUCOSE | IL18 | INSULIN |
| ADIPOQ | CRP | GLUCOSE | IL18 | LEP |
| ADIPOQ | CRP | GLUCOSE | IL18 | PLAT |
| ADIPOQ | CRP | GLUCOSE | INSULIN | PLAT |
| ADIPOQ | CRP | GLUCOSE | LEP | PLAT |
| ANG | CCL2 | CRP | FTH1 | GLUCOSE |
| ANG | CCL2 | CRP | GLUCOSE | HBA1C |
| ANG | CCL2 | CRP | GLUCOSE | INSULIN |
| ANG | CRP | FTH1 | GLUCOSE | HBA1C |
| ANG | CRP | FTH1 | GLUCOSE | INSULIN |
| ANG | CRP | GLUCOSE | HBA1C | IL18 |
| ANG | CRP | GLUCOSE | HBA1C | INSULIN |
| ANG | CRP | GLUCOSE | HBA1C | TRIG |
| ANG | CRP | GLUCOSE | IL18 | INSULIN |
| ANG | CRP | GLUCOSE | INSULIN | PLAT |
| C3 | CCL2 | CRP | GLUCOSE | INSULIN |
| C3 | CRP | GLUCOSE | HBA1C | IL18 |
| C3 | CRP | GLUCOSE | HBA1C | INSULIN |
| CCL2 | CDK5 | CRP | GLUCOSE | HBA1C |

FIGURE 39 (continued)

| | | | | |
|---|---|---|---|---|
| CCL2 | CDK5 | CRP | GLUCOSE | INSULIN |
| CCL2 | CRP | ENG | FTH1 | GLUCOSE |
| CCL2 | CRP | FTH1 | GLUCOSE | HBA1C |
| CCL2 | CRP | FTH1 | GLUCOSE | INSULIN |
| CCL2 | CRP | FTH1 | GLUCOSE | LEP |
| CCL2 | CRP | GLUCOSE | HBA1C | HDL |
| CCL2 | CRP | GLUCOSE | HBA1C | IGFBP1 |
| CCL2 | CRP | GLUCOSE | HBA1C | IL18 |
| CCL2 | CRP | GLUCOSE | HBA1C | INSULIN |
| CCL2 | CRP | GLUCOSE | HBA1C | PLAT |
| CCL2 | CRP | GLUCOSE | HBA1C | TRIG |
| CCL2 | CRP | GLUCOSE | HSPA1B | INSULIN |
| CCL2 | CRP | GLUCOSE | IL18 | INSULIN |
| CCL2 | CRP | GLUCOSE | INSULIN | PLAT |
| CDK5 | CRP | GLUCOSE | HBA1C | IL18 |
| CDK5 | CRP | GLUCOSE | HBA1C | INSULIN |
| CRP | ENG | FTH1 | GLUCOSE | HBA1C |
| CRP | ENG | FTH1 | GLUCOSE | IL18 |
| CRP | ENG | FTH1 | GLUCOSE | INSULIN |
| CRP | ENG | GLUCOSE | HBA1C | IL18 |
| CRP | ENG | GLUCOSE | HBA1C | INSULIN |
| CRP | ENG | GLUCOSE | HBA1C | TRIG |
| CRP | ENG | GLUCOSE | IL18 | INSULIN |
| CRP | FTH1 | GLUCOSE | GPT | INSULIN |
| CRP | FTH1 | GLUCOSE | HBA1C | HDL |
| CRP | FTH1 | GLUCOSE | HBA1C | IL18 |
| CRP | FTH1 | GLUCOSE | HBA1C | IL2RA |
| CRP | FTH1 | GLUCOSE | HBA1C | INSULIN |
| CRP | FTH1 | GLUCOSE | HBA1C | LEP |
| CRP | FTH1 | GLUCOSE | HBA1C | PLAT |
| CRP | FTH1 | GLUCOSE | HBA1C | TRIG |
| CRP | FTH1 | GLUCOSE | IL18 | INSULIN |
| CRP | FTH1 | GLUCOSE | INSULIN | PLAT |
| CRP | GLUCOSE | GPT | HBA1C | IL18 |
| CRP | GLUCOSE | GPT | HBA1C | INSULIN |
| CRP | GLUCOSE | HBA1C | HDL | IL18 |
| CRP | GLUCOSE | HBA1C | HDL | INSULIN |
| CRP | GLUCOSE | HBA1C | HDL | PLAT |
| CRP | GLUCOSE | HBA1C | HSPA1B | IL18 |
| CRP | GLUCOSE | HBA1C | HSPA1B | INSULIN |

FIGURE 39 (continued)

| CRP | GLUCOSE | HBA1C | IGFBP1 | IL18 |
|---|---|---|---|---|
| CRP | GLUCOSE | HBA1C | IGFBP2 | IL18 |
| CRP | GLUCOSE | HBA1C | IGFBP2 | INSULIN |
| CRP | GLUCOSE | HBA1C | IL18 | INSULIN |
| CRP | GLUCOSE | HBA1C | IL18 | LEP |
| CRP | GLUCOSE | HBA1C | IL18 | PLAT |
| CRP | GLUCOSE | HBA1C | IL18 | TRIG |
| CRP | GLUCOSE | HBA1C | IL18 | VEGF |
| CRP | GLUCOSE | HBA1C | IL2RA | INSULIN |
| CRP | GLUCOSE | HBA1C | INSULIN | PLAT |
| CRP | GLUCOSE | HBA1C | INSULIN | TRIG |
| CRP | GLUCOSE | HBA1C | INSULIN | VEGF |
| CRP | GLUCOSE | HBA1C | PLAT | TRIG |
| CRP | GLUCOSE | HSPA1B | IL18 | INSULIN |
| CRP | GLUCOSE | IL18 | INSULIN | PLAT |
| FTH1 | GLUCOSE | HBA1C | IL18 | INSULIN |
| FTH1 | GLUCOSE | HBA1C | IL18 | LEP |
| FTH1 | GLUCOSE | HBA1C | INSULIN | PLAT |
| GLUCOSE | HBA1C | IL18 | INSULIN | PLAT |

FIGURE 40

| ADIPOQ | ANG  | CRP     | FTH1    | GLUCOSE | HBA1C   |
|--------|------|---------|---------|---------|---------|
| ADIPOQ | ANG  | CRP     | FTH1    | GLUCOSE | INSULIN |
| ADIPOQ | ANG  | CRP     | GLUCOSE | HBA1C   | IL18    |
| ADIPOQ | CCL2 | CRP     | FTH1    | GLUCOSE | HBA1C   |
| ADIPOQ | CCL2 | CRP     | FTH1    | GLUCOSE | INSULIN |
| ADIPOQ | CCL2 | CRP     | FTH1    | GLUCOSE | LEP     |
| ADIPOQ | CCL2 | CRP     | GLUCOSE | HBA1C   | IL18    |
| ADIPOQ | CCL2 | CRP     | GLUCOSE | HBA1C   | INSULIN |
| ADIPOQ | CCL2 | CRP     | GLUCOSE | HBA1C   | PLAT    |
| ADIPOQ | CCL2 | CRP     | GLUCOSE | INSULIN | PLAT    |
| ADIPOQ | CDK5 | CRP     | FTH1    | GLUCOSE | HBA1C   |
| ADIPOQ | CRP  | ENG     | FTH1    | GLUCOSE | HBA1C   |
| ADIPOQ | CRP  | ENG     | FTH1    | GLUCOSE | INSULIN |
| ADIPOQ | CRP  | ENG     | FTH1    | GLUCOSE | LEP     |
| ADIPOQ | CRP  | FTH1    | GLUCOSE | HBA1C   | IL18    |
| ADIPOQ | CRP  | FTH1    | GLUCOSE | HBA1C   | INSULIN |
| ADIPOQ | CRP  | FTH1    | GLUCOSE | HBA1C   | LEP     |
| ADIPOQ | CRP  | FTH1    | GLUCOSE | HBA1C   | PLAT    |
| ADIPOQ | CRP  | FTH1    | GLUCOSE | IL18    | LEP     |
| ADIPOQ | CRP  | FTH1    | GLUCOSE | INSULIN | PLAT    |
| ADIPOQ | CRP  | FTH1    | GLUCOSE | LEP     | PLAT    |
| ADIPOQ | CRP  | GLUCOSE | HBA1C   | IL18    | INSULIN |
| ADIPOQ | CRP  | GLUCOSE | HBA1C   | IL18    | LEP     |
| ADIPOQ | CRP  | GLUCOSE | HBA1C   | IL18    | PLAT    |
| ADIPOQ | CRP  | GLUCOSE | HBA1C   | INSULIN | PLAT    |
| ADIPOQ | CRP  | GLUCOSE | HBA1C   | LEP     | PLAT    |
| ADIPOQ | CRP  | GLUCOSE | HBA1C   | PLAT    | TRIG    |
| ADIPOQ | CRP  | GLUCOSE | IL18    | LEP     | PLAT    |
| ANG    | CCL2 | CRP     | FTH1    | GLUCOSE | HBA1C   |
| ANG    | CCL2 | CRP     | FTH1    | GLUCOSE | INSULIN |
| ANG    | CCL2 | CRP     | GLUCOSE | HBA1C   | INSULIN |
| ANG    | CRP  | ENG     | FTH1    | GLUCOSE | HBA1C   |
| ANG    | CRP  | ENG     | FTH1    | GLUCOSE | INSULIN |
| ANG    | CRP  | FTH1    | GLUCOSE | HBA1C   | IL18    |
| ANG    | CRP  | FTH1    | GLUCOSE | HBA1C   | IL2RA   |
| ANG    | CRP  | FTH1    | GLUCOSE | HBA1C   | INSULIN |
| ANG    | CRP  | FTH1    | GLUCOSE | HBA1C   | LEP     |
| ANG    | CRP  | FTH1    | GLUCOSE | HBA1C   | TRIG    |
| ANG    | CRP  | FTH1    | GLUCOSE | INSULIN | PLAT    |
| ANG    | CRP  | GLUCOSE | HBA1C   | IL18    | INSULIN |

FIGURE 40 (continued)

| | | | | | |
|---|---|---|---|---|---|
| ANG | CRP | GLUCOSE | HBA1C | IL18 | PLAT |
| ANG | CRP | GLUCOSE | HBA1C | INSULIN | PLAT |
| C3 | CCL2 | CRP | FTH1 | GLUCOSE | HBA1C |
| C3 | CCL2 | CRP | GLUCOSE | HBA1C | INSULIN |
| C3 | CRP | FTH1 | GLUCOSE | HBA1C | INSULIN |
| C3 | CRP | GLUCOSE | HBA1C | IL18 | INSULIN |
| CCL2 | CDK5 | CRP | FTH1 | GLUCOSE | HBA1C |
| CCL2 | CDK5 | CRP | FTH1 | GLUCOSE | INSULIN |
| CCL2 | CDK5 | CRP | GLUCOSE | HBA1C | INSULIN |
| CCL2 | CRP | ENG | FTH1 | GLUCOSE | HBA1C |
| CCL2 | CRP | ENG | FTH1 | GLUCOSE | INSULIN |
| CCL2 | CRP | ENG | GLUCOSE | HBA1C | INSULIN |
| CCL2 | CRP | FTH1 | GLUCOSE | GPT | HBA1C |
| CCL2 | CRP | FTH1 | GLUCOSE | GPT | INSULIN |
| CCL2 | CRP | FTH1 | GLUCOSE | HBA1C | IGFBP1 |
| CCL2 | CRP | FTH1 | GLUCOSE | HBA1C | IL18 |
| CCL2 | CRP | FTH1 | GLUCOSE | HBA1C | INSULIN |
| CCL2 | CRP | FTH1 | GLUCOSE | HBA1C | LEP |
| CCL2 | CRP | FTH1 | GLUCOSE | HBA1C | PLAT |
| CCL2 | CRP | FTH1 | GLUCOSE | HBA1C | TRIG |
| CCL2 | CRP | FTH1 | GLUCOSE | INSULIN | PLAT |
| CCL2 | CRP | GLUCOSE | GPT | HBA1C | INSULIN |
| CCL2 | CRP | GLUCOSE | HBA1C | HSPA1B | INSULIN |
| CCL2 | CRP | GLUCOSE | HBA1C | IL18 | INSULIN |
| CCL2 | CRP | GLUCOSE | HBA1C | IL18 | PLAT |
| CCL2 | CRP | GLUCOSE | HBA1C | INSULIN | PLAT |
| CCL2 | CRP | GLUCOSE | HBA1C | PLAT | TRIG |
| CCL2 | CRP | GLUCOSE | IL18 | INSULIN | PLAT |
| CCL2 | FTH1 | GLUCOSE | HBA1C | INSULIN | PLAT |
| CDK5 | CRP | FTH1 | GLUCOSE | HBA1C | INSULIN |
| CRP | ENG | FTH1 | GLUCOSE | GPT | INSULIN |
| CRP | ENG | FTH1 | GLUCOSE | HBA1C | IL18 |
| CRP | ENG | FTH1 | GLUCOSE | HBA1C | INSULIN |
| CRP | ENG | FTH1 | GLUCOSE | HBA1C | LEP |
| CRP | ENG | FTH1 | GLUCOSE | HBA1C | TRIG |
| CRP | ENG | FTH1 | GLUCOSE | IL18 | INSULIN |
| CRP | ENG | FTH1 | GLUCOSE | IL2RA | INSULIN |
| CRP | ENG | FTH1 | GLUCOSE | INSULIN | PLAT |
| CRP | ENG | FTH1 | GLUCOSE | INSULIN | TRIG |
| CRP | ENG | FTH1 | GLUCOSE | INSULIN | VEGF |

FIGURE 40 (continued)

| CRP | ENG | GLUCOSE | HBA1C | IL18 | INSULIN |
|---|---|---|---|---|---|
| CRP | ENG | GLUCOSE | HBA1C | IL18 | PLAT |
| CRP | ENG | GLUCOSE | HBA1C | IL18 | TRIG |
| CRP | ENG | GLUCOSE | HBA1C | INSULIN | PLAT |
| CRP | FTH1 | GLUCOSE | GPT | HBA1C | INSULIN |
| CRP | FTH1 | GLUCOSE | HBA1C | HGF | INSULIN |
| CRP | FTH1 | GLUCOSE | HBA1C | HSPA1B | INSULIN |
| CRP | FTH1 | GLUCOSE | HBA1C | IL18 | INSULIN |
| CRP | FTH1 | GLUCOSE | HBA1C | IL18 | LEP |
| CRP | FTH1 | GLUCOSE | HBA1C | IL18 | PLAT |
| CRP | FTH1 | GLUCOSE | HBA1C | IL2RA | INSULIN |
| CRP | FTH1 | GLUCOSE | HBA1C | INSULIN | LEP |
| CRP | FTH1 | GLUCOSE | HBA1C | INSULIN | PLAT |
| CRP | FTH1 | GLUCOSE | HBA1C | INSULIN | TRIG |
| CRP | FTH1 | GLUCOSE | HBA1C | INSULIN | VEGF |
| CRP | GLUCOSE | GPT | HBA1C | IL18 | INSULIN |
| CRP | GLUCOSE | HBA1C | HSPA1B | IL18 | INSULIN |
| CRP | GLUCOSE | HBA1C | IL18 | INSULIN | PLAT |
| CRP | GLUCOSE | HBA1C | IL18 | PLAT | TRIG |
| FTH1 | GLUCOSE | HBA1C | IL18 | INSULIN | PLAT |

FIGURE 41

| | | | | | | |
|---|---|---|---|---|---|---|
| ADIPOQ | ANG | CRP | FTH1 | GLUCOSE | HBA1C | IL18 |
| ADIPOQ | ANG | CRP | FTH1 | GLUCOSE | HBA1C | INSULIN |
| ADIPOQ | ANG | CRP | FTH1 | GLUCOSE | HBA1C | LEP |
| ADIPOQ | ANG | CRP | FTH1 | GLUCOSE | HBA1C | PLAT |
| ADIPOQ | ANG | CRP | GLUCOSE | HBA1C | IL18 | PLAT |
| ADIPOQ | ANG | CRP | GLUCOSE | HBA1C | INSULIN | PLAT |
| ADIPOQ | C3 | CRP | FTH1 | GLUCOSE | HBA1C | INSULIN |
| ADIPOQ | C3 | CRP | FTH1 | GLUCOSE | HBA1C | LEP |
| ADIPOQ | CCL2 | CRP | ENG | FTH1 | GLUCOSE | HBA1C |
| ADIPOQ | CCL2 | CRP | ENG | FTH1 | GLUCOSE | LEP |
| ADIPOQ | CCL2 | CRP | FTH1 | GLUCOSE | HBA1C | INSULIN |
| ADIPOQ | CCL2 | CRP | FTH1 | GLUCOSE | HBA1C | LEP |
| ADIPOQ | CCL2 | CRP | FTH1 | GLUCOSE | HBA1C | PLAT |
| ADIPOQ | CCL2 | CRP | FTH1 | GLUCOSE | LEP | PLAT |
| ADIPOQ | CCL2 | CRP | GLUCOSE | HBA1C | IL18 | PLAT |
| ADIPOQ | CCL2 | CRP | GLUCOSE | HBA1C | INSULIN | PLAT |
| ADIPOQ | CDK5 | CRP | FTH1 | GLUCOSE | HBA1C | LEP |
| ADIPOQ | CRP | ENG | FTH1 | GLUCOSE | HBA1C | IL18 |
| ADIPOQ | CRP | ENG | FTH1 | GLUCOSE | HBA1C | INSULIN |
| ADIPOQ | CRP | ENG | FTH1 | GLUCOSE | HBA1C | LEP |
| ADIPOQ | CRP | ENG | FTH1 | GLUCOSE | HBA1C | PLAT |
| ADIPOQ | CRP | ENG | FTH1 | GLUCOSE | IL18 | LEP |
| ADIPOQ | CRP | ENG | FTH1 | GLUCOSE | INSULIN | PLAT |
| ADIPOQ | CRP | ENG | FTH1 | GLUCOSE | LEP | PLAT |
| ADIPOQ | CRP | FTH1 | GLUCOSE | GPT | HBA1C | LEP |
| ADIPOQ | CRP | FTH1 | GLUCOSE | HBA1C | HSPA1B | LEP |
| ADIPOQ | CRP | FTH1 | GLUCOSE | HBA1C | IL18 | INSULIN |
| ADIPOQ | CRP | FTH1 | GLUCOSE | HBA1C | IL18 | LEP |
| ADIPOQ | CRP | FTH1 | GLUCOSE | HBA1C | IL18 | PLAT |
| ADIPOQ | CRP | FTH1 | GLUCOSE | HBA1C | INSULIN | LEP |
| ADIPOQ | CRP | FTH1 | GLUCOSE | HBA1C | INSULIN | PLAT |
| ADIPOQ | CRP | FTH1 | GLUCOSE | HBA1C | LEP | PLAT |
| ADIPOQ | CRP | GLUCOSE | HBA1C | IL18 | INSULIN | PLAT |
| ADIPOQ | CRP | GLUCOSE | HBA1C | IL18 | LEP | PLAT |
| ANG | CCL2 | CRP | FTH1 | GLUCOSE | HBA1C | IL18 |
| ANG | CCL2 | CRP | FTH1 | GLUCOSE | HBA1C | INSULIN |
| ANG | CCL2 | CRP | FTH1 | GLUCOSE | HBA1C | LEP |
| ANG | CCL2 | CRP | FTH1 | GLUCOSE | HBA1C | PLAT |
| ANG | CCL2 | CRP | FTH1 | GLUCOSE | INSULIN | PLAT |
| ANG | CCL2 | CRP | GLUCOSE | HBA1C | INSULIN | PLAT |

FIGURE 41 (continued)

| | | | | | | |
|---|---|---|---|---|---|---|
| ANG | CDK5 | CRP | FTH1 | GLUCOSE | HBA1C | INSULIN |
| ANG | CRP | ENG | FTH1 | GLUCOSE | HBA1C | IL18 |
| ANG | CRP | ENG | FTH1 | GLUCOSE | HBA1C | INSULIN |
| ANG | CRP | FTH1 | GLUCOSE | GPT | HBA1C | INSULIN |
| ANG | CRP | FTH1 | GLUCOSE | HBA1C | HSPA1B | INSULIN |
| ANG | CRP | FTH1 | GLUCOSE | HBA1C | IL18 | INSULIN |
| ANG | CRP | FTH1 | GLUCOSE | HBA1C | IL18 | LEP |
| ANG | CRP | FTH1 | GLUCOSE | HBA1C | IL18 | PLAT |
| ANG | CRP | FTH1 | GLUCOSE | HBA1C | IL2RA | INSULIN |
| ANG | CRP | FTH1 | GLUCOSE | HBA1C | INSULIN | LEP |
| ANG | CRP | FTH1 | GLUCOSE | HBA1C | INSULIN | PLAT |
| ANG | CRP | FTH1 | GLUCOSE | HBA1C | INSULIN | TRIG |
| ANG | CRP | FTH1 | GLUCOSE | HBA1C | PLAT | TRIG |
| ANG | CRP | GLUCOSE | HBA1C | IL18 | INSULIN | PLAT |
| C3 | CCL2 | CRP | FTH1 | GLUCOSE | HBA1C | INSULIN |
| C3 | CRP | ENG | FTH1 | GLUCOSE | HBA1C | INSULIN |
| C3 | CRP | FTH1 | GLUCOSE | HBA1C | IL18 | INSULIN |
| CCL2 | CDK5 | CRP | FTH1 | GLUCOSE | HBA1C | INSULIN |
| CCL2 | CRP | ENG | FTH1 | GLUCOSE | GPT | HBA1C |
| CCL2 | CRP | ENG | FTH1 | GLUCOSE | GPT | INSULIN |
| CCL2 | CRP | ENG | FTH1 | GLUCOSE | HBA1C | IL18 |
| CCL2 | CRP | ENG | FTH1 | GLUCOSE | HBA1C | INSULIN |
| CCL2 | CRP | ENG | FTH1 | GLUCOSE | HBA1C | LEP |
| CCL2 | CRP | ENG | FTH1 | GLUCOSE | HBA1C | PLAT |
| CCL2 | CRP | ENG | FTH1 | GLUCOSE | HBA1C | TRIG |
| CCL2 | CRP | ENG | FTH1 | GLUCOSE | INSULIN | PLAT |
| CCL2 | CRP | FTH1 | GLUCOSE | GPT | HBA1C | INSULIN |
| CCL2 | CRP | FTH1 | GLUCOSE | HBA1C | HSPA1B | INSULIN |
| CCL2 | CRP | FTH1 | GLUCOSE | HBA1C | IL18 | INSULIN |
| CCL2 | CRP | FTH1 | GLUCOSE | HBA1C | IL18 | LEP |
| CCL2 | CRP | FTH1 | GLUCOSE | HBA1C | IL18 | PLAT |
| CCL2 | CRP | FTH1 | GLUCOSE | HBA1C | INSULIN | LEP |
| CCL2 | CRP | FTH1 | GLUCOSE | HBA1C | INSULIN | PLAT |
| CCL2 | CRP | FTH1 | GLUCOSE | HBA1C | INSULIN | VEGF |
| CCL2 | CRP | FTH1 | GLUCOSE | HBA1C | LEP | PLAT |
| CCL2 | CRP | GLUCOSE | HBA1C | IL18 | INSULIN | PLAT |
| CDK5 | CRP | ENG | FTH1 | GLUCOSE | HBA1C | INSULIN |
| CRP | ENG | FTH1 | GLUCOSE | GPT | HBA1C | IL18 |
| CRP | ENG | FTH1 | GLUCOSE | GPT | HBA1C | INSULIN |
| CRP | ENG | FTH1 | GLUCOSE | GPT | HBA1C | LEP |

FIGURE 41 (continued)

| CRP | ENG | FTH1 | GLUCOSE | HBA1C | HDL | INSULIN |
|---|---|---|---|---|---|---|
| CRP | ENG | FTH1 | GLUCOSE | HBA1C | HGF | INSULIN |
| CRP | ENG | FTH1 | GLUCOSE | HBA1C | HSPA1B | INSULIN |
| CRP | ENG | FTH1 | GLUCOSE | HBA1C | IGFBP2 | INSULIN |
| CRP | ENG | FTH1 | GLUCOSE | HBA1C | IL18 | INSULIN |
| CRP | ENG | FTH1 | GLUCOSE | HBA1C | IL18 | LEP |
| CRP | ENG | FTH1 | GLUCOSE | HBA1C | IL18 | PLAT |
| CRP | ENG | FTH1 | GLUCOSE | HBA1C | IL18 | TRIG |
| CRP | ENG | FTH1 | GLUCOSE | HBA1C | IL2RA | INSULIN |
| CRP | ENG | FTH1 | GLUCOSE | HBA1C | INSULIN | LEP |
| CRP | ENG | FTH1 | GLUCOSE | HBA1C | INSULIN | PLAT |
| CRP | ENG | FTH1 | GLUCOSE | HBA1C | INSULIN | SERPINE1 |
| CRP | ENG | FTH1 | GLUCOSE | HBA1C | INSULIN | TRIG |
| CRP | ENG | FTH1 | GLUCOSE | HBA1C | INSULIN | VEGF |
| CRP | ENG | FTH1 | GLUCOSE | HBA1C | LEP | TRIG |
| CRP | ENG | GLUCOSE | HBA1C | IL18 | INSULIN | PLAT |
| CRP | FTH1 | GLUCOSE | HBA1C | HSPA1B | IL18 | INSULIN |
| CRP | FTH1 | GLUCOSE | HBA1C | IL18 | INSULIN | PLAT |
| CRP | FTH1 | GLUCOSE | HBA1C | IL2RA | INSULIN | PLAT |
| CRP | FTH1 | GLUCOSE | HBA1C | INSULIN | PLAT | TRIG |

FIGURE 42

| ADIPOQ | CCL2 | CRP | ENG | FTH1 | GLUCOSE | HBA1C | INSULIN |
|---|---|---|---|---|---|---|---|
| ADIPOQ | CCL2 | CRP | ENG | FTH1 | GLUCOSE | HBA1C | LEP |
| ADIPOQ | CCL2 | CRP | ENG | FTH1 | GLUCOSE | HBA1C | PLAT |
| ADIPOQ | CCL2 | CRP | ENG | FTH1 | GLUCOSE | INSULIN | PLAT |
| ADIPOQ | CCL2 | CRP | ENG | FTH1 | GLUCOSE | LEP | PLAT |
| ADIPOQ | CCL2 | CRP | FTH1 | GLUCOSE | HBA1C | HSPA1B | LEP |
| ADIPOQ | CCL2 | CRP | FTH1 | GLUCOSE | HBA1C | IL18 | INSULIN |
| ADIPOQ | CCL2 | CRP | FTH1 | GLUCOSE | HBA1C | IL18 | LEP |
| ADIPOQ | CCL2 | CRP | FTH1 | GLUCOSE | HBA1C | IL18 | PLAT |
| ADIPOQ | CCL2 | CRP | FTH1 | GLUCOSE | HBA1C | INSULIN | LEP |
| ADIPOQ | CCL2 | CRP | FTH1 | GLUCOSE | HBA1C | INSULIN | PLAT |
| ADIPOQ | CCL2 | CRP | FTH1 | GLUCOSE | HBA1C | LEP | PLAT |
| ADIPOQ | CCL2 | CRP | GLUCOSE | HBA1C | IL18 | INSULIN | PLAT |
| ADIPOQ | CRP | ENG | FTH1 | GLUCOSE | GPT | HBA1C | INSULIN |
| ADIPOQ | CRP | ENG | FTH1 | GLUCOSE | GPT | HBA1C | LEP |
| ADIPOQ | CRP | ENG | FTH1 | GLUCOSE | HBA1C | HSPA1B | INSULIN |
| ADIPOQ | CRP | ENG | FTH1 | GLUCOSE | HBA1C | HSPA1B | LEP |
| ADIPOQ | CRP | ENG | FTH1 | GLUCOSE | HBA1C | IL18 | INSULIN |
| ADIPOQ | CRP | ENG | FTH1 | GLUCOSE | HBA1C | IL18 | LEP |
| ADIPOQ | CRP | ENG | FTH1 | GLUCOSE | HBA1C | IL18 | PLAT |
| ADIPOQ | CRP | ENG | FTH1 | GLUCOSE | HBA1C | INSULIN | LEP |
| ADIPOQ | CRP | ENG | FTH1 | GLUCOSE | HBA1C | INSULIN | PLAT |
| ADIPOQ | CRP | ENG | FTH1 | GLUCOSE | HBA1C | INSULIN | VEGF |
| ADIPOQ | CRP | ENG | FTH1 | GLUCOSE | HBA1C | LEP | PLAT |
| ADIPOQ | CRP | ENG | FTH1 | GLUCOSE | HBA1C | LEP | TRIG |
| ADIPOQ | CRP | ENG | FTH1 | GLUCOSE | HBA1C | LEP | VEGF |
| ADIPOQ | CRP | ENG | FTH1 | GLUCOSE | HBA1C | PLAT | TRIG |
| ADIPOQ | CRP | ENG | FTH1 | GLUCOSE | IL18 | LEP | PLAT |
| ADIPOQ | CRP | FTH1 | GLUCOSE | GPT | HBA1C | INSULIN | PLAT |
| ADIPOQ | CRP | FTH1 | GLUCOSE | GPT | HBA1C | LEP | PLAT |
| ADIPOQ | CRP | FTH1 | GLUCOSE | HBA1C | HSPA1B | IL18 | LEP |
| ADIPOQ | CRP | FTH1 | GLUCOSE | HBA1C | HSPA1B | INSULIN | PLAT |
| ADIPOQ | CRP | FTH1 | GLUCOSE | HBA1C | HSPA1B | LEP | PLAT |
| ADIPOQ | CRP | FTH1 | GLUCOSE | HBA1C | IL18 | INSULIN | LEP |
| ADIPOQ | CRP | FTH1 | GLUCOSE | HBA1C | IL18 | INSULIN | PLAT |
| ADIPOQ | CRP | FTH1 | GLUCOSE | HBA1C | IL18 | LEP | PLAT |
| ADIPOQ | CRP | FTH1 | GLUCOSE | HBA1C | IL2RA | INSULIN | PLAT |
| ADIPOQ | CRP | FTH1 | GLUCOSE | HBA1C | INSULIN | LEP | PLAT |
| ADIPOQ | CRP | FTH1 | GLUCOSE | HBA1C | INSULIN | PLAT | TRIG |
| ADIPOQ | CRP | FTH1 | GLUCOSE | HBA1C | LEP | PLAT | TRIG |

FIGURE 42 (continued)

| ADIPOQ | CRP | FTH1 | GLUCOSE | HBA1C | LEP | PLAT | VEGF |
|---|---|---|---|---|---|---|---|
| ADIPOQ | CRP | GLUCOSE | HBA1C | IL18 | INSULIN | LEP | PLAT |
| CCL2 | CRP | ENG | FTH1 | GLUCOSE | GPT | HBA1C | INSULIN |
| CCL2 | CRP | ENG | FTH1 | GLUCOSE | GPT | HBA1C | LEP |
| CCL2 | CRP | ENG | FTH1 | GLUCOSE | GPT | HBA1C | PLAT |
| CCL2 | CRP | ENG | FTH1 | GLUCOSE | GPT | INSULIN | PLAT |
| CCL2 | CRP | ENG | FTH1 | GLUCOSE | HBA1C | HGF | INSULIN |
| CCL2 | CRP | ENG | FTH1 | GLUCOSE | HBA1C | HSPA1B | INSULIN |
| CCL2 | CRP | ENG | FTH1 | GLUCOSE | HBA1C | IGFBP1 | INSULIN |
| CCL2 | CRP | ENG | FTH1 | GLUCOSE | HBA1C | IGFBP1 | PLAT |
| CCL2 | CRP | ENG | FTH1 | GLUCOSE | HBA1C | IL18 | INSULIN |
| CCL2 | CRP | ENG | FTH1 | GLUCOSE | HBA1C | IL18 | LEP |
| CCL2 | CRP | ENG | FTH1 | GLUCOSE | HBA1C | IL18 | PLAT |
| CCL2 | CRP | ENG | FTH1 | GLUCOSE | HBA1C | IL2RA | INSULIN |
| CCL2 | CRP | ENG | FTH1 | GLUCOSE | HBA1C | INSULIN | LEP |
| CCL2 | CRP | ENG | FTH1 | GLUCOSE | HBA1C | INSULIN | PLAT |
| CCL2 | CRP | ENG | FTH1 | GLUCOSE | HBA1C | INSULIN | TRIG |
| CCL2 | CRP | ENG | FTH1 | GLUCOSE | HBA1C | INSULIN | VEGF |
| CCL2 | CRP | ENG | FTH1 | GLUCOSE | HBA1C | LEP | PLAT |
| CCL2 | CRP | ENG | FTH1 | GLUCOSE | HBA1C | LEP | TRIG |
| CCL2 | CRP | ENG | FTH1 | GLUCOSE | HBA1C | PLAT | TRIG |
| CCL2 | CRP | FTH1 | GLUCOSE | GPT | HBA1C | INSULIN | PLAT |
| CCL2 | CRP | FTH1 | GLUCOSE | HBA1C | HGF | INSULIN | PLAT |
| CCL2 | CRP | FTH1 | GLUCOSE | HBA1C | HSPA1B | IL18 | INSULIN |
| CCL2 | CRP | FTH1 | GLUCOSE | HBA1C | HSPA1B | INSULIN | PLAT |
| CCL2 | CRP | FTH1 | GLUCOSE | HBA1C | IGFBP1 | INSULIN | PLAT |
| CCL2 | CRP | FTH1 | GLUCOSE | HBA1C | IL18 | INSULIN | PLAT |
| CCL2 | CRP | FTH1 | GLUCOSE | HBA1C | IL2RA | INSULIN | PLAT |
| CCL2 | CRP | FTH1 | GLUCOSE | HBA1C | INSULIN | LEP | PLAT |
| CCL2 | CRP | FTH1 | GLUCOSE | HBA1C | INSULIN | PLAT | TRIG |
| CCL2 | CRP | FTH1 | GLUCOSE | HBA1C | INSULIN | PLAT | VEGF |
| CCL2 | CRP | GLUCOSE | HBA1C | HSPA1B | IL18 | INSULIN | PLAT |
| CRP | ENG | FTH1 | GLUCOSE | GPT | HBA1C | IL18 | INSULIN |
| CRP | ENG | FTH1 | GLUCOSE | GPT | HBA1C | IL18 | LEP |
| CRP | ENG | FTH1 | GLUCOSE | GPT | HBA1C | IL2RA | INSULIN |
| CRP | ENG | FTH1 | GLUCOSE | GPT | HBA1C | INSULIN | LEP |
| CRP | ENG | FTH1 | GLUCOSE | GPT | HBA1C | INSULIN | PLAT |
| CRP | ENG | FTH1 | GLUCOSE | HBA1C | HGF | IL18 | INSULIN |
| CRP | ENG | FTH1 | GLUCOSE | HBA1C | HGF | INSULIN | PLAT |
| CRP | ENG | FTH1 | GLUCOSE | HBA1C | HSPA1B | IL18 | INSULIN |

FIGURE 42 (continued)

| CRP | ENG | FTH1 | GLUCOSE | HBA1C | HSPA1B | IL18 | LEP |
|-----|-----|------|---------|-------|--------|------|-----|
| CRP | ENG | FTH1 | GLUCOSE | HBA1C | HSPA1B | INSULIN | PLAT |
| CRP | ENG | FTH1 | GLUCOSE | HBA1C | IGFBP1 | IL18 | INSULIN |
| CRP | ENG | FTH1 | GLUCOSE | HBA1C | IL18 | IL2RA | INSULIN |
| CRP | ENG | FTH1 | GLUCOSE | HBA1C | IL18 | INSULIN | LEP |
| CRP | ENG | FTH1 | GLUCOSE | HBA1C | IL18 | INSULIN | PLAT |
| CRP | ENG | FTH1 | GLUCOSE | HBA1C | IL18 | INSULIN | TRIG |
| CRP | ENG | FTH1 | GLUCOSE | HBA1C | IL18 | INSULIN | VEGF |
| CRP | ENG | FTH1 | GLUCOSE | HBA1C | IL18 | LEP | PLAT |
| CRP | ENG | FTH1 | GLUCOSE | HBA1C | IL18 | LEP | TRIG |
| CRP | ENG | FTH1 | GLUCOSE | HBA1C | IL18 | PLAT | TRIG |
| CRP | ENG | FTH1 | GLUCOSE | HBA1C | IL2RA | INSULIN | PLAT |
| CRP | ENG | FTH1 | GLUCOSE | HBA1C | INSULIN | LEP | PLAT |
| CRP | ENG | FTH1 | GLUCOSE | HBA1C | INSULIN | PLAT | TRIG |
| CRP | ENG | FTH1 | GLUCOSE | HBA1C | INSULIN | PLAT | VEGF |
| CRP | ENG | FTH1 | GLUCOSE | HBA1C | LEP | PLAT | TRIG |
| CRP | FTH1 | GLUCOSE | HBA1C | HSPA1B | IL18 | INSULIN | PLAT |
| CRP | FTH1 | GLUCOSE | HBA1C | IL18 | INSULIN | LEP | PLAT |
| CRP | FTH1 | GLUCOSE | HBA1C | IL18 | INSULIN | PLAT | TRIG |
| CRP | FTH1 | GLUCOSE | HBA1C | IL18 | INSULIN | PLAT | VEGF |

FIGURE 43

| ADIPOQ | CCL2 | CRP | ENG | FTH1 | GLUCOSE | GPT | HBA1C | INSULIN |
|---|---|---|---|---|---|---|---|---|
| ADIPOQ | CCL2 | CRP | ENG | FTH1 | GLUCOSE | GPT | HBA1C | LEP |
| ADIPOQ | CCL2 | CRP | ENG | FTH1 | GLUCOSE | GPT | HBA1C | PLAT |
| ADIPOQ | CCL2 | CRP | ENG | FTH1 | GLUCOSE | HBA1C | HSPA1B | INSULIN |
| ADIPOQ | CCL2 | CRP | ENG | FTH1 | GLUCOSE | HBA1C | HSPA1B | LEP |
| ADIPOQ | CCL2 | CRP | ENG | FTH1 | GLUCOSE | HBA1C | HSPA1B | PLAT |
| ADIPOQ | CCL2 | CRP | ENG | FTH1 | GLUCOSE | HBA1C | IL18 | INSULIN |
| ADIPOQ | CCL2 | CRP | ENG | FTH1 | GLUCOSE | HBA1C | IL18 | LEP |
| ADIPOQ | CCL2 | CRP | ENG | FTH1 | GLUCOSE | HBA1C | IL18 | PLAT |
| ADIPOQ | CCL2 | CRP | ENG | FTH1 | GLUCOSE | HBA1C | INSULIN | LEP |
| ADIPOQ | CCL2 | CRP | ENG | FTH1 | GLUCOSE | HBA1C | INSULIN | PLAT |
| ADIPOQ | CCL2 | CRP | ENG | FTH1 | GLUCOSE | HBA1C | LEP | PLAT |
| ADIPOQ | CCL2 | CRP | ENG | FTH1 | GLUCOSE | HBA1C | PLAT | TRIG |
| ADIPOQ | CCL2 | CRP | ENG | FTH1 | GLUCOSE | HSPA1B | LEP | PLAT |
| ADIPOQ | CCL2 | CRP | ENG | FTH1 | GLUCOSE | IL18 | LEP | PLAT |
| ADIPOQ | CCL2 | CRP | ENG | FTH1 | GLUCOSE | INSULIN | LEP | PLAT |
| ADIPOQ | CCL2 | CRP | FTH1 | GLUCOSE | GPT | HBA1C | INSULIN | PLAT |
| ADIPOQ | CCL2 | CRP | FTH1 | GLUCOSE | GPT | HBA1C | LEP | PLAT |
| ADIPOQ | CCL2 | CRP | FTH1 | GLUCOSE | HBA1C | HSPA1B | INSULIN | PLAT |
| ADIPOQ | CCL2 | CRP | FTH1 | GLUCOSE | HBA1C | HSPA1B | LEP | PLAT |
| ADIPOQ | CCL2 | CRP | FTH1 | GLUCOSE | HBA1C | IL18 | INSULIN | PLAT |
| ADIPOQ | CCL2 | CRP | FTH1 | GLUCOSE | HBA1C | IL18 | LEP | PLAT |
| ADIPOQ | CCL2 | CRP | FTH1 | GLUCOSE | HBA1C | INSULIN | LEP | PLAT |
| ADIPOQ | CCL2 | CRP | FTH1 | GLUCOSE | HBA1C | INSULIN | PLAT | VEGF |
| ADIPOQ | CCL2 | CRP | FTH1 | GLUCOSE | HBA1C | LEP | PLAT | TRIG |
| ADIPOQ | CCL2 | CRP | FTH1 | GLUCOSE | HBA1C | LEP | PLAT | VEGF |
| ADIPOQ | CRP | ENG | FTH1 | GLUCOSE | GPT | HBA1C | IL18 | INSULIN |
| ADIPOQ | CRP | ENG | FTH1 | GLUCOSE | GPT | HBA1C | IL18 | LEP |
| ADIPOQ | CRP | ENG | FTH1 | GLUCOSE | GPT | HBA1C | IL18 | PLAT |
| ADIPOQ | CRP | ENG | FTH1 | GLUCOSE | GPT | HBA1C | INSULIN | LEP |
| ADIPOQ | CRP | ENG | FTH1 | GLUCOSE | GPT | HBA1C | INSULIN | PLAT |
| ADIPOQ | CRP | ENG | FTH1 | GLUCOSE | GPT | HBA1C | LEP | PLAT |
| ADIPOQ | CRP | ENG | FTH1 | GLUCOSE | HBA1C | HGF | INSULIN | PLAT |
| ADIPOQ | CRP | ENG | FTH1 | GLUCOSE | HBA1C | HGF | LEP | PLAT |
| ADIPOQ | CRP | ENG | FTH1 | GLUCOSE | HBA1C | HSPA1B | IL18 | LEP |
| ADIPOQ | CRP | ENG | FTH1 | GLUCOSE | HBA1C | HSPA1B | INSULIN | LEP |
| ADIPOQ | CRP | ENG | FTH1 | GLUCOSE | HBA1C | HSPA1B | INSULIN | PLAT |
| ADIPOQ | CRP | ENG | FTH1 | GLUCOSE | HBA1C | HSPA1B | LEP | PLAT |
| ADIPOQ | CRP | ENG | FTH1 | GLUCOSE | HBA1C | IGFBP1 | INSULIN | PLAT |
| ADIPOQ | CRP | ENG | FTH1 | GLUCOSE | HBA1C | IGFBP1 | LEP | PLAT |

FIGURE 43 (continued)

| ADIPOQ | CRP | ENG | FTH1 | GLUCOSE | HBA1C | IL18 | INSULIN | LEP |
|---|---|---|---|---|---|---|---|---|
| ADIPOQ | CRP | ENG | FTH1 | GLUCOSE | HBA1C | IL18 | INSULIN | PLAT |
| ADIPOQ | CRP | ENG | FTH1 | GLUCOSE | HBA1C | IL18 | LEP | PLAT |
| ADIPOQ | CRP | ENG | FTH1 | GLUCOSE | HBA1C | IL18 | LEP | TRIG |
| ADIPOQ | CRP | ENG | FTH1 | GLUCOSE | HBA1C | IL18 | LEP | VEGF |
| ADIPOQ | CRP | ENG | FTH1 | GLUCOSE | HBA1C | IL18 | PLAT | TRIG |
| ADIPOQ | CRP | ENG | FTH1 | GLUCOSE | HBA1C | IL2RA | INSULIN | PLAT |
| ADIPOQ | CRP | ENG | FTH1 | GLUCOSE | HBA1C | IL2RA | LEP | PLAT |
| ADIPOQ | CRP | ENG | FTH1 | GLUCOSE | HBA1C | INSULIN | LEP | PLAT |
| ADIPOQ | CRP | ENG | FTH1 | GLUCOSE | HBA1C | INSULIN | PLAT | TRIG |
| ADIPOQ | CRP | ENG | FTH1 | GLUCOSE | HBA1C | INSULIN | PLAT | VEGF |
| ADIPOQ | CRP | ENG | FTH1 | GLUCOSE | HBA1C | LEP | PLAT | TRIG |
| ADIPOQ | CRP | ENG | FTH1 | GLUCOSE | HBA1C | LEP | PLAT | VEGF |
| ADIPOQ | CRP | ENG | FTH1 | GLUCOSE | HSPA1B | IL18 | LEP | PLAT |
| ADIPOQ | CRP | FTH1 | GLUCOSE | GPT | HBA1C | IL18 | INSULIN | PLAT |
| ADIPOQ | CRP | FTH1 | GLUCOSE | HBA1C | HSPA1B | IL18 | INSULIN | PLAT |
| ADIPOQ | CRP | FTH1 | GLUCOSE | HBA1C | HSPA1B | IL18 | LEP | PLAT |
| ADIPOQ | CRP | FTH1 | GLUCOSE | HBA1C | IGFBP1 | IL18 | INSULIN | PLAT |
| ADIPOQ | CRP | FTH1 | GLUCOSE | HBA1C | IL18 | INSULIN | LEP | PLAT |
| ADIPOQ | CRP | FTH1 | GLUCOSE | HBA1C | IL18 | LEP | PLAT | TRIG |
| ADIPOQ | ENG | FTH1 | GLUCOSE | HBA1C | HSPA1B | IL18 | LEP | PLAT |
| CCL2 | CRP | ENG | FTH1 | GLUCOSE | GPT | HBA1C | HSPA1B | INSULIN |
| CCL2 | CRP | ENG | FTH1 | GLUCOSE | GPT | HBA1C | IL18 | INSULIN |
| CCL2 | CRP | ENG | FTH1 | GLUCOSE | GPT | HBA1C | IL18 | LEP |
| CCL2 | CRP | ENG | FTH1 | GLUCOSE | GPT | HBA1C | IL2RA | INSULIN |
| CCL2 | CRP | ENG | FTH1 | GLUCOSE | GPT | HBA1C | INSULIN | LEP |
| CCL2 | CRP | ENG | FTH1 | GLUCOSE | GPT | HBA1C | INSULIN | PLAT |
| CCL2 | CRP | ENG | FTH1 | GLUCOSE | GPT | HBA1C | INSULIN | VEGF |
| CCL2 | CRP | ENG | FTH1 | GLUCOSE | GPT | HBA1C | LEP | PLAT |
| CCL2 | CRP | ENG | FTH1 | GLUCOSE | HBA1C | HGF | INSULIN | PLAT |
| CCL2 | CRP | ENG | FTH1 | GLUCOSE | HBA1C | HSPA1B | IL18 | INSULIN |
| CCL2 | CRP | ENG | FTH1 | GLUCOSE | HBA1C | HSPA1B | IL18 | LEP |
| CCL2 | CRP | ENG | FTH1 | GLUCOSE | HBA1C | HSPA1B | INSULIN | LEP |
| CCL2 | CRP | ENG | FTH1 | GLUCOSE | HBA1C | HSPA1B | INSULIN | PLAT |
| CCL2 | CRP | ENG | FTH1 | GLUCOSE | HBA1C | HSPA1B | LEP | PLAT |
| CCL2 | CRP | ENG | FTH1 | GLUCOSE | HBA1C | IGFBP1 | INSULIN | PLAT |
| CCL2 | CRP | ENG | FTH1 | GLUCOSE | HBA1C | IL18 | INSULIN | LEP |
| CCL2 | CRP | ENG | FTH1 | GLUCOSE | HBA1C | IL18 | INSULIN | PLAT |
| CCL2 | CRP | ENG | FTH1 | GLUCOSE | HBA1C | IL18 | LEP | PLAT |
| CCL2 | CRP | ENG | FTH1 | GLUCOSE | HBA1C | IL2RA | INSULIN | PLAT |

FIGURE 43 (continued)

| CCL2 | CRP | ENG | FTH1 | GLUCOSE | HBA1C | INSULIN | LEP | PLAT |
|---|---|---|---|---|---|---|---|---|
| CCL2 | CRP | ENG | FTH1 | GLUCOSE | HBA1C | INSULIN | PLAT | TRIG |
| CCL2 | CRP | ENG | FTH1 | GLUCOSE | HBA1C | INSULIN | PLAT | VEGF |
| CCL2 | CRP | ENG | FTH1 | GLUCOSE | HBA1C | LEP | PLAT | TRIG |
| CCL2 | CRP | FTH1 | GLUCOSE | HBA1C | HSPA1B | IL18 | INSULIN | PLAT |
| CCL2 | CRP | FTH1 | GLUCOSE | HBA1C | IL18 | INSULIN | LEP | PLAT |
| CRP | ENG | FTH1 | GLUCOSE | GPT | HBA1C | HSPA1B | IL18 | INSULIN |
| CRP | ENG | FTH1 | GLUCOSE | GPT | HBA1C | IL18 | INSULIN | LEP |
| CRP | ENG | FTH1 | GLUCOSE | GPT | HBA1C | IL18 | INSULIN | PLAT |
| CRP | ENG | FTH1 | GLUCOSE | GPT | HBA1C | IL2RA | INSULIN | PLAT |
| CRP | ENG | FTH1 | GLUCOSE | GPT | HBA1C | INSULIN | LEP | PLAT |
| CRP | ENG | FTH1 | GLUCOSE | HBA1C | HGF | IL18 | INSULIN | PLAT |
| CRP | ENG | FTH1 | GLUCOSE | HBA1C | HSPA1B | IL18 | INSULIN | LEP |
| CRP | ENG | FTH1 | GLUCOSE | HBA1C | HSPA1B | IL18 | INSULIN | PLAT |
| CRP | ENG | FTH1 | GLUCOSE | HBA1C | IGFBP1 | IL18 | INSULIN | PLAT |
| CRP | ENG | FTH1 | GLUCOSE | HBA1C | IL18 | IL2RA | INSULIN | PLAT |
| CRP | ENG | FTH1 | GLUCOSE | HBA1C | IL18 | INSULIN | LEP | PLAT |
| CRP | ENG | FTH1 | GLUCOSE | HBA1C | IL18 | INSULIN | PLAT | TRIG |
| CRP | ENG | FTH1 | GLUCOSE | HBA1C | IL18 | INSULIN | PLAT | VEGF |
| CRP | ENG | FTH1 | GLUCOSE | HBA1C | IL18 | LEP | PLAT | TRIG |

FIGURE 44

| |
|---|
| ADIPOQ; CCL2; CRP; ENG; FTH1; GLUCOSE; GPT; HBA1C; HSPA1B; LEP |
| ADIPOQ; CCL2; CRP; ENG; FTH1; GLUCOSE; GPT; HBA1C; IL18; LEP |
| ADIPOQ; CCL2; CRP; ENG; FTH1; GLUCOSE; GPT; HBA1C; IL18; PLAT |
| ADIPOQ; CCL2; CRP; ENG; FTH1; GLUCOSE; GPT; HBA1C; INSULIN; LEP |
| ADIPOQ; CCL2; CRP; ENG; FTH1; GLUCOSE; GPT; HBA1C; INSULIN; PLAT |
| ADIPOQ; CCL2; CRP; ENG; FTH1; GLUCOSE; GPT; HBA1C; LEP; PLAT |
| ADIPOQ; CCL2; CRP; ENG; FTH1; GLUCOSE; HBA1C; HGF; INSULIN; PLAT |
| ADIPOQ; CCL2; CRP; ENG; FTH1; GLUCOSE; HBA1C; HGF; LEP; PLAT |
| ADIPOQ; CCL2; CRP; ENG; FTH1; GLUCOSE; HBA1C; HSPA1B; IL18; LEP |
| ADIPOQ; CCL2; CRP; ENG; FTH1; GLUCOSE; HBA1C; HSPA1B; INSULIN; LEP |
| ADIPOQ; CCL2; CRP; ENG; FTH1; GLUCOSE; HBA1C; HSPA1B; INSULIN; PLAT |
| ADIPOQ; CCL2; CRP; ENG; FTH1; GLUCOSE; HBA1C; HSPA1B; LEP; PLAT |
| ADIPOQ; CCL2; CRP; ENG; FTH1; GLUCOSE; HBA1C; IGFBP1; INSULIN; PLAT |
| ADIPOQ; CCL2; CRP; ENG; FTH1; GLUCOSE; HBA1C; IGFBP1; LEP; PLAT |
| ADIPOQ; CCL2; CRP; ENG; FTH1; GLUCOSE; HBA1C; IL18; INSULIN; PLAT |
| ADIPOQ; CCL2; CRP; ENG; FTH1; GLUCOSE; HBA1C; IL18; LEP; PLAT |
| ADIPOQ; CCL2; CRP; ENG; FTH1; GLUCOSE; HBA1C; IL2RA; INSULIN; PLAT |
| ADIPOQ; CCL2; CRP; ENG; FTH1; GLUCOSE; HBA1C; IL2RA; LEP; PLAT |
| ADIPOQ; CCL2; CRP; ENG; FTH1; GLUCOSE; HBA1C; INSULIN; LEP; PLAT |
| ADIPOQ; CCL2; CRP; ENG; FTH1; GLUCOSE; HBA1C; INSULIN; PLAT; TRIG |
| ADIPOQ; CCL2; CRP; ENG; FTH1; GLUCOSE; HBA1C; INSULIN; PLAT; VEGF |
| ADIPOQ; CCL2; CRP; ENG; FTH1; GLUCOSE; HBA1C; LEP; PLAT; TRIG |
| ADIPOQ; CCL2; CRP; ENG; FTH1; GLUCOSE; HBA1C; LEP; PLAT; VEGF |
| ADIPOQ; CCL2; CRP; ENG; FTH1; GLUCOSE; HSPA1B; INSULIN; LEP; PLAT |
| ADIPOQ; CCL2; CRP; FTH1; GLUCOSE; GPT; HBA1C; INSULIN; LEP; PLAT |
| ADIPOQ; CCL2; CRP; FTH1; GLUCOSE; HBA1C; HSPA1B; IL18; INSULIN; PLAT |
| ADIPOQ; CCL2; CRP; FTH1; GLUCOSE; HBA1C; HSPA1B; IL18; LEP; PLAT |
| ADIPOQ; CCL2; CRP; FTH1; GLUCOSE; HBA1C; HSPA1B; INSULIN; LEP; PLAT |
| ADIPOQ; CCL2; CRP; FTH1; GLUCOSE; HBA1C; IL18; INSULIN; LEP; PLAT |
| ADIPOQ; CRP; ENG; FTH1; GLUCOSE; GPT; HBA1C; HGF; LEP; PLAT |
| ADIPOQ; CRP; ENG; FTH1; GLUCOSE; GPT; HBA1C; HSPA1B; IL18; LEP |
| ADIPOQ; CRP; ENG; FTH1; GLUCOSE; GPT; HBA1C; HSPA1B; LEP; PLAT |
| ADIPOQ; CRP; ENG; FTH1; GLUCOSE; GPT; HBA1C; IGFBP1; LEP; PLAT |
| ADIPOQ; CRP; ENG; FTH1; GLUCOSE; GPT; HBA1C; IL18; INSULIN; LEP |
| ADIPOQ; CRP; ENG; FTH1; GLUCOSE; GPT; HBA1C; IL18; INSULIN; PLAT |
| ADIPOQ; CRP; ENG; FTH1; GLUCOSE; GPT; HBA1C; IL18; LEP; PLAT |
| ADIPOQ; CRP; ENG; FTH1; GLUCOSE; GPT; HBA1C; IL2RA; INSULIN; PLAT |
| ADIPOQ; CRP; ENG; FTH1; GLUCOSE; GPT; HBA1C; IL2RA; LEP; PLAT |
| ADIPOQ; CRP; ENG; FTH1; GLUCOSE; GPT; HBA1C; INSULIN; LEP; PLAT |
| ADIPOQ; CRP; ENG; FTH1; GLUCOSE; GPT; HBA1C; LEP; PLAT; TRIG |

FIGURE 44 (continued)

| |
|---|
| ADIPOQ; CRP; ENG; FTH1; GLUCOSE; GPT; HBA1C; LEP; PLAT; VEGF |
| ADIPOQ; CRP; ENG; FTH1; GLUCOSE; HBA1C; HGF; IL18; INSULIN; PLAT |
| ADIPOQ; CRP; ENG; FTH1; GLUCOSE; HBA1C; HGF; IL18; LEP; PLAT |
| ADIPOQ; CRP; ENG; FTH1; GLUCOSE; HBA1C; HGF; INSULIN; LEP; PLAT |
| ADIPOQ; CRP; ENG; FTH1; GLUCOSE; HBA1C; HSPA1B; IL18; INSULIN; PLAT |
| ADIPOQ; CRP; ENG; FTH1; GLUCOSE; HBA1C; HSPA1B; IL18; LEP; PLAT |
| ADIPOQ; CRP; ENG; FTH1; GLUCOSE; HBA1C; HSPA1B; INSULIN; LEP; PLAT |
| ADIPOQ; CRP; ENG; FTH1; GLUCOSE; HBA1C; HSPA1B; LEP; PLAT; TRIG |
| ADIPOQ; CRP; ENG; FTH1; GLUCOSE; HBA1C; HSPA1B; LEP; PLAT; VEGF |
| ADIPOQ; CRP; ENG; FTH1; GLUCOSE; HBA1C; IGFBP1; IL18; INSULIN; PLAT |
| ADIPOQ; CRP; ENG; FTH1; GLUCOSE; HBA1C; IGFBP1; IL18; LEP; PLAT |
| ADIPOQ; CRP; ENG; FTH1; GLUCOSE; HBA1C; IGFBP1; INSULIN; LEP; PLAT |
| ADIPOQ; CRP; ENG; FTH1; GLUCOSE; HBA1C; IL18; IL2RA; INSULIN; PLAT |
| ADIPOQ; CRP; ENG; FTH1; GLUCOSE; HBA1C; IL18; IL2RA; LEP; PLAT |
| ADIPOQ; CRP; ENG; FTH1; GLUCOSE; HBA1C; IL18; INSULIN; LEP; PLAT |
| ADIPOQ; CRP; ENG; FTH1; GLUCOSE; HBA1C; IL18; INSULIN; PLAT; TRIG |
| ADIPOQ; CRP; ENG; FTH1; GLUCOSE; HBA1C; IL18; INSULIN; PLAT; VEGF |
| ADIPOQ; CRP; ENG; FTH1; GLUCOSE; HBA1C; IL18; LEP; PLAT; TRIG |
| ADIPOQ; CRP; ENG; FTH1; GLUCOSE; HBA1C; IL18; LEP; PLAT; VEGF |
| ADIPOQ; CRP; ENG; FTH1; GLUCOSE; HBA1C; IL2RA; INSULIN; LEP; PLAT |
| ADIPOQ; CRP; ENG; FTH1; GLUCOSE; HBA1C; IL2RA; LEP; PLAT; TRIG |
| ADIPOQ; CRP; ENG; FTH1; GLUCOSE; HBA1C; INSULIN; LEP; PLAT; TRIG |
| ADIPOQ; CRP; ENG; FTH1; GLUCOSE; HBA1C; INSULIN; LEP; PLAT; VEGF |
| ADIPOQ; CRP; ENG; FTH1; GLUCOSE; HBA1C; LEP; PLAT; TRIG; VEGF |
| ADIPOQ; CRP; FTH1; GLUCOSE; HBA1C; HSPA1B; IL18; INSULIN; LEP; PLAT |
| CCL2; CRP; ENG; FTH1; GLUCOSE; GPT; HBA1C; HGF; INSULIN; PLAT |
| CCL2; CRP; ENG; FTH1; GLUCOSE; GPT; HBA1C; HSPA1B; IL18; INSULIN |
| CCL2; CRP; ENG; FTH1; GLUCOSE; GPT; HBA1C; HSPA1B; INSULIN; LEP |
| CCL2; CRP; ENG; FTH1; GLUCOSE; GPT; HBA1C; HSPA1B; INSULIN; PLAT |
| CCL2; CRP; ENG; FTH1; GLUCOSE; GPT; HBA1C; IGFBP1; INSULIN; PLAT |
| CCL2; CRP; ENG; FTH1; GLUCOSE; GPT; HBA1C; IL18; INSULIN; PLAT |
| CCL2; CRP; ENG; FTH1; GLUCOSE; GPT; HBA1C; IL18; LEP; PLAT |
| CCL2; CRP; ENG; FTH1; GLUCOSE; GPT; HBA1C; IL2RA; INSULIN; PLAT |
| CCL2; CRP; ENG; FTH1; GLUCOSE; GPT; HBA1C; INSULIN; LEP; PLAT |
| CCL2; CRP; ENG; FTH1; GLUCOSE; GPT; HBA1C; INSULIN; PLAT; TRIG |
| CCL2; CRP; ENG; FTH1; GLUCOSE; GPT; HBA1C; INSULIN; PLAT; VEGF |
| CCL2; CRP; ENG; FTH1; GLUCOSE; HBA1C; HGF; HSPA1B; INSULIN; PLAT |
| CCL2; CRP; ENG; FTH1; GLUCOSE; HBA1C; HGF; IL18; INSULIN; PLAT |
| CCL2; CRP; ENG; FTH1; GLUCOSE; HBA1C; HGF; INSULIN; LEP; PLAT |
| CCL2; CRP; ENG; FTH1; GLUCOSE; HBA1C; HSPA1B; IGFBP1; INSULIN; PLAT |

FIGURE 44 (continued)

| |
|---|
| CCL2; CRP; ENG; FTH1; GLUCOSE; HBA1C; HSPA1B; IL18; INSULIN; LEP |
| CCL2; CRP; ENG; FTH1; GLUCOSE; HBA1C; HSPA1B; IL18; INSULIN; PLAT |
| CCL2; CRP; ENG; FTH1; GLUCOSE; HBA1C; HSPA1B; IL18; LEP; PLAT |
| CCL2; CRP; ENG; FTH1; GLUCOSE; HBA1C; HSPA1B; IL2RA; INSULIN; PLAT |
| CCL2; CRP; ENG; FTH1; GLUCOSE; HBA1C; HSPA1B; INSULIN; LEP; PLAT |
| CCL2; CRP; ENG; FTH1; GLUCOSE; HBA1C; HSPA1B; INSULIN; PLAT; TRIG |
| CCL2; CRP; ENG; FTH1; GLUCOSE; HBA1C; HSPA1B; INSULIN; PLAT; VEGF |
| CCL2; CRP; ENG; FTH1; GLUCOSE; HBA1C; HSPA1B; LEP; PLAT; TRIG |
| CCL2; CRP; ENG; FTH1; GLUCOSE; HBA1C; IL18; INSULIN; LEP; PLAT |
| CCL2; CRP; ENG; FTH1; GLUCOSE; HBA1C; IL18; INSULIN; PLAT; TRIG |
| CCL2; CRP; ENG; FTH1; GLUCOSE; HBA1C; IL18; INSULIN; PLAT; VEGF |
| CCL2; CRP; ENG; FTH1; GLUCOSE; HBA1C; IL18; LEP; PLAT; TRIG |
| CCL2; CRP; ENG; FTH1; GLUCOSE; HBA1C; INSULIN; LEP; PLAT; TRIG |
| CCL2; CRP; ENG; FTH1; GLUCOSE; HBA1C; INSULIN; LEP; PLAT; VEGF |
| CCL2; CRP; ENG; FTH1; GLUCOSE; HBA1C; INSULIN; PLAT; TRIG; VEGF |
| CCL2; ENG; FTH1; GLUCOSE; HBA1C; HSPA1B; IL18; INSULIN; LEP; PLAT |
| CRP; ENG; FTH1; GLUCOSE; GPT; HBA1C; IL18; IL2RA; INSULIN; PLAT |
| CRP; ENG; FTH1; GLUCOSE; GPT; HBA1C; IL18; INSULIN; LEP; PLAT |
| CRP; ENG; FTH1; GLUCOSE; HBA1C; HSPA1B; IL18; INSULIN; LEP; PLAT |
| CRP; ENG; FTH1; GLUCOSE; HBA1C; IL18; INSULIN; LEP; PLAT; TRIG |

FIGURE 45

| ADIPOQ | CCL2 | CRP | ENG | FTHI | GLUCOSE | GPT | HBA1C | HGF | INSULIN | PLAT |
|---|---|---|---|---|---|---|---|---|---|---|
| ADIPOQ | CCL2 | CRP | ENG | FTHI | GLUCOSE | GPT | HBA1C | HGF | LEP | PLAT |
| ADIPOQ | CCL2 | CRP | ENG | FTHI | GLUCOSE | GPT | HBA1C | HSPA1B | IL18 | LEP |
| ADIPOQ | CCL2 | CRP | ENG | FTHI | GLUCOSE | GPT | HBA1C | HSPA1B | INSULIN | PLAT |
| ADIPOQ | CCL2 | CRP | ENG | FTHI | GLUCOSE | GPT | HBA1C | HSPA1B | LEP | PLAT |
| ADIPOQ | CCL2 | CRP | ENG | FTHI | GLUCOSE | GPT | HBA1C | IGFBP1 | INSULIN | PLAT |
| ADIPOQ | CCL2 | CRP | ENG | FTHI | GLUCOSE | GPT | HBA1C | IGFBP1 | LEP | PLAT |
| ADIPOQ | CCL2 | CRP | ENG | FTHI | GLUCOSE | GPT | HBA1C | IL18 | INSULIN | PLAT |
| ADIPOQ | CCL2 | CRP | ENG | FTHI | GLUCOSE | GPT | HBA1C | IL18 | LEP | PLAT |
| ADIPOQ | CCL2 | CRP | ENG | FTHI | GLUCOSE | GPT | HBA1C | IL2RA | INSULIN | PLAT |
| ADIPOQ | CCL2 | CRP | ENG | FTHI | GLUCOSE | GPT | HBA1C | IL2RA | LEP | PLAT |
| ADIPOQ | CCL2 | CRP | ENG | FTHI | GLUCOSE | GPT | HBA1C | INSULIN | LEP | PLAT |
| ADIPOQ | CCL2 | CRP | ENG | FTHI | GLUCOSE | GPT | HBA1C | INSULIN | PLAT | TRIG |
| ADIPOQ | CCL2 | CRP | ENG | FTHI | GLUCOSE | GPT | HBA1C | INSULIN | PLAT | VEGF |
| ADIPOQ | CCL2 | CRP | ENG | FTHI | GLUCOSE | GPT | HBA1C | LEP | PLAT | TRIG |
| ADIPOQ | CCL2 | CRP | ENG | FTHI | GLUCOSE | GPT | HBA1C | LEP | PLAT | VEGF |
| ADIPOQ | CCL2 | CRP | ENG | FTHI | GLUCOSE | HBA1C | HGF | HSPA1B | LEP | PLAT |
| ADIPOQ | CCL2 | CRP | ENG | FTHI | GLUCOSE | HBA1C | HGF | IL18 | INSULIN | PLAT |
| ADIPOQ | CCL2 | CRP | ENG | FTHI | GLUCOSE | HBA1C | HGF | IL18 | LEP | PLAT |
| ADIPOQ | CCL2 | CRP | ENG | FTHI | GLUCOSE | HBA1C | HGF | INSULIN | LEP | PLAT |
| ADIPOQ | CCL2 | CRP | ENG | FTHI | GLUCOSE | HBA1C | HSPA1B | IGFBP1 | LEP | LEP |
| ADIPOQ | CCL2 | CRP | ENG | FTHI | GLUCOSE | HBA1C | HSPA1B | IL18 | INSULIN | PLAT |
| ADIPOQ | CCL2 | CRP | ENG | FTHI | GLUCOSE | HBA1C | HSPA1B | IL18 | LEP | PLAT |
| ADIPOQ | CCL2 | CRP | ENG | FTHI | GLUCOSE | HBA1C | HSPA1B | IL2RA | INSULIN | PLAT |
| ADIPOQ | CCL2 | CRP | ENG | FTHI | GLUCOSE | HBA1C | HSPA1B | IL2RA | LEP | PLAT |
| ADIPOQ | CCL2 | CRP | ENG | FTHI | GLUCOSE | HBA1C | HSPA1B | INSULIN | LEP | PLAT |

FIGURE 45 (continued)

| ADIPOQ | CCL2 | CRP | ENG | FTHI | GLUCOSE | HBA1C | HSPA1B | INSULIN | PLAT | TRIG |
|---|---|---|---|---|---|---|---|---|---|---|
| ADIPOQ | CCL2 | CRP | ENG | FTHI | GLUCOSE | HBA1C | HSPA1B | LEP | PLAT | TRIG |
| ADIPOQ | CCL2 | CRP | ENG | FTHI | GLUCOSE | HBA1C | HSPA1B | LEP | PLAT | VEGF |
| ADIPOQ | CCL2 | CRP | ENG | FTHI | GLUCOSE | HBA1C | IGFBP1 | IL18 | INSULIN | PLAT |
| ADIPOQ | CCL2 | CRP | ENG | FTHI | GLUCOSE | HBA1C | IGFBP1 | IL18 | LEP | PLAT |
| ADIPOQ | CCL2 | CRP | ENG | FTHI | GLUCOSE | HBA1C | IGFBP1 | INSULIN | LEP | PLAT |
| ADIPOQ | CCL2 | CRP | ENG | FTHI | GLUCOSE | HBA1C | IL18 | IL2RA | LEP | PLAT |
| ADIPOQ | CCL2 | CRP | ENG | FTHI | GLUCOSE | HBA1C | IL18 | INSULIN | LEP | PLAT |
| ADIPOQ | CCL2 | CRP | ENG | FTHI | GLUCOSE | HBA1C | IL18 | INSULIN | PLAT | TRIG |
| ADIPOQ | CCL2 | CRP | ENG | FTHI | GLUCOSE | HBA1C | IL18 | INSULIN | PLAT | VEGF |
| ADIPOQ | CCL2 | CRP | ENG | FTHI | GLUCOSE | HBA1C | IL18 | LEP | PLAT | TRIG |
| ADIPOQ | CCL2 | CRP | ENG | FTHI | GLUCOSE | HBA1C | IL18 | LEP | PLAT | VEGF |
| ADIPOQ | CCL2 | CRP | ENG | FTHI | GLUCOSE | HBA1C | IL2RA | INSULIN | LEP | PLAT |
| ADIPOQ | CCL2 | CRP | ENG | FTHI | GLUCOSE | HBA1C | INSULIN | LEP | PLAT | TRIG |
| ADIPOQ | CCL2 | CRP | ENG | FTHI | GLUCOSE | HBA1C | INSULIN | LEP | PLAT | VEGF |
| ADIPOQ | CCL2 | CRP | ENG | FTHI | HBA1C | HSPA1B | IL18 | PLAT | TRIG | VEGF |
| ADIPOQ | CRP | ENG | FTHI | GLUCOSE | GPT | HBA1C | HGF | IL18 | INSULIN | PLAT |
| ADIPOQ | CRP | ENG | FTHI | GLUCOSE | GPT | HBA1C | HGF | IL18 | LEP | PLAT |
| ADIPOQ | CRP | ENG | FTHI | GLUCOSE | GPT | HBA1C | HSPA1B | IL18 | INSULIN | PLAT |
| ADIPOQ | CRP | ENG | FTHI | GLUCOSE | GPT | HBA1C | HSPA1B | IL18 | LEP | PLAT |
| ADIPOQ | CRP | ENG | FTHI | GLUCOSE | GPT | HBA1C | HSPA1B | IL2RA | LEP | PLAT |
| ADIPOQ | CRP | ENG | FTHI | GLUCOSE | GPT | HBA1C | HSPA1B | INSULIN | LEP | PLAT |
| ADIPOQ | CRP | ENG | FTHI | GLUCOSE | GPT | HBA1C | IGFBP1 | LEP | PLAT | VEGF |
| ADIPOQ | CRP | ENG | FTHI | GLUCOSE | GPT | HBA1C | IGFBP1 | IL18 | LEP | PLAT |
| ADIPOQ | CRP | ENG | FTHI | GLUCOSE | GPT | HBA1C | IGFBP1 | INSULIN | LEP | PLAT |

FIGURE 45 (continued)

| | | | | | | | | | | |
|---|---|---|---|---|---|---|---|---|---|---|
| ADIPOQ | CRP | ENG | FTH1 | GLUCOSE | GPT | HBA1C | IL18 | IL2RA | INSULIN | PLAT |
| ADIPOQ | CRP | ENG | FTH1 | GLUCOSE | GPT | HBA1C | IL18 | IL2RA | LEP | PLAT |
| ADIPOQ | CRP | ENG | FTH1 | GLUCOSE | GPT | HBA1C | IL18 | INSULIN | LEP | PLAT |
| ADIPOQ | CRP | ENG | FTH1 | GLUCOSE | GPT | HBA1C | IL18 | LEP | PLAT | TRIG |
| ADIPOQ | CRP | ENG | FTH1 | GLUCOSE | GPT | HBA1C | IL18 | LEP | PLAT | VEGF |
| ADIPOQ | CRP | ENG | FTH1 | GLUCOSE | GPT | HBA1C | IL2RA | INSULIN | LEP | PLAT |
| ADIPOQ | CRP | ENG | FTH1 | GLUCOSE | GPT | HBA1C | INSULIN | LEP | PLAT | TRIG |
| ADIPOQ | CRP | ENG | FTH1 | GLUCOSE | GPT | HBA1C | INSULIN | LEP | PLAT | VEGF |
| ADIPOQ | CRP | ENG | FTH1 | GLUCOSE | GPT | HBA1C | LEP | PLAT | TRIG | VEGF |
| ADIPOQ | CRP | ENG | FTH1 | GLUCOSE | HBA1C | HGF | HSPA1B | IL18 | LEP | PLAT |
| ADIPOQ | CRP | ENG | FTH1 | GLUCOSE | HBA1C | HGF | IL18 | INSULIN | LEP | PLAT |
| ADIPOQ | CRP | ENG | FTH1 | GLUCOSE | HBA1C | HSPA1B | IGFBP1 | IL18 | LEP | PLAT |
| ADIPOQ | CRP | ENG | FTH1 | GLUCOSE | HBA1C | HSPA1B | IL18 | IL2RA | INSULIN | PLAT |
| ADIPOQ | CRP | ENG | FTH1 | GLUCOSE | HBA1C | HSPA1B | IL18 | IL2RA | LEP | PLAT |
| ADIPOQ | CRP | ENG | FTH1 | GLUCOSE | HBA1C | HSPA1B | IL18 | INSULIN | LEP | PLAT |
| ADIPOQ | CRP | ENG | FTH1 | GLUCOSE | HBA1C | HSPA1B | IL18 | LEP | PLAT | TRIG |
| ADIPOQ | CRP | ENG | FTH1 | GLUCOSE | HBA1C | HSPA1B | IL18 | LEP | PLAT | TRIG |
| ADIPOQ | CRP | ENG | FTH1 | GLUCOSE | HBA1C | HSPA1B | IL2RA | INSULIN | PLAT | VEGF |
| ADIPOQ | CRP | ENG | FTH1 | GLUCOSE | HBA1C | HSPA1B | INSULIN | LEP | PLAT | PLAT |
| ADIPOQ | CRP | ENG | FTH1 | GLUCOSE | HBA1C | HSPA1B | LEP | PLAT | TRIG | VEGF |
| ADIPOQ | CRP | ENG | FTH1 | GLUCOSE | HBA1C | IGFBP1 | IL18 | INSULIN | LEP | PLAT |
| ADIPOQ | CRP | ENG | FTH1 | GLUCOSE | HBA1C | IL18 | IL2RA | INSULIN | LEP | PLAT |
| ADIPOQ | CRP | ENG | FTH1 | GLUCOSE | HBA1C | IL18 | INSULIN | LEP | PLAT | TRIG |
| ADIPOQ | CRP | ENG | FTH1 | GLUCOSE | HBA1C | IL18 | INSULIN | LEP | PLAT | VEGF |
| ADIPOQ | CRP | ENG | FTH1 | GLUCOSE | HBA1C | IL18 | LEP | PLAT | TRIG | VEGF |
| ADIPOQ | CRP | ENG | FTH1 | GLUCOSE | HBA1C | IL18 | LEP | PLAT | TRIG | VEGF |
| ADIPOQ | CRP | ENG | FTH1 | GLUCOSE | HBA1C | IL18 | PLAT | TRIG | VEGF | VEGF |
| CCL2 | CRP | ENG | FTH1 | GLUCOSE | GPT | HBA1C | HSPA1B | IL18 | INSULIN | PLAT |

FIGURE 45 (continued)

| CCL2 | CRP | ENG | FTH1 | GLUCOSE | GPT | HBA1C | HSPA1B | IL2RA | INSULIN | PLAT |
|---|---|---|---|---|---|---|---|---|---|---|
| CCL2 | CRP | ENG | FTH1 | GLUCOSE | GPT | HBA1C | HSPA1B | INSULIN | LEP | PLAT |
| CCL2 | CRP | ENG | FTH1 | GLUCOSE | GPT | HBA1C | IL18 | IL2RA | INSULIN | PLAT |
| CCL2 | CRP | ENG | FTH1 | GLUCOSE | GPT | HBA1C | IL18 | INSULIN | LEP | PLAT |
| CCL2 | CRP | ENG | FTH1 | GLUCOSE | GPT | HBA1C | IL18 | INSULIN | PLAT | VEGF |
| CCL2 | CRP | ENG | FTH1 | GLUCOSE | GPT | HBA1C | IL2RA | INSULIN | LEP | PLAT |
| CCL2 | CRP | ENG | FTH1 | GLUCOSE | GPT | HBA1C | INSULIN | LEP | PLAT | TRIG |
| CCL2 | CRP | ENG | FTH1 | GLUCOSE | GPT | HBA1C | INSULIN | LEP | PLAT | VEGF |
| CCL2 | CRP | ENG | FTH1 | GLUCOSE | HBA1C | HGF | HSPA1B | IL18 | INSULIN | PLAT |
| CCL2 | CRP | ENG | FTH1 | GLUCOSE | HBA1C | HSPA1B | IGFBP1 | IL18 | INSULIN | PLAT |
| CCL2 | CRP | ENG | FTH1 | GLUCOSE | HBA1C | HSPA1B | IL18 | IL2RA | INSULIN | PLAT |
| CCL2 | CRP | ENG | FTH1 | GLUCOSE | HBA1C | HSPA1B | IL18 | INSULIN | LEP | PLAT |
| CCL2 | CRP | ENG | FTH1 | GLUCOSE | HBA1C | HSPA1B | IL18 | INSULIN | PLAT | TRIG |
| CCL2 | CRP | ENG | FTH1 | GLUCOSE | HBA1C | HSPA1B | IL18 | INSULIN | PLAT | VEGF |
| CCL2 | CRP | ENG | FTH1 | GLUCOSE | HBA1C | HSPA1B | IL18 | LEP | PLAT | TRIG |
| CCL2 | CRP | ENG | FTH1 | GLUCOSE | HBA1C | HSPA1B | IL2RA | INSULIN | LEP | PLAT |
| CCL2 | CRP | ENG | FTH1 | GLUCOSE | HBA1C | HSPA1B | IL2RA | INSULIN | PLAT | TRIG |
| CCL2 | CRP | ENG | FTH1 | GLUCOSE | HBA1C | HSPA1B | INSULIN | LEP | PLAT | TRIG |
| CCL2 | CRP | ENG | FTH1 | GLUCOSE | HBA1C | HSPA1B | INSULIN | LEP | PLAT | VEGF |
| CCL2 | CRP | ENG | FTH1 | GLUCOSE | HBA1C | IL18 | INSULIN | LEP | PLAT | TRIG |

FIGURE 46

| ADIPOQ | CCL2 | CRP | ENG | FTHI | GLUCOSE | GPT | HBA1C | | | |
|---|---|---|---|---|---|---|---|---|---|---|
| ADIPOQ | CCL2 | CRP | ENG | FTHI | GLUCOSE | GPT | HBA1C | HGF | HSPA1B | INSULIN | PLAT |
| ADIPOQ | CCL2 | CRP | ENG | FTHI | GLUCOSE | GPT | HBA1C | HGF | HSPA1B | LEP | PLAT |
| ADIPOQ | CCL2 | CRP | ENG | FTHI | GLUCOSE | GPT | HBA1C | HGF | IL18 | INSULIN | PLAT |
| ADIPOQ | CCL2 | CRP | ENG | FTHI | GLUCOSE | GPT | HBA1C | HGF | IL18 | LEP | PLAT |
| ADIPOQ | CCL2 | CRP | ENG | FTHI | GLUCOSE | GPT | HBA1C | HGF | IL2RA | INSULIN | PLAT |
| ADIPOQ | CCL2 | CRP | ENG | FTHI | GLUCOSE | GPT | HBA1C | HGF | INSULIN | LEP | PLAT |
| ADIPOQ | CCL2 | CRP | ENG | FTHI | GLUCOSE | GPT | HBA1C | HGF | LEP | PLAT | VEGF |
| ADIPOQ | CCL2 | CRP | ENG | FTHI | GLUCOSE | GPT | HBA1C | HSPA1B | IGFBP1 | LEP | PLAT |
| ADIPOQ | CCL2 | CRP | ENG | FTHI | GLUCOSE | GPT | HBA1C | HSPA1B | IL18 | INSULIN | PLAT |
| ADIPOQ | CCL2 | CRP | ENG | FTHI | GLUCOSE | GPT | HBA1C | HSPA1B | IL18 | LEP | PLAT |
| ADIPOQ | CCL2 | CRP | ENG | FTHI | GLUCOSE | GPT | HBA1C | HSPA1B | IL2RA | INSULIN | PLAT |
| ADIPOQ | CCL2 | CRP | ENG | FTHI | GLUCOSE | GPT | HBA1C | HSPA1B | IL2RA | LEP | PLAT |
| ADIPOQ | CCL2 | CRP | ENG | FTHI | GLUCOSE | GPT | HBA1C | HSPA1B | INSULIN | LEP | PLAT |
| ADIPOQ | CCL2 | CRP | ENG | FTHI | GLUCOSE | GPT | HBA1C | HSPA1B | INSULIN | PLAT | TRIG |
| ADIPOQ | CCL2 | CRP | ENG | FTHI | GLUCOSE | GPT | HBA1C | HSPA1B | LEP | PLAT | TRIG |
| ADIPOQ | CCL2 | CRP | ENG | FTHI | GLUCOSE | GPT | HBA1C | HSPA1B | LEP | PLAT | VEGF |
| ADIPOQ | CCL2 | CRP | ENG | FTHI | GLUCOSE | GPT | HBA1C | IGFBP1 | IL18 | INSULIN | PLAT |
| ADIPOQ | CCL2 | CRP | ENG | FTHI | GLUCOSE | GPT | HBA1C | IGFBP1 | IL18 | LEP | PLAT |
| ADIPOQ | CCL2 | CRP | ENG | FTHI | GLUCOSE | GPT | HBA1C | IGFBP1 | INSULIN | LEP | PLAT |
| ADIPOQ | CCL2 | CRP | ENG | FTHI | GLUCOSE | GPT | HBA1C | IGFBP1 | LEP | PLAT | TRIG |
| ADIPOQ | CCL2 | CRP | ENG | FTHI | GLUCOSE | GPT | HBA1C | IL18 | IL2RA | PLAT | VEGF |
| ADIPOQ | CCL2 | CRP | ENG | FTHI | GLUCOSE | GPT | HBA1C | IL18 | IL2RA | INSULIN | PLAT |
| ADIPOQ | CCL2 | CRP | ENG | FTHI | GLUCOSE | GPT | HBA1C | IL18 | INSULIN | LEP | PLAT |
| ADIPOQ | CCL2 | CRP | ENG | FTHI | GLUCOSE | GPT | HBA1C | IL18 | LEP | PLAT | VEGF |
| ADIPOQ | CCL2 | CRP | ENG | FTHI | GLUCOSE | GPT | HBA1C | IL18 | PLAT | TRIG | |
| ADIPOQ | CCL2 | CRP | ENG | FTHI | GLUCOSE | GPT | HBA1C | IL18 | PLAT | VEGF | |

FIGURE 46 (continued)

| | | | | | | | | | | | | |
|---|---|---|---|---|---|---|---|---|---|---|---|---|
| ADIPOQ | CCL2 | CRP | ENG | FTH1 | GLUCOSE | GPT | HBA1C | IL2RA | INSULIN | LEP | PLAT |
| ADIPOQ | CCL2 | CRP | ENG | FTH1 | GLUCOSE | GPT | HBA1C | INSULIN | LEP | PLAT | TRIG |
| ADIPOQ | CCL2 | CRP | ENG | FTH1 | GLUCOSE | GPT | HBA1C | INSULIN | LEP | PLAT | VEGF |
| ADIPOQ | CCL2 | CRP | ENG | FTH1 | GLUCOSE | GPT | HBA1C | LEP | PLAT | TRIG | VEGF |
| ADIPOQ | CCL2 | CRP | ENG | FTH1 | GLUCOSE | HBA1C | HGF | HSPA1B | IL18 | INSULIN | PLAT |
| ADIPOQ | CCL2 | CRP | ENG | FTH1 | GLUCOSE | HBA1C | HGF | HSPA1B | IL18 | LEP | PLAT |
| ADIPOQ | CCL2 | CRP | ENG | FTH1 | GLUCOSE | HBA1C | HGF | HSPA1B | INSULIN | LEP | PLAT |
| ADIPOQ | CCL2 | CRP | ENG | FTH1 | GLUCOSE | HBA1C | HGF | IL18 | LEP | PLAT | VEGF |
| ADIPOQ | CCL2 | CRP | ENG | FTH1 | GLUCOSE | HBA1C | HGF | IL18 | INSULIN | PLAT | TRIG |
| ADIPOQ | CCL2 | CRP | ENG | FTH1 | GLUCOSE | HBA1C | HGF | IL18 | LEP | PLAT | TRIG |
| ADIPOQ | CCL2 | CRP | ENG | FTH1 | GLUCOSE | HBA1C | HGF | INSULIN | LEP | PLAT | VEGF |
| ADIPOQ | CCL2 | CRP | ENG | FTH1 | GLUCOSE | HBA1C | HGF | INSULIN | LEP | PLAT | PLAT |
| ADIPOQ | CCL2 | CRP | ENG | FTH1 | GLUCOSE | HBA1C | HSPA1B | IGFBP1 | IL18 | LEP | PLAT |
| ADIPOQ | CCL2 | CRP | ENG | FTH1 | GLUCOSE | HBA1C | HSPA1B | IGFBP1 | IL18 | LEP | PLAT |
| ADIPOQ | CCL2 | CRP | ENG | FTH1 | GLUCOSE | HBA1C | HSPA1B | IGFBP1 | IL2RA | INSULIN | PLAT |
| ADIPOQ | CCL2 | CRP | ENG | FTH1 | GLUCOSE | HBA1C | HSPA1B | IGFBP1 | INSULIN | LEP | PLAT |
| ADIPOQ | CCL2 | CRP | ENG | FTH1 | GLUCOSE | HBA1C | HSPA1B | IGFBP1 | LEP | PLAT | TRIG |
| ADIPOQ | CCL2 | CRP | ENG | FTH1 | GLUCOSE | HBA1C | HSPA1B | IL18 | IL2RA | PLAT | VEGF |
| ADIPOQ | CCL2 | CRP | ENG | FTH1 | GLUCOSE | HBA1C | HSPA1B | IL18 | IL2RA | INSULIN | PLAT |
| ADIPOQ | CCL2 | CRP | ENG | FTH1 | GLUCOSE | HBA1C | HSPA1B | IL18 | INSULIN | LEP | PLAT |
| ADIPOQ | CCL2 | CRP | ENG | FTH1 | GLUCOSE | HBA1C | HSPA1B | IL18 | INSULIN | LEP | PLAT |
| ADIPOQ | CCL2 | CRP | ENG | FTH1 | GLUCOSE | HBA1C | HSPA1B | IL18 | LEP | PLAT | TRIG |
| ADIPOQ | CCL2 | CRP | ENG | FTH1 | GLUCOSE | HBA1C | HSPA1B | IL18 | LEP | PLAT | VEGF |
| ADIPOQ | CCL2 | CRP | ENG | FTH1 | GLUCOSE | HBA1C | HSPA1B | IL18 | LEP | PLAT | VEGF |
| ADIPOQ | CCL2 | CRP | ENG | FTH1 | GLUCOSE | HBA1C | HSPA1B | IL2RA | INSULIN | LEP | PLAT |

FIGURE 46 (continued)

| ADIPOQ | CCL2 | CRP | ENG | FTHI | GLUCOSE | HBA1C | HSPA1B | IL2RA | LEP | PLAT | TRIG |
| --- | --- | --- | --- | --- | --- | --- | --- | --- | --- | --- | --- |
| ADIPOQ | CCL2 | CRP | ENG | FTHI | GLUCOSE | HBA1C | HSPA1B | IL2RA | LEP | PLAT | VEGF |
| ADIPOQ | CCL2 | CRP | ENG | FTHI | GLUCOSE | HBA1C | HSPA1B | INSULIN | LEP | PLAT | TRIG |
| ADIPOQ | CCL2 | CRP | ENG | FTHI | GLUCOSE | HBA1C | HSPA1B | INSULIN | LEP | PLAT | VEGF |
| ADIPOQ | CCL2 | CRP | ENG | FTHI | GLUCOSE | HBA1C | HSPA1B | LEP | TRIG | PLAT | VEGF |
| ADIPOQ | CCL2 | CRP | ENG | FTHI | GLUCOSE | HBA1C | IGFBP1 | IL18 | INSULIN | LEP | PLAT |
| ADIPOQ | CCL2 | CRP | ENG | FTHI | GLUCOSE | HBA1C | IGFBP1 | IL18 | LEP | PLAT | TRIG |
| ADIPOQ | CCL2 | CRP | ENG | FTHI | GLUCOSE | HBA1C | IGFBP1 | IL18 | LEP | PLAT | VEGF |
| ADIPOQ | CCL2 | CRP | ENG | FTHI | GLUCOSE | HBA1C | IGFBP1 | INSULIN | LEP | PLAT | TRIG |
| ADIPOQ | CCL2 | CRP | ENG | FTHI | GLUCOSE | HBA1C | IGFBP1 | INSULIN | LEP | PLAT | VEGF |
| ADIPOQ | CCL2 | CRP | ENG | FTHI | GLUCOSE | HBA1C | IL18 | IL2RA | INSULIN | LEP | PLAT |
| ADIPOQ | CCL2 | CRP | ENG | FTHI | GLUCOSE | HBA1C | IL18 | INSULIN | LEP | PLAT | TRIG |
| ADIPOQ | CCL2 | CRP | ENG | FTHI | GLUCOSE | HBA1C | IL18 | INSULIN | LEP | PLAT | VEGF |
| ADIPOQ | CCL2 | CRP | ENG | FTHI | GLUCOSE | HBA1C | IL18 | LEP | PLAT | TRIG | VEGF |
| ADIPOQ | CCL2 | CRP | ENG | FTHI | GLUCOSE | HBA1C | INSULIN | LEP | PLAT | TRIG | VEGF |
| ADIPOQ | CRP | ENG | FTHI | GLUCOSE | GPT | HBA1C | HGF | HSPA1B | IL18 | LEP | PLAT |
| ADIPOQ | CRP | ENG | FTHI | GLUCOSE | GPT | HBA1C | HGF | IL18 | INSULIN | LEP | PLAT |
| ADIPOQ | CRP | ENG | FTHI | GLUCOSE | GPT | HBA1C | HSPA1B | IGFBP1 | IL18 | LEP | PLAT |
| ADIPOQ | CRP | ENG | FTHI | GLUCOSE | GPT | HBA1C | HSPA1B | IL18 | IL2RA | LEP | PLAT |
| ADIPOQ | CRP | ENG | FTHI | GLUCOSE | GPT | HBA1C | HSPA1B | IL18 | INSULIN | LEP | PLAT |
| ADIPOQ | CRP | ENG | FTHI | GLUCOSE | GPT | HBA1C | HSPA1B | IL18 | LEP | PLAT | TRIG |
| ADIPOQ | CRP | ENG | FTHI | GLUCOSE | GPT | HBA1C | HSPA1B | IL2RA | INSULIN | PLAT | VEGF |
| ADIPOQ | CRP | ENG | FTHI | GLUCOSE | GPT | HBA1C | HSPA1B | INSULIN | LEP | PLAT | TRIG |
| ADIPOQ | CRP | ENG | FTHI | GLUCOSE | GPT | HBA1C | HSPA1B | INSULIN | LEP | PLAT | VEGF |
| ADIPOQ | CRP | ENG | FTHI | GLUCOSE | GPT | HBA1C | IGFBP1 | IL18 | INSULIN | LEP | PLAT |
| ADIPOQ | CRP | ENG | FTHI | GLUCOSE | GPT | HBA1C | IL18 | IL2RA | INSULIN | LEP | PLAT |

FIGURE 46 (continued)

| ADIPOQ | CRP | ENG | FTH1 | GLUCOSE | GPT | HBA1C | IL18 | INSULIN | LEP | PLAT | TRIG |
| --- | --- | --- | --- | --- | --- | --- | --- | --- | --- | --- | --- |
| ADIPOQ | CRP | ENG | FTH1 | GLUCOSE | GPT | HBA1C | IL18 | INSULIN | LEP | PLAT | VEGF |
| ADIPOQ | CRP | ENG | FTH1 | GLUCOSE | GPT | HBA1C | INSULIN | LEP | PLAT | TRIG | VEGF |
| ADIPOQ | CRP | ENG | FTH1 | GLUCOSE | HBA1C | HGF | HSPA1B | IL18 | INSULIN | LEP | PLAT |
| ADIPOQ | CRP | ENG | FTH1 | GLUCOSE | HBA1C | HGF | HSPA1B | IL18 | INSULIN | LEP | TRIG |
| ADIPOQ | CRP | ENG | FTH1 | GLUCOSE | HBA1C | HSPA1B | IGFBP1 | IL18 | LEP | PLAT | PLAT |
| ADIPOQ | CRP | ENG | FTH1 | GLUCOSE | HBA1C | HSPA1B | IGFBP1 | IL18 | INSULIN | LEP | TRIG |
| ADIPOQ | CRP | ENG | FTH1 | GLUCOSE | HBA1C | HSPA1B | IL18 | IL2RA | LEP | PLAT | PLAT |
| ADIPOQ | CRP | ENG | FTH1 | GLUCOSE | HBA1C | HSPA1B | IL18 | INSULIN | LEP | PLAT | TRIG |
| ADIPOQ | CRP | ENG | FTH1 | GLUCOSE | HBA1C | HSPA1B | IL18 | INSULIN | LEP | PLAT | VEGF |
| ADIPOQ | CRP | ENG | FTH1 | GLUCOSE | HBA1C | HSPA1B | IL18 | LEP | PLAT | TRIG | VEGF |
| ADIPOQ | CRP | ENG | FTH1 | GLUCOSE | HBA1C | IL18 | IL2RA | INSULIN | LEP | PLAT | TRIG |
| ADIPOQ | CRP | ENG | FTH1 | GLUCOSE | HBA1C | IL18 | INSULIN | LEP | PLAT | TRIG | VEGF |
| CCL2 | CRP | ENG | FTH1 | GLUCOSE | GPT | HBA1C | HSPA1B | IL18 | IL2RA | TRIG | PLAT |
| CCL2 | CRP | ENG | FTH1 | GLUCOSE | GPT | HBA1C | HSPA1B | IL18 | INSULIN | LEP | PLAT |
| CCL2 | CRP | ENG | FTH1 | GLUCOSE | GPT | HBA1C | HSPA1B | IL2RA | INSULIN | LEP | PLAT |
| CCL2 | CRP | ENG | FTH1 | GLUCOSE | HBA1C | HGF | HSPA1B | IL18 | INSULIN | LEP | PLAT |
| CCL2 | CRP | ENG | FTH1 | GLUCOSE | HBA1C | HSPA1B | IGFBP1 | IL18 | INSULIN | LEP | PLAT |
| CCL2 | CRP | ENG | FTH1 | GLUCOSE | HBA1C | HSPA1B | IL18 | INSULIN | LEP | PLAT | TRIG |
| CCL2 | CRP | ENG | FTH1 | GLUCOSE | HBA1C | HSPA1B | IL18 | INSULIN | LEP | PLAT | VEGF |

FIGURE 47

| ADIPOQ | CCL2 | CRP | ENG | FTH1 | GLUCOSE | GPT | HBA1C | HGF | HSPA1B | IL18 | INSULIN | PLAT |
|---|---|---|---|---|---|---|---|---|---|---|---|---|
| ADIPOQ | CCL2 | CRP | ENG | FTH1 | GLUCOSE | GPT | HBA1C | HGF | HSPA1B | IL18 | LEP | PLAT |
| ADIPOQ | CCL2 | CRP | ENG | FTH1 | GLUCOSE | GPT | HBA1C | HGF | HSPA1B | INSULIN | LEP | PLAT |
| ADIPOQ | CCL2 | CRP | ENG | FTH1 | GLUCOSE | GPT | HBA1C | HGF | HSPA1B | LEP | PLAT | TRIG |
| ADIPOQ | CCL2 | CRP | ENG | FTH1 | GLUCOSE | GPT | HBA1C | HGF | HSPA1B | LEP | PLAT | VEGF |
| ADIPOQ | CCL2 | CRP | ENG | FTH1 | GLUCOSE | GPT | HBA1C | HGF | IGFBP1 | IL18 | LEP | PLAT |
| ADIPOQ | CCL2 | CRP | ENG | FTH1 | GLUCOSE | GPT | HBA1C | HGF | IGFBP1 | INSULIN | LEP | PLAT |
| ADIPOQ | CCL2 | CRP | ENG | FTH1 | GLUCOSE | GPT | HBA1C | HGF | IL18 | INSULIN | LEP | PLAT |
| ADIPOQ | CCL2 | CRP | ENG | FTH1 | GLUCOSE | GPT | HBA1C | HGF | IL18 | LEP | PLAT | TRIG |
| ADIPOQ | CCL2 | CRP | ENG | FTH1 | GLUCOSE | GPT | HBA1C | HGF | IL18 | LEP | PLAT | VEGF |
| ADIPOQ | CCL2 | CRP | ENG | FTH1 | GLUCOSE | GPT | HBA1C | HGF | IL2RA | INSULIN | LEP | PLAT |
| ADIPOQ | CCL2 | CRP | ENG | FTH1 | GLUCOSE | GPT | HBA1C | HGF | INSULIN | LEP | PLAT | TRIG |
| ADIPOQ | CCL2 | CRP | ENG | FTH1 | GLUCOSE | GPT | HBA1C | HGF | INSULIN | LEP | PLAT | VEGF |
| ADIPOQ | CCL2 | CRP | ENG | FTH1 | GLUCOSE | GPT | HBA1C | HSPA1B | IGFBP1 | IL18 | INSULIN | PLAT |
| ADIPOQ | CCL2 | CRP | ENG | FTH1 | GLUCOSE | GPT | HBA1C | HSPA1B | IGFBP1 | IL18 | LEP | PLAT |
| ADIPOQ | CCL2 | CRP | ENG | FTH1 | GLUCOSE | GPT | HBA1C | HSPA1B | IGFBP1 | INSULIN | LEP | PLAT |
| ADIPOQ | CCL2 | CRP | ENG | FTH1 | GLUCOSE | GPT | HBA1C | HSPA1B | IGFBP1 | LEP | PLAT | TRIG |
| ADIPOQ | CCL2 | CRP | ENG | FTH1 | GLUCOSE | GPT | HBA1C | HSPA1B | IL18 | IL2RA | PLAT | VEGF |
| ADIPOQ | CCL2 | CRP | ENG | FTH1 | GLUCOSE | GPT | HBA1C | HSPA1B | IL18 | IL2RA | INSULIN | PLAT |
| ADIPOQ | CCL2 | CRP | ENG | FTH1 | GLUCOSE | GPT | HBA1C | HSPA1B | IL18 | INSULIN | LEP | PLAT |
| ADIPOQ | CCL2 | CRP | ENG | FTH1 | GLUCOSE | GPT | HBA1C | HSPA1B | IL18 | INSULIN | LEP | PLAT |
| ADIPOQ | CCL2 | CRP | ENG | FTH1 | GLUCOSE | GPT | HBA1C | HSPA1B | IL18 | LEP | PLAT | TRIG |
| ADIPOQ | CCL2 | CRP | ENG | FTH1 | GLUCOSE | GPT | HBA1C | HSPA1B | IL18 | LEP | PLAT | VEGF |
| ADIPOQ | CCL2 | CRP | ENG | FTH1 | GLUCOSE | GPT | HBA1C | HSPA1B | IL2RA | INSULIN | LEP | PLAT |
| ADIPOQ | CCL2 | CRP | ENG | FTH1 | GLUCOSE | GPT | HBA1C | IL2RA | IL2RA | LEP | PLAT | VEGF |

FIGURE 47 (continued)

| ADIPOQ | CCL2 | CRP | ENG | FTH1 | GLUCOSE | GPT | HBA1C | HSPA1B | INSULIN | LEP | PLAT | TRIG |
|---|---|---|---|---|---|---|---|---|---|---|---|---|
| ADIPOQ | CCL2 | CRP | ENG | FTH1 | GLUCOSE | GPT | HBA1C | HSPA1B | INSULIN | LEP | PLAT | VEGF |
| ADIPOQ | CCL2 | CRP | ENG | FTH1 | GLUCOSE | GPT | HBA1C | HSPA1B | LEP | PLAT | TRIG | VEGF |
| ADIPOQ | CCL2 | CRP | ENG | FTH1 | GLUCOSE | GPT | HBA1C | IGFBP1 | IL18 | LEP | INSULIN | PLAT |
| ADIPOQ | CCL2 | CRP | ENG | FTH1 | GLUCOSE | GPT | HBA1C | IGFBP1 | IL18 | LEP | PLAT | TRIG |
| ADIPOQ | CCL2 | CRP | ENG | FTH1 | GLUCOSE | GPT | HBA1C | IGFBP1 | IL18 | LEP | PLAT | VEGF |
| ADIPOQ | CCL2 | CRP | ENG | FTH1 | GLUCOSE | GPT | HBA1C | IGFBP1 | IL2RA | INSULIN | LEP | PLAT |
| ADIPOQ | CCL2 | CRP | ENG | FTH1 | GLUCOSE | GPT | HBA1C | IGFBP1 | INSULIN | LEP | PLAT | TRIG |
| ADIPOQ | CCL2 | CRP | ENG | FTH1 | GLUCOSE | GPT | HBA1C | IGFBP1 | INSULIN | LEP | PLAT | VEGF |
| ADIPOQ | CCL2 | CRP | ENG | FTH1 | GLUCOSE | GPT | HBA1C | IL18 | IL2RA | INSULIN | LEP | PLAT |
| ADIPOQ | CCL2 | CRP | ENG | FTH1 | GLUCOSE | GPT | HBA1C | IL18 | INSULIN | LEP | PLAT | TRIG |
| ADIPOQ | CCL2 | CRP | ENG | FTH1 | GLUCOSE | GPT | HBA1C | IL18 | INSULIN | LEP | PLAT | VEGF |
| ADIPOQ | CCL2 | CRP | ENG | FTH1 | GLUCOSE | GPT | HBA1C | IL2RA | INSULIN | LEP | PLAT | TRIG |
| ADIPOQ | CCL2 | CRP | ENG | FTH1 | GLUCOSE | GPT | HBA1C | IL2RA | INSULIN | LEP | PLAT | VEGF |
| ADIPOQ | CCL2 | CRP | ENG | FTH1 | GLUCOSE | GPT | HBA1C | INSULIN | LEP | PLAT | TRIG | VEGF |
| ADIPOQ | CCL2 | CRP | ENG | FTH1 | GLUCOSE | HBA1C | HGF | HSPA1B | IGFBP1 | IL18 | PLAT | TRIG |
| ADIPOQ | CCL2 | CRP | ENG | FTH1 | GLUCOSE | HBA1C | HGF | HSPA1B | IGFBP1 | INSULIN | IL18 | PLAT |
| ADIPOQ | CCL2 | CRP | ENG | FTH1 | GLUCOSE | HBA1C | HGF | HSPA1B | IL18 | IL2RA | INSULIN | PLAT |
| ADIPOQ | CCL2 | CRP | ENG | FTH1 | GLUCOSE | HBA1C | HGF | HSPA1B | IL18 | INSULIN | LEP | PLAT |
| ADIPOQ | CCL2 | CRP | ENG | FTH1 | GLUCOSE | HBA1C | HGF | HSPA1B | IL18 | LEP | PLAT | TRIG |
| ADIPOQ | CCL2 | CRP | ENG | FTH1 | GLUCOSE | HBA1C | HGF | HSPA1B | IL18 | LEP | PLAT | VEGF |
| ADIPOQ | CCL2 | CRP | ENG | FTH1 | GLUCOSE | HBA1C | HGF | HSPA1B | IL2RA | INSULIN | LEP | PLAT |
| ADIPOQ | CCL2 | CRP | ENG | FTH1 | GLUCOSE | HBA1C | HGF | HSPA1B | INSULIN | LEP | PLAT | TRIG |
| ADIPOQ | CCL2 | CRP | ENG | FTH1 | GLUCOSE | HBA1C | HGF | HSPA1B | INSULIN | LEP | PLAT | VEGF |
| ADIPOQ | CCL2 | CRP | ENG | FTH1 | GLUCOSE | HBA1C | HGF | IGFBP1 | IL18 | INSULIN | LEP | PLAT |

FIGURE 47 (continued)

| ADIPOQ | CCL2 | CRP | ENG | FTH1 | GLUCOSE | HBA1C | HGF | IL18 | INSULIN | LEP | PLAT | TRIG |
|---|---|---|---|---|---|---|---|---|---|---|---|---|
| ADIPOQ | CCL2 | CRP | ENG | FTH1 | GLUCOSE | HBA1C | HGF | IL18 | INSULIN | LEP | PLAT | VEGF |
| ADIPOQ | CCL2 | CRP | ENG | FTH1 | GLUCOSE | HBA1C | HSPA1B | IGFBP1 | IL18 | INSULIN | PLAT | |
| ADIPOQ | CCL2 | CRP | ENG | FTH1 | GLUCOSE | HBA1C | HSPA1B | IGFBP1 | IL2RA | LEP | PLAT | |
| ADIPOQ | CCL2 | CRP | ENG | FTH1 | GLUCOSE | HBA1C | HSPA1B | IGFBP1 | IL2RA | LEP | PLAT | |
| ADIPOQ | CCL2 | CRP | ENG | FTH1 | GLUCOSE | HBA1C | HSPA1B | IGFBP1 | IL18 | INSULIN | LEP | PLAT |
| ADIPOQ | CCL2 | CRP | ENG | FTH1 | GLUCOSE | HBA1C | HSPA1B | IGFBP1 | IL18 | LEP | PLAT | TRIG |
| ADIPOQ | CCL2 | CRP | ENG | FTH1 | GLUCOSE | HBA1C | HSPA1B | IGFBP1 | IL18 | LEP | PLAT | VEGF |
| ADIPOQ | CCL2 | CRP | ENG | FTH1 | GLUCOSE | HBA1C | HSPA1B | IGFBP1 | IL2RA | LEP | PLAT | |
| ADIPOQ | CCL2 | CRP | ENG | FTH1 | GLUCOSE | HBA1C | HSPA1B | IGFBP1 | IL2RA | INSULIN | PLAT | VEGF |
| ADIPOQ | CCL2 | CRP | ENG | FTH1 | GLUCOSE | HBA1C | HSPA1B | IGFBP1 | INSULIN | LEP | PLAT | TRIG |
| ADIPOQ | CCL2 | CRP | ENG | FTH1 | GLUCOSE | HBA1C | HSPA1B | IL18 | INSULIN | LEP | PLAT | VEGF |
| ADIPOQ | CCL2 | CRP | ENG | FTH1 | GLUCOSE | HBA1C | HSPA1B | IL18 | IL2RA | LEP | PLAT | TRIG |
| ADIPOQ | CCL2 | CRP | ENG | FTH1 | GLUCOSE | HBA1C | HSPA1B | IL18 | IL2RA | LEP | TRIG | |
| ADIPOQ | CCL2 | CRP | ENG | FTH1 | GLUCOSE | HBA1C | HSPA1B | IL18 | IL2RA | LEP | PLAT | VEGF |
| ADIPOQ | CCL2 | CRP | ENG | FTH1 | GLUCOSE | HBA1C | HSPA1B | IL18 | INSULIN | LEP | PLAT | TRIG |
| ADIPOQ | CCL2 | CRP | ENG | FTH1 | GLUCOSE | HBA1C | HSPA1B | IL18 | LEP | PLAT | TRIG | |
| ADIPOQ | CCL2 | CRP | ENG | FTH1 | GLUCOSE | HBA1C | HSPA1B | IL2RA | INSULIN | LEP | PLAT | VEGF |
| ADIPOQ | CCL2 | CRP | ENG | FTH1 | GLUCOSE | HBA1C | HSPA1B | IL2RA | INSULIN | LEP | PLAT | TRIG |
| ADIPOQ | CCL2 | CRP | ENG | FTH1 | GLUCOSE | HBA1C | HSPA1B | INSULIN | LEP | PLAT | VEGF | |
| ADIPOQ | CCL2 | CRP | ENG | FTH1 | GLUCOSE | HBA1C | IGFBP1 | IL18 | INSULIN | LEP | TRIG | |
| ADIPOQ | CCL2 | CRP | ENG | FTH1 | GLUCOSE | HBA1C | IGFBP1 | IL18 | LEP | PLAT | VEGF | |
| ADIPOQ | CCL2 | CRP | ENG | FTH1 | GPT | HBA1C | IL18 | INSULIN | LEP | PLAT | TRIG | |
| ADIPOQ | CRP | ENG | FTH1 | GLUCOSE | GPT | HBA1C | HGF | INSULIN | IL18 | TRIG | PLAT | VEGF |
| ADIPOQ | CRP | ENG | FTH1 | GLUCOSE | GPT | HBA1C | HGF | IL18 | INSULIN | LEP | PLAT | VEGF |
| ADIPOQ | CRP | ENG | FTH1 | GLUCOSE | | HBA1C | HSPA1B | IGFBP1 | IL2RA | LEP | PLAT | PLAT |

FIGURE 47 (continued)

| ADIPOQ | CRP | ENG | FTH1 | GLUCOSE | GPT | HBA1C | HSPA1B | IGFBP1 | IL18 | INSULIN | LEP | PLAT |
|---|---|---|---|---|---|---|---|---|---|---|---|---|
| ADIPOQ | CRP | ENG | FTH1 | GLUCOSE | GPT | HBA1C | HSPA1B | IGFBP1 | IL18 | LEP | PLAT | VEGF |
| ADIPOQ | CRP | ENG | FTH1 | GLUCOSE | GPT | HBA1C | HSPA1B | IL18 | IL2RA | INSULIN | LEP | PLAT |
| ADIPOQ | CRP | ENG | FTH1 | GLUCOSE | GPT | HBA1C | HSPA1B | IL18 | IL2RA | LEP | PLAT | VEGF |
| ADIPOQ | CRP | ENG | FTH1 | GLUCOSE | GPT | HBA1C | HSPA1B | IL18 | INSULIN | LEP | PLAT | TRIG |
| ADIPOQ | CRP | ENG | FTH1 | GLUCOSE | GPT | HBA1C | HSPA1B | IL18 | INSULIN | LEP | PLAT | VEGF |
| ADIPOQ | CRP | ENG | FTH1 | GLUCOSE | GPT | HBA1C | HSPA1B | IL18 | LEP | PLAT | TRIG | VEGF |
| ADIPOQ | CRP | ENG | FTH1 | GLUCOSE | GPT | HBA1C | HSPA1B | IL18 | INSULIN | LEP | PLAT | VEGF |
| ADIPOQ | CRP | ENG | FTH1 | GLUCOSE | GPT | HBA1C | IL18 | IL2RA | INSULIN | LEP | TRIG | VEGF |
| ADIPOQ | CRP | ENG | FTH1 | GLUCOSE | GPT | HGF | HSPA1B | IL18 | INSULIN | LEP | PLAT | TRIG |
| ADIPOQ | CRP | ENG | FTH1 | GLUCOSE | HBA1C | HGF | HSPA1B | IL18 | IL2RA | INSULIN | LEP | PLAT |
| ADIPOQ | CRP | ENG | FTH1 | GLUCOSE | HBA1C | HGF | HSPA1B | IL18 | INSULIN | LEP | PLAT | VEGF |
| ADIPOQ | CRP | ENG | FTH1 | GLUCOSE | HBA1C | HSPA1B | IGFBP1 | IL18 | INSULIN | LEP | PLAT | TRIG |
| ADIPOQ | CRP | ENG | FTH1 | GLUCOSE | HBA1C | HSPA1B | IL18 | IL2RA | INSULIN | LEP | PLAT | TRIG |
| ADIPOQ | CRP | ENG | FTH1 | GLUCOSE | HBA1C | HSPA1B | IL18 | IL2RA | INSULIN | LEP | PLAT | VEGF |
| ADIPOQ | CRP | ENG | FTH1 | GLUCOSE | HBA1C | HSPA1B | IL18 | INSULIN | LEP | PLAT | TRIG | VEGF |
| CCL2 | CRP | ENG | FTH1 | GLUCOSE | GPT | HBA1C | HSPA1B | IGFBP1 | IL18 | INSULIN | TRIG | PLAT |
| CCL2 | CRP | ENG | FTH1 | GLUCOSE | GPT | HBA1C | HSPA1B | IL18 | IL2RA | INSULIN | LEP | PLAT |
| CCL2 | CRP | ENG | FTH1 | GLUCOSE | GPT | HBA1C | HSPA1B | IL18 | INSULIN | LEP | PLAT | TRIG |
| CCL2 | CRP | ENG | FTH1 | GLUCOSE | GPT | HBA1C | HSPA1B | IL18 | INSULIN | LEP | PLAT | VEGF |

FIGURE 48

| |
|---|
| ADIPOQ; CCL2; CRP; ENG; FTH1; GLUCOSE; GPT; HBA1C; HGF; HSPA1B; IGFBP1; IL18; LEP; PLAT |
| ADIPOQ; CCL2; CRP; ENG; FTH1; GLUCOSE; GPT; HBA1C; HGF; HSPA1B; IGFBP1; INSULIN; LEP; PLAT |
| ADIPOQ; CCL2; CRP; ENG; FTH1; GLUCOSE; GPT; HBA1C; HGF; HSPA1B; IGFBP1; LEP; PLAT; VEGF |
| ADIPOQ; CCL2; CRP; ENG; FTH1; GLUCOSE; GPT; HBA1C; HGF; HSPA1B; IL18; IL2RA; INSULIN; PLAT |
| ADIPOQ; CCL2; CRP; ENG; FTH1; GLUCOSE; GPT; HBA1C; HGF; HSPA1B; IL18; IL2RA; LEP; PLAT |
| ADIPOQ; CCL2; CRP; ENG; FTH1; GLUCOSE; GPT; HBA1C; HGF; HSPA1B; IL18; INSULIN; LEP; PLAT |
| ADIPOQ; CCL2; CRP; ENG; FTH1; GLUCOSE; GPT; HBA1C; HGF; HSPA1B; IL18; LEP; PLAT; TRIG |
| ADIPOQ; CCL2; CRP; ENG; FTH1; GLUCOSE; GPT; HBA1C; HGF; HSPA1B; IL18; LEP; PLAT; VEGF |
| ADIPOQ; CCL2; CRP; ENG; FTH1; GLUCOSE; GPT; HBA1C; HGF; HSPA1B; IL2RA; INSULIN; LEP; PLAT |
| ADIPOQ; CCL2; CRP; ENG; FTH1; GLUCOSE; GPT; HBA1C; HGF; HSPA1B; INSULIN; LEP; PLAT; TRIG |
| ADIPOQ; CCL2; CRP; ENG; FTH1; GLUCOSE; GPT; HBA1C; HGF; HSPA1B; INSULIN; LEP; PLAT; VEGF |
| ADIPOQ; CCL2; CRP; ENG; FTH1; GLUCOSE; GPT; HBA1C; HGF; HSPA1B; LEP; PLAT; TRIG; VEGF |
| ADIPOQ; CCL2; CRP; ENG; FTH1; GLUCOSE; GPT; HBA1C; HGF; IGFBP1; IL18; INSULIN; LEP; PLAT |
| ADIPOQ; CCL2; CRP; ENG; FTH1; GLUCOSE; GPT; HBA1C; HGF; IGFBP1; IL2RA; INSULIN; LEP; PLAT |
| ADIPOQ; CCL2; CRP; ENG; FTH1; GLUCOSE; GPT; HBA1C; HGF; IGFBP1; INSULIN; LEP; PLAT; VEGF |
| ADIPOQ; CCL2; CRP; ENG; FTH1; GLUCOSE; GPT; HBA1C; HGF; IL18; IL2RA; INSULIN; LEP; PLAT |
| ADIPOQ; CCL2; CRP; ENG; FTH1; GLUCOSE; GPT; HBA1C; HGF; IL18; INSULIN; LEP; PLAT; TRIG |
| ADIPOQ; CCL2; CRP; ENG; FTH1; GLUCOSE; GPT; HBA1C; HGF; IL2RA; INSULIN; LEP; PLAT; VEGF |
| ADIPOQ; CCL2; CRP; ENG; FTH1; GLUCOSE; GPT; HBA1C; HGF; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; PLAT |
| ADIPOQ; CCL2; CRP; ENG; FTH1; GLUCOSE; GPT; HBA1C; HSPA1B; IGFBP1; IL18; IL2RA; LEP; PLAT |
| ADIPOQ; CCL2; CRP; ENG; FTH1; GLUCOSE; GPT; HBA1C; HSPA1B; IGFBP1; IL18; INSULIN; LEP; PLAT |
| ADIPOQ; CCL2; CRP; ENG; FTH1; GLUCOSE; GPT; HBA1C; HSPA1B; IGFBP1; IL18; LEP; PLAT; VEGF |
| ADIPOQ; CCL2; CRP; ENG; FTH1; GLUCOSE; GPT; HBA1C; HSPA1B; IGFBP1; IL18; LEP; PLAT; TRIG |
| ADIPOQ; CCL2; CRP; ENG; FTH1; GLUCOSE; GPT; HBA1C; HSPA1B; IGFBP1; IL18; LEP; PLAT; VEGF |

FIGURE 48 (continued)

| |
|---|
| ADIPOQ; CCL2; CRP; ENG; FTH1; GLUCOSE; GPT; HBA1C; HSPA1B; IGFBP1; IL2RA; INSULIN; LEP; PLAT |
| ADIPOQ; CCL2; CRP; ENG; FTH1; GLUCOSE; GPT; HBA1C; HSPA1B; IGFBP1; IL2RA; LEP; PLAT; TRIG |
| ADIPOQ; CCL2; CRP; ENG; FTH1; GLUCOSE; GPT; HBA1C; HSPA1B; IGFBP1; IL2RA; LEP; PLAT; VEGF |
| ADIPOQ; CCL2; CRP; ENG; FTH1; GLUCOSE; GPT; HBA1C; HSPA1B; IGFBP1; INSULIN; LEP; PLAT; TRIG |
| ADIPOQ; CCL2; CRP; ENG; FTH1; GLUCOSE; GPT; HBA1C; HSPA1B; IGFBP1; INSULIN; LEP; PLAT; VEGF |
| ADIPOQ; CCL2; CRP; ENG; FTH1; GLUCOSE; GPT; HBA1C; HSPA1B; IGFBP1; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT |
| ADIPOQ; CCL2; CRP; ENG; FTH1; GLUCOSE; GPT; HBA1C; HSPA1B; IL18; IL2RA; INSULIN; PLAT; VEGF |
| ADIPOQ; CCL2; CRP; ENG; FTH1; GLUCOSE; GPT; HBA1C; HSPA1B; IL18; IL2RA; LEP; PLAT; TRIG |
| ADIPOQ; CCL2; CRP; ENG; FTH1; GLUCOSE; GPT; HBA1C; HSPA1B; IL18; IL2RA; LEP; PLAT; VEGF |
| ADIPOQ; CCL2; CRP; ENG; FTH1; GLUCOSE; GPT; HBA1C; HSPA1B; IL18; INSULIN; LEP; PLAT; TRIG |
| ADIPOQ; CCL2; CRP; ENG; FTH1; GLUCOSE; GPT; HBA1C; HSPA1B; IL18; INSULIN; LEP; PLAT; VEGF |
| ADIPOQ; CCL2; CRP; ENG; FTH1; GLUCOSE; GPT; HBA1C; HSPA1B; IL18; INSULIN; PLAT; TRIG; VEGF |
| ADIPOQ; CCL2; CRP; ENG; FTH1; GLUCOSE; GPT; HBA1C; HSPA1B; IL18; LEP; PLAT; TRIG; VEGF |
| ADIPOQ; CCL2; CRP; ENG; FTH1; GLUCOSE; GPT; HBA1C; HSPA1B; IL2RA; INSULIN; LEP; PLAT; TRIG |
| ADIPOQ; CCL2; CRP; ENG; FTH1; GLUCOSE; GPT; HBA1C; HSPA1B; IL2RA; INSULIN; LEP; PLAT; VEGF |
| ADIPOQ; CCL2; CRP; ENG; FTH1; GLUCOSE; GPT; HBA1C; HSPA1B; INSULIN; LEP; PLAT; TRIG; VEGF |
| ADIPOQ; CCL2; CRP; ENG; FTH1; GLUCOSE; GPT; HBA1C; IGFBP1; IL18; IL2RA; INSULIN; LEP; PLAT |
| ADIPOQ; CCL2; CRP; ENG; FTH1; GLUCOSE; GPT; HBA1C; IGFBP1; IL18; IL2RA; LEP; PLAT; VEGF |
| ADIPOQ; CCL2; CRP; ENG; FTH1; GLUCOSE; GPT; HBA1C; IGFBP1; IL18; INSULIN; LEP; PLAT; TRIG |
| ADIPOQ; CCL2; CRP; ENG; FTH1; GLUCOSE; GPT; HBA1C; IGFBP1; IL18; LEP; PLAT; TRIG; VEGF |
| ADIPOQ; CCL2; CRP; ENG; FTH1; GLUCOSE; GPT; HBA1C; IGFBP1; IL2RA; INSULIN; LEP; PLAT; VEGF |
| ADIPOQ; CCL2; CRP; ENG; FTH1; GLUCOSE; GPT; HBA1C; IGFBP1; INSULIN; LEP; PLAT; TRIG; VEGF |
| ADIPOQ; CCL2; CRP; ENG; FTH1; GLUCOSE; GPT; HBA1C; IL18; IL2RA; INSULIN; LEP; PLAT; TRIG |

FIGURE 48 (continued)

| |
|---|
| ADIPOQ; CCL2; CRP; ENG; FTH1; GLUCOSE; GPT; HBA1C; IL18; IL2RA; INSULIN; LEP; PLAT; VEGF |
| ADIPOQ; CCL2; CRP; ENG; FTH1; GLUCOSE; GPT; HBA1C; IL18; IL2RA; INSULIN; LEP; PLAT; TRIG; VEGF |
| ADIPOQ; CCL2; CRP; ENG; FTH1; GLUCOSE; GPT; HBA1C; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; LEP; PLAT |
| ADIPOQ; CCL2; CRP; ENG; FTH1; GLUCOSE; HBA1C; HGF; HSPA1B; IGFBP1; IL18; INSULIN; LEP; PLAT |
| ADIPOQ; CCL2; CRP; ENG; FTH1; GLUCOSE; HBA1C; HGF; HSPA1B; IGFBP1; IL18; LEP; PLAT; TRIG |
| ADIPOQ; CCL2; CRP; ENG; FTH1; GLUCOSE; HBA1C; HGF; HSPA1B; IGFBP1; IL18; LEP; PLAT; VEGF |
| ADIPOQ; CCL2; CRP; ENG; FTH1; GLUCOSE; HBA1C; HGF; HSPA1B; IGFBP1; INSULIN; LEP; PLAT; TRIG |
| ADIPOQ; CCL2; CRP; ENG; FTH1; GLUCOSE; HBA1C; HGF; HSPA1B; IL18; IL2RA; INSULIN; LEP; PLAT |
| ADIPOQ; CCL2; CRP; ENG; FTH1; GLUCOSE; HBA1C; HGF; HSPA1B; IL18; IL2RA; LEP; PLAT; TRIG |
| ADIPOQ; CCL2; CRP; ENG; FTH1; GLUCOSE; HBA1C; HGF; HSPA1B; IL18; INSULIN; LEP; PLAT; TRIG |
| ADIPOQ; CCL2; CRP; ENG; FTH1; GLUCOSE; HBA1C; HGF; HSPA1B; IL18; INSULIN; LEP; PLAT; VEGF |
| ADIPOQ; CCL2; CRP; ENG; FTH1; GLUCOSE; HBA1C; HGF; HSPA1B; IL18; LEP; PLAT; TRIG; VEGF |
| ADIPOQ; CCL2; CRP; ENG; FTH1; GLUCOSE; HBA1C; HGF; HSPA1B; IL2RA; INSULIN; LEP; PLAT; TRIG |
| ADIPOQ; CCL2; CRP; ENG; FTH1; GLUCOSE; HBA1C; HGF; HSPA1B; INSULIN; LEP; PLAT; TRIG; VEGF |
| ADIPOQ; CCL2; CRP; ENG; FTH1; GLUCOSE; HBA1C; HGF; IL18; INSULIN; LEP; PLAT; TRIG; VEGF |
| ADIPOQ; CCL2; CRP; ENG; FTH1; GLUCOSE; HBA1C; HSPA1B; IGFBP1; IL18; IL2RA; INSULIN; LEP; PLAT |
| ADIPOQ; CCL2; CRP; ENG; FTH1; GLUCOSE; HBA1C; HSPA1B; IGFBP1; IL18; IL2RA; LEP; PLAT; TRIG |
| ADIPOQ; CCL2; CRP; ENG; FTH1; GLUCOSE; HBA1C; HSPA1B; IGFBP1; IL18; IL2RA; LEP; PLAT; VEGF |
| ADIPOQ; CCL2; CRP; ENG; FTH1; GLUCOSE; HBA1C; HSPA1B; IGFBP1; IL18; INSULIN; LEP; PLAT; TRIG |
| ADIPOQ; CCL2; CRP; ENG; FTH1; GLUCOSE; HBA1C; HSPA1B; IGFBP1; IL18; INSULIN; LEP; PLAT; VEGF |
| ADIPOQ; CCL2; CRP; ENG; FTH1; GLUCOSE; HBA1C; HSPA1B; IGFBP1; IL2RA; INSULIN; LEP; PLAT; TRIG |
| ADIPOQ; CCL2; CRP; ENG; FTH1; GLUCOSE; HBA1C; HSPA1B; IGFBP1; INSULIN; LEP; PLAT; TRIG; VEGF |
| ADIPOQ; CCL2; CRP; ENG; FTH1; GLUCOSE; HBA1C; HSPA1B; IL18; IL2RA; INSULIN; LEP; PLAT; TRIG |
| ADIPOQ; CCL2; CRP; ENG; FTH1; GLUCOSE; HBA1C; HSPA1B; IL18; IL2RA; LEP; PLAT; TRIG; VEGF |
| ADIPOQ; CCL2; CRP; ENG; FTH1; GLUCOSE; HBA1C; HSPA1B; IL18; IL2RA; INSULIN; LEP; PLAT; VEGF |
| ADIPOQ; CCL2; CRP; ENG; FTH1; GLUCOSE; HBA1C; HSPA1B; IL2RA; LEP; PLAT; TRIG; VEGF |

FIGURE 48 (continued)

| Row |
|---|
| ADIPOQ; CCL2; CRP; ENG; FTH1; GLUCOSE; HBA1C; HSPA1B; IL18; INSULIN; LEP; PLAT; TRIG; VEGF |
| ADIPOQ; CCL2; CRP; ENG; FTH1; GLUCOSE; HBA1C; HSPA1B; IL2RA; INSULIN; LEP; PLAT; TRIG; VEGF |
| ADIPOQ; CCL2; CRP; ENG; FTH1; GLUCOSE; HBA1C; IGFBP1; IL18; INSULIN; LEP; PLAT; TRIG; VEGF |
| ADIPOQ; CRP; ENG; FTH1; GLUCOSE; GPT; HBA1C; HGF; HSPA1B; IGFBP1; IL18; INSULIN; LEP; PLAT |
| ADIPOQ; CRP; ENG; FTH1; GLUCOSE; GPT; HBA1C; HGF; HSPA1B; IL18; IL2RA; INSULIN; LEP; PLAT |
| ADIPOQ; CRP; ENG; FTH1; GLUCOSE; GPT; HBA1C; HGF; HSPA1B; IL18; INSULIN; LEP; PLAT; TRIG |
| ADIPOQ; CRP; ENG; FTH1; GLUCOSE; GPT; HBA1C; HGF; HSPA1B; IL18; INSULIN; LEP; PLAT; VEGF |
| ADIPOQ; CRP; ENG; FTH1; GLUCOSE; GPT; HBA1C; HSPA1B; IGFBP1; IL18; IL2RA; INSULIN; LEP; PLAT |
| ADIPOQ; CRP; ENG; FTH1; GLUCOSE; GPT; HBA1C; HSPA1B; IGFBP1; IL18; INSULIN; LEP; PLAT; TRIG |
| ADIPOQ; CRP; ENG; FTH1; GLUCOSE; GPT; HBA1C; HSPA1B; IGFBP1; IL18; INSULIN; LEP; PLAT; VEGF |
| ADIPOQ; CRP; ENG; FTH1; GLUCOSE; GPT; HBA1C; HSPA1B; IGFBP1; IL18; LEP; PLAT; TRIG; VEGF |
| ADIPOQ; CRP; ENG; FTH1; GLUCOSE; GPT; HBA1C; HSPA1B; IL18; IL2RA; INSULIN; LEP; PLAT; TRIG |
| ADIPOQ; CRP; ENG; FTH1; GLUCOSE; GPT; HBA1C; HSPA1B; IL18; IL2RA; INSULIN; LEP; PLAT; VEGF |
| ADIPOQ; CRP; ENG; FTH1; GLUCOSE; GPT; HBA1C; HSPA1B; IL18; INSULIN; LEP; PLAT; TRIG; VEGF |
| ADIPOQ; CRP; ENG; FTH1; GLUCOSE; HBA1C; HGF; HSPA1B; IL18; IL2RA; INSULIN; LEP; PLAT; TRIG |
| ADIPOQ; CRP; ENG; FTH1; GLUCOSE; HBA1C; HGF; HSPA1B; IL18; INSULIN; LEP; PLAT; TRIG; VEGF |
| ADIPOQ; CRP; ENG; FTH1; GLUCOSE; HBA1C; HSPA1B; IGFBP1; IL18; IL2RA; INSULIN; LEP; PLAT; TRIG |
| ADIPOQ; CRP; ENG; FTH1; GLUCOSE; HBA1C; HSPA1B; IL18; IL2RA; INSULIN; LEP; PLAT; TRIG; VEGF |

FIGURE 49

| |
|---|
| ADIPOQ; CCL2; CRP; ENG; FTH1; GLUCOSE; GPT; HBA1C; HGF; HSPA1B; IGFBP1; IL18; IL2RA; INSULIN; PLAT |
| ADIPOQ; CCL2; CRP; ENG; FTH1; GLUCOSE; GPT; HBA1C; HGF; HSPA1B; IGFBP1; IL18; IL2RA; LEP; PLAT |
| ADIPOQ; CCL2; CRP; ENG; FTH1; GLUCOSE; GPT; HBA1C; HGF; HSPA1B; IGFBP1; IL18; INSULIN; LEP; PLAT |
| ADIPOQ; CCL2; CRP; ENG; FTH1; GLUCOSE; GPT; HBA1C; HGF; HSPA1B; IGFBP1; IL18; INSULIN; PLAT; VEGF |
| ADIPOQ; CCL2; CRP; ENG; FTH1; GLUCOSE; GPT; HBA1C; HGF; HSPA1B; IGFBP1; IL18; LEP; PLAT; TRIG |
| ADIPOQ; CCL2; CRP; ENG; FTH1; GLUCOSE; GPT; HBA1C; HGF; HSPA1B; IGFBP1; IL18; LEP; PLAT; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT |
| ADIPOQ; CCL2; CRP; ENG; FTH1; GLUCOSE; GPT; HBA1C; HGF; HSPA1B; IGFBP1; IL2RA; LEP; PLAT; TRIG |
| ADIPOQ; CCL2; CRP; ENG; FTH1; GLUCOSE; GPT; HBA1C; HGF; HSPA1B; IGFBP1; IL2RA; LEP; PLAT; VEGF |
| ADIPOQ; CCL2; CRP; ENG; FTH1; GLUCOSE; GPT; HBA1C; HGF; HSPA1B; IGFBP1; INSULIN; LEP; PLAT; TRIG |
| ADIPOQ; CCL2; CRP; ENG; FTH1; GLUCOSE; GPT; HBA1C; HGF; HSPA1B; IGFBP1; INSULIN; LEP; PLAT; VEGF |
| ADIPOQ; CCL2; CRP; ENG; FTH1; GLUCOSE; GPT; HBA1C; HGF; HSPA1B; IGFBP1; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT |
| ADIPOQ; CCL2; CRP; ENG; FTH1; GLUCOSE; GPT; HBA1C; HGF; HSPA1B; IL18; IL2RA; INSULIN; PLAT; VEGF |
| ADIPOQ; CCL2; CRP; ENG; FTH1; GLUCOSE; GPT; HBA1C; HGF; HSPA1B; IL18; IL2RA; LEP; PLAT; TRIG |
| ADIPOQ; CCL2; CRP; ENG; FTH1; GLUCOSE; GPT; HBA1C; HGF; HSPA1B; IL18; IL2RA; LEP; PLAT; VEGF |
| ADIPOQ; CCL2; CRP; ENG; FTH1; GLUCOSE; GPT; HBA1C; HGF; HSPA1B; IL18; INSULIN; LEP; PLAT; TRIG |
| ADIPOQ; CCL2; CRP; ENG; FTH1; GLUCOSE; GPT; HBA1C; HGF; HSPA1B; IL18; INSULIN; LEP; PLAT; VEGF |
| ADIPOQ; CCL2; CRP; ENG; FTH1; GLUCOSE; GPT; HBA1C; HGF; HSPA1B; IL18; INSULIN; PLAT; TRIG; VEGF |
| ADIPOQ; CCL2; CRP; ENG; FTH1; GLUCOSE; GPT; HBA1C; HGF; HSPA1B; IL18; LEP; PLAT; TRIG; VEGF |
| ADIPOQ; CCL2; CRP; ENG; FTH1; GLUCOSE; GPT; HBA1C; HGF; HSPA1B; IL2RA; INSULIN; LEP; PLAT; TRIG |
| ADIPOQ; CCL2; CRP; ENG; FTH1; GLUCOSE; GPT; HBA1C; HGF; HSPA1B; IL2RA; INSULIN; LEP; PLAT; VEGF |
| ADIPOQ; CCL2; CRP; ENG; FTH1; GLUCOSE; GPT; HBA1C; HGF; HSPA1B; IL2RA; LEP; PLAT; TRIG; VEGF |
| ADIPOQ; CCL2; CRP; ENG; FTH1; GLUCOSE; GPT; HBA1C; HGF; HSPA1B; INSULIN; LEP; PLAT; TRIG; VEGF |
| ADIPOQ; CCL2; CRP; ENG; FTH1; GLUCOSE; GPT; HBA1C; HGF; IGFBP1; IL18; IL2RA; INSULIN; LEP; PLAT |
| ADIPOQ; CCL2; CRP; ENG; FTH1; GLUCOSE; GPT; HBA1C; HGF; IGFBP1; IL18; IL2RA; INSULIN; LEP; PLAT |
| ADIPOQ; CCL2; CRP; ENG; FTH1; GLUCOSE; GPT; HBA1C; HGF; IGFBP1; IL18; IL2RA; LEP; PLAT; VEGF |
| ADIPOQ; CCL2; CRP; ENG; FTH1; GLUCOSE; GPT; HBA1C; HGF; IGFBP1; IL18; INSULIN; LEP; PLAT; TRIG |

FIGURE 49 (continued)

| |
|---|
| ADIPOQ; CCL2; CRP; ENG; FTH1; GLUCOSE; GPT; HBA1C; HGF; IGFBP1; IL18; INSULIN; LEP; PLAT; VEGF |
| ADIPOQ; CCL2; CRP; ENG; FTH1; GLUCOSE; GPT; HBA1C; HGF; IGFBP1; IL18; LEP; PLAT; TRIG; VEGF |
| ADIPOQ; CCL2; CRP; ENG; FTH1; GLUCOSE; GPT; HBA1C; HGF; IGFBP1; IL2RA; INSULIN; LEP; PLAT; TRIG |
| ADIPOQ; CCL2; CRP; ENG; FTH1; GLUCOSE; GPT; HBA1C; HGF; IGFBP1; IL2RA; INSULIN; LEP; PLAT; VEGF |
| ADIPOQ; CCL2; CRP; ENG; FTH1; GLUCOSE; GPT; HBA1C; HGF; IGFBP1; INSULIN; LEP; PLAT; TRIG; VEGF |
| ADIPOQ; CCL2; CRP; ENG; FTH1; GLUCOSE; GPT; HBA1C; HGF; IL18; IL2RA; INSULIN; LEP; PLAT; TRIG |
| ADIPOQ; CCL2; CRP; ENG; FTH1; GLUCOSE; GPT; HBA1C; HGF; IL18; IL2RA; INSULIN; LEP; PLAT; VEGF |
| ADIPOQ; CCL2; CRP; ENG; FTH1; GLUCOSE; GPT; HBA1C; HGF; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT |
| ADIPOQ; CCL2; CRP; ENG; FTH1; GLUCOSE; GPT; HBA1C; HSPA1B; IGFBP1; IL18; IL2RA; INSULIN; PLAT; TRIG |
| ADIPOQ; CCL2; CRP; ENG; FTH1; GLUCOSE; GPT; HBA1C; HSPA1B; IGFBP1; IL18; IL2RA; INSULIN; PLAT; VEGF |
| ADIPOQ; CCL2; CRP; ENG; FTH1; GLUCOSE; GPT; HBA1C; HSPA1B; IGFBP1; IL18; IL2RA; LEP; PLAT; TRIG |
| ADIPOQ; CCL2; CRP; ENG; FTH1; GLUCOSE; GPT; HBA1C; HSPA1B; IGFBP1; IL18; IL2RA; LEP; PLAT; VEGF |
| ADIPOQ; CCL2; CRP; ENG; FTH1; GLUCOSE; GPT; HBA1C; HSPA1B; IGFBP1; IL18; INSULIN; LEP; PLAT; TRIG |
| ADIPOQ; CCL2; CRP; ENG; FTH1; GLUCOSE; GPT; HBA1C; HSPA1B; IGFBP1; IL18; INSULIN; LEP; PLAT; VEGF |
| ADIPOQ; CCL2; CRP; ENG; FTH1; GLUCOSE; GPT; HBA1C; HSPA1B; IGFBP1; IL18; INSULIN; PLAT; TRIG; VEGF |
| ADIPOQ; CCL2; CRP; ENG; FTH1; GLUCOSE; GPT; HBA1C; HSPA1B; IGFBP1; IL18; LEP; PLAT; TRIG; VEGF |
| ADIPOQ; CCL2; CRP; ENG; FTH1; GLUCOSE; GPT; HBA1C; HSPA1B; IGFBP1; IL2RA; INSULIN; LEP; PLAT; TRIG |
| ADIPOQ; CCL2; CRP; ENG; FTH1; GLUCOSE; GPT; HBA1C; HSPA1B; IGFBP1; IL2RA; INSULIN; LEP; PLAT; VEGF |
| ADIPOQ; CCL2; CRP; ENG; FTH1; GLUCOSE; GPT; HBA1C; HSPA1B; IGFBP1; IL2RA; INSULIN; PLAT; TRIG; VEGF |
| ADIPOQ; CCL2; CRP; ENG; FTH1; GLUCOSE; GPT; HBA1C; HSPA1B; IGFBP1; IL2RA; LEP; PLAT; TRIG; VEGF |
| ADIPOQ; CCL2; CRP; ENG; FTH1; GLUCOSE; GPT; HBA1C; HSPA1B; IGFBP1; INSULIN; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT; TRIG |
| ADIPOQ; CCL2; CRP; ENG; FTH1; GLUCOSE; GPT; HBA1C; HSPA1B; IL18; IL2RA; INSULIN; LEP; PLAT; VEGF |
| ADIPOQ; CCL2; CRP; ENG; FTH1; GLUCOSE; GPT; HBA1C; HSPA1B; IL18; IL2RA; INSULIN; PLAT; TRIG; VEGF |
| ADIPOQ; CCL2; CRP; ENG; FTH1; GLUCOSE; GPT; HBA1C; HSPA1B; IL18; IL2RA; LEP; PLAT; TRIG; VEGF |

FIGURE 49 (continued)

| |
|---|
| ADIPOQ; CCL2; CRP; ENG; FTH1; GLUCOSE; GPT; HBA1C; HSPA1B; IL18; INSULIN; LEP; PLAT; TRIG; VEGF |
| ADIPOQ; CCL2; CRP; ENG; FTH1; GLUCOSE; GPT; HBA1C; HSPA1B; IL2RA; INSULIN; LEP; PLAT; TRIG; VEGF |
| ADIPOQ; CCL2; CRP; ENG; FTH1; GLUCOSE; GPT; HBA1C; IGFBP1; IL18; IL2RA; INSULIN; LEP; PLAT; TRIG |
| ADIPOQ; CCL2; CRP; ENG; FTH1; GLUCOSE; GPT; HBA1C; IGFBP1; IL18; IL2RA; INSULIN; LEP; PLAT; VEGF |
| ADIPOQ; CCL2; CRP; ENG; FTH1; GLUCOSE; GPT; HBA1C; IGFBP1; IL18; IL2RA; LEP; PLAT; TRIG; VEGF |
| ADIPOQ; CCL2; CRP; ENG; FTH1; GLUCOSE; GPT; HBA1C; IGFBP1; IL18; INSULIN; LEP; PLAT; TRIG; VEGF |
| ADIPOQ; CCL2; CRP; ENG; FTH1; GLUCOSE; GPT; HBA1C; IGFBP1; IL2RA; INSULIN; LEP; PLAT; TRIG; VEGF |
| ADIPOQ; CCL2; CRP; ENG; FTH1; GLUCOSE; GPT; HBA1C; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT |
| ADIPOQ; CCL2; CRP; ENG; FTH1; GLUCOSE; HBA1C; HGF; HSPA1B; IGFBP1; IL18; IL2RA; LEP; PLAT; TRIG |
| ADIPOQ; CCL2; CRP; ENG; FTH1; GLUCOSE; HBA1C; HGF; HSPA1B; IGFBP1; IL18; IL2RA; LEP; PLAT; VEGF |
| ADIPOQ; CCL2; CRP; ENG; FTH1; GLUCOSE; HBA1C; HGF; HSPA1B; IGFBP1; IL18; INSULIN; LEP; PLAT; TRIG |
| ADIPOQ; CCL2; CRP; ENG; FTH1; GLUCOSE; HBA1C; HGF; HSPA1B; IGFBP1; IL18; INSULIN; LEP; PLAT; VEGF |
| ADIPOQ; CCL2; CRP; ENG; FTH1; GLUCOSE; HBA1C; HGF; HSPA1B; IGFBP1; IL18; LEP; PLAT; TRIG; VEGF |
| ADIPOQ; CCL2; CRP; ENG; FTH1; GLUCOSE; HBA1C; HGF; HSPA1B; IGFBP1; IL2RA; INSULIN; LEP; PLAT; TRIG |
| ADIPOQ; CCL2; CRP; ENG; FTH1; GLUCOSE; HBA1C; HGF; HSPA1B; IGFBP1; INSULIN; LEP; PLAT; TRIG; VEGF |
| ADIPOQ; CCL2; CRP; ENG; FTH1; GLUCOSE; HBA1C; HGF; HSPA1B; IL18; IL2RA; INSULIN; LEP; PLAT; TRIG |
| ADIPOQ; CCL2; CRP; ENG; FTH1; GLUCOSE; HBA1C; HGF; HSPA1B; IL18; IL2RA; INSULIN; LEP; PLAT; VEGF |
| ADIPOQ; CCL2; CRP; ENG; FTH1; GLUCOSE; HBA1C; HGF; HSPA1B; IL18; IL2RA; LEP; PLAT; TRIG; VEGF |
| ADIPOQ; CCL2; CRP; ENG; FTH1; GLUCOSE; HBA1C; HGF; HSPA1B; IL18; INSULIN; LEP; PLAT; TRIG; VEGF |
| ADIPOQ; CCL2; CRP; ENG; FTH1; GLUCOSE; HBA1C; HGF; HSPA1B; IL2RA; INSULIN; LEP; PLAT; TRIG; VEGF |
| ADIPOQ; CCL2; CRP; ENG; FTH1; GLUCOSE; HBA1C; HGF; IGFBP1; IL18; IL2RA; INSULIN; LEP; PLAT; TRIG |
| ADIPOQ; CCL2; CRP; ENG; FTH1; GLUCOSE; HBA1C; HGF; IGFBP1; IL18; IL2RA; INSULIN; LEP; PLAT; VEGF |
| ADIPOQ; CCL2; CRP; ENG; FTH1; GLUCOSE; HBA1C; HSPA1B; IGFBP1; IL18; IL2RA; INSULIN; LEP; PLAT; TRIG |
| ADIPOQ; CCL2; CRP; ENG; FTH1; GLUCOSE; HBA1C; HSPA1B; IGFBP1; IL18; IL2RA; INSULIN; LEP; PLAT; VEGF |
| ADIPOQ; CCL2; CRP; ENG; FTH1; GLUCOSE; HBA1C; IGFBP1; IL18; IL2RA; INSULIN; LEP; PLAT; TRIG; VEGF |

FIGURE 49 (continued)

| |
|---|
| ADIPOQ; CCL2; CRP; ENG; FTH1; GLUCOSE; HBA1C; HSPA1B; IGFBP1; IL18; INSULIN; LEP; PLAT; TRIG; VEGF |
| ADIPOQ; CCL2; CRP; ENG; FTH1; GLUCOSE; HBA1C; HSPA1B; IGFBP1; IL2RA; INSULIN; LEP; PLAT; TRIG; VEGF |
| ADIPOQ; CCL2; CRP; ENG; FTH1; GLUCOSE; HBA1C; HSPA1B; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT |
| ADIPOQ; CRP; ENG; FTH1; GLUCOSE; GPT; HBA1C; HGF; HSPA1B; IGFBP1; IL18; INSULIN; LEP; PLAT; TRIG |
| ADIPOQ; CRP; ENG; FTH1; GLUCOSE; GPT; HBA1C; HGF; HSPA1B; IGFBP1; IL18; INSULIN; LEP; PLAT; VEGF |
| ADIPOQ; CRP; ENG; FTH1; GLUCOSE; GPT; HBA1C; HGF; HSPA1B; IL18; IL2RA; INSULIN; LEP; PLAT; TRIG |
| ADIPOQ; CRP; ENG; FTH1; GLUCOSE; GPT; HBA1C; HGF; HSPA1B; IL18; IL2RA; INSULIN; LEP; PLAT; VEGF |
| ADIPOQ; CRP; ENG; FTH1; GLUCOSE; GPT; HBA1C; HSPA1B; IGFBP1; IL18; IL2RA; INSULIN; LEP; PLAT; TRIG |
| ADIPOQ; CRP; ENG; FTH1; GLUCOSE; GPT; HBA1C; HSPA1B; IGFBP1; IL18; IL2RA; INSULIN; LEP; PLAT; VEGF |
| ADIPOQ; CRP; ENG; FTH1; GLUCOSE; GPT; HBA1C; HSPA1B; IGFBP1; IL18; INSULIN; LEP; PLAT; TRIG; VEGF |
| ADIPOQ; CRP; ENG; FTH1; GLUCOSE; GPT; HBA1C; HSPA1B; IL18; IL2RA; INSULIN; LEP; PLAT; TRIG; VEGF |
| ADIPOQ; CRP; ENG; FTH1; GLUCOSE; HBA1C; HGF; HSPA1B; IGFBP1; IL18; IL2RA; INSULIN; LEP; PLAT; TRIG |
| ADIPOQ; CRP; ENG; FTH1; GLUCOSE; HBA1C; HGF; HSPA1B; IGFBP1; IL18; IL2RA; INSULIN; LEP; PLAT; VEGF |
| ADIPOQ; CRP; ENG; FTH1; GLUCOSE; HBA1C; HGF; HSPA1B; IGFBP1; IL18; INSULIN; LEP; PLAT; TRIG; VEGF |
| ADIPOQ; CRP; ENG; FTH1; GLUCOSE; HBA1C; HGF; HSPA1B; IL18; IL2RA; INSULIN; LEP; PLAT; TRIG; VEGF |
| ADIPOQ; CRP; ENG; FTH1; GLUCOSE; HBA1C; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IL18; IL2RA; INSULIN; LEP; PLAT; VEGF |
| CCL2; CRP; ENG; FTH1; GLUCOSE; GPT; HBA1C; HSPA1B; IGFBP1; IL18; IL2RA; INSULIN; LEP; PLAT; VEGF |

FIGURE 50

| |
|---|
| ADIPOQ; CCL2; CRP; ENG; FTH1; GLUCOSE; GPT; HBA1C; HGF; HSPA1B; IGFBP1; IL18; IL2RA; INSULIN; LEP; PLAT |
| ADIPOQ; CCL2; CRP; ENG; FTH1; GLUCOSE; GPT; HBA1C; HGF; HSPA1B; IGFBP1; IL18; IL2RA; INSULIN; LEP; TRIG |
| ADIPOQ; CCL2; CRP; ENG; FTH1; GLUCOSE; GPT; HBA1C; HGF; HSPA1B; IGFBP1; IL18; IL2RA; INSULIN; LEP; VEGF |
| ADIPOQ; CCL2; CRP; ENG; FTH1; GLUCOSE; GPT; HBA1C; HGF; HSPA1B; IGFBP1; IL18; IL2RA; INSULIN; PLAT; TRIG |
| ADIPOQ; CCL2; CRP; ENG; FTH1; GLUCOSE; GPT; HBA1C; HGF; HSPA1B; IGFBP1; IL18; IL2RA; INSULIN; PLAT; VEGF |
| ADIPOQ; CCL2; CRP; ENG; FTH1; GLUCOSE; GPT; HBA1C; HGF; HSPA1B; IGFBP1; IL18; IL2RA; LEP; PLAT; TRIG |
| ADIPOQ; CCL2; CRP; ENG; FTH1; GLUCOSE; GPT; HBA1C; HGF; HSPA1B; IGFBP1; IL18; IL2RA; LEP; PLAT; VEGF |
| ADIPOQ; CCL2; CRP; ENG; FTH1; GLUCOSE; GPT; HBA1C; HGF; HSPA1B; IGFBP1; IL18; IL2RA; LEP; TRIG; VEGF |
| ADIPOQ; CCL2; CRP; ENG; FTH1; GLUCOSE; GPT; HBA1C; HGF; HSPA1B; IGFBP1; IL18; IL2RA; PLAT; TRIG; VEGF |
| ADIPOQ; CCL2; CRP; ENG; FTH1; GLUCOSE; GPT; HBA1C; HGF; HSPA1B; IGFBP1; IL18; INSULIN; LEP; PLAT; TRIG |
| ADIPOQ; CCL2; CRP; ENG; FTH1; GLUCOSE; GPT; HBA1C; HGF; HSPA1B; IGFBP1; IL18; INSULIN; LEP; PLAT; VEGF |
| ADIPOQ; CCL2; CRP; ENG; FTH1; GLUCOSE; GPT; HBA1C; HGF; HSPA1B; IGFBP1; IL18; INSULIN; LEP; TRIG; VEGF |
| ADIPOQ; CCL2; CRP; ENG; FTH1; GLUCOSE; GPT; HBA1C; HGF; HSPA1B; IGFBP1; IL18; INSULIN; PLAT; TRIG; VEGF |
| ADIPOQ; CCL2; CRP; ENG; FTH1; GLUCOSE; GPT; HBA1C; HGF; HSPA1B; IGFBP1; IL18; LEP; PLAT; TRIG; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT; TRIG |
| ADIPOQ; CCL2; CRP; ENG; FTH1; GLUCOSE; GPT; HBA1C; HGF; HSPA1B; IGFBP1; IL2RA; INSULIN; LEP; PLAT; VEGF |
| ADIPOQ; CCL2; CRP; ENG; FTH1; GLUCOSE; GPT; HBA1C; HGF; HSPA1B; IGFBP1; IL2RA; INSULIN; LEP; TRIG; VEGF |
| ADIPOQ; CCL2; CRP; ENG; FTH1; GLUCOSE; GPT; HBA1C; HGF; HSPA1B; IGFBP1; IL2RA; INSULIN; PLAT; TRIG; VEGF |
| ADIPOQ; CCL2; CRP; ENG; FTH1; GLUCOSE; GPT; HBA1C; HGF; HSPA1B; IGFBP1; IL2RA; LEP; PLAT; TRIG; VEGF |
| ADIPOQ; CCL2; CRP; ENG; FTH1; GLUCOSE; GPT; HBA1C; HGF; HSPA1B; IGFBP1; INSULIN; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT; TRIG |
| ADIPOQ; CCL2; CRP; ENG; FTH1; GLUCOSE; GPT; HBA1C; HGF; HSPA1B; IL18; IL2RA; INSULIN; LEP; PLAT; VEGF |
| ADIPOQ; CCL2; CRP; ENG; FTH1; GLUCOSE; GPT; HBA1C; HGF; HSPA1B; IL18; IL2RA; INSULIN; LEP; TRIG; VEGF |
| ADIPOQ; CCL2; CRP; ENG; FTH1; GLUCOSE; GPT; HBA1C; HGF; HSPA1B; IL18; IL2RA; INSULIN; PLAT; TRIG; VEGF |
| ADIPOQ; CCL2; CRP; ENG; FTH1; GLUCOSE; GPT; HBA1C; HGF; HSPA1B; IL18; IL2RA; LEP; PLAT; TRIG; VEGF |
| ADIPOQ; CCL2; CRP; ENG; FTH1; GLUCOSE; GPT; HBA1C; HGF; HSPA1B; IL18; INSULIN; LEP; PLAT; TRIG; VEGF |
| ADIPOQ; CCL2; CRP; ENG; FTH1; GLUCOSE; GPT; HBA1C; HGF; HSPA1B; IL2RA; INSULIN; LEP; PLAT; TRIG; VEGF |

FIGURE 50 (continued)

| |
|---|
| ADIPOQ; CCL2; CRP; ENG; FTH1; GLUCOSE; GPT; HBA1C; HGF; IGFBP1; IL18; IL2RA; INSULIN; LEP; PLAT; TRIG |
| ADIPOQ; CCL2; CRP; ENG; FTH1; GLUCOSE; GPT; HBA1C; HGF; IGFBP1; IL18; IL2RA; INSULIN; LEP; PLAT; VEGF |
| ADIPOQ; CCL2; CRP; ENG; FTH1; GLUCOSE; GPT; HBA1C; HGF; IGFBP1; IL18; IL2RA; INSULIN; LEP; PLAT; TRIG; VEGF |
| ADIPOQ; CCL2; CRP; ENG; FTH1; GLUCOSE; GPT; HBA1C; HGF; IGFBP1; IL18; IL2RA; LEP; PLAT; TRIG; VEGF |
| ADIPOQ; CCL2; CRP; ENG; FTH1; GLUCOSE; GPT; HBA1C; HGF; IGFBP1; IL18; INSULIN; LEP; PLAT; TRIG; VEGF |
| ADIPOQ; CCL2; CRP; ENG; FTH1; GLUCOSE; GPT; HBA1C; HGF; IGFBP1; IL2RA; INSULIN; LEP; PLAT; TRIG; VEGF |
| ADIPOQ; CCL2; CRP; ENG; FTH1; GLUCOSE; GPT; HBA1C; HGF; IL18; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT; TRIG |
| ADIPOQ; CCL2; CRP; ENG; FTH1; GLUCOSE; GPT; HBA1C; HSPA1B; IGFBP1; IL18; IL2RA; INSULIN; LEP; PLAT; VEGF |
| ADIPOQ; CCL2; CRP; ENG; FTH1; GLUCOSE; GPT; HBA1C; HSPA1B; IGFBP1; IL18; IL2RA; INSULIN; PLAT; TRIG; VEGF |
| ADIPOQ; CCL2; CRP; ENG; FTH1; GLUCOSE; GPT; HBA1C; HSPA1B; IGFBP1; IL18; IL2RA; LEP; PLAT; TRIG; VEGF |
| ADIPOQ; CCL2; CRP; ENG; FTH1; GLUCOSE; GPT; HBA1C; HSPA1B; IGFBP1; IL18; INSULIN; LEP; PLAT; TRIG; VEGF |
| ADIPOQ; CCL2; CRP; ENG; FTH1; GLUCOSE; GPT; HBA1C; HSPA1B; IL18; IL2RA; INSULIN; LEP; PLAT; TRIG; VEGF |
| ADIPOQ; CCL2; CRP; ENG; FTH1; GLUCOSE; GPT; HBA1C; HGF; HSPA1B; IGFBP1; IL18; IL2RA; INSULIN; LEP; PLAT; TRIG |
| ADIPOQ; CCL2; CRP; ENG; FTH1; GLUCOSE; GPT; HGF; HSPA1B; IGFBP1; IL18; IL2RA: INSULIN; LEP; PLAT; VEGF |
| ADIPOQ; CCL2; CRP; ENG; FTH1; GLUCOSE; GPT; HGF; HSPA1B; IGFBP1; IL18; IL2RA: INSULIN; LEP; PLAT; TRIG |
| ADIPOQ; CCL2; CRP; ENG; FTH1; GLUCOSE; GPT; HGF; HSPA1B; IGFBP1; IL18; IL2RA: INSULIN; PLAT; TRIG; VEGF |
| ADIPOQ; CCL2; CRP; ENG; FTH1; GLUCOSE; GPT; HGF; HSPA1B; IGFBP1; IL18; IL2RA: LEP; PLAT; TRIG; VEGF |
| ADIPOQ; CCL2; CRP; ENG; FTH1; GLUCOSE; GPT; HGF; HSPA1B; IGFBP1; IL18; INSULIN; LEP; PLAT; TRIG; VEGF |
| ADIPOQ; CCL2; CRP; ENG; FTH1; GLUCOSE; GPT; HSPA1B; IGFBP1; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT; TRIG |
| ADIPOQ; CCL2; CRP; ENG; FTH1; GLUCOSE; HBA1C; HGF; HSPA1B; IGFBP1; IL18; IL2RA; INSULIN; LEP; PLAT; VEGF |
| ADIPOQ; CCL2; CRP; ENG; FTH1; GLUCOSE; HBA1C; HGF; HSPA1B; IGFBP1; IL18; IL2RA; INSULIN; LEP; TRIG; VEGF |

FIGURE 50 (continued)

| |
|---|
| ADIPOQ; CCL2; CRP; ENG; FTH1; GLUCOSE; HBA1C; HGF; HSPA1B; IGFBP1; IL18; IL2RA; INSULIN; PLAT; TRIG; VEGF |
| ADIPOQ; CCL2; CRP; ENG; FTH1; GLUCOSE; HBA1C; HGF; HSPA1B; IGFBP1; IL18; IL2RA; LEP; PLAT; TRIG; VEGF |
| ADIPOQ; CCL2; CRP; ENG; FTH1; GLUCOSE; HBA1C; HGF; HSPA1B; IGFBP1; IL18; INSULIN; LEP; PLAT; TRIG; VEGF |
| ADIPOQ; CCL2; CRP; ENG; FTH1; GLUCOSE; HBA1C; HGF; HSPA1B; IGFBP1; IL2RA; INSULIN; LEP; PLAT; TRIG; VEGF |
| ADIPOQ; CCL2; CRP; ENG; FTH1; GLUCOSE; HBA1C; HGF; HSPA1B; IL18; IL2RA; INSULIN; LEP; PLAT; TRIG; VEGF |
| ADIPOQ; CCL2; CRP; ENG; FTH1; GLUCOSE; HBA1C; HGF; IGFBP1; IL18; IL2RA; INSULIN; LEP; PLAT; TRIG; VEGF |
| ADIPOQ; CCL2; CRP; ENG; FTH1; GLUCOSE; HBA1C; HSPA1B; IGFBP1; IL18; IL2RA; INSULIN; LEP; PLAT; TRIG; VEGF |
| ADIPOQ; CCL2; CRP; ENG; FTH1; GLUCOSE; HGF; HSPA1B; IGFBP1; IL18; IL2RA; INSULIN; LEP; PLAT; TRIG; VEGF |
| ADIPOQ; CCL2; CRP; ENG; FTH1; GPT; HBA1C; HGF; HSPA1B; IGFBP1; IL18; IL2RA; INSULIN; LEP; PLAT; TRIG |
| ADIPOQ; CCL2; CRP; ENG; FTH1; GPT; HBA1C; HGF; HSPA1B; IGFBP1; IL18; IL2RA; INSULIN; LEP; PLAT; VEGF |
| ADIPOQ; CCL2; CRP; ENG; FTH1; GPT; HBA1C; HGF; HSPA1B; IGFBP1; IL18; IL2RA; INSULIN; LEP; TRIG; VEGF |
| ADIPOQ; CCL2; CRP; ENG; FTH1; GPT; HBA1C; HGF; HSPA1B; IGFBP1; IL18; IL2RA; INSULIN; PLAT; TRIG; VEGF |
| ADIPOQ; CCL2; CRP; ENG; FTH1; GPT; HBA1C; HGF; HSPA1B; IGFBP1; IL18; IL2RA; LEP; PLAT; TRIG; VEGF |
| ADIPOQ; CCL2; CRP; ENG; FTH1; GPT; HBA1C; HGF; HSPA1B; IGFBP1; IL18; INSULIN; LEP; PLAT; TRIG; VEGF |
| ADIPOQ; CCL2; CRP; ENG; FTH1; GPT; HBA1C; HGF; HSPA1B; IGFBP1; IL2RA; INSULIN; LEP; PLAT; TRIG; VEGF |
| ADIPOQ; CCL2; CRP; ENG; FTH1; GPT; HBA1C; HGF; HSPA1B; IL18; IL2RA; INSULIN; LEP; PLAT; TRIG; VEGF |
| ADIPOQ; CCL2; CRP; ENG; FTH1; GPT; HBA1C; HGF; IGFBP1; IL18; IL2RA; INSULIN; LEP; PLAT; TRIG; VEGF |
| ADIPOQ; CCL2; CRP; ENG; FTH1; GPT; HBA1C; HSPA1B; IGFBP1; IL18; IL2RA; INSULIN; LEP; PLAT; TRIG; VEGF |
| ADIPOQ; CCL2; CRP; ENG; FTH1; GPT; HGF; HSPA1B; IGFBP1; IL18; IL2RA; INSULIN; LEP; PLAT; TRIG; VEGF |
| ADIPOQ; CCL2; CRP; ENG; GLUCOSE; GPT; HBA1C; HGF; HSPA1B; IGFBP1; IL18; IL2RA; INSULIN; LEP; PLAT; TRIG |
| ADIPOQ; CCL2; CRP; ENG; GLUCOSE; GPT; HBA1C; HGF; HSPA1B; IGFBP1; IL18; IL2RA; INSULIN; LEP; PLAT; VEGF |
| ADIPOQ; CCL2; CRP; ENG; GLUCOSE; GPT; HBA1C; HGF; HSPA1B; IGFBP1; IL18; IL2RA; INSULIN; LEP; TRIG; VEGF |
| ADIPOQ; CCL2; CRP; ENG; GLUCOSE; GPT; HBA1C; HGF; HSPA1B; IGFBP1; IL18; IL2RA; INSULIN; PLAT; TRIG; VEGF |
| ADIPOQ; CCL2; CRP; ENG; GLUCOSE; GPT; HBA1C; HGF; HSPA1B; IGFBP1; IL18; IL2RA; LEP; PLAT; TRIG; VEGF |
| ADIPOQ; CCL2; CRP; ENG; GLUCOSE; GPT; HBA1C; HGF; HSPA1B; IGFBP1; IL18; INSULIN; LEP; PLAT; TRIG; VEGF |
| ADIPOQ; CCL2; CRP; ENG; GLUCOSE; GPT; HBA1C; HGF; HSPA1B; IGFBP1; IL2RA; INSULIN; LEP; PLAT; TRIG; VEGF |
| ADIPOQ; CCL2; CRP; ENG; GLUCOSE; GPT; HBA1C; HGF; HSPA1B; IL18; IL2RA; INSULIN; LEP; PLAT; TRIG; VEGF |
| ADIPOQ; CCL2; CRP; ENG; GLUCOSE; GPT; HBA1C; HGF; IGFBP1; IL18; IL2RA; INSULIN; LEP; PLAT; TRIG; VEGF |
| ADIPOQ; CCL2; CRP; ENG; GLUCOSE; GPT; HBA1C; HSPA1B; IGFBP1; IL18; IL2RA; INSULIN; LEP; PLAT; TRIG; VEGF |
| ADIPOQ; CCL2; CRP; ENG; GLUCOSE; GPT; HGF; HSPA1B; IGFBP1; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT; TRIG |
| ADIPOQ; CRP; ENG; FTH1; GLUCOSE; GPT; HBA1C; HGF; HSPA1B; IGFBP1; IL18; IL2RA; INSULIN; LEP; PLAT; VEGF |
| ADIPOQ; CRP; ENG; FTH1; GLUCOSE; GPT; HBA1C; HGF; HSPA1B; IGFBP1; IL18; IL2RA; INSULIN; LEP; TRIG; VEGF |
| ADIPOQ; CRP; ENG; FTH1; GLUCOSE; GPT; HBA1C; HGF; HSPA1B; IGFBP1; IL18; IL2RA; INSULIN; PLAT; TRIG; VEGF |

FIGURE 50 (continued)

| |
|---|
| ADIPOQ; CRP; ENG; FTH1; GLUCOSE; GPT; HBA1C; HGF; HSPA1B; IGFBP1; IL18; IL2RA; LEP; PLAT; TRIG; VEGF |
| ADIPOQ; CRP; ENG; FTH1; GLUCOSE; GPT; HBA1C; HGF; HSPA1B; IGFBP1; IL18; INSULIN; LEP; PLAT; TRIG; VEGF |
| ADIPOQ; CRP; ENG; FTH1; GLUCOSE; GPT; HBA1C; HGF; HSPA1B; IGFBP1; IL2RA; INSULIN; LEP; PLAT; TRIG; VEGF |
| ADIPOQ; CRP; ENG; FTH1; GLUCOSE; GPT; HBA1C; HGF; HSPA1B; IL18; IL2RA; INSULIN; LEP; PLAT; TRIG; VEGF |
| ADIPOQ; CRP; ENG; FTH1; GLUCOSE; GPT; HBA1C; HGF; IGFBP1; IL18; IL2RA; INSULIN; LEP; PLAT; TRIG; VEGF |
| ADIPOQ; CRP; ENG; FTH1; GLUCOSE; GPT; HBA1C; HSPA1B; IGFBP1; IL18; IL2RA; INSULIN; LEP; PLAT; TRIG; VEGF |
| ADIPOQ; CRP; ENG; FTH1; GLUCOSE; GPT; HGF; HSPA1B; IGFBP1; IL18; IL2RA; INSULIN; LEP; PLAT; TRIG; VEGF |
| ADIPOQ; CRP; ENG; FTH1; GLUCOSE; HBA1C; HGF; HSPA1B; IGFBP1; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IGFBP1; IL18; IL2RA; INSULIN; LEP; PLAT; TRIG |
| CCL2; CRP; ENG; FTH1; GLUCOSE; GPT; HBA1C; HGF; HSPA1B; IGFBP1; IL18; IL2RA; INSULIN; LEP; PLAT; VEGF |
| CCL2; CRP; ENG; FTH1; GLUCOSE; GPT; HBA1C; HGF; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IGFBP1; IL18; IL2RA; INSULIN; PLAT; TRIG; VEGF |
| CCL2; CRP; ENG; FTH1; GLUCOSE; GPT; HBA1C; HGF; HSPA1B; IGFBP1; IL18; IL2RA; LEP; PLAT; TRIG; VEGF |
| CCL2; CRP; ENG; FTH1; GLUCOSE; GPT; HBA1C; HGF; HSPA1B; IGFBP1; IL18; INSULIN; LEP; PLAT; TRIG; VEGF |
| CCL2; CRP; ENG; FTH1; GLUCOSE; GPT; HBA1C; HGF; HSPA1B; IGFBP1; IL2RA; INSULIN; LEP; PLAT; TRIG; VEGF |
| CCL2; CRP; ENG; FTH1; GLUCOSE; GPT; HBA1C; HGF; HSPA1B; IL18; IL2RA; INSULIN; LEP; PLAT; TRIG; VEGF |
| CCL2; CRP; ENG; FTH1; GLUCOSE; GPT; HBA1C; HGF; IGFBP1; IL18; IL2RA; INSULIN; LEP; PLAT; TRIG; VEGF |
| CCL2; CRP; ENG; FTH1; GLUCOSE; GPT; HBA1C; HSPA1B; IGFBP1; IL18; IL2RA; INSULIN; LEP; PLAT; TRIG; VEGF |
| CCL2; CRP; ENG; FTH1; GLUCOSE; GPT; HGF; HSPA1B; IGFBP1; IL18; IL2RA; INSULIN; LEP; PLAT; TRIG; VEGF |
| CCL2; CRP; ENG; FTH1; GLUCOSE; HBA1C; HGF; HSPA1B; IGFBP1; IL18; IL2RA; INSULIN; LEP; PLAT; TRIG; VEGF |
| CCL2; CRP; ENG; FTH1; GPT; HBA1C; HGF; HSPA1B; IGFBP1; IL18; IL2RA; INSULIN; LEP; PLAT; TRIG; VEGF |
| CCL2; ENG; FTH1; GLUCOSE; GPT; HBA1C; HGF; HSPA1B; IGFBP1; IL18; IL2RA; INSULIN; LEP; PLAT; TRIG; VEGF |
| CRP; ENG; FTH1; GLUCOSE; GPT; HBA1C; HGF; HSPA1B; IGFBP1; IL18; IL2RA; INSULIN; LEP; PLAT; TRIG; VEGF |

FIGURE 51

| |
|---|
| ADIPOQ; CCL2; CRP; ENG; FTH1; GLUCOSE; GPT; HBA1C; HGF; HSPA1B; IGFBP1; IL18; IL2RA; INSULIN; LEP; PLAT; TRIG |
| ADIPOQ; CCL2; CRP; ENG; FTH1; GLUCOSE; GPT; HBA1C; HGF; HSPA1B; IGFBP1; IL18; IL2RA; INSULIN; LEP; PLAT; VEGF |
| ADIPOQ; CCL2; CRP; ENG; FTH1; GLUCOSE; GPT; HBA1C; HGF; HSPA1B; IGFBP1; IL18; IL2RA; INSULIN; LEP; TRIG; VEGF |
| ADIPOQ; CCL2; CRP; ENG; FTH1; GLUCOSE; GPT; HBA1C; HGF; HSPA1B; IGFBP1; IL18; IL2RA; INSULIN; PLAT; TRIG; VEGF |
| ADIPOQ; CCL2; CRP; ENG; FTH1; GLUCOSE; GPT; HBA1C; HGF; HSPA1B; IGFBP1; IL18; IL2RA; INSULIN; LEP; PLAT; TRIG; VEGF |
| ADIPOQ; CCL2; CRP; ENG; FTH1; GLUCOSE; GPT; HBA1C; HGF; HSPA1B; IGFBP1; IL18; IL2RA; LEP; PLAT; TRIG; VEGF |
| ADIPOQ; CCL2; CRP; ENG; FTH1; GLUCOSE; GPT; HBA1C; HGF; HSPA1B; IGFBP1; IL18; INSULIN; LEP; PLAT; TRIG; VEGF |
| ADIPOQ; CCL2; CRP; ENG; FTH1; GLUCOSE; GPT; HBA1C; HGF; HSPA1B; IGFBP1; IL2RA; INSULIN; LEP; PLAT; TRIG; VEGF |
| ADIPOQ; CCL2; CRP; ENG; FTH1; GLUCOSE; GPT; HBA1C; HGF; HSPA1B; IL18; IL2RA; INSULIN; LEP; PLAT; TRIG; VEGF |
| ADIPOQ; CCL2; CRP; ENG; FTH1; GLUCOSE; GPT; HBA1C; HGF; IGFBP1; IL18; IL2RA; INSULIN; LEP; PLAT; TRIG; VEGF |
| ADIPOQ; CCL2; CRP; ENG; FTH1; GLUCOSE; GPT; HBA1C; HSPA1B; IGFBP1; IL18; IL2RA; INSULIN; LEP; PLAT; TRIG; VEGF |
| ADIPOQ; CCL2; CRP; ENG; FTH1; GLUCOSE; GPT; HGF; HSPA1B; IGFBP1; IL18; IL2RA; INSULIN; LEP; PLAT; TRIG; VEGF |
| ADIPOQ; CCL2; CRP; ENG; FTH1; GLUCOSE; HBA1C; HGF; HSPA1B; IGFBP1; IL18; IL2RA; INSULIN; LEP; PLAT; TRIG; VEGF |
| ADIPOQ; CCL2; CRP; ENG; FTH1; GPT; HBA1C; HGF; HSPA1B; IGFBP1; IL18; IL2RA; INSULIN; LEP; PLAT; TRIG; VEGF |
| ADIPOQ; CCL2; CRP; ENG; GLUCOSE; GPT; HBA1C; HGF; HSPA1B; IGFBP1; IL18; IL2RA; INSULIN; LEP; PLAT; TRIG; VEGF |
| ADIPOQ; CCL2; CRP; FTH1; GLUCOSE; GPT; HBA1C; HGF; HSPA1B; IGFBP1; IL18; IL2RA; INSULIN; LEP; PLAT; TRIG; VEGF |
| ADIPOQ; CCL2; ENG; FTH1; GLUCOSE; GPT; HBA1C; HGF; HSPA1B; IGFBP1; IL18; IL2RA; INSULIN; LEP; PLAT; TRIG; VEGF |
| ADIPOQ; CRP; ENG; FTH1; GLUCOSE; GPT; HBA1C; HGF; HSPA1B; IGFBP1; IL18; IL2RA; INSULIN; LEP; PLAT; TRIG; VEGF |
| CCL2; CRP; ENG; FTH1; GLUCOSE; GPT; HBA1C; HGF; HSPA1B; IGFBP1; IL18; IL2RA; INSULIN; LEP; PLAT; TRIG; VEGF |

DIABETES-RELATED BIOMARKERS AND METHODS OF USE THEREOF

CROSS-REFERENCE TO RELATED APPLICATIONS

This application is a continuation of U.S. patent application Ser. No. 12/106,070, filed Apr. 18, 2008, now U.S. Pat. No. 8,119,358, which is a continuation-in-part of U.S. patent application Ser. No. 11/788,260, filed Apr. 18, 2007, now abandoned which is a continuation-in-part of U.S. patent application Ser. No. 11/546,874, filed Oct. 11, 2006, now abandoned which claims priority from U.S. Provisional Patent Application No. 60/725,462 filed Oct. 11, 2005. U.S. patent application Ser. No. 12/106,070, filed Apr. 18, 2008, also claims priority from U.S. Provisional Patent Application No. 61/002,609, filed Nov. 8, 2007. These related applications are incorporated by reference herein in their entirety.

STATEMENT REGARDING FEDERALLY SPONSORED RESEARCH OR DEVELOPMENT

Not applicable.

FIELD OF THE INVENTION

The invention relates to biomarkers associated with Diabetes, methods of using the biomarkers to determine the risk that an individual will develop Diabetes, and methods of screening a population to identify persons at risk for developing Diabetes and other pre-diabetic conditions.

BACKGROUND OF THE INVENTION

Diabetes mellitus is a serious illness characterized by a loss of the ability to regulate blood glucose levels. The World Health Organization (WHO) estimates that more than 180 million people worldwide have Diabetes. This number is likely to more than double by 2030. In 2005, an estimated 1.1 million people died from Diabetes; this estimate likely undercounts deaths caused by Diabetes, as Diabetes contributes to other diseases, such as heart disease and kidney disease, that may be listed as the cause of death. Almost 80% of Diabetes deaths occur in low and middle-income countries. See URL World-Wide-Web.who.int/mediacentre/factsheets/fs312/en/index.html.

Diabetes Mellitus is subdivided into Type 1 Diabetes and Type 2 Diabetes. Type 1 Diabetes (insulin-dependent Diabetes or childhood-onset Diabetes) results from a lack of insulin production due to an autoimmune mediated destruction of the beta cells of the pancreas. Patients require daily administration of insulin for survival and are at risk for ketoacidosis. Patients with Type 1 Diabetes exhibit little or no insulin secretion as manifested by low or undetectable levels of insulin or plasma C-peptide (also known in the art as "soluble C-peptide").

Type 2 Diabetes (non-insulin-dependent Diabetes or adult-onset Diabetes) results from insensitivity to insulin, and accounts for 90% of Diabetes worldwide. Gestational Diabetes is a loss of blood sugar control (hyperglycemia) that occurs during pregnancy. Type 2 Diabetes is characterized by disorders of insulin action and insulin secretion, either of which may be the predominant feature. Type 2 Diabetes patients are characterized with a relative, rather than absolute, insulin deficiency and are insulin resistant. At least initially, and often throughout their lifetime, these individuals do not need supplemental insulin treatment to survive. Type 2 Diabetes accounts for 90-95% of all cases of Diabetes and can go undiagnosed for many years because the hyperglycemia is often not severe enough to provoke noticeable symptoms of Diabetes or symptoms are simply not recognized. The majority of patients with Type 2 Diabetes are obese, and obesity itself may cause or aggravate insulin resistance. Many of those who are not obese by traditional weight criteria may have an increased percentage of body fat distributed predominantly in the abdominal region (visceral fat). Whereas patients with this form of Diabetes may have insulin levels that appear normal or elevated, the high blood glucose levels in these diabetic patients would be expected to result in even higher insulin values had their beta cell function been normal. Thus, insulin secretion is often defective and insufficient to compensate for the insulin resistance. On the other hand, some hyperglycemic individuals have essentially normal insulin action, but markedly impaired insulin secretion.

Pre-diabetics often have fasting glucose levels between normal and frank diabetic levels. Abnormal glucose tolerance, or "impaired glucose tolerance" can be an indication that an individual is on the path toward Diabetes; it requires the use of a 2-hour oral glucose tolerance test for its detection. However, it has been shown that impaired glucose tolerance is by itself entirely asymptomatic and unassociated with any functional disability. Indeed, insulin secretion is typically greater in response to a mixed meal than in response to a pure glucose load; as a result, most persons with impaired glucose tolerance are rarely, if ever, hyperglycemic in their daily lives, except when they undergo diagnostic glucose tolerance tests. Thus, the importance of impaired glucose tolerance resides exclusively in its ability to identify persons at increased risk of future disease (Stern et al, 2002)

Diabetes is generally diagnosed by determining blood glucose levels after fasting overnight (fasting plasma glucose level) or by determining blood glucose levels after fasting, followed by ingestion of glucose and a blood glucose measurement two hours after glucose administration (a glucose tolerance test). In studies conducted by Stern and colleagues (Stern et al., Diabetes Care 25:1851-1856, (2002)), the sensitivity and false-positive rates of impaired glucose tolerance as a predictor of future conversion to Type 2 Diabetes was 50.9% and 10.2%, respectively, representing an area under the Receiver-Operating Characteristic Curve of 77.5% (with a 95% confidence interval of 74.3-80.7%) and a P-value (calculated using Hosmer-Lemeshow goodness-of-fit) of 0.20. Because of the inconvenience associated with the two-hour glucose tolerance test, as well as the cost of the test, the test is seldom used in routine clinical practice. Moreover, patients whose Diabetes is diagnosed solely on the basis of an oral glucose tolerance test have a high rate of reversion to normal on follow-up and may in fact represent false-positive diagnoses (Burke et al., Diabetes Care 21:1266-1270 (1998)). Stern and others reported that such cases were almost 5 times more likely to revert to non-diabetic status after 7 to 8 years of follow-up compared with persons meeting conventional fasting or clinical diagnostic criteria.

Beyond glucose and HBA1c, several single time point biomarker measurements have been attempted for the use of risk assessment for future Diabetes. U.S. Patent Application No. 2003/0100486 proposes C-Reactive Protein (CRP) and Interleukin-6 (IL-6), both markers of systemic inflammation, used alone and as an adjunct to the measurement of HBA1c. However, for practical reasons relating to clinical performance, specifically poor specificity and high false positive rates, these tests have not been adopted.

Often a person with impaired glucose tolerance will be found to have at least one or more of the common arteriovascular disease risk factors (e.g., dyslipidemia and hypertension). This clustering has been termed "Syndrome X," or "Metabolic Syndrome" by some researchers and can be indicative of a diabetic or pre-diabetic condition. Alone, each component of the cluster conveys increased arteriovascular and diabetic disease risk, but together as a combination they become much more significant. This means that the management of persons with hyperglycemia and other features of Metabolic Syndrome should focus not only on blood glucose control but also include strategies for reduction of other arteriovascular disease risk factors. Furthermore, such risk factors are non-specific for Diabetes or pre-Diabetes and are not in themselves a basis for a diagnosis of Diabetes, or of diabetic status.

Risk prediction for Diabetes, pre-Diabetes, or a pre-diabetic condition can also encompass multi-variate risk prediction algorithms and computed indices that assess and estimate a subject's absolute risk for developing Diabetes, pre-Diabetes, or a pre-diabetic condition with reference to a historical cohort. Risk assessment using such predictive mathematical algorithms and computed indices has increasingly been incorporated into guidelines for diagnostic testing and treatment, and encompass indices obtained from and validated with, inter alia, multi-stage, stratified samples from a representative population. A plurality of conventional Diabetes risk factors is incorporated into predictive models. A notable example of such algorithms include the Framingham study (Kannel, W. B. et al, (1976) Am. J. Cardiol. 38: 46-51) and modifications of the Framingham Study, such as the National Cholesterol Education Program Expert Panel on Detection, Evaluation, and Treatment of High Blood Cholesterol in Adults (Adult Treatment Panel III).

Other Diabetes risk prediction algorithms include, without limitation, the San Antonio Heart Study (Stern, M. P. et al, (1984) Am. J. Epidemiol. 120: 834-851; Stern, M. P. et al, (1993) Diabetes 42: 706-714; Burke, J. P. et al, (1999) Arch. Intern. Med. 159: 1450-1456), Archimedes (Eddy, D. M. and Schlessinger, L. (2003) Diabetes Care 26(11): 3093-3101; Eddy, D. M. and Schlessinger, L. (2003) Diabetes Care 26(11): 3102-3110), the Finnish-based Diabetes Risk Score (Lindström, J. and Tuomilehto, J. (2003) Diabetes Care 26(3): 725-731), and the Ely Study (Griffin, S. J. et al, (2000) Diabetes Metab. Res. Rev. 16: 164-171), the contents of which are expressly incorporated herein by reference.

Despite the numerous studies and algorithms that have been used to assess the risk of Diabetes, pre-Diabetes, or a pre-diabetic condition, a need exists for accurate methods of assessing such risks or conditions. Furthermore, due to issues of practicality and the difficulty of the risk computations involved, there has been little adoption of such an approach by the primary care physician that is most likely to initially encounter the pre-diabetic or undiagnosed early diabetic. Clearly, there remains a need for more practical methods of assessing the risk of future Diabetes.

It is well documented that pre-Diabetes can be present for ten or more years before the detection of glycemic disorders like Diabetes. Treatment of pre-diabetics with drugs such as acarbose, metformin, troglitazone and rosiglitazone can postpone or prevent Diabetes; yet few pre-diabetics are treated. A major reason, as indicated above, is that no simple and unambiguous laboratory test exists to determine the actual risk of an individual to develop Diabetes. Furthermore, even in individuals known to be at risk of Diabetes, glycemic control remains the primary therapeutic monitoring endpoint, and is subject to the same limitations as its use in the prediction and diagnosis of frank Diabetes. Thus, there remains a need in the art for methods of identifying, diagnosing, and treatment of these individuals who are not yet diabetics, but who are at significant risk of developing Diabetes.

Accordingly, there remains a need for a relatively inexpensive and convenient method for screening persons at risk for developing Diabetes. Such a test could be used for screening a large population to identify persons at risk for Diabetes, or for testing a single person to determine that individual's risk of developing Diabetes.

SUMMARY OF THE INVENTION

The instant invention relates to use of biomarkers for evaluating the risk that an individual will become diabetic, or for identifying members of a population at risk of developing Diabetes, and methods of calculating such risks, advising individuals of such risks, providing diagnostic test systems for calculating such risks, and various other embodiments as described herein.

In one embodiment, the invention provides novel panels of biomarkers which can be measured and used to evaluate the risk that an individual will develop Diabetes in the future, for example, the risk that an individual will develop Diabetes in the next 1, 2, 2.5, 5, 7.5, or 10 years. Exemplary preferred panels are shown in the Figures. Each panel depicted in a Figure is contemplated as an individual embodiment of the invention. Each panel defines a set of markers that can be employed for methods, improvements, kits, computer readable media, systems, and other aspects of the invention which employ such sets of markers.

In another embodiment, the invention embraces a method of calculating a Diabetes risk score, comprising (a) obtaining inputs about an individual comprising the level of biomarkers in at least one biological sample from said individual; and (b) calculating a Diabetes risk score from said inputs; wherein said biomarkers comprise (i) at least three biomarkers selected from RDMARKERS, or (ii) at least three biomarkers, where two biomarkers are selected from ADIPOQ; CRP; GLUCOSE; GPT; HBA1C; HSPA1B; IGFBP1; IGFBP2; INS; LEP; and TRIG; and one biomarker is selected from the ALLDBRISKS, CPs, and TLRFs of Table 1, Table 2, and Table 3; or (iii) at least three biomarkers, where at least one biomarker is selected from GLUCOSE and HBA1C; at least one biomarker is selected from ADIPOQ, CRP, GPT, HSPA1B, IGFBP1, IGFBP2, INS, LEP, and TRIG; and at least one biomarker is selected from the ALLDBRISKS, CPs, and TLRFs of Table 1, Table 2, and Table 3.

In a related embodiment the invention is a method, of evaluating risk for developing a diabetic condition, the method comprising: (a) obtaining biomarker measurement data, wherein the biomarker measurement data is representative of measurements of biomarkers in at least one biological sample from an individual; and (b) evaluating risk for developing a diabetic condition based on an output from a model, wherein the model is executed based on an input of the biomarker measurement data; wherein the biomarkers comprise: (i) at least three biomarkers, where three of the biomarkers are selected from the RDMARKER sets listed in FIG. 6A; or (ii) at least four biomarkers selected from RDMARKERS; or (iii) at least three biomarkers, where two biomarkers are selected from ADIPOQ; CRP; GLUCOSE; GPT; HBA1C; HSPA1B; IGFBP1; IGFBP2; INS. LEP; and TRIG; and one biomarker is selected from the ALLDBRISKS, CPs, and TLRFs of Table 1, Table 2, and Table 3; or (iv) at least three biomarkers, where at least one biomarker is selected from GLUCOSE and HBA1C; at least one biomarker is selected from ADIPOQ, CRP, GPT, HSPA1B, IGFBP1, IGFBP2, INS, LEP, and TRIG; and at least one biomarker is selected from the ALL- DBRISKS, CPs, and TLRFs of Table 1, Table 2, and Table 3; or (v) at least three biomarkers, where at least two biomarkers are selected from the biomarkers within the group consisting of Core Biomarkers I and Core Biomarkers II and at least a third biomarker is selected from any of the biomarkers listed in Table 4.

In yet another related embodiment, the invention is method of evaluating risk for developing a diabetic condition comprising: obtaining biomarker measurements from at least one biological sample from an individual who is a subject that has not been previously diagnosed as having Diabetes, pre-Diabetes, or a pre-diabetic condition; comparing the biomarker measurement to normal control levels; and evaluating the risk for the individual developing a diabetic condition from the comparison; wherein the biomarkers are defined as set forth in the preceding paragraph.

Similarly, the invention includes method of evaluating risk for developing a diabetic condition, the method comprising: obtaining biomarker measurement data, wherein the biomarker measurement data is representative of measurements of biomarkers in at least one biological sample from an individual; and evaluating risk for developing a diabetic condition based on an output from a model, wherein the model is executed based on an input of the biomarker measurement data; wherein said biomarkers are defined as above.

In another embodiment, the at least three RDMARKERS are selected from the combinations of FIG. 6A.

In another embodiment, the biomarkers comprise at least four biomarkers selected from RDMARKERS.

In another embodiment, the at least four biomarkers selected from RDMARKERS are selected from the combinations in FIG. 6B.

In other embodiments, the biomarkers comprise at least five, at least six, at least seven, at least eight, at least nine, at least ten, or eleven biomarkers selected from RDMARKERS.

In some variations, the step of evaluating risk comprises computing an index value using the model based on the biomarker measurement data, wherein the index value is correlated with risk of developing a diabetic condition in the subject. Optionally, evaluating risk comprises normalizing the biomarker measurement data to reference values.

In another embodiment, the combination of biomarkers used excludes any combination of biomarkers specifically identified in US Patent Publication No. 2007/0218519. In another embodiment, the combination of biomarkers used excludes any combination of biomarkers generically identified in US Patent Application Publication No. 2007/0218519.

In other embodiments, the biomarkers comprise at least five, at least six, at least seven, at least eight, at least nine, at least ten, or eleven biomarkers selected from RDMARKERS.

In another embodiment, the combination of biomarkers used excludes any combination of biomarkers specifically identified in International Publication No. WO 2007/044860. In another embodiment, the combination of biomarkers used excludes any combination of biomarkers generically identified in International Publication No. WO 2007/044860.

In another embodiment, the invention embraces a method of calculating a Diabetes risk score, comprising (a) obtaining inputs about an individual comprising the level of biomarkers in at least one biological sample from said individual; and (b) calculating a Diabetes risk score from said inputs; wherein said biomarkers comprise (i) at least three biomarkers, where three of the biomarkers are selected from the RDMARKER sets listed in FIG. 6A; or (ii) at least four biomarkers selected from RDMARKERS; or (iii) at least three biomarkers, where two biomarkers are selected from ADIPOQ; CRP; GLUCOSE; GPT; HBA1C; HSPA1B; IGFBP1; IGFBP2; IN; LEP; and TRIG; and one biomarker is selected from the ALLDBRISKS, CPs, and TLRFs of Table 1, Table 2, and Table 3; or (iv) at least three biomarkers, where at least one biomarker is selected from GLUCOSE and HBA1C; at least one biomarker is selected from ADIPOQ, CRP, GPT, HSPA1B, IGFBP1, IGFBP2, INS, LEP, and TRIG; and at least one biomarker is selected from the ALLDBRISKS, CPs, and TLRFs of Table 1, Table 2, and Table 3. In other embodiments, the biomarkers comprise at least four, at least five, at least six, at least seven, at least eight, at least nine, at least ten, or at least eleven biomarkers selected from RDMARKERS.

The invention can alternatively be defined as an improvement over existing methodologies. For example, in a method of evaluating the risk of developing a diabetic condition in a subject by measuring one or more of Clinical Parameters and Traditional Laboratory Risk Factors, an embodiment of the invention is an improvement comprising: obtaining biomarker measurement data that is representative of measurements of at least two biomarkers in a sample from the subject, wherein the at least two biomarkers are selected from the group consisting of Core Biomarkers I and Core Biomarkers II; and evaluating the risk of developing a diabetic condition in the subject based on an output from a model, wherein the model is executed based on an input of the biomarker measurement data.

Alternatively, in a method of evaluating the risk of developing a diabetic condition in a subject by measuring one or more of Clinical Parameters and Traditional Laboratory Risk Factors, an embodiment of the invention is an improvement comprising: obtaining biomarker measurement data that is representative of measurements of at least two biomarkers in a sample from the subject, wherein the at least two biomarkers are selected from the group consisting of ADIPOQ; CRP; FGA; INS; LEP; AGER; AHSG; ANG; APOE; CD14; FTH1; IGFBP1; IL2RA; VCAM1; VEGF; and VWF; and evaluating the risk of developing a diabetic condition in the subject based on an output from a model, wherein the model is executed based on an input of the biomarker measurement data.

In some variations of the invention, the obtaining biomarker measurement data step comprises measuring the level of at least one of the biomarkers in at least one biological sample from said individual. Optionally, the method includes a step (prior to the step of obtaining biomarker measurement data) of obtaining at least one biological sample from the individual.

In some variations, obtaining biomarker measurement data comprises obtaining data representative of a measurement of the level of at least one biomarker from a preexisting record (that contains such information about the individual).

In another embodiment, the invention embraces a method comprising advising an individual of said individual's risk of developing Diabetes, wherein said risk is based on factors comprising a Diabetes risk score, and wherein said Diabetes risk score is calculated as described above. The advising can be performed by a health care practitioner, including, but not limited to, a physician, nurse, nurse practitioner, pharmacist, pharmacist's assistant, physician's assistant, laboratory technician, dietician, or nutritionist, or by a person working under the direction of a health care practitioner. The advising can be performed by a health maintenance organization, a hospital, a clinic, an insurance company, a health care company, or a national, federal, state, provincial, municipal, or local health care agency or health care system. The health care practitioner or person working under the direction of a health care practitioner obtains the medical history of the individual from the individual or from the medical records of the individual. The advising can be done automatically, for example, by a computer, microprocessor, or dedicated device for delivering such advice. The advising can be done by a health care practitioner or a person working under the direction of a health care practitioner via a computer, such as by electronic mail or text message.

In some embodiments of the invention, the Diabetes risk score is calculated automatically. The Diabetes risk score can be calculated by a computer, a calculator, a programmable calculator, or any other device capable of computing, and can be communicated to the individual by a health care practitioner, including, but not limited to, a physician, nurse, nurse practitioner, pharmacist, pharmacist's assistant, physician's assistant, laboratory technician, dietician, or nutritionist, or by a person working under the direction of a health care practitioner, or by an organization such as a health maintenance organization, a hospital, a clinic, an insurance company, a health care company, or a national, federal, state, provincial, municipal, or local health care agency or health care system, or automatically, for example, by a computer, microprocessor, or dedicated device for delivering such advice.

In some embodiments, the individual has not been diagnosed to have Diabetes. In some embodiments, the individual has not been diagnosed to have a Diabetes-related condition, such as metabolic syndrome, Syndrome X, or other Diabetes-related condition.

In another embodiment, the invention embraces a method of providing a Diabetes risk score, comprising calculating a Diabetes risk score as described above, and providing the Diabetes risk score to a person, organization, or database. In other embodiments, at least one biomarker input is obtained from a preexisting record, such as a record stored in a database, data structure, other electronic medical record, or paper, microfiche, or other non-electronic record.

In another embodiment, at least one biomarker input is obtained from one or more biological samples collected from the individual, such as from a blood sample, saliva sample, urine sample, cerebrospinal fluid sample, sample of another bodily fluid, or other biological sample including, but not limited to, those described herein.

In another embodiment, the invention comprises providing two or more Diabetes risk scores to a person, organization, or database, where the two or more Diabetes risk scores are derived from biomarker information representing the biomarker status of the individual at two or more points in time. In any of the foregoing embodiments, the entity performing the method can receive consideration for performing any one or more steps of the methods described.

In another embodiment, the invention embraces a method of ranking or grouping a population of individuals, comprising obtaining a Diabetes risk score for individuals comprised within said population, wherein said Diabetes risk score is calculated as described above; and ranking individuals within the population relative to the remaining individuals in the population or dividing the population into at least two groups, based on factors comprising said obtained Diabetes risk scores. The ranking or grouping of the population of individuals can be utilized for one or more of the following purposes: to determine an individual's eligibility for health insurance; an individual's premium for health insurance; to determine an individual's premium for membership in a health care plan, health maintenance organization, or preferred provider organization; to assign health care practitioners to an individual in a health care plan, health maintenance organization, or preferred provider organization; to recommend therapeutic intervention or lifestyle intervention to an individual or group of individuals; to manage the health care of an individual or group of individuals; to monitor the health of an individual or group of individuals; or to monitor the health care treatment, therapeutic intervention, or lifestyle intervention for an individual or group of individuals.

In another embodiment, the invention embraces one or more data structures or databases comprising values for (a) at least three biomarkers, where three of the biomarkers are selected from the RDMARKER sets listed in FIG. 6A; or (b) at least four biomarkers selected from RDMARKERS; or (c) at least three biomarkers, where two biomarkers are selected from ADIPOQ; CRP; GLUCOSE; GPT; HBA1C; HSPA1B; IGFBP1; IGFBP2; INS; LEP; and TRIG; and one biomarker is selected from the ALLDBRISKS, CPs, and TLRFs of Table 1, Table 2, and Table 3; or (d) at least three biomarkers, where at least one biomarker is selected from GLUCOSE and HBA1C; at least one biomarker is selected from ADIPOQ, CRP, GPT, HSPA1B, IGFBP1, IGFBP2, INS, LEP, and TRIG; and at least one biomarker is selected from the ALLDBRISKS, CPs, and TLRFs of Table 1, Table 2, and Table 3.

In another embodiment, the invention embraces a combination of biomarkers comprising at least three biomarkers selected from RDMARKERS, where the combination of biomarkers is selected from the combinations in FIG. 6A; a combination of biomarkers comprising at least four biomarkers selected from RDMARKERS; or a combination of biomarkers comprising at least four biomarkers selected from the combinations in FIG. 6B.

In another embodiment, the invention embraces a diagnostic test system comprising (1) means for obtaining test results comprising levels of multiple biomarkers in at least one biological sample; (2) means for collecting and tracking test results for one or more individual biological sample; (3) means for calculating an index value from inputs using a DRS Formula, wherein said inputs comprise measured levels of biomarkers, and further wherein said measured levels of biomarkers comprise the levels of (a) at least three biomarkers selected from RDMARKERS, or (b) at least three biomarkers, where two biomarkers are selected from ADIPOQ; CRP; GLUCOSE; GPT; HBA1C; HSPA1B; IGFBP1; IGFBP2; INS; LEP; and TRIG; and one biomarker is selected from the ALLDBRISKS, CPs, and TLRFs of Table 1, Table 2, and Table 3; or (c) at least three biomarkers, where at least one biomarker is selected from GLUCOSE and HBA1C; at least one biomarker is selected from ADIPOQ, CRP, GPT, HSPA1B, IGFBP1, IGFBP2, INS, LEP, and TRIG; and at least one biomarker is selected from the ALLDBRISKS, CPs, and TLRFs of Table 1, Table 2, and Table 3; and (4) means for reporting said index value. In one embodiment, said index value is a Diabetes risk score; the Diabetes risk score can be calculated according to any of the methods described herein. The means for collecting and tracking test results for one or more individuals can comprise a data structure or database. The means for calculating a Diabetes risk score can comprise a computer, microprocessor, programmable calculator, dedicated device, or any other device capable of calculating the Diabetes risk score. The means for reporting the Diabetes risk score can comprise a visible display, an audio output, a link to a data structure or database, or a printer.

A "diagnostic system is any system capable of carrying out the methods of the invention, including computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like.

Still another embodiment of the invention is a kit comprising reagents for measuring a group of biomarkers, wherein the group of biomarkers are defined as described in any of the preceding paragraphs, or panels containing figures, or other descriptions of preferred sets or panels of markers found herein. In some variations, such reagents are packaged together. In some variations, the kit further includes an analysis tool for evaluating risk of an individual developing a diabetic condition from measurements of the group of biomarkers from at least one biological sample from the individual.

Still another embodiment of the invention is a computer readable medium having computer executable instructions for evaluating risk for developing a diabetic condition, the computer readable medium comprising: a routine, stored on the computer readable medium and adapted to be executed by a processor, to store biomarker measurement data representing a set or panel of biomarkers; and a routine stored on the computer readable medium and adapted to be executed by a processor to analyze the biomarker measurement data to evaluate a risk for developing a diabetic condition. The preferred sets or panels of biomarkers are defined as described in any of the preceding paragraphs, or panels containing figures, or other descriptions of preferred sets or panels of markers found herein.

Another embodiment of the invention is a diagnostic test system. For example, the invention includes a diagnostic test system comprising: means for obtaining test results data representing levels of multiple biomarkers in at least one biological sample; means for collecting and tracking test results data for one or more individual biological samples; means for computing an index value from biomarker measurement data according to a DRS Formula, wherein said biomarker measurement data is representative of measured levels of biomarkers, and further wherein said measured levels of biomarkers comprise the levels of a set or panel of biomarkers as defined elsewhere herein; and means for reporting said index value. In some variations of the diagnostic test system, the index value is a Diabetes risk score. In some preferred variations, the Diabetes risk score is computed according to the methods described herein for computing such scores. In some variations, the means for collecting and tracking test results data representing for one or more individuals comprises a data structure or database. In some variations, the means for computing a Diabetes risk score comprises a computer or microprocessor. In some variations, the means for reporting the Diabetes risk score comprises a visible display, an audio output, a link to a data structure or database, or a printer.

A related embodiment of the invention is a medical diagnostic test system for evaluating risk for developing a diabetic condition, the system comprising: a data collection tool adapted to collect biomarker measurement data representative of measurements of biomarkers in at least one biological sample from an individual; and an analysis tool comprising a statistical analysis engine adapted to generate a representation of a correlation between a risk for developing a diabetic condition and measurements of the biomarkers, wherein the representation of the correlation is adapted to be executed to generate a result; and an index computation tool adapted to analyze the result to determine the individual's risk for developing a diabetic condition and represent the result as an index value; wherein said biomarkers are defined as a set or panel as described elsewhere herein. In some variations, the analysis tool comprises a first analysis tool comprising a first statistical analysis engine, the system further comprising a second analysis tool comprising a second statistical analysis engine adapted to select the representation of the correlation between the risk for developing a diabetic condition and measurements of the biomarkers from among a plurality of representations capable of representing the correlation. In some variations, the system further comprising a reporting tool adapted to generate a report comprising the index value.

Still another embodiment of the invention is a method developing a model for evaluation of risk for developing a diabetic condition, the method comprising: obtaining biomarker measurement data, wherein the biomarker measurement data is representative of measurements of biomarkers from a population and includes endpoints of the population; inputting the biomarker measurement data of at least a subset of the population into a model; training the model for endpoints using the inputted biomarker measurement data to derive a representation of a correlation between a risk of developing a diabetic condition and measurements of biomarkers in at least one biological sample from an individual; wherein said biomarkers for which measurement data is obtained comprise a set or panel of markers of the invention as defined elsewhere herein.

Other embodiments of the invention are directed to therapeutic or prophylactic treatment of a subject indentified as having a condition, or at risk for a condition, according to procedures described herein. For example, the invention includes a method of prophylaxis for Diabetes comprising: obtaining risk score data representing a Diabetes risk score for an individual, wherein the Diabetes risk score is computed according to a method or improvement of the invention; and generating prescription treatment data representing a prescription for a treatment regimen to delay or prevent the onset of Diabetes to an individual identified by the Diabetes risk score as being at elevated risk for Diabetes.

A related embodiment of the invention is a method of prophylaxis for Diabetes comprising: evaluating risk, for at least one subject, of developing a diabetic condition according to the method or improvement of the invention; and treating a subject identified as being at elevated risk for a diabetic condition with a treatment regimen to delay or prevent the onset of Diabetes. A variety of suitable treatment regimens are described below in greater detail.

A further embodiment of the invention is a method of evaluating the current status of a diabetic condition in an individual comprising obtaining biomarker measurement data and evaluating the current status of a diabetic condition in the individual based on an output from a model, wherein the biomarkers are any biomarker of the invention.

Another embodiment of the invention is a method of evaluating risk for developing a diabetic condition in an individual with a known glucose class, the method comprising obtaining biomarker measurement data and evaluating risk for developing a diabetic condition based on an output from a model, wherein the biomarkers are any biomarker of the invention.

Still another aspect of the invention is a method of ranking or grouping a population of individuals, comprising: obtaining Diabetes risk score data representing a Diabetes risk score for individuals comprised within said population, wherein said Diabetes risk score is calculated according to a method or improvement described herein; and ranking individuals within the population relative to the remaining individuals in the population or dividing the population into at least two groups, based on factors comprising said obtained Diabetes risk score data. In some variations, such a method further comprises using ranking data representing the ranking or grouping of the population of individuals for one or more of the following purposes: to determine an individual's eligibility for health insurance; to determine an individual's premium for health insurance; to determine an individual's premium for membership in a health care plan, health maintenance organization, or preferred provider organization; to assign health care practitioners to an individual in a health care plan, health maintenance organization, or preferred provider organization. Optionally, the method further comprises using ranking data representing the ranking or grouping of the population of individuals for one or more purposes selected from the group consisting of: to recommend therapeutic intervention or lifestyle intervention to an individual or group of individuals; to manage the health care of an individual or group of individuals; to monitor the health of an individual or group of individuals; or to monitor the health care treatment, therapeutic intervention, or lifestyle intervention for an individual or group of individuals.

The foregoing summary is not intended to define every aspect of the invention, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations specifically mentioned above. With respect to aspects of the invention described as a genus, all individual species are individually considered separate aspects of the invention. With respect to aspects described as a range, all sub-ranges and individual values are specifically contemplated.

Although the applicant(s) invented the full scope of the claims appended hereto, the claims appended hereto are not intended to encompass within their scope the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 1 depicts the combinations of panels falling within the fitted AUC (AUCf) level indicated in the column indicated by "Cutoff," as measured and calculated from the base population of Example 2. Eighty-four markers are analyzed (there are 84 possible panels of 1 marker, 3,486 possible panels of two markers, and 95,284 possible panels of 3 markers). The columns labeled "C" indicate the number of marker panels that met the AUC cutoff; the columns labeled "P" indicate the percentage of all marker panels of that given size. The 84 markers include the 75 parameters listed in FIG. 2, plus markers for Activity, Glucose Tolerance, Diet, Sex, two markers for Family History (differing in degree), Alcohol, Smoking Intervention, and Diet Intervention as measured in base population of Example 2.

FIG. 2 depicts particularly useful 3-panel combinations from an evaluation of the 75 parameters listed as measured and calculated from the base population of Example 2.

FIG. 5 is a table summarizing the univariate logistic regression results for the biomarkers listed in FIG. 8, as measured and calculated from the base population of Example 2. This includes the measured values and variances of certain selected studied within the examples given, including their concentration or other measurement units, mathematical normalization transformations (used in model formula and multi-biomarker index construction), transformed mean and standard deviation values, and back-transformed mean biomarker concentration or other value as measured for both the Total Cases (Converter to type 2 Diabetes, n=83) and Total Controls (Non-Converter to Type 2 Diabetes, n=236) described, as well as a comparison of the individual predictability with a statistical p-value given, using a two-tailed t-test for the null hypothesis (the probability that the odds ratio is 1).

FIG. 6 (A-I) contains tables summarizing enumeration of fitted logistic regression models for various three-panel through eleven-panel ALLDBRISK combinations possible from a starting set of the 11 selected ALLDBRISK (Tier 1-2), as measured and calculated from the base population of Example 2.

FIG. 6A depicts 7 particularly useful combinations of panels of three biomarkers; each panel can be used alone, or with additional biomarkers in combination to the three markers listed.

FIG. 6B depicts 25 particularly useful combinations of panels of four biomarkers; each panel can be used alone, or with additional biomarkers in combination to the four markers listed.

FIG. 6C depicts 65 particularly useful combinations of panels of five biomarkers; each panel can be used alone, or with additional biomarkers in combination to the five markers listed.

FIG. 6D depicts 134 particularly useful combinations of panels of six biomarkers; each panel can be used alone, or with additional biomarkers in combination to the six markers listed.

FIG. 6E depicts 147 particularly useful combinations of panels of seven biomarkers; each panel can be used alone, or with additional biomarkers in combination to the seven markers listed.

FIG. 6F depicts 100 particularly useful combinations of panels of eight biomarkers; each panel can be used alone, or with additional biomarkers in combination to the eight markers listed.

FIG. 6G depicts 44 particularly useful combinations of panels of nine biomarkers; each panel can be used alone, or with additional biomarkers in combination to the nine markers listed.

FIG. 6H depicts 11 particularly useful combinations of panels of ten biomarkers; each panel can be used alone, or with additional biomarkers in combination to the ten markers listed.

FIG. 6I depicts a particularly useful combination of a panel of eleven biomarkers; the panel can be used alone, or with additional biomarkers in combination to the eleven markers listed.

FIG. 7 depicts is a table summarizing the complete enumeration of fitted logistic regression models for all three-panel, four-panel, five-panel, six-panel, and seven-panel ALLDBRISK combinations possible from a starting set of 26 selected ALLDBRISK (Tier 1-3), as measured and calculated from the base population of Example 2.

FIG. 8 is a table containing key ALLDBRISK markers, including clinical parameters, traditional laboratory risk factors, and together with Tier 1, Tier 2 and Tier 3 ALLDBRISK biomarkers, that are used in the predictive models according to the present invention, as measured and calculated from the base population of Example 2. These are identified based on the commonly used gene symbol as described herein.

FIG. 9 is a table depicting categories of physiological functions, giving groups of exemplar ALLDBRISK markers for each function.

FIG. 10 depicts useful univariate biomarkers. is a table summarizing the nine significant ALLDBRISK marker measured values and variances of certain biomarkers studied, including their concentration or other measurement units, mathematical normalization transformations (used in model formula and multi-biomarker index construction), transformed mean and standard deviation values, and back-transformed mean biomarker concentration or other value as measured for both the Total Cases (Converter to type 2 Diabetes Events, n=83) and Total Controls (Non-Converter to type 2 Diabetes, n=236) of the study, as well as a comparison of the individual predictability with a statistical p-value given, using a two-tailed t-test for the null hypothesis (the probability that the odds ratio is 1), as measured and calculated from the base population of Example 2.

FIG. 11A is a list of 18 significant interaction variables produced from pairs of ALLDBRISK makers among all possible two marker combinations that showed significant predictability using a two-tailed test for the null hypothesis (the probability that the odds ratio is 1) after a Dunn-Sidak multiple testing correction, as measured and calculated from the base population of Example 2. FIG. 11B lists the 16 unique markers that were a component of the significant interaction variables, as measured and calculated from the base population of Example 2.

FIG. 12 is a list of 18 ALLDBRISK identified through various heuristic models, as measured and calculated from the base population of Example 2.

FIG. 14 shows the correlation performance to OGTT for three DRS scores, trained to predict Diabetes as calculated in the base population of Example 2.

FIG. 15 is a table containing key biomarkers, including clinical parameters, traditional laboratory risk factors, and together with core and additional biomarkers, that are used in the predictive models according to the present invention.

FIG. 18 is a table showing the results of univariate analysis of parameter variances, biomarker transformations, and biomarker mean back-transformed concentration values as measured for both the Case (Converter to Diabetes) and Control (Non-Converter to Diabetes) arm of the Base Population of Example 1.

FIG. 21 is a table summarizing the characteristics considered in various predictive models and model types of the present invention, using various model parameters, as measured in the Base Population of Example 1.

FIG. 25 are tables showing univariate ANOVA analysis of parameter variances including biomarker transformation and biomarker mean back-transformed concentration values across non-converters, converters, and diabetics arms, as measured and calculated at baseline in the Total Population of Example 2.

FIGS. 26A-26I are tables summarizing the cross-correlation of clinical parameters and biomarkers of the present invention, as measured in the Total Population of Example 2.

FIG. 29 is a table showing the representation of all parameters tested in Example 1 and Example 2 and according to the ALLDBRISK biomarker categories used in the invention.

FIGS. 30A-30D are tables showing biomarker selection under various scenarios of classification model types and Base and Total Populations of Example 1 and Example 2, respectively.

FIG. 31 are tables showing the complete enumeration of fitted LDA models for all potential univariate, bivariate, and trivariate combinations as measured and calculated in for both Total and Base Populations in Example 1 and Example 2, and encompassing all 53 and 49 biomarkers recorded, respectively, for each study as potential model parameters.

FIG. 36 depicts the combinations of panels falling within the fitted AUCf level indicated in the column indicated by "Bins," as measured and calculated from the base population of Example 8. Sixty-five markers are analyzed (there are 65 possible panels of 1 marker, 2,080 possible panels of two markers, and 43,680 possible panels of 3 markers). The columns labeled "C" indicate the number of marker panels that met the AUC cutoff; the columns labeled "P" indicate the percentage of all marker panels of that given size. The 65 markers include all blood-borne biomarkers measured on stored samples or captured in the clinical annotations (i.e. measured at baseline).

FIG. 37 depicts selected particularly useful combinations of panels of three biomarkers; each panel can be used alone, or with additional biomarkers in combination to the three markers listed. These panels represent enumeration of fitted logistic regression models from a starting set of 65 selected ALLDBRISK, as measured and calculated from a larger base population of Example 8 and meet a predetermined cut off level (0.75 AUC or better).

FIG. 38 depicts selected particularly useful combinations of panels of four biomarkers; each panel can be used alone, or with additional biomarkers in combination to the four markers listed. These panels represent enumeration of fitted logistic regression models from a starting set of 26 selected ALLDBRISK, as measured and calculated from a larger base population of Example 8 and meet a predetermined cut off level (0.75 AUC or better).

FIG. 39 depicts selected particularly useful combinations of panels of five biomarkers; each panel can be used alone, or with additional biomarkers in combination to the five markers listed. These panels represent enumeration of fitted logistic regression models from a starting set of 26 selected ALLDBRISK, as measured and calculated from a larger base population of Example 8 and meet a predetermined cut off level (0.75 AUC or better).

FIG. 40 depicts selected particularly useful combinations of panels of six biomarkers; each panel can be used alone, or with additional biomarkers in combination to the six markers listed. These panels represent enumeration of fitted logistic regression models from a starting set of 26 selected ALLDBRISK, as measured and calculated from a larger base population of Example 8 and meet a predetermined cut off level (0.75 AUC or better).

FIG. 41 depicts selected particularly useful combinations of panels of seven biomarkers; each panel can be used alone, or with additional biomarkers in combination to the seven markers listed. These panels represent enumeration of fitted logistic regression models from a starting set of 26 selected ALLDBRISK, as measured and calculated from a larger base population of Example 8 and meet a predetermined cut off level (0.75 AUC or better).

FIG. 42 depicts selected particularly useful combinations of panels of eight biomarkers; each panel can be used alone, or with additional biomarkers in combination to the eight markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 43 depicts selected particularly useful combinations of panels of nine biomarkers; each panel can be used alone, or with additional biomarkers in combination to the nine markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 44 depicts selected particularly useful combinations of panels of ten biomarkers; each panel can be used alone, or with additional biomarkers in combination to the ten markers listed. These panels represent enumeration of fitted logistic regression models from a starting set of 185 selected ALLDBRISK, as measured and calculated from a larger base population of Example 8 and meet a predetermined cut off level (0.75 AUC or better).

FIG. 45 depicts selected particularly useful combinations of panels of eleven biomarkers; each panel can be used alone, or with additional biomarkers in combination to the eleven markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 46 depicts selected particularly useful combinations of panels of twelve biomarkers; each panel can be used alone, or with additional biomarkers in combination to the twelve markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 47 depicts selected particularly useful combinations of panels of thirteen biomarkers; each panel can be used alone, or with additional biomarkers in combination to the thirteen markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 48 depicts selected particularly useful combinations of panels of fourteen biomarkers; each panel can be used alone, or with additional biomarkers in combination to the fourteen markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 49 depicts selected particularly useful combinations of panels of fifteen biomarkers; each panel can be used alone, or with additional biomarkers in combination to the fifteen markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 50 depicts selected particularly useful combinations of panels of sixteen biomarkers; each panel can be used alone, or with additional biomarkers in combination to the sixteen markers listed. These panels represent enumeration of fitted logistic regression models from a starting set of 18 selected ALLDBRISK, as measured and calculated from a larger base population of Example 8 and meet a predetermined cut off level (0.75 AUC or better).

FIG. 51 depicts selected particularly useful combinations of panels of seventeen biomarkers; each panel can be used alone, or with additional biomarkers in combination to the six markers listed. These panels represent enumeration of fitted logistic regression models from a starting set of 18 selected ALLDBRISK, as measured and calculated from a larger base population of Example 8 and meet a predetermined cut off level (0.75 AUC or better).

DETAILED DESCRIPTION OF THE INVENTION

Figure 3:
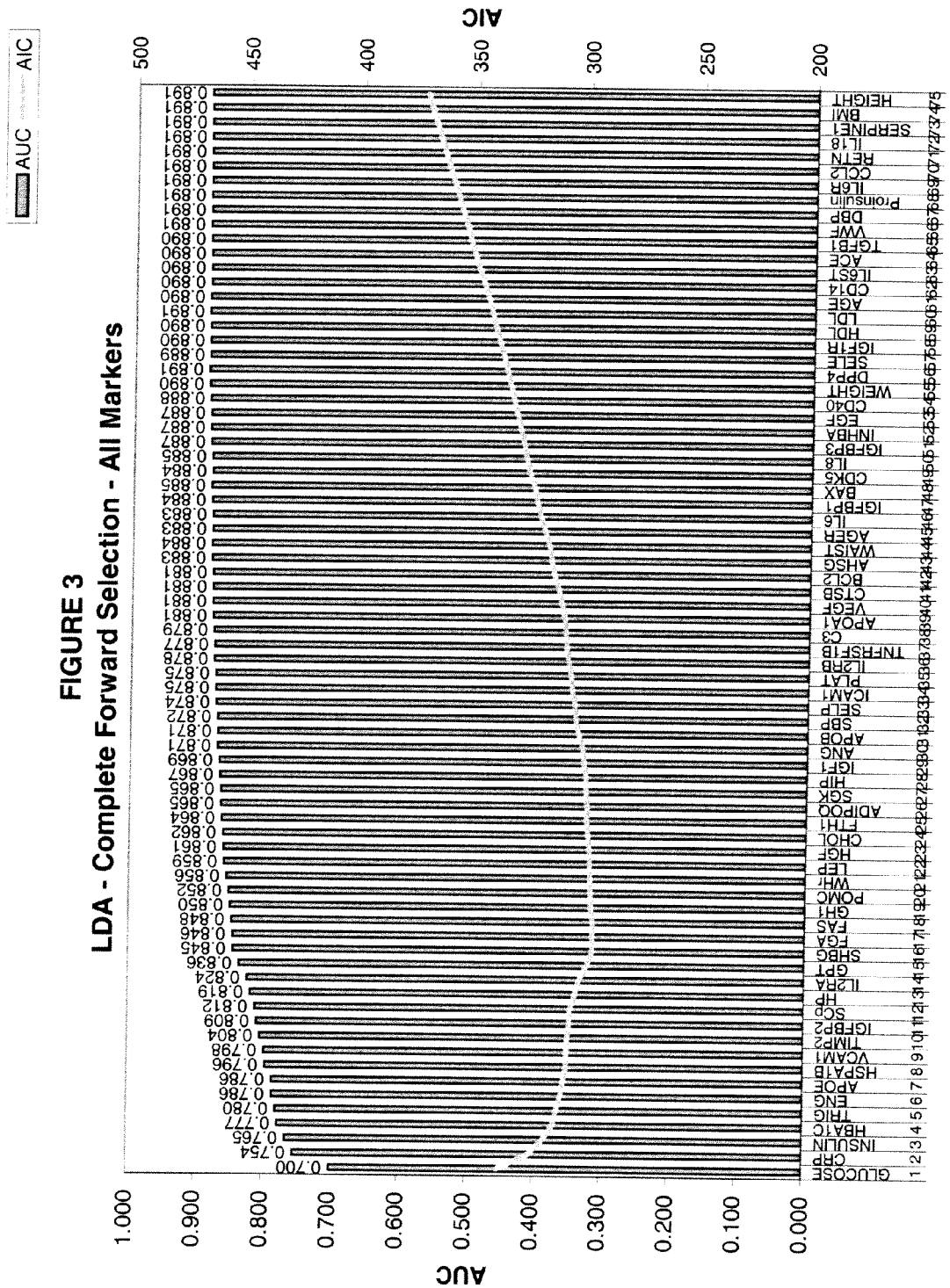
FIG. 3 depicts a full forward selection graph against the 75 parameters evaluated, depicting the ROC curve calculated AUCf statistics for multiple expanding "best forward selected" LDA models as measured and calculated from the base population of Example 2, starting from a single ALLDBRISK marker and then at each step adding one more incremental forward selected ALLDBRISK. This continues through 75 selected quantitative ALLDBRISK selected from a total set of markers. The AIC is superimposed on the graph as a black line.

The present invention relates to the identification of biomarkers associated with subjects having Diabetes, pre-Diabetes, or a pre-diabetic condition, or who are pre-disposed to developing Diabetes, pre-Diabetes, or a pre-diabetic condition. Accordingly, the present invention features methods for identifying subjects who are at risk of developing Diabetes, pre-Diabetes, or a pre-diabetic condition, including those subjects who are asymptomatic for Diabetes, pre-Diabetes, or a pre-diabetic condition by detection of the biomarkers disclosed herein. These biomarkers are also useful for monitoring subjects undergoing treatments and therapies for Diabetes, pre-Diabetes, or pre-diabetic conditions, and for selecting or modifying therapies and treatments that would be efficacious in subjects having Diabetes, pre-Diabetes, or a pre-diabetic condition, wherein selection and use of such treatments and therapies slow the progression of Diabetes, pre-Diabetes, or pre-diabetic conditions, or prevent their onset.

Definitions

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

"Biomarker" in the context of the present invention encompasses, without limitation, proteins, nucleic acids, and metabolites, together with their polymorphisms, mutations, variants, modifications, subunits, fragments, protein-ligand complexes, and degradation products, protein-ligand complexes, elements, related metabolites, and other analytes or sample-derived measures. Biomarkers can also include mutated proteins or mutated nucleic acids. Biomarkers also encompass non-blood borne factors, non-analyte physiological markers of health status, or other factors or markers not measured from samples (e.g., biological samples such as bodily fluids), such as "clinical parameters" defined herein, as well as "traditional laboratory risk factors", also defined herein. Biomarkers also include any calculated indices created mathematically or combinations of any one or more of the foregoing measurements, including temporal trends and differences. The term "analyte" as used herein can mean any substance to be measured and can encompass electrolytes and elements, such as calcium.

"RDMARKER" or "RDMARKERS" refers to a biomarker or biomarkers selected from the group consisting of ADIPOQ; CRP; GLUCOSE; GPT (or ALT); HBA1C; HSPA1B; IGFBP1; IGFBP2; INS; LEP; and TRIG.

Clinical parameters" or "CPs" encompasses all non-sample or non-analyte biomarkers of subject health status or other characteristics, such as, without limitation, age (AGE), race or ethnicity (RACE), gender (SEX), diastolic blood pressure (DBP) and systolic blood pressure (SBP), family history (FHX, including FH×1 for 1 parent and FH×2 for 2 parents), height (HT), weight (WT), waist (Waist) and hip (Hip) circumference, Waist-Hip ratio (WHr), body-mass index (BMI), past Gestational Diabetes Mellitus (GDM), and resting heart rate.

"Consideration" encompasses anything of value, including, but not limited to, monetary consideration, as well as non-monetary consideration including, but not limited to, related services or products, discounts on services or products, favored supplier relationships, more rapid reimbursements, etc.

"Diabetic condition" in the context of the present invention comprises type I and type II Diabetes mellitus, and pre-Diabetes (defined herein). It is also known in the art that Diabetic-related conditions include Diabetes and the pre-diabetic condition (defined herein).

"Diabetes mellitus" in the context of the present invention encompasses Type 1 Diabetes, both autoimmune and idiopathic and Type 2 Diabetes (referred to herein as "Diabetes" or "T2DM"). The World Health Organization defines the diagnostic value of fasting plasma glucose concentration to 7.0 mmol/l (126 mg/dl) and above for Diabetes mellitus (whole blood 6.1 mmol/l or 110 mg/dl), or 2-hour glucose level greater than or equal to 11.1 mmol/L (greater than or equal to 200 mg/dL). Other values suggestive of or indicating high risk for Diabetes mellitus include elevated arterial pressure greater than or equal to 140/90 mm Hg; elevated plasma triglycerides (greater than or equal to 1.7 mmol/L; 150 mg/dL) and/or low HDL-cholesterol (<0.9 mmol/L, 35 mg/dl for men; <1.0 mmol/L, 39 mg/dL women); central obesity (males: waist to hip ratio>0.90; females: waist to hip ratio>0.85) and/or body mass index exceeding 30 kg/m2; microalbuminuria, where the urinary albumin excretion rate greater than or equal to 20 µg/min or albumin:creatinine ratio greater than or equal to 30 mg/g).

"Gestational Diabetes" refers to glucose intolerance during pregnancy. This condition results in high blood sugar that starts or is first diagnosed during pregnancy.

"FN" is false negative, which for a disease state test means classifying a disease subject incorrectly as non-disease or normal.

"FP" is false positive, which for a disease state test means classifying a normal subject incorrectly as having disease.

The terms "formula," "algorithm," and "model" are used interchangeably for any mathematical equation, algorithmic, analytical or programmed process, or statistical technique that takes one or more continuous or categorical inputs (herein called "parameters") and calculates an output value, sometimes referred to as an "index" or "index value." Non-limiting examples of "formulas" include sums, ratios, and regression operators, such as coefficients or exponents, biomarker value transformations and normalizations (including, without limitation, those normalization schemes based on clinical parameters, such as gender, age, or ethnicity), rules and guidelines, statistical classification models, and neural networks trained on historical populations. Of particular use for the biomarkers are linear and non-linear equations and statistical classification analyses to determine the relationship between levels of biomarkers detected in a subject sample and the subject's risk of Diabetes. In panel and combination construction, of particular interest are structural and synactic statistical classification algorithms, and methods of risk index construction, utilizing pattern recognition features, including established techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), as well as other related decision tree classification techniques, Shruken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, among others. Many of these techniques are useful either combined with a ALLDBRISK selection technique, such as forward selection, backwards selection, or stepwise selection, complete enumeration of all potential panels of a given size, genetic algorithms, or they may themselves include biomarker selection methodologies in their own technique. These may be coupled with information criteria, such as Akaike's Information Criterion (AIC) or Bayes Information Criterion (BIC), in order to quantify the tradeoff between additional biomarkers and model improvement, and to aid in minimizing overfit. The resulting predictive models may be validated in other studies, or cross-validated in the study they were originally trained in, using such techniques as Leave-One-Out (LOO) and 10-Fold cross-validation (10-Fold CV).

A "DRS Formula" is a formula developed as described herein and used to calculate a Diabetes risk score from inputs comprising the results from biomarker testing as described herein. A DRS Formula is the preferred means for calculating a Diabetes risk score.

A "Health economic utility function" is a formula that is derived from a combination of the expected probability of a range of clinical outcomes in an idealized applicable patient population, both before and after the introduction of a diagnostic or therapeutic intervention into the standard of care. It encompasses estimates of the accuracy, effectiveness and performance characteristics of such intervention, and a cost and/or value measurement (a utility) associated with each outcome, which may be derived from actual health system costs of care (services, supplies, devices and drugs, etc.) and/or as an estimated acceptable value per quality adjusted life year (QALY) resulting in each outcome. The sum, across all predicted outcomes, of the product of the predicted population size for an outcome multiplied by the respective outcome's expected utility is the total health economic utility of a given standard of care. The difference between (i) the total health economic utility calculated for the standard of care with the intervention versus (ii) the total health economic utility for the standard of care without the intervention results in an overall measure of the health economic cost or value of the intervention. This may itself be divided amongst the entire patient group being analyzed (or solely amongst the intervention group) to arrive at a cost per unit intervention, and to guide such decisions as market positioning, pricing, and assumptions of health system acceptance. Such health economic utility functions are commonly used to compare the cost-effectiveness of the intervention, but may also be transformed to estimate the acceptable value per QALY the health care system is willing to pay, or the acceptable cost-effective clinical performance characteristics required of a new intervention.

For diagnostic (or prognostic) interventions of the invention, as each outcome (which in a disease classifying diagnostic test may be a TP, FP, TN, or FN) bears a different cost, a health economic utility function may preferentially favor sensitivity over specificity, or PPV over NPV based on the clinical situation and individual outcome costs and value, and thus provides another measure of health economic performance and value which may be different from more direct clinical or analytical performance measures. These different measurements and relative trade-offs generally will converge only in the case of a perfect test, with zero error rate (aka zero predicted subject outcome misclassifications or FP and FN), which all performance measures will favor over imperfection, but to differing degrees.

"Impaired glucose tolerance" (IGT) is a pre-diabetic condition defined as having a blood glucose level that is higher than normal, but not high enough to be classified as Diabetes Mellitus. A subject with IGT will have two-hour glucose levels of 140 to 199 mg/dL (7.8 to 11.0 mmol) on the 75-g oral glucose tolerance test. These glucose levels are above normal but below the level that is diagnostic for Diabetes. Subjects with impaired glucose tolerance or impaired fasting glucose have a significant risk of developing Diabetes and thus are an important target group for primary prevention.

"Insulin resistance" refers to a diabetic or pre-diabetic condition in which the cells of the body become resistant to the effects of insulin, that is, the normal response to a given amount of insulin is reduced. As a result, higher levels of insulin are needed in order for insulin to exert its effects.

The oral glucose tolerance test (OGTT) is principally used for diagnosis of Diabetes Mellitus or pre-diabetic conditions when blood glucose levels are equivocal, during pregnancy, or in epidemiological studies (Definition, Diagnosis and Classification of Diabetes Mellitus and its Complications, Part 1, World Health Organization, 1999). The OGTT should be administered in the morning after at least 3 days of unrestricted diet (greater than 150 g of carbohydrate daily) and usual physical activity. A reasonable (30-50 g) carbohydrate-containing meal should be consumed on the evening before the test. The test should be preceded by an overnight fast of 8-14 hours, during which water may be consumed. After collection of the fasting blood sample, the subject should drink 75 g of anhydrous glucose or 82.5 g of glucose monohydrate in 250-300 ml of water over the course of 5 minutes. For children, the test load should be 1.75 g of glucose per kg body weight up to a total of 75 g of glucose. Timing of the test is from the beginning of the drink. Blood samples must be collected 2 hours after the test load. As previously noted, a diagnosis of impaired glucose tolerance (IGT) has been noted as being only 50% sensitive, with a >10% false positive rate, for a 7.5 year conversion to Diabetes when used at the WHO cut-off points. This is a significant problem for the clinical utility of the test, as even relatively high risk ethnic groups have only a 10% rate of conversion to Diabetes over such a period unless otherwise enriched by other risk factors; in an unselected general population, the rate of conversion over such periods is typically estimated at 5-6%, or less than 1% per annum.

"Measuring" or "measurement" means assessing the presence, absence, quantity or amount (which can be an effective amount) of either a given substance within a clinical or subject-derived sample, including the derivation of qualitative or quantitative concentration levels of such substances, or otherwise evaluating the values or categorization of a subject's clinical parameters.

"Negative predictive value" or "NPV" is calculated by TN/(TN+FN) or the true negative fraction of all negative test results. It also is inherently impacted by the prevalence of the disease and pre-test probability of the population intended to be tested. See, e.g., O'Marcaigh A S, Jacobson R M, "Estimating The Predictive Value Of A Diagnostic Test, How To Prevent Misleading Or Confusing Results," Clin. Ped. 1993, 32(8): 485-491, which discusses specificity, sensitivity, and positive and negative predictive values of a test, e.g., a clinical diagnostic test. Often, for binary disease state classification approaches using a continuous diagnostic test measurement, the sensitivity and specificity is summarized by Receiver Operating Characteristics (ROC) curves according to Pepe et al, "Limitations of the Odds Ratio in Gauging the Performance of a Diagnostic, Prognostic, or Screening Marker," Am. J. Epidemiol 2004, 159 (9): 882-890, and summarized by the Area Under the Curve (AUC) or c-statistic, an indicator that allows representation of the sensitivity and specificity of a test, assay, or method over the entire range of test (or assay) cut points with just a single value. See also, e.g., Shultz, "Clinical Interpretation Of Laboratory Procedures," chapter 14 in Teitz, Fundamentals of Clinical Chemistry, Burtis and Ashwood (eds.), 4th edition 1996, W.B. Saunders Company, pages 192-199; and Zweig et al., "ROC Curve Analysis: An Example Showing The Relationships Among Serum Lipid And Apolipoprotein Concentrations In Identifying Subjects With Coronory Artery Disease," Clin. Chem., 1992, 38(8): 1425-1428. An alternative approach using likelihood functions, odds ratios, information theory, predictive values, calibration (including goodness-of-fit), and reclassification measurements is summarized according to Cook, "Use and Misuse of the Receiver Operating Characteristic Curve in Risk Prediction," Circulation 2007, 115: 928-935. Hazard ratios and absolute and relative risk ratios within subject cohorts defined by a test are a further measurement of clinical accuracy and utility. In this last, multiple methods are frequently used to defining abnormal or disease values, including reference limits, discrimination limits, and risk thresholds as per Vasan, "Biomarkers of Cardiovascular Disease Molecular Basis and Practical Considerations," Circulation 2006, 113: 2335-2362.

Analytical accuracy refers to the repeatability and predictability of the measurement process itself, and may be summarized in such measurements as coefficients of variation, and tests of concordance and calibration of the same samples or controls with different times, users, equipment and/or reagents. These and other considerations in evaluating new biomarkers are also summarized in Vasan, Circulation 2006, 113: 2335-2362.

"Normal glucose levels" is used interchangeably with the term "normoglycemic" and "normal" and refers to a fasting venous plasma glucose concentration of less than 6.1 mmol/L (110 mg/dL). Although this amount is arbitrary, such values have been observed in subjects with proven normal glucose tolerance, although some may have IGT as measured by oral glucose tolerance test (OGTT). Glucose levels above normoglycemic are considered a pre-diabetic condition.

"Performance" is a term that relates to the overall usefulness and quality of a diagnostic or prognostic test, including, among others, clinical and analytical accuracy, other analytical and process characteristics, such as use characteristics (e.g., stability, ease of use), health economic value, and relative costs of components of the test. Any of these factors may be the source of superior performance and thus usefulness of the test.

"Positive predictive value" or "PPV" is calculated by TP/(TP+FP) or the true positive fraction of all positive test results. It is inherently impacted by the prevalence of the disease and pre-test probability of the population intended to be tested.

"Pre-Diabetes" or "pre-Diabetic," in the context of the present invention indicates the physiological state, in an individual or in a population, and absent any therapeutic intervention (diet, exercise, pharmaceutical, or otherwise) of having a higher than normal expected rate of disease conversion to frank Type 2 Diabetes Mellitus. Pre-Diabetes can also refer to those subjects or individuals, or a population of subjects or individuals who will, or are predicted to convert to frank Type 2 Diabetes Mellitus within a given time period or time horizon at a higher rate than that of the general, unselected population. Such absolute predicted rate of conversion to frank Type 2 Diabetes Mellitus in pre-Diabetes populations may be as low as 1 percent or more per annum, but preferably 2 percent per annum or more. It may also be stated in terms of a relative risk from normal between quartiles of risk or as a likelihood ratio between differing biomarker and index scores, including those coming from the invention. Unless otherwise noted, and without limitation, when a categorical positive diagnosis of pre-Diabetes is stated here, it is defined experimentally with reference to the group of subjects with a predicted conversion rate to Type 2 Diabetes mellitus of two percent (2%) or greater per annum over the coming 5.0 years, or ten percent (10%) or greater in the entire period, of those testing at a given threshold value (the selected pre-Diabetes clinical cutoff). When a continuous measure of Diabetes conversion risk is produced, pre-Diabetes encompasses any expected annual rate of conversion above that seen in a normal reference or general unselected normal prevalence population. When a complete study is retrospectively discussed in the Examples, pre-Diabetes encompasses the baseline condition of all of the "Converters" or "Cases" arms, each of whom converted to Type 2 Diabetes Mellitus during the study.

In an unselected individual population, pre-Diabetes overlaps with, but is not necessarily a complete superset of, or contained subset within, all those with "pre-diabetic conditions;" as many who will convert to Diabetes in a given time horizon are now apparently healthy, and with no obvious pre-diabetic condition, and many have pre-diabetic conditions but will not convert in a given time horizon; such is the diagnostic gap and need to be fulfilled by the invention. Taken as a population, individuals with pre-Diabetes have a predictable risk of conversion to Diabetes (absent therapeutic intervention) compared to individuals without pre-Diabetes and otherwise risk matched.

"Pre-diabetic condition" refers to a metabolic state that is intermediate between normal glucose homeostasis and metabolism and states seen in frank Diabetes Mellitus. Pre-diabetic conditions include, without limitation, Metabolic Syndrome ("Syndrome X"), Impaired Glucose Tolerance (IGT), and Impaired Fasting Glycemia (IFG). IGT refers to post-prandial abnormalities of glucose regulation, while IFG refers to abnormalities that are measured in a fasting state. The World Health Organization defines values for IFG as a fasting plasma glucose concentration of 6.1 mmol/L (100 mg/dL) or greater (whole blood 5.6 mmol/L; 100 mg/dL), but less than 7.0 mmol/L (126 mg/dL) (whole blood 6.1 mmol/L; 110 mg/dL). Metabolic syndrome according to the National Cholesterol Education Program (NCEP) criteria are defined as having at least three of the following: blood pressure greater than or equal to 130/85 mm Hg; fasting plasma glucose greater than or equal to 6.1 mmol/L; waist circumference>102 cm (men) or >88 cm (women); triglycerides greater than or equal to 1.7 mmol/L; and HDL cholesterol<1.0 mmol/L (men) or 1.3 mmol/L (women). Many individuals with pre-diabetic conditions will not convert to T2DM.

"Risk" in the context of the present invention, relates to the probability that an event will occur over a specific time period, as in the conversion to frank Diabetes, and can can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1−p) where p is the probability of event and (1−p) is the probability of no event) to no-conversion. Alternative continuous measures which may be assessed in the context of the present invention include time to Diabetes conversion and therapeutic Diabetes conversion risk reduction ratios.

"Risk evaluation," or "evaluation of risk" in the context of the present invention encompasses making a prediction of the probability, odds, or likelihood that an event or disease state may occur, the rate of occurrence of the event or conversion from one disease state to another, i.e., from a normoglycemic condition to a pre-diabetic condition or pre-Diabetes, or from a pre-diabetic condition to pre-Diabetes or Diabetes. Risk evaluation can also comprise prediction of future glucose, HBA1c scores or other indices of Diabetes, either in absolute or relative terms in reference to a previously measured population. The methods of the present invention may be used to make continuous or categorical measurements of the risk of conversion to Type 2 Diabetes, thus diagnosing and defining the risk spectrum of a category of subjects defined as pre-diabetic. In the categorical scenario, the invention can be used to discriminate between normal and pre-Diabetes subject cohorts. In other embodiments, the present invention may be used so as to discriminate pre-Diabetes from Diabetes, or Diabetes from normal. Such differing use may require different biomarker combinations in individual panels, mathematical algorithm, and/or cut-off points, but be subject to the same aforementioned measurements of accuracy for the intended use.

A "sample" in the context of the present invention is a biological sample isolated from a subject and can include, by way of example and not limitation, whole blood, serum, plasma, blood cells, endothelial cells, tissue biopsies, lymphatic fluid, ascites fluid, interstitital fluid (also known as "extracellular fluid" and encompasses the fluid found in spaces between cells, including, inter alia, gingival crevicular fluid), bone marrow, cerebrospinal fluid (CSF), saliva, mucous, sputum, sweat, urine, or any other secretion, excretion, or other bodily fluids. "Blood sample" refers to whole blood or any fraction thereof, including blood cells, serum and plasma; serum is a preferred blood sample.

"Sensitivity" is calculated by TP/(TP+FN) or the true positive fraction of disease subjects.

"Specificity" is calculated by TN/(TN+FP) or the true negative fraction of non-disease or normal subjects.

By "statistically significant", it is meant that the alteration is greater than what might be expected to happen by chance alone (which could be a "false positive"). Statistical significance can be determined by any method known in the art. Commonly used measures of significance include the p-value, which presents the probability of obtaining a result at least as extreme as a given data point, assuming the data point was the result of chance alone. A result is often considered highly significant at a p-value of 0.05 or less.

A "subject" in the context of the present invention is preferably a mammal. The mammal can be a human, non-human primate, mouse, rat, dog, cat, horse, or cow, but are not limited to these examples. Mammals other than humans can be advantageously used as subjects that represent animal models of Diabetes Mellitus, pre-Diabetes, or pre-diabetic conditions. A subject can be male or female. A subject can be one who has been previously diagnosed or identified as having Diabetes, pre-Diabetes, or a pre-diabetic condition, and optionally has already undergone, or is undergoing, a therapeutic intervention for the Diabetes, pre-Diabetes, or pre-diabetic condition. Alternatively, a subject can also be one who has not been previously diagnosed as having Diabetes, pre-Diabetes, or a pre-diabetic condition. For example, a subject can be one who exhibits one or more risk factors for Diabetes, pre-Diabetes, or a pre-diabetic condition, or a subject who does not exhibit Diabetes risk factors, or a subject who is asymptomatic for Diabetes, pre-Diabetes, or pre-diabetic conditions. A subject can also be one who is suffering from or at risk of developing Diabetes, pre-Diabetes, or a pre-diabetic condition.

"TN" is true negative, which for a disease state test means classifying a non-disease or normal subject correctly.

"TP" is true positive, which for a disease state test means correctly classifying a disease subject.

"Traditional laboratory risk factors" or "TLRFs" correspond to biomarkers isolated or derived from subject samples and which are currently evaluated in the clinical laboratory and used in traditional global risk assessment algorithms, such as Stern, Framingham, Finland Diabetes Risk Score, ARIC Diabetes, and Archimedes. Traditional laboratory risk factors commonly tested from subject blood samples include, but are not limited to, total cholesterol (CHOL), LDL (LDL/LDLC), HDL (HDL/HDLC), VLDL (VLDLC), triglycerides (TRIG), glucose (including, without limitation, the fasting plasma glucose (Glucose) and the oral glucose tolerance test (OGTT)) and HBA1c (HBA1C) levels.

The RDMARKER set of biomarkers of the invention are selected from adiponectin (ADIPOQ), C-reactive protein (CRP); glucose (GLUCOSE); glutamic-pyruvate transaminase (GPT or ALT); glycosylated hemoglobin (HBA1C); heat shock 70 kDa protein 1B (HSPA1B); insulin-like growth factor binding protein 1 (IGFBP1); insulin-like growth factor binding protein 2 (IGFBP2); insulin (INS, INSULIN-M, proinsulin and SCp), leptin (LEP) and triglycerides (TRIG). The biomarker GPT may be analyzed by measuring the GPT protein level or measuring the enzymatic activity as an alanine aminotransferase (ALT). The GPT enzymatic activity (ALT activity) may be measured using conventional methods known in the art. These markers are individually known; see US 2007/0218519 and US 2007/0259377, which are incorporated by reference herein in their entirety, for descriptions of the individual markers.

Diagnostic and Prognostic Indications of the Invention

The invention provides improved diagnosis and prognosis of Diabetes, pre-Diabetes, or a pre-diabetic condition. The risk of developing Diabetes, pre-Diabetes, or a pre-diabetic condition can be detected with a pre-determined level of predictability by measuring various biomarkers such as RDMARKERs, ALLDBRISKs, CPs, and TLRFs (including, but not limited to, proteins, nucleic acids, polymorphisms, metabolites, and other analytes in a test sample from a subject), and comparing the measured values to reference or index values, often utilizing mathematical algorithms or formula in order to combine information from results of multiple individual biomarkers and from non-analyte clinical parameters into a single measurement or index. Subjects identified as having an increased risk of Diabetes, pre-Diabetes, or a pre-diabetic condition can optionally be selected to receive treatment regimens, such as administration of prophylactic or therapeutic compounds such as "Diabetes-modulating agents" as defined herein, or implementation of exercise regimens or dietary supplements to prevent or delay the onset of Diabetes, pre-Diabetes, or a pre-diabetic condition.

The amount of the biomarker can be measured in a test sample and compared to the "normal control level", utilizing techniques such as reference limits, discrimination limits, or risk defining thresholds to define cutoff points and abnormal values for Diabetes, pre-Diabetes, and pre-diabetic conditions, all as described in Vasan, 2006. The normal control level means the level of one or more biomarkers or combined biomarker indices typically found in a subject not suffering from Diabetes, pre-Diabetes, or a pre-diabetic condition. Such normal control level and cutoff points may vary based on whether a biomarker is used alone or in a formula combining with other biomarkers into an index. Alternatively, the normal control level can be a database of biomarker patterns from previously tested subjects who did not convert to Diabetes over a clinically relevant time horizon.

The present invention may be used to make continuous or categorical measurements of the risk of conversion to Type 2 Diabetes, thus diagnosing and defining the risk spectrum of a category of subjects defined as pre-diabetic. In the categorical scenario, the methods of the present invention can be used to discriminate between normal and pre-Diabetes subject cohorts. In other embodiments, the present invention may be used so as to discriminate pre-Diabetes from Diabetes, or Diabetes from normal. Such differing use may require different biomarker combinations in individual panels, mathematical algorithms, and/or cut-off points, but subject to the same aforementioned measurements of accuracy for the intended use.

Identifying the pre-diabetic subject enables the selection and initiation of various therapeutic interventions or treatment regimens in order to delay, reduce or prevent that subject's conversion to a frank Diabetes disease state. Levels of an effective amount of biomarkers also allows for the course of treatment of Diabetes, pre-Diabetes or a pre-diabetic condition to be monitored. In this method, a biological sample can be provided from a subject undergoing treatment regimens or therapeutic interventions, e.g., drug treatments, for Diabetes. Such treatment regimens or therapeutic interventions can include, but are not limited to, exercise regimens, dietary modification, dietary supplementation, bariatric surgical intervention, administration of pharmaceuticals, and treatment with therapeutics or prophylactics used in subjects diagnosed or identified with Diabetes, pre-Diabetes, or a pre-diabetic condition. If desired, biological samples are obtained from the subject at various time points before, during, or after treatment.

The present invention can also be used to screen patient or subject populations in any number of settings. For example, a health maintenance organization, public health entity or school health program can screen a group of subjects to identify those requiring interventions, as described above, or for the collection of epidemiological data. Insurance companies (e.g., health, life, or disability) may screen applicants in the process of determining coverage or pricing, or existing clients for possible intervention. Data collected in such population screens, particularly when tied to any clinical progression to conditions like Diabetes, pre-Diabetes, or a pre-diabetic condition, will be of value in the operations of, for example, health maintenance organizations, public health programs and insurance companies. Such data arrays or collections can be stored in machine-readable media and used in any number of health-related data management systems to provide improved healthcare services, cost effective healthcare, improved insurance operation, etc. See, for example, U.S. patent application No.; U.S. Patent Application No. 2002/0038227; U.S. Patent Application No. US 2004/0122296; U.S. Patent Application No. US 2004/0122297; and U.S. Pat. No. 5,018,067. Such systems can access the data directly from internal data storage or remotely from one or more data storage sites as further detailed herein. Thus, in a health-related data management system, wherein risk of developing a diabetic condition for a subject or a population comprises analyzing Diabetes risk factors, the present invention provides an improvement comprising use of a data array encompassing the biomarker measurements as defined herein and/or the resulting evaluation of risk from those biomarker measurements.

A machine-readable storage medium can comprise a data storage material encoded with machine readable data or data arrays which, when using a machine programmed with instructions for using said data, is capable of use for a variety of purposes, such as, without limitation, subject information relating to Diabetes risk factors over time or in response to Diabetes-modulating drug therapies, drug discovery, and the like. Measurements of effective amounts of the biomarkers of the invention and/or the resulting evaluation of risk from those biomarkers can implemented in computer programs executing on programmable computers, comprising, inter alia, a processor, a data storage system (including volatile and non-volatile memory and/or storage elements), at least one input device, and at least one output device. Program code can be applied to input data to perform the functions described above and generate output information. The output information can be applied to one or more output devices, according to methods known in the art. The computer may be, for example, a personal computer, microcomputer, or workstation of conventional design.

Each program can be implemented in a high level procedural or object oriented programming language to communicate with a computer system. However, the programs can be implemented in assembly or machine language, if desired. The language can be a compiled or interpreted language. Each such computer program can be stored on a storage media or device (e.g., ROM or magnetic diskette or others as defined elsewhere in this disclosure) readable by a general or special purpose programmable computer, for configuring and operating the computer when the storage media or device is read by the computer to perform the procedures described herein. The health-related data management system of the invention may also be considered to be implemented as a computer-readable storage medium, configured with a computer program, where the storage medium so configured causes a computer to operate in a specific and predefined manner to perform various functions described herein. Levels of an effective amount of biomarkers can then be determined and compared to a reference value, e.g. a control subject or population whose diabetic state is known or an index value or baseline value. The reference sample or index value or baseline value may be taken or derived from one or more subjects who have been exposed to the treatment, or may be taken or derived from one or more subjects who are at low risk of developing Diabetes, pre-Diabetes, or a pre-diabetic condition, or may be taken or derived from subjects who have shown improvements in Diabetes risk factors (such as clinical parameters or traditional laboratory risk factors as defined herein) as a result of exposure to treatment. Alternatively, the reference sample or index value or baseline value may be taken or derived from one or more subjects who have not been exposed to the treatment. For example, samples may be collected from subjects who have received initial treatment for Diabetes, pre-Diabetes, or a pre-diabetic condition and subsequent treatment for Diabetes, pre-Diabetes, or a pre-diabetic condition to monitor the progress of the treatment. A reference value can also comprise a value derived from risk prediction algorithms or computed indices from population studies such as those disclosed herein.

Figure 33:
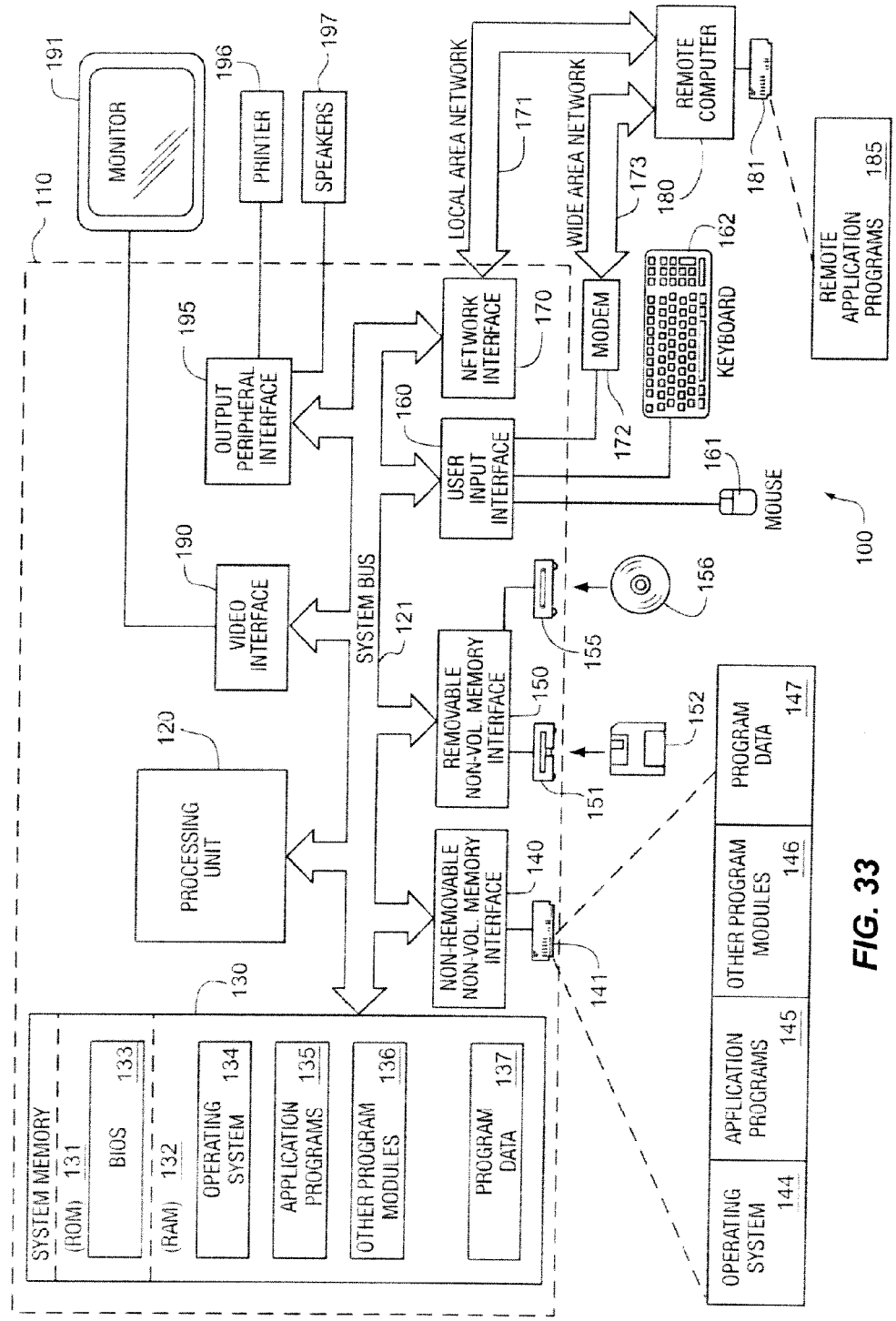
FIG. 33 illustrates an example of a suitable computing system environment 100 on which a system for the steps of the claimed method and apparatus may be implemented.

FIG. 33 illustrates an example of a suitable computing system environment 100 on which a system for the steps of the claimed method and apparatus may be implemented. The computing system environment 100 is only one example of a suitable computing environment and is not intended to suggest any limitation as to the scope of use or functionality of the method of apparatus of the claims. Neither should the computing environment 100 be interpreted as having any dependency or requirement relating to any one or combination of components illustrated in the exemplary operating environment 100.

The steps of the claimed method and system are operational with numerous other general purpose or special purpose computing system environments or configurations. Examples of well known computing systems, environments, and/or configurations that may be suitable for use with the methods or system of the claims include, but are not limited to, personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, and the like, including those systems, environments, configurations and means described elsewhere within this disclosure.

The steps of the claimed method and system may be described in the general context of computer-executable instructions, such as program modules, being executed by a computer. Generally, program modules include routines, programs, objects, components, data structures, etc. that perform particular tasks or implement particular abstract data types. The methods and apparatus may also be practiced in distributed computing environments where tasks are performed by remote processing devices that are linked through a communications network. In both integrated and distributed computing environments, program modules may be located in both local and remote computer storage media including memory storage devices.

With reference to FIG. 33, an exemplary system for implementing the steps of the claimed method and system includes a general purpose computing device in the form of a computer 110. Components of computer 110 may include, but are not limited to, a processing unit 120, a system memory 130, and a system bus 121 that couples various system components including the system memory to the processing unit 120. The system bus 121 may be any of several types of bus structures including a memory bus or memory controller, a peripheral bus, and a local bus using any of a variety of bus architectures. By way of example, and not limitation, such architectures include Industry Standard Architecture (USA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

Computer 110 typically includes a variety of computer readable media. Computer readable media can be any available media that can be accessed by computer 110 and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 110. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The system memory 130 includes computer storage media in the form of volatile and/or nonvolatile memory such as read only memory (ROM) 131 and random access memory (RAM) 132. A basic input/output system 133 (BIOS), containing the basic routines that help to transfer information between elements within computer 110, such as during start-up, is typically stored in ROM 131. RAM 132 typically contains data and/or program modules that are immediately accessible to and/or presently being operated on by processing unit 120. By way of example, and not limitation, FIG. 33 illustrates operating system 134, application programs 135, other program modules 136, and program data 137.

The computer 110 may also include other removable/non-removable, volatile/nonvolatile computer storage media. By way of example only, FIG. 33 illustrates a hard disk drive 140 that reads from or writes to non-removable, nonvolatile magnetic media, a magnetic disk drive 151 that reads from or writes to a removable, nonvolatile magnetic disk 152, and an optical disk drive 155 that reads from or writes to a removable, nonvolatile optical disk 156 such as a CD ROM or other optical media. Other removable/non-removable, volatile/nonvolatile computer storage media that can be used in the exemplary operating environment include, but are not limited to, magnetic tape cassettes, flash memory cards, digital versatile disks, digital video tape, solid state RAM, solid state ROM, and the like. The hard disk drive 141 is typically connected to the system bus 121 through a non-removable memory interface such as interface 140, and magnetic disk drive 151 and optical disk drive 155 are typically connected to the system bus 121 by a removable memory interface, such as interface 150.

The drives and their associated computer storage media discussed above and illustrated in FIG. 33, provide storage of computer readable instructions, data structures, program modules and other data for the computer 110. In FIG. 33, for example, hard disk drive 141 is illustrated as storing operating system 144, application programs 145, other program modules 146, and program data 147. Note that these components can either be the same as or different from operating system 134, application programs 135, other program modules 136, and program data 137. Operating system 144, application programs 145, other program modules 146, and program data 147 are given different numbers here to illustrate that, at a minimum, they are different copies. A user may enter commands and information into the computer 20 through input devices such as a keyboard 162 and pointing device 161, commonly referred to as a mouse, trackball or touch pad. Other input devices (not shown) may include a microphone, joystick, game pad, satellite dish, scanner, or the like. These and other input devices are often connected to the processing unit 120 through a user input interface 160 that is coupled to the system bus, but may be connected by other interface and bus structures, such as a parallel port, game port or a universal serial bus (USB). A monitor 191 or other type of display device is also connected to the system bus 121 via an interface, such as a video interface 190. In addition to the monitor, computers may also include other peripheral output devices such as speakers 197 and printer 196, which may be connected through an output peripheral interface 190.

The biomarkers of the present invention can thus be used to generate a "reference biomarker profile" of those subjects who do not have Diabetes, pre-Diabetes, or a pre-diabetic condition such as impaired glucose tolerance, and would not be expected to develop Diabetes, pre-Diabetes, or a pre-diabetic condition. The biomarkers disclosed herein can also be used to generate a "subject biomarker profile" taken from subjects who have Diabetes, pre-Diabetes, or a pre-diabetic condition like impaired glucose tolerance. The subject biomarker profiles can be compared to a reference biomarker profile to diagnose or identify subjects at risk for developing Diabetes, pre-Diabetes or a pre-diabetic condition, to monitor the progression of disease, as well as the rate of progression of disease, and to monitor the effectiveness of Diabetes, pre-Diabetes or pre-diabetic condition treatment modalities. The reference and subject biomarker profiles of the present invention can be contained in a machine-readable medium, such as but not limited to, analog tapes like those readable by a VCR, CD-ROM, DVD-ROM, USB flash media, among others. Such machine-readable media can also contain additional test results, such as, without limitation, measurements of clinical parameters and traditional laboratory risk factors. Alternatively or additionally, the machine-readable media can also comprise subject information such as medical history and any relevant family history. The machine-readable media can also contain information relating to other Diabetes-risk algorithms and computed indices such as those described herein.

Differences in the genetic makeup of subjects can result in differences in their relative abilities to metabolize various drugs, which may modulate the symptoms or risk factors of Diabetes, pre-Diabetes or a pre-diabetic condition. Subjects that have Diabetes, pre-Diabetes, or a pre-diabetic condition, or at risk for developing Diabetes, pre-Diabetes, or a pre-diabetic condition can vary in age, ethnicity, body mass index (BMI), total cholesterol levels, blood glucose levels, blood pressure, LDL and HDL levels, and other parameters. Accordingly, use of the biomarkers disclosed herein, both alone and together in combination with known genetic factors for drug metabolism, allow for a pre-determined level of predictability that a putative therapeutic or prophylactic to be tested in a selected subject will be suitable for treating or preventing Diabetes, pre-Diabetes, or a pre-diabetic condition in the subject.

To identify therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in Diabetes or pre-Diabetes risk factors (e.g., clinical parameters or traditional laboratory risk factors) as a result of such treatment or exposure.

Agents for reducing the risk of Diabetes, pre-Diabetes, pre-diabetic conditions, or diabetic complications include, without limitation of the following, insulin, hypoglycemic agents, anti-inflammatory agents, lipid reducing agents, antihypertensives such as calcium channel blockers, beta-adrenergic receptor blockers, cyclooxygenase-2 inhibitors, angiotensin system inhibitors, ACE inhibitors, rennin inhibitors, together with other common risk factor modifying agents (herein "Diabetes-modulating drugs").

The term "insulin (INS)" includes mature insulin (insulin-M), pro-insulin and soluble c-peptide (SCp). "Insulin" includes rapid acting forms, such as Insulin lispro rDNA origin: HUMALOG (1.5 mL, 10 mL, Eli Lilly and Company, Indianapolis, Ind.), Insulin Injection (Regular Insulin) form beef and pork (regular ILETIN I, Eli Lilly], human: rDNA: HUMULIN R (Eli Lilly), NOVOLIN R (Novo Nordisk, New York, N.Y.), Semisynthetic: VELOSULIN Human (Novo Nordisk), rDNA Human, Buffered: VELOSULIN BR, pork: regular Insulin (Novo Nordisk), purified pork: Pork Regular ILETIN II (Eli Lilly), Regular Purified Pork Insulin (Novo Nordisk), and Regular (Concentrated) ILETIN II U-500 (500 units/mL, Eli Lilly); intermediate-acting forms such as Insulin Zinc Suspension, beef and pork: LENTE ILETIN G I (Eli Lilly), Human, rDNA: HUMULIN L (Eli Lilly), NOVOLIN L (Novo Nordisk), purified pork: LENTE ILETIN II (Eli Lilly), Isophane Insulin Suspension (NPH): beef and pork: NPH ILETIN I (Eli Lilly), Human, rDNA: HUMULIN N (Eli Lilly), Novolin N (Novo Nordisk), purified pork: Pork NPH Iletin II (Eli Lilly), NPH-N (Novo Nordisk); and long-acting forms such as Insulin zinc suspension, extended (UL-TRALENTE, Eli Lilly), human, rDNA: HUMULIN U (Eli Lilly).

"Hypoglycemic" agents are preferably oral hypoglycemic agents and include, without limitation, first-generation sulfonylureas: Acetohexamide (Dymelor), Chlorpropamide (Diabinese), Tolbutamide (Orinase); second-generation sulfonylureas: Glipizide (Glucotrol, Glucotrol XL), Glyburide (Diabeta; Micronase; Glynase), Glimepiride (Amaryl); Biguanides: Metformin (Glucophage); Alpha-glucosidase inhibitors: Acarbose (Precose), Miglitol (Glyset), Thiazolidinediones: Rosiglitazone (Avandia), Pioglitazone (Actos), Troglitazone (Rezulin); Meglitinides: Repaglinide (Prandin); and other hypoglycemics such as Acarbose; Buformin; Butoxamine Hydrochloride; Camiglibose; Ciglitazone; Englitazone Sodium; Darglitazone Sodium; Etoformin Hydrochloride; Gliamilide; Glibomuride; Glicetanile Gliclazide Sodium; Gliflumide; Glucagon; Glyhexamide; Glymidine Sodium; Glyoctamide; Glyparamide; Linogliride; Linogliride Fumarate; Methyl Palmoxirate; Palmoxirate Sodium; Pirogliride Tartrate; Proinsulin Human; Seglitide Acetate; Tolazamide; Tolpyrramide; Zopolrestat.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isofluprednone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Morniflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium. An important anti-inflammatory agent is aspirin.

Preferred anti-inflammatory agents are cytokine inhibitors. Important cytokine inhibitors include cytokine antagonists (e.g., IL-6 receptor antagonists), aza-alkyl lysophospholipids (AALP), and Tumor Necrosis Factor-alpha (TNF-alpha) inhibitors, such as anti-TNF-alpha antibodies, soluble TNF receptor, TNF-alpha, anti-sense nucleic acid molecules, multivalent guanylhydrazone (CNI-1493), N-acetylcysteine, pentoxiphylline, oxpentifylline, carbocyclic nucleoside analogues, small molecule S9a, RP 55778 (a TNF-alpha synthesis inhibitor), Dexanabinol (HU-211, is a synthetic cannabinoid devoid of cannabimimetic effects, inhibits TNF-alpha production at a post-transcriptional stage), MDL 201,449A (9-[(1R,3R)-trans-cyclopentan-3-ol]adenine, and trichodimerol (BMS-182123). Preferred TNF-alpha inhibitors are Etanercept (ENBREL, Immunex, Seattle) and Infliximab (REMICADE, Centocor, Malvern, Pa.).

"Lipid reducing agents" include gemfibrozil, cholystyramine, colestipol, nicotinic acid, and HMG-CoA reductase inhibitors. HMG-CoA reductase inhibitors useful for administration, or co-administration with other agents according to the invention include, but are not limited to, simvastatin (U.S. Pat. No. 4,444,784), lovastatin (U.S. Pat. No. 4,231,938), pravastatin sodium (U.S. Pat. No. 4,346,227), fluvastatin (U.S. Pat. No. 4,739,073), atorvastatin (U.S. Pat. No. 5,273,995), cerivastatin, and numerous others described in U.S. Pat. Nos. 5,622,985, 5,135,935, 5,356,896, 4,920,109, 5,286,895, 5,262,435, 5,260,332, 5,317,031, 5,283,256, 5,256,689, 5,182,298, 5,369,125, 5,302,604, 5,166,171, 5,202,327, 5,276,021, 5,196,440, 5,091,386, 5,091,378, 4,904,646, 5,385,932, 5,250,435, 5,132,312, 5,130,306, 5,116,870, 5,112,857, 5,102,911, 5,098,931, 5,081,136, 5,025,000, 5,021,453, 5,017,716, 5,001,144, 5,001,128, 4,997,837, 4,996,234, 4,994,494, 4,992,429, 4,970,231, 4,968,693, 4,963,538, 4,957,940, 4,950,675, 4,946,864, 4,946,860, 4,940,800, 4,940,727, 4,939,143, 4,929,620, 4,923,861, 4,906,657, 4,906,624 and 4,897,402, the disclosures of which patents are incorporated herein by reference.

"Calcium channel blockers" are a chemically diverse class of compounds having important therapeutic value in the control of a variety of diseases including several cardiovascular disorders, such as hypertension, angina, and cardiac arrhythmias (Fleckenstein, Cir. Res. v. 52, (suppl. 1), p. 13-16 (1983); Fleckenstein, Experimental Facts and Therapeutic Prospects, John Wiley, New York (1983); McCall, D., Curr Pract Cardiol, v. 10, p. 1-11 (1985)). Calcium channel blockers are a heterogeneous group of drugs that belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, aminone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hydroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hyd-roxypropoxy)-3-pyridenecarbonitrilHCl, 1-butylamino-3-(2,5-dichlorophenoxy-)-2-propanol, 1-isopropylamino-3-(4-(2- cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol, 7-(2-hydroxy-3-t-butylaminpropoxy)phthalide. The above-identified compounds can be used as isomeric mixtures, or in their respective levorotating or dextrorotating form.

A number of selective "COX-2 inhibitors" are known in the art and include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 "N-benzyl indol-3-yl butanoic acid derivatives as cyclooxygenase inhibitors"; U.S. Pat. No. 5,677,318 "Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihy-drofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenyl-heterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., J. Pharmacol. Exp. Ther. 247(1), 1-7 (1988)); 4,5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenol and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alany-1-(4, thiazolyl)-L-alanyl(35,45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl)methyl]1H-imidazole-5-yl[methylan-e]-2-thiophenepropanoic acid, Smith Kline Beecham Pharmaceuticals, Pa.); Losartan (DUP753/MK954, DuPont Merck Pharmaceutical Company); Remikirin (RO42-5892, F. Hoffman LaRoche AG); A.sub.2 agonists (Marion Merrill Dow) and certain non-peptide heterocycles (G. D. Searle and Company).

"Angiotensin converting enzyme (ACE) inhibitors" include amino acids and derivatives thereof, peptides, including di- and tri-peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazepril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di- and tri-peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S.

Pat. Nos. 5,071,837, 5,064,965, 5,063,207, 5,036,054, 5,036, 053, 5,034,512, and 4,894,437).

Other Diabetes-modulating drugs include, but are not limited to, lipase inhibitors such as cetilistat (ATL-962); synthetic amylin analogs such as Symlin pramlintide with or without recombinant leptin; sodium-glucose cotransporter 2 (SGLT2) inhibitors like sergliflozin (869682; KGT-1251), YM543, dapagliflozin, GlaxoSmithKline molecule 189075, and Sanofi-Aventis molecule AVE2268; dual adipose triglyceride lipase and PI3 kinase activators like Adyvia (ID 1101); antagonists of neuropeptide Y2, Y4, and Y5 receptors like Nastech molecule PYY3-36, synthetic analog of human hormones PYY3-36 and pancreatic polypeptide (7™ molecule TM30338); Shionogi molecule S-2367; cannabinoid CB1 receptor antagonists such as rimonabant (Acomplia), taranabant, CP-945,598, Solvay molecule SLV319, Vernalis molecule V24343; hormones like oleoyl-estrone; inhibitors of serotonin, dopamine, and norepinephrine (also known in the art as "triple monoamine reuptake inhibitors") like tesofensine (Neurosearch molecule NS2330); inhibitors of norepinephrine and dopamine reuptake, like Contrave (bupropion plus opioid antagonist naltrexone) and Excalia (bupropion plus anticonvulsant zonisaminde); inhibitors of 11β-hydroxysteroid dehydrogenase type 1 (11b-HSD1) like Incyte molecule INCB13739; inhibitors of cortisol synthesis such as ketoconazole (DiObex molecule D10-902); inhibitors of gluconeogenesis such as Metabasis/Daiichi molecule CS-917; glucokinase activators like Roche molecule R1440; antisense inhibitors of protein tyrosine phosphatase-1B such as ISIS 113715; as well as other agents like NicOx molecule NCX 4016; injections of gastrin and epidermal growth factor (EGF) analogs such as Islet Neogenesis Therapy (E1-I.N.T.); and betahistine (Obecure molecule OBE101).

A subject cell (i.e., a cell isolated from a subject) can be incubated in the presence of a candidate agent and the pattern of biomarker expression in the test sample is measured and compared to a reference profile, e.g., a Diabetes reference expression profile or a non-Diabetes reference expression profile or an index value or baseline value. The test agent can be any compound or composition or combination thereof. For example, the test agents are agents frequently used in Diabetes treatment regimens and are described herein.

Additionally, any of the aforementioned methods can be used separately or in combination to assess if a subject has shown an "improvement in Diabetes risk factors" or moved within the risk spectrum of pre-Diabetes. Such improvements include, without limitation, a reduction in body mass index (BMI), a reduction in blood glucose levels, an increase in HDL levels, a reduction in systolic and/or diastolic blood pressure, an increase in insulin levels, or combinations thereof.

A subject suffering from or at risk of developing Diabetes or a pre-diabetic condition may also be suffering from or at risk of developing arteriovascular disease, hypertension, or obesity. Type 2 Diabetes in particular and arteriovascular disease have many risk factors in common, and many of these risk factors are highly correlated with one another. The relationship among these risk factors may be attributable to a small number of physiological phenomena, perhaps even a single phenomenon. Subjects suffering from or at risk of developing Diabetes, arteriovascular disease, hypertension or obesity are identified by methods known in the art.

Because of the interrelationship between Diabetes and arteriovascular disease, some or all of the individual biomarkers and biomarker panels of the present invention may overlap or be encompassed by biomarkers of arteriovascular disease, and indeed may be useful in the diagnosis of the risk of arteriovascular disease.

Performance and Accuracy Measures of the Invention

The performance and thus absolute and relative clinical usefulness of the invention may be assessed in multiple ways as noted above. Amongst the various assessments of performance, the invention is intended to provide accuracy in clinical diagnosis and prognosis. The accuracy of a diagnostic or prognostic test, assay, or method concerns the ability of the test, assay, or method to distinguish between subjects having Diabetes, pre-Diabetes, or a pre-diabetic condition, or at risk for Diabetes, pre-Diabetes, or a pre-diabetic condition, is based on whether the subjects have an "effective amount" or a "significant alteration" in the levels of a biomarker. By "effective amount" or "significant alteration," it is meant that the measurement of the biomarker is different than the predetermined cut-off point (or threshold value) for that biomarker and therefore indicates that the subject has Diabetes, pre-Diabetes, or a pre-diabetic condition for which the biomarker is a determinant. The difference in the level of biomarker between normal and abnormal is preferably statistically significant and may be an increase in biomarker level or a decrease in biomarker level. As noted below, and without any limitation of the invention, achieving statistical significance, and thus the preferred analytical and clinical accuracy, generally but not always requires that combinations of several biomarkers be used together in panels and combined with mathematical algorithms in order to achieve a statistically significant biomarker index.

In the categorical diagnosis of a disease state, changing the cut point or threshold value of a test (or assay) usually changes the sensitivity and specificity, but in a qualitatively inverse relationship. Therefore, in assessing the accuracy and usefulness of a proposed medical test, assay, or method for assessing a subject's condition, one should always take both sensitivity and specificity into account and be mindful of what the cut point is at which the sensitivity and specificity are being reported because sensitivity and specificity may vary significantly over the range of cut points. Use of statistics such as AUC, encompassing all potential cut point values, is preferred for most categorical risk measures using the invention, while for continuous risk measures, statistics of goodness-of-fit and calibration to observed results or other gold standards, are preferred.

Using such statistics, an "acceptable degree of diagnostic accuracy", is herein defined as a test or assay (such as the test of the invention for determining the clinically significant presence of biomarkers, which thereby indicates the presence of Diabetes, pre-Diabetes, or a pre-diabetic condition) in which the AUC (area under the ROC curve for the test or assay) is at least 0.60, desirably at least 0.65, more desirably at least 0.70, preferably at least 0.75, more preferably at least 0.80, and most preferably at least 0.85.

By a "very high degree of diagnostic accuracy", it is meant a test or assay in which the AUC (area under the ROC curve for the test or assay) is at least 0.80, desirably at least 0.85, more desirably at least 0.875, preferably at least 0.90, more preferably at least 0.925, and most preferably at least 0.95.

The predictive value of any test depends both on the sensitivity and specificity of the test, and on the prevalence of the condition in the population being tested. This notion, based on Bayes' theorem, provides that the greater the likelihood that the condition being screened for is present in a subject or in the population (pre-test probability), the greater the validity of a positive test and the greater the likelihood that the result is a true positive. Thus, the problem with using any test in any population where there is a low likelihood of the condition being present is that a positive result has more limited value (i.e., a positive test is more likely to be a false positive). Similarly, in populations at very high risk, a negative test result is more likely to be a false negative.

As a result, ROC and AUC can be misleading as to the clinical utility of a test in low disease prevalence tested populations (defined as those with less than 1% rate of occurrences (incidence) per annum, or less than 10% cumulative prevalence over a specified time horizon). Alternatively, absolute risk and relative risk ratios as defined elsewhere in this disclosure can be employed to determine the degree of clinical utility. Populations of subjects to be tested can also be categorized into quartiles by the test's measurement values, where the top quartile (25% of the population) comprises the group of subjects with the highest relative risk for developing Diabetes, pre-Diabetes, or a pre-diabetic condition and the bottom quartile comprising the group of subjects having the lowest relative risk for developing Diabetes, pre-Diabetes, or a pre-diabetic condition. Generally, values derived from tests or assays having over 2.5 times the relative risk from top to bottom quartile in a low prevalence population are considered to have a "high degree of diagnostic accuracy," and those with five to seven times the relative risk for each quartile are considered to have a "very high degree of diagnostic accuracy." Nonetheless, values derived from tests or assays having only 1.2 to 2.5 times the relative risk for each quartile remain clinically useful are widely used as risk factors for a disease; such is the case with total cholesterol and for many inflammatory biomarkers with respect to their prediction of future cardiovascular events. Often such lower diagnostic accuracy tests must be combined with additional parameters in order to derive meaningful clinical thresholds for therapeutic intervention, as is done with the aforementioned global risk assessment indices.

A health economic utility function is an yet another means of measuring the performance and clinical value of a given test, consisting of weighting the potential categorical test outcomes based on actual measures of clinical and economic value for each. Health economic performance is closely related to accuracy, as a health economic utility function specifically assigns an economic value for the benefits of correct classification and the costs of misclassification of tested subjects. As a performance measure, it is not unusual to require a test to achieve a level of performance which results in an increase in health economic value per test (prior to testing costs) in excess of the target price of the test.

In general, alternative methods of determining diagnostic accuracy are commonly used for continuous measures, when a disease category or risk category (such as pre-Diabetes) has not yet been clearly defined by the relevant medical societies and practice of medicine, where thresholds for therapeutic use are not yet established, or where there is no existing gold standard for diagnosis of the pre-disease. For continuous measures of risk, measures of diagnostic accuracy for a calculated index are typically based on curve fit and calibration between the predicted continuous value and the actual observed values (or a historical index calculated value) and utilize measures such as R squared, Hosmer-Lemeshow P-value statistics and confidence intervals. It is not unusual for predicted values using such algorithms to be reported including a confidence interval (usually 90% or 95% CI) based on a historical observed cohort's predictions, as in the test for risk of future breast cancer recurrence commercialized by Genomic Health, Inc. (Redwood City, Calif.).

In general, by defining the degree of diagnostic accuracy, i.e., cut points on a ROC curve, defining an acceptable AUC value, and determining the acceptable ranges in relative concentration of what constitutes an effective amount of the biomarkers of the invention allows one of skill in the art to use the biomarkers to diagnose or identify subjects with a pre-determined level of predictability and performance.

Calculation of the Diabetes Risk Score ("DRS")

After selection of a set of biomarkers as disclosed in the instant invention, well-known techniques such as cross-correlation, Principal Components Analysis (PCA), factor rotation, Logistic Regression (LogReg), Linear Discriminant Analysis (LDA), Eigengene Linear Discriminant Analysis (ELDA), Support Vector Machines (SVM), Random Forest (RF), Recursive Partitioning Tree (RPART), related decision tree classification techniques, Shrunken Centroids (SC), StepAIC, Kth-Nearest Neighbor, Boosting, Decision Trees, Neural Networks, Bayesian Networks, Support Vector Machines, and Hidden Markov Models, Linear Regression or classification algorithms, Nonlinear Regression or classification algorithms, analysis of variants (ANOVA), hierarchical analysis or clustering algorithms; hierarchical algorithms using decision trees; kernel based machine algorithms such as kernel partial least squares algorithms, kernel matching pursuit algorithms, kernel Fisher's discriminate analysis algorithms, or kernel principal components analysis algorithms, or other mathematical and statistical methods can be used to develop a DRS Formula for calculation of Diabetes risk score. A selected population of individuals is used, where historical information is available regarding the values of biomarkers in the population and their clinical outcomes. To calculate a Diabetes risk score for a given individual, biomarker values are obtained from one or more samples collected from the individual and used as input data (inputs into a DRS Formula fitted to the actual historical data obtained from the selected population of individuals.

Implementation of Biomarker Tests

Tests to measure biomarkers and biomarker panels can be implemented on a wide variety of diagnostic test systems. Diagnostic test systems are apparatuses that typically include means for obtaining test results from biological samples. Examples of such means include modules that automate the testing (e.g., biochemical, immunological, nucleic acid detection assays). Some diagnostic test systems are designed to handle multiple biological samples and can be programmed to run the same or different tests on each sample. Diagnostic test systems typically include means for collecting, storing and/or tracking test results for each sample, usually in a data structure or database. Examples include well-known physical and electronic data storage devices (e.g., hard drives, flash memory, magnetic tape, paper print-outs). It is also typical for diagnostic test systems to include means for reporting test results. Examples of reporting means include visible display, a link to a data structure or database, or a printer. The reporting means can be nothing more than a data link to send test results to an external device, such as a data structure, data base, visual display, or printer.

One embodiment of the present invention comprises a diagnostic test system that has been adapted to aide in the identification of individuals at risk of developing Diabetes. The test system employs means to apply a DRS Formula to inputs that include the levels of biomarkers measured from a biomarker panel in accordance with the description herein. Typically, test results from a biomarker panel of the present invention serve as inputs to a computer or microprocessor programmed with the DRS Formula. When the inputs include all the inputs for a Diabetes risk score, then the diagnostic test system can include the score in the reported test results. If some factors apart from the biomarkers tested in the system are used to calculate the final risk score, then these factors can be supplied to the diagnostic test system so that it can complete the risk score calculation, or the DRS Formula can produce an index score that will reported and externally combined with the other inputs to calculate a final risk score.

A number of diagnostic test systems are available for use in implementing the present invention and exemplify further means for carrying out the invention. One such device is the Abbott Architect® System, a high throughput, fully automated, clinical chemistry analyzer (ARCHITECT is a registered trademark of Abbott Laboratories, Abbott Park, Ill. 60064 United States of America, for data management and laboratory automation systems comprised of computer hardware and software for use in the field of medical diagnostics). The Architect® system is described at URL World-Wide-Web.abbottdiagnostics.com/pubs/2006/ 2006_AACC_Wilson_c16000.pdf (Wilson, C. et al., "Clinical Chemistry Analyzer Sub-System Level Performance," American Association for Clinical Chemistry Annual Meeting, Chicago, Ill., Jul. 23-27, 2006, and in Kisner H J, "Product development: the making of the Abbott ARCHITECT," Clin Lab Manage Rev. 1997 November-December; 11(6): 419-21; Ognibene A et al., "A new modular chemiluminescence immunoassay analyser evaluated," Clin Chem Lab Med. 2000 March; 38(3):251-60; Park J W et al., "Three-year experience in using total laboratory automation system," Southeast Asian J Trop Med Public Health. 2002; 33 Suppl 2:68-73; Pauli D et al., "The Abbott Architect c8000: analytical performance and productivity characteristics of a new analyzer applied to general chemistry testing," Clin Lab. 2005; 51(1-2):31-41. Another useful system is the Abbott AxSYM® and AxSYM® Plus systems, which is described, along with other Abbott systems, at URL World-Wide-Web.abbottdiagnostics.com/Products/Instruments_by_Platform/.

Other devices useful for implementation of the tests to measure biomarkers are the Johnson & Johnson Vitros® system (VITROS is a registered trademark of Johnson & Johnson Corp., New Brunswick, N.J., United States of America, for medical equipment, namely, chemistry analyzer apparatus used to generate diagnostic test results from blood and other body fluids by professionals in hospitals, laboratories, clinics and doctor's offices), see URL World-Wide-Web.jnjgateway.com/home.jhtml?loc=USENG&page=menu& nodekey=/Prod_Info/Specialty/Diagnostics/Laboratory_ and_Transfusion_Medicine/Chemistry_Immunodiagnostics; and the Dade-Behring Dimension® system (DIMENSION is a registered trademark of Dade Behring Inc., Deerfield Ill., United States of America for medical diagnostic analyzers for the analysis of bodily fluids, and computer hardware and computer software for use in operating the analyzers and for use in analyzing the data generated by the analyzers), see URL diagnostics.siemens.com/webapp/wcs/ stores/servlet/PSGenericDisplay~q_catalogId~e_-111~a_ langId~e_-111~a_pageId~e__94489~a_storeId~e__10001. htm.

The tests for the biomarker panels of the invention can be carried out by laboratories such as those which are certified under the Clinical Laboratory Improvement Amendments of the United States (42 U.S.C. §263(a)), or other federal, national, state, provincial, or other law of any country, state, or province governing the operation of laboratories which analyze samples for clinical purposes. Such laboratories include, for example, Laboratory Corporation of America, with headquarters at 358 South Main Street, Burlington, N.C. 27215, United States of America; Quest Diagnostics, with corporate headquarters at 3 Giralda Farms, Madison, N.J. 07940, United States of America; and hospital-based reference laboratories and clinical chemistry laboratories.

Relative Performance of the Invention

Only a minority of individual ALLDBRISK achieve an acceptable degree of diagnostic accuracy as defined above. Using a representative list of ALLDBRISK in each study, an exhaustive analysis of all potential univariate, bivariate, and trivariate combinations was used to derive a best fit LDA model to predict risk of conversion to Diabetes in each of the Example populations (see FIG. 31). For every possible ALLDBRISK combination of a given panel size an LDA model was developed and then analyzed for its AUC statistics.

It is immediately apparent from the figure that there is a very low likelihood of high accuracy individual biomarkers, and even high accuracy combinations utilizing multiple biomarkers are infrequent. As demonstrated in FIG. 31, none of the individual ALLDBRISK, out of the 53 and 49 ALLDBRISK tested in Example 1 and Example 2, respectively, presented herein, achieved an AUC of 0.75 for the prediction of Diabetes in a best fit univariate model. The individual ALLDBRISK parameters tested included many of the traditional laboratory risk factors and clinical parameters commonly used in global risk assessment and indices for Diabetes and arteriovascular disease.

Only two single ALLDBRISK, fasting glucose and insulin, even achieved an AUC of 0.70 in a univariate model; neither of these two biomarkers consistently did so in all of the population cohorts in the presented studies. Despite this lack of a very high level of diagnostic accuracy, fasting glucose remains the most common method of predicting the risk of Diabetes, and furthermore remains the primary method and definition used for the diagnosis of frank Diabetes.

In the Examples, achieving an accuracy defined by an AUC of 0.75 or above required a minimum combination of two or more biomarkers as taught in the invention herein. Across all of the examples, only three such two ALLDBRISK combinations yielded bivariate models which met this hurdle, and only when used within the Base population cohorts of each Example, which had more selected (narrower) population selection (including only those with both a BMI greater than or equal to 25 and age greater than or equal to 39) than the total population of each Example. Such two biomarker combinations occurred at an approximate rate of only one in a thousand potential combinations.

However, as demonstrated above, several of the other biomarkers are useful in trivariate combinations of three ALLDBRISK, many of which achieved both acceptable performance either with or without including either glucose or insulin. Notably, in two separate studies, a representative set of 53 and 49 biomarkers selected out of the 266 ALLDBRISK, clinical parameters and traditional laboratory risk factors, were tested, and of these, certain combinations of three or more ALLDBRISK were found to exhibit superior performance. These are key aspects of the invention.

Notably, this analysis of FIG. 31 demonstrated that no single biomarker was required to practice the invention at an acceptable level of diagnostic accuracy, although several individually identified biomarkers are parts of the most preferred embodiments as disclosed below. It is a feature of the invention that the information lost due to removing one ALLDBRISK can often be replaced through substitution with one or more other ALLDBRISK, and generically by increasing the panel size, subject to the need to increase the study size in order for studies examining very large models encompassing many ALLDBRISK to remain statistically significant. It is also a feature of the invention that overall performance and accuracy can often be improved by adding additional biomarkers (e.g., ALLDBRISK, traditional laboratory risk factors, and clinical parameters) as additional inputs to a formula or model, as demonstrated above in the relative performance of univariate, bivariate, and trivariate models, and below in the performance of larger models.

The ultimate determinant and gold standard of true risk of conversion to Diabetes is actual conversions within a sufficiently large study population and observed over the length of time claimed, as was done in the Examples contained herein. However, this is problematic, as it is necessarily a retrospective point of view. As a result, subjects suffering from or at risk of developing Diabetes, pre-Diabetes, or a pre-diabetic condition are commonly diagnosed or identified by methods known in the art, generally using either traditional laboratory risk factors or other non-analyte clinical parameters, and future risk is estimated based on historical experience and registry studies. Such methods include, but are not limited to, measurement of systolic and diastolic blood pressure, measurements of body mass index, in vitro determination of total cholesterol, LDL, HDL, insulin, and glucose levels from blood samples, oral glucose tolerance tests, stress tests, measurement of high sensitivity C-reactive protein (CRP), electrocardiogram (ECG), c-peptide levels, anti-insulin antibodies, anti-beta cell-antibodies, and glycosylated hemoglobin (HBA1c).

For example, Diabetes is frequently diagnosed by measuring fasting blood glucose, insulin, or HBA1c levels. Normal adult glucose levels are 60-126 mg/dl. Normal insulin levels are 7 mU/mL±3 mU. Normal HBA1c levels are generally less than 6%. Hypertension is diagnosed by a blood pressure consistently at or above 140/90. Risk of arteriovascular disease can also be diagnosed by measuring cholesterol levels. For example, LDL cholesterol above 137 or total cholesterol above 200 is indicative of a heightened risk of arteriovascular disease. Obesity is diagnosed for example, by body mass index. Body mass index (BMI) is measured (kg/m2 (or lb/in2×704.5)). Alternatively, waist circumference (estimates fat distribution), waist-to-hip ratio (estimates fat distribution), skinfold thickness (if measured at several sites, estimates fat distribution), or bioimpedance (based on principle that lean mass conducts current better than fat mass (i.e. fat mass impedes current), estimates % fat) is measured. The parameters for normal, overweight, or obese individuals is as follows: Underweight: BMI<18.5; Normal: BMI 18.5 to 24.9; Overweight: BMI=25 to 29.9. Overweight individuals are characterized as having a waist circumference of >94 cm for men or >80 cm for women and waist to hip ratios of >0.95 in men and >0.80 in women. Obese individuals are characterized as having a BMI of 30 to 34.9, being greater than 20% above "normal" weight for height, having a body fat percentage >30% for women and 25% for men, and having a waist circumference >102 cm (40 inches) for men or 88 cm (35 inches) for women. Individuals with severe or morbid obesity are characterized as having a BMI of >35.

As noted above, risk prediction for Diabetes, pre-Diabetes, or a pre-diabetic condition can also encompass risk prediction algorithms and computed indices that assess and estimate a subject's absolute risk for developing Diabetes, pre-Diabetes, or a pre-diabetic condition with reference to a historical cohort. Risk assessment using such predictive mathematical algorithms and computed indices has increasingly been incorporated into guidelines for diagnostic testing and treatment, and encompass indices obtained from and validated with, inter alia, multi-stage, stratified samples from a representative population.

Despite the numerous studies and algorithms that have been used to assess the risk of Diabetes, pre-Diabetes, or a pre-diabetic condition, the evidence-based, multiple risk factor assessment approach is only moderately accurate for the prediction of short- and long-term risk of manifesting Diabetes, pre-Diabetes, or a pre-diabetic condition in individual asymptomatic or otherwise healthy subjects. Such risk prediction algorithms can be advantageously used in combination with the ALLDBRISK of the present invention to distinguish between subjects in a population of interest to determine the risk stratification of developing Diabetes, pre-Diabetes, or a pre-diabetic condition. The ALLDBRISK and methods of use disclosed herein provide tools that can be used in combination with such risk prediction algorithms to assess, identify, or diagnose subjects who are asymptomatic and do not exhibit the conventional risk factors.

The data derived from risk factors, risk prediction algorithms and from the methods of the present invention can be combined and compared by known statistical techniques in order to compare the relative performance of the invention to the other techniques.

Furthermore, the application of such techniques to panels of multiple ALLDBRISK is encompassed by or within the ambit of the present invention, as is the use of such combinations and formulae to create single numerical "risk indices" or "risk scores" encompassing information from multiple ALLDBRISK inputs.

Selection of Biomarkers

The biomarkers and methods of the present invention allow one of skill in the art to identify, diagnose, or otherwise assess those subjects who do not exhibit any symptoms of Diabetes, pre-Diabetes, or a pre-diabetic condition, but who nonetheless may be at risk for developing Diabetes, pre-Diabetes, or experiencing symptoms characteristic of a pre-diabetic condition.

Two hundred and sixty-six (266) analyte-based biomarkers have been identified as being found to have altered or modified presence or concentration levels in subjects who have Diabetes, or who exhibit symptoms characteristic of a pre-diabetic condition, or have pre-Diabetes (as defined herein), including such subjects as are insulin resistant, have altered beta cell function or are at risk of developing Diabetes based upon known clinical parameters or traditional laboratory risk factors, such as family history of Diabetes, low activity level, poor diet, excess body weight (especially around the waist), age greater than 45 years, high blood pressure, high levels of triglycerides, HDL cholesterol of less than 35, previously identified impaired glucose tolerance, previous Diabetes during pregnancy (Gestational Diabetes Mellitus or GDM) or giving birth to a baby weighing more than nine pounds, and ethnicity Biomarkers can be selected from various groups as outlined in the instant specification to form a panel of n markers. For example, one embodiment of the invention embraces a method of evaluating the risk of developing Diabetes or another Diabetes-related condition, comprising measuring the levels of at least three biomarkers, where two biomarkers are selected from ADIPOQ; CRP; GLUCOSE; GPT; HBA1C; HSPA1B; IGFBP1; IGFBP2; INS; LEP; and TRIG; and one biomarker is selected from the ALLDBRISKS, CPs, and TLRFs of Table 1, Table 2, and Table 3; and using the measured levels of the biomarkers to evaluate the risk of developing Diabetes or a Diabetes-related condition. In this instance, n is 3. When selecting from different groups, unique biomarkers should be used; e.g., in the immediately preceding example, if ADIPOQ is selected from the group of ADIPOQ; CRP; GLUCOSE; GPT; HBA1C; HSPA1B; IGFBP1; IGFBP2; INS; LEP; and TRIG, then ADIPOQ should not also be selected from the markers of Table 1, Table 2, and Table 3.

Diabetes-related conditions include Diabetes and the pre-diabetic conditions defined above.

Table 1 comprises several biomarkers, collectively referred to as ALLDBRISK, which are analyte-based or individual history-based biomarkers for use in the present invention. One skilled in the art will recognize that the ALLDBRISKS presented herein encompasses all forms and variants, including but not limited to, polymorphisms, isoforms, mutants, derivatives, precursors including nucleic acids and pro-proteins, cleavage products, receptors (including soluble and transmembrane receptors), ligands, protein-ligand complexes, and post-translationally modified variants (such as cross-linking or glycosylation), fragments, and degradation products, as well as any multi-unit nucleic acid, protein, and glycoprotein structures comprised of any of the ALLDBRISKS as constituent subunits of the fully assembled structure.

TABLE 1

| ALLDBRISK | Official Name | Common Name | Entrez Gene Link |
|---|---|---|---|
| 1 | ATP-binding cassette, sub-family C (CFTR/MRP), member 8 | sulfonylurea receptor (SUR1), HI; SUR; HHF1; MRP8; PHHI; SUR1; ABC36; HRINS | ABCC8 |
| 2 | ATP-binding cassette, sub-family C (CFTR/MRP), member 9 | sulfonylurea receptor (SUR2a), SUR2; ABC37; CMD1O; FLJ36852 | ABCC9 |
| 3 | angiotensin I converting enzyme (peptidyl-dipeptidase A) 1 | angiotensin-converting enzyme (ACE) - ACE1, CD143, DCP, DCP1, CD143 antigen; angiotensin I converting enzyme; angiotensin converting enzyme, somatic isoform; carboxycathepsin; dipeptidyl carboxypeptidase 1; kininase II; peptidase P; peptidyl-dipeptidase A; testicular ECA | ACE |
| 4 | adenylate cyclase activating polypeptide 1 (pituitary) | adenylate cyclase activating polypeptide | ADCYAP1 |
| 5 | adiponectin, C1Q and collagen domain containing | Adiponectin - ACDC, ACRP30, APM-1, APM1, GBP28, glycosylated adiponectin, adiponectin, adipocyte, C1Q and collagen domain containing; adipocyte, C1Q and collagen domain-containing; adiponectin; adipose most abundant gene transcript 1; gelatin-binding protein 28 | ADIPOQ |
| 6 | adiponectin receptor 1 | G Protein Coupled Receptor AdipoR1 - ACDCR1, CGI-45, PAQR1, TESBP1A | ADIPOR1 |
| 7 | adiponectin receptor 2 | G Protein Coupled Receptor AdipoR2 - ACDCR2, PAQR2 | ADIPOR2 |
| 8 | Adrenomedullin | adrenomedullin - AM, preproadrenomedullin | ADM |
| 9 | adrenergic, beta-2-, receptor, surface | G Protein-Coupled Beta-2 Adrenoceptor - ADRB2R, ADRBR, B2AR, BAR, BETA2AR, beta-2 adrenergic receptor; beta-2 adrenoceptor; catecholamine receptor | ADRB2 |
| 10 | advanced glycosylation end product-specific receptor | RAGE - advanced glycosylation end product-specific receptor RAGE3; advanced glycosylation end product-specific receptor variant sRAGE1; advanced glycosylation end product-specific receptor variant sRAGE2; receptor for advanced glycosylation end-products; soluble receptor | AGER |
| 11 | agouti related protein homolog (mouse) | AGRT, ART, ASIP2, & Agouti-related transcript, mouse, homolog of; agouti (mouse) related protein; agouti related protein homolog | AGRP |
| 12 | angiotensinogen (serpin peptidase inhibitor, clade A, member 8) | angiotensin I; pre-angiotensinogen; angiotensin II precursor; angiotensinogen (serine (or cysteine) peptidase inhibitor, clade A, member 8); angiotensinogen (serine (or cysteine) proteinase inhibitor, clade A (alpha-1 antiproteinase, antitrypsin), member 8) | AGT |
| 13 | angiotensin II receptor, type 1 | G protein-Coupled Receptor AGTR1A - AG2S, AGTR1A, AGTR1B, AT1, AT1B, AT2R1, AT2R1A, AT2R1B, HAT1R, angiotensin receptor 1; angiotensin receptor 1B; type-1B angiotensin II receptor | AGTR1 |
| 14 | angiotensin II receptor-associated protein | angiotensin II - ATRAP, ATI receptor-associated protein; angiotensin II, type I receptor-associated protein | AGTRAP |
| 15 | alpha-2-HS-glycoprotein | A2HS, AHS, FETUA, HSGA, Alpha-2HS-glycoprotein; fetuin-A | AHSG |

TABLE 1-continued

| ALLDBRISK | Official Name | Common Name | Entrez Gene Link |
|---|---|---|---|
| 16 | v-akt murine thymoma viral oncogene homolog 1 | Ser/Thr kinase Akt - PKB, PRKBA, RAC, RAC-ALPHA, RAC-alpha serine/threonine-protein kinase; murine thymoma viral (v-akt) oncogene homolog-1; protein kinase B; rac protein kinase alpha | AKT1 |
| 17 | v-akt murine thymoma viral oncogene homolog 2 | PKBBETA, PRKBB, RAC-BETA, Murine thymoma viral (v-akt) homolog-2; rac protein kinase beta | AKT2 |
| 18 | Albumin | Ischemia-modified albumin (IMA) - cell growth inhibiting protein 42; growth-inhibiting protein 20; serum albumin | ALB |
| 19 | Alstrom syndrome 1 | ALSS | ALMS1 |
| 20 | archidonate 12-lipoxygenase | LOG12, 12(S)-lipoxygenase; platelet-type 12-lipoxygenase/arachidonate 12-lipoxygenase | ALOX12 |
| 21 | Angiogenin, ribonuclease, RNase A family, 5 | Angiogenin, MGC71966, RNASE4, RNASE5, angiogenin, ribonuclease, RNase A family, 5 | ANG |
| 22 | ankyrin repeat domain 23 | DARP, MARP3, Diabetes related ankyrin repeat protein; muscle ankyrin repeat protein 3 | ANKRD23 |
| 23 | apelin, AGTRL 1 Ligand | XNPEP2, apelin, peptide ligand for APJ receptor | APLN |
| 24 | apolipoprotein A-I | apolipoproteins A-1 and B, amyloidosis; apolipoprotein A-I, preproprotein; apolipoprotein A1; preproapolipoprotein | APOA1 |
| 25 | apolipoprotein A-II | Apolipoprotein A-II | APOA2 |
| 26 | apolipoprotein B (including Ag(x) antigen) | apolipoproteins A-1 and B - Apolipoprotein B, FLDB, apoB-100; apoB-48; apolipoprotein B; apolipoprotein B48 | APOB |
| 27 | apolipoprotein E | APO E - AD2, apoprotein, Alzheimer disease 2 (APOE*E4-associated, late onset); apolipoprotein E precursor; apolipoprotein E3 | APOE |
| 28 | aryl hydrocarbon receptor nuclear translocator | dioxin receptor, nuclear translocator; hypoxia-inducible factor 1, beta subunit | ARNT |
| 29 | Aryl hydrocarbon receptor nuclear translocator-like | Bmal1, TIC; JAP3; MOP3; BMAL1; PASD3; BMAL1c; bHLH-PAS protein JAP3; member of PAS superfamily 3; ARNT-like protein 1, brain and muscle; basic-helix-loop-helix-PAS orphan MOP3 | ARNTL |
| 30 | arrestin, beta 1 | beta arrestin - ARB1, ARR1, arrestin beta 1 | ARRB1 |
| 31 | arginine vasopressin (neurophysin II, antidiuretic hormone, Diabetes insipidus, neurohypophyseal) | copeptin - ADH, ARVP, AVP-NPII, AVRP, VP, arginine vasopressin-neurophysin II; vasopressin-neurophysin II-copeptin, vasopressin | AVP |
| 32 | bombesin receptor subtype 3 | G-protein coupled receptor; bombesin receptor subtype 3 | BRS3 |
| 33 | Betacellulin | betacellulin | BTC |
| 34 | benzodiazepine receptor (peripheral) | PBR - DBI, IBP, MBR, PBR, PKBS, PTBR, mDRC, pk18, benzodiazepine peripheral binding site; mitochondrial benzodiazapine receptor; peripheral benzodiazepine receptor; peripheral-type benzodiazepine receptor | BZRP |
| 35 | complement component 3 | complement C3 - acylation-stimulating protein cleavage product; complement component C3, ASP; CPAMD1 | C3 |
| 36 | complement component 4A (Rodgers blood group) | complement C4 - C4A anaphylatoxin; Rodgers form of C4; acidic C4; c4 propeptide; complement component 4A; complement component C4B | C4A |
| 37 | complement component 4B (Childo blood group) | C4A, C4A13, C4A91, C4B1, C4B12, C4B2, C4B3, C4B5, C4F, CH, CO4, CPAMD3, C4 complement C4d region; Chido form of C4; basic C4; complement C4B; complement component 4B; complement component 4B, centromeric; complement component 4B, telomeric; complement component C4B | C4B |
| 38 | complement component 5 | anaphylatoxin C5a analog - CPAMD4 | C5 |
| 39 | Calpain-10 | calcium-activated neutral protease | CAPN10 |
| 40 | Cholecystokinin | cholecystokinin | CCK |

TABLE 1-continued

| ALLDBRISK | Official Name | Common Name | Entrez Gene Link |
|---|---|---|---|
| 41 | cholecystokinin (CCK)-A receptor | CCK-A; CCK-A; CCKRA; CCK1-R; cholecystokinin-1 receptor; cholecystokinin type-A receptor | CCKAR |
| 42 | chemokine (C-C motif) ligand 2 | Monocyte chemoattractant protein-1 (MCP-1) - GDCF-2, GDCF-2 HC11, HC11, HSMCR30, MCAF, MCP-1, MCP1, SCYA2, SMC-CF, monocyte chemoattractant protein-1; monocyte chemotactic and activating factor; monocyte chemotactic protein 1, homologous to mouse Sig-je; monocyte secretory protein JE; small inducible cytokine A2; small inducible cytokine A2 (monocyte chemotactic protein 1, homologous to mouse Sig-je); small inducible cytokine subfamily A (Cys-Cys), member 2 | CCL2 |
| 43 | CD14 molecule | CD14 antigen - monocyte receptor | CD14 |
| 44 | CD163 molecule | CD163 - M130, MM130 - CD163 antigen; macrophage-associated antigen, macrophage-specific antigen | CD163 |
| 45 | CD36 molecule (thrombospondin receptor) | fatty acid translocase, FAT; GP4; GP3B; GPIV; PASIV; SCARB3, PAS-4 protein; collagen type I; glycoprotein IIIb; cluster determinant 36; fatty acid translocase; thrombospondin receptor; collagen type I receptor; platelet glycoprotein IV; platelet collagen receptor; scavenger receptor class B, member 3; leukocyte differentiation antigen CD36; CD36 antigen (collagen type I receptor, thrombospondin receptor) | CD36 |
| 46 | CD38 molecule | T10; CD38 antigen (p45); cyclic ADP-ribose hydrolase; ADP-ribosyl cyclase/cyclic ADP-ribose hydrolase | CD38 |
| 47 | CD3d molecule, delta (CD3-TCR complex) | CD3-DELTA, T3D, CD3D antigen, delta polypeptide; CD3d antigen, delta polypeptide (TiT3 complex); T-cell receptor T3 delta chain | CD3D |
| 48 | CD3g molecule, gamma (CD3-TCR complex) | T3G; CD3-GAMMA, T3G, CD3G gamma; CD3g antigen, gamma polypeptide (TiT3 complex); T-cell antigen receptor complex, gamma subunit of T3; T-cell receptor T3 gamma chain; T-cell surface glycoprotein CD3 gamma chain precursor | CD3G |
| 49 | CD40 molecule, TNF receptor superfamily member 5 | Bp50, CDW40, TNFRSF5, p50, B cell surface antigen CD40; B cell-associated molecule; CD40 antigen; CD40 antigen (TNF receptor superfamily member 5); CD40 type II isoform; CD40L receptor; nerve growth factor receptor-related B-lymphocyte activation molecule; tumor necrosis factor receptor superfamily, member 5 | CD40 |
| 50 | CD40 ligand (TNF superfamily, member 5, hyper-IgM syndrome) | CD40 Ligand (CD40L) (also called soluble CD40L vs. platelet-bound CD40L), CD154, CD40L, HIGM1, IGM, IMD3, T-BAM, TNFSF5, TRAP, gp39, hCD40L, CD40 antigen ligand; CD40 ligand; T-B cell-activating molecule; TNF-related activation protein; tumor necrosis factor (ligand) superfamily member 5; tumor necrosis factor (ligand) superfamily, member 5 (hyper-IgM syndrome); tumor necrosis factor ligand superfamily member 5 | CD40LG |
| 51 | CD68 molecule | GP110; SCARD1; macrosialin; CD68 antigen; macrophage antigen CD68; scavenger receptor class D, member 1 | CD68 |
| 52 | cyclin-dependent kinase 5 | PSSALRE; cyclin-dependent kinase 5 | CDK5 |
| 53 | complement factor D (adipsin) | ADN, DF, PFD, C3 convertase activator; D component of complement (adipsin); adipsin; complement factor D; properdin factor D | CFD |

TABLE 1-continued

| ALLDBRISK | Official Name | Common Name | Entrez Gene Link |
|---|---|---|---|
| 54 | CASP8 and FADD-like apoptosis regulator | FLIP - caspase 8 inhibitor, CASH; FLIP; MRIT; CLARP; FLAME; Casper; c-FLIP; FLAME-1; I-FLICE; USURPIN; c-FLIPL; c-FLIPR; c-FLIPS; CASP8AP1, usurpin beta; FADD-like anti-apoptotic molecule; Inhibitor of FLICE; Caspase-related inducer of apoptosis; Caspase homolog; Caspase-like apoptosis regulatory protein | CFLAR |
| 55 | Clock homolog (mouse) | clock protein; clock (mouse) homolog; circadian locomoter output cycles kaput protein | CLOCK |
| 56 | chymase 1, mast cell | chymase 1 - CYH, MCT1, chymase 1 preproprotein transcript E; chymase 1 preproprotein transcript I; chymase, heart; chymase, mast cell; mast cell protease I | CMA1 |
| 57 | cannabinoid receptor 1 (brain) | cannabinoid receptor 1 - CANN6, CB-R, CB1, CB1A, CB1K5, CNR, central cannabinoid receptor | CNR1 |
| 58 | cannabinoid receptor 2 (macrophage) | cannabinoid receptor 2 (macrophage), CB2, CX5 | CNR2 |
| 59 | Cortistatin | CST-14; CST-17; CST-29; cortistatin-14; cortistatin-17; cortistatin-29; preprocortistatin | CORT |
| 60 | carnitine palmitoyltransferase I | CPT1; CPT1-L; L-CPT1, carnitine palmitoyltransferase I; liver | CPT1A |
| 61 | carnitine palmitoyltransferase II | CPT1, CPTASE | CPT2 |
| 62 | complement component (3b/4b) receptor 1 | complement receptor CR1; KN; C3BR; CD35; CD35 antigen; C3b/C4b receptor; C3-binding protein; Knops blood group antigen; complement component receptor 1; complement component (3b/4b) receptor 1, including Knops blood group system | CR1 |
| 63 | complement component (3d/Epstein Barr virus) receptor 2 | complement receptor CR2; C3DR; CD21 | CR2 |
| 64 | CREB binding protein (Rubinstein-Taybi syndrome) | Cbp; CBP; RTS; RSTS, CREB-binding protein | CREBBP |
| 65 | C-reactive protein, pentraxin-related | C-Reactive Protein, CRP, PTX1 | CRP |
| 66 | CREB regulated transcription coactivator 2 | Torc2 (transcriptional coactivator); transducer of regulated cAMP response element-binding protein (CREB) 2 | CRTC2 |
| 67 | colony stimulating factor 1 (macrophage) | M-CSF - colony stimulating factor 1; macrophage colony stimulating factor | CSF1 |
| 68 | cathepsin B | cathepsin B - procathepsin B, APPS; CPSB, APP secretase; amyloid precursor protein secretase; cathepsin B1; cysteine protease; preprocathepsin B | CTSB |
| 69 | cathepsin L | CATL, MEP, major excreted protein | CTSL |
| 70 | cytochrome P450, family 19, subfamily A, polypeptide 1 | ARO, ARO1, CPV1, CYAR, CYP19, P-450AROM, aromatase; cytochrome P450, family 19; cytochrome P450, subfamily XIX (aromatization of androgens); estrogen synthetase; flavoprotein-linked monooxygenase; microsomal monooxygenase | CYP19A1 |
| 71 | Dio-2, death inducer-obliterator 1 | death associated transcription factor 1; BYE1; DIO1; DATF1; DIDO2; DIDO3; DIO-1 | DIDO1 |
| 72 | dipeptidyl-peptidase 4 (CD26, adenosine deaminase complexing protein 2) | dipeptidylpeptidase IV - ADABP, ADCP2, CD26, DPPIV, TP103, T-cell activation antigen CD26; adenosine deaminase complexing protein 2; dipeptidylpeptidase IV; dipeptidylpeptidase IV (CD26, adenosine deaminase complexing protein 2) | DPP4 |
| 73 | epidermal growth factor (beta-urogastrone) | URG - urogastrone | EGF |
| 74 | early growth response 1 | zinc finger protein 225; transcription factor ETR103; early growth response protein 1; nerve growth factor-induced protein A | EGR1 |
| 75 | epididymal sperm binding protein 1 | E12, HE12, epididymal secretory protein | ELSPBP1 |

TABLE 1-continued

| ALLDBRISK | Official Name | Common Name | Entrez Gene Link |
|---|---|---|---|
| 76 | ectonucleotide pyrophosphatase/phosphodiesterase 1 | ENPP1 - M6S1, NPP1, NPPS, PC-1, PCA1, PDNP1, Ly-41 antigen; alkaline phosphodiesterase 1; membrane component, chromosome 6, surface marker 1; phosphodiesterase I/nucleotide pyrophosphatase 1; plasma-cell membrane glycoprotein 1 | ENPP1 |
| 77 | E1A binding protein p300 | p300, E1A binding protein p300, E1A-binding protein, 300 kD; E1A-associated protein p300 | EP300 |
| 78 | coagulation factor XIII, A1 polypeptide | Coagulation Factor XIII - Coagulation factor XIII A chain; Coagulation factor XIII, A polypeptide; TGase; (coagulation factor XIII, A1 polypeptide); coagulation factor XIII A1 subunit; factor XIIIa, coagulation factor XIII A1 subunit | F13A1 |
| 79 | coagulation factor VIII, procoagulant component (hemophilia A) | Factor VIII, AHF, F8 protein, F8B, F8C, FVIII, HEMA, coagulation factor VIII; coagulation factor VIII, isoform b; coagulation factor VIIIc; factor VIII F8B; procoagulant component, isoform b | F8 |
| 80 | fatty acid binding protein 4, adipocyte | fatty acid binding protein 4, adipocyte - A-FABP | FABP4 |
| 81 | Fas (TNF receptor superfamily, member 6) | soluble Fas/APO-1 (sFas), ALPS1A, APO-1, APT1, Apo-1 Fas, CD95, FAS1, FASTM, TNFRSF6, APO-1 cell surface antigen; CD95 antigen; Fas antigen; apoptosis antigen 1; tumor necrosis factor receptor superfamily, member 6 | FAS |
| 82 | Fas ligand (TNF superfamily, member 6) | Fas ligand (sFasL), APT1LG1, CD178, CD95L, FASL, TNFSF6, CD95 ligand; apoptosis (APO-1) antigen ligand 1; fas ligand; tumor necrosis factor (ligand) superfamily, member 6 | FASLG |
| 83 | free fatty acid receptor 1 | G protein-coupled receptor 40 - FFA1R, GPR40, G protein-coupled receptor 40 | FFAR1 |
| 84 | fibrinogen alpha chain | Fibrin, Fib2, fibrinogen, A alpha polypeptide; fibrinogen, alpha chain, isoform alpha preproprotein; fibrinogen, alpha polypeptide | FGA |
| 85 | forkhead box A2 | (Foxa2); HNF3B; TCF3B; hepatic nuclear factor-3-beta; hepatocyte nuclear factor 3, beta | FOXA2 |
| 86 | forkhead box O1A | FKH1; FKHR; FOXO1; forkhead (*Drosophila*) homolog 1 (rhabdomyosarcoma); forkhead, *Drosophila*, homolog of, in rhabdomyosarcoma | FOXO1A |
| 87 | Ferritin | FTH; PLIF; FTHL6; PIG15; apoferritin; placenta immunoregulatory factor; proliferation-inducing protein 15 | FTH1 |
| 88 | glutamate decarboxylase 2 | glutamic acid decarboxylase (GAD65) antibodies; Glutamate decarboxylase-2 (pancreas); glutamate decarboxylase 2 (pancreatic islets and brain, 65 kD) | GAD2 |
| 89 | Galanin | GALN; GLNN; galanin-related peptide | GAL |
| 90 | Gastrin | gastrin - GAS | GAST |
| 91 | glucagon | glucagon-like peptide-1, GLP-1, GLP2, GRPP, glicentin-related polypeptide; glucagon-like peptide 1; glucagon-like peptide 2 | GCG |
| 92 | Glucokinase | hexokinase 4, maturity to onset Diabetes of the young 2; GK; GLK; HK4; HHF3; HKIV; HXKP; MODY2 | GCK |
| 93 | gamma-glutamyltransferase 1 | GGT; GTG; CD224; glutamyl transpeptidase; gamma-glutamyl transpeptidase | GGT1 |
| 94 | growth hormone 1 | growth hormone - GH, GH-N, GHN, hGH-N, pituitary growth hormone | GH1 |
| 95 | ghrelin/obestatin preprohormone | ghrelin - MTLRP, ghrelin, obestatin, ghrelin; ghrelin precursor; ghrelin, growth hormone secretagogue receptor ligand; motilin-related peptide | GHRL |
| 96 | gastric inhibitory polypeptide | glucose-dependent insulinotropic peptide | GIP |
| 97 | gastric inhibitory polypeptide receptor | GIP Receptor | GIPR |
| 98 | glucagon-like peptide 1 receptor | glucagon-like peptide 1 receptor | GLP1R |

TABLE 1-continued

| ALLDBRISK | Official Name | Common Name | Entrez Gene Link |
|---|---|---|---|
| 99 | guanine nucleotide binding protein (G protein), beta polypeptide 3 | G-protein beta-3 subunit - G protein, beta-3 subunit; GTP-binding regulatory protein beta-3 chain; guanine nucleotide-binding protein G(I)/G(S)/G(T) beta subunit 3; guanine nucleotide-binding protein, beta-3 subunit; hypertension associated protein; transducin beta chain 3 | GNB3 |
| 100 | glutamic-pyruvate transaminase (alanine aminotransferase) | glutamic-pyruvate transaminase (alanine aminotransferase), AAT1, ALT1, GPT1 | GPT |
| 101 | gastrin releasing peptide (bombesin) | bombesin; BN; GRP-10; proGRP; preproGRP; neuromedin C; pre-progastrin releasing peptide | GRP |
| 102 | gelsolin (amyloidosis, Finnish type) | Gelsolin | GSN |
| 103 | Hemoglobin | CD31; alpha-1 globin; alpha-1-globin; alpha-2 globin; alpha-2-globin; alpha one globin; hemoglobin alpha 2; hemoglobin alpha-2; hemoglobin alpha-1 chain; hemoglobin alpha 1 globin chain, glycosylated hemoglobin, HBA1c | HBA1 |
| 104 | hemoglobin, beta | HBD, beta globin | HBB |
| 105 | hypocretin (orexin) neuropeptide precursor | orexin A; OX; PPOX | HCRT |
| 106 | hepatocyte growth factor (hepapoietin A; scatter factor) | Hepatocyte growth factor (HGF) - F-TCF, HGFB, HPTA, SF, fibroblast-derived tumor cytotoxic factor; hepatocyte growth factor; hepatopoietin A; lung fibroblast-derived mitogen; scatter factor | HGF |
| 107 | hepatocyte nuclear factor 4, alpha | hepatocyte nuclear factor 4 - HNF4, HNF4a7, HNF4a8, HNF4a9, MODY, MODY1, NR2A1, NR2A21, TCF, TCF14, HNF4-alpha; hepatic nuclear factor 4 alpha; hepatocyte nuclear factor 4 alpha; transcription factor-14 | HNF4A |
| 108 | haptoglobin | haptoglobin - hp2-alpha | HP |
| 109 | hydroxysteroid (11-beta) dehydrogenase 1 | Corticosteroid 11-beta-dehydrogenase, isozyme 1; HDL; 11-DH; HSD11; HSD11B; HSD11L; 11-beta-HSD1 | HSD11B1 |
| 110 | heat shock 70 kDa protein 1B | HSP70-2, heat shock 70 kD protein 1B | HSPA1B |
| 111 | islet amyloid polypeptide | Amylin - DAP, IAP, Islet amyloid polypeptide (Diabetes-associated peptide; amylin) | IAPP |
| 112 | intercellular adhesion molecule 1 (CD54), human rhinovirus receptor | soluble intercellular adhesion molecule-1, BB2, CD54, P3.58, 60 bp after segment 1; cell surface glycoprotein; cell surface glycoprotein P3.58; intercellular adhesion molecule 1 | ICAM1 |
| 113 | Intercellular adhesion molecule 3 (CD50), | CD50, CDW50, ICAM-R intercellular adhesion molecule-3 | ICAM3 |
| 114 | interferon, gamma | IFNG: IFG; IFI | IFNG |
| 115 | insulin-like growth factor 1 (somatomedin C) | IGF-1: somatomedin C. insulin-like growth factor-1 | IGF1 |
| 116 | insulin-like growth factor 2 (somatomedin A) | IGF-II polymorphisms (somatomedin A) - C11orf43, INSIGF, pp9974, insulin-like growth factor 2; insulin-like growth factor II; insulin-like growth factor type 2; putative insulin-like growth factor II associated protein | IGF2 |
| 117 | insulin-like growth factor binding protein 1 | insulin-like growth factor binding protein-1 (IGFBP-1) - AFBP, IBP1, IGF-BP25, PP12, hIGFBP-1, IGF-binding protein 1; alpha-pregnancy-associated endometrial globulin; amniotic fluid binding protein; binding protein-25; binding protein-26; binding protein-28; growth hormone independent-binding protein; placental protein 12 | IGFBP1 |
| 118 | insulin-like growth factor binding protein 3 | insulin-like growth factor binding protein 3: IGF-binding protein 3 - BP-53, IBP3, IGF-binding protein 3; acid stable subunit of the 140 K IGF complex; binding protein 29; binding protein 53; growth hormone-dependent binding protein | IGFBP3 |
| 119 | inhibitor of kappa light polypeptide gene enhancer in B-cells, kinase beta | ikk-beta; IKK2; IKKB; NFKBIKB; IKK-beta; nuclear factor NF-kappa-B inhibitor kinase beta; inhibitor of nuclear factor kappa B kinase beta subunit | IKBKB |

TABLE 1-continued

| ALLDBRISK | Official Name | Common Name | Entrez Gene Link |
|---|---|---|---|
| 120 | interleukin 10 | IL-10, CSIF, IL-10, IL10A, TGIF, cytokine synthesis inhibitory factor | IL10 |
| 121 | interleukin 18 (interferon-gamma-inducing factor) | IL-18 - IGIF, IL-18, IL-1g, IL1F4, IL-1 gamma; interferon-gamma-inducing factor; interleukin 18; interleukin-1 gamma; interleukin-18 | IL18 |
| 122 | interleukin 1, alpha | IL 1 - IL-1A, IL1, IL1-ALPHA, IL1F1, IL1A (IL1F1); hematopoietin-1; preinterleukin 1 alpha; pro-interleukin-1-alpha | IL1A |
| 123 | interleukin 1, beta | interleukin-1 beta (IL-1 beta) - IL-1, IL1-BETA, IL1F2, catabolin; preinterleukin 1 beta; pro-interleukin-1-beta | IL1B |
| 124 | interleukin 1 receptor antagonist | interleukin-1 receptor antagonist (IL-1Ra) - ICIL-1RA, IL-1ra3, IL1F3, IL1RA, IRAP, IL1RN (IL1F3); intracellular IL-1 receptor antagonist type II; intracellular interleukin-1 receptor antagonist (icIL-1ra); type II interleukin-1 receptor antagonist | IL1RN |
| 125 | interleukin 2 | interleukin-2 (IL-2) - IL-2, TCGF, lymphokine, T cell growth factor; aldesleukin; interleukin-2; involved in regulation of T-cell clonal expansion | IL2 |
| 126 | interleukin 2 receptor, alpha | Interleukin-2 receptor; IL-2RA; IL2RA; RP11-536K7.1; CD25; IDDM10; IL2R; TCGFR; interleukin 2 receptor, alpha chain | IL2RA |
| 127 | interleukin 6 (interferon, beta 2) | Interleukin-6 (IL-6), BSF2, HGF, HSF, IFNB2, IL-6 | IL6 |
| 128 | interleukin 6 receptor | interleukin-6 receptor, soluble (sIL-6R) - CD126, IL-6R-1, IL-6R-alpha, IL6RA, CD126 antigen; interleukin 6 receptor alpha subunit | IL6R |
| 129 | interleukin 6 signal transducer (gp130, oncostatin M receptor) | CD130, CDw130, GP130, GP130-RAPS, IL6R-beta; CD130 antigen; IL6ST nirs variant 3; gp130 of the rheumatoid arthritis antigenic peptide-bearing soluble form; gp130 transducer chain; interleukin 6 signal transducer; interleukin receptor beta chain; membrane glycoprotein gp130; oncostatin M receptor | Il6ST |
| 130 | interleukin 8 | Interleukin-8 (IL-8), 3-10C, AMCF-I, CXCL8, GCP-1, GCP1, IL-8, K60, LECT, LUCT, LYNAP, MDNCF, MONAP, NAF, NAP-1, NAP1, SCYB8, TSG-1, b-ENAP, CXC chemokine ligand 8; LUCT/interleukin-8; T cell chemotactic factor; beta-thromboglobulin-like protein; chemokine (C—X—C motif) ligand 8; emoctakin; granulocyte chemotactic protein 1; lymphocyte-derived neutrophil-activating factor; monocyte derived neutrophil-activating protein; monocyte-derived neutrophil chemotactic factor; neutrophil-activating factor; neutrophil-activating peptide 1; neutrophil-activating protein 1; protein 3-10C; small inducible cytokine subfamily B, member 8 | IL8 |
| 131 | inhibin, beta A (activin A, activin AB alpha polypeptide) | activin A - EDF, FRP, Inhibin, beta-1; inhibin beta A | INHBA |
| 132 | insulin | Insulin (mature polypeptide) | INSULIN-M |
| 133 | insulin receptor | CD220, HHF5 | INSR |
| 134 | insulin promoter factor-1 | IPF-1, PDX-1 (pancreatic and duodenal homeobox factor-1) | IPF1 |
| 135 | insulin receptor substrate 1 | HIRS-1 | IRS1 |
| 136 | insulin receptor substrate-2 | IRS2 | IRS2 |
| 137 | potassium inwardly-rectifying channel, subfamily J, member 11 | ATP gated K+ channels, Kir 6.2; BIR; HHF2; PHHI; IKATP; KIR6.2 | KCNJ11 |
| 138 | potassium inwardly-rectifying channel, subfamily J, member 8 | ATP gated K+ channels, Kir 6.1 | KCNJ8 |
| 139 | klotho | klotho | KL |
| 140 | kallikrein B, plasma (Fletcher factor) 1 | kallikrein 3 - KLK3 - Kallikrein, plasma; kallikrein 3, plasma; kallikrein B plasma; kininogenin; plasma kallikrein B1 | KLKB1 |

TABLE 1-continued

| ALLDBRISK | Official Name | Common Name | Entrez Gene Link |
|---|---|---|---|
| 141 | leptin (obesity homolog, mouse) | leptin - OB, OBS, leptin; leptin (murine obesity homolog); obesity; obesity (murine homolog, leptin) | LEP |
| 142 | leptin receptor | leptin receptor, soluble - CD295, OBR, OB receptor | LEPR |
| 143 | legumain | putative cysteine protease 1 - AEP, LGMN1, PRSC1, asparaginyl endopeptidase; cysteine protease 1; protease, cysteine, 1 (legumain) | LGMN |
| 144 | lipoprotein, Lp(a) | lipoprotein (a) [Lp(a)], AK38, APOA, LP, Apolipoprotein Lp(a); antiangiogenic AK38 protein; apolipoprotein(a) | LPA |
| 145 | lipoprotein lipase | LPL - LIPD | LPL |
| 146 | v-maf musculoaponeurotic fibrosarcoma oncogene homolog A (avian) | MafA (transcription factor) - RIPE3b1, hMafA, v-maf musculoaponeurotic fibrosarcoma oncogene homolog A | MAFA |
| 147 | mitogen-activated protein kinase 8 interacting protein 1 | IB1, JIP-1, JIP1, PRKM8IP, JNK-interacting protein 1; PRKM8 interacting protein; islet-brain 1 | MAPK8IP1 |
| 148 | mannose-binding lectin (protein C) 2, soluble (opsonic defect) | COLEC1, HSMBPC, MBL, MBP, MBP1, Mannose-binding lectin 2, soluble (opsonic defect); mannan-binding lectin; mannan-binding protein; mannose binding protein; mannose-binding protein C; soluble mannose-binding lectin | MBL2 |
| 149 | melanocortin 4 receptor | G protein coupled receptor MC4 | MC4R |
| 150 | melanin-concentrating hormone receptor 1 | G Protein-Coupled Receptor 24 - GPR24, MCH1R, SLC1, G protein-coupled receptor 24; G-protein coupled receptor 24 isoform 1, GPCR24 | MCHR1 |
| 151 | matrix metallopeptidase 12 (macrophage elastase) | Matrix Metalloproteinases (MMP), HME, MME, macrophage elastase; macrophage metalloelastase; matrix metalloproteinase 12; matrix metalloproteinase 12 (macrophage elastase) | MMP12 |
| 152 | matrix metallopeptidase 14 (membrane-inserted) | Matrix Metalloproteinases (MMP), MMP-X1, MT1-MMP, MTMMP1, matrix metalloproteinase 14; matrix metalloproteinase 14 (membrane-inserted); membrane type 1 metalloprotease; membrane-type matrix metalloproteinase 1; membrane-type-1 matrix metalloproteinase | MMP14 |
| 153 | matrix metallopeptidase 2 (gelatinase A, 72 kDa gelatinase, 72 kDa type IV collagenase) | Matrix Metalloproteinases (MMP), MMP-2, CLG4, CLG4A, MMP-II, MONA, TBE-1, 72 kD type IV collagenase; collagenase type IV-A; matrix metalloproteinase 2; matrix metalloproteinase 2 (gelatinase A, 72 kD gelatinase, 72 kD type IV collagenase); matrix metalloproteinase 2 (gelatinase A, 72 kDa gelatinase, 72 kDa type IV collagenase); matrix metalloproteinase-II; neutrophil gelatinase | MMP2 |
| 154 | matrix metallopeptidase 9 (gelatinase B, 92 kDa gelatinase, 92 kDa type IV collagenase) | Matrix Metalloproteinases (MMP), MMP-9, CLG4B, GELB, 92 kD type IV collagenase; gelatinase B; macrophage gelatinase; matrix metalloproteinase 9; matrix metalloproteinase 9 (gelatinase B, 92 kD gelatinase, 92 kD type IV collagenase); matrix metalloproteinase 9 (gelatinase B, 92 kDa gelatinase, 92 kDa type IV collagenase); type V collagenase | MMP9 |
| 155 | nuclear receptor co-repressor 1 | NCoR; thyroid hormone- and retinoic acid receptor-associated corepressor 1 | NCOR1 |
| 156 | neurogenic differentiation 1 | neuroD (transcription factor) - BETA2, BHF-1, NEUROD | NEUROD1 |
| 157 | nuclear factor of kappa light polypeptide gene enhancer in B-cells 1(p105) | nuclear factor, kappa B (NFKB); DNA binding factor KBF1; nuclear factor NF-kappa-B p50 subunit; nuclear factor kappa-B DNA binding subunit | NFKB1 |
| 158 | nerve growth factor, beta polypeptide | B-type neurotrophic growth factor (BNGF) - beta-nerve growth factor; nerve growth factor, beta subunit | NGFB |
| 159 | non-insulin-dependent Diabetes Mellitus (common, type 2) 1 | NIDDM1 | NIDDM1 |

TABLE 1-continued

| ALLDBRISK | Official Name | Common Name | Entrez Gene Link |
|---|---|---|---|
| 160 | non-insulin-dependent Diabetes Mellitus (common, type 2) 2 | NIDDM2 | NIDDM2 |
| 161 | Noninsulin-dependent Diabetes Mellitus 3 | NIDDM3 | NIDDM3 |
| 162 | nischarin (imidazoline receptor) | imidazoline receptor; IRAS; I-1 receptor candidate protein; imidazoline receptor candidate; imidazoline receptor antisera selected | NISCH |
| 163 | NF-kappaB repressing factor | NRF; ITBA4 gene; transcription factor NRF; NF-kappa B repressing factor; NF-kappa B-repressing factor | NKRF |
| 164 | neuronatin | Peg5 | NNAT |
| 165 | nitric oxide synthase 2A | NOS, type II; nitric oxide synthase, macrophage | NOS2A |
| 166 | Niemann-Pick disease, type C2 | epididymal secreting protein 1 - HE1, NP-C2, epididymal secretory protein; epididymal secretory protein E1; tissue-specific secretory protein | NPC2 |
| 167 | natriuretic peptide precursor B | B-type Natriuretic Peptide (BNP), BNP, brain type natriuretic peptide, pro-BNP?, NPPB | NPPB |
| 168 | nuclear receptor subfamily 1, group D, member 1 | Human Nuclear Receptor NR1D1 - EAR1, THRA1, THRAL, ear-1, hRev, Rev-erb-alpha; thyroid hormone receptor, alpha-like | NR1D1 |
| 169 | nuclear respiratory factor 1 | NRF1; ALPHA-PAL; alpha palindromic-binding protein | NRF1 |
| 170 | oxytocin, prepro-(neurophysin I) | oxytocin - OT, OT-NPI, oxytocin-neurophysin I; oxytocin-neurophysin I, preproprotein | OXT |
| 171 | purinergic receptor P2Y, G-protein coupled, 10 | G Protein Coupled Receptor P2Y10 - P2Y10, G-protein coupled purinergic receptor P2Y10; P2Y purinoceptor 10; P2Y-like receptor | P2RY10 |
| 172 | purinergic receptor P2Y, G-protein coupled, 12 | G Protein-Coupled Receptor P2Y12 - ADPG-R, HORK3, P2T(AC), P2Y(AC), P2Y(ADP), P2Y(cyc), P2Y12, SP1999, ADP-glucose receptor; G-protein coupled receptor SP1999; Gi-coupled ADP receptor HORK3; P2Y purinoceptor 12; platelet ADP receptor; purinergic receptor P2RY12; purinergic receptor P2Y, G-protein coupled 12; purinergic receptor P2Y12; putative G-protein coupled receptor | P2RY12 |
| 173 | purinergic receptor P2Y, G-protein coupled, 2 | Purinoceptor 2 Type Y (P2Y2) - HP2U, P2RU1, P2U, P2U1, P2UR, P2Y2, P2Y2R, ATP receptor; P2U nucleotide receptor; P2U purinoceptor 1; P2Y purinoceptor 2; purinergic receptor P2Y2; purinoceptor P2Y2 | P2RY2 |
| 174 | progestagen-associated endometrial protein (placental protein 14, pregnancy-associated endometrial alpha-2-globulin, alpha uterine protein) | glycodelin-A; glycodelin-F; glycodelin-S; progesterone-associated endometrial protein | PAEP |
| 175 | paired box gene 4 | Pax4 (transcription factor) - paired domain gene 4 | PAX4 |
| 176 | pre-B-cell colony enhancing factor 1 | visfatin; nicotinamide phosphoribosyltransferase | PBEF1 |
| 177 | phosphoenolpyruvate carboxykinase 1 (PEPCK1) | PEPCK1; PEP carboxykinase; phosphopyruvate carboxylase; phosphoenolpyruvate carboxylase | PCK1 |
| 178 | proprotein convertase subtilisin/kexin type 1 | proprotein convertase 1 (PC1, PC3, PCSK1, cleaves pro-insulin) | PCSK1 |
| 179 | placental growth factor, vascular endothelial growth factor-related protein | placental growth factor - PLGF, PlGF-2 | PGF |
| 180 | phosphoinositide-3-kinase, catalytic, alpha polypeptide | PI3K, p110-alpha, PI3-kinase p110 subunit alpha; PtdIns-3-kinase p110; phosphatidylinositol 3-kinase, catalytic, 110-KD, alpha; phosphatidylinositol 3-kinase, catalytic, alpha polypeptide; phosphatidylinositol-4,5-bisphosphate 3-kinase catalytic subunit, alpha isoform | PIK3CA |
| 181 | phosphoinositide-3-kinase, regulatory subunit 1 (p85 alpha) | phophatidylinositol 3-kinase; phosphatidylinositol 3-kinase, regulatory, 1; phosphatidylinositol 3-kinase-associated p-85 alpha; phosphoinositide-3-kinase, regulatory subunit, polypeptide | PIK3R1 |

TABLE 1-continued

| ALLDBRISK | Official Name | Common Name | Entrez Gene Link |
|---|---|---|---|
| | | 1 (p85 alpha); phosphatidylinositol 3-kinase, regulatory subunit, polypeptide 1 (p85 alpha) | |
| 182 | phospholipase A2, group XIIA | PLA2G12, group XII secreted phospholipase A2; group XIIA secreted phospholipase A2 | PLA2G12A |
| 183 | phospholipase A2, group IID | phospholipase A2, secretory - SPLASH, sPLA2S, secretory phospholipase A2s | PLA2G2D |
| 184 | plasminogen activator, tissue | tissue Plasminogen Activator (tPA), T-PA, TPA, alteplase; plasminogen activator, tissue type; reteplase; t-plasminogen activator; tissue plasminogen activator (t-PA) | PLAT |
| 185 | patatin-like phospholipase domain containing 2 | Adipose tissue lipase, ATGL - ATGL, TTS-2.2, adipose triglyceride lipase; desnutrin; transport-secretion protein 2.2; triglyceride hydrolase | PNPLA2 |
| 186 | proopiomelanocortin (adrenocorticotropin/beta-lipotropin/ alpha-melanocyte stimulating hormone/ beta-melanocyte stimulating hormone/ beta-endorphin) | proopiomelanocortin - beta-LPH; beta-MSH; alpha-MSH; gamma-LPH; gamma-MSH; corticotropin; beta-endorphin; met-enkephalin; lipotropin beta; lipotropin gamma; melanotropin beta; N-terminal peptide; melanotropin alpha; melanotropin gamma; pro-ACTH-endorphin; adrenocorticotropin; pro-opiomelanocortin; corticotropin-lipotropin; adrenocorticotropic hormone; alpha-melanocyte-stimulating hormone; corticotropin-like intermediary peptide | POMC |
| 187 | paraoxonase 1 ESA, PON, Paraoxonase | paraoxonase - ESA, PON, Paraoxonase | PON1 |
| 188 | peroxisome proliferative activated receptor, alpha | Peroxisome proliferator-activated receptor (PPAR), NR1C1, PPAR, hPPAR, PPAR alpha | PPARA |
| 189 | peroxisome proliferative activated receptor, delta | Peroxisome proliferator-activated receptor (PPAR), FAAR, NR1C2, NUC1, NUCI, NUCII, PPAR-beta, PPARB, nuclear hormone receptor 1, PPAR Delta | PPARD |
| 190 | peroxisome proliferative activated receptor, gamma | Peroxisome proliferator-activated receptor (PPAR), HUMPPARG, NR1C3, PPARG1, PPARG2, PPAR gamma; peroxisome proliferative activated receptor gamma; peroxisome proliferator activated-receptor gamma; peroxisome proliferator-activated receptor gamma 1; ppar gamma2 | PPARG |
| 191 | peroxisome proliferative activated receptor, gamma, coactivator 1 | Pgc1 alpha; PPAR gamma coactivator-1; ligand effect modulator-6; PPAR gamma coactivator variant form3 | PPARGC1A |
| 192 | protein phosphatase 1, regulatory (inhibitor) subunit 3A (glycogen and sarcoplasmic reticulum binding subunit, skeletal muscle) | PP1G, PPP1R3, protein phosphatase 1 glycogen-associated regulatory subunit; protein phosphatase 1 glycogen-binding regulatory subunit 3; protein phosphatase type-1 glycogen targeting subunit; serine/threonine specific protein phosphatase; type-1 protein phosphatase skeletal muscle glycogen targeting subunit | PPP1R3A |
| 193 | protein phosphatase 2A, regulatory subunit B' (PR 53) | protein phosphatase 2A - PP2A, PR53, PTPA, PP2A, subunit B'; phosphotyrosyl phosphatase activator; protein phosphatase 2A, regulatory subunit B' | PPP2R4 |
| 194 | protein kinase, AMP-activated, beta 1 non-catalytic subunit | on list as adenosine monophosphate kinase? - AMPK, HAMPKb, 5'-AMP-activated protein kinase beta-1 subunit; AMP-activated protein kinase beta 1 non-catalytic subunit; AMP-activated protein kinase beta subunit; AMPK beta-1 chain; AMPK beta 1; protein kinase, AMP-activated, noncatalytic, beta-1 | PRKAB1 |
| 195 | protein kinase, cAMP-dependent, catalytic, alpha | PKA (kinase) - PKACA, PKA C-alpha; cAMP-dependent protein kinase catalytic subunit alpha; cAMP-dependent protein kinase catalytic subunit alpha, isoform 1; protein kinase A catalytic subunit | PRKACA |
| 196 | protein kinase C, epsilon | PKC-epsilon - PKCE, nPKC-epsilon | PRKCE |

TABLE 1-continued

| ALLDBRISK | Official Name | Common Name | Entrez Gene Link |
|---|---|---|---|
| 197 | proteasome (prosome, macropain) 26S subunit, non-ATPase, 9 (Bridge-1) | Bridge-1; homolog of rat Bridge 1; 26S proteasome regulatory subunit p27; proteasome 26S non-ATPase regulatory subunit 9 | PSMD9 |
| 198 | prostaglandin E synthase | mPGES - MGST-IV, MGST1-L1, MGST1L1, PGES, PIG12, PP102, PP1294, TP53I12 Other Designations: MGST1-like 1; glutathione S-transferase 1-like 1; microsomal glutathione S-transferase 1-like 1; p53-induced apoptosis protein 12; p53-induced gene 12; tumor protein p53 inducible protein 12 | PTGES |
| 199 | prostaglandin-endoperoxide synthase 2 (prostaglandin G/H synthase and cyclooxygenase) | Cyclo-oxygenase-2 (COX-2) - COX-2, COX2, PGG/HS, PGHS-2, PHS-2, hCox-2, cyclooxygenase 2b; prostaglandin G/H synthase and cyclooxygenase; prostaglandin-endoperoxide synthase 2 | PTGS2 |
| 200 | protein tyrosine phosphatase, mitochondrial 1 | PTPMT1 - PLIP, PNAS-129, NB4 apoptosis/differentiation related protein; PTEN-like phosphatase | PTPMT1 |
| 201 | Peptide YY | PYY1 | PYY |
| 202 | retinol binding protein 4, plasma (RBP4) | RBP4; retinol-binding protein 4, plasma; retinol-binding protein 4, interstitial | RBP4 |
| 203 | regenerating islet-derived 1 alpha (pancreatic stone protein, pancreatic thread protein) | regenerating gene product (Reg); protein-X; lithostathine 1 alpha; pancreatic thread protein; regenerating protein I alpha; islet cells regeneration factor; pancreatic stone protein, secretory; islet of langerhans regenerating protein | REG1A |
| 204 | resistin | resistin - ADSF, FIZZ3, RETN1, RSTN, XCP1, C/EBP-epsilon regulated myeloid-specific secreted cysteine-rich protein precursor 1; found in inflammatory zone 3 | RETN |
| 205 | ribosomal protein S6 kinase, 90 kDa, polypeptide 1 | S6-kinase 1 - HU-1, RSK, RSK1, S6K-alpha 1, (ribosomal protein S6 kinase, 90 kD, polypeptide 1); p90-RSK 1; ribosomal protein S6 kinase alpha 1; ribosomal protein S6 kinase, 90 kD, 1; ribosomal protein S6 kinase, 90 kD, polypeptide 1 | RPS6KA1 |
| 206 | Ras-related associated with Diabetes | RAD, RAD1, REM3, RAS (RAD and GEM) like GTP binding 3 | RRAD |
| 207 | serum amyloid A1 | Serum Amyloid A (SAA), PIG4, SAA, TP53I4, tumor protein p53 inducible protein 4 | SAA1 |
| 208 | selectin E (endothelial adhesion molecule 1) | E-selectin, CD62E, ELAM, ELAM1, ESEL, LECAM2, leukocyte endothelial cell adhesion molecule 2; selectin E, endothelial adhesion molecule 1 | SELE |
| 209 | selectin P (granule membrane protein 140 kDa, antigen CD62) | CD62, CD62P, FLJ45155, GMP140, GRMP, PADGEM, PSEL; antigen CD62; granulocyte membrane protein; selectin P; selectin P (granule membrane protein 140 kD, antigen CD62) | SELP |
| 210 | serpin peptidase inhibitor, clade A (alpha-1 antiproteinase, antitrypsin), member 6 | corticosteroid-binding globulin; transcortin; corticosteroid binding globulin; serine (or cysteine) proteinase inhibitor, clade A (alpha-1 antiproteinase, antitrypsin), member 6 | SERPINA6 |
| 211 | serpin peptidase inhibitor, clade E (nexin, plasminogen activator inhibitor type 1), member 1 | plasminogen activator inhibitor-1 - PAI, PAI-1, PAI1, PLANH1, plasminogen activator inhibitor, type I; plasminogen activator inhibitor-1; serine (or cysteine) proteinase inhibitor, clade E (nexin, plasminogen activator inhibitor type 1), member 1 | SERPINE1 |
| 212 | serum/glucocorticoid regulated kinase | Serum/Glucocorticoid Regulated Kinase 1 - SGK1, serine/threonine protein kinase SGK; serum and glucocorticoid regulated kinase | SGK |
| 213 | sex hormone-binding globulin | sex hormone-binding globulin (SHBG) - ABP, Sex hormone-binding globulin (androgen binding protein) | SHBG |
| 214 | thioredoxin interacting protein | Sirt1; SIR2alpha; sir2-like 1; sirtuin type 1; sirtuin (silent mating type information regulation 2, S. cerevisiae, homolog) 1 | SIRT1 |

TABLE 1-continued

| ALLDBRISK | Official Name | Common Name | Entrez Gene Link |
|---|---|---|---|
| 215 | solute carrier family 2, member 10 | glucose transporter 10 (GLUT10); ATS | SLC2A10 |
| 216 | solute carrier family 2, member 2 | glucose transporter 2 (GLUT2) | SLC2A2 |
| 217 | solute carrier family 2, member 4 | glucose transporter 4 (GLUT4) | SLC2A4 |
| 218 | solute carrier family 7 (cationic amino acid transporter, y+ system), member 1(ERR) | ERR - ATRC1, CAT-1, ERR, HCAT1, REC1L, amino acid transporter, cationic 1; ecotropic retroviral receptor | SLC7A1 |
| 219 | SNF1-like kinase 2 | Sik2; salt-inducible kinase 2; salt-inducible serine/threonine kinase 2 | SNF1LK2 |
| 220 | suppressor of cytokine signaling 3 | CIS3, Cish3, SOCS-3, SSI-3, SSI3, STAT induced STAT inhibitor 3; cytokine-induced SH2 protein 3 | SOCS3 |
| 221 | v-src sarcoma (Schmidt-Ruppin A-2) viral oncogene homolog (avian) | ASV, SRC1, c-SRC, p60-Src, proto-oncogene tyrosine-protein kinase SRC; protooncogene SRC, Rous sarcoma; tyrosine kinase pp60c-src; tyrosine-protein kinase SRC-1 | SRC |
| 222 | sterol regulatory element binding transcription factor 1 | sterol regulatory element-binding protein 1c (SREBP-1c) | SREBF1 |
| 223 | solute carrier family 2, member 4 | SMST, somatostatin-14, somatostatin-28 | SST |
| 224 | somatostatin receptor 2 | somatostatin receptor subtype 2 | SSTR2 |
| 225 | somatostatin receptor 5 | somatostatin receptor 5 - somatostatin receptor subtype 5 | SSTR5 |
| 226 | transcription factor 1, hepatic; LF-B1, hepatic nuclear factor (HNF1) | HNF1α; albumin proximal factor; hepatic nuclear factor 1; maturity onset Diabetes of the young 3; Interferon production regulator factor (HNF1) | TCF1 |
| 227 | transcription factor 2, hepatic; LF-B3; variant hepatic nuclear factor | hepatocyte nuclear factor 2 - FJHN, HNF1B, HNF1beta, HNF2, LFB3, MODY5, VHNF1, transcription factor 2 | TCF2 |
| 228 | transcription factor 7-like 2 (T-cell specific, HMG-box) | TCF7L2 - TCF-4, TCF4 | TCF7L2 |
| 229 | transforming growth factor, beta 1 (Camurati-Engelmann disease) | TGF-beta: TGF-beta 1 protein; diaphyseal dysplasia 1, progressive; transforming growth factor beta 1; transforming growth factor, beta 1; transforming growth factor-beta 1, CED, DPD1, TGFB | TGFB1 |
| 230 | transglutaminase 2 (C polypeptide, protein-glutamine-gamma-glutamyltransferase) | TG2, TGC, C polypeptide; TGase C; TGase-H; protein-glutamine-gamma-glutamyltransferase; tissue transglutaminase; transglutaminase 2; transglutaminase C | TGM2 |
| 231 | thrombospondin 1 | thrombospondin - THBS, TSP, TSP1, thrombospondin-1p180 | THBS1 |
| 232 | thrombospondin, type I, domain containing 1 | TMTSP, UNQ3010, thrombospondin type I domain-containing 1; thrombospondin, type I, domain 1; transmembrane molecule with thrombospondin module | THSD1 |
| 233 | TIMP metallopeptidase inhibitor | CSC-21K; tissue inhibitor of metalloproteinase; tissue inhibitor of metalloproteinase 2 precursor; tissue inhibitor of metalloproteinases 2 | TIMP2 |
| 234 | tumor necrosis factor (TNF superfamily, member 2) | TNF-alpha (tumour necrosis factor-alpha) - DIF, TNF-alpha, TNFA, TNFSF2, APC1 protein; TNF superfamily, member 2; TNF, macrophage-derived; TNF, monocyte-derived; cachectin; tumor necrosis factor alpha | TNF |
| 235 | tumor necrosis factor receptor superfamily, member 11b (osteoprotegerin) | MGC29565, OCIF, OPG, TR1; osteoclastogenesis inhibitory factor; osteoprotegerin | TNFRSF11B |
| 236 | tumor necrosis factor receptor superfamily, member 1A | tumor necrosis factor receptor 1 gene R92Q polymorphism - CD120a, FPF, TBP1, TNF-R, TNF-R-I, TNF-R55, TNFAR, TNFR1, TNFR55, TNFR60, p55, p55-R, p60, tumor necrosis factor binding protein 1; tumor necrosis factor receptor 1; tumor necrosis factor receptor type 1; tumor necrosis factor-alpha receptor | TNFRSF1A |
| 237 | tumor necrosis factor receptor superfamily, member 1B | soluble necrosis factor receptor - CD120b, TBPII, TNF-R-II, TNF-R75, TNFBR, TNFR2, TNFR80, p75, p75TNFR, p75 TNF receptor; tumor | TNFRSF1B |

TABLE 1-continued

| ALLDBRISK | Official Name | Common Name | Entrez Gene Link |
|---|---|---|---|
| | | necrosis factor beta receptor; tumor necrosis factor binding protein 2; tumor necrosis factor receptor 2 | |
| 238 | tryptophan hydroxylase 2 | enzyme synthesizing serotonin; neuronal tryptophan hydroxylase, NTPH | TPH2 |
| 239 | thyrotropin-releasing hormone | thyrotropin-releasing hormone | TRH |
| 240 | transient receptor potential cation channel, subfamily V, member 1 | vanilloid receptor 1 - VR1, capsaicin receptor; transient receptor potential vanilloid 1a; transient receptor potential vanilloid 1b; vanilloid receptor subtype 1, capsaicin receptor; transient receptor potential vanilloid subfamily 1 (TRPV1) | TRPV1 |
| 241 | thioredoxin interacting protein | thioredoxin binding protein 2; upregulated by 1,25-dihydroxyvitamin D-3 | TXNIP |
| 242 | thioredoxin reductase 2 | TR; TR3; SELZ; TRXR2; TR-BETA; selenoprotein Z; thioredoxin reductase 3; thioredoxin reductase beta | TXNRD2 |
| 243 | urocortin 3 (stresscopin) | archipelin, urocortin III, SCP, SPC, UCNIII, stresscopin; urocortin 3 | UCN3 |
| 244 | uncoupling protein 2 (mitochondrial, proton carrier) | UCPH, uncoupling protein 2; uncoupling protein-2 | UCP2 |
| 245 | upstream transcription factor 1 | major late transcription factor 1 | USF1 |
| 246 | urotensin 2 | PRO1068, U-II, UCN2, UII | UTS2 |
| 247 | vascular cell adhesion molecule 1 | (soluble) vascular cell adhesion molecule-1, CD106, INCAM-100, CD106 antigen, VCAM-1 | VCAM1 |
| 248 | vascular endothelial growth factor | VEGF - VEGFA, VPF, vascular endothelial growth factor A; vascular permeability factor | VEGF |
| 249 | vimentin | vimentin | VIM |
| 250 | vasoactive intestinal peptide | vasoactive intestinal peptide - PHM27 | VIP |
| 251 | vasoactive intestinal peptide receptor 1 | vasoactive intestinal peptide receptor 1 - HVR1, II, PACAP-R-2, RCD1, RDC1, VIPR, VIRG, VPAC1, PACAP type II receptor; VIP receptor, type I; pituitary adenylate cyclase activating polypeptide receptor, type II | VIPR1 |
| 252 | vasoactive intestinal peptide receptor 2 | Vasoactive Intestinal Peptide Receptor 2 - VPAC2 | VIPR2 |
| 253 | von Willebrand factor | von Willebrand factor, F8VWF, VWD, coagulation factor VIII VWF | VWF |
| 254 | Wolfram syndrome 1 (wolframin) | DFNA14, DFNA38, DFNA6, DIDMOAD, WFRS, WFS, WOLFRAMIN | WFS1 |
| 255 | X-ray repair complementing defective repair in Chinese hamster cells 6 | Ku autoantigen, 70 kDa; Ku autoantigen p70 subunit; thyroid-lupus autoantigen p70; CTC box binding factor 75 kDa subunit; thyroid autoantigen 70 kD (Ku antigen); thyroid autoantigen 70 kDa (Ku antigen); ATP-dependent DNA helicase II, 70 kDa subunit | XRCC6 |
| 256 | c-peptide | c-peptide, soluble c-peptide | SCp |
| 257 | cortisol | cortisol - hydrocortisone is the synthetic form | |
| 258 | vitamin D3 | vitamin D3 | |
| 259 | estrogen | estrogen | |
| 260 | estradiol | estradiol | |
| 261 | digitalis-like factor | digitalis-like factor | |
| 262 | oxyntomodulin | oxyntomodulin | |
| 263 | dehydroepiandrosterone sulfate (DHEAS) | dehydroepiandrosterone sulfate (DHEAS) | |
| 264 | serotonin (5-hydroxytryptamine) | serotonin (5-hydroxytryptamine) | |
| 265 | anti-CD38 autoantibodies | anti-CD38 autoantibodies | |
| 266 | gad65 autoantibody | gad65 autoantibody epitopes | |
| 267 | Proinsulin | | PROINS |
| 268 | endoglin | END; ORW; HHT1; ORW1; CD105; FLJ41744; RP11-228B15.2 | ENG |
| 269 | interleukin 2 receptor, beta | CD122; P70-75; CD122 antigen; OTTHUMP00000028799; high affinity IL-2 receptor beta subunit | IL2RB |
| 270 | insulin-like growth factor binding protein 2 | IBP2; IGF-BP53 | IGFBP2 |
| 271 | insulin-like growth factor 1 receptor | CD221, IGFIR, JTK13, MGC142170, MGC142172, MGC18216 | IGF1R |

TABLE 2

| # | Clinical Parameter ("CPs") |
|---|---|
| 272 | Age (AGE) |
| 273 | Body Mass Index (BMI) |
| 274 | Diastolic Blood Pressure (DBP) |
| 275 | Family History (FHX) (or FHX1—one parent with Diabetes; and FHX2—two parents with Diabetes) |
| 276 | Gestational Diabetes Mellitus (GDM), Past |
| 277 | Height (HT) |
| 278 | Hip Circumference (Hip) |
| 279 | Race (RACE) |
| 280 | Sex (SEX) |
| 281 | Systolic Blood Pressure (SBP) |
| 282 | Waist Circumference (Waist) |
| 283 | Weight (WT) |

(and other combinations thereof, including Waist to Hip Ratio (WHr)).

TABLE 3

| # | Traditional Laboratory Risk Factors ("TLRFs") |
|---|---|
| 284 | Cholesterol (CHOL) |
| 285 | Glucose (fasting plasma glucose (FPG/Glucose) or with oral glucose tolerance test (OGTT)) |
| 286 | HBA1c (Glycosylated Hemoglobin (HBA1/HBA1C) |
| 287 | High Density Lipoprotein (HDL/HDLC) |
| 288 | Low Density Lipoprotein (LDL/LDLC) |
| 289 | Very Low Density Lipoprotein (VLDLC) |
| 290 | Triglycerides (TRIG) |

One skilled in the art will note that the above listed ALLDBRISK markers ("ALLDBRISKS") come from a diverse set of physiological and biological pathways, including many which are not commonly accepted to be related to Diabetes. These groupings of different ALLDBRISK markers, even within those high significance segments, may presage differing signals of the stage or rate of the progression of the disease. Such distinct groupings of ALLDBRISK markers may allow a more biologically detailed and clinically useful signal from the ALLDBRISK markers as well as opportunities for pattern recognition within the ALLDBRISK algorithms combining the multiple ALLDBRISK signals.

The present invention concerns, in one aspect, a subset of ALLDBRISK markers; other ALLDBRISKS and even biomarkers which are not listed in the above Table 1, but related to these physiological and biological pathways, may prove to be useful given the signal and information provided from these studies. To the extent that other biomarker pathway participants (i.e., other biomarker participants in common pathways with those biomarkers contained within the list of ALLDBRISKS in the above Table 1) are also relevant pathway participants in pre-Diabetes, Diabetes, or a pre-diabetic condition, they may be functional equivalents to the biomarkers thus far disclosed in Table 1.

These other pathway participants are also considered ALLDBRISKS in the context of the present invention, provided they additionally share certain defined characteristics of a good biomarker, which would include both involvement in the herein disclosed biological processes and also analytically important characteristics such as the bioavailability of said biomarkers at a useful signal to noise ratio, and in a useful sample matrix such as blood serum. Such requirements typically limit the diagnostic usefulness of many members of a biological pathway, and frequently occurs only in pathway members that constitute secretory substances, those accessible on the plasma membranes of cells, as well as those that are released into the serum upon cell death, due to apoptosis or for other reasons such as endothelial remodeling or other cell turnover or cell necrotic processes, whether or not they are related to the disease progression of pre-Diabetes, a pre-diabetic condition, and Diabetes. However, the remaining and future biomarkers that meet this high standard for ALLDBRISKS are likely to be quite valuable.

Furthermore, other unlisted biomarkers will be very highly correlated with the biomarkers listed as ALLDBRISKS in Table 1 (for the purpose of this application, any two variables will be considered to be "very highly correlated" when they have a correlation (R) of 0.4 or greater). The present invention encompasses such functional and statistical equivalents to the aforementioned ALLDBRISKS. Furthermore, the statistical utility of such additional ALLDBRISKS is substantially dependent on the cross-correlation between multiple biomarkers and any new biomarkers will often be required to operate within a panel in order to elaborate the meaning of the underlying biology.

One or more, preferably two or more of the listed ALLDBRISKS can be detected in the practice of the present invention. For example, two (2), three (3), four (4), five (5), ten (10), fifteen (15), twenty (20), forty (40), fifty (50), seventy-five (75), one hundred (100), one hundred and twenty five (125), one hundred and fifty (150), one hundred and seventy-five (175), two hundred (200), two hundred and ten (210), two hundred and twenty (220), two hundred and thirty (230), two hundred and forty (240), two hundred and fifty (250), two hundred and sixty (260) or more ALLDBRISKS can be detected. In some aspects, all ALLDBRISKS listed herein can be detected. Preferred ranges from which the number of ALLDBRISKS can be detected include ranges bounded by any minimum selected from between one and all known ALLDBRISKS, particularly up to two, five, ten, twenty, twenty-five, thirty, forty, fifty, seventy-five, one hundred, one hundred and twenty five, one hundred and fifty, one hundred and seventy-five, two hundred, two hundred and ten, two hundred and twenty, two hundred and thirty, two hundred and forty, two hundred and fifty, paired with any maximum up to the total known ALLDBRISKS, particularly up to five, ten, twenty, fifty, and seventy-five. Particularly preferred ranges include two to five (2-5), two to ten (2-10), two to fifty (2-50), two to seventy-five (2-75), two to one hundred (2-100), five to ten (5-10), five to twenty (5-20), five to fifty (5-50), five to seventy-five (5-75), five to one hundred (5-100), ten to twenty (10-20), ten to fifty (10-50), ten to seventy-five (10-75), ten to one hundred (10-100), twenty to fifty (20-50), twenty to seventy-five (20-75), twenty to one hundred (20-100), fifty to seventy-five (50-75), fifty to one hundred (50-100), one hundred to one hundred and twenty-five (100-125), one hundred and twenty-five to one hundred and fifty (125-150), one hundred and fifty to one hundred and seventy five (150-175), one hundred and seventy-five to two hundred (175-200), two hundred to two hundred and ten (200-210), two hundred and ten to two hundred and twenty (210-220), two hundred and twenty to two hundred and thirty (220-230), two hundred and thirty to two hundred and forty (230-240), two hundred and forty to two hundred and fifty (240-250), two hundred and fifty to two hundred and sixty (250-260), and two hundred and sixty to more than two hundred and sixty (260+).

Construction of ALLDBRISK Panels

Groupings of ALLDBRISKS can be included in "panels." A "panel" within the context of the present invention means a group of biomarkers (whether they are ALLDBRISKS, clinical parameters, or traditional laboratory risk factors) that includes more than one ALLDBRISK. A panel can also comprise additional biomarkers, e.g., clinical parameters, traditional laboratory risk factors, known to be present or associated with Diabetes, in combination with a selected group of the ALLDBRISKS listed in Table 1.

As noted above, many of the individual ALLDBRISKS, clinical parameters, and traditional laboratory risk factors listed, when used alone and not as a member of a multi-biomarker panel of ALLDBRISKS, have little or no clinical use in reliably distinguishing individual normal (or "normoglycemic"), pre-Diabetes, and Diabetes subjects from each other in a selected general population, and thus cannot reliably be used alone in classifying any patient between those three states. Even where there are statistically significant differences in their mean measurements in each of these populations, as commonly occurs in studies which are sufficiently powered, such biomarkers may remain limited in their applicability to an individual subject, and contribute little to diagnostic or prognostic predictions for that subject. A common measure of statistical significance is the p-value, which indicates the probability that an observation has arisen by chance alone; preferably, such p-values are 0.05 or less, representing a 5% or less chance that the observation of interest arose by chance. Such p-values depend significantly on the power of the study performed.

As discussed above, in the study populations of the below Examples, none of the individual ALLDBRISKS demonstrated a very high degree of diagnostic accuracy when used by itself for the diagnosis of pre-Diabetes, even though many showed statistically significant differences between the subject populations of the Examples (as seen in FIG. 5). However, when each ALLDBRISK is taken individually to assess the individual subjects of the population, such ALLDBRISKS are of limited use in the intended risk indications for the invention (as is shown in FIG. 5). The few exceptions to this were generally in their use distinguishing frank Diabetes from normal, where several of the biomarkers (for example, glucose, insulin, HBA1c) are part of the clinical definition and symptomatic pathology of Diabetes itself.

Combinations of multiple clinical parameters used singly alone or together in formulas is another approach, but also generally has difficulty in reliably achieving a high degree of diagnostic accuracy for individual subjects when tested across multiple study populations except when the blood-borne biomarkers are included. Even when individual ALLDBRISKS that are traditionally used blood-borne biomarkers of Diabetes are added to clinical parameters, as with glucose and HDLC within the Diabetes risk index of Stern (2002), it is difficult to reliably achieve a high degree of diagnostic accuracy for individual subjects when tested across multiple study populations. Used herein, for a formula or biomarker (including ALLDBRISKS, clinical parameters, and traditional laboratory risk factors) to "reliably achieve" a given level of diagnostic accuracy meant to achieve this metric under cross-validation (such as LOO-CV or 10-Fold CV within the original population) or in more than one population (e.g., demonstrate it beyond the original population in which the formula or biomarker was originally measured and trained). It is recognized that biological variability is such that it is unlikely that any given formula or biomarker will achieve the same level of diagnostic accuracy in every individual population in which it can be measured, and that substantial similarity between such training and validation populations is assumed and, indeed, required.

Despite this individual ALLDBRISK performance, and the general performance of formulas combining only the traditional clinical parameters and few traditional laboratory risk factors, the present inventors have noted that certain specific combinations of two or more ALLDBRISKS can also be used as multi-biomarker panels comprising combinations of ALLDBRISKS that are known to be involved in one or more physiological or biological pathways, and that such information can be combined and made clinically useful through the use of various formulae, including statistical classification algorithms and others, combining and in many cases extending the performance characteristics of the combination beyond that of the individual ALLDBRISKS. These specific combinations show an acceptable level of diagnostic accuracy, and, when sufficient information from multiple ALLDBRISKS is combined in a trained formula, often reliably achieve a high level of diagnostic accuracy transportable from one population to another.

The general concept of how two less specific or lower performing ALLDBRISKS are combined into novel and more useful combinations for the intended indications, is a key aspect of the invention. Multiple biomarkers can often yield better performance than the individual components when proper mathematical and clinical algorithms are used; this is often evident in both sensitivity and specificity, and results in a greater AUC. Secondly, there is often novel unperceived information in the existing biomarkers, as such was necessary in order to achieve through the new formula an improved level of sensitivity or specificity. This hidden information may hold true even for biomarkers which are generally regarded to have suboptimal clinical performance on their own. In fact, the suboptimal performance in terms of high false positive rates on a single biomarker measured alone may very well be an indicator that some important additional information is contained within the biomarker results—information which would not be elucidated absent the combination with a second biomarker and a mathematical formula.

Several statistical and modeling algorithms known in the art can be used to both assist in ALLDBRISK selection choices and optimize the algorithms combining these choices. Statistical tools such as factor and cross-biomarker correlation/covariance analyses allow more rationale approaches to panel construction. Mathematical clustering and classification tree showing the Euclidean standardized distance between the ALLDBRISKS can be advantageously used. While such grouping may or may not give direct insight into the biology and desired informational content targets for ideal pre-Diabetes formula, it is the result of a method of factor analysis intended to group collections of ALLDBRISK with similar information content (see Examples below for more statistical techniques commonly employed). Pathway informed seeding of such statistical classification techniques also may be employed, as may rational approaches based on the selection of individual ALLDBRISK based on their participation across in particular pathways or physiological functions.

Ultimately, formula such as statistical classification algorithms can be directly used to both select ALLDBRISK and to generate and train the optimal formula necessary to combine the results from multiple ALLDBRISK into a single index. Often, techniques such as forward (from zero potential explanatory parameters) and backwards selection (from all available potential explanatory parameters) are used, and information criteria, such as AIC or BIC, are used to quantify the tradeoff between the performance and diagnostic accuracy of the panel and the number of ALLDBRISK used. The position of the individual ALLDBRISK on a forward or backwards selected panel can be closely related to its provision of incremental information content for the algorithm, so the order of contribution is highly dependent on the other constituent ALLDBRISK in the panel.

The inventors have observed that certain ALLDBRISK are frequently selected across many different formulas and model types for biomarker selection and model formula construction. One aspect of the present invention relates to selected key biomarkers that are categorized based on the frequency of the presence of the ALLDBRISK and in the best fit models of given types taken across multiple population studies, such as those shown in Examples 1 and 2 herein.

One such grouping of several classes of ALLDBRISK is presented below in Table 4 and again in FIG. 15.

ten, at least eleven, or at least twelve biomarkers can be selected from Core Biomarkers I and II, or from Additional Biomarkers I and II.

Using the categories presented above and without intending to limit the practice of the invention, several panel selection approaches can be used independently or, when larger panels are desired, in combination in order to achieve improvements in the diagnostic accuracy of a ALLDBRISK panel over the individual ALLDBRISK. A preferred One approach involves first choosing one or more ALLDBRISK

TABLE 4

| Clinical Parameters | Traditional Laboratory Risk Factors | Core Biomarkers I | Core Biomarkers II | Additional. Biomarkers I | Additional Biomarkers II |
|---|---|---|---|---|---|
| Age (AGE) Body Mass Index (BMI) Diastolic Blood Pressure (DBP) Family History (FHX) Gestational Diabetes Mellitus (GDM), Past Height (HT) Hip Circumference (Hip) Race (RACE) Sex (SEX) Systolic Blood Pressure (SBP) Waist Circumference (Waist) Weight (WT) | Cholesterol (CHOL) Glucose (fasting plasma glucose (FPG/Glucose) or with oral glucose tolerance test (OGTT)) HBA1c (Glycosylated Hemoglobin (HBA1/HBA1C) High Density Lipoprotein (HDL/HDLC) Low Density Lipoprotein (LDL/LDLC) Very Low Density Lipoprotein (VLDLC) Triglycerides (TRIG) | Adiponectin (ADIPOQ) C-Reactive Protein (CRP) Fibrinogen alpha chain (FGA) Insulin, Pro-insulin, and soluble C-Peptide (any and/or all of which, INS) Leptin (LEP) | Advanced Glycosylation End Product-Specific Receptor (AGER) Alpha-2-HS-Glycoprotein (AHSG) Angiogenin (ANG) Apolipoprotein E (APOE) CD14 molecule (CD14) Ferritin (FTH1) Insulin-like growth factor binding protein 1 (IGFBP1) Interleukin 2 Receptor, Alpha (IL2RA) Vascular Cell Adhesion Molecule 1 (VCAM1) Vascular Endothelial Growth Factor (VEGF) Von Willebrand Factor (VWF) | Chemokine (C-C motif) ligand 2 aka monocyte chemoattractant protein-1 (CCL2) Cyclin-dependent kinase 5 (CDK5) Complement Component 3 (C3) Fas aka TNF receptor superfamily, member 6 (FAS) Hepatocyte Growth Factor (HGF) Interleukin 18 (IL18) Inhibin, Beta A aka Activin-A (INHBA) Resistin (RETN) Selectin-P (SELP) Tumor Necrosis Factor Receptor Superfamily, member 1 B (TNFRSF1B) | Angiotensin-Converting Enzyme (ACE) Complement Component C4 (C4A) Complement Factor D (Adipsin) (CFD) Dipeptidyl-Peptidase 4 (CD26) (DPP4) Haptoglobin (HP) Interleukin 8 (IL8) Matrix Metallopeptidase 2 (MMP2) Selectin E (SELE) Tumor Necrosis Factor (TNF-Alpha) (TNF) Tumor Necrosis Factor Superfamily Member 1A (TNFRSF1A) |

In the context of the present invention, and without limitation of the foregoing, Table 4 above may be used to construct an ALLDBRISK panel comprising a series of individual ALLDBRISK. The table, derived using the above statistical and pathway informed classification techniques, is intended to assist in the construction of preferred embodiments of the invention by choosing individual ALLDBRISK from selected categories of multiple ALLDBRISK. Preferably, at least two biomarkers from one or more of the above lists of Clinical Parameters, Traditional Laboratory Risk Factors, Core Biomarkers I and II, and Additional Biomarkers I and II are selected, however, the invention also concerns selection of at least two, at least three, at least four, at least five, at least six, at least seven, at least eight, at least nine, at least ten, at least eleven, and at least twelve of these biomarkers, and larger panels up to the entire set of biomarkers listed herein. For example, at least two, at least three, at least four, at least five, at least six, at least seven, at least eight, at least nine, at least from the column labeled Core Biomarkers I, which represents those ALLDBRISK most frequently chosen using the various selection formula. While biomarker substitutions are possible with this approach, several biomarker selection formulas, across multiple studies and populations, have demonstrated and confirmed the importance of those ALLDBRISK listed in the Core Biomarkers I column shown above for the discrimination of subjects likely to convert to Diabetes (pre-Diabetics) from those who are not likely to do so. In general, for smaller panels, the higher performing ALLDBRISK panels generally contain ALLDBRISK chosen first from the list in the Core Biomarker I column, with the highest levels of performance when several ALLDBRISK are chosen from this category. ALLDBRISK in the Core Biomarker II column can also be chosen first, and, in sufficiently large panels may also achieve high degrees of accuracy, but generally are most useful in combination with the ALLDBRISK in the Core Biomarker I column shown above.

Panels of ALLDBRISK chosen in the above fashion may also be supplemented with one or more ALLDBRISK chosen from either or both of the columns labeled Additional Biomarkers I and Additional Biomarkers II or from the columns labeled "Traditional Laboratory Risk Factors" and "Clinical Parameters." Of the Traditional Laboratory Risk Factors, preference is given to Glucose and HBA1c. Of the Clinical Parameters, preference is given to measures of blood pressure (SBP and DBP) and of waist or hip circumference. Such Additional Biomarkers can be added to panels constructed from one or more ALLDBRISK from the Core Biomarker I and/or Core Biomarker II columns.

Finally, such Additional Biomarkers can also be used individually as initial seeds in construction of several panels together with other ALLDBRISK. The ALLDBRISK identified in the Additional Biomarkers I and Additional Biomarkers II column are identified as common substitution strategies for Core Biomarkers particularly in larger panels, and panels so constructive often still arrive at acceptable diagnostic accuracy and overall ALLDBRISK panel performance. In fact, as a group, some substitutions of Core Biomarkers for Additional Biomarkers are beneficial for panels over a certain size, and can result in different models and selected sets of ALLDBRISK in the panels selected using forward versus stepwise (looking back and testing each previous ALLDBRISK's individual contribution with each new ALLDBRISK addition to a panel) selection formula. Multiple biomarker substitutes for individual Core Biomarkers may also be derived from substitution analysis (presenting only a constrained set of biomarkers, without the relevant Core Biomarker, to the selection formula used, and comparing the before and after panels constructed) and replacement analysis (replacing the relevant Core Biomarker with every other potential biomarker parameter, reoptimizing the formula coefficients or weights appropriately, and ranking the best replacements by a performance criteria).

Figure 24:
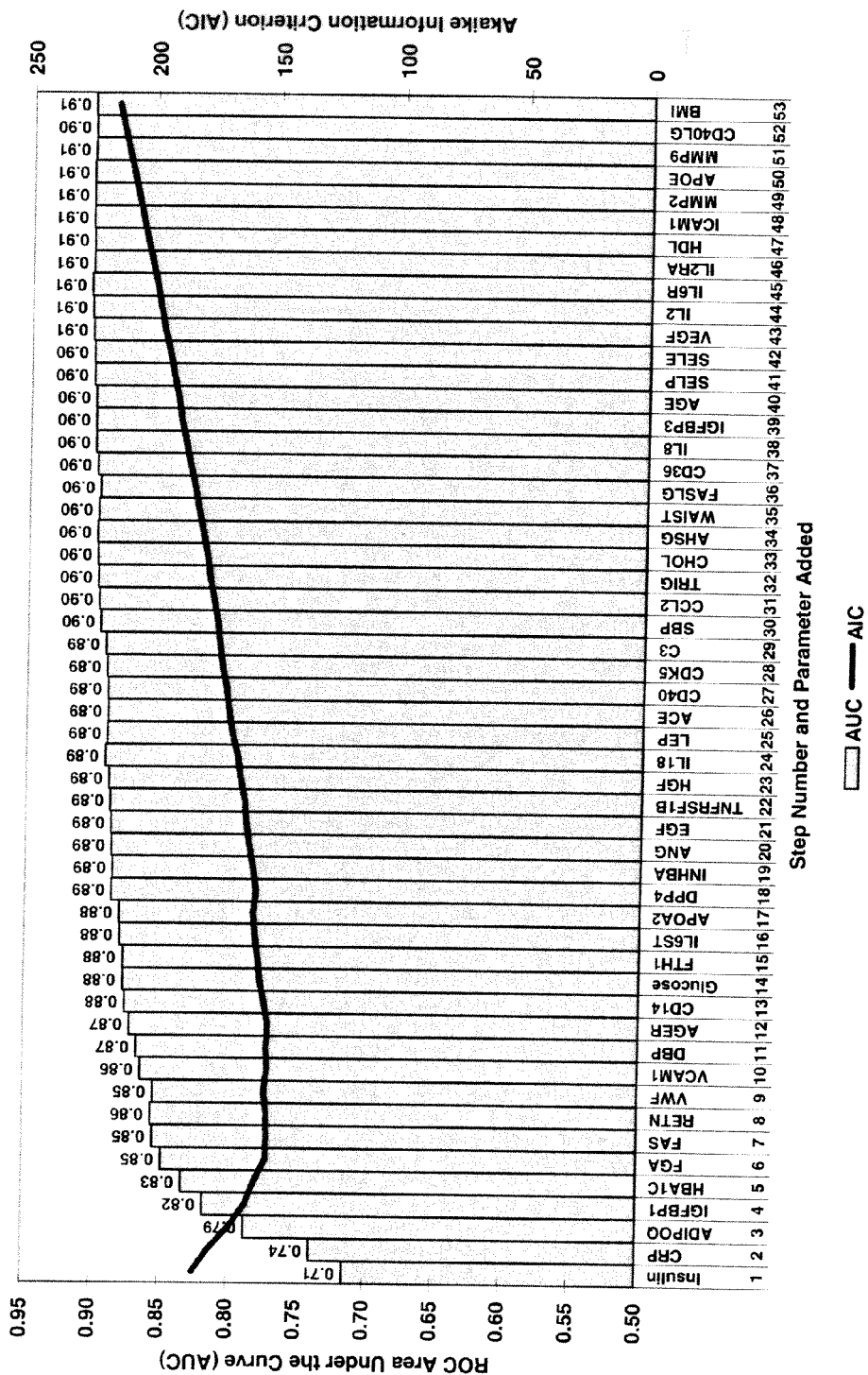
FIG. 24 is a graph showing the entire LDA forward-selected set of all tested biomarkers with model AUC and Akaike Information Criterion (AIC) statistics at each biomarker addition step, as measured and calculated in the Base Population of Example 1.
Figure 26A:
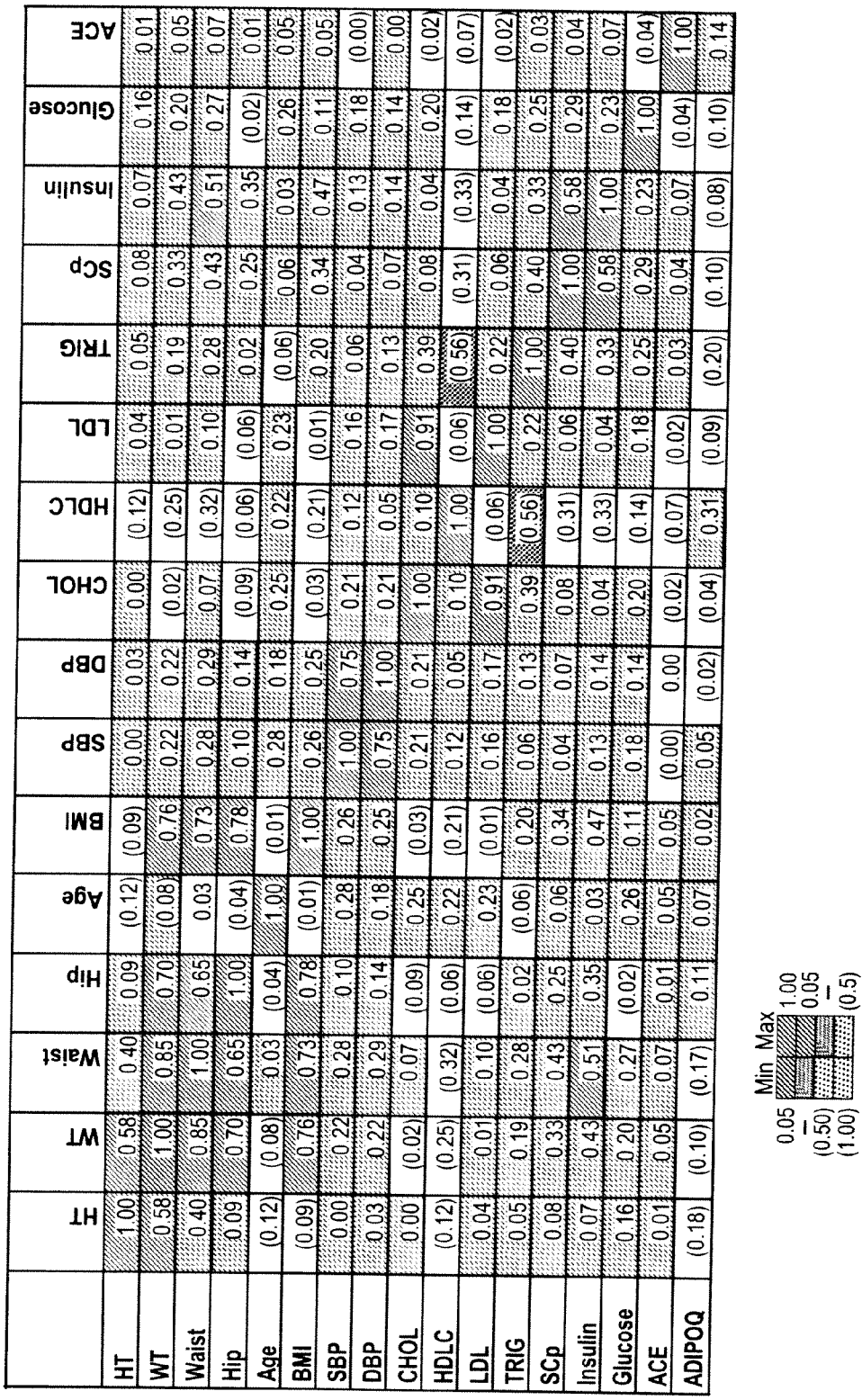
Figure 26C:
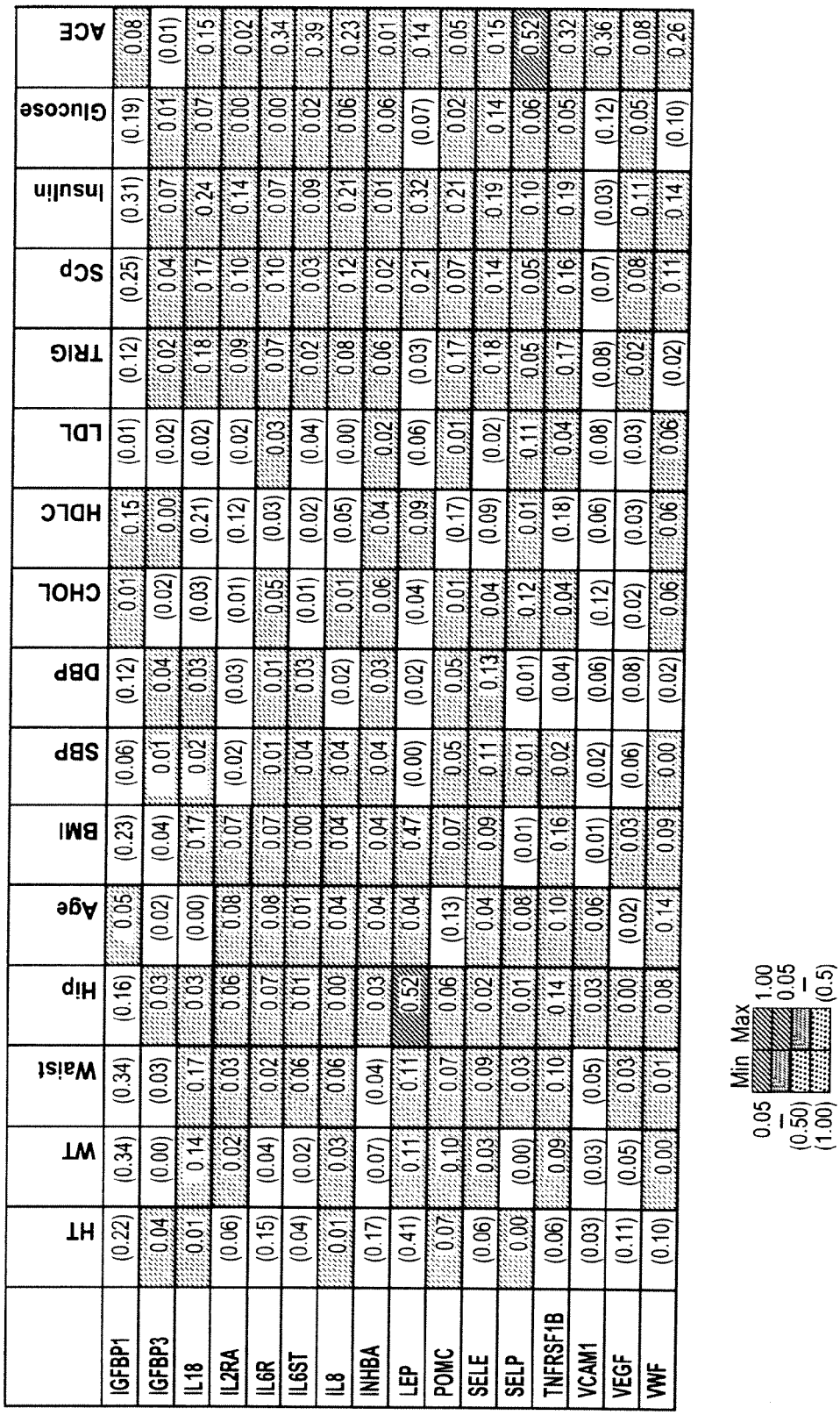
Figure 26D:
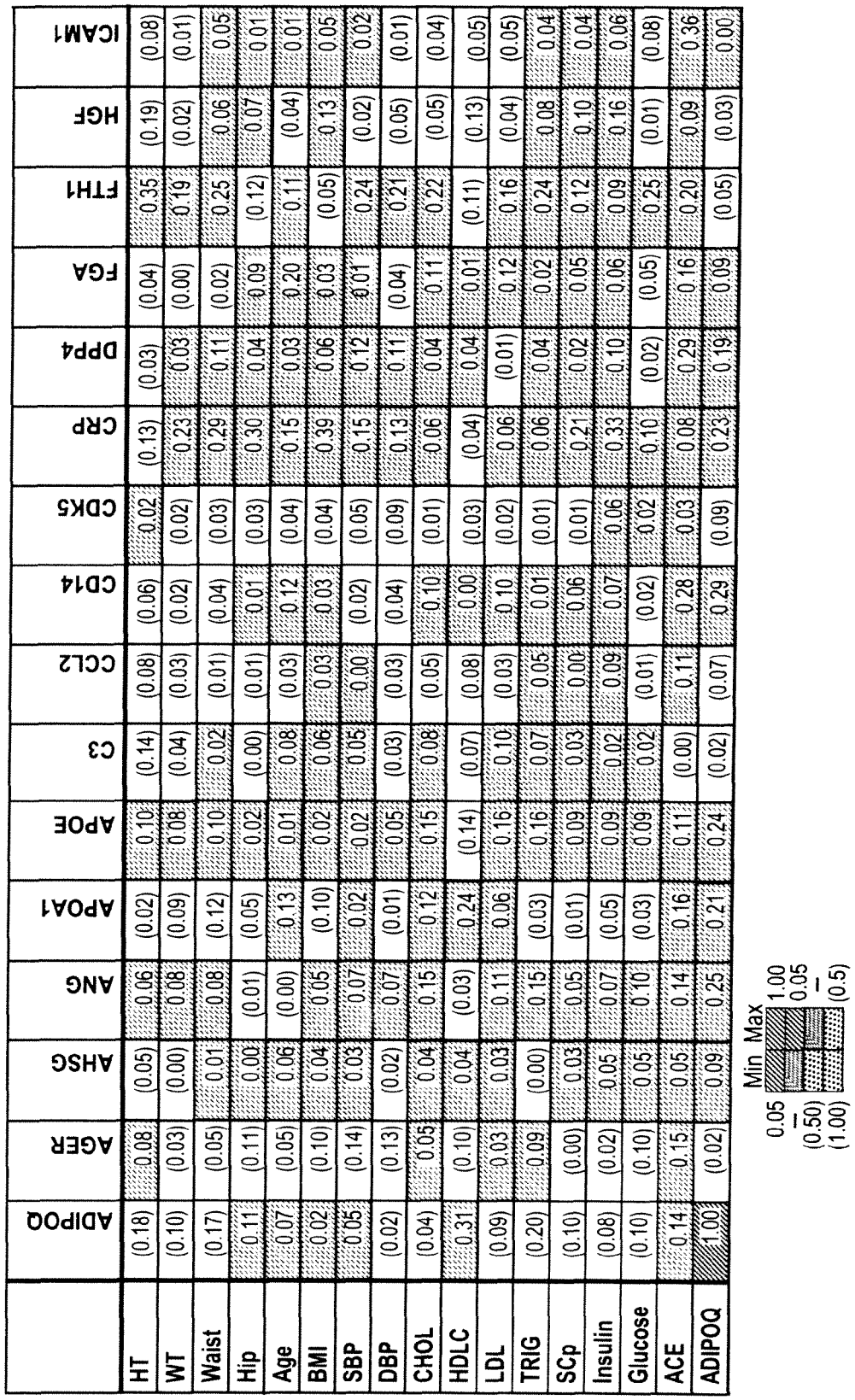
Figure 26E:
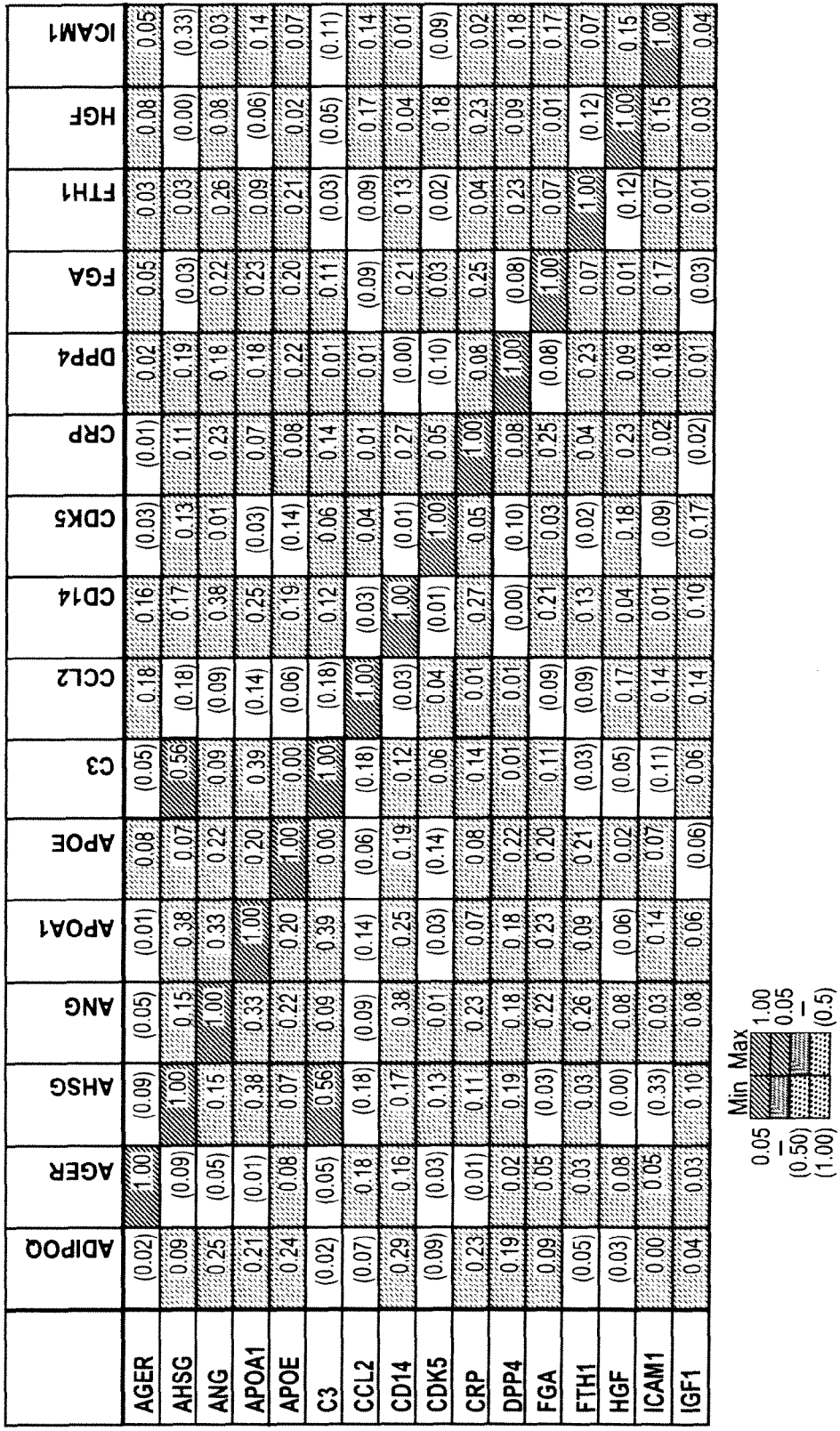
Figure 26F:
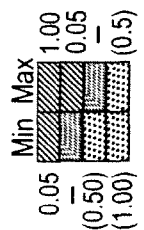
Figure 26G:
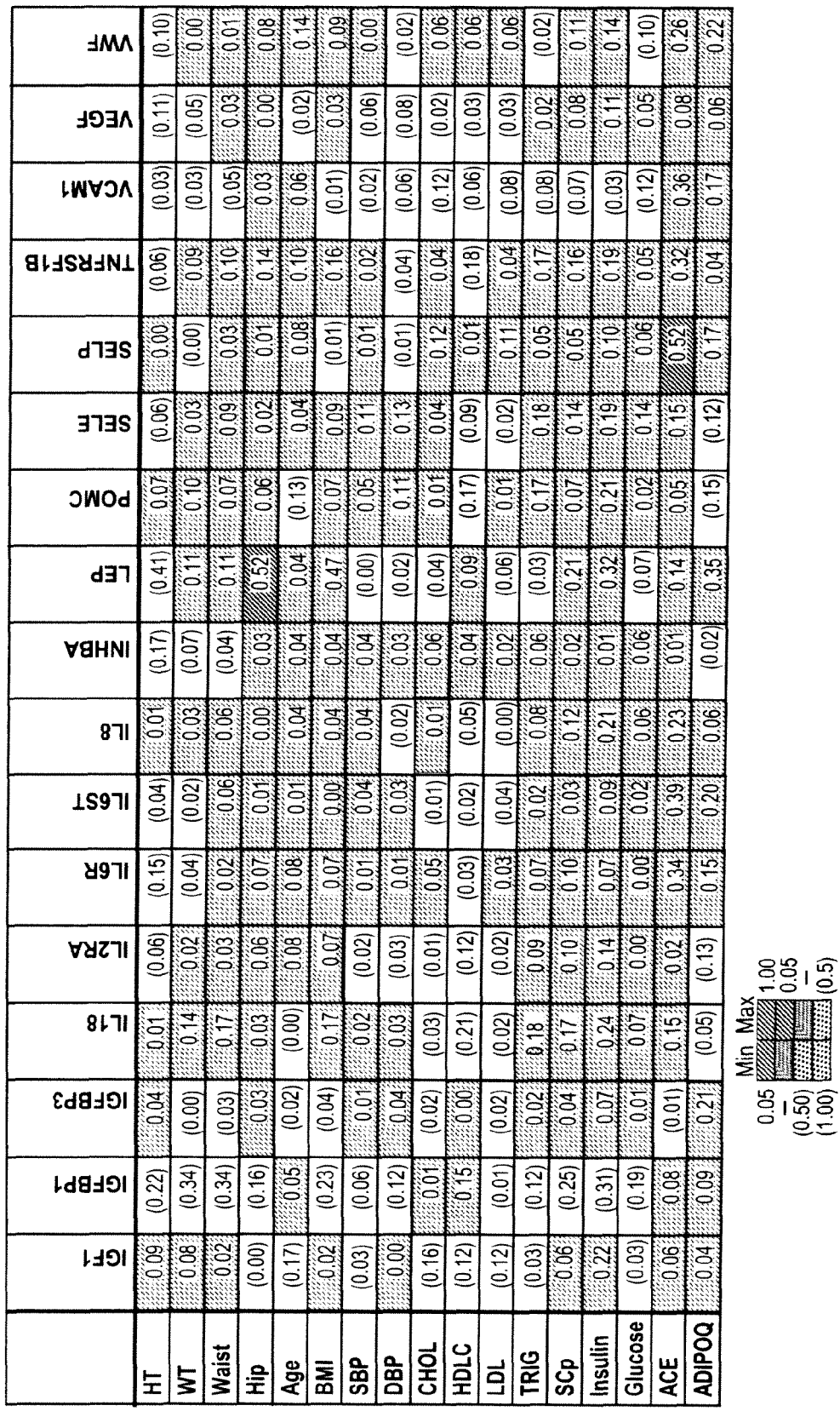
Figure 26H:
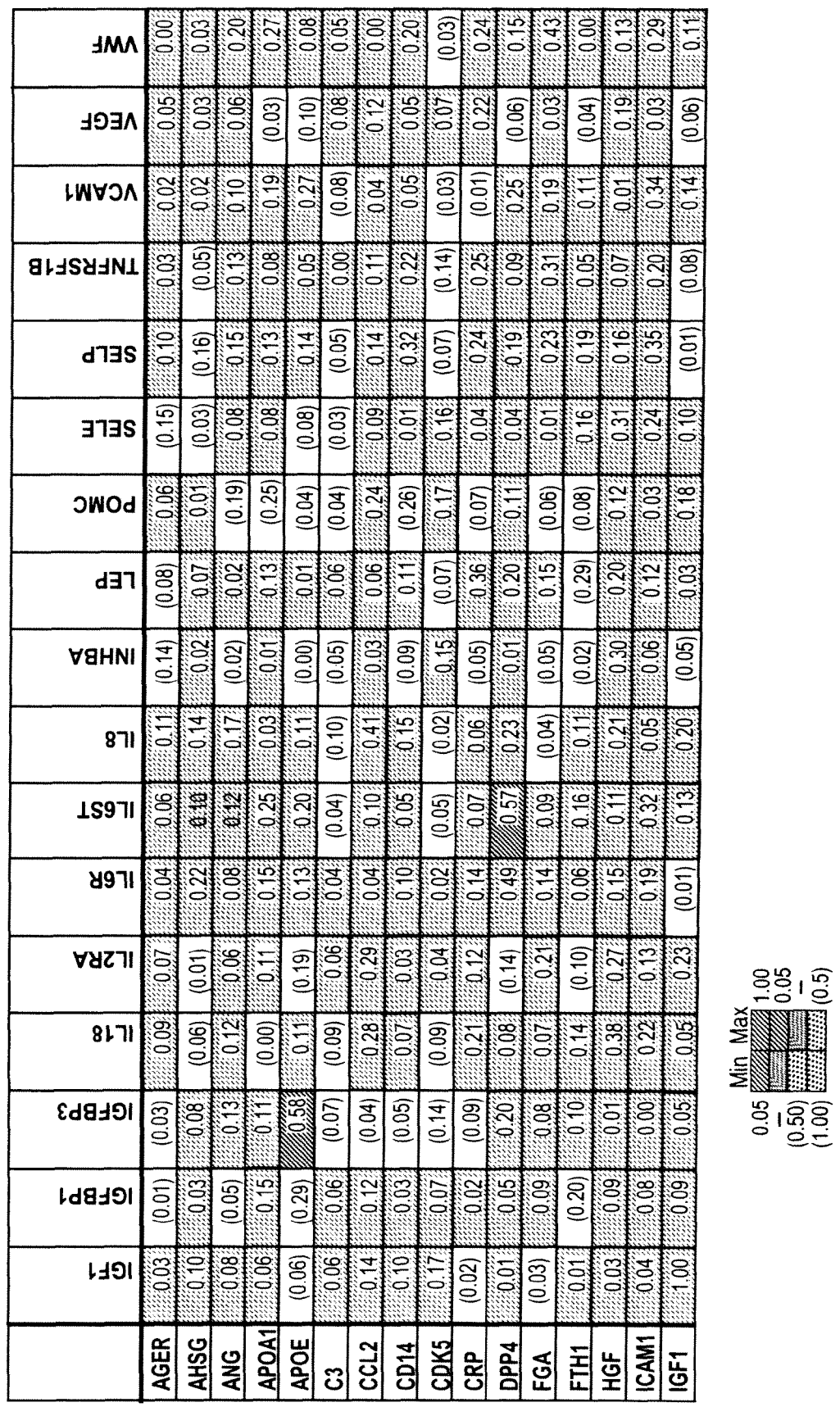
Figure 26I:
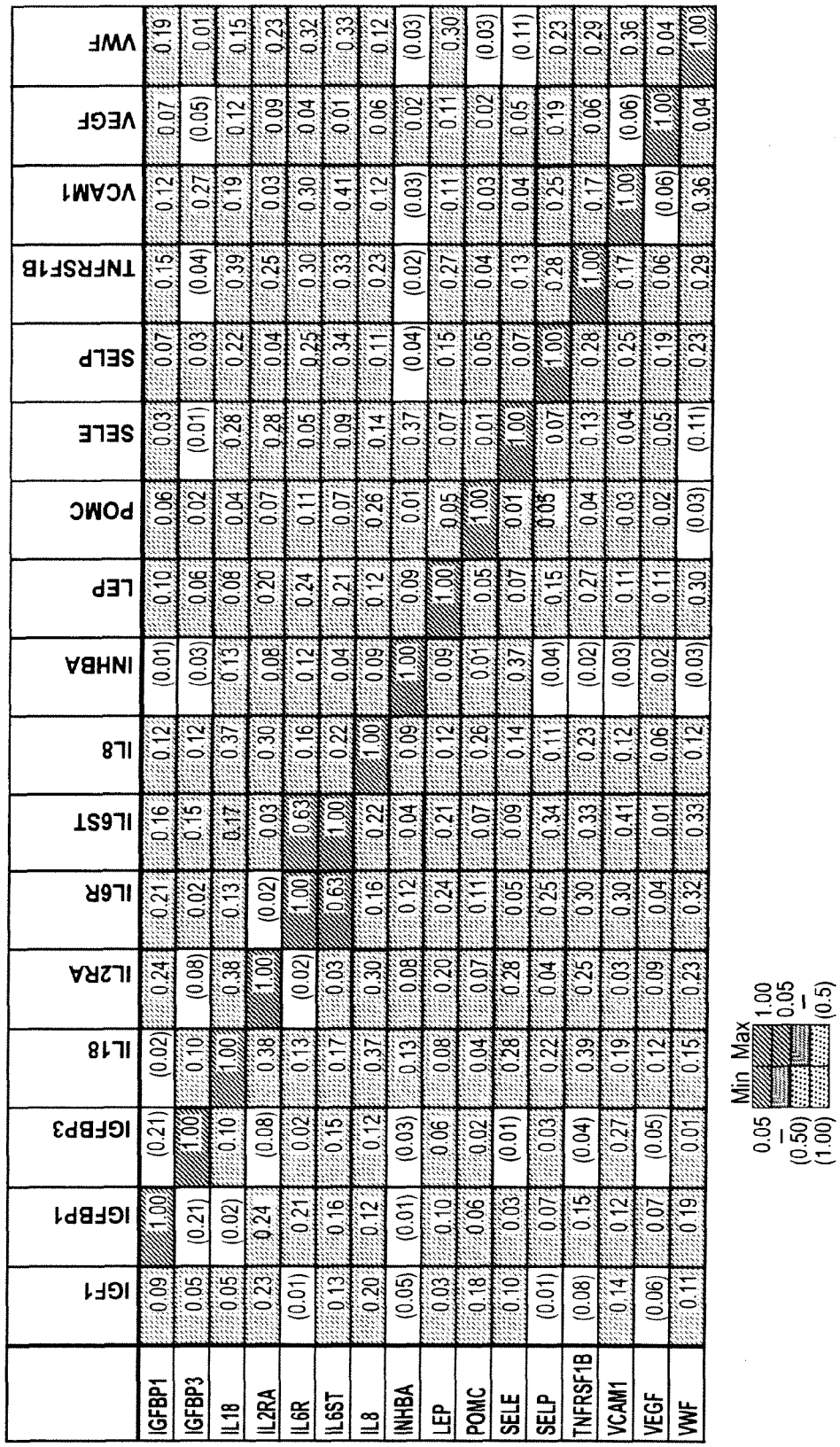
Figure 27:
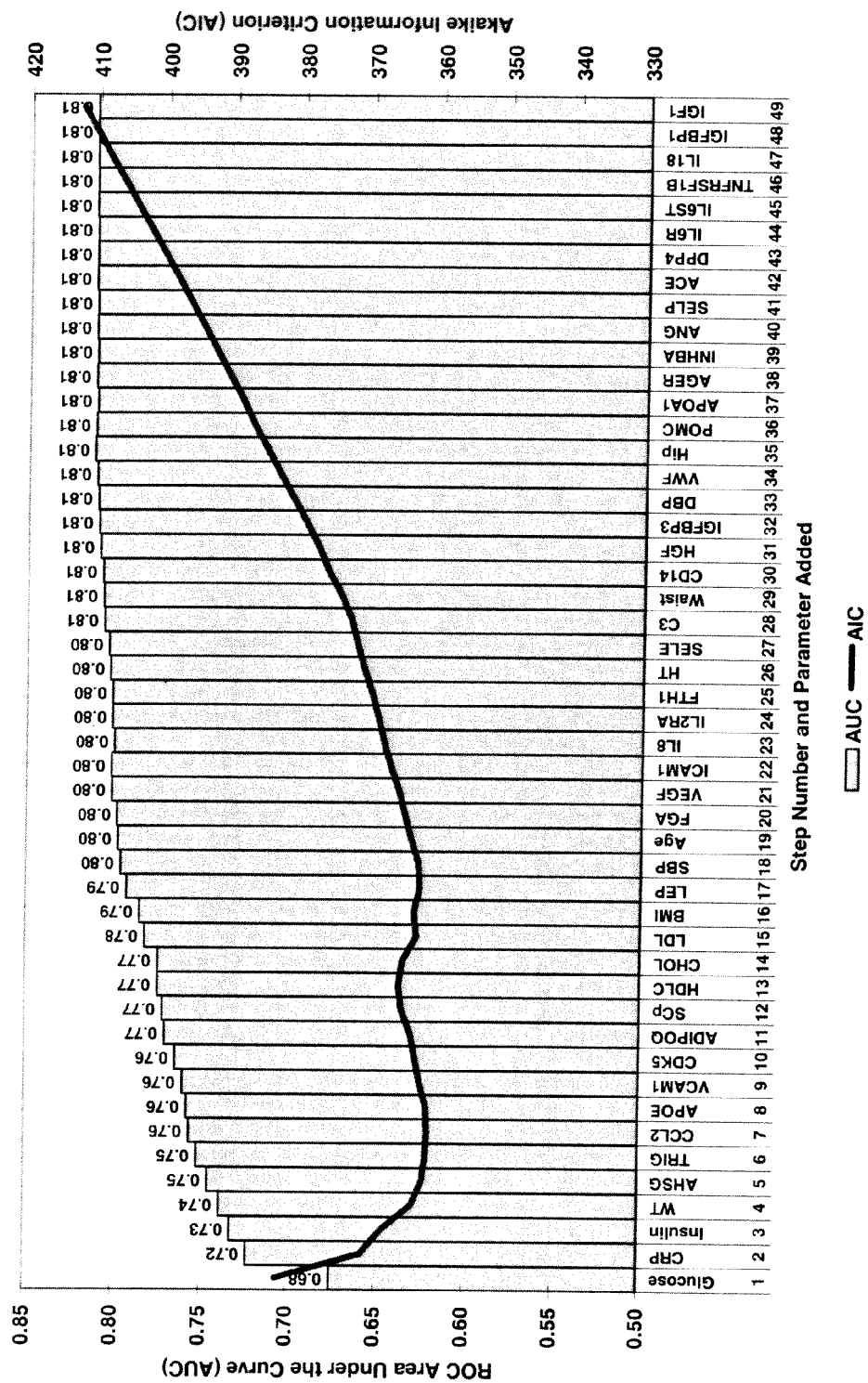
FIG. 27 is a graph showing the entire LDA forward-selected set of tested parameters with model AUC and AIC statistics at each biomarker addition step as measured and calculated in the Total Population of Example 2.
Figure 28:
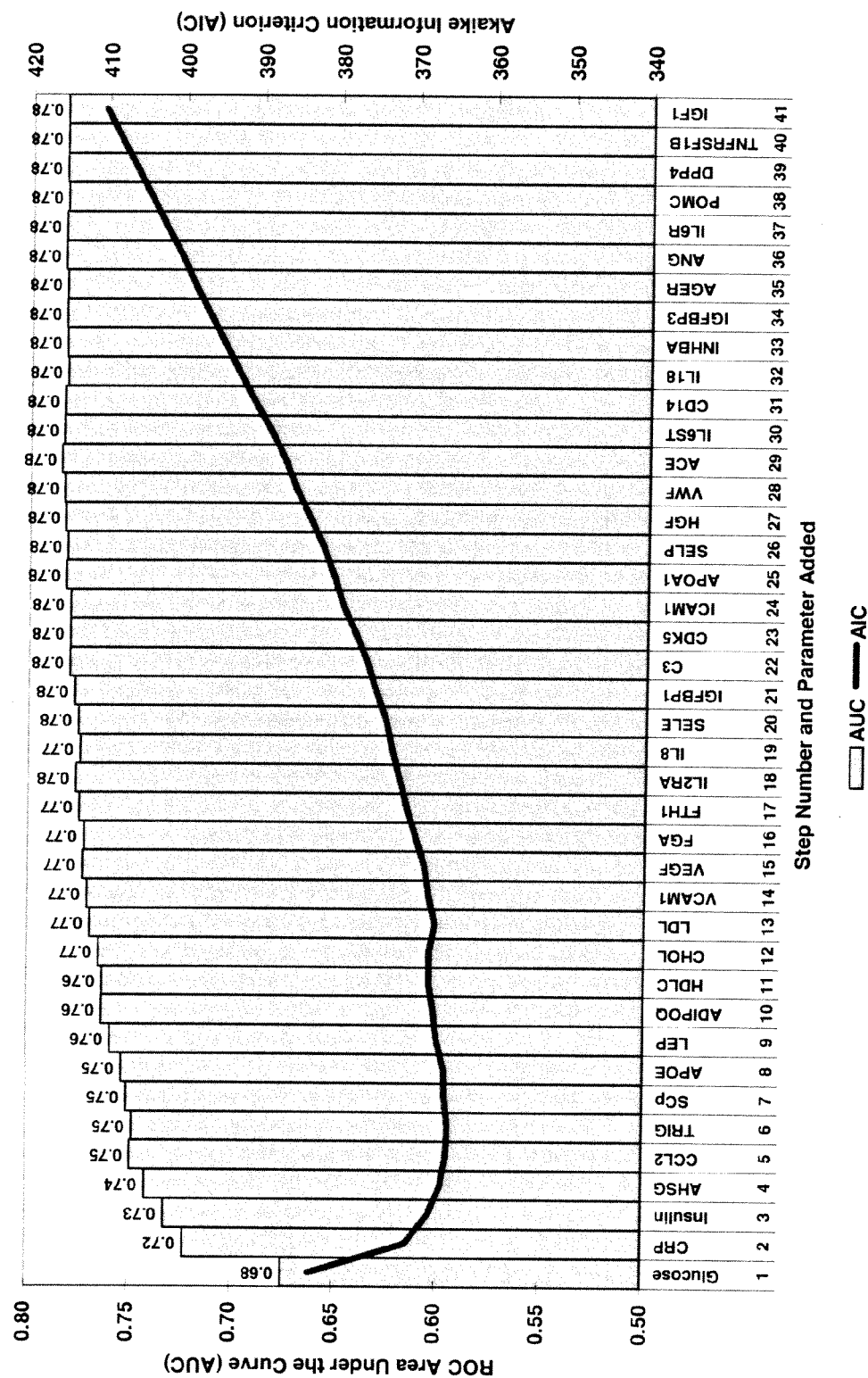
FIG. 28 is a graph showing LDA forward-selected set of blood parameters (excluding clinical parameters) alone with model characteristics at each biomarker addition step as measured and calculated in the Total Population of Example 2.

As implied above, in all such panel construction techniques, initial and subsequent Core or Additional Biomarkers, or Traditional Laboratory Risk Factors or Clinical Parameters, may also be deliberately selected from a field of many potential ALLDBRISK by ALLDBRISK selection formula, including the actual performance of each derived statistical classifier algorithm itself in a training subject population, in order to maximize the improvement in performance at each incremental addition of a ALLDBRISK. In this manner, many acceptably performing panels can be constructed using any number of ALLDBRISK up to the total set measured in one's individual practice of the invention (as summarized in FIG. 21, and in detail in FIGS. 24, 27 and 28 for the relevant Example populations). This technique is also of great use when the number of potential ALLDBRISK is constrained for other reasons of practicality or economics, as the order of ALLDBRISK selection is demonstrated in the Examples to vary upon the total ALLDBRISK available to the formula used in selection. It is a feature of the invention that the order and identity of the specific ALLDBRISK selected under any given formula may vary based on both the starting list of potential biomarker parameters presented to the formula (the total pool from which biomarkers may be selected to form panels) as well as due to the training population characteristics and level of diversity, as shown in the Examples below.

Figure 16:
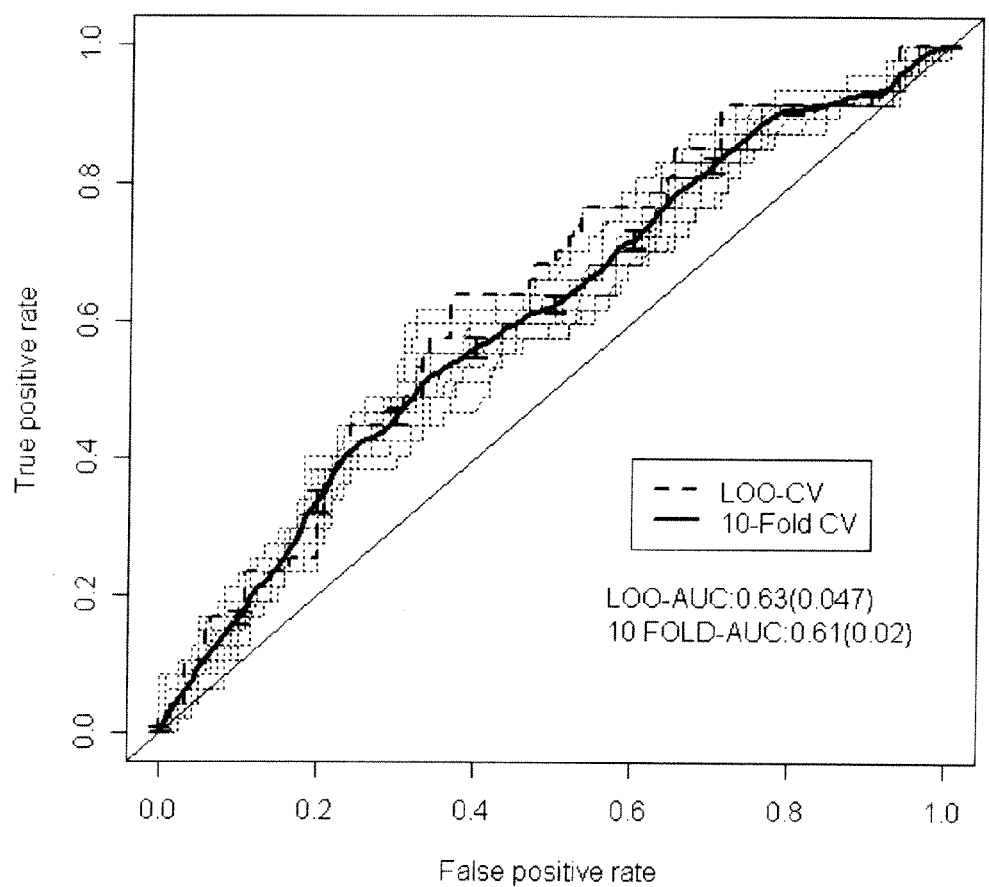
FIG. 16 is a graph depicting the Receiver Operator Characteristic (ROC) curve of a Linear Discriminant Analysis (LDA) classification model derived solely from the Clinical Parameters (and excluding the use of any blood-borne biomarkers of the present invention), as measured and calculated for the Base Population of Example 1, and including Area Under the Curve (AUC) and cross-validation statistics using Leave One Out (LOO) and 10-Fold methods.

Examples of specific ALLDBRISK panel construction derived using the above general techniques are also disclosed herein in the Examples, without limitation of the foregoing, our techniques of biomarker panel construction, or the applicability of alternative ALLDBRISK or biomarkers from functionally equivalent classes which are also involved in the same constituent physiological and biological pathways. Of particular note are the panels summarized in FIG. 21 for Example 1, and FIGS. 16A and 16B, which include ALLDBRISK shown in the above Tables 1 and 2 together with Traditional Laboratory Risk Factors and Clinical Parameters, and describe their AUC performance in fitted formulas within the relevant identified population and biomarker sets.

In another embodiment, FIGS. 8, 9, 10, 11, and 12 are of particular use for constructing panels. FIG. 8 indicates key groups of markers of use in the construction of panels according to the invention by the categories of Clinical Parameters (CPs), Traditional Laboratory Risk Factors (TLRFs), Tier 1 and Tier 2 Markers (both together, RDMARKERS), and other Tier 3 Markers. Preferably, ALLDBRISK panels are constructed using two or more RDMARKERS first, with the option then supplementing with other Tier 3, CPs and TLRF Markers.

FIG. 9 indicates certain biological groupings of markers useful in the construction of panels, categorized into general functional categories with exemplar ALLDBRISKS listed in each of the categories of Glycemic Control, Acute Phase Response/Signaling, Lipoprotein Metabolism, Adipocyte Signaling, Liver/Heptatic Signaling, and Inflammatory Blood/Endothelial Cell Signaling. Other ALLDBRISK markers in the indicated physiological functions may also be of use in the practice of the invention, provided they are functional or statistical equivalents of these exemplar markers, and also provided they share the aforementioned desirable characteristics of a good biomarker. Preferably, one marker from each of Glycemic Control and Acute Phase Response/Signaling is first chosen in the practice of the invention, with the option then of supplementing with one or more from one or more of the other categories of Lipoprotein Metabolism, Adipocyte Signaling, Liver/Heptatic Signaling, and Inflammatory Blood/Endothelial Cell Signaling.

FIGS. 10, 11 and 12 comprise other groupings of markers found useful in the construction of panels according to the practice of the invention, and panels may be constructed from these, or these may be used to supplement existing panels in selected populations. FIG. 10 provides individual markers found to be significantly altered in Converters versus Non-Converters. FIG. 11 comprises "synthetic interaction markers" formed from the product of two constituent markers transformed values (transformed according to FIG. 5) which are found to be significantly altered in Converters versus Non-Converters, as well as a listing of the individual marker constituents commonly found in such synthetic interaction markers. FIG. 12 comprises a listing of markers of interest obtained when various aforementioned heuristic formula are used in marker selection and algorithm construction, including Linear Discriminant Analysis, forward selection, stepwise selection, backwards selection, Kruskal-Wallis, and Eigengene-based Linear Discriminant Analysis, further explained below.

Construction of Clinical Algorithms

Any formula may be used to combine ALLDBRISK results into indices useful in the practice of the invention. As indicated above, and without limitation, such indices may indicate, among the various other indications, the probability, likelihood, absolute or relative risk, time to or rate of conversion from one to another disease states, or make predictions of future biomarkers measurements of Diabetes such as Glucose or HBA1c used for Diabetes in the diagnosis of the frank disease. This may be for a specific time period or horizon, or for remaining lifetime risk, or simply be provided as an index relative to another reference subject population.

Although various preferred formula are described here, several other model and formula types beyond those mentioned herein and in the definitions above are well known to one skilled in the art. The actual model type or formula used may itself be selected from the field of potential models based on the performance and diagnostic accuracy characteristics of its results in a training population. The specifics of the formula itself may commonly be derived from ALLDBRISK results in the relevant training population. Amongst other uses, such formula may be intended to map the feature space derived from one or more ALLDBRISK inputs to a set of subject classes (e.g. useful in predicting class membership of subjects as normal, pre-Diabetes, Diabetes), to derive an estimation of a probability function of risk using a Bayesian approach (e.g. the risk of Diabetes), or to estimate the class-conditional probabilities, then use Bayes' rule to produce the class probability function as in the previous case.

Preferred formulas include the broad class of statistical classification algorithms, and in particular the use of discriminant analysis. The goal of discriminant analysis is to predict class membership from a previously identified set of features. In the case of linear discriminant analysis (LDA), the linear combination of features is identified that maximizes the separation among groups by some criteria. Features can be identified for LDA using an eigengene based approach with different thresholds (ELDA) or a stepping algorithm based on a multivariate analysis of variance (MANOVA). Forward, backward, and stepwise algorithms can be performed that minimize the probability of no separation based on the Hotelling-Lawley statistic.

Eigengene-based Linear Discriminant Analysis (ELDA) is a feature selection technique developed by Shen et al. (2006). The formula selects features (e.g. biomarkers) in a multivariate framework using a modified eigen analysis to identify features associated with the most important eigenvectors. "Important" is defined as those eigenvectors that explain the most variance in the differences among samples that are trying to be classified relative to some threshold.

A support vector machine (SVM) is a classification formula that attempts to find a hyperplane that separates two classes. This hyperplane contains support vectors, data points that are exactly the margin distance away from the hyperplane. In the likely event that no separating hyperplane exists in the current dimensions of the data, the dimensionality is expanded greatly by projecting the data into larger dimensions by taking non-linear functions of the original variables (Venables and Ripley, 2002). Although not required, filtering of features for SVM often improves prediction. Features (e.g., biomarkers) can be identified for a support vector machine using a non-parametric Kruskal-Wallis (KW) test to select the best univariate features. A random forest (RF, Breiman, 2001) or recursive partitioning (RPART, Breiman et al., 1984) can also be used separately or in combination to identify biomarker combinations that are most important. Both KW and RF require that a number of features be selected from the total. RPART creates a single classification tree using a subset of available biomarkers.

Other formula may be used in order to pre-process the results of individual ALLDBRISK measurement into more valuable forms of information, prior to their presentation to the predictive formula. Most notably, normalization of biomarker results, using either common mathematical transformations such as logarithmic or logistic functions, as normal or other distribution positions, in reference to a population's mean values, etc. are all well known to those skilled in the art (as shown in FIG. 5, and described in Example 1, such transformation and normalization of individual biomarker concentrations may commonly be performed in the practice of the invention). Of particular interest are a set of normalizations based on Clinical Parameters such as age, gender, race, or sex, where specific formula are used solely on subjects within a class or continuously combining a Clinical Parameter as an input. In other cases, analyte-based biomarkers can be combined into calculated variables (much as BMI is a calculation using Height and Weight) which are subsequently presented to a formula.

In addition to the individual parameter values of one subject potentially being normalized, an overall predictive formula for all subjects, or any known class of subjects, may itself be recalibrated or otherwise adjusted based on adjustment for a population's expected prevalence and mean biomarker parameter values, according to the technique outlined in D'Agostino et al. (2001) JAMA 286:180-187, or other similar normalization and recalibration techniques. Such epidemiological adjustment statistics may be captured, confirmed, improved and updated continuously through a registry of past data presented to the model, which may be machine readable or otherwise, or occasionally through the retrospective query of stored samples or reference to historical studies of such parameters and statistics. Additional examples that may be the subject of formula recalibration or other adjustments include statistics used in studies by Pepe, M. S. et al, 2004 on the limitations of odds ratios; Cook, N. R., 2007 relating to ROC curves; and Vasan, R. S., 2006 regarding biomarkers of cardiovascular disease.

Finally, the numeric result of a classifier formula itself may be transformed post-processing by its reference to an actual clinical population and study results and observed endpoints, in order to calibrate to absolute risk and provide confidence intervals for varying numeric results of the classifier or risk formula. An example of this is the presentation of absolute risk, and confidence intervals for that risk, derived using an actual clinical study, chosen with reference to the output of the recurrence score formula in the Oncotype Dx product of Genomic Health, Inc. (Redwood City, Calif.). A further modification is to adjust for smaller sub-populations of the study based on the output of the classifier or risk formula and defined and selected by their Clinical Parameters, such as age or sex.

Summary of Algorithm Development Process and Application of Algorithms

Figure 34:
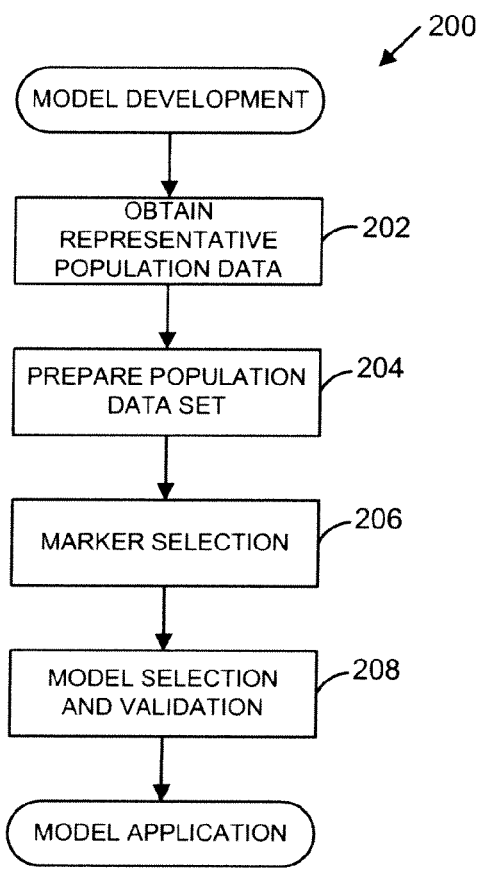
FIG. 34 is a flow diagram of an example method for developing a model which may be used to evaluate a risk of a person, or group of people, for developing a diabetic condition.

FIG. 34 is a flow diagram of an example method 200 for developing a model which may be used to evaluate a risk of a person, or group of people, for developing a diabetic condition. The method 200 may be implemented using the example computing system environment 100 of FIG. 33 and will be used to explain the operation of the environment 100. However, it should be recognized that the method 200 could be implemented by a system different than the computing system environment 100. At a block 202, biomarker data from a representative population, as has been described herein, is obtained from a data storage device, such as the system memory 130, an internal or external database, or other computer storage media. The biomarker data may be initially derived through a variety of means, including prospective (longitudinal) studies to involving observations of the representative population over a period of time, retrospective studies of samples of a representative population that queries the samples and/or from a retrospective epidemiological data storage containing the results from previous studies, such as an NIH database. The biomarker data may be derived from a single study or multiple studies, and generally includes data pertaining to the desired indication and endpoint of the representative population, including values of the biomarkers described herein, clinical annotations (which may include endpoints), and most particularly the desired endpoints for training an algorithm for use in the invention, across many subjects.

At a block 204, the representative population data set is prepared as needed to meet the requirements of the model or analysis that will be used for biomarker selection, as described below. For example, data set preparation may include preparing the biomarker values from each subject within the representative population, or a chosen subset thereof. However, the raw biomarker data alone may not be entirely useful for the purposes of model training. As such, various data preparation methods may be used to prepare the data, such as gap fill techniques (e.g., nearest neighbor interpolation or other pattern recognition), quality checks, data combination using of various formulae (e.g., statistical classification algorithms), normalization and/or transformations, such as logarithmic functions to change the distribution of data to meet model requirements (e.g., base 10, natural log, etc.). Again, the particular data preparation procedures are dependent upon the model or models that will be trained using the representative population data. The particular data preparation techniques for various different model types are known, and need not be described further.

At a block 206, the particular biomarkers are selected to be subsequently used in the training of the model used to evaluate a risk of developing a diabetic condition. Biomarker selection may involve utilizing a selection model to validate the representative population data set and selecting the biomarker data from the data set that provides the most reproducible results. Examples of data set validation may include, but are not limited to, cross-validation and bootstrapping. From the marker selection, the model to be used in evaluating a risk of developing a diabetic condition may be determined and selected. However, it is noted that not all models provide the same results with the same data set. For example, different models may utilize different numbers of biomarkers and produce different results, thereby adding significance to the combination of biomarkers on the selected model. Accordingly, multiple selection models may be chosen and utilized with the representative population data set, or subsets of the data set, in order to identify the optimal model for risk evaluation. Examples of the particular models, including statistical models, algorithms, etc., which may be used for selecting the biomarkers have been described above.

For each selection model used with the data set, or subset thereof, the biomarkers are selected based on each biomarker's statistical significance in the model. When input to each model, the biomarkers are selected based on various criteria for statistical significance, and may further involve cumulative voting and weighting. Tests for statistical significance may include exit-tests and analysis of variance (ANOVA). The model may include classification models (e.g., LDA, logistic regression, SVM, RF, tree models, etc.) and survival models (e.g., cox), many examples of which have been described above.

It is noted that while biomarkers may be applied individually to each selection model to identify the statistically significant biomarkers, in some instances individual biomarkers alone may not be fully indicative of a risk for a diabetic condition, in which case combinations of biomarkers may be applied to the selection model. For example, rather than utilizing univariate biomarker selection, multivariate biomarker selection may be utilized. That is, a biomarker may not be a good indicator when used as a univariate input to the selection model, but may be a good indicator when used in combination with other biomarkers (i.e., a multivariate input to the model), because each marker may bring additional information to the combination that would not be indicative if taken alone.

At a block 208, the model to be used for evaluating risk is selected, trained and validated. In particular, leading candidate models may be selected based on one or more performance criteria, examples of which have been described above. For example, from using the data set, or data subsets, with various models, not only are the models used to determine statistically significant biomarkers, but the results may be used to select the optimal models along with the biomarkers. As such, the evaluation model used to evaluate risk may include one of those used as a selection model, including classification models and survival models. Combinations of models markers, including marker subsets, may be compared and validated in subsets and individual data sets. The comparison and validation may be repeated many times to train and validate the model and to choose an appropriate model, which is then used as an evaluation model for evaluating risk of a diabetic condition.

Figure 35:
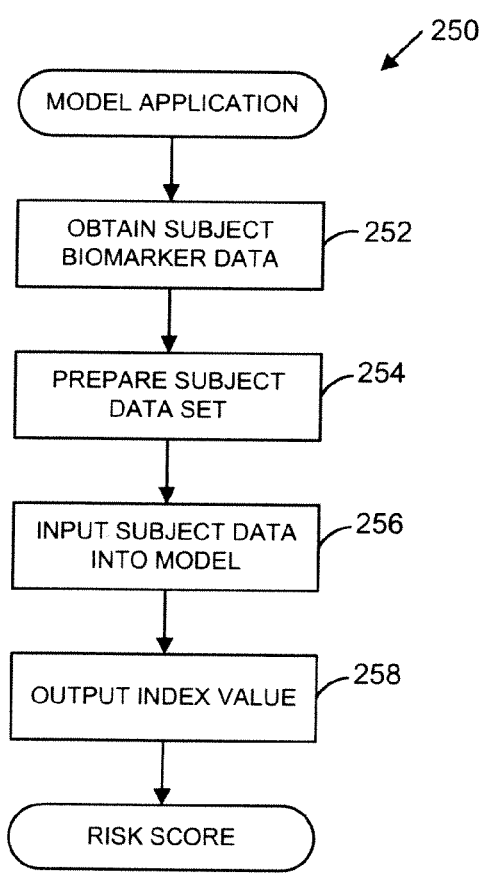
FIG. 35 is a flow diagram of an example method for using a model to evaluate a risk of a subject (e.g., a person, or group of people) developing a diabetic condition.

FIG. 35 is a flow diagram of an example method 250 for using a model to evaluate a risk of a subject (e.g., a person, or group of people) developing a diabetic condition. At a block 252, biomarker data from the subject is obtained from a data storage device, which may be the same as, or different from, the data storage device discussed above with reference to FIG. 34. The subject biomarker data may be initially derived through a variety of means, including self-reports, physical examination, laboratory testing and existing medical records, charts or databases. As with the representative population biomarker data at block 204 of FIG. 34, the subject biomarker data at block 254 may be prepared using transforms, logs, combinations, normalization, etc. as needed according to the model type selected and trained in FIG. 34. Once the data has been prepared, at a block 256, the subject biomarker data is input into the evaluation model, and at a block 258 the evaluation model outputs an index value (e.g., risk score, relative risk, time to conversion, etc.). Many examples have been provided herein as to how a model may be used to evaluate the subject biomarkers and output an index value, e.g. see Example 7.

Modifications for Therapeutic Intervention Panels

An ALLDBRISK panel can be constructed and formula derived specifically to enhance performance for use also in subjects undergoing therapeutic interventions, or a separate panel and formula may alternatively be used solely in such patient populations. An aspect of the invention is the use of specific known characteristics of ALLDBRISKS and their changes in such subjects for such panel construction and formula derivation. Such modifications may enhance the performance of various indications noted above in Diabetes prevention, and diagnosis, therapy, monitoring, and prognosis of Diabetes and pre-Diabetes.

Several of the ALLDBRISKS disclosed herein are known to those skilled in the art to vary predictably under therapeutic intervention, whether lifestyle (e.g. diet and exercise), surgical (e.g. bariatric surgery) or pharmaceutical (e.g, one of the various classes of drugs mentioned herein or known to modify common risk factors or risk of Diabetes) intervention. For example, a PubMed search using the terms "Adiponectin drug," will return over 700 references, many with respect to the changes or non-changes in the levels of adiponectin (ADIPOQ) in subjects treated with various individual Diabetes-modulating agents. Similar evidence of variance under therapeutic intervention is widely available for many of the biomarkers listed in Table 1, such as CRP, FGA, INS, LEP, among others. Certain of the biomarkers listed, most particularly the Clinical Parameters and the Traditional Laboratory Risk Factors, (and including such biomarkers as GLUCOSE, SBP, DBP, CHOL, HDL, and HBA1c), are traditionally used as surrogate or primary endpoint markers of efficacy for entire classes of Diabetes-modulating agents, thus most certainly changing in a statistically significant way.

Still others, including genetic biomarkers, such as those polymorphisms known in the PPARG and INSR (and generally all genetic biomarkers absent somatic mutation), are similarly known not to vary in their measurement under particular therapeutic interventions. Such variation may or may not impact the general validity of a given panel, but will often impact the index values reported, and may require different marker selection, the formula to be re-optimized or other changes to the practice of the invention. Alternative model calibrations may also be practiced in order to adjust the normally reported results under a therapeutic intervention, including the use of manual table lookups and adjustment factors.

Such properties of the individual ALLDBRISKS can thus be anticipated and exploited to select, guide, and monitor therapeutic interventions. For example, specific ALLDBRISKS may be added to, or subtracted from, the set under consideration in the construction of the ALLDBRISK panels, based on whether they are known to vary, or not to vary, under therapeutic intervention. Alternatively, such ALLDBRISKS may be individually normalized or formula recalibrated to adjust for such effects according to the above and other means well known to those skilled in the art.

Combination with Clinical Parameters

Any of the aforementioned Clinical Parameters may be used in the practice of the invention as an ALLDBRISK input to a formula or as a pre-selection criteria defining a relevant population to be measured using a particular ALLDBRISK panel and formula. As noted above, Clinical Parameters may also be useful in the biomarker normalization and pre-processing, or in ALLDBRISK selection, panel construction, formula type selection and derivation, and formula result post-processing.

Endpoints of the Invention

One embodiment of the invention is to tailor ALLDBRISK panels and formulas to the population and end point or use that is intended. For example, the ALLDBRISK panels and formulas may used for assessment of subjects for primary prevention and diagnosis and for secondary prevention and management. For the primary assessment, the ALLDBRISK panels and formulas may be used for prediction and risk stratification for conditions, for the diagnosis of diabetic conditions, for the prognosis of glucose level and rate of change and for indication for future diagnosis. For secondary prevention and management, the ALLDBRISK panels and formulas may be used for prognosis, risk stratification for Diabetes complications. The ALLDBRISK panels and formulas may be used for clinical decision support, such as determining whether to defer intervention to next visit, to recommend normal preventive check-ups, to recommend increased visit frequency, to recommend increased testing and to recommend therapeutic intervention. The ALLDBRISK panels and formulas may also be useful for intervention in subjects with diabetic conditions, such as therapeutic selection and response, adjustment and dosing of therapy, monitoring ongoing therapeutic efficiency and indication for change in therapeutic intervention.

The disease endpoints of the invention include type I and type II Diabetes Mellitus and other diabetic conditions and pre-diabetic conditions. The ALLDBRISK panels and formulas may be used to evaluate the current status of the disease endpoints by aiding in the diagnosis of latent type II Diabetes Mellitus, and aiding in the determination of severity of the type II Diabetes Mellitus and determination of the subclass of type II Diabetes Mellitus. The ALLDBRISK panels and formulas are also useful for determining the future status of intervention such as determining the prognosis of future type II Diabetes Mellitus with therapy, intervention and drug therapy. The invention may be tailored to a specific intervention, drug class, therapeutic class or therapy or drug therapy or a combination thereof.

The surrogate endpoints of the invention include measuring HBA1c, glucose (FPG and OGTT), and glucose class (normal glucose tolerance (NGT), IGT, IFG AND T2DM). The ALLDBRISK panels and formulas are useful for determining the current status of the surrogate endpoints by diagnosing glucose class with or without fasting. The future status of surrogate endpoints may be determined using the ALLDBRISK panels and formulas of the invention such as determination of the prognosis of future glucose class. The ALLDBRISK panels and formulas are also useful for determining the future status of intervention such as determination of prognosis of future glucose class with drug therapy.

The complication endpoints of diabetic conditions include eye retinopathy, microvascular damage, liver damage, limb amputation and cardiovascular complications to name a few. The ALLDBRISK panels and formulas may be used to evaluate the current status of the disease endpoints by aiding in the diagnosis of liver damage. The future status of complication endpoints may be determined using the ALLDBRISK panels and formulas such as determination of the prognosis of future retinopathy. The ALLDBRISK panels and formulas are also useful for determining the future status of intervention such as determining the prognosis of future retinopathy with therapy or drug therapy.

Measurement of ALLDBRISKS

Biomarkers may be measured in using several techniques designed to achieve more predictable subject and analytical variability. On subject variability, many of the above ALLDBRISKS are commonly measured in a fasting state, and most commonly in the morning, providing a reduced level of subject variability due to both food consumption and metabolism and diurnal variation. The invention hereby claims all fasting and temporal-based sampling procedures using the ALLDBRISKS described herein. Pre-processing adjustments of ALLDBRISK results may also be intended to reduce this effect.

The actual measurement of levels of the ALLDBRISKS can be determined at the protein or nucleic acid level using any method known in the art. For example, at the nucleic acid level, Northern and Southern hybridization analysis, as well as ribonuclease protection assays using probes which specifically recognize one or more of these sequences can be used to determine gene expression. Alternatively, levels of ALLDBRISKS can be measured using reverse-transcription-based PCR assays (RT-PCR), e.g., using primers specific for the differentially expressed sequence of genes. Levels of ALLDBRISKS can also be determined at the protein level, e.g., by measuring the levels of peptides encoded by the gene products described herein, or activities thereof. Such methods are well known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed.

The ALLDBRISK proteins, polypeptides, mutations, and polymorphisms thereof can be detected in any suitable manner, but is typically detected by contacting a sample from the subject with an antibody which binds the ALLDBRISK protein, polypeptide, mutation, or polymorphism and then detecting the presence or absence of a reaction product. The antibody may be monoclonal, polyclonal, chimeric, or a fragment of the foregoing, as discussed in detail above, and the step of detecting the reaction product may be carried out with any suitable immunoassay. The sample from the subject is typically a biological fluid as described above, and may be the same sample of biological fluid used to conduct the method described above.

Immunoassays carried out in accordance with the present invention may be homogeneous assays or heterogeneous assays. In a homogeneous assay the immunological reaction usually involves the specific antibody (e.g., anti-ALLD-BRISK protein antibody), a labeled analyte, and the sample of interest. The signal arising from the label is modified, directly or indirectly, upon the binding of the antibody to the labeled analyte. Both the immunological reaction and detection of the extent thereof can be carried out in a homogeneous solution. Immunochemical labels which may be employed include free radicals, radioisotopes, fluorescent dyes, enzymes, bacteriophages, or coenzymes.

In a heterogeneous assay approach, the reagents are usually the sample, the antibody, and means for producing a detectable signal. Samples as described above may be used. The antibody can be immobilized on a support, such as a bead (such as protein A and protein G agarose beads), plate or slide, and contacted with the specimen suspected of containing the antigen in a liquid phase. The support is then separated from the liquid phase and either the support phase or the liquid phase is examined for a detectable signal employing means for producing such signal. The signal is related to the presence of the analyte in the sample. Means for producing a detectable signal include the use of radioactive labels, fluorescent labels, or enzyme labels. For example, if the antigen to be detected contains a second binding site, an antibody which binds to that site can be conjugated to a detectable group and added to the liquid phase reaction solution before the separation step. The presence of the detectable group on the solid support indicates the presence of the antigen in the test sample. Examples of suitable immunoassays include, but are not limited to oligonucleotides, immunoblotting, immunoprecipitation, immunofluorescence methods, chemiluminescence methods, electrochemiluminescence (ECL) or enzyme-linked immunoassays.

Those skilled in the art will be familiar with numerous specific immunoassay formats and variations thereof which may be useful for carrying out the method disclosed herein. See generally E. Maggio, Enzyme-Immunoassay, (1980) (CRC Press, Inc., Boca Raton, Fla.); see also U.S. Pat. No. 4,727,022 to Skold et al. titled "Methods for Modulating Ligand-Receptor Interactions and their Application," U.S. Pat. No. 4,659,678 to Forrest et al. titled "Immunoassay of Antigens," U.S. Pat. No. 4,376,110 to David et al., titled "Immunometric Assays Using Monoclonal Antibodies," U.S. Pat. No. 4,275,149 to Litman et al., titled "Macromolecular Environment Control in Specific Receptor Assays," U.S. Pat. No. 4,233,402 to Maggio et al., titled "Reagents and Method Employing Channeling," and U.S. Pat. No. 4,230,767 to Boguslaski et al., titled "Heterogeneous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein may likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies can also be useful for detecting post-translational modifications of ALLDBRISK proteins, polypeptides, mutations, and polymorphisms, such as tyrosine phosphorylation, threonine phosphorylation, serine phosphorylation, glycosylation (e.g., O-GlcNAc). Such antibodies specifically detect the phosphorylated amino acids in a protein or proteins of interest, and can be used in immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF) (Wirth, U. et al. (2002) Proteomics 2(10): 1445-51).

For ALLDBRISK proteins, polypeptides, mutations, and polymorphisms known to have enzymatic activity, the activities can be determined in vitro using enzyme assays known in the art. Such assays include, without limitation, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the database entries for the ALLDBRISK sequences, expression of the ALLDBRISK sequences can be detected (if present) and measured using techniques well known to one of ordinary skill in the art. For example, sequences within the sequence database entries corresponding to ALLDBRISK sequences, or within the sequences disclosed herein, can be used to construct probes for detecting ALLDBRISK RNA sequences in, e.g., Northern blot hybridization analyses or methods which specifically, and, preferably, quantitatively amplify specific nucleic acid sequences. As another example, the sequences can be used to construct primers for specifically amplifying the ALLDBRISK sequences in, e.g., amplification-based detection methods such as reverse-transcription based polymerase chain reaction (RT-PCR). When alterations in gene expression are associated with gene amplification, deletion, polymorphisms, and mutations, sequence comparisons in test and reference populations can be made by comparing relative amounts of the examined DNA sequences in the test and reference cell populations.

Expression of the genes disclosed herein can be measured at the RNA level using any method known in the art. For example, Northern hybridization analysis using probes which specifically recognize one or more of these sequences can be used to determine gene expression. Alternatively, expression can be measured using reverse-transcription-based PCR assays (RT-PCR), e.g., using primers specific for the differentially expressed sequences. RNA can also be quantified using, for example, other target amplification methods (e.g., TMA, SDA, NASBA), or signal amplification methods (e.g., bDNA), and the like.

Alternatively, ALLDBRISK protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. (See, WO 04/056456 and WO 04/088309, each of which are hereby incorporated by reference in their entireties) In this regard, other ALLDBRISK analytes can be measured using the above-mentioned detection methods, or other methods known to the skilled artisan. For example, circulating calcium ions (Ca2+) can be detected in a sample using fluorescent dyes such as the Fluo series, Fura-2A, Rhod-2, among others. Other ALLDBRISK metabolites can be similarly detected using reagents that specifically designed or tailored to detect such metabolites.

Kits

The invention also includes a ALLDBRISK-detection reagent, e.g., nucleic acids that specifically identify one or more ALLDBRISK nucleic acids by having homologous nucleic acid sequences, such as oligonucleotide sequences or aptamers, complementary to a portion of the ALLDBRISK nucleic acids or antibodies to proteins encoded by the ALLDBRISK nucleic acids packaged together in the form of a kit. The oligonucleotides can be fragments of the ALLDBRISK genes. For example the oligonucleotides can be 200, 150, 100, 50, 25, 10 or less nucleotides in length. The kit may contain in separate containers a nucleic acid or antibody (either already bound to a solid matrix or packaged separately with reagents for binding them to the matrix), control formulations (positive and/or negative), and/or a detectable label such as fluorescein, green fluorescent protein, rhodamine, cyanine dyes, Alexa dyes, luciferase, radiolabels, among others. Instructions (e.g., written, tape, VCR, CD-ROM, etc.) for carrying out the assay may be included in the kit. The assay may for example be in the form of a Northern hybridization or a sandwich ELISA as known in the art.

For example, ALLDBRISK detection reagents can be immobilized on a solid matrix such as a porous strip to form at least one ALLDBRISK detection site. The measurement or detection region of the porous strip may include a plurality of sites containing a nucleic acid. A test strip may also contain sites for negative and/or positive controls. Alternatively, control sites can be located on a separate strip from the test strip. Optionally, the different detection sites may contain different amounts of immobilized nucleic acids, e.g., a higher amount in the first detection site and lesser amounts in subsequent sites. Upon the addition of test sample, the number of sites displaying a detectable signal provides a quantitative indication of the amount of ALLDBRISKS present in the sample. The detection sites may be configured in any suitably detectable shape and are typically in the shape of a bar or dot spanning the width of a test strip.

Alternatively, the kit contains a nucleic acid substrate array comprising one or more nucleic acid sequences. The nucleic acids on the array specifically identify one or more nucleic acid sequences represented by ALLDBRISKS 1-271. In various embodiments, the expression of 2, 3, 4, 5, 6, 7, 8, 9, 10, 15, 20, 25, 40, 50, 100, 125, 150, 175, 200, 210, 220, 230, 240, 250, 260 or more of the sequences represented by ALLDBRISKS 1-271 can be identified by virtue of binding to the array. The substrate array can be on, e.g., a solid substrate, e.g., a "chip" as described in U.S. Pat. No. 5,744,305. Alternatively, the substrate array can be a solution array, e.g., xMAP (Luminex, Austin, Tex.), Cyvera (Illumina, San Diego, Calif.), CellCard (Vitra Bioscience, Mountain View, Calif.) and Quantum Dots' Mosaic (Invitrogen, Carlsbad, Calif.).

Suitable sources for antibodies for the detection of ALLDBRISK include commercially available sources such as, for example, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. However, the skilled artisan can routinely make antibodies, nucleic acid probes, e.g., oligonucleotides, aptamers, siRNAs, antisense oligonucleotides, against any of the ALLDBRISK in Table 1.

Above starting after Table 3, the invention is described in relation to the ALLDBRISKS marker set. It is understood that further embodiments of the invention include the above discussion in relation to the RDMARKERS and the above discussion is reincorporated herein substituting RDMARKERS as appropriate.

EXAMPLES

Materials and Methods: Source Reagents: A large and diverse array of vendors that were used to source immunoreagents as a starting point for assay development, such as, but not limited to, Abazyme, Abnova, Affinity Biologicals, AntibodyShop, Biogenesis, Biosense Laboratories, Calbiochem, Cell Sciences, Chemicon International, Chemokine, Clontech, Cytolab, DAKO, Diagnostic BioSystems, eBioscience, Endocrine Technologies, Enzo Biochem, Eurogentec, Fusion Antibodies, Genesis Biotech, GloboZymes, Haematologic Technologies, Immunodetect, Immunodiagnostik, Immunometrics, Immunostar, Immunovision, Biogenex, Invitrogen, Jackson ImmunoResearch Laboratory, KMI Diagnostics, Koma Biotech, LabFrontier Life Science Institute, Lee Laboratories, Lifescreen, Maine Biotechnology Services, Mediclone, MicroPharm Ltd., ModiQuest, Molecular Innovations, Molecular Probes, Neoclone, Neuromics, New England Biolabs, Novocastra, Novus Biologicals, Oncogene Research Products, Orbigen, Oxford Biotechnology, Panvera, PerkinElmer Life Sciences, Pharmingen, Phoenix Pharmaceuticals, Pierce Chemical Company, Polymun Scientific, Polysiences, Inc., Promega Corporation, Proteogenix, Protos Immunoresearch, QED Biosciences, Inc., R&D Systems, Repligen, Research Diagnostics, Roboscreen, Santa Cruz Biotechnology, Seikagaku America, Serological Corporation, Serotec, SigmaAldrich, StemCell Technologies, Synaptic Systems GmbH, Technopharm, Terra Nova Biotechnology, TiterMax, Trillium Diagnostics, Upstate Biotechnology, US Biological, Vector Laboratories, Wako Pure Chemical Industries, and Zeptometrix. A search for capture antibodies, detection antibodies, and analytes was performed to configure a working sandwich immunoassay. The reagents were ordered and received into inventory.

Immunoassays were developed in three steps: Prototyping, Validation, and Kit Release. Prototyping was conducted using standard ELISA formats when the two antibodies used in the assay were from different host species. Using standard conditions, anti-host secondary antibodies conjugated with horse radish peroxidase were evaluated in a standard curve. If a good standard curve was detected, the assay proceeded to the next step. Assays that had the same host antibodies went directly to the next step (e.g., mouse monoclonal sandwich assays).

Validation of working assays was performed using the Zeptosense detection platform from Singulex, Inc. (St. Louis, Mo.). The detection antibody was first conjugated to the fluorescent dye Alexa 647. The conjugations used standard NHS ester chemistry, for example, according to the manufacturer. Once the antibody was labeled, the assay was tested in a sandwich assay format using standard conditions. Each assay well was solubilized in a denaturing buffer, and the material was read on the Zeptosense platform.

Once a working Zeptosense standard curve was demonstrated, assays were typically applied to 24-96 serum samples to determine the normal distribution of the target analyte across clinical samples. The amount of serum required to measure the biomarker within the linear dynamic range of the assay was determined, and the assay proceeded to kit release. For the initial validated assays, 0.004 microliters were used per well on average.

Each component of the kit including manufacturer, catalog numbers, lot numbers, stock and working concentrations, standard curve, and serum requirements were compiled into a standard operating procedures for each biomarker assay. This kit was then released for use to test clinical samples.

Example 1

Example 1 presents the practice of the invention in a risk matched (age, sex, BMI, among others) case-control study design. Subjects which converted to Diabetes were initially selected and risk matched based on baseline characteristic with subjects who did not convert to Diabetes, drawing from a larger longitudinal general population study. For purposes of formula discovery, subjects were selected from the larger study with the following characteristics: Converters (C): conversion to Diabetes must have been within 5 years; Non-Converters (NC): must have had at least 8 years of follow-up with no documentation of conversion to Diabetes.

Both the "Total Population" of all such subjects and a selected "Base Population" sub-population were analyzed. The Base Population was comprised of all subjects within the Total Population who additionally met the inclusion criteria of AGE equal to or greater than 39 years and BMI equal to or greater than 25 kg/m$^2$.

Descriptive statistics summarizing each of the Example 1 study population arms are presented below in Table 5. (Note that HOMA-IR=Homeostasis Model Assessment—Insulin Resistance.)

TABLE 5

Baseline characteristics of converters and non-converters in Example 1

| | | Example 1 | | | |
|---|---|---|---|---|---|
| | | Total Population | | Base Population | |
| Variables | Levels | C (n = 60) | NC (n = 177) | C (n = 47) | NC (n = 120) |
| Glucose tolerance status baseline | NGT | 20 | 91 | 14 | 55 |
| | IFG | 6 | 22 | 5 | 18 |
| | IGT | 21 | 47 | 18 | 34 |
| | IFG-IGT | 13 | 17 | 10 | 13 |
| Sex | female | 28 | 84 | 22 | 60 |
| | male | 32 | 93 | 25 | 60 |
| Family HX DD (parents and sibs) | No | 8 | 21 | 6 | 14 |
| | Yes | 52 | 156 | 41 | 106 |
| Waist | Mean | 96.98 | 92.8 | 98.73 | 94.7 |
| | SD | 11.725 | 11.679 | 10.37 | 10.865 |
| | Median | 97.5 | 92.5 | 100 | 94 |
| | Min | 72 | 67.5 | 73 | 75 |
| | Max | 127 | 138 | 127 | 138 |
| | N | 60 | 177 | 47 | 120 |
| Age | Mean | 52.11 | 50.85 | 55.5 | 54.8 |
| | SD | 11.826 | 11.957 | 8.214 | 8.981 |
| | Median | 51.99 | 51.11 | 56.83 | 55.32 |
| | Min | 14.1 | 17.87 | 41.37 | 39.26 |
| | Max | 72.47 | 74.72 | 72.47 | 74.72 |
| | N | 60 | 177 | 47 | 120 |
| BMI | Mean | 28.84 | 27.76 | 29.32 | 28.71 |
| | SD | 3.889 | 4.108 | 3.557 | 3.348 |
| | Median | 28.12 | 27.17 | 28.55 | 27.72 |
| | Min | 21.98 | 19.94 | 25.14 | 25.03 |
| | Max | 43.71 | 44.55 | 43.71 | 44.55 |
| | N | 60 | 177 | 47 | 120 |
| SBP | Mean | 142.76 | 132.53 | 145.78 | 136.64 |
| | SD | 22.819 | 16.886 | 21.471 | 16.863 |
| | Median | 139.5 | 132 | 141 | 136.25 |
| | Min | 105 | 99 | 105 | 99 |
| | Max | 199 | 185 | 196 | 185 |
| | N | 60 | 177 | 47 | 120 |
| DBP | Mean | 84.78 | 81.25 | 86.47 | 83.17 |
| | SD | 10.506 | 9.653 | 10.017 | 9.422 |
| | Median | 85 | 80 | 88 | 82 |
| | Min | 62 | 56 | 67 | 60 |
| | Max | 109 | 110 | 109 | 110 |
| | N | 60 | 177 | 47 | 120 |
| CHOL | Mean | 5.9 | 5.92 | 5.94 | 6.13 |
| | SD | 1.177 | 1.245 | 1.163 | 1.253 |
| | Median | 5.67 | 5.81 | 5.71 | 6.02 |
| | Min | 4.08 | 3.39 | 4.08 | 3.77 |
| | Max | 10.04 | 12.51 | 10.04 | 12.51 |
| | N | 57 | 168 | 44 | 114 |
| HDLC | Mean | 1.28 | 1.36 | 1.22 | 1.36 |
| | SD | 0.319 | 0.31 | 0.281 | 0.33 |
| | Median | 1.25 | 1.34 | 1.16 | 1.34 |
| | Min | 0.724 | 0.776 | 0.724 | 0.776 |
| | Max | 1.959 | 2.109 | 1.893 | 2.109 |
| | N | 56 | 167 | 44 | 115 |
| TRIG | Mean | 1.7 | 1.49 | 1.75 | 1.51 |
| | SD | 1.113 | 0.88 | 0.959 | 0.79 |
| | Median | 1.58 | 1.21 | 1.62 | 1.27 |
| | Min | 0.61 | 0.508 | 0.63 | 0.587 |
| | Max | 6.57 | 6.78 | 5.56 | 3.90 |
| | N | 57 | 168 | 44 | 114 |
| Insulin | Mean | 13.09 | 8.45 | 14.04 | 8.61 |
| | SD | 8.684 | 4.553 | 9.217 | 4.393 |
| | Median | 10.5 | 7.05 | 12.92 | 7.46 |
| | Min | 2.58 | 2.72 | 2.58 | 2.90 |
| | Max | 55.50 | 27.42 | 55.50 | 24.69 |
| | N | 59 | 171 | 46 | 117 |

TABLE 5-continued

Baseline characteristics of converters and non-converters in Example 1

| | | Example 1 | | | |
|---|---|---|---|---|---|
| | | Total Population | | Base Population | |
| Variables | Levels | C (n = 60) | NC (n = 177) | C (n = 47) | NC (n = 120) |
| Glucose | Mean | 5.94 | 5.84 | 5.94 | 5.89 |
| | SD | 0.601 | 0.572 | 0.616 | 0.569 |
| | Median | 5.94 | 5.82 | 6.05 | 5.93 |
| | Min | 4.24 | 4.63 | 4.24 | 4.63 |
| | Max | 6.89 | 6.89 | 6.89 | 6.89 |
| | N | 60 | 177 | 47 | 120 |
| Glucose 120 min | Mean | 7.92 | 6.82 | 8.05 | 6.92 |
| | SD | 2.121 | 1.541 | 2.186 | 1.437 |
| | Median | 7.95 | 6.78 | 8.14 | 7.01 |
| | Min | 4.52 | 2.60 | 4.52 | 3.62 |
| | Max | 15.82 | 10.396 | 15.82 | 10.396 |
| | N | 60 | 177 | 47 | 120 |
| HBA1C | Mean | 5.75 | 5.44 | 5.79 | 5.51 |
| | SD | 0.443 | 0.511 | 0.427 | 0.55 |
| | Median | 5.7 | 5.4 | 5.8 | 5.5 |
| | Min | 4.80 | 3.90 | 5.10 | 3.90 |
| | Max | 7.14 | 7.05 | 7.14 | 7.05 |
| | N | 53 | 138 | 41 | 93 |
| HOMA | Mean | 3.5 | 2.22 | 3.75 | 2.28 |
| | SD | 2.46 | 1.26 | 2.615 | 1.232 |
| | Median | 2.86 | 1.85 | 3.49 | 1.91 |
| | Min | 0.59 | 0.62 | 0.59 | 0.70 |
| | Max | 16.30 | 7.37 | 16.30 | 7.13 |
| | N | 59 | 171 | 46 | 117 |

Baseline (at study entry) samples were tested. The total ALLDBRISKS measured in this population are presented in FIG. 15 of US 2007/0259377 (FIG. 29 herein), in the Example 1 column.

Prior to statistical methods being applied, each ALLDBRISK assay plate was reviewed for pass/fail criteria. Parameters taken into consideration included number of samples within range of the standard curve, serum control within the range of the standard curve, CVs of samples and dynamic range of assay.

A best fit Clinical Parameter only model was calculated in order to have a baseline to measure improvement from the incorporation of analyte-based ALLDBRISKS into the potential formulas. FIG. 2 of US 2007/0259377 (FIG. 16 herein), depicts a ROC curve of an LDA classification model derived only from the Clinical Parameters as measured and calculated for the Base Population of Example 1. FIG. 2 of US 2007/0259377 (FIG. 16 herein) also contains the AUC as well as LOO and 10-Fold cross-validation methods. No blood-borne biomarkers were measured in this analysis.

Figure 17:
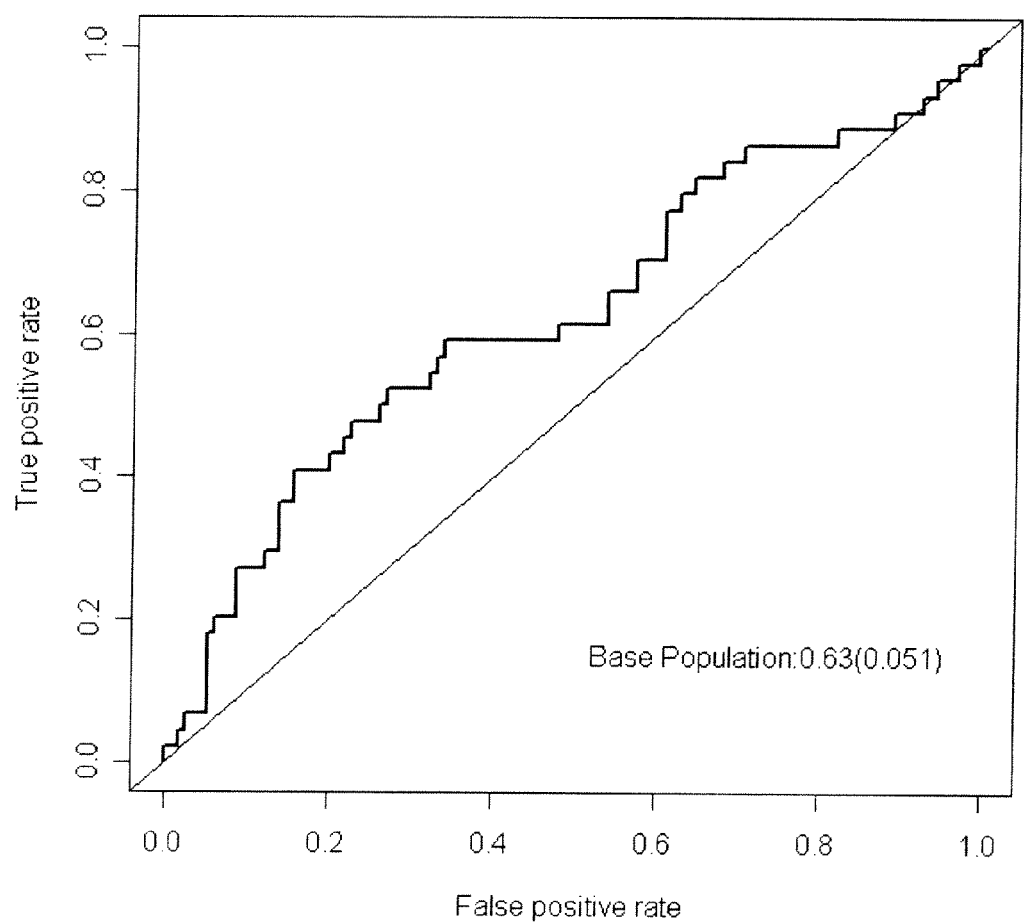
FIG. 17 is a graph showing a representative clinical global risk assessment index according to the Stern model of Diabetes risk, as measured and calculated for the Base Population of Example 1.
Figure 19A:
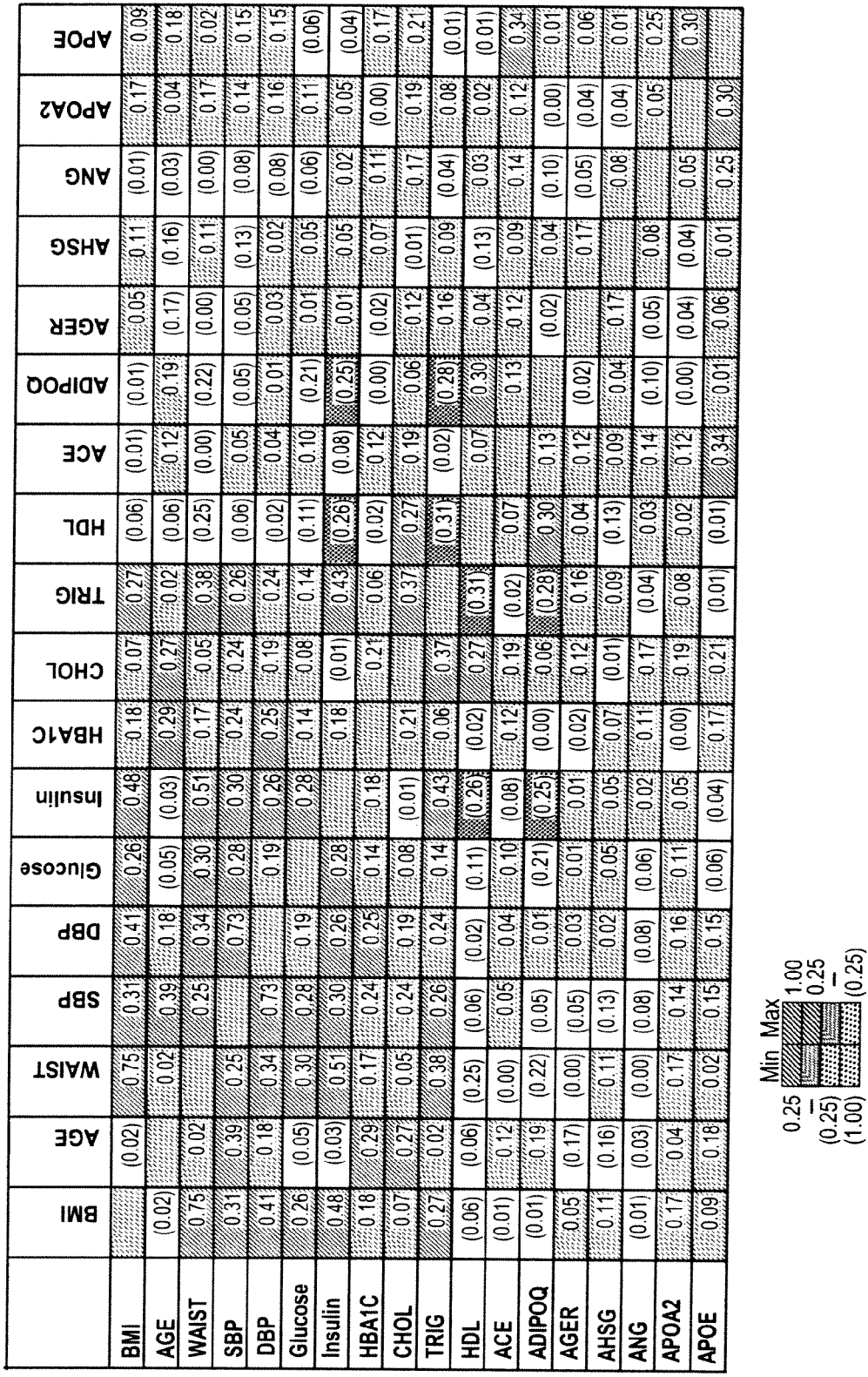
FIGS. 19A-19I are tables summarizing the results of cross-correlation analysis of clinical parameters and biomarkers of the present invention, as measured in the Base Population of Example 1.
Figure 19B:
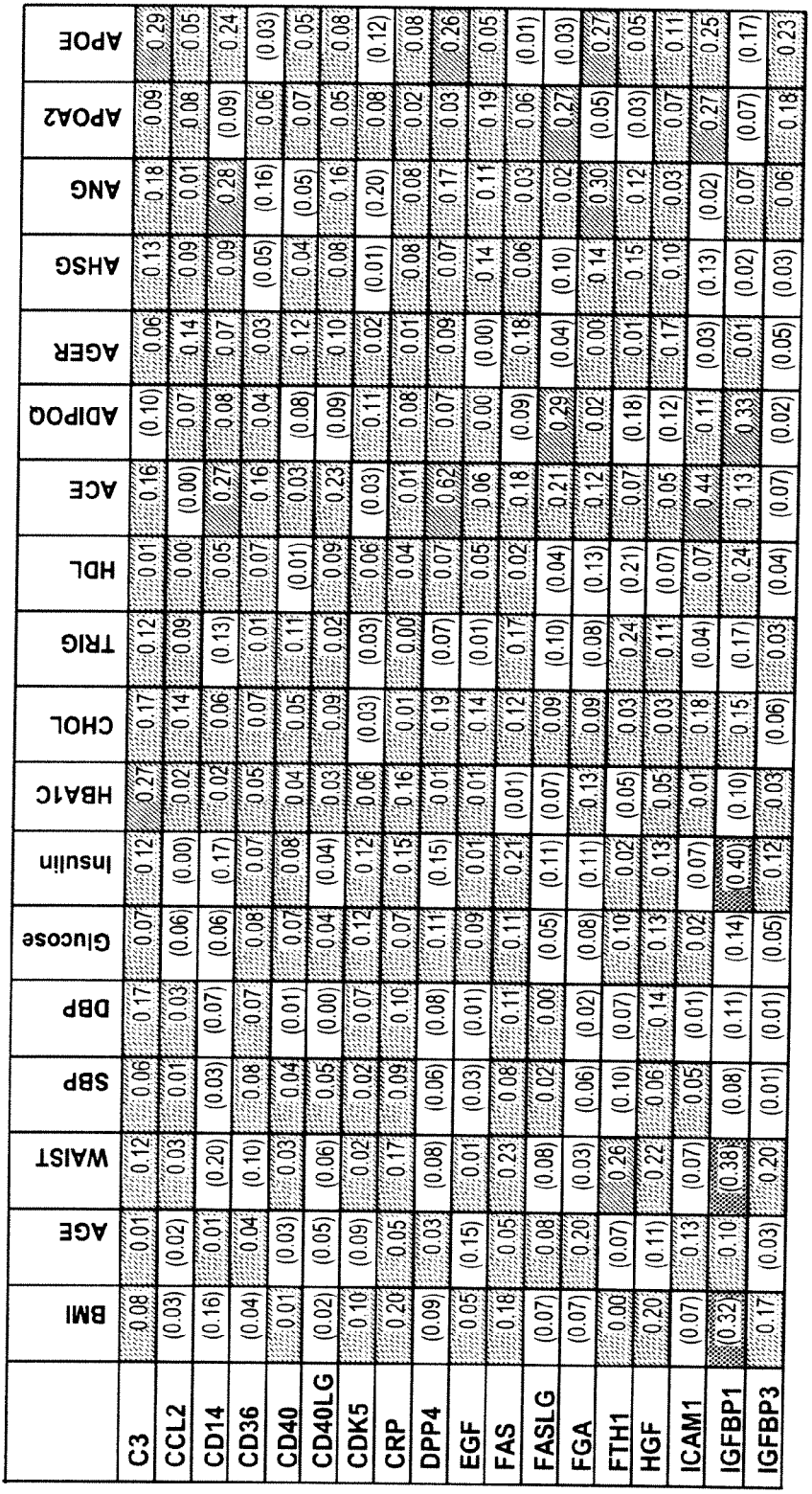
Figure 19C:
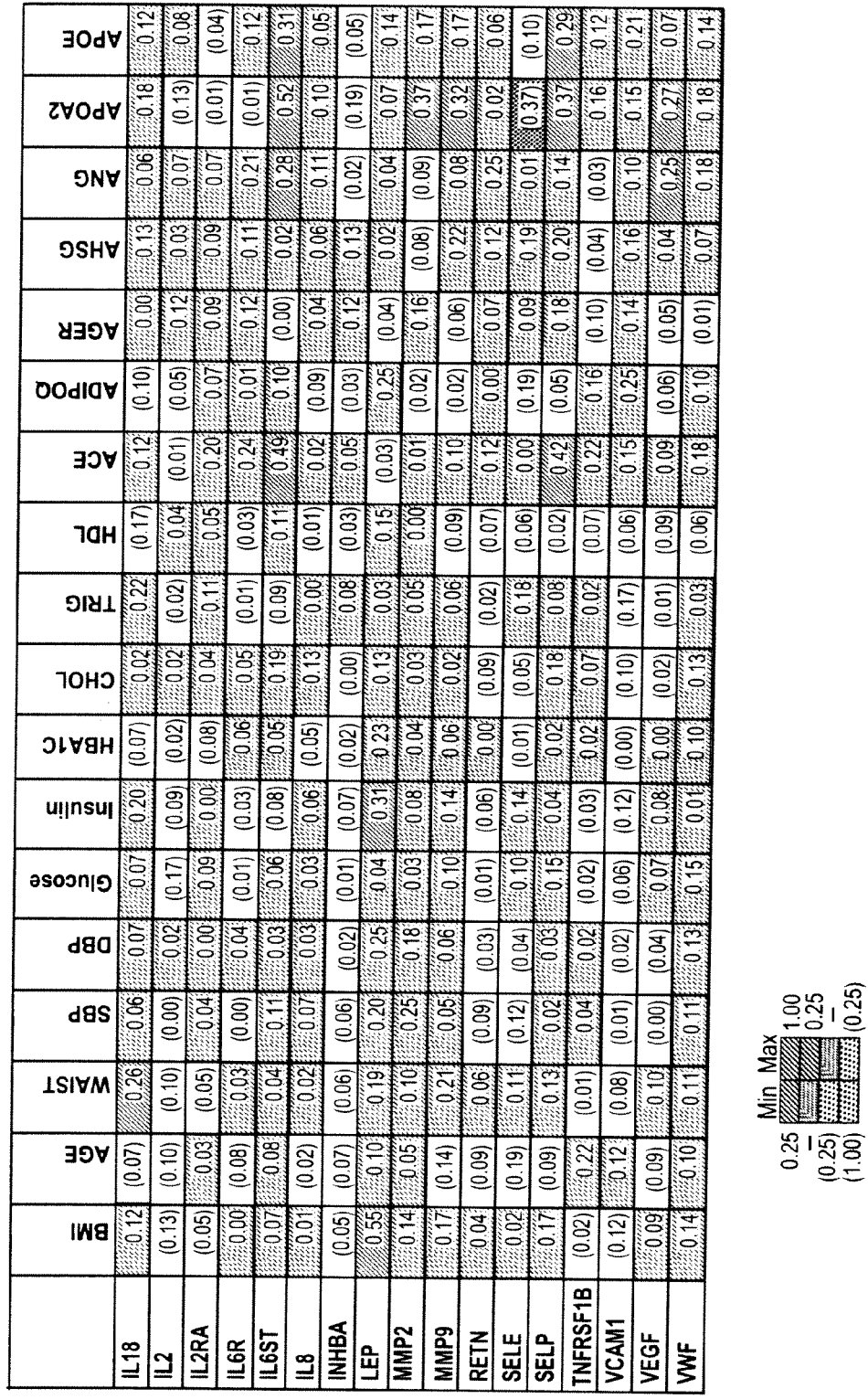
Figure 19D:
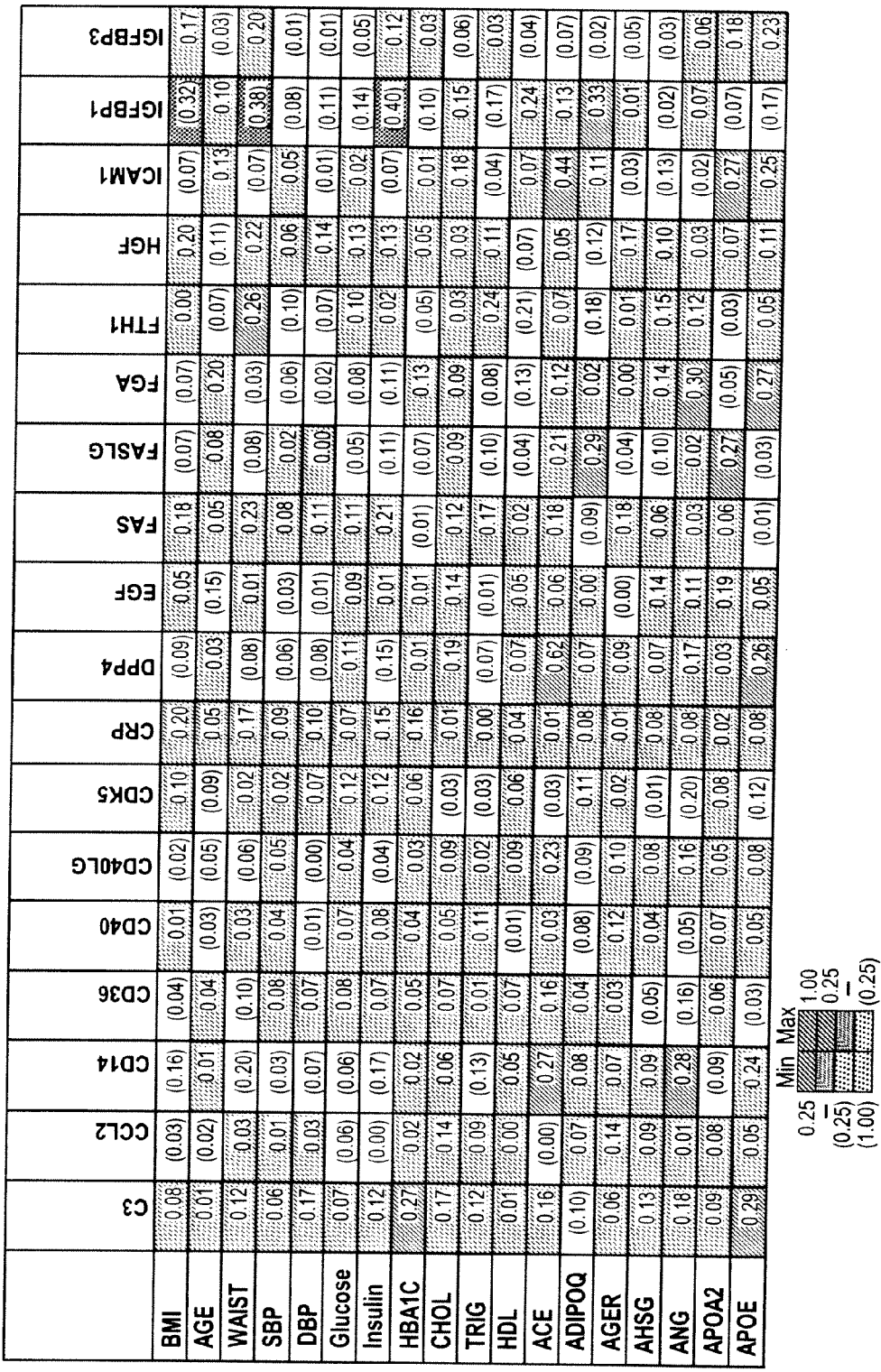
Figure 19E:
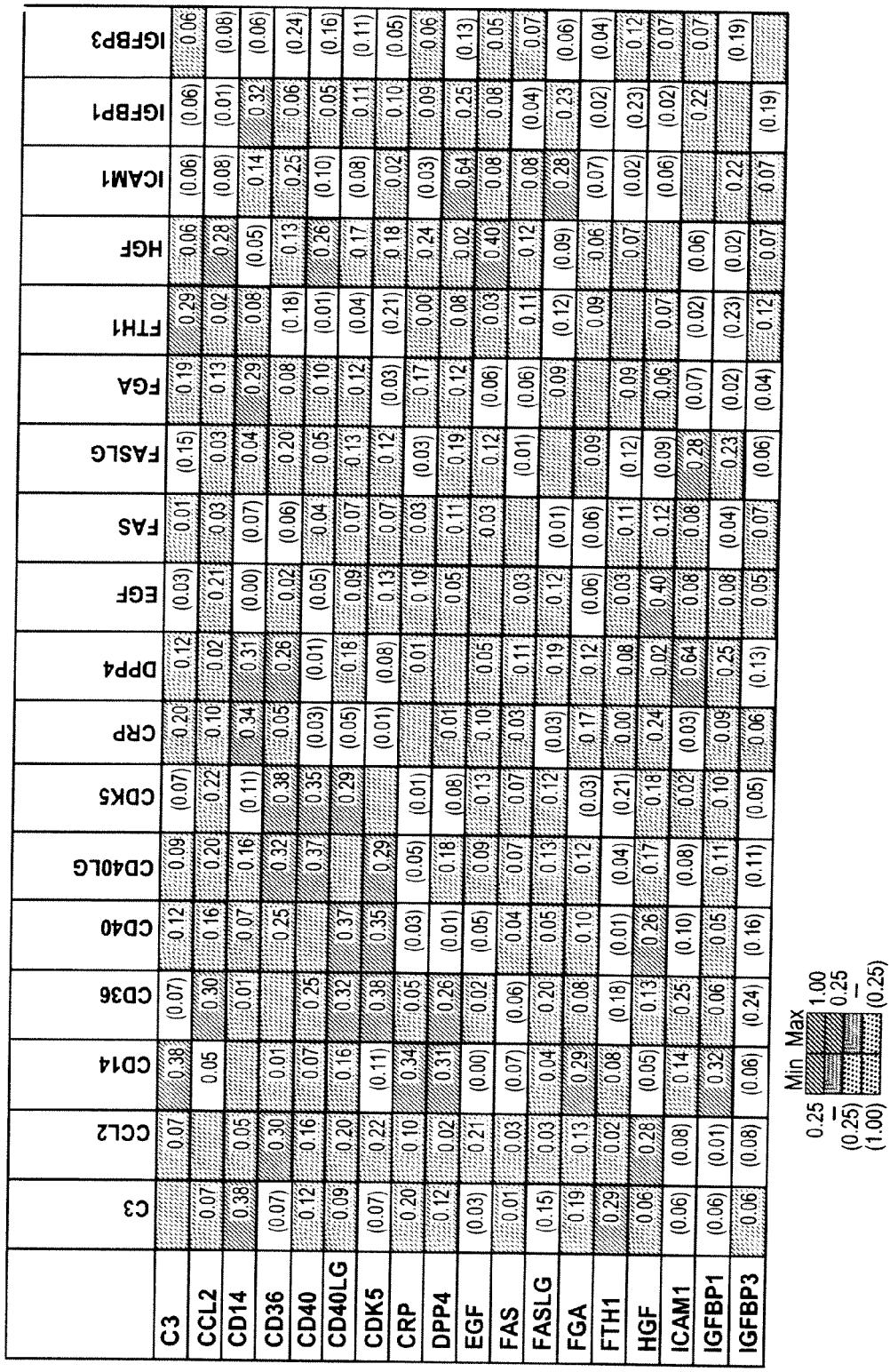
Figure 19F:
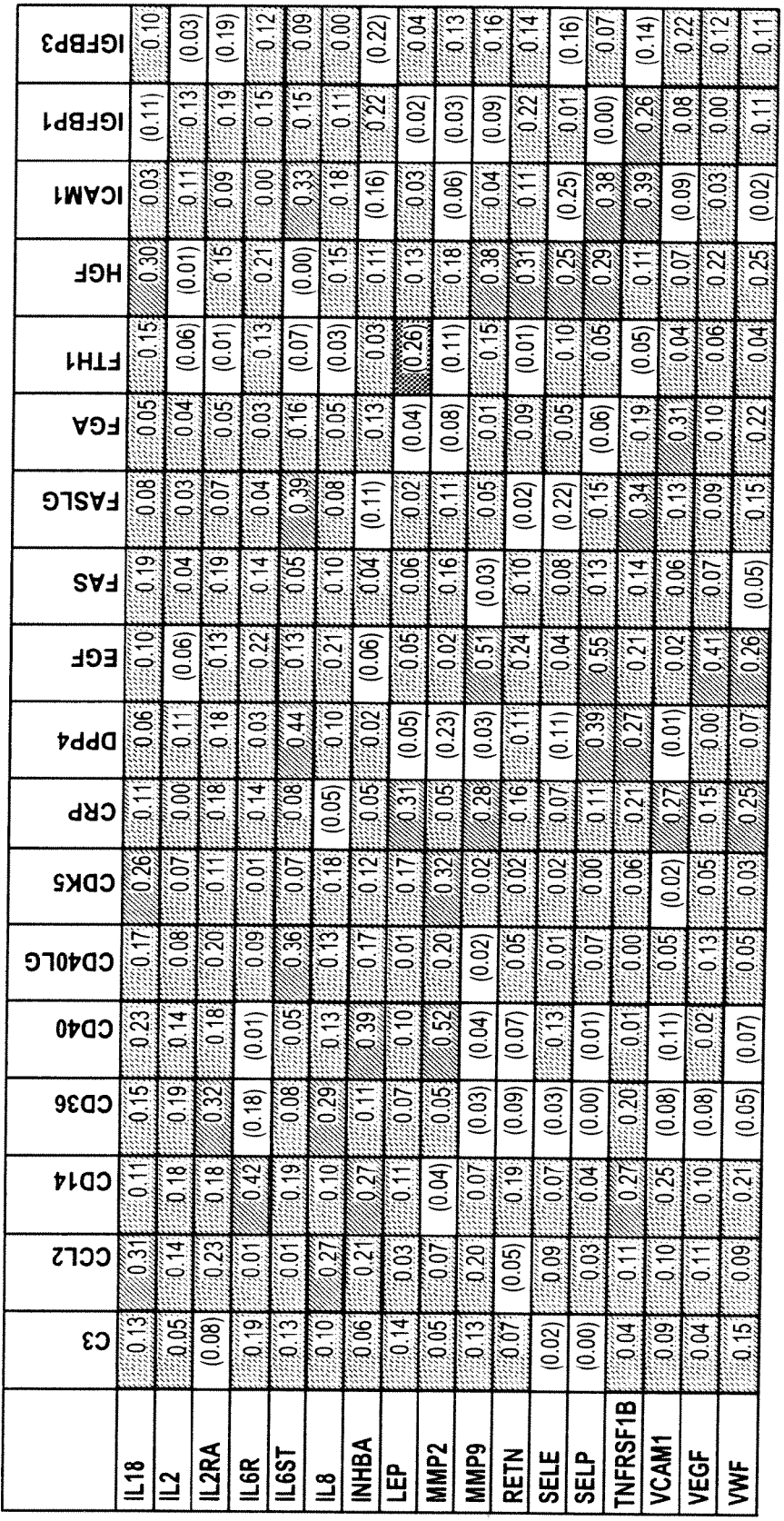
Figure 19G:
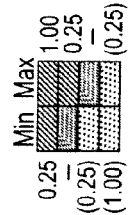
Figure 19H:
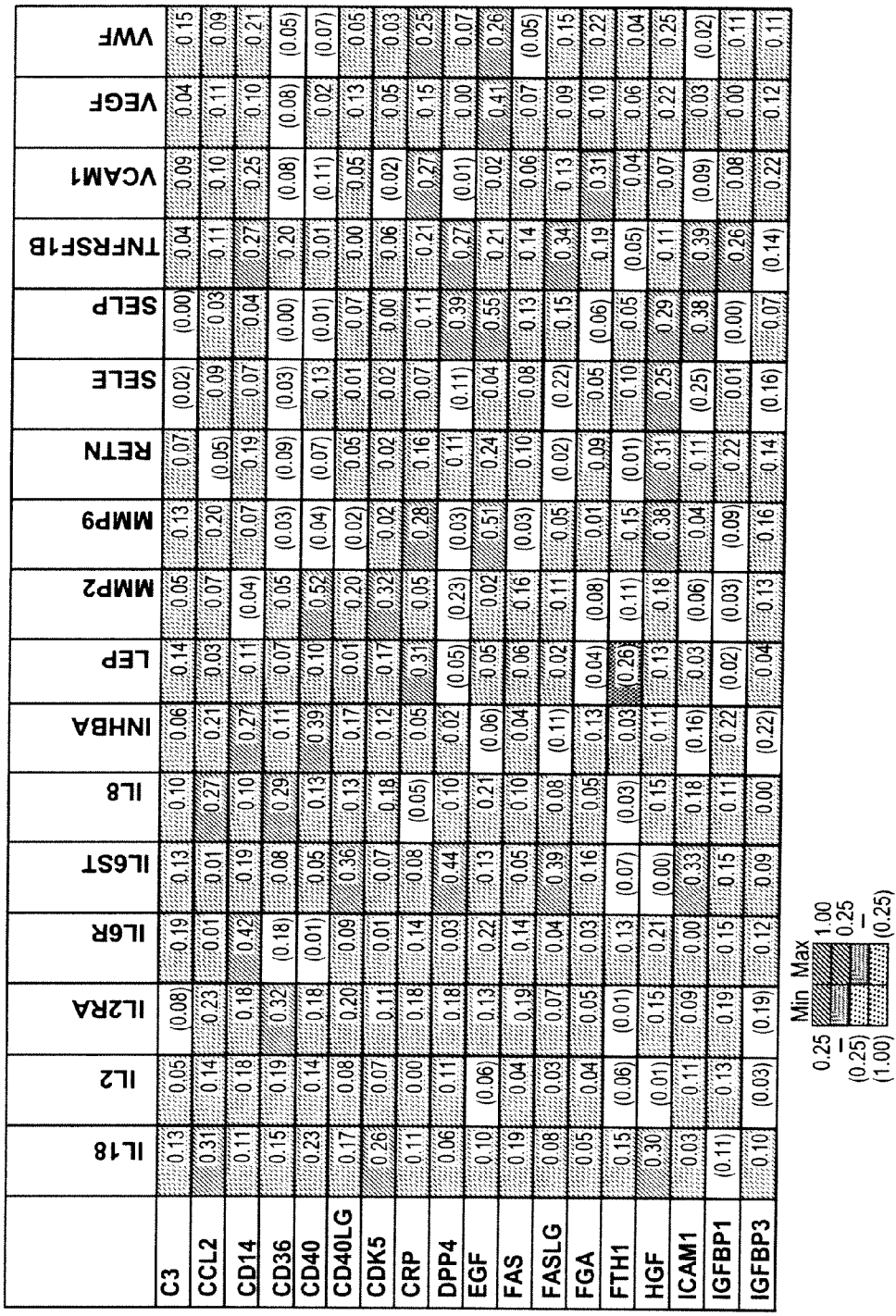
Figure 19I:
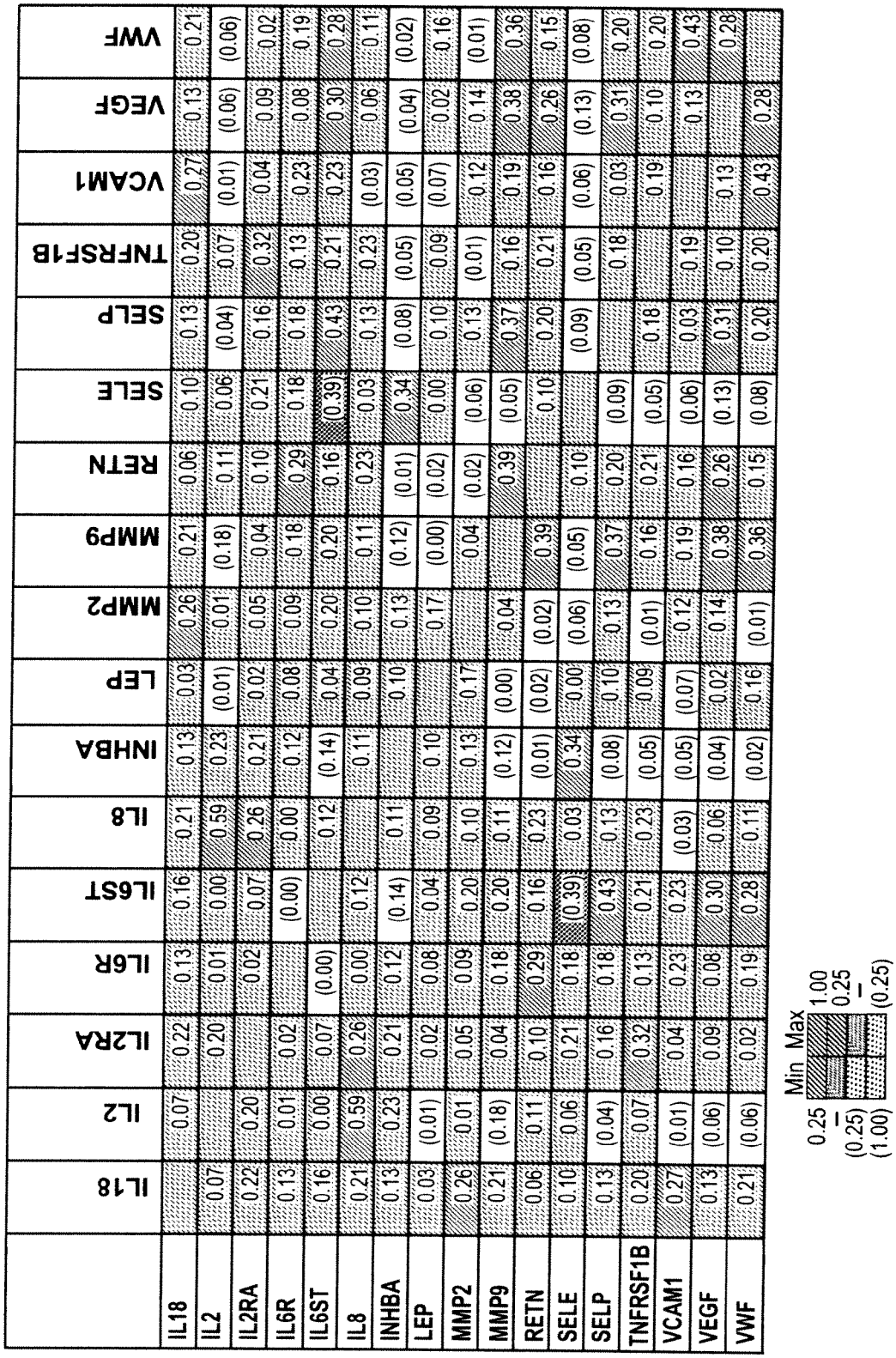

Baseline comparison was also calculated using a common literature global Diabetes risk index encompassing selected Clinical Parameter plus selected common Traditional Risk Factors. FIG. 3 of US 2007/0259377 (FIG. 17 herein), is a graphical representation of a clinical global risk assessment index according to the Stern model of Diabetes risk, measured and calculated for the Base Population of Example 1.

Figure 4:
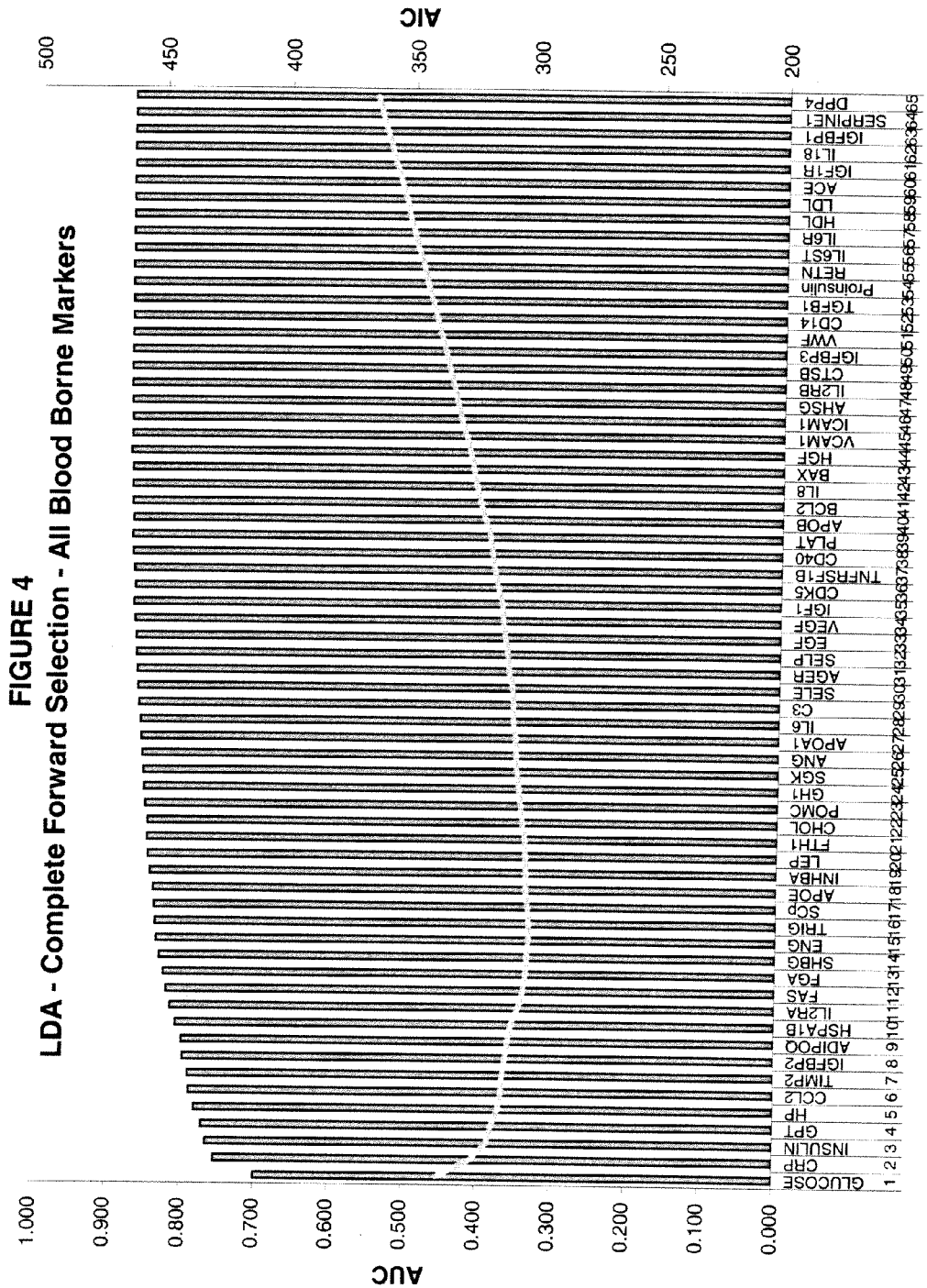
FIG. 4 is a chart depicting the ROC curve calculated AUCf statistics for multiple expanding "best forward selected" LDA models as measured and calculated from the base population of Example 2, starting from a single ALLDBRISK and then at each step adding one more incremental forward selected ALLDBRISK. This continues through 65 selected quantitative blood-borne ALLDBRISK selected from the set of markers in FIG. 3. The AIC is superimposed on the graph as a black line.

Prior to formula analysis, ALLDBRISK parameters were transformed, according to the methodologies shown for each ALLDBRISK in FIG. 4 of US 2007/0259377 (FIG. 18 herein), and missing results were imputed. If the amount of missing data was greater than 1%, various imputation techniques were employed to evaluate the effect on the results, otherwise the k-nearest neighbor method (library EMV, R Project) was used using correlation as the distance metric and 6 nearest neighbors to estimate the missing values.

Excessive covariation, multicolinearity, between variables were evaluated graphically and by computing pairwise correlation coefficients. When the correlation coefficients exceeded 0.75, a strong lack of independence between biomarkers was indicated, suggesting that they should be evaluated separately. Univariate summary statistics including means, standard deviations, and odds ratios were computed using logistic regression.

FIG. 4 of US 2007/0259377 (FIG. 18 herein) is a table that summarizes the results of univariate analysis of parameters variances, biomarker transformations, and biomarker mean back-transformed concentration values measured for both Converter and Non-Converter arms within Base Population of Example 1.

FIG. 5 of US 2007/0259377 (FIG. 19 herein) presents a table summarizing a cross-correlation analysis of clinical parameters and biomarkers as disclosed herein, as measured in the Base Population of Example 1.

Figure 20A:
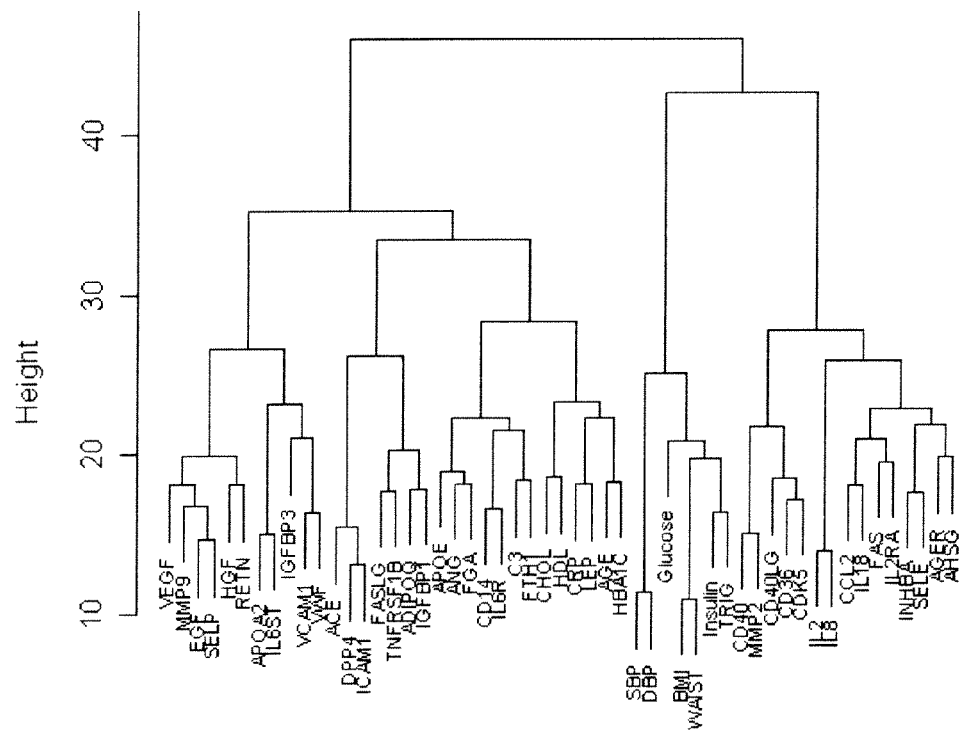
FIG. 20A is a graphical tree representation of the results of hierarchical clustering and Principal Component Analysis (PCA) of clinical parameters and biomarkers of the present invention, as measured in the Base Population of Example 1.
Figure 20B:
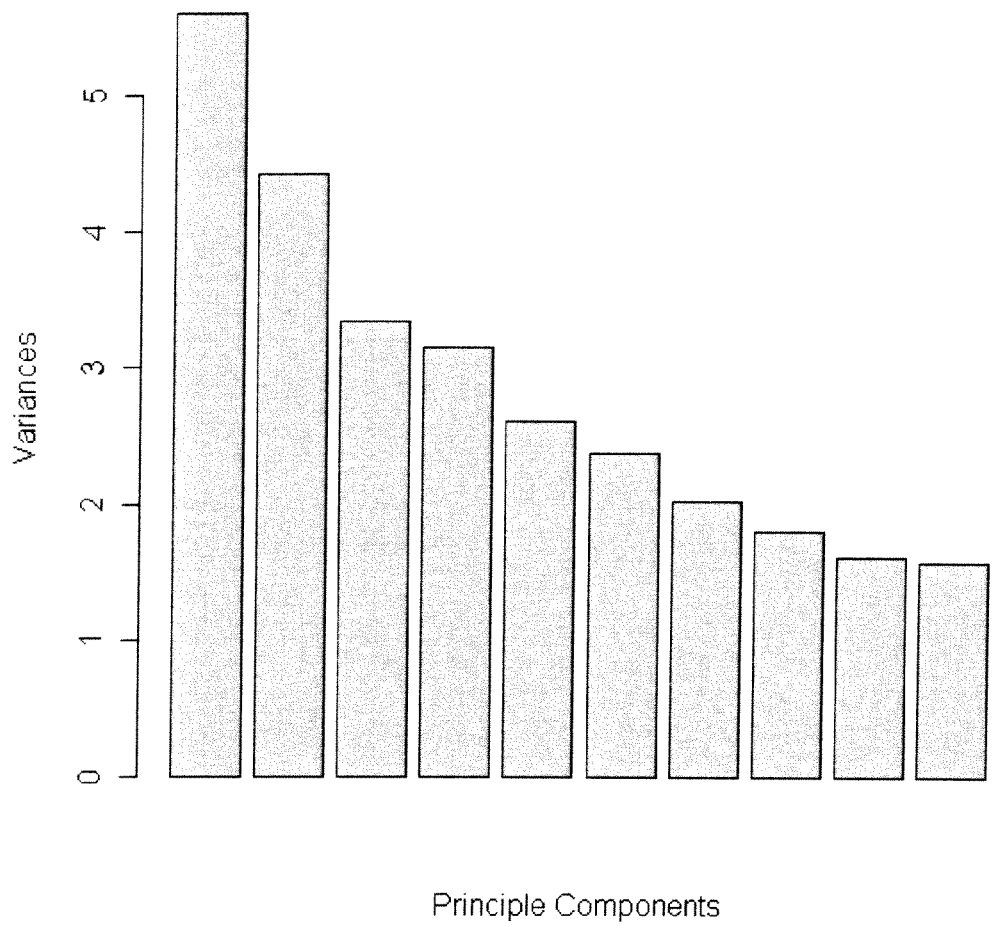
FIG. 20B is a bar graph representing the results of hierarchical clustering and PCA of clinical parameters and biomarkers of the present invention, as measured in the Base Population of Example 1.
Figure 20C:
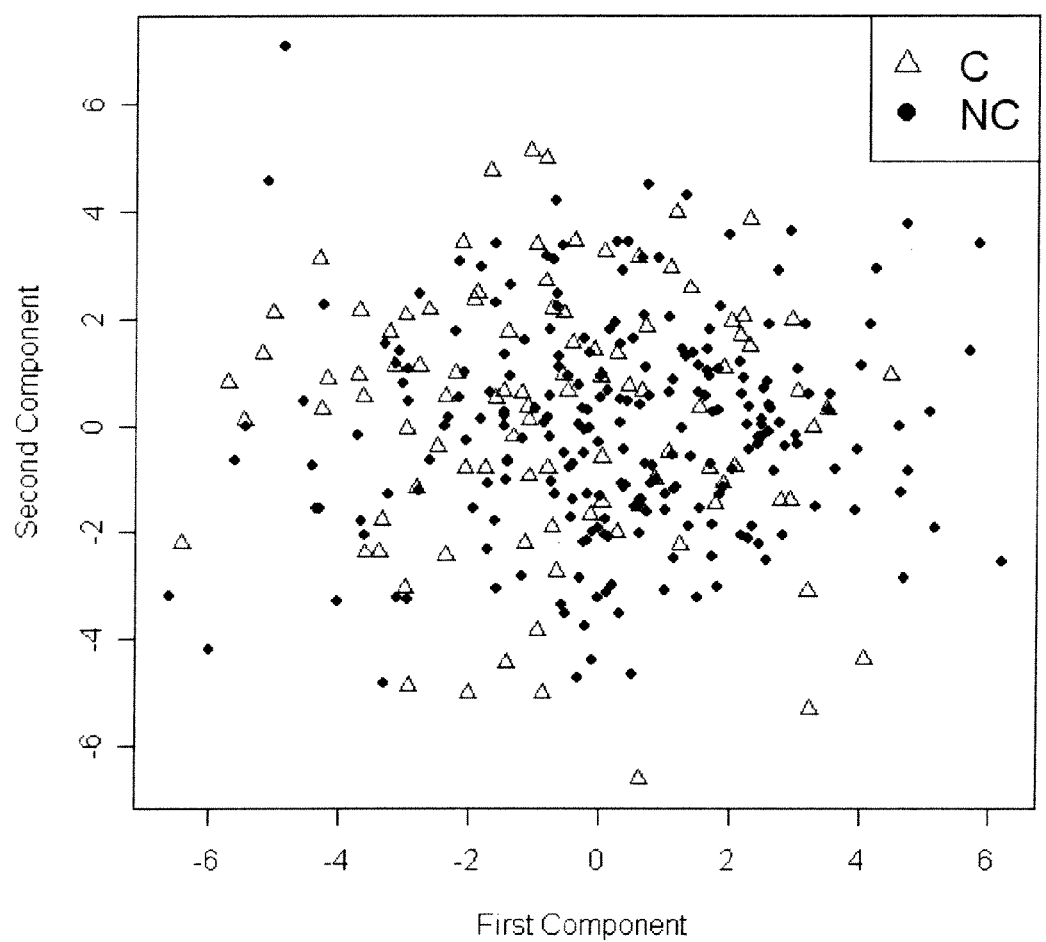
FIG. 20C is a scatter plot of the results of hierarchical clustering and PCA of clinical parameters and biomarkers of the present invention, as measured in the Base Population of Example 1.

FIGS. 6A through 6C of US 2007/0259377 (FIGS. 20A-20C herein) depict various graphical representations of the results of hierarchical clustering and Principal Component Analysis (PCA) of clinical parameters and biomarkers of the invention, as measured in the Base Population of Example 1.

Biomarker Selection and Model Building

Characteristics of the Base Population of Example 1 were considered in various predictive models, model types, and model parameters, and the AUC results of these formula are summarized in FIG. 7 of US 2007/0259377 (FIG. 21 herein). In general, Linear Discriminant Analysis (LDA) formula maintained the most predictable performance under cross-validation.

As an example LDA model, the below coefficients represent the terms of the linear discriminant (LD) of the respective LDA models, given in the form of:

LD=coefficient1\*biomarker1+
    coefficient2\*biomarker2+
    coefficient3\*biomarker3+

The terms "biomarker1," "biomarker2," "biomarker3" . . . represent the transformed values of the respective parameter as presented above in FIG. 4, with concentrations generally being log transformed, DBP being transformed using the square root function, and HBA1C value being used raw. Transformations were performed to correct the biomarkers for violations of univariate normality.

For a given subject, the posterior probability of conversion to Type 2 Diabetes Mellitus within a five year horizon under the relevant LDA is approximated by $1/(1+\text{EXP}(-1*\text{LD}))$. If the solution is >0.5, the subject was classified by the model as a converter.

Table 6 shows the results of ELDA and LDA SWS analysis on a selected set of ALLDBRISK and Traditional Blood Risk Factors in Cohort A Samples

TABLE 6

| ELDA | | LDA SWS | |
|---|---|---|---|
| DBP | −0.28145 | Insulin | −2.78863 |
| Insulin | −1.71376 | HBA1C | −0.76414 |
| HBA1C | −0.73139 | ADIPOQ | 1.818677 |
| ADIPOQ | 1.640633 | CRP | −0.83886 |
| CRP | −0.92502 | FAS | 1.041641 |
| FGA | 0.955317 | FGA | 0.827067 |
| | | IGFBP1 | −1.2481 |

Model Validation

To validate both the biomarker selection process and the underlying predictive algorithm, extensive cross-validation incorporating both feature selection and algorithm estimation was used. Two common cross-validation schemes to determine model performance were used. A leave-one-out CV is known to produce nearly unbiased prediction error estimates, but the estimate is often criticized to be highly variable. A 10-fold cross-validation, on the other hand, reduces the variability, but can introduce bias in the error estimates (Braga-Neto and Dougherty, 2004). To reduce the bias in this estimate the 10-fold cross validation was repeated 10 times such that the training samples were randomly divided 100 times into training groups consisting of 90% of the samples and test groups consisting of the remaining 10% of the samples. Such repeated 10-fold CV estimator has been recommended as an overall error estimator of choice in terms of reduced variance (Kohavi, 1995). The model performance characteristics were then averaged over all 10 of the cross validations.

Biomarker importance was estimated by ranking the features by their appearance frequencies in all the CV steps, because biomarker selection was carried out within the CV loops. Model quality was evaluated based on the model with the largest area under the ROC curve as well as sensitivity and specificity at the limit of the region of the ROC curve with the greatest area (i.e. the inflection point of the sensitivity plots).

Figure 22:
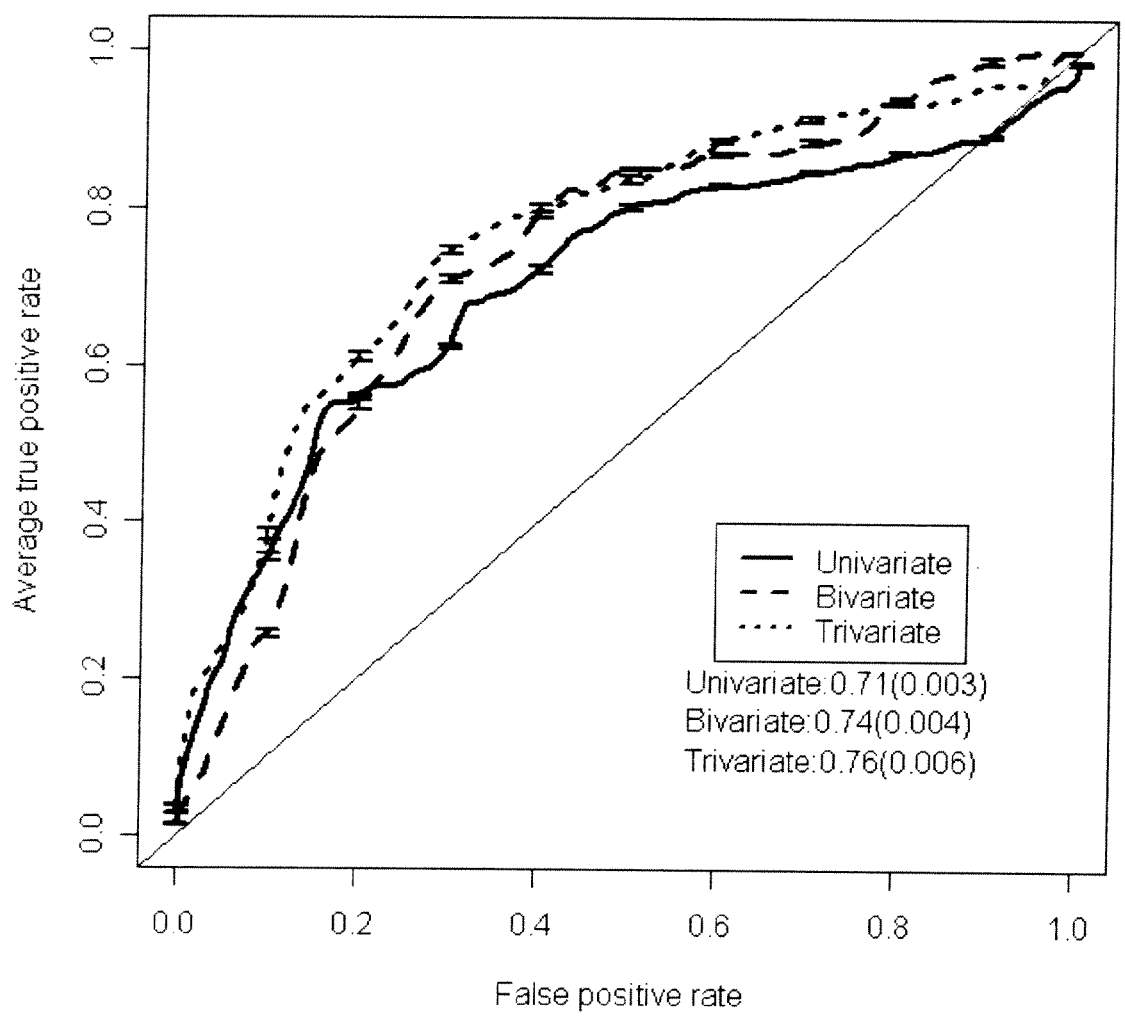
FIG. 22 is a graphical representative of the ROC curves for the leading univariate, bivariate, and trivariate LDA models by AUC, as measured and calculated in the Base Population of Example 1. The legend AUC represents the mean AUC of 10-Fold cross-validations for each model, with error bars indicating the standard deviation of the AUCs.
Figure 23:
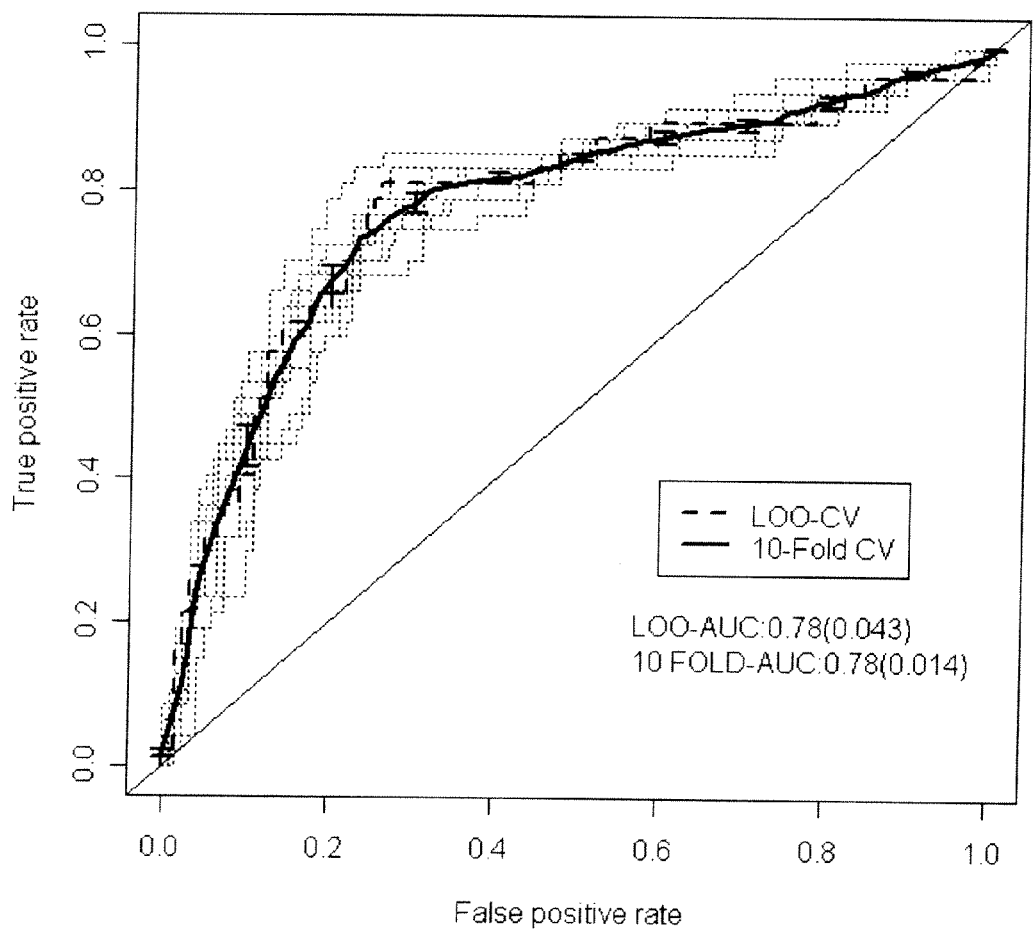
FIG. 23 is a graphical representation of the ROC curves for the LDA stepwise selection model, as measured and calculated in the Base Population of Example 1, using the same format as in FIG. 8.

FIG. 8 of US 2007/0259377 (FIG. 22 herein) is a graph showing the ROC curves for the leading univariate, bivariate, and trivariate LDA models by AUC, as measured and calculated in the Base Population of Example 1, whereas FIG. 9 of US 2007/0259377 (FIG. 23 herein) graphically shows ROC curves for the LDA stepwise selection model, also as measured and calculated in the Base Population of Example 1. The entire LDA forward-selected set of all tested parameters with model AUC and Akaike Information Criterion (AIC) statistics at each biomarker addition step is shown in the graph of FIG. 10 of US 2007/0259377 (FIG. 24 herein), as measured and calculated in the Base Population of Example 1.

Example 2

Example 2 demonstrates the practice of the invention in a separate general longitudinal population-based study, with a comparably selected Base sub-population and a frank Diabetes sub-analysis.

As in Example 1, for purposes of model discovery, subjects were selected from the sample sets with the following characteristics:

Converters (C): conversion to Diabetes must have been within 5 years

Non-Converters (NC): must have had at least 8 years of follow-up with no documentation of Diabetes.

As in Example 1, both the "Total Population" of all such subjects and a selected "Base Population" sub-population were analyzed. The Base Population was comprised of all subjects within the Total Population who additionally met the inclusion criteria of AGE equal to or greater than 39 years and BMI equal to or greater than 25 kg/m2.

Descriptive statistics summarizing each of the Example 2 study population arms are presented below in Table 7.

TABLE 7

Baseline Characteristics of Example 2 and Subsets

| | | Example 2 | | | | |
|---|---|---|---|---|---|---|
| | | Total Population | | Base Population | | |
| Variables | Levels | C (n = 100) | NC (n = 236) | C (n = 83) | NC (n = 236) | Diabetic (n = 48) |
| HeartThrombosis | No | 95 | 225 | 78 | 225 | 45 |
| | Yes | 0 | 1 | 0 | 1 | 1 |
| PhysicalActivity | Active | 12 | 32 | 12 | 32 | 4 |
| | Athelete | 0 | 3 | 0 | 3 | 1 |
| | Sit | 26 | 50 | 24 | 50 | 21 |
| | Walk | 60 | 146 | 45 | 146 | 21 |
| Familial History | No | 94 | 211 | 78 | 211 | 45 |
| of CVD | Yes | 6 | 25 | 5 | 25 | 3 |
| Glucose tolerance | NGT | 21 | 163 | 14 | 163 | 0 |
| status baseline | IFG | 18 | 39 | 15 | 39 | 0 |
| | IGT | 59 | 27 | 52 | 27 | 0 |
| | SDM | 0 | 0 | 0 | 0 | 27 |
| | KDM | 0 | 0 | 0 | 0 | 21 |
| Diet | average | 57 | 160 | 46 | head | 27 |
| | healthy | 13 | 34 | 13 | 34 | 9 |
| | unhealthy | 23 | 31 | 18 | 31 | 9 |
| Sex | female | 39 | 91 | 31 | 91 | 19 |
| | male | 61 | 145 | 52 | 145 | 29 |
| Family HX DD | No | 71 | 182 | 57 | 182 | 32 |
| (parents and sibs) | Yes | 29 | 54 | 26 | 54 | 16 |
| Family HX DB | No | 97 | 236 | 81 | 236 | 47 |
| (children) | Yes | 3 | 0 | 2 | 0 | 1 |
| High Risk | No | 9 | 79 | 5 | 79 | 0 |
| | Yes | 91 | 157 | 78 | 157 | 48 |
| Smoking | Not Offered | 59 | 90 | 53 | 90 | 39 |
| Intervention | Declined | 21 | 43 | 16 | 43 | 6 |
| | Accepted | 11 | 24 | 9 | 24 | 3 |
| Diet and Exercise | Not Offered | 14 | 62 | 9 | 62 | 12 |
| Intervention | Declined | 22 | 36 | 19 | 36 | 11 |
| | Accepted | 55 | 59 | 50 | 59 | 25 |
| Height | Mean | 172.4 | 172.97 | 172.43 | 172.97 | 170.85 |
| | SD | 9.112 | 9.486 | 9.445 | 9.486 | 10.664 |
| | Median | 172 | 173 | 172 | 173 | 170.5 |
| | Min | 148 | 151 | 148 | 151 | 149 |

TABLE 7-continued

Baseline Characteristics of Example 2 and Subsets

| | | Example 2 | | | | |
|---|---|---|---|---|---|---|
| | | Total Population | | Base Population | | |
| Variables | Levels | C (n = 100) | NC (n = 236) | C (n = 83) | NC (n = 236) | Diabetic (n = 48) |
| | Max | 192 | 195 | 192 | 195 | 194 |
| | N | 100 | 236 | 83 | 236 | 48 |
| Weight | Mean | 87.44 | 86.35 | 90.61 | 86.35 | 90.98 |
| | SD | 16.398 | 14.457 | 14.968 | 14.457 | 18.396 |
| | Median | 84.5 | 84.45 | 88 | 84.45 | 86.3 |
| | Min | 49.8 | 57 | 67.2 | 57 | 64.3 |
| | Max | 126 | 183 | 126 | 183 | 141.2 |
| | N | 100 | 236 | 83 | 236 | 48 |
| Waist | Mean | 96.05 | 93.39 | 98.49 | 93.39 | 101.31 |
| | SD | 12.567 | 11.05 | 11.651 | 11.05 | 13.246 |
| | Median | 94.5 | 93 | 96 | 93 | 99 |
| | Min | 66 | 68 | 72 | 68 | 79 |
| | Max | 125 | 165 | 125 | 165 | 136 |
| | N | 100 | 235 | 83 | 235 | 48 |
| Hip | Mean | 105.34 | 105.37 | 106.72 | 105.37 | 108.02 |
| | SD | 9.47 | 9.774 | 9.021 | 9.774 | 11.412 |
| | Median | 105.5 | 104 | 107 | 104 | 105.5 |
| | Min | 81 | 88 | 81 | 88 | 91 |
| | Max | 135 | 165 | 135 | 165 | 151 |
| | N | 100 | 235 | 83 | 235 | 48 |
| Age | Mean | 49.6 | 48.81 | 50.07 | 48.81 | 51.26 |
| | SD | 6.786 | 6.325 | 6.325 | 6.325 | 6.426 |
| | Median | 50 | 49.8 | 50 | 49.8 | 50.15 |
| | Min | 34.7 | 39.7 | 39.8 | 39.7 | 39.8 |
| | Max | 60.5 | 60.3 | 60.5 | 60.3 | 60.8 |
| | N | 100 | 236 | 83 | 236 | 48 |
| BMI | Mean | 29.36 | 28.82 | 30.42 | 28.82 | 31.13 |
| | SD | 4.656 | 4.115 | 4.051 | 4.115 | 5.472 |
| | Median | 28.7 | 27.65 | 29.7 | 27.65 | 29.8 |
| | Min | 18.7 | 25 | 25 | 25 | 25 |
| | Max | 45.2 | 55.7 | 45.2 | 55.7 | 48.9 |
| | N | 100 | 236 | 83 | 236 | 48 |
| Units of alcohol intake per week | Mean | 12.61 | 13.68 | 12.3 | 13.68 | 15.55 |
| | SD | 13.561 | 28.03 | 13.419 | 28.03 | 22.115 |
| | Median | 6 | 8 | 6 | 8 | 6.5 |
| | Min | 0 | 0 | 0 | 0 | 0 |
| | Max | 59 | 330 | 59 | 330 | 102 |
| | N | 95 | 219 | 79 | 219 | 44 |
| SBP | Mean | 138.07 | 133.91 | 139.18 | 133.91 | 144.15 |
| | SD | 18.265 | 18.508 | 15.798 | 18.508 | 23.448 |
| | Median | 140 | 130 | 140 | 130 | 140 |
| | Min | 104 | 100 | 110 | 100 | 100 |
| | Max | 195 | 198 | 180 | 198 | 212 |
| | N | 100 | 236 | 83 | 236 | 48 |
| DBP | Mean | 87.28 | 84.91 | 87.61 | 84.91 | 87.1 |
| | SD | 12.874 | 11.708 | 12.151 | 11.708 | 10.446 |
| | Median | 85 | 85 | 85 | 85 | 87 |
| | Min | 58 | 60 | 66 | 60 | 60 |
| | Max | 140 | 128 | 140 | 128 | 110 |
| | N | 100 | 236 | 83 | 236 | 48 |
| CHOL | Mean | 5.92 | 5.81 | 5.95 | 5.81 | 5.85 |
| | SD | 1.092 | 1.033 | 1.033 | 1.033 | 1.015 |
| | Median | 5.8 | 5.7 | 5.8 | 5.7 | 5.9 |
| | Min | 3.4 | 3.5 | 3.6 | 3.5 | 4.1 |
| | Max | 9.2 | 9 | 8.5 | 9 | 7.7 |
| | N | 100 | 236 | 83 | 236 | 48 |
| HDLC | Mean | 1.29 | 1.35 | 1.26 | 1.35 | 1.25 |
| | SD | 0.352 | 0.388 | 0.343 | 0.388 | 0.35 |
| | Median | 1.23 | 1.29 | 1.21 | 1.29 | 1.21 |
| | Min | 0.66 | 0.6 | 0.66 | 0.6 | 0.74 |
| | Max | 2.19 | 3.37 | 2.19 | 3.37 | 2.6 |
| | N | 100 | 236 | 83 | 236 | 48 |
| LDL | Mean | 3.8 | 3.75 | 3.83 | 3.75 | 3.62 |
| | SD | 0.992 | 0.912 | 0.952 | 0.912 | 0.843 |
| | Median | 3.7 | 3.7 | 3.72 | 3.7 | 3.6 |
| | Min | 1.61 | 1.2 | 2.1 | 1.2 | 1.6 |
| | Max | 6.62 | 6.86 | 6.62 | 6.86 | 5.4 |
| | N | 97 | 232 | 80 | 232 | 45 |
| TRIG | Mean | 1.92 | 1.6 | 2 | 1.6 | 2.2 |
| | SD | 1.107 | 1.454 | 1.143 | 1.454 | 1.444 |
| | Median | 1.6 | 1.3 | 1.6 | 1.3 | 1.9 |

TABLE 7-continued

Baseline Characteristics of Example 2 and Subsets

| | | Example 2 | | | | |
| --- | --- | --- | --- | --- | --- | --- |
| | | Total Population | | Base Population | | |
| Variables | Levels | C (n = 100) | NC (n = 236) | C (n = 83) | NC (n = 236) | Diabetic (n = 48) |
| | Min | 0.5 | 0.4 | 0.6 | 0.4 | 0.6 |
| | Max | 5.6 | 15.2 | 5.6 | 15.2 | 7 |
| | N | 100 | 236 | 83 | 236 | 48 |
| SCp0 | Mean | 652.08 | 595.81 | 670.23 | 595.81 | 706.33 |
| | SD | 197.944 | 177.582 | 197.384 | 177.582 | 195.637 |
| | Median | 659.5 | 564 | 706.5 | 564 | 727 |
| | Min | 280 | 273 | 280 | 273 | 10 |
| | Max | 972 | 988 | 972 | 988 | 996 |
| | N | 72 | 209 | 56 | 209 | 33 |
| Insulin | Mean | 63.14 | 45.85 | 67.24 | 45.85 | 71.26 |
| | SD | 39.01 | 28.065 | 40.203 | 28.065 | 38.414 |
| | Median | 53.5 | 37 | 57 | 37 | 62 |
| | Min | 12 | 10 | 12 | 10 | 26 |
| | Max | 210 | 164 | 210 | 164 | 217 |
| | N | 100 | 236 | 83 | 236 | 47 |
| Ins120 | Mean | 382.89 | 213.13 | 401.88 | 213.13 | 464.34 |
| | SD | 231.912 | 157.625 | 227.478 | 157.625 | 295.239 |
| | Median | 323.5 | 181 | 351.5 | 181 | 441 |
| | Min | 55 | 11 | 55 | 11 | 53 |
| | Max | 958 | 913 | 958 | 913 | 990 |
| | N | 90 | 224 | 74 | 224 | 32 |
| Glucose | Mean | 5.95 | 5.61 | 6 | 5.61 | 8.91 |
| | SD | 0.55 | 0.504 | 0.528 | 0.504 | 3.843 |
| | Median | 6 | 5.6 | 6 | 5.6 | 7.3 |
| | Min | 4.7 | 4.1 | 4.7 | 4.1 | 4.9 |
| | Max | 6.8 | 6.9 | 6.8 | 6.9 | 21 |
| | N | 100 | 236 | 83 | 236 | 48 |
| Glucose 120 min | Mean | 8.07 | 6.08 | 8.22 | 6.08 | 12.5 |
| | SD | 1.876 | 1.543 | 1.791 | 1.543 | 4.349 |
| | Median | 8.5 | 6 | 8.6 | 6 | 12.5 |
| | Min | 4 | 2.4 | 4 | 2.4 | 4.2 |
| | Max | 11 | 10.7 | 11 | 10.7 | 25.6 |
| | N | 98 | 229 | 81 | 229 | 36 |

ALLDBRISK biomarkers were run on baseline samples in the same manner as described for the samples derived from Example 2.

FIG. 11 of US 2007/0259377 (FIG. 25 herein) shows tables that summarize univariate ANOVA analyses of parameter variances, including biomarker transformation and biomarker mean back-transformed concentration values across non-converters, converters, and diabetic populations, as measured and calculated at baseline in the Total Population of Example 2. Cross-correlation of clinical parameters and selected biomarkers are shown in FIG. 12 of US 2007/0259377, (FIG. 26 herein) which was measured in the Total Populations of Example 2.

Figure 13:
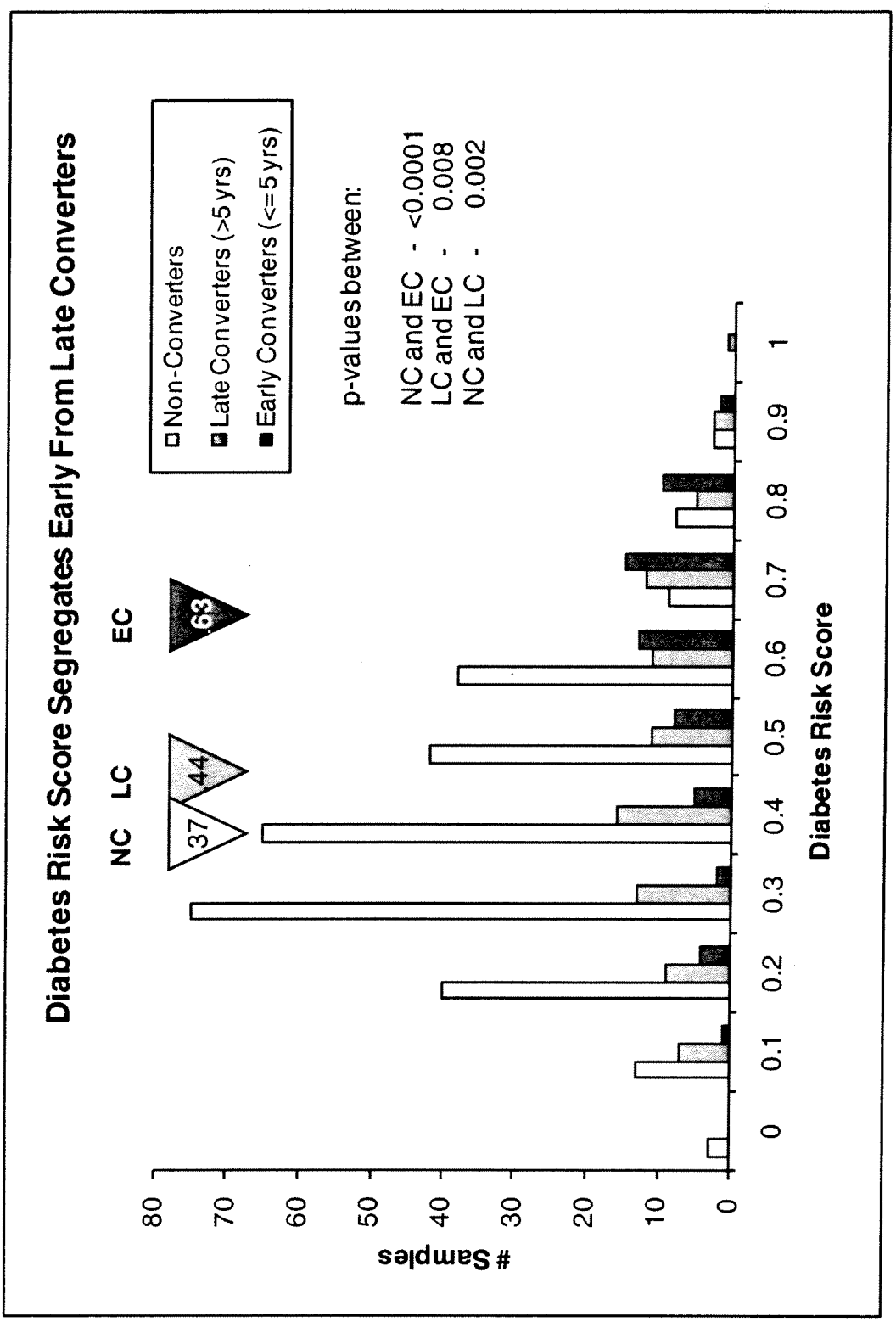
FIG. 13 depicts an analysis of DRS scores from the base population of Example 1. Three populations have been segregated by their DRS (p<0.0001; Kruskal-Wallis Test): Non-Converters (NC), Late Converters (LC, >5 years to conversion) and Early Converters (EC, <5 years to conversion). The highest risk group, EC, which converts to Diabetes in less than 5 years, has a median DRS of 0.63, compared to the NC group with a score of 0.37 (p<0.0001). It is also possible to separate the LC group, who convert to Diabetes in >5 years, from the EC group (p=0.008).

FIG. 13 of US 2007/0259377 (FIG. 27 herein) is a graphical representation of the entire LDA forward-selected set of tested parameters with model AUC and AIC statistics at each biomarker addition step, as measured and calculated in the Total Population of Example 2, while FIG. 14 of US 2007/0259377 (FIG. 28 herein) graphically shows an LDA forward-selected set of blood-borne biomarkers (excluding clinical parameters) alone with model characteristics at each biomarker addition step as described herein in the same population.

Example 3

Example 3 is a study of the differences and similarities between the results obtained in the two previous Examples.

FIG. 29 is a tabular representation of all parameters tested in Example 1 and Example 2, according to the ALLDBRISK biomarker categories disclosed herein.

Tables summarizing ALLDBRISK biomarker selection under various scenarios of classification model types and base and total populations of Examples 1 and 2 are shown in FIGS. 16A and 16B, respectively.

Figure 32:
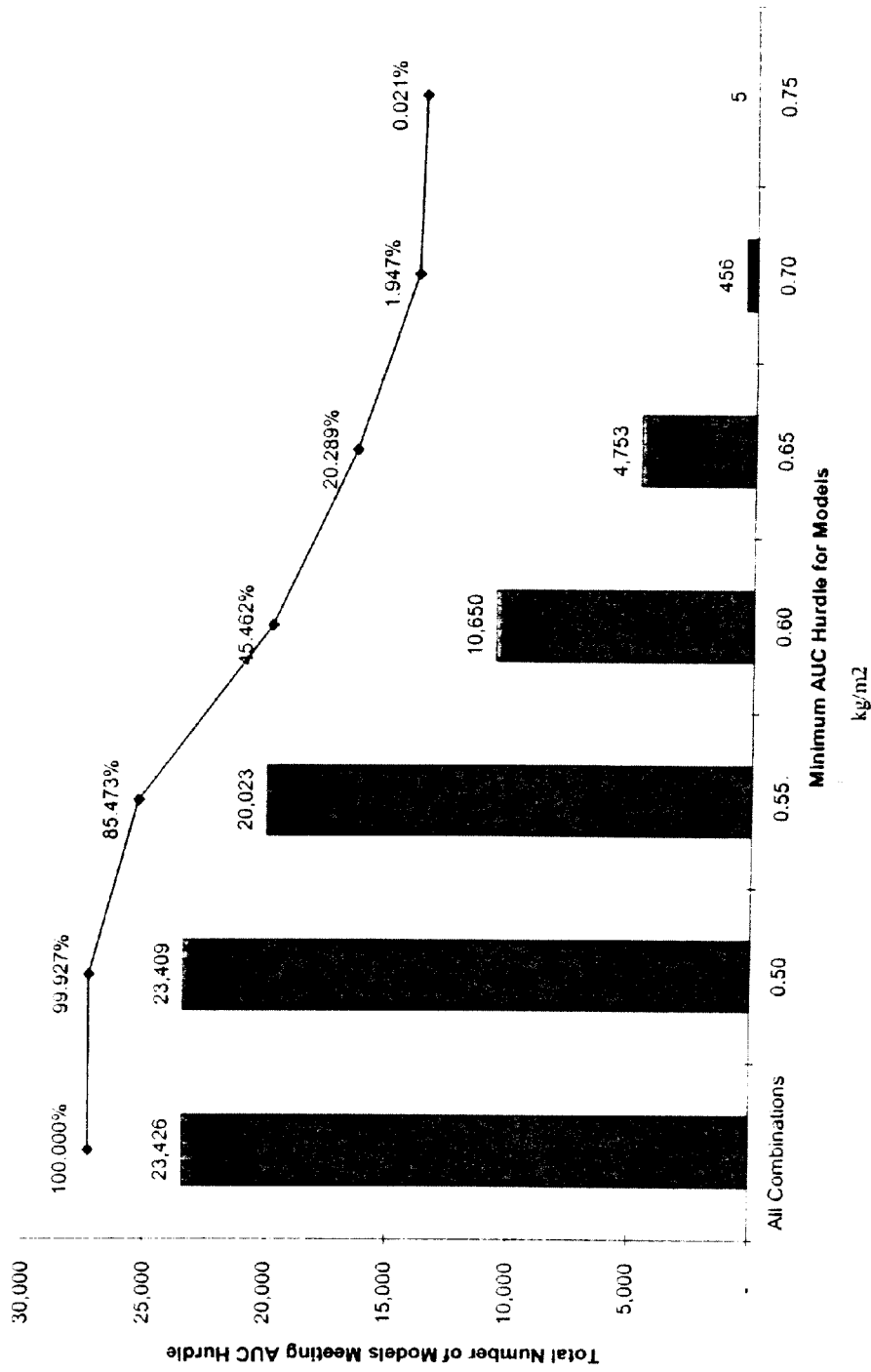
FIG. 32 is a graph showing the number and percentage of the total univariate, bivariate, and trivariate models of FIG. 31 which meet various AUC hurdles using the Total Population of Example 1.

FIG. 31 further summarizes the complete enumeration of fitted LDA models for all potential univariate, bivariate, and trivariate combinations as measured and calculated for both Total and Base Populations of Examples 1 and 2, and encompassing all 53 and 49 ALLDBRISK parameters recorded, respectively, for each study as potential model parameters. A graphical representation of the data presented in FIG. 31 is shown in FIG. 32, which shows the number and percentage of the total univariate, bivariate, and trivariate models that meet various AUC hurdles using the Total Population of Example 1.

Example 4

Example of a Diabetes Risk Score Based on Nine Biomarkers

The parameter D is computed using the following formula: D=−13.56*glucose−0.62*CRP−0.70*insulin−0.89*GPT−0.92*HSPA1B+0.04*IGFBP2+0.66*ADIPOQ−0.67*LEP−0.69*TRIG. The Diabetes Risk Score, or DRS, is given by the formula DRS=exp(D)/[1+exp(D)].

Example 5

In the same overall study population as Example 1, over a mean 7.7 year study period, 148 of 2753 individuals converted to type 2 Diabetes. Each converter was matched in a 1:2 ratio (296 subjects) with non-converters. Unrelated subjects were matched for age at study entry and age of diagnosis or last follow-up visit, glucose tolerance status, BMI, gender and presence (or absence) of a family history of Diabetes. Baseline test results for the subjects (e.g. BMI, age, SBP, DBP, fasting glucose, 2 hour glucose, total cholesterol, HDL cholesterol, triglycerides and serum insulin) were used in conjunction with biomarker quantitation.

An analysis of the population was performed using Diabetes risk scores calculated according to the instant invention. The highest risk group, EC, which converts to Diabetes in less than 5 years, has a median DRS of 0.63, compared to the NC group with a score of 0.37 (p<0.0001). It is also possible to separate the LC group, who convert to Diabetes in >5 years, from the EC group (p=0.008). Thus, populations at low, medium, and high risk can be identified, and the time to conversion can be predicted.

Example 6

A DRS score may also correlate and predict OGTT. FIG. 14 shows the correlation performance of three such scores, trained to predict Diabetes.

The disclosures of all publications, patents, patent applications and published patent applications referred to herein by an identifying citation are hereby incorporated herein by reference in their entirety. In particular, US 2007/0218519, International Patent Application No. WO 2007/044860, and US 2007/0259377 are hereby incorporated herein by reference in their entirety.

Although the foregoing invention has been described in some detail by way of illustration and example for purposes of clarity of understanding, it is apparent to those skilled in the art that certain minor changes and modifications will be practiced. Therefore, the description and examples should not be construed as limiting the scope of the invention.

Example 7

This is an description of calculating Risk using the algorithm LDA and the formula set out in Example 4 (DRS=exp (D)/[1+exp (D)]).

Marker Selection

An exemplary data set collected from human subjects included 632 observations in this data set and 65 potential blood-borne biomarkers (Inputs). To reduce the number of Inputs, three broad marker selection algorithms were used: Univariate marker selection, exhaustive small model searches, and bootstrap replicates of common heuristic marker selection techniques. The bootstrap marker selection process included forward, backward, and stepwise selection based on Akaike's information criteria (AIC) and Hoetelling's $T^2$, Analysis of variance based filters, random forest filters and Eigengene-based linear discriminant analysis. These selection techniques were used on 100 bootstrap replicates and the marker counts were tabulated and averaged. To control for model size, marker counts were weighted by 1/k where k is the size of the model. Markers were selected for modeling based on a permutation test as follows: Algorithm outputs were permuted and the 100 bootstrap replicates were used to calculate weighted marker count averages of the six selection techniques. This process was repeated 20 times and the 95 percentile of the weighted marker count averages was used as a cutoff to identify markers that were selected significantly more than random. Similar permutation techniques were used to identify univariate features and exhaustive searches that were different from random.

Algorithm Construction

The markers selected as described above were then combined to calculate coefficients that result in a functioning model. Logistic regression and/or linear discriminant analysis were used to estimate coefficients based on maximum likelihood and least-squares means, respectively. Initially, individual markers were evaluated for linearity using decile plots and transformations were attempted if strong departures are noted. Models including all markers were then constructed and the coefficients were examined to determine if all were necessary. The ability to reduce the marker number is evaluated using regression models of principle components of the Inputs, backward selection, and bootstrapping methods. The remaining parameters were used to produce an algorithm is that is a linear model constructed at a prior probability of 50% group membership for the each of the two model outputs. This weighting is useful in balancing sensitivity and specificity of the resulting model when the number of cases and controls (also known as converters and non-converters, respectively) are imbalanced. Cases refer to the samples that were being analyzed to determine if different than the control.

For illustrative purposes, exemplary coefficients for selected biomarkers with the resulting intercept for analysis are set out in Table 8 below. The transformed values for the biomarkers are also set out under subject 20311 (1) and 77884 (0).

TABLE 8

|  | LDA.BWD | LDA.SWS | LDA.KW10 | LDA.RF10 | LDA.ELDA3 | LDA.ELDA2 | 20311 (1) | 77884 (0) |
|---|---|---|---|---|---|---|---|---|
| Intercept | −26.4567 | −27.9154 | −25.1138 | −25.4264 | −5.96578 | −13.1593 |  |  |
| ADIPOQ | −0.66724 | −0.74205 |  | −0.13523 |  | −0.47984 | 3.837386 | 3.59833 |
| CHOL | −2.66393 |  |  |  |  |  | 0.90309 | 0.690196 |
| CRP | 0.70821 | 0.717325 | 0.603214 |  | 0.514556 | 0.6277 | 4.136395 | 2.709206 |
| DPP4 |  |  |  | 0.078344 |  |  | 2.624639 | 2.55854 |
| ENG | −1.12999 | −1.14016 |  |  |  |  | 0.433883 | −0.025635 |
| FTH1 | 0.711809 | 0.706316 | 0.473219 | 0.389999 | 0.620951 | 0.586941 | 3.600816 | 3.079284 |
| GH1 |  |  |  |  | −0.23073 | −0.04613 | −0.331038 | −0.607982 |
| GLUCOSE | 17.46311 | 17.41075 | 17.37771 | 16.54193 |  | 19.69818 | 0.812913 | 0.653213 |
| GPT | 1.087745 | 1.021178 |  |  |  | 0.788968 | 0.325215 | 0.441237 |
| HBA1C | 12.05816 | 11.23972 | 9.050276 | 10.31996 |  |  | 0.770852 | 0.755875 |
| HDL |  |  | 0.390531 |  |  |  | 0.269513 | 0.093422 |
| HGF |  |  | 0.026509 |  |  | −0.10911 | −0.201097 | −0.417961 |
| HSPA1B |  |  |  |  |  | 0.789939 | 1.238439 | 0.348427 |
| IGFBP1 |  |  |  |  |  | 0.045342 | 0.294254 | 0.918387 |

TABLE 8-continued

|         | LDA.BWD  | LDA.SWS  | LDA.KW10 | LDA.RF10 | LDA.ELDA3 | LDA.ELDA2 | 20311 (1) | 77884 (0) |
|---------|----------|----------|----------|----------|-----------|-----------|-----------|-----------|
| IGFBP2  |          |          |          |          | −0.00518  | −0.01889  | 20.68154  | 14.95522  |
| IL18    |          |          | 0.759557 | 1.049944 | 0.808142  | 0.820012  | −0.702241 | −0.627808 |
| IL2RA   |          |          | 0.60912  |          |           | 0.74837   | −0.787264 | −0.301986 |
| INSULIN | 0.665954 | 0.882926 | 1.194011 | 1.36753  | 1.576526  | 1.103641  | 1.869232  | 0.954243  |
| LEP     | 0.696587 | 0.69285  |          |          |           | 0.658789  | 1.016614  | 0.35699   |
| PLAT    | −0.99971 | −0.94709 |          |          |           |           | 1.024778  | 0.885599  |
| SELE    |          |          |          |          |           | −0.51067  | 1.978515  | 2.085064  |
| SELP    |          |          |          |          |           | −0.2501   | 2.539756  | 2.537585  |
| SERPINE1|          |          |          |          | 0.019556  | −0.08744  | 7.794406  | 4.859024  |
| SGK     |          |          |          |          |           | −0.39277  | 3.019246  | 3.989198  |
| SHBG    |          |          |          |          |           | −0.39018  | 4.185424  | 3.527613  |
| TRIG    | 0.846546 |          | 0.591921 | 0.495268 | 0.848019  | 0.171855  | 0.079181  | −0.09691  |
| VCAM1   | 0.995924 | 1.073903 |          | 0.497995 |           |           | 2.726349  | 2.497237  |
| VEGF    |          |          |          |          |           | 0.653159  | −0.53022  | −1.569929 |
| VWF     |          |          |          | 0.226829 |           | −0.08     | 4.484484  | 3.835305  |

Calculation of Risk

The algorithm produced a linear predictor, lp, that is related to group membership of a sample (e.g. case or controls), assuming a 50% prior probability of belonging to a group of converters being a case. This lp can be converted to a convenient score for an individual subject (DRS) on a 0-10 scale using the following equation:

$$DRS = 10 \cdot e^{lp}/(1+e^{lp})$$

This score correlates with the absolute risk of conversion at a specified prior probability (assuming a specified probability of 50%). Changing the prior probability that was used to construct the algorithm to a probability that reflects the actual percentage of "cases" in the population (based on epidemiology data of that population) effectively shifts the linear model by changing the intercept term, $\alpha$, as follows:

$$\alpha' = \alpha + \ln(\pi_1/\pi_0)$$

Where $\alpha'$ is the new intercept, $\alpha$ is the intercept assuming a 50% prior, $\pi_1$ is the prior probability of being a case and $\pi_0$ is the prior probability of being a control. The remaining coefficients stay the same and a new linear predictor, lp', is computed. From this Risk (is computed as follows:

$$Risk = e^{lp'}/(1+e^{lp'})$$

The Risk is the probability that a subject would become a case (a converter). For example, a risk of 25% indicates that 25% of the people with a similar DRS will convert to a diabetic within 5 years.

Example Calculation of Risk

To calculate risk for algorithm LDA.BWD in Table 8, the following biomarker value coefficients and intercept were used: intercept 26.4567, ADIPOQ coefficient −0.66724, CHOL coefficient −2.66393, CRP coefficient 0.70821, ENG coefficient −1.12999, FTH1 coefficient 0.711809, GLUCOSE coefficient 17.46311, GPT coefficient 1.087745, HBA1C coefficient 12.05816, INSULIN coefficient 665954, LEP coefficient 0.696587, PLAT coefficient −0.99971, TRIG coefficient 0.846546, and VCAM1 coefficient 0.995924.

For two subjects the transformed biomarker values (concentration measured) as indicated in Table 8, the lp and score were calculated as follows and set out in Table 9.

$$lp = (ADIPOQ \cdot -0.66724) + (CHOL \cdot -2.66393) + (CRP \cdot 0.70821) + (ENG \cdot -1.12999) + (FTH1 \cdot 0.711809) + (GLUCOSE \cdot 17.46311) + (GPT \cdot 1.087745) + (HBA1C \cdot 12.05816) + (INSULIN \cdot 665954) + (LEP \cdot 0.696587) + (PLAT \cdot -0.99971) + (TRIG \cdot 0.846546) + (VCAM1 \cdot 0.995924) + -26.4567$$

$$DRS = 10 \cdot e^{lp}/(1+e^{lp})$$

TABLE 9

| Subjects | Group | lp       | DRS      |
|----------|-------|----------|----------|
| 77884    | 0     | 1.426083 | 8.062902 |
| 20311    | 1     | −2.41455 | 0.820701 |

To calculate Risk the prior predictability is shifted in view of the epidemiology data of the population that the subject being analyzed is a member. In this example the prior predictability is shifted to 12.5%, and using the following equation the resulting new intercept ($\alpha'$) is −28.4026

$$\alpha' = \alpha + \ln(\pi_1/\pi_0)$$

Using the new intercept the adjusted linear predictor (lp') and Risk is calculated using the following equations. The risk scores are set out in Table 12.

$$lp = (ADIPOQ \cdot -0.66724) + (CHOL \cdot -2.66393) + (CRP \cdot 0.70821) + (ENG \cdot -1.12999) + (FTH1 \cdot 0.711809) + (GLUCOSE \cdot 17.46311) + (GPT \cdot 1.087745) + (HBA1C \cdot 12.05816) + (INSULIN \cdot 665954) + (LEP \cdot 0.696587) + (PLAT \cdot -0.99971) + (TRIG \cdot 0.846546) + (VCAM1 \cdot 0.995924) + -24.5108$$

$$Risk = e^{lp'}/(1+e^{lp'})$$

TABLE 10

| Subjects | Group | lp'      | Score    | Risk     |
|----------|-------|----------|----------|----------|
| 77884    | 0     | −0.51983 | 8.062902 | 0.372893 |
| 20311    | 1     | −4.36046 | 0.820701 | 0.012611 |

Example 8

Example 8 demonstrates the practice of the invention in an expanded general longitudinal population-based study, with a comparably selected Base sub-population and a frank Diabetes sub-analysis.

As in Example 1, for purposes of model discovery, subjects were selected from the sample sets with the following characteristics:

Converters (C): conversion to Diabetes by the 5$^{th}$ year examination

Non-Converters (NC): must have had at least 5 years of follow-up with no documentation of Diabetes.

As in Example 1, both the "Total Population" of all such subjects and a selected "Base Population" sub-population were analyzed. The Base Population was comprised of all subjects within the Total Population who additionally met the inclusion criteria of AGE equal to or greater than 39 years and BMI equal to or greater than 25 kg/m².

Descriptive statistics summarizing the expanded Total Population study arms used in Example 8 are presented below in Table 11.

TABLE 11

|  | Converters | Non-Converters | p |
|---|---|---|---|
| N | 160 | 472 | |
| Male | 110 (68.8%) | 279 (59.1%) | 0.031 |
| NFG/NGT | 12 (7.6%) | 226 (49.7%) | <0.0001 |
| IFG only | 46 (29.1%) | 174 (38.2%) | 0.0433 |
| IGT Only | 25 (15.8%) | 19 (4.2%) | <0.0001 |
| Both IFG and IGT | 75 (47.5%) | 36 (7.9%) | <0.0001 |
| Family History | 48 (30%) | 98 (20.8%) | 0.0223 |
| Age (yrs) | 50.15 (45.2-55) | 49.8 (44.8-54.8) | <0.0001 |
| Height (cm) | 172 (166-179.125) | 172 (166-179) | 0.9277 |
| Weight (kg) | 88.75 (80.375-100.025) | 84 (76.7-93.2) | 0.0001 |
| BMI (kg/m2) | 29.7 (27.475-32.85) | 27.55 (26.1-30.125) | <0.0001 |
| Waist (cm) | 97 (90.5-108.5) | 93 (86-98.5) | <0.0001 |
| Hip (cm) | 106 (101.5-113) | 104 (100-109) | 0.004 |
| Total Cholesterol (mmol/l) | 5.8 (5.1-6.5) | 5.7 (5-6.4) | 0.2513 |
| HDL Cholesterol (mmol/l) | 1.2 (1.01-1.43) | 1.3 (1.09-1.57) | 0.0013 |
| LDL Cholesterol (mmol/l) | 3.645 (3.12-4.4) | 3.605 (3.0525-4.3) | 0.6898 |
| Triglycerides (mmol/l) | 1.6 (1.275-2.2) | 1.3 (0.9-1.8) | <0.0001 |
| SBP (mm Hg) | 140 (130-150) | 130 (120-144.25) | <0.0001 |
| DBP (mm Hg) | 90 (80-96) | 85 (80-90) | 0.0008 |
| Fasting Insulin (pmol/l) | 57.5 (37-81.25) | 40 (27-59) | <0.0001 |
| 2-hour Insulin (pmol/l) | 324.5 (210-486.25) | 186 (100-298) | <0.0001 |
| Fasting Glucose (mmol/l) | 6.1 (5.7-6.5) | 5.6 (5.3-6) | <0.0001 |
| 2-hour Glucose (mmol/l) | 8.4 (7.1-9.475) | 6.1 (5.1-7) | <0.0001 |
| HBA1C (%) | 6.1 (5.8-6.4) | 5.9 (5.6-6.1) | <0.0001 |

What is claimed is:

1. A method for monitoring a treatment regimen to delay or prevent an individual's conversion to a frank Diabetes disease state, the method comprising:
   (a) obtaining from at least one biological sample isolated from said individual undergoing said treatment regimen measurements of biomarkers comprising the biomarkers ADIPOQ (Adiponectin), GLUCOSE and CRP (C-Reactive Protein), and further comprising at least one biomarker selected from the group consisting of HBA1C (Glycosylated Hemoglobin), IGFBP1 (Insulin-like growth factor binding protein 1), IGFBP2 (Insulin-like growth factor binding protein 2), Insulin, LEP (Leptin) and TRIG (Triglycerides);
   (b) calculating the individual's risk for developing a diabetic condition from the output of a model, wherein the inputs to said model comprise said measurements, and further wherein said model was developed by fitting data from a longitudinal study of a selected population of individuals and said fitted data comprises levels of said biomarkers and conversion to Diabetes in said selected population of individuals; and
   (c) comparing the calculated risk for said individual to a previously calculated risk obtained from at least one earlier sample from said individual.

2. A method according to claim 1 wherein at least one of said biomarker measurements is obtained by a method selected from the group consisting of immunoassay and enzymatic activity assay.

3. A method according to claim 1 further comprising advising said individual or a health care practitioner of said change in calculated risk.

4. A method according to claim 2 further comprising advising said individual or a health care practitioner of said change in calculated risk.

5. A method according to claim 1 wherein said biomarkers comprise HBA1C.

6. A method according to claim 2 wherein said biomarkers comprise HBA1C.

7. A method according to claim 1 wherein said biomarkers comprise Insulin.

8. A method according to claim 2 wherein said biomarkers comprise Insulin.

9. A method according to claim 5 wherein said biomarkers further comprise Insulin.

10. A method according to claim 6 wherein said biomarkers further comprise Insulin.

11. A method according to claim 1 wherein said biomarkers further comprise a marker selected from IL2RA (Interleukin 2 Receptor, Alpha) and ferritin.

12. A method according to claim 2 wherein said biomarkers further comprise a marker selected from IL2RA (Interleukin 2 Receptor, Alpha) and ferritin.

13. A method according to claim 1 wherein said isolated biological sample is serum or plasma.

14. A method according to claim 2 wherein said isolated biological sample is serum or plasma.

15. A method for monitoring a treatment regimen or to delay, or prevent an individual's conversion to a frank Diabetes disease state, the method comprising:
   (a) obtaining from at least one biological sample isolated from said individual undergoing said treatment regimen measurements of biomarkers comprising the biomarkers ADIPOQ (Adiponectin), GLUCOSE and CRP (C-Reactive Protein), and further comprising at least one biomarker selected from the group consisting of HBA1C (Glycosylated Hemoglobin), IGFBP1 (Insulin-like growth factor binding protein 1), IGFBP2 (Insulin-like growth factor binding protein 2), Insulin, LEP (Leptin) and TRIG (Triglycerides);
   (b) calculating the individual's risk for developing a diabetic condition from the output of a model, wherein the inputs to said model comprise said measurements, and further wherein said model was developed by fitting data from a longitudinal study of a selected population of individuals and said fitted data comprises levels of said biomarkers and conversion to Diabetes in said selected population of individuals;

(c) storing said calculated risk on electronic data storage means (d) comparing the calculated risk for said individual to a previously calculated risk obtained from at least one earlier sample from said individual.

16. A method according to claim 15 wherein at least one of said biomarker measurements is obtained by a method selected from the group consisting of immunoassay and enzymatic activity assay.

17. A method according to claim 15 further comprising advising said individual or a health care practitioner of said change in calculated risk.

18. A method according to claim 16 further comprising advising said individual or a health care practitioner of said change in calculated risk.

19. A method according to claim 15 wherein said biomarkers comprise HBA1C.

20. A method according to claim 16 wherein said biomarkers comprise HBA1C.

21. A method according to claim 15 wherein said biomarkers comprise Insulin.

22. A method according to claim 16 wherein said biomarkers comprise Insulin.

23. A method according to claim 19 wherein said biomarkers further comprise Insulin.

24. A method according to claim 20 wherein said biomarkers further comprise Insulin.

25. A method according to claim 15 wherein said biomarkers further comprise a marker selected from IL2RA (Interleukin 2 Receptor, Alpha) and ferritin.

26. A method according to claim 16 wherein said biomarkers further comprise a marker selected from IL2RA (Interleukin 2 Receptor, Alpha) and ferritin.

27. A method according to claim 15 wherein said isolated biological sample is serum or plasma.

28. A method according to claim 16 wherein said isolated biological sample is serum or plasma.

29. A method for monitoring a treatment regimen to delay or prevent an individual's conversion to a frank Diabetes disease state, the method comprising:

(a) obtaining from at least one biological sample isolated from said individual undergoing said treatment regimen measurements of biomarkers comprising the biomarkers ADIPOQ (Adiponectin), GLUCOSE and CRP (C-Reactive Protein), and further comprising at least one biomarker selected from the group consisting of HBA1C (Glycosylated Hemoglobin), IGFBP1 (Insulin-like growth factor binding protein 1), IGFBP2 (Insulin-like growth factor binding protein 2), Insulin, LEP (Leptin) and TRIG (Triglycerides);

(b) calculating the individual's risk for developing a diabetic condition from the output of a model, wherein the inputs to said model comprise said measurements, and further wherein said model was developed by fitting data from a longitudinal study of a selected population of individuals and said fitted data comprises levels of said biomarkers and conversion to Diabetes in said selected population of individuals;

(c) storing said calculated risk on electronic data storage means (d) comparing the calculated risk for said individual to a previously calculated risk obtained from at least one earlier sample from said individual and (f) advising said individual or a health care practitioner of whether there has been a change in calculated risk.

30. A method according to claim 20 wherein at least one of said biomarker measurements is obtained by a method selected from the group consisting of immunoassay and enzymatic activity assay.

31. A method according to claim 20 wherein said biomarkers comprise HBA1C.

32. A method according to claim 30 wherein said biomarkers comprise HBA1C.

33. A method according to claim 20 wherein said biomarkers comprise Insulin.

34. A method according to claim 30 wherein said biomarkers comprise Insulin.

35. A method according to claim 20 wherein said biomarkers further comprise a marker selected from IL2RA (Interleukin 2 Receptor, Alpha) and ferritin.

36. A method according to claim 30 said wherein said biomarkers further comprise a marker selected from IL2RA (Interleukin 2 Receptor, Alpha) and ferritin.

37. A method according to claim 20 wherein said isolated biological sample is serum or plasma.

38. A method according to claim 30 wherein said isolated biological sample is serum or plasma.

* * * * *